(12) United States Patent
Sun et al.

(10) Patent No.: US 6,833,247 B2

(45) Date of Patent: Dec. 21, 2004

(54) REGULATED PROSTATE CANCER GENES

(75) Inventors: Zairen Sun, Rockville, MD (US); Xuan Li, Silver Spring, MD (US); Gilbert Jay, North Bethesda, MD (US)

(73) Assignee: Origene Technologies, Inc., Rockville, MD (US)

( * ) Notice: Subject to any disclaimer, the term of this patent is extended or adjusted under 35 U.S.C. 154(b) by 0 days.

(21) Appl. No.: 10/144,198

(22) Filed: May 14, 2002

(65) Prior Publication Data

US 2003/0219748 A1 Nov. 27, 2003

(51) Int. Cl.[7] .......................... C12Q 1/68; C12P 19/34; C12N 5/00

(52) U.S. Cl. .......................... 435/6; 435/91.1; 435/325; 435/375

(58) Field of Search .......................... 514/44; 536/24.1, 536/24.5; 435/91.2, 6

(56) References Cited

U.S. PATENT DOCUMENTS 6,391,543 B2 * 5/2002 Billing-Medel et al. ....... 435/6

OTHER PUBLICATIONS

Nagase et al. 2002 (Accession No. AB033070).*
Hong, W. 2001 (Accession No. AF413080).*
Phillips, S. 1999 (Accession No. AL031003).*
Waterson, R.H. 2000 (Accession No. AC036236).*
Drmanac et al. 2001 (Accession No. AAS73915).*
Sugano et al. 2000 (Accession No. AK000682).*

* cited by examiner

*Primary Examiner*—Karen A. Lacourciere
*Assistant Examiner*—Terra C. Gibbs
(74) *Attorney, Agent, or Firm*—Millen, White, Zelano & Branigan, P.C.

(57) ABSTRACT

The present invention relates to all facets of novel polynucleotides, the polypeptides they encode, antibodies and specific binding partners thereto, and their applications to research, diagnosis, drug discovery, therapy, clinical medicine, forensic science and medicine, etc. The polynucleotides are differentially-regulated in prostate cancer and are therefore useful in variety of ways, including, but not limited to, as molecular markers, as drug targets, and for detecting, diagnosing, staging, monitoring, prognosticating, preventing or treating, determining predisposition to, etc., diseases and conditions, to prostate cancer.

14 Claims, 22 Drawing Sheets

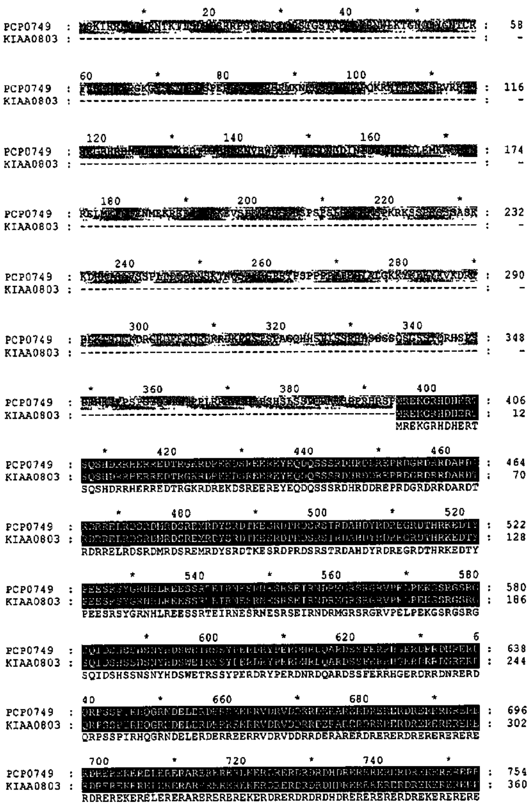

```
              *         20          *         40          *
PCP0749 : MSKIRRRRMENTKTTSDRRRRPSYRRRGSSTGSTARRRRDWLKTCNQRYGNTCR : 58
KIAA0803 : -------------------------------------------------------- : -

              60          *         80          *        100          *
PCP0749 : FYRRRRRGKGRRRNRRRSPERRRRRRRERMKNRRRRRLRRQKRNTRRSSRRVRRRR : 116
KIAA0803 : -------------------------------------------------------- : -

             120          *        140          *        160          *
PCP0749 : SRGRHRRRRRRRRKERTRRRRRENVEWPRRRRQRSDNRQDINRRRRRESLEMKRRRRR : 174
KIAA0803 : -------------------------------------------------------- : -

             180          *        200          *        220          *
PCP0749 : RELMRRRRRNMEKRERRRRREVSRRRRRSRRSPSPSLRRRRRSPKRKSSRRGSSASK : 232
KIAA0803 : -------------------------------------------------------- : -

             240          *        260          *        280          *
PCP0749 : KDRRRRRVSSPLTRRORNSKTNRRRRRRPRTPSPPPRRRRRNATGKKYRRRKYKVKDRP : 290
KIAA0803 : -------------------------------------------------------- : -

             300          *        320          *        340
PCP0749 : PRRRRDCRRDRCRDRRRRRDRRRRRREKPRRSTARQHHSRLSSRRRGGGSQSRSSTQRHSRS : 348
KIAA0803 : -------------------------------------------------------- : -

              *        360          *        380          *        400
PCP0749 : RRHRRRRTPSPSSRRRRRRRRPLRRRRRRRRSHSLSSRRRRRRRPRHRSPMREKGRHDHERT : 406
KIAA0803 : -----------------------------------------------MREKGRHDHERT : 12
                                                         MREKGRHDHERT

              *        420          *        440          *        460
PCP0749 : SQSHDRRHERREDTRGKRDREKDSREEREYEQDQSSSRDHRDDREPRDGRDRRDARDT : 464
KIAA0803 : SQSHDRRHERREDTRGKRDREKDSREEREYEQDQSSSRDHRDDREPRDGRDRRDARDT : 70
          SQSHDRRHERREDTRGKRDREKDSREEREYEQDQSSSRDHRDDREPRDGRDRRDARDT

              *        480          *        500          *        520
PCP0749 : RDRRELRDSRDMRDSREMRDYSRDTKESRDPRDSRSTRDAHDYRDREGRDTHRKEDTY : 522
KIAA0803 : RDRRELRDSRDMRDSREMRDYSRDTKESRDPRDSRSTRDAHDYRDREGRDTHRKEDTY : 128
          RDRRELRDSRDMRDSREMRDYSRDTKESRDPRDSRSTRDAHDYRDREGRDTHRKEDTY

              *        540          *        560          *        580
PCP0749 : PEESRSYGRNHLREESSRTEIRNESRNESRSEIRNDRMGRSRGRVPELPEKGSRGSRG : 580
KIAA0803 : PEESRSYGRNHLREESSRTEIRNESRNESRSEIRNDRMGRSRGRVPELPEKGSRGSRG : 186
          PEESRSYGRNHLREESSRTEIRNESRNESRSEIRNDRMGRSRGRVPELPEKGSRGSRG

              *        600          *        620          *          6
PCP0749 : SQIDSHSSNSNYHDSWETRSSYPERDRYPERDNRDQARDSSFERRHGERDRRDNRERI : 638
KIAA0803 : SQIDSHSSNSNYHDSWETRSSYPERDRYPERDNRDQARDSSFERRHGERDRRDNRERI : 244
          SQIDSHSSNSNYHDSWETRSSYPERDRYPERDNRDQARDSSFERRHGERDRRDNRERD

           40          *        660          *        680          *
PCP0749 : QRPSSPIRHQGRNDELERDERRRERRVDRVDDRRDERARERDRERERDRERERERERE : 696
KIAA0803 : QRPSSPIRHQGRNDELERDERRRERRVDRVDDRRDERARERDRERERDRERERERERE : 302
          QRPSSPIRHQGRNDELERDERRRERRVDRVDDRRDERARERDRERERDRERERERERE

             700          *        720          *        740          *
PCP0749 : RDREREKERELERERARERERREKERDRERDRDRDHDRERERERERDREKERERERE : 754
KIAA0803 : RDREREKERELERERARERERREKERDRERDRDRDHDRERERERERDREKERERERE : 360
          RDREREKERELERERARERERREKERDRERDRDRDHDRERERERERDREKERERERE
```

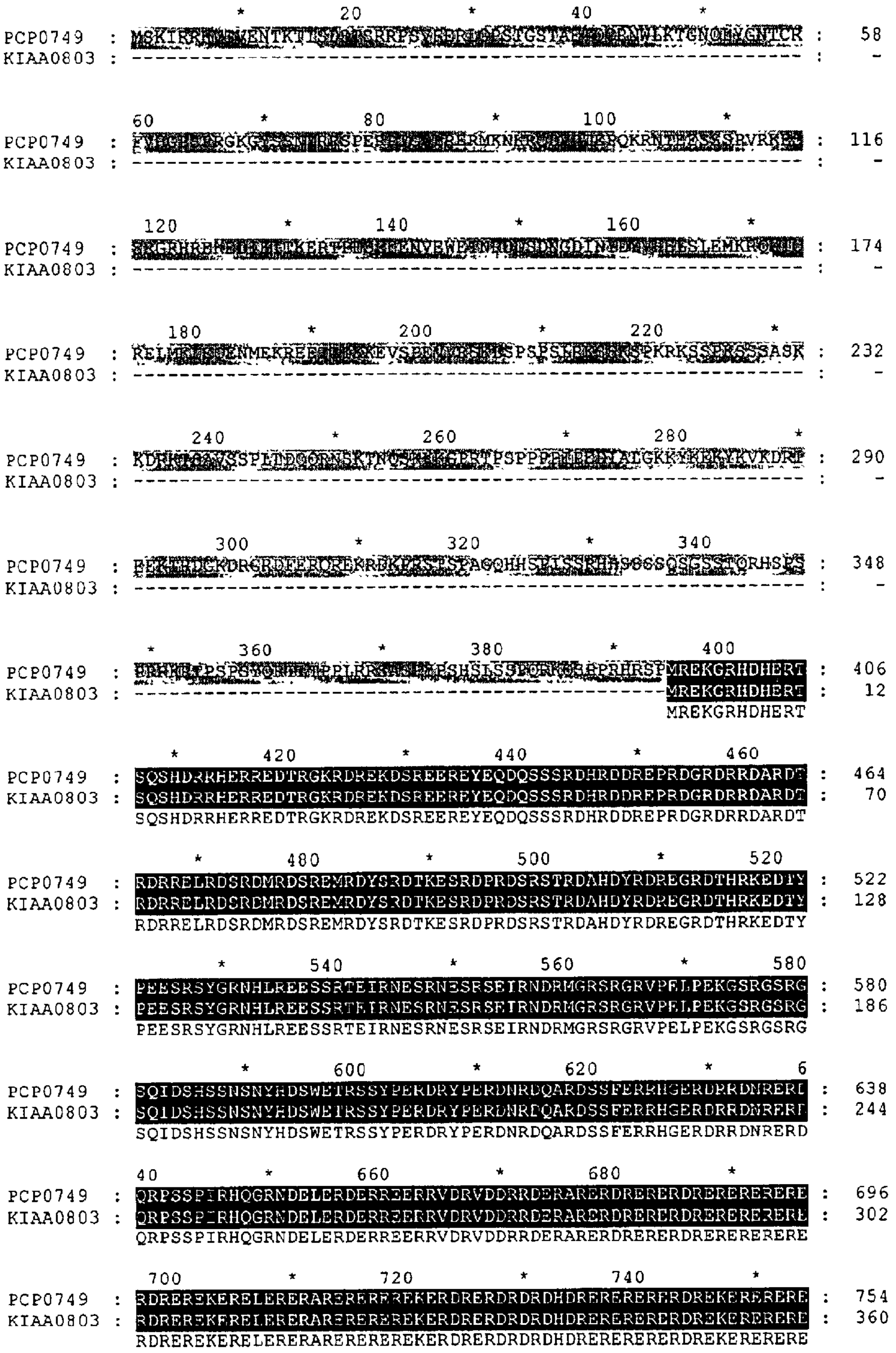

FIG. 1A

```
             760        *       780         *       800         *
PCP0749  : ERERERERERERERERERERERERARERDKERERQRDWEDKDKGRDDRREKREEIREDRN : 812
KIAA0803 : ERERERERERERERERERERERERARERDKERERQRDWEDKDKGRDDRREKREEIREDRN : 418
           ERERERERERERERERERERERERARERDKERERQRDWEDKDKGRDDRREKREEIREDRN

             820        *       840         *       860         *
PCP0749  : PRDGHDERKSKKRYRNEGSPSPRQSPKRRREHSPDSDAYNSGDDKNEKHRLLSQVVRP : 870
KIAA0803 : PRDGHDERKSKKRYRNEGSPSPRQSPKRRREHSPDSDAYNSGDDKNEKHRLLSQVVRP : 476
           PRDGHDERKSKKRYRNEGSPSPRQSPKRRREHSPDSDAYNSGDDKNEKHRLLSQVVRP

               880        *       900         *       920
PCP0749  : QESRSLSPSHLTEDRQGRWKEEDRKPERKESSRRYEEQELKEKVSSVDKQREQTEILE : 928
KIAA0803 : QESRSLSPSHLTEDRQGRWKEEDRKPERKESSRRYEEQELKEKVSSVDKQREQTEILE : 534
           QESRSLSPSHLTEDRQGRWKEEDRKPERKESSRRYEEQELKEKVSSVDKQREQTEILE

            *       940         *       960         *       980
PCP0749  : SSRMRAQDIIGHHQSEDRETSDRAHDENKKKAKIQKKPIKKKKEDDVGIERGNIETTS : 986
KIAA0803 : SSRMRAQDIIGHHQSEDRETSDRAHDENKKKAKIQKKPIKKKKEDDVGIERGNIETTS : 592
           SSRMRAQDIIGHHQSEDRETSDRAHDENKKKAKIQKKPIKKKKEDDVGIERGNIETTS

             *      1000        *      1020         *      1040
PCP0749  : EDGQVFSPKKGQKKKSIEKKRKKSKGDSDISDEEAAQQSKKKRGPRTPPITTKEELVE : 1044
KIAA0803 : EDGQVFSPKKGQKKKSIEKKRKKSKGDSDISDEEAAQQSKKKRGPRTPPITTKEELVE : 650
           EDGQVFSPKKGQKKKSIEKKRKKSKGDSDISDEEAAQQSKKKRGPRTPPITTKEELVE

              *      1060        *      1080         *      1100
PCP0749  : MCNGKNGILEDSQKKEDTAFSDWSDEDVPDRTEVTEAEHTATATTPGSTPSPLSSLLP : 1102
KIAA0803 : MCNGKNGILEDSQKKEDTAFSDWSDEDVPDRTEVTEAEHTATATTPGSTPSPLSSLLP : 708
           MCNGKNGILEDSQKKEDTAFSDWSDEDVPDRTEVTEAEHTATATTPGSTPSPLSSLLP

               *      1120        *      1140         *      1160
PCP0749  : PPPPVATATATTVPATLAATTAAAATSFSTSAITISTSATPTNTTNNTFANEDSHRKC : 1160
KIAA0803 : PPPPVATATATTVPATLAATTAAAATSFSTSAITISTSATPTNTTNNTFANEDSHRKC : 766
           PPPPVATATATTVPATLAATTAAAATSFSTSAITISTSATPTNTTNNTFANEDSHRKC

                *      1180        *      1200         *      12
PCP0749  : HRTRVEKVETPHVTIEDAQHRKPMDQKRSSSLGSNRSNRSHTSGRLRSPSNDSAHRSG : 1218
KIAA0803 : HRTRVEKVETPHVTIEDAQHRKPMDQKRSSSLGSNRSNRSHTSGRLRSPSNDSAHRSG : 824
           HRTRVEKVETPHVTIEDAQHRKPMDQKRSSSLGSNRSNRSHTSGRLRSPSNDSAHRSG

           20       *      1240        *      1260         *
PCP0749  : DDQSGRKRVLHSGSRDREKTKSLEITGERKSRIDQLKRGEPSRSTSSDRQDSRSHSSR : 1276
KIAA0803 : DDQSGRKRVLHSGSRDREKTKSLEITGERKSRIDQLKRGEPSRSTSSDRQDSRSHSSR : 882
           DDQSGRKRVLHSGSRDREKTKSLEITGERKSRIDQLKRGEPSRSTSSDRQDSRSHSSR

           1280         *      1300        *      1320         *
PCP0749  : RSSPESDRQVHSRSGSFDSRDRLQERDRYEHDRERERERRDTRQREWDRDADKDWPRN : 1334
KIAA0803 : RSSPESDRQVHSRSGSFDSRDRLQERDRYEHDRERERERRDTRQREWDRDADKDWPRN : 940
           RSSPESDRQVHSRSGSFDSRDRLQERDRYEHDRERERERRDTRQREWDRDADKDWPRN

             1340         *      1360        *      1380         *
PCP0749  : RDRDRLRERERERERDKRRDLDRERERLISDSVERDRDRDRDRTFESSQIESVKRCEA : 1392
KIAA0803 : RDRDRLRERERERERDKRRDLDRERERLISDSVERDRDRDRDRTFESSQIESVKRCEA : 998
           RDRDRLRERERERERDKRRDLDRERERLISDSVERDRDRDRDRTFESSQIESVKRCEA

               1400         *      1420        *      1440         *
PCP0749  : KLEGEHERDLESTSRDSLALDKERMDKDLGSVQGFEDTNKSERTESLEAGDDESKLDD : 1450
KIAA0803 : KLEGEHERDLESTSRDSLALDKERMDKDLGSVQGFEDTNKSERTESLEAGDDESKLDD : 1056
           KLEGEHERDLESTSRDSLALDKERMDKDLGSVQGFEDTNKSERTESLEAGDDESKLDD

                 1460         *      1480        *      1500
PCP0749  : AHSLGSGAGEGYEPISDDELDEILAGDAEKRREDQQDEEKMPDPLDVIDVDWSGLMPKH : 1508
KIAA0803 : AHSLGSGAGEGYEPISDDELDEILAGDAEKRREDQQDEEKMPDPLDVIDVDWSGLMPKH : 1114
           AHSLGSGAGEGYEPISDDELDEILAGDAEKRREDQQDEEKMPDPLDVIDVDWSGLMPKH

             *      1520         *      1540        *      1560
PCP0749  : PKEPREPGAALLKFTPGAVMLRVGISKKLAGSELFAKVKETCQRLLEKPKGSFILL : 1564
KIAA0803 : PKEPREPGAALLKFTPGAVMLRVGISKKLAGSELFAKVKETCQRLLEKPKGSFILL : 1170
           PKEPREPGAALLKFTPGAVMLRVGISKKLAGSELFAKVKETCQRLLEKPKGSFILL
```

FIG. 1B

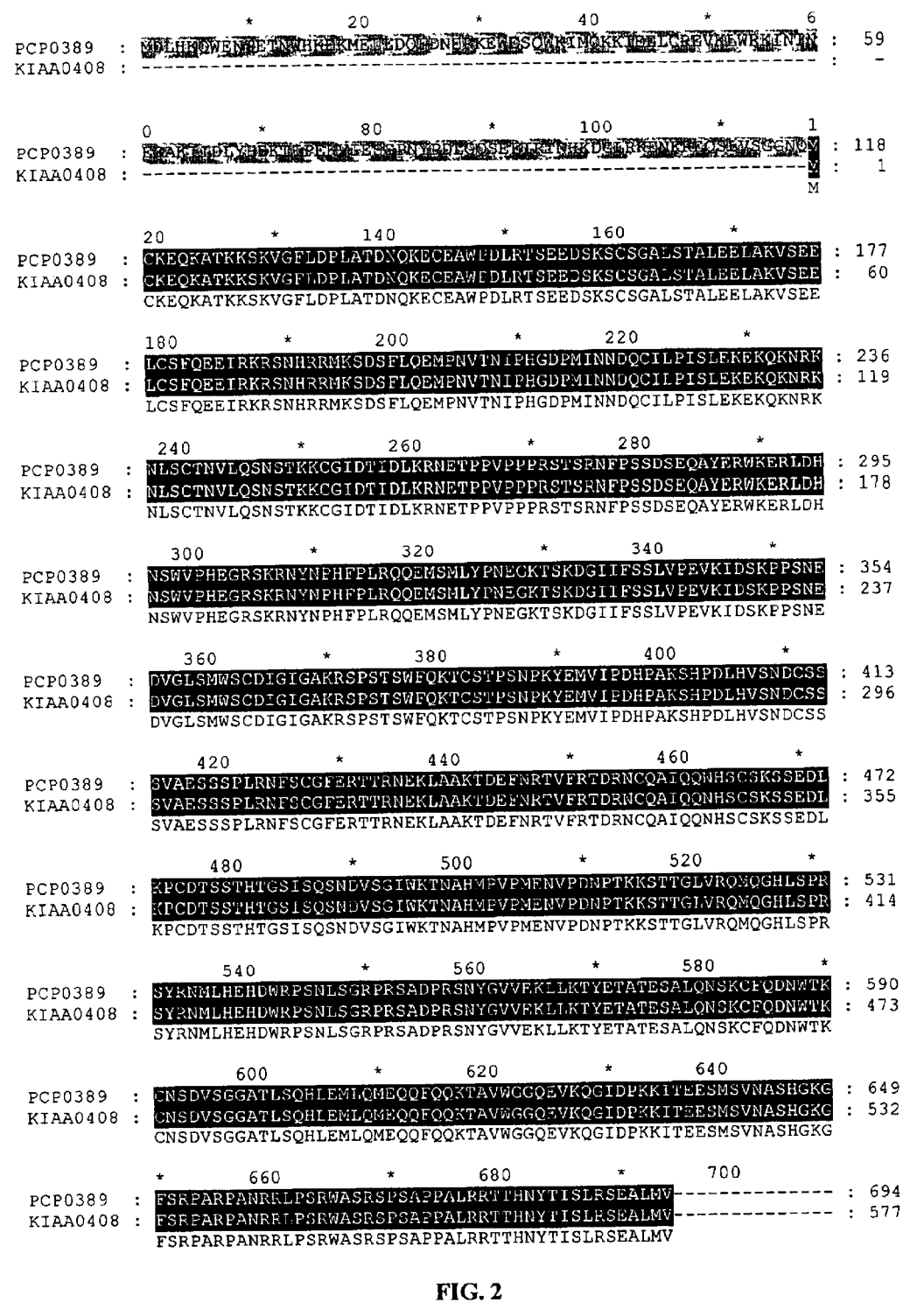

```
                 *        20         *        40         *        6
PCP0389  : [illegible]                                                : 59
KIAA0408 : ----------------------------------------------------------- : -

           0         *        80         *       100         *        1
PCP0389  : [illegible]                                               M : 118
KIAA0408 : ----------------------------------------------------------M : 1
                                                                      M

           20        *       140         *       160         *
PCP0389  : CKEQKATKKSKVGFLDPLATDNQKECEAWPDLRTSEEDSKSCSGALSTALEELAKVSEE : 177
KIAA0408 : CKEQKATKKSKVGFLDPLATDNQKECEAWPDLRTSEEDSKSCSGALSTALEELAKVSEE : 60
           CKEQKATKKSKVGFLDPLATDNQKECEAWPDLRTSEEDSKSCSGALSTALEELAKVSEE

           180       *       200         *       220         *
PCP0389  : LCSFQEEIRKRSNHRRMKSDSFLQEMPNVTNIPHGDPMINNDQCILPISLEKEKQKNRK : 236
KIAA0408 : LCSFQEEIRKRSNHRRMKSDSFLQEMPNVTNIPHGDPMINNDQCILPISLEKEKQKNRK : 119
           LCSFQEEIRKRSNHRRMKSDSFLQEMPNVTNIPHGDPMINNDQCILPISLEKEKQKNRK

            240      *       260         *       280         *
PCP0389  : NLSCTNVLQSNSTKKCGIDTIDLKRNETPPVPPPRSTSRNFPSSDSEQAYERWKERLDH : 295
KIAA0408 : NLSCTNVLQSNSTKKCGIDTIDLKRNETPPVPPPRSTSRNFPSSDSEQAYERWKERLDH : 178
           NLSCTNVLQSNSTKKCGIDTIDLKRNETPPVPPPRSTSRNFPSSDSEQAYERWKERLDH

             300     *       320         *       340         *
PCP0389  : NSWVPHEGRSKRNYNPHFPLRQQEMSMLYPNEGKTSKDGIIFSSLVPEVKIDSKPPSNE : 354
KIAA0408 : NSWVPHEGRSKRNYNPHFPLRQQEMSMLYPNEGKTSKDGIIFSSLVPEVKIDSKPPSNE : 237
           NSWVPHEGRSKRNYNPHFPLRQQEMSMLYPNEGKTSKDGIIFSSLVPEVKIDSKPPSNE

              360    *       380         *       400         *
PCP0389  : DVGLSMWSCDIGIGAKRSPSTSWFQKTCSTPSNPKYEMVIPDHPAKSHPDLHVSNDCSS : 413
KIAA0408 : DVGLSMWSCDIGIGAKRSPSTSWFQKTCSTPSNPKYEMVIPDHPAKSHPDLHVSNDCSS : 296
           DVGLSMWSCDIGIGAKRSPSTSWFQKTCSTPSNPKYEMVIPDHPAKSHPDLHVSNDCSS

               420   *       440         *       460         *
PCP0389  : SVAESSSPLRNFSCGFERTTRNEKLAAKTDEFNRTVFRTDRNCQAIQQNHSCSKSSEDL : 472
KIAA0408 : SVAESSSPLRNFSCGFERTTRNEKLAAKTDEFNRTVFRTDRNCQAIQQNHSCSKSSEDL : 355
           SVAESSSPLRNFSCGFERTTRNEKLAAKTDEFNRTVFRTDRNCQAIQQNHSCSKSSEDL

                480  *       500         *       520         *
PCP0389  : KPCDTSSTHTGSISQSNDVSGIWKTNAHMPVPMENVPDNPTKKSTTGLVRQMQGHLSPR : 531
KIAA0408 : KPCDTSSTHTGSISQSNDVSGIWKTNAHMPVPMENVPDNPTKKSTTGLVRQMQGHLSPR : 414
           KPCDTSSTHTGSISQSNDVSGIWKTNAHMPVPMENVPDNPTKKSTTGLVRQMQGHLSPR

                 540   *     560         *       580         *
PCP0389  : SYRNMLHEHDWRPSNLSGRPRSADPRSNYGVVEKLLKTYETATESALQNSKCFQDNWTK : 590
KIAA0408 : SYRNMLHEHDWRPSNLSGRPRSADPRSNYGVVEKLLKTYETATESALQNSKCFQDNWTK : 473
           SYRNMLHEHDWRPSNLSGRPRSADPRSNYGVVEKLLKTYETATESALQNSKCFQDNWTK

                 600     *     620           *     640
PCP0389  : CNSDVSGGATLSQHLEMLQMEQQFQQKTAVWGGQEVKQGIDPKKITEESMSVNASHGKG : 649
KIAA0408 : CNSDVSGGATLSQHLEMLQMEQQFQQKTAVWGGQEVKQGIDPKKITEESMSVNASHGKG : 532
           CNSDVSGGATLSQHLEMLQMEQQFQQKTAVWGGQEVKQGIDPKKITEESMSVNASHGKG

            *     660      *       680         *        700
PCP0389  : FSRPARPANRRLPSRWASRSPSAPPALRRTTHNYTISLRSEALMV-------------- : 694
KIAA0408 : FSRPARPANRRLPSRWASRSPSAPPALRRTTHNYTISLRSEALMV-------------- : 577
           FSRPARPANRRLPSRWASRSPSAPPALRRTTHNYTISLRSEALMV
```

FIG. 2

```
                         *        20         *        40         *
PCP0814   : MERAPCHRLRARGTRKARAGAWRGGLRECLSKGMERPAAREPHGPDALRRFQGLLLDR :  58
NM_030817 : ---------------------------------MERPAAREPHGPDALRRFQGLLLDR :  25
                                             MERPAAREPHGPDALRRFQGLLLDR

            60         *        80         *       100         *
PCP0814   : RGRLHRQVLRLREVARRLERLRRRSLVANVAGSSLSATGALAAIVGLSLSPVTLGTSL : 116
NM_030817 : RGRLHRQVLRLREVARRLERLRRRSLVANVAGSSLSATGALAAIVGLSLSPVTLGTSL :  83
            RGRLHRQVLRLREVARRLERLRRRSLVANVAGSSLSATGALAAIVGLSLSPVTLGTSL

             120         *       140         *       160         *
PCP0814   : LVSAVGLGVATAGGAVTITSDLSLIFCNSRELRRVQEIAATCQDQMREILSCLEFFCR : 174
NM_030817 : LVSAVGLGVATAGGAVTITSDLSLIFCNSRELRRVQEIAATCQDQMREILSCLEFFCR : 141
            LVSAVGLGVATAGGAVTITSDLSLIFCNSRELRRVQEIAATCQDQMREILSCLEFFCR

               180         *       200         *       220         *
PCP0814   : WQGCGDRQLLQCGRNASIALYNSVYFIVFFGSRGFLIPRRAEGDTKVSQAVLKAKIQK : 232
NM_030817 : WQGCGDRQLLQCGRNASIALYNSVYFIVFFGSRGFLIPRRAEGDTKVSQAVLKAKIQK : 199
            WQGCGDRQLLQCGRNASIALYNSVYFIVFFGSRGFLIPRRAEGDTKVSQAVLKAKIQK

                 240         *       260         *
PCP0814   : LAESLESCTGALDELSEQLESRVQLCTKSSRGHDLKISADQRAGLFF : 279
NM_030817 : LAESLESCTGALDELSEQLESRVQLCTKSSRGHDLKISADQRAGLFF : 246
            LAESLESCTGALDELSEQLESRVQLCTKSSRGHDLKISADQRAGLFF
```

FIG. 3

```
                        *        20         *        40         *
PCP0623   : MNGDMPHVPITTLAGIASLTDLLNQLPLPSPLPATTTKSLLFNARIAEEVNCLLACR :  57
NM_015384 : --------------------------------------------------------- :   -
NM_133433 : --------------------------------------------------------- :   -

             60         *        80         *       100         *
PCP0623   : DDNLVSQLVHSLNQVSTDHIELKDNLGSDDPEGDIPVLLQAVLARSPNVFREKSMQN : 114
NM_015384 : --------------------------------------------------------- :   -
NM_133433 : --------------------------------------------------------- :   -

               120         *       140         *       160         *
PCP0623   : RYVQSGMMMSQYKLSQNSMHSSPASSNYQQTTISHSPSSRFVPPQTSSGNRFMPQQN : 171
NM_015384 : --------------------------------------------------------- :   -
NM_133433 : --------------------------------------------------------- :   -

                 180         *       200         *       220
PCP0623   : SPVPSPYAPQSPAGYMPYSHPSSYTTHPQMQQASVSSPIVAGGLRNIHDNKVSGPLS : 228
NM_015384 : --------------------------------------------------------- :   -
NM_133433 : --------------------------------------------------------- :   -

              *       240         *       260         *       280
PCP0623   : GNSANHHADNPRHGSSEDYLHMVHRLSSDDGDSSTMRNAASFPLRSPQPVCSPAGSE : 285
NM_015384 : --------------------------------------------------------- :   -
NM_133433 : --------------------------------------------------------- :   -

                *       300         *       320         *       340
PCP0623   : GTPKGSRPPLILQSQSLPCSSPRDVPPDILLDSPERKQKKQKKMKLGKDEKEQSEKA : 342
NM_015384 : --------------------------------------------------------- :   -
NM_133433 : --------------------------------------------------------- :   -

                  *       360         *       380         *       40
PCP0623   : AMYDIISSPSKDSTKLTLRLSRVRSSDMDQQEDMISGVENSNVSENDIPFNVQYPGQ : 399
NM_015384 : --------------------------------------------------------- :   -
NM_133433 : --------------------------------------------------------- :   -

            0         *       420         *       440         *
PCP0623   : TSKTPITPQDINRPLNAAQCLSQQEQTAFLPANQVPVLQQNTSVAAKQPQTSVVQNQ : 456
NM_015384 : --------------------------------------------------------- :   -
NM_133433 : --------------------------------------------------------- :   -

              460         *       480         *       500         *
PCP0623   : QQISQQGPIYDEVELDALAEIERIERESAIERERFSKEVQDKDKPLKKRKQDSYPQE : 513
NM_015384 : --------------------------------------------------------- :   -
NM_133433 : --------------------------------------------------------- :   -

                520         *       540         *       560         *
PCP0623   : AGGATGGNRPASQETGSTGNGSRPALMVSIDLHQAGRVDSQASITQDSDSIKKPEEI : 570
NM_015384 : --------------------------MVSIDLHQAGRVDSQASITQDSDSIKKPEEI :  31
NM_133433 : --------------------------MVSIDLHQAGRVDSQASITQDSDSIKKPEEI :  31

                  580         *       600         *       620
PCP0623   : KQCNDAPVSVLQEDIVGSLKSTPENHPETPKKKSDPELSKSEMKQSESRLAESKPNE : 627
NM_015384 : KQCNDAPVSVLQEDIVGSLKSTPENHPETPKKKSDPELSKSEMKQSESRLAESKPNE :  88
NM_133433 : KQCNDAPVSVLQEDIVGSLKSTPENHPETPKKKSDPELSKSEMKQSESRLAESKPNE :  88
```

FIG. 4A

```
                  *       640        *       660        *       680
PCP0623   : NRLVETKSSENKLETKVETQTEELKQNESRTTECKQNESTIVEPKQNENRLSDTKPN :  684
NM_015384 : NRLVETKSSENKLETKVETQTEELKQNESRTTECKQNESTIVEPKQNENRLSDTKPN :  145
NM_133433 : NRLVETKSSENKLETKVETQTEELKQNESRTTECKQNESTIVEPKQNENRLSDTKPN :  145

                  *       700        *       720        *       740
PCP0623   : DNKQNNGRSETTKSRPETPKQKGESRPETPKQKSDGHPETPKQKGDGRPETPKQKGE :  741
NM_015384 : DNKQNNGRSETTKSRPETPKQKGESRPETPKQKSDGHPETPKQKGDGRPETPKQKGE :  202
NM_133433 : DNKQNNGRSETTKSRPETPKQKGESRPETPKQKSDGHPETPKQKGDGRPETPKQKGE :  202

                  *       760        *       780        *         8
PCP0623   : SRPETPKQKNEGRPETPKHRHDNRRDSGKPSTEKKPEVSKHKQDTKSDSPRLKSERA :  798
NM_015384 : SRPETPKQKNEGRPETPKHRHDNRRDSGKPSTEKKPEVSKHKQDTKSDSPRLKSERA :  259
NM_133433 : SRPETPKQKNEGRPETPKHRHDNRRDSGKPSTEKKPEVSKHKQDTKSDSPRLKSERA :  259

            00        *       820        *       840        *
PCP0623   : EALKQRPDGRSVSESLRRDHDNKQKSDDRGESERHRGDQSRVRRPETLRSSSRNEHG :  855
NM_015384 : EALKQRPDGRSVSESLRRDHDNKQKSDDRGESERHRGDQSRVRRPETLRSSSRNEHG :  316
NM_133433 : EALKQRPDGRSVSESLRRDHDNKQKSDDRGESERHRGDQSRVRRPETLRSSSRNEHG :  316

                860        *       880        *       900        *
PCP0623   : IKSDSSKTDKLERKHRHESGDSRERPSSGEQKSRPDSPRVKQGDSNKSRSDKLGFKS :  912
NM_015384 : IKSDSSKTDKLERKHRHESGDSRERPSSGEQKSRPDSPRVKQGDSNKSRSDKLGFKS :  373
NM_133433 : IKSDSSKTDKLERKHRHESGDSRERPSSGEQKSRPDSPRVKQGDSNKSRSDKLGFKS :  373

                    920        *       940        *       960
PCP0623   : PTSKDDKRTEGNKSKVDTNKAHPDNKAEFPSYLLGGRSGALKNFVIPKIKRDKDGNV :  969
NM_015384 : PTSKDDKRTEGNKSKVDTNKAHPDNKAEFPSYLLGGRSGALKNFVIPKIKRDKDGNV :  430
NM_133433 : PTSKDDKRTEGNKSKVDTNKAHPDNKAEFPSYLLGGRSGALKNFVIPKIKRDKDGNV :  430

            *       980        *      1000        *      1020
PCP0623   : TQETKKMEMKGEPKDKVEKIGLVEDLNKGAKPVVVLQKLSLDDVQKLIKDREDKSRS : 1026
NM_015384 : TQETKKMEMKGEPKDKVEKIGLVEDLNKGAKPVVVLQKLSLDDVQKLIKDREDKSRS :  487
NM_133433 : TQETKKMEMKGEPKDKVEKIGLVEDLNKGAKPVVVLQKLSLDDVQKLIKDREDKSRS :  487

                *      1040        *      1060        *      1080
PCP0623   : SLKPIKNKPSKSNKGSIDQSVLKELPPELLAEIESTMPLCERVKMNKRKRSTVNEKP : 1083
NM_015384 : SLKPIKNKPSKSNKGSIDQSVLKELPPELLAEIESTMPLCERVKMNKRKRSTVNEKP :  544
NM_133433 : SLKPIKNKPSKSNKGSIDQSVLKELPPELLAEIESTKPLCERVKMNKRKRSTVNEKP :  544

                  *      1100        *      1120        *      1140
PCP0623   : KYAEISSDEDNDSDEAFESSRKRHKKDDDKAWEYEERDRRSSGDHRRSGHSHEGRRS : 1140
NM_015384 : KYAEISSDEDNDSDEAFESSRKRHKKDDDKAWEYEERDRRSSGDHRRSGHSHEGRRS :  601
NM_133433 : KYAEISSDEDNDSDEAFESSRKRHKKDDDKAWEYEERDRRSSGDHRRSGHSHEGRRS :  601

                    *      1160        *      1180        *         1
PCP0623   : SGGGRYRNRSPSDSDMEDYSPPPSLSEVARKMKKKEKQKKRKAYEPKLTPEEMMDSS : 1197
NM_015384 : SGGGRYRNRSPSDSDMEDYSPPPSLSEVARKMKKKEKQKKRKAYEPKLTPEEMMDSS :  658
NM_133433 : SGGGRYRNRSPSDSDMEDYSPPPSLSEVARKMKKKEKQKKRKAYEPKLTPEEMMDSS :  658

            200        *      1220        *      1240        *
PCP0623   : TFKRFTASIENILDNLEDMDFTAFGDDDEIPQELLLGKHQLNELGSESAKIKAMGIM : 1254
NM_015384 : TFKRFTASIENILDNLEDMDFTAFGDDDEIPQELLLGKHQLNELGSESAKIKAMGIM :  715
NM_133433 : TFKRFTASIENILDNLEDMDFTAFGDDDEIPQELLLGKHQLNELGSESAKIKAMGIM :  715
```

FIG. 4B

```
                 1260        *      1280        *      1300        *
PCP0623    : DKLSTDKTVKVLNILEKNIQDGSKLSTLLNHNNDTEEEERLWRDLIMERVTKSADAC : 1311
NM_015384  : DKLSTDKTVKVLNILEKNIQDGSKLSTLLNHNNDTEEEERLWRDLIMERVTKSADAC :  772
NM_133433  : DKLSTDKTVKVLNILEKNIQDGSKLSTLLNHNNDTEEEERLWRDLIMERVTKSADAC :  772

                    1320        *      1340        *      1360
PCP0623    : LTTINIMTSPNMPKAVYIEDVIERVIQYTKFHLQNTLYPQYDPVYRLDPHGGGLLSS : 1368
NM_015384  : LTTINIMTSPNMPKAVYIEDVIERVIQYTKFHLQNTLYPQYDPVYRLDPHGGGLLSS :  829
NM_133433  : LTTINIMTSPNMPKAVYIEDVIERVIQYTKFHLQNTLYPQYDPVYRLDPHGGGLLSS :  829

                *      1380        *      1400        *      1420
PCP0623    : KAKRAKCSTHKQRVIVMLYNKVCDIVSSLSELLEIQLLTDTTILQVSSMGITPFFVE : 1425
NM_015384  : KAKRAKCSTHKQRVIVMLYNKVCDIVSSLSELLEIQLLTDTTILQVSSMGITPFFVE :  886
NM_133433  : KAKRAKCSTHKQRVIVMLYNKVCDIVSSLSELLEIQLLTDTTILQVSSMGITPFFVE :  886

                  *      1440        *      1460        *      1480
PCP0623    : NVSELQLCAIKLVTAVFSRYEKHRQLILEEIFTSLARLPTSKRSLRNFRLNSSDMDG : 1482
NM_015384  : NVSELQLCAIKLVTAVFSRYEKHRQLILEEIFTSLARLPTSKRSLRNFRLNSSDMDG :  943
NM_133433  : NVSELQLCAIKLVTAVFSRYEKHRQLILEEIFTSLARLPTSKRSLRNFRLNSSDMDG :  943

                    *      1500        *      1520        *      154
PCP0623    : EPMYIQMVTALVLQLIQCVVHLPSSEKDSNAEEDSNKKIDQDVVITNSYETAMRTAQ : 1539
NM_015384  : EPMYIQMVTALVLQLIQCVVHLPSSEKDSNAEEDSNKKIDQDVVITNSYETAMRTAQ : 1000
NM_133433  : EPMYIQMVTALVLQLIQCVVHLPSSEKDSNAEEDSNKKIDQDVVITNSYETAMRTAQ : 1000

             0         *      1560        *      1580        *
PCP0623    : NFLSIFLKKCGSKQGEEDYRPLFENFVQDLLSTVNKPEWPAAELLLSLLGRLLVHQF : 1596
NM_015384  : NFLSIFLKKCGSKQGEEDYRPLFENFVQDLLSTVNKPEWPAAELLLSLLGRLLVHQF : 1057
NM_133433  : NFLSIFLKKCGSKQGEEDYRPLFENFVQDLLSTVNKPEWPAAELLLSLLGRLLVHQF : 1057

             1600        *      1620        *      1640        *
PCP0623    : SNKSTEMALRVASLDYLGTVAARLRKDAVTSKMDQGSIERILKQVSGGEDEIQQLQK : 1653
NM_015384  : SNKSTEMALRVASLDYLGTVAARLRKDAVTSKMDQGSIERILKQVSGGEDEIQQLQK : 1114
NM_133433  : SNKSTEMALRVASLDYLGTVAARLRKDAVTSKMDQGSIERILKQVSGGEDEIQQLQK : 1114

               1660        *      1680        *      1700        *
PCP0623    : ALLDYLDENTETDPSLVFSRKFYIAQWFRDTTLETEKAMKSQKDEESSEGTHHAKEI : 1710
NM_015384  : ALLDYLDENTETDPSLVFSRKFYIAQWFRDTTLETEKAMKSQKDEESSEGTHHAKEI : 1171
NM_133433  : ALLDYLDENTETDPSLVFSRKFYIAQWFRDTTLETEKAMKSQKDEESSEGTHHAKEI : 1171

                  1720        *      1740        *      1760
PCP0623    : ETTGQIMHRAENRKKFLRSIIKTTPSQFSTLKMNSDTVDYDDACLIVRYLASMRPFA : 1767
NM_015384  : ETTGQIMHRAENRKKFLRSIIKTTPSQFSTLKMNSDTVDYDDACLIVRYLASMRPFA : 1228
NM_133433  : ETTGQIMHRAENRKKFLRSIIKTTPSQFSTLKMNSDTVDYDDACLIVRYLASMRPFA : 1228

               *      1780        *      1800        *      1820
PCP0623    : QSFDIYLTQILRVLGENAIAVRTKAMKCLSEVVAVDPSILARLDMQRGVHGRLMDNS : 1824
NM_015384  : QSFDIYLTQILRVLGENAIAVRTKAMKCLSEVVAVDPSILARLDMQRGVHGRLMDNS : 1285
NM_133433  : QSFDIYLTQILRVLGENAIAVRTKAMKCLSEVVAVDPSILARLDMQRGVHGRLMDNS : 1285

                 *      1840        *      1860        *      1880
PCP0623    : TSVREAAVELLGRFVLCRPQLAEQYYDMLIERILDTGISVRKRVIKILRDICIEQPT : 1881
NM_015384  : TSVREAAVELLGRFVLCRPQLAEQYYDMLIERILDTGISVRKRVIKILRDICIEQPT : 1342
NM_133433  : TSVREAAVELLGRFVLCRPQLAEQYYDMLIERILDTGISVRKRVIKILRDICIEQPT : 1342
```

FIG. 4C

```
                     *       1900          *       1920          *         19
PCP0623   : FPKITEMCVKMIRRVNDEEGIKKLVNETFQKLWFTPTPHNDKEAMTRKILNITDVVA : 1938
NM_015384 : FPKITEMCVKMIRRVNDEEGIKKLVNETFQKLWFTPTPHNDKEAMTRKILNITDVVA : 1399
NM_133433 : FPKITEMCVKMIRRVNDEEGIKKLVNETFQKLWFTPTPHNDKEAMTRKILNITDVVA : 1399

            40       *       1960          *       1980          *
PCP0623   : ACRDTGYDWFEQLLQNLLKSEEDSSYKPVKKACTQLVDNLVEHILKYEESLADSDNK : 1995
NM_015384 : ACRDTGYDWFEQLLQNLLKSEEDSSYKPVKKACTQLVDNLVEHILKYEESLADSDNK : 1456
NM_133433 : ACRDTGYDWFEQLLQNLLKSEEDSSYKPVKKACTQLVDNLVEHILKYEESLADSDNK : 1456

             2000          *       2020          *       2040          *
PCP0623   : GVNSGRLVACITTLFLFSKIRPQLMVKHAMTMQPYLTTKCSTQNDFMVICNVAKILE : 2052
NM_015384 : GVNSGRLVACITTLFLFSKIRPQLMVKHAMTMQPYLTTKCSTQNDFMVICNVAKILE : 1513
NM_133433 : GVNSGRLVACITTLFLFSKIRPQLMVKHAMTMQPYLTTKCSTQNDFMVICNVAKILE : 1513

                2060         *       2080          *       2100
PCP0623   : LVVPLMEHPSETFLATIEEDLMKLIIKYGMTVVQHCVSCLGAVVNKVTQNFKFVWAC : 2109
NM_015384 : LVVPLMEHPSETFLATIEEDLMKLIIKYGMTVVQHCVSCLGAVVNKVTQNFKFVWAC : 1570
NM_133433 : LVVPLMEHPSETFLATIEEDLMKLIIKYGMTVVQHCVSCLGAVVNKVTQNFKFVWAC : 1570

            *      2120          *       2140          *       2160
PCP0623   : FNRYYGAISKLKSQHQEDPNNTSLLTNKPALLRSLFTVGALCRHFDFDLEDFKGNSK : 2166
NM_015384 : FNRYYGAISKLKSQHQEDPNNTSLLTNKPALLRSLFTVGALCRHFDFDLEDFKGNSK : 1627
NM_133433 : FNRYYGAISKLKSQHQEDPNNTSLLTNKPALLRSLFTVGALCRHFDFDLEDFKGNSK : 1627

              *      2180          *       2200          *       2220
PCP0623   : VNIKDKVLELLMYFTKHSDEEVQTKAIIGLGFAFIQHPSLMFEQEVKNLYNNILSDK : 2223
NM_015384 : VNIKDKVLELLMYFTKHSDEEVQTKAIIGLGFAFIQHPSLMFEQEVKNLYNNILSDK : 1684
NM_133433 : VNIKDKVLELLMYFTKHSDEEVQTKAIIGLGFAFIQHPSLMFEQEVKNLYNNILSDK : 1684

                *      2240          *       2260          *       2280
PCP0623   : NSSVNLKIQVLKNLQTYLQEEDTRMQQADRDWKKVAKQEDLKEMGDVSSGMSSSIMQ : 2280
NM_015384 : NSSVNLKIQVLKNLQTYLQEEDTRMQQADRDWKKVAKQEDLKEMGDVSSGMSSSIMQ : 1741
NM_133433 : NSSVNLKIQVLKNLQTYLQEEDTRMQQADRDWKKVAKQEDLKEMGDVSSGMSSSIMQ : 1741

                  *      2300          *       2320          *         2
PCP0623   : LYLKQVLEAFFHTQSSVRHFALNVIALILNQGLIHPVQCVPYLIAMGTDPEPAMRNK : 2337
NM_015384 : LYLKQVLEAFFHTQSSVRHFALNVIALTLNQGLTHPVQCVPYLIAMGTDPEPAMRNK : 1798
NM_133433 : LYLKQVLEAFFHTQSSVRHFALNVIALTLNQGLIHPVQCVPYLIAMGTDPEPAMRNK : 1798

            340        *       2360          *       2380          *
PCP0623   : ADQQLVETDKKYAGFIHMKAVAGMKMSYQVQQAINTCLKDPVRGFRQDESSSALCSH : 2394
NM_015384 : ADQQLVETDKKYAGFIHMKAVAGMKMSYQVQQAINTCLKDPVRGFRQDESSSALCSH : 1855
NM_133433 : ADQQLVETDKKYAGFIHMKAVAGMKMSYQVQQAINTCLKDPVRGFRQDESSSALCSH : 1855

              2400         *       2420          *       2440          *
PCP0623   : LYSMIRGNRQHRRAFLISLLNLFDDTAKTDVTMLLYIADNLACFPYQTQEEPLFIMH : 2451
NM_015384 : LYSMIRGNRQHRRAFLISLLNLFDDTAKTDVTMLLYIADNLACFPYQTQEEPLFIMH : 1912
NM_133433 : LYSMIRGNRQHRRAFLISLLNLFDDTAKTDVTMLLYIADNLACFPYQTQEEPLFIMH : 1912

                2460         *       2480          *       2500
PCP0623   : HTDITLSVSGSNLLQSFKESMVKDKRKERKSSPSKENESSDSEEEVSRPRKSRKRVD : 2508
NM_015384 : HTDITLSVSGSNLLQSFKESMVKDKRKERKSSPSKENESSDSEEEVSRPRKSRKRVD : 1969
NM_133433 : HTDITLSVSGSNLLQSFKESMVKDKRKERKSSPSKENESSDSEEEVSRPRKSRKRVD : 1969
```

FIG. 4D

```
                 *       2520         *       2540         *       2560
PCP0623   : SDSDSDSEDDINSVMKCLPENSAPLIEFANVSQGILLLLMLKQHLKNLCGFSDSKIQ : 2565
NM_015384 : SDSDSDSEDDINSVMKCLPENSAPLIEFANVSQGILLLLMLKQHLKNLCGFSDSKIQ : 2026
NM_133433 : SDSDSDSEDDINSVMKCLPENSAPLIEFANVSQGILLLLMLKQHLKNLCGFSDSKIQ : 2026

                    *       2580         *       2600         *       2620
PCP0623   : KYSPSESAKVYDKAINRKTGVHFHPKQTLDFLRSDMANSKITEEVKRSIVKQYLDFK : 2622
NM_015384 : KYSPSESAKVYDKAINRKTGVHFHPKQTLDFLRSDMANSKITEEVKRSIVKQYLDFK : 2083
NM_133433 : KYSPSESAKVYDKAINRKTGVHFHPKQTLDFLRSDMANSKITEEVKRSIVKQYLDFK : 2083

                       *       2640         *       2660         *       268
PCP0623   : LLMEHLDPDEEEEEEGEVSASTNARNKAITSLLGGGSPKNNTAAETEDDESDGEDRGG : 2679
NM_015384 : LLMEHLDPDEEEEEEGEVSASTNARNKAITSLLGGGSPKNNTAAETEDDESDGEDRGG : 2140
NM_133433 : LLMEHLDPDEEEEEEGEVSASTNARNKAITSLLGGGSPKNNTAAETEDDESDGEDRGG : 2140

            0        *       2700         *       2720         *
PCP0623   : GTSGVKRRRSQRISQRIT--------------------------------------- : 2697
NM_015384 : GTSGVKRRRSQRISQRIT--------------------------------------- : 2158
NM_133433 : GTSGSLRRSKRNSDSTELAAQMNESVDVMDVIAICCPKYKDRPQIARVVQKTSSGFS : 2197

            2740         *       2760         *       2780         *
PCP0623   : --------------------------------------------------------- :    -
NM_015384 : --------------------------------------------------------- :    -
NM_133433 : VQWMAGSYSGSWTEAKRRDGRKLVPWVDTIKESDIIYKKIALTSANKLTNKVVQTLR : 2254

               2800
PCP0623   : ----------- :    -
NM_015384 : ----------- :    -
NM_133433 : SLYAAKDGTSS : 2265
```

FIG. 4E

```
                         *        20         *        40         *
PCP0815   : MADESERS-SRLSVPCGEP-AALGGDASEEDHPQVCAKCCAQFTDPTEFLAHQNACS :  55
XM_033473 : MSRRKQRKPQQLISDCEGPSASENGDASEEDHPQVCAKCCAQFTDPTEFLAHQNACS :  57
            M    2R    L   C  P A   GDASEEDHPQVCAKCCAQFTDPTEFLAHQNACS

             60         *        80         *       100         *
PCP0815   : TDPPVMVIIGGQENPNNSSASSEPRPEGHNNPQVMDTEHSNPPDSGSSVPTDPTWGP : 112
XM_033473 : TDPPVMVIIGGQENPNNSSASSEPRPEGHNNPQVMDTEHSNPPDSGSSVPTDPTWGP : 114
            TDPPVMVIIGGQENPNNSSASSEPRPEGHNNPQVMDTEHSNPPDSGSSVPTDPTWGP

               120         *       140         *       160         *
PCP0815   : ERRGEESSGHFLVAATGTAAGGGGGLILASPKLGATPLPPESTPAPPPPPPPPPPPG : 169
XM_033473 : ERRGEESSGHFLVAATGTAAGGGGGLILASPKLGATPLPPESTPAPPPPPPPPPPPG : 171
            ERRGEES GHFLVAATGTAAGGGGGLILASPKLGATPLPPESTPAPPPPPPPPPPPG

                 180         *       200         *       220
PCP0815   : VGSGHLNIPLILEELRVLQQRQIHQMQMTEQICRQVLLLGSLGQTVGAPASPSELPG : 226
XM_033473 : VGSGHLNIPLILEELRVLQQRQIHQMQMTEQICRQVLLLGSLGQTVGAPASPSELPG : 228
            VGSGHLNIPLILEELRVLQQRQIHQMQMTEQICRQVLLLGSLGQTVGAPASPSELPG

              *       240         *       260         *       280
PCP0815   : TGTASSTKPLLPLFSPIKPVQTSKTLASSSSSSSSSSGAETPKQAFFHLYHPLGSQH : 283
XM_033473 : TGTASSTKPLLPLFSPIKPVQTSKTLASSSSSSSSSSGAETPKQAFFHLYHPLGSQH : 285
            TGTASSTKPLLPLFSPIKPVQTSKTLASSSSSSSSSSGAETPKQAFFHLYHPLGSQH

                *       300         *       320         *       340
PCP0815   : PFSAGGVGRSHKPTPAPSPALPGSTDQLIASPHLAFPSTTGLLAAQCLGAARGLEAT : 340
XM_033473 : PFSAGGVGRSHKPTPAPSPALPGSTDQLIASPHLAFPSTTGLLAAQCLGAARGLEAT : 342
            PFSAGGVGRSHKPTPAPSPALPGSTDQLIASPHLAFPSTTGLLAAQCLGAARGLEAT

                  *       360         *       380         *        40
PCP0815   : ASPGLLKPKNGSGELSYGEVMGPLEKPGGRHKCRFCAKVFGSDSALQIHLRSHTGER : 397
XM_033473 : ASPGLLKPKNGSGELSYGEVMGPLEKPGGRHKCRFCAKVFGSDSALQIHLRSHTGER : 399
            ASPGLLKPKNGSGELSYGEVMGPLEKPGGRHKCRFCAKVFGSDSALQIHLRSHTGER

            0        *       420         *       440         *
PCP0815   : PYKCNVCGNRFTTRGNLKVHFHRHREKYPHVQMNPHPVPEHLDYVITSSGLPYGMSV : 454
XM_033473 : PYKCNVCGNRFTTRGNLKVHFHRHREKYPHVQMNPHPVPEHLDYVITSSGLPYGMSV : 456
            PYKCNVCGNRFTTRGNLKVHFHRHREKYPHVQMNPHPVPEHLDYVITSSGLPYGMSV

             460         *       480         *       500         *
PCP0815   : PPEKAEEEAATPGGGVERKPLVASTTALSATESLTLLSTSAGTATAPGLPAFNKFVL : 511
XM_033473 : PPEKAEEEAATPGGGVERKPLVASTTALSATESLTLLSTSAGTATAPGLPAFNKFVL : 513
            PPEKAEEEAATPGGGVERKPLVASTTALSATESLTLLSTSAGTATAPGLPAFNKFVL

                520         *       540         *       560         *
PCP0815   : MKAVEPKNKADENTPPGSEGSAISGVAESSTATRMQLSKLVTSLPSWALLTNHFKST : 568
XM_033473 : MKAVEPKNKADENTPPGSEGSAISGVAESSTATRMQLSKLVTSLPSWALLTNHFKST : 570
            MKAVEPKNKADENTPPGSEGSAISGVAESSTATRMQLSKLVTSLPSWALLTNHFKST

                  580         *       600         *       620
PCP0815   : GSFPFPYVLEPLGASPSETSKLQQLVEKIDRQGAVAVTSAASGAPTTSAPAPSSSAS : 625
XM_033473 : GSFPFPYVLEPLGASPSETSKLQQLVEKIDRQGAVAVTSAASGAPTTSAPAPSSSAS : 627
            GSFPFPYVLEPLGASPSETSKLQQLVEKIDRQGAVAVTSAASGAPTTSAPAPSSSAS

              *       640         *       660         *       680
PCP0815   : SGPNQCVICLRVLSCPRALRLHYGQHGGERPFKCKVCGRAFSTRGNLRAHFVGHKAS : 682
XM_033473 : SGPNQCVICLRVLSCPRALRLHYGQHGGERPFKCKVCGRAFSTRGNLRAHFVGHKAS : 684
            SGPNQCVICLRVLSCPRALRLHYGQHGGERPFKCKVCGRAFSTRGNLRAHFVGHKAS
```

FIG. 5A

```
                  *      700       *       720       *      740
PCP0815    : PAARAQNSCPICQKKFTNAVTLQQHVRMHLGGQIPNGGTALPEGGGAAQENGSEQST : 739
XM_033473  : PAARAQNSCPICQKKFTNAVTLQQHVRMHLGGQIPNGGTALPEGGGAAQENGSEQST : 741
             PAARAQNSCPICQKKFTNAVTLQQHVRMHLGGQIPNGGTALPEGGGAAQENGSEQST

                  *      760       *       780       *       8
PCP0815    : VSGAGSFPQQQSQQPSPEEELSEEEEEEEDEEEEEDVTDEDSLAGRGSESGGEKAISV : 796
XM_033473  : VSGAGSFPQQQSQQPSPEEELSEEEEEEEDEEEEEDVTDEDSLAGRGSESGGEKAISV : 798
             VSGAGSFPQQQSQQPSPEEELSEEEEEEEDEEEEEDVTDEDSLAGRGSESGGEKAISV

             00        *      820       *      840        *
PCP0815    : RGDSEEASGAEEEVGTVAAAATAGKEMDSNEKTTQQSSLPPPPPPDSLDQPQPMEQG : 853
XM_033473  : RGDSEEASGAEEEVGTVAAAATAGKEMDSNEKTTQQSSLPPPPPPDSLDQPQPMEQG : 855
             RGDSEEASGAEEEVGTVAAAATAGKEMDSNEKTTQQSSLPPPPPPDSLDQPQPMEQG

               860       *      880       *      900        *
PCP0815    : SSGVLGGKEEGGKPERSSSPASALTPEGEATSVTLVEELSLQEAMRKEPGESSSRKA : 910
XM_033473  : SSGVLGGKEEGGKPERSSSPASALTPEGEATSVTLVEELSLQEAMRKEPGESSSRKA : 912
             SSGVLGGKEEGGKPERSSSPASALTPEGEATSVTLVEELSLQEAMRKEPGESSSRKA

                 920       *      940       *      960
PCP0815    : CEVCGQAFPSQAALEEHQKTHPKEGPLFTCVFCRQGFLERATLKKHMLLAHHQNQYV : 967
XM_033473  : CEVCGQAFPSQAALEEHQKTHPKEGPLFTCVFCRQGFLERATLKKHMLLAHHQVQRE : 969
             CEVCGQAFPSQAALEEHQKTHPKEGPLFTCVFCRQGFLERATLKKHMLLAHHQ Q

             *       980       *      1000        *      1020
PCP0815    : APLSNGLPMKPWNSSSTSTPTPSLAPPVE-EGLSTVASKVPPTM------------- : 1010
XM_033473  : A------PHGPQNTAALSLV-PGCSPSITSTGLSHEPRKDDPTIE------------- : 1007
             A      P  P N    S   P   P 6   GL     K  PT6

                  *      1040       *      1060        *
PCP0815    : ---------------------GSREAKEKEAPHLEQPEAEKAPPEKKELIEKK : 1041
XM_033473  : ------------------------------------------------------ :  -
```

FIG. 5B

```
              *         20          *         40          *
PCP0840   : [MCTRAR FESNT...RSCGGH...DTIL.TPN.ED.D.PKV.EKOET.QPGLVA.] :  58
XM_059862 : ------------------------------------------------------- :   -

            60          *         80          *        100          *
PCP0840   : [SVTNK.M.D.R.QD.SH.KQ.S....T...SV.S...SRP.H.SCS..R...R..] : 116
XM_059862 : ------------------------------------------------------- :   -

                120         *        140          *        160          *
PCP0840   : [......]SSTP-TGSEYDE.EVDYEESDSDESWTTESAISSEAILSSMCMNGGEEKPF : 173
XM_059862 : -------[MN.PF.]SEYDE.EVDYE.SDSDESWTTESAISSEAILSSMCMNGGEEKPF :  51
                     P  SEYDEEEVDYEESDSDESWTTESAISSEAILSSMCMNGGEEKPF

               180         *        200          *        220          *
PCP0840   : ACPVPGCKKRYKNVNGIKYHAKNGHRTQIRVRKPFKCRCGKSYKTAQGLRHHTINFHP : 231
XM_059862 : ACPVPGCKKRYKNVNGIKYHAKNGHRTQIRVRKPFKCRCGKSYKTAQGLRHHTINFHP : 109
            ACPVPGCKKRYKNVNGIKYHAKNGHRTQIRVRKPFKCRCGKSYKTAQGLRHHTINFHP

                240
PCP0840   : PVSAEIIRKMQQ : 243
XM_059862 : PVSAEIIRKMQQ : 121
            PVSAEIIRKMQQ
```

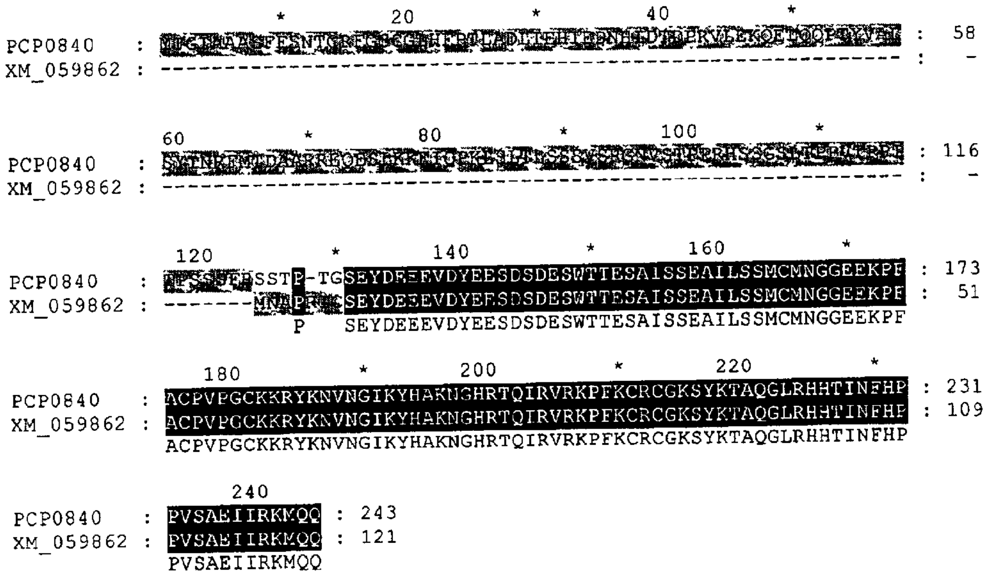

FIG. 6

```
                     *        20        *        40         *
PCP0424A  : MACREGAGSRRARSNGCRLPRRGRRRGGRRRTVGPGPIHCRGRRALGPRVFRVMEALI :  58
NM_012062 : -----------------------------------------------------MEALI :   5
PCP0424B  : MACREGAGSRRARSNGCRLPRRGRRRGGRRRTVGPGPIHCRGRRALGPRVFRVMEALI :  58
NM_012063 : -----------------------------------------------------MEALI :   5
PCP0424C  : MACREGAGSRRARSNGCRLPRRGRRRGGRRRTVGPGPIHCRGRRALGPRVFRVMEALI :  58
NM_005690 : -----------------------------------------------------MEALI :   5
                                                                 MEALI

              60         *        80         *       100         *
PCP0424A  : PVINKLQDVFNTVGADIIQLPQIVVVGTQSSGKSSVLESLVGRDLLPRGTGIVTRRPL : 116
NM_012062 : PVINKLQDVFNTVGADIIQLPQIVVVGTQSSGKSSVLESLVGRDLLPRGTGIVTRRPL :  63
PCP0424B  : PVINKLQDVFNTVGADIIQLPQIVVVGTQSSGKSSVLESLVGRDLLPRGTGIVTRRPL : 116
NM_012063 : PVINKLQDVFNTVGADIIQLPQIVVVGTQSSGKSSVLESLVGRDLLPRGTGIVTRRPL :  63
PCP0424C  : PVINKLQDVFNTVGADIIQLPQIVVVGTQSSGKSSVLESLVGRDLLPRGTGIVTRRPL : 116
NM_005690 : PVINKLQDVFNTVGADIIQLPQIVVVGTQSSGKSSVLESLVGRDLLPRGTGIVTRRPL :  63
            PVINKLQDVFNTVGADIIQLPQIVVVGTQSSGKSSVLESLVGRDLLPRGTGIVTRRPL

              120        *       140         *       160         *
PCP0424A  : ILQLVHVTQEDKRKTTGEENGVEAEEWGKFLHTKNKLYTDFDEIRQEIENETERISGN : 174
NM_012062 : ILQLVHVTQEDKRKTTGEENGVEAEEWGKFLHTKNKLYTDFDEIRQEIENETERISGN : 121
PCP0424B  : ILQLVHVTQEDKRKTTGEENGVEAEEWGKFLHTKNKLYTDFDEIRQEIENETERISGN : 174
NM_012063 : ILQLVHVTQEDKRKTTGEENGVEAEEWGKFLHTKNKLYTDFDEIRQEIENETERISGN : 121
PCP0424C  : ILQLVHVTQEDKRKTTGEENGVEAEEWGKFLHTKNKLYTDFDEIRQEIENETERISGN : 174
NM_005690 : ILQLVHVTQEDKRKTTGEENGVEAEEWGKFLHTKNKLYTDFDEIRQEIENETERISGN : 121
            ILQLVHVTQEDKRKTTGEENGVEAEEWGKFLHTKNKLYTDFDEIRQEIENETERISGN

                180        *       200         *       220         *
PCP0424A  : NKGVSPEPIHLKIFSPNVVNLTLVDLPGMTKVPVGDQPKDIELQIRELILRFISNPNS : 232
NM_012062 : NKGVSPEPIHLKIFSPNVVNLTLVDLPGMTKVPVGDQPKDIELQIRELILRFISNPNS : 179
PCP0424B  : NKGVSPEPIHLKIFSPNVVNLTLVDLPGMTKVPVGDQPKDIELQIRELILRFISNPNS : 232
NM_012063 : NKGVSPEPIHLKIFSPNVVNLTLVDLPGMTKVPVGDQPKDIELQIRELILRFISNPNS : 179
PCP0424C  : NKGVSPEPIHLKIFSPNVVNLTLVDLPGMTKVPVGDQPKDIELQIRELILRFISNPNS : 232
NM_005690 : NKGVSPEPIHLKIFSPNVVNLTLVDLPGMTKVPVGDQPKDIELQIRELILRFISNPNS : 179
            NKGVSPEPIHLKIFSPNVVNLTLVDLPGMTKVPVGDQPKDIELQIRELILRFISNPNS

                240        *       260         *       280         *
PCP0424A  : IILAVTAANTDMATSEALKISREVDPDGRRTLAVITKLDLMDAGTDAMDVLMGRVIPV : 290
NM_012062 : IILAVTAANTDMATSEALKISREVDPDGRRTLAVITKLDLMDAGTDAMDVLMGRVIPV : 237
PCP0424B  : IILAVTAANTDMATSEALKISREVDPDGRRTLAVITKLDLMDAGTDAMDVLMGRVIPV : 290
NM_012063 : IILAVTAANTDMATSEALKISREVDPDGRRTLAVITKLDLMDAGTDAMDVLMGRVIPV : 237
PCP0424C  : IILAVTAANTDMATSEALKISREVDPDGCRTLAVITKLDLMDAGTDAMDVLMGRVIPV : 290
NM_005690 : IILAVTAANTDMATSEALKISREVDPDGCRTLAVITKLDLMDAGTDAMDVLMGRVIPV : 237
            IILAVTAANTDMATSEALKISREVDPDG RTLAVITKLDLMDAGTDAMDVLMGRVIPV

                300        *       320         *       340
PCP0424A  : KLGIIGVVNRSQLDINNKKSVTDSIRDEYAFLQKKYPSLANRNGTKYLARTLNRLLMH : 348
NM_012062 : KLGIIGVVNRSQLDINNKKSVTDSIRDEYAFLQKKYPSLANRNGTKYLARTLNRLLMH : 295
PCP0424B  : KLGIIGVVNRSQLDINNKKSVTDSIRDEYAFLQKKYPSLANRNGTKYLARTLNRLLMH : 348
NM_012063 : KLGIIGVVNRSQLDINNKKSVTDSIRDEYAFLQKKYPSLANRNGTKYLARTLNRLLMH : 295
PCP0424C  : KLGIIGVVNRSQLDINNKKSVTDSIRDEYAFLQKKYPSLANRNGTKYLARTLNRLLMH : 348
NM_005690 : KLGIIGVVNRSQLDINNKKSVTDSIRDEYAFLQKKYPSLANRNGTKYLARTLNRLLMH : 295
            KLGIIGVVNRSQLDINNKKSVTDSIRDEYAFLQKKYPSLANRNGTKYLARTLNRLLMH

              *       360         *       380         *       400
PCP0424A  : HIRDCLPELKTRINVLAAQYQSLLNSYGEPVDDKSATLLQLITKFATEYCNTIEGTAK : 406
NM_012062 : HIRDCLPELKTRINVLAAQYQSLLNSYGEPVDDKSATLLQLITKFATEYCNTIEGTAK : 353
PCP0424B  : HIRDCLPELKTRINVLAAQYQSLLNSYGEPVDDKSATLLQLITKFATEYCNTIEGTAK : 406
NM_012063 : HIRDCLPELKTRINVLAAQYQSLLNSYGEPVDDKSATLLQLITKFATEYCNTIEGTAK : 353
PCP0424C  : HIRDCLPELKTRINVLAAQYQSLLNSYGEPVDDKSATLLQLITKFATEYCNTIEGTAK : 406
NM_005690 : HIRDCLPELKTRINVLAAQYQSLLNSYGEPVDDKSATLLQLITKFATEYCNTIEGTAK : 353
            HIRDCLPELKTRINVLAAQYQSLLNSYGEPVDDKSATLLQLITKFATEYCNTIEGTAK
```

FIG. 7A

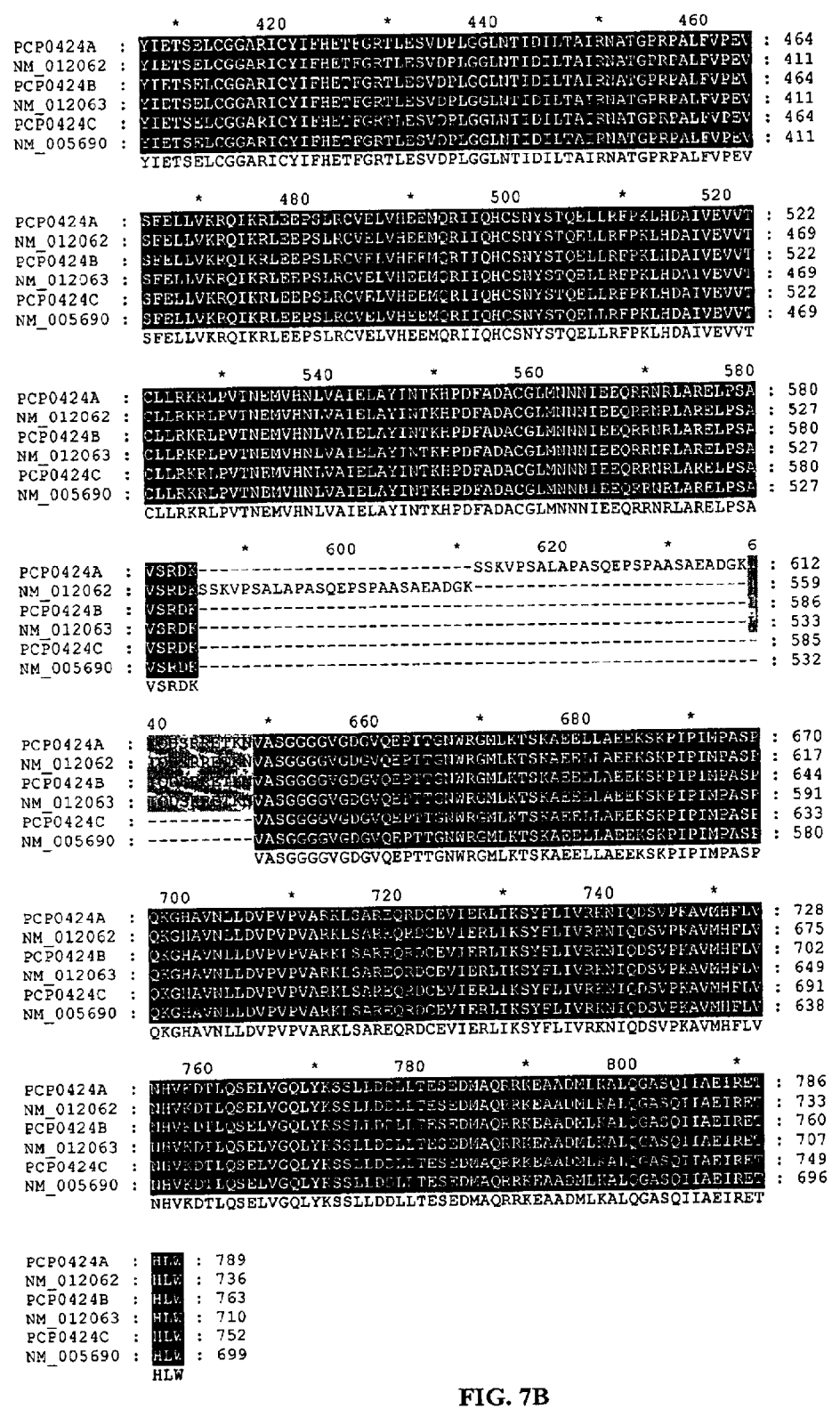

```
                    *         420         *         440         *         460
PCP0424A  : YIETSELCGGARICYIFHETFGRTLESVDPLGGLNTIDILTAIRNATGPRPALFVPEV : 464
NM_012062 : YIETSELCGGARICYIFHETFGRTLESVDPLGGLNTIDILTAIRNATGPRPALFVPEV : 411
PCP0424B  : YIETSELCGGARICYIFHETFGRTLESVDPLGGLNTIDILTAIRNATGPRPALFVPEV : 464
NM_012063 : YIETSELCGGARICYIFHETFGRTLESVDPLGGLNTIDILTAIRNATGPRPALFVPEV : 411
PCP0424C  : YIETSELCGGARICYIFHETFGRTLESVDPLGGLNTIDILTAIRNATGPRPALFVPEV : 464
NM_005690 : YIETSELCGGARICYIFHETFGRTLESVDPLGGLNTIDILTAIRNATGPRPALFVPEV : 411
            YIETSELCGGARICYIFHETFGRTLESVDPLGGLNTIDILTAIRNATGPRPALFVPEV

                    *         480         *         500         *         520
PCP0424A  : SFELLVKRQIKRLEEPSLRCVELVHEEMQRIIQHCSNYSTQELLRFPKLHDAIVEVVT : 522
NM_012062 : SFELLVKRQIKRLEEPSLRCVELVHEEMQRIIQHCSNYSTQELLRFPKLHDAIVEVVT : 469
PCP0424B  : SFELLVKRQIKRLEEPSLRCVELVHEEMQRIIQHCSNYSTQELLRFPKLHDAIVEVVT : 522
NM_012063 : SFELLVKRQIKRLEEPSLRCVELVHEEMQRIIQHCSNYSTQELLRFPKLHDAIVEVVT : 469
PCP0424C  : SFELLVKRQIKRLEEPSLRCVELVHEEMQRIIQHCSNYSTQELLRFPKLHDAIVEVVT : 522
NM_005690 : SFELLVKRQIKRLEEPSLRCVELVHEEMQRIIQHCSNYSTQELLRFPKLHDAIVEVVT : 469
            SFELLVKRQIKRLEEPSLRCVELVHEEMQRIIQHCSNYSTQELLRFPKLHDAIVEVVT

                    *         540         *         560         *         580
PCP0424A  : CLLRKRLPVTNEMVHNLVAIELAYINTKHPDFADACGLMNNNIEEQRRNRLARELPSA : 580
NM_012062 : CLLRKRLPVTNEMVHNLVAIELAYINTKHPDFADACGLMNNNIEEQRRNRLARELPSA : 527
PCP0424B  : CLLRKRLPVTNEMVHNLVAIELAYINTKHPDFADACGLMNNNIEEQRRNRLARELPSA : 580
NM_012063 : CLLRKRLPVTNEMVHNLVAIELAYINTKHPDFADACGLMNNNIEEQRRNRLARELPSA : 527
PCP0424C  : CLLRKRLPVTNEMVHNLVAIELAYINTKHPDFADACGLMNNNIEEQRRNRLARELPSA : 580
NM_005690 : CLLRKRLPVTNEMVHNLVAIELAYINTKHPDFADACGLMNNNIEEQRRNRLARELPSA : 527
            CLLRKRLPVTNEMVHNLVAIELAYINTKHPDFADACGLMNNNIEEQRRNRLARELPSA

                    *         600         *         620         *         6
PCP0424A  : VSRDK-----------------------SSKVPSALAPASQEPSPAASAEADGK     : 612
NM_012062 : VSRDKSSKVPSALAPASQEPSPAASAEADGK------------------------   : 559
PCP0424B  : VSRDK-------------------------------------------------   : 586
NM_012063 : VSRDK-------------------------------------------------   : 533
PCP0424C  : VSRDK-------------------------------------------------   : 585
NM_005690 : VSRDK-------------------------------------------------   : 532
            VSRDK

           40         *         660         *         680         *
PCP0424A  : XXXXXXXXXXVASGGGGVGDGVQEPITGNWRGMLKTSKAEELLAEEKSKPIPIMPASP : 670
NM_012062 : XXXXXXXXXXVASGGGGVGDGVQEPITGNWRGMLKTSKAEELLAEEKSKPIPIMPASP : 617
PCP0424B  : XXXXXXXXXXVASGGGGVGDGVQEPITGNWRGMLKTSKAEELLAEEKSKPIPIMPASP : 644
NM_012063 : XXXXXXXXXXVASGGGGVGDGVQEPITGNWRGMLKTSKAEELLAEEKSKPIPIMPASP : 591
PCP0424C  : ----------VASGGGGVGDGVQEPTTGNWRGMLKTSKAEELLAEEKSKPIPIMPASP : 633
NM_005690 : ----------VASGGGGVGDGVQEPTTGNWRGMLKTSKAEELLAEEKSKPIPIMPASP : 580
            VASGGGGVGDGVQEPTTGNWRGMLKTSKAEELLAEEKSKPIPIMPASP

              700         *         720         *         740         *
PCP0424A  : QKGHAVNLLDVPVPVARKLSAREQRDCEVIERLIKSYFLIVRKNIQDSVPKAVMHFLV : 728
NM_012062 : QKGHAVNLLDVPVPVARKLSAREQRDCEVIERLIKSYFLIVRKNIQDSVPKAVMHFLV : 675
PCP0424B  : QKGHAVNLLDVPVPVARKLSAREQRDCEVIERLIKSYFLIVRKNIQDSVPKAVMHFLV : 702
NM_012063 : QKGHAVNLLDVPVPVARKLSAREQRDCEVIERLIKSYFLIVRKNIQDSVPKAVMHFLV : 649
PCP0424C  : QKGHAVNLLDVPVPVARKLSAREQRDCEVIERLIKSYFLIVRKNIQDSVPKAVMHFLV : 691
NM_005690 : QKGHAVNLLDVPVPVARKLSAREQRDCEVIERLIKSYFLIVRKNIQDSVPKAVMHFLV : 638
            QKGHAVNLLDVPVPVARKLSAREQRDCEVIERLIKSYFLIVRKNIQDSVPKAVMHFLV

              760         *         780         *         800         *
PCP0424A  : NHVKDTLQSELVGQLYKSSLLDDLLTESEDMAQRRKEAADMLKALQGASQIIAEIRET : 786
NM_012062 : NHVKDTLQSELVGQLYKSSLLDDLLTESEDMAQRRKEAADMLKALQGASQIIAEIRET : 733
PCP0424B  : NHVKDTLQSELVGQLYKSSLLDDLLTESEDMAQRRKEAADMLKALQGASQIIAEIRET : 760
NM_012063 : NHVKDTLQSELVGQLYKSSLLDDLLTESEDMAQRRKEAADMLKALQGASQIIAEIRET : 707
PCP0424C  : NHVKDTLQSELVGQLYKSSLLDDLLTESEDMAQRRKEAADMLKALQGASQIIAEIRET : 749
NM_005690 : NHVKDTLQSELVGQLYKSSLLDDLLTESEDMAQRRKEAADMLKALQGASQIIAEIRET : 696
            NHVKDTLQSELVGQLYKSSLLDDLLTESEDMAQRRKEAADMLKALQGASQIIAEIRET

PCP0424A  : HLW : 789
NM_012062 : HLW : 736
PCP0424B  : HLW : 763
NM_012063 : HLW : 710
PCP0424C  : HLW : 752
NM_005690 : HLW : 699
            HLW
```

FIG. 7B

```
                          *        20         *        40         *        60
PCP0816    : MAEPGHSHILSARVRGRTERRIPRLWRLLLWAGTAFQVTQGTGPELHACKESEYHYEYTA :  60
XM_042775  : MAEPGHSHILSARVRGRTERRIPRLWRLLLWAGTAFQVTQGTGPELHACKESEYHYEYTA :  60

                          *        80         *       100         *       120
PCP0816    : CDSTGSRWRVAVPHTPGLCTSLPDPVKGTECSFSCNAGEFLDMKDQSCKPCAEGRYSLGT : 120
XM_042775  : CDSTGSRWRVAVPHTPGLCTSLPDPIKGTECSFSCNAGEFLDMKDQSCKPCAEGRYSLGT : 120

                          *       140         *       160         *       180
PCP0816    : GIRFDEWDELPHGFASLSANMELDDSAAESTGNCTSSKWVPRGDYIASNTDECTATLMYA : 180
XM_042775  : GIRFDEWDELPHGFASLSANMELDDSAAESTGNCTSSKWVPRGDYIASNTDECTATLMYA : 180

                          *       200         *       220         *       240
PCP0816    : VNLKQSGTVNFEYYYPDSSIIFEFFVQNDQCQPNADDSRWMKTTEKGWEFHSVELNRGNN : 240
XM_042775  : VNLKQSGTVNFEYYYPDSSIIFEFFVQNDQCQPNADDSRWMKTTEKGWEFHSVELNRGNN : 240

                          *       260         *       280         *       300
PCP0816    : VLYWRTTAFSVWTKVPKPVLVRNIAITSVAYTSKCFPCKPGTYADKQGSSECKPCPANTY : 300
XM_042775  : VLYWRTTAFSVWTKVPKPVLVRNIAIT--------------------------------- : 267

                          *       320         *       340         *       360
PCP0816    : SNRGETSCHQCPRDKNSEKGSSSCNVRPACTDKDYFYTHTACDANGETQLMYKWAKPKIC : 360
XM_042775  : -----------------EKGSSSCNVRPACTDKDYFYTHTACDANGETQLMYKWAKPKIC : 310

                          *       380         *       400         *       420
PCP0816    : SEDLEGAVKLPASGVKTHCPPCNPGFFKTNNSTCQPCPYGSYSNGSDCTRCPAGTEPAVG : 420
XM_042775  : SEDLEGAVKLPASGVKTHCPPCNPGFFKTNNSTCQPCPYGSYSNGSDCTRCPAGTEPAVG : 370

                          *       440         *       460         *       480
PCP0816    : FEYKWWNTLPTNMETTVLSGINFEYKGMTGWEVAGDHIYTAAGASDNDFMILTLVVPGFR : 480
XM_042775  : FEYKWWNTLPTNMETTVLSGINFEYKGMTGWEVAGDHIYTAAGASDNDFMILTLVVPGFR : 430

                          *       500         *       520         *       540
PCP0816    : PPQSVMADTENKEVARITFVFETLCSVNCELYFMVGVNSRTNTPVETWKGSKGKQSYTYI : 540
XM_042775  : PPQSVMADTENKEVARITFVFETLCSVNCELYFMVGVNSRTNTPVETWKGSKGKQSYTYI : 490

                          *       560         *       580         *       600
PCP0816    : IEENTTTSFTWAFQRTTFHEASRKYTNDVAKIYSINVTNVMNGVASYCRPCALEASDVGS : 600
XM_042775  : IEENTTTSFTWAFQRTTFHEASRKYTNDVAKIYSINVTNVMNGVASYCRPCALEASDVGS : 550

                          *       620         *       640         *       660
PCP0816    : SCTSCPAGYYIDRDSGTCHSCPPNTILKAHQPYGVQACVPCGPGTKNNKIHSLCYNDCTF : 660
XM_042775  : SCTSCPAGYYIDRDSGTCHSCPTNTILKAHQPYGVQACVPCGPGTKNNKIHSLCYNDCTF : 610

                          *       680         *       700         *       720
PCP0816    : SRNTPTRTFNYNFSALANTVTLAGGPSFTSKGLKYFHHFTLSLCGNQGRKMSVCTDNVTD : 720
XM_042775  : SRNTPTRTFNYNFSALANTVTLAGGPSFTSKGLKYFHHFTLSLCGNQGRKMSVCTDNVTD : 670
```

FIG. 8A

```
                      *      740        *       760        *       780
PCP0816   : LRIPEGESGFSKSITAYVCQAVIIPPEVTGYKAGVSSQPVSLADRLIGVTTDMTLDGITS :  780
XM_042775 : LRIPEGESGFSKSITAYVCQAVIIPPEVTGYKAGVSSQPVSLADRLIGVTTDMTLDGITS :  730

                      *      800        *       820        *       840
PCP0816   : PAELFHLESLGIPDVIFFYRSNDVTQSCSSGRSTTIRVRCSPQKTVPGSLLLPGTCSDGT :  840
XM_042775 : PAELFHLESLGIPDVIFFYRSNDVTQSCSSGRSTTIRVRCSPQKTVPGSLLLPGTCSDGT :  790

                      *      860        *       880        *       900
PCP0816   : CDGCNFHFLWESAAACPLCSVADYHAIVSSCVAGIQKTTYVWREPKLCSGGISLPEQRVT :  900
XM_042775 : CDGCNFHFLWESAAACPLCSVADYHAIVSSCVAGIQKTTYVWREPKLCSGGISLPEQRVT :  850

                      *      920        *       940        *       960
PCP0816   : ICKTIDFWLKVGISAGTCTAILLTVLTCYFWKKNQKLEYKYSKLVMNATLKDCDLPAADS :  960
XM_042775 : ICKTIDFWLKVGISAGTCTAILLTVLTCYFWKKNQKLEYKYSKLVMNATLKDCDLPAADS :  910

                      *      980        *       1000       *
PCP0816   : CAIMEGEDVEDDLIFTSKKSLFGKIKSFTSKRTPDGEWQSVPLKTSSQGPD[illegible] : 1013
XM_042775 : CAIMEGEDVEDDLIFTSKKSLFGKIKSFTSKQ-P-----APV-TISLSEDS--  :  954
```

FIG. 8B

```
              *        20         *        40         *        60
PCP0480  : MTMTLHTKASGMALLHQIQGNELEPLNRPQLKIPLERPLGEVYLDSSKPAVYNYPEGAAY :  60
NM_000125: MTMTLHTKASGMALLHQIQGNELEPLNRPQLKIPLERPLGEVYLDSSKPAVYNYPEGAAY :  60

              *        80         *       100         *       120
PCP0480  : EFNAAAAANAQVYGQTGLPYGPGSEAAAFGSKGLGGFPPPLMSVSPSPLMLLHPPPQLSPF : 120
NM_000125: EFNAAAAANAQVYGQTGLPYGPGSEAAAFGSKGLGGFPPPLMSVSPSPLMLLHPPPQLSPF : 120

              *       140         *       160         *       180
PCP0480  : LQPHGQQVPYYLENEPSGYTVREAGPPAFYRXVESEQESSRVSHWMXXXFM--------- : 171
NM_000125: LQPHGQQVPYYLENEPSGYTVREAGPPAFYRPNSENRRXXXERLXSTNXXXXXXXXXXX : 180

              *       200         *       220         *       240
PCP0480  : ----------------------------------------------------------- :   -
NM_000125: XXXXXXXXXXXXXXXXXXXXXXXXXXXXXXXXXXXXXXXXXXXXXXXXXXXXXXXXXXX : 240

              *       260         *       280         *       300
PCP0480  : ----------------------------------------------------------- :   -
NM_000125: XXXXXXXXXXXXXXXXXXXXXXXXXXXXXXXXXXXXXXXXXXXXXXXXXXXXXXXXXXX : 300

              *       320         *       340         *       360
PCP0480  : ----------------------------------------------------------- :   -
NM_000125: XXXXXXXXXXXXXXXXXXXXXXXXXXXXXXXXXXXXXXXXXXXXXXXXXXXXXXXXXXX : 360

              *       380         *       400         *       420
PCP0480  : ----------------------------------------------------------- :   -
NM_000125: XXXXXXXXXXXXXXXXXXXXXXXXXXXXXXXXXXXXXXXXXXXXXXXXXXXXXXXXXXX : 420

              *       440         *       460         *       480
PCP0480  : ----------------------------------------------------------- :   -
NM_000125: XXXXXXXXXXXXXXXXXXXXXXXXXXXXXXXXXXXXXXXXXXXXXXXXXXXXXXXXXXX : 480

              *       500         *       520         *       540
PCP0480  : ----------------------------------------------------------- :   -
NM_000125: XXXXXXXXXXXXXXXXXXXXXXXXXXXXXXXXXXXXXXXXXXXXXXXXXXXXXXXXXXX : 540

              *       560         *       580         *
PCP0480  : ---------------------------------------------------------- :   -
NM_000125: XXXXXXXXXXXXXXXXXXXXXXXXXXXXXXXXXXXXXXXXXXXXXXXXXXXXXXXXXX : 595
```

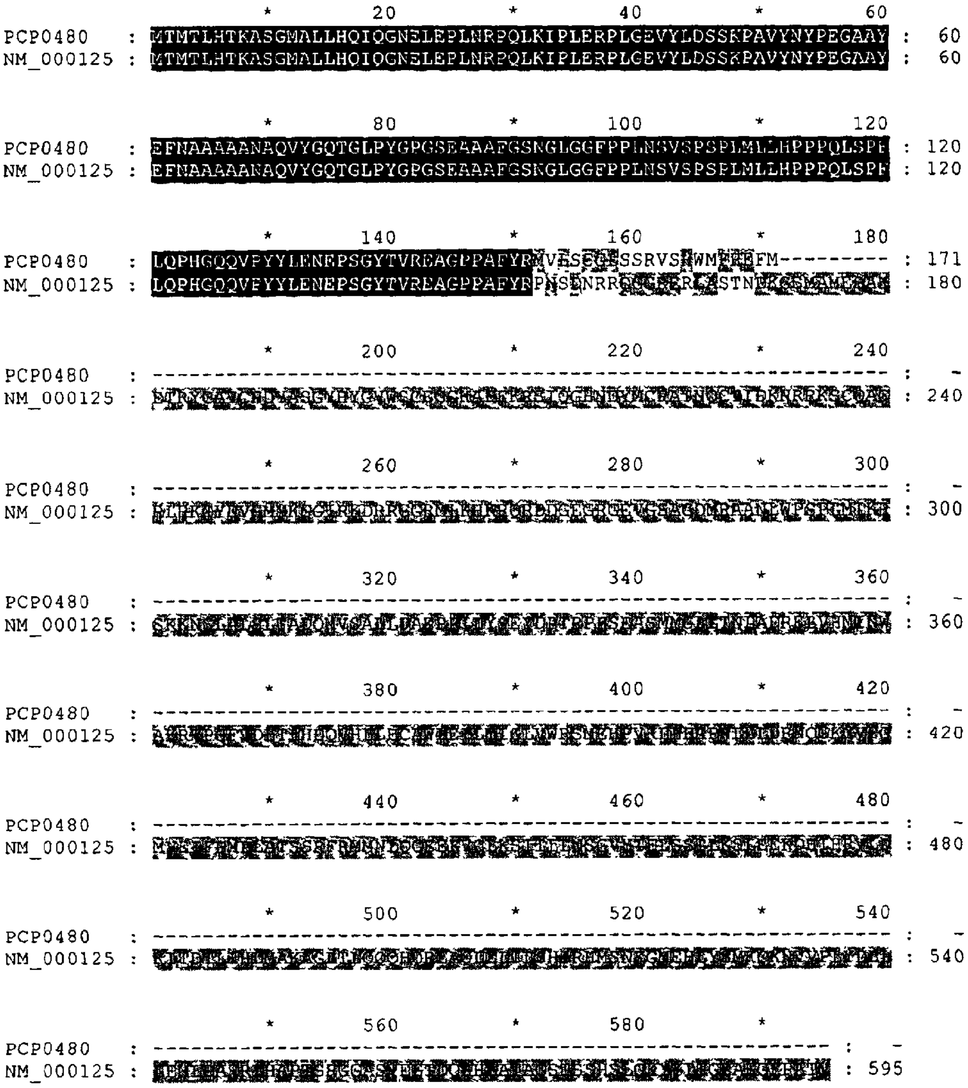

FIG. 9

```
                       *        20         *        40         *        60
XM_094949 : ---------MIKDWTKEHVKKWVNEDLKINEQYGQILLSEEVTGLVLQELTEKDLVEMGL :  51
PC0382    : MSKQVSLPEMIKDWTKEHVKKWVNEDLKINEQYGQILLSEEVTGLVLQELTEKDLVEMGL :  60

                       *        80         *       100         *       120
XM_094949 : PWGPALLIKRSYNKLNSKSPESDNHDPGQLDNSKPSKTEHQKNPKHTKKEEENSMSSNID : 111
PC0382    : PWGPALLIKRSYNKLNSKSPESDNHDPGQLDNSKPSKTEHQKNPKHTKKEEENSMSSNID : 120

                       *       140         *       160         *       180
XM_094949 : YDPREIRDIKQEESILMKENVLDEVANAKHKKKGKLKPEQLTCMPYPFDQFHDSHRYIEH : 171
PC0382    : YDPREIRDIKQEESILMKENVLDEVANAKHKKKGKLKPEQLTCMPYPFDQFHDSHRYIEH : 180

                       *       200         *       220         *       240
XM_094949 : YTLQPETGALNLIDPIHEFKALINTETATEVDIKMKFSNEVFRFASACMNSRTNGTIHFG : 231
PC0382    : YTLQPETGALNLIDPIHEFKALINTETATEVDIKMKFSNEVFRFASACMNSRTNGTIHFG : 240

                       *       260         *       280         *       300
XM_094949 : VKDKPHGEIVGVKITSKAAFIDHFNVMIKKYFEESEINEAKKCIREPRFVEVLLQNNTPS : 291
PC0382    : VKDKPHGEIVGVKITSKAAFIDHFNVMIKKYFEESEINEAKKCIREPRFVEVLLQNNTPS : 300

                       *       320         *       340         *       360
XM_094949 : DRFVIEVDTIPKHSICNDKYFYIQMQICKDKIWKQNQNLSLFVREGASSRDILANSKQRD : 351
PC0382    : DRFVIEVDTIPKHSICNDKYFYIQMQICKDKIWKQNQNLSLFVREGASSRDILANSKQRD : 360

                       *       380         *       400         *       420
XM_094949 : VDFKAFLQNLKSLVASRKEAEEEYGMKAMKKESEGLKLVKLLIGNRDSLDNSYYDWYILV : 411
PC0382    : VDFKAFLQNLKSLVASRKEAEEEYGMKAMKKESEGLKLVKLLIGNRDSLDNSYYDWYILV : 420

                       *       440         *       460         *       480
XM_094949 : TNKCHPNQIKHLDFLKEIKWFAVLEFDPESMINGVVKAYKESRVANLHFPNQYEDKTTNM : 471
PC0382    : TNKCHPNQIKHLDFLKEIKWFAVLEFDPESMINGVVKAYKESRVANLHFPNQYEDKTTNM : 480

                       *       500         *       520         *       540
XM_094949 : WEKISTLNLYQQPSWIFCNGRSDLKSETYKPLEPHLWQRERASEVRKLILFLTDENIMTR : 531
PC0382    : WEKISTLNLYQQPSWIFCNGRSDLKSETYKPLEPHLWQRERASEVRKLILFLTDENIMTR : 540

                       *       560         *       580         *       600
XM_094949 : GKFLVVFLLLSSVESPGDPLIETFWAFYQALKGMENMLCISVHSHIYQRWKDLLQTRMKM : 591
PC0382    : GKFLVVFLLLSSVESPGDPLIETFWAFYQALKGMENMLCISVHSHIYQRWKDLLQTRTKM : 600

                       *       620         *       640         *       660
XM_094949 : EDELTNHSISTLNIELVNSTILKLKSVTRSSRRFLPARGSSSVILEKKKEDVLTALEILC : 651
PC0382    : EDELTNHSISTLNIELVNSTILKLKSVTRSSRRFLPARGSSSVILEKKKEDVLTALEILC : 660

                       *       680         *       700         *       720
XM_094949 : ENECTETDIEKDKSKFLEFKKSKEEHFYRGGKVSWWNFYFSSENYSSDFVKRDSYEKLKI : 711
PC0382    : ENECTETDIEKDKSKFLEFKKSKEEHFYRGGKVSWWNFYFSSENYSSDFVKRDSYEKLKI : 720

                       *       740         *       760         *       780
XM_094949 : LIHCWAESPKPIFAKIINLYHHPGCGGTTLAMHVLWDLKKNFRCAVLKNKTTDFAEIAEC : 771
PC0382    : LIHCWAESPKPIFAKIINLYHHPGCGGTTLAMHVLWDLKKNFRCAVLKNKTTDFAEIAEC : 780
```

FIG. 10A

```
                  *       800         *       820         *       840
XM_094949 : VINLVTYRAKSHQDYIPVLLLVDDFEEQENVYFLQNAIHSVLAEKDLRYEKTLVIILNCM :  831
PC0382    : VINLVTYRAKSHQDYIPVLLLVDDFEEQENVYFLQNAIHSVLAEKDLRYEKTLVIILNCM :  840

                  *       860         *       880         *       900
XM_094949 : RSRNFDESAKLADSIALNYQLSSKEQRAFGAKLKEIEKQHKNCENFYSFMIMKSNFDETY :  891
PC0382    : RSRNFDESAKLADSIALNYQLSSKEQRAFGAKLKEIEKQHKNCENFYSFMIMKSNFDETY :  900

                  *       920         *       940         *       960
XM_094949 : IENVVRNILKGQDVDSKEAQLISFLALLSSYVTDSTISVSQCEIFLGIIYTSTPWEPESL :  951
PC0382    : IENVVRNILKGQDVDSKEAQLISFLALLSSYVTDSTISVSQCEIFLGIIYTSTPWEPESL :  960

                  *       980         *      1000         *      1020
XM_094949 : EDKMGTYSTLLIKTEVAEYGRYTGVRIIHPLIALYCLKELERSYHLDKCQIALNILEENL : 1011
PC0382    : EDKMGTYSTLLIKTEVAEYGRYTGVRIIHPLIALYCLKELERSYHLDKCQIALNILEENL : 1020

                  *      1040         *      1060         *      1080
XM_094949 : FYDSGIGRDKFQHDVQTLLLTRQRKVYGDETDTLFSPLMEALQNKDIEKVLSAGSRRFPQ : 1071
PC0382    : FYDSGIGRDKFQHDVQTLLLTRQRKVYGDETDTLFSPLMEALQNKDIEKVLSAGSRRFPQ : 1080

                  *      1100         *      1120         *      1140
XM_094949 : NAFICQALARHFYIKEKDFNTALDWARQAKMKAPKNSYISDTLGQVYKSEIKWWLDGNKN : 1131
PC0382    : NAFICQALARHFYIKEKDFNTALDWARQAKMKAPKNSYISDTLGQVYKSEIKWWLDGNKN : 1140

                  *      1160         *      1180         *      1200
XM_094949 : CRSITVNDLTHLLEAAEKASRAFKESQRQTDSKNYETENWSPQKSQRRYDMYNTACFLGE : 1191
PC0382    : CRSITVNDLTHLLEAAEKASRAFKESQRQTDSKNYETENWSPQKSQRRYDMYNTACFLGE : 1200

                  *      1220         *      1240         *      1260
XM_094949 : IEVGLYTIQILQLTPFFHKENELSKKHMVQFLSGKWTIPPDPRNECYLALSKFTSHLKNL : 1251
PC0382    : IEVGLYTIQILQLTPFFHKENELSKKHMVQFLSGKWTIPPDPRNECYLALSKFTSHLKNL : 1260

                  *      1280         *      1300         *      1320
XM_094949 : QSDLKRCFDFFIDYMVLLKMRYTQKEIAEIMLSKKVSRCFRKYTELFCHLDPCLLQSKES : 1311
PC0382    : QSDLKRCFDFFIDYMVLLKMRYTQKEIAEIMLSKKVSRCFRKYTELFCHLDPCLLQSKES : 1320

                  *      1340         *      1360         *      1380
XM_094949 : QLLQEENCRKKLEALRADRFAGLLEYLNPNYKDATTMESIVNEYAFLLQQNSKKPMTNEK : 1371
PC0382    : QLLQEENCRKKLEALRADRFAGLLEYLNPNYKDATTMESIVNEYAFLLQQNSKKPMTNEK : 1380

                  *      1400         *      1420         *      1440
XM_094949 : QNSILANIILSCLKPNSKLIQPLTTLKKQLREVLQFVGLSHQYPGPYFLACLLFWPENQL : 1431
PC0382    : QNSILANIILSCLKPNSKLIQPLTTLKKQLREVLQFVGLSHQYPGPYFLACLLFWPENQL : 1440

                  *      1460         *      1480         *      1500
XM_094949 : LDQDSKLIEKYVSSLNRSFRGQYKRMCRSKQASTLFYLGKRKGLNSIVHKAKIEQYFDKA : 1491
PC0382    : LDQDSKLIEKYVSSLNRSFRGQYKRMCRSKQASTLFYLGKRKGLNSIVHKAKIEQYFDKA : 1500

                  *      1520         *      1540         *      1560
XM_094949 : QNTNSLWHSGDVWKKNEVKDLLRRLTGQAEGKLISVEYGTEEKIKIPVISVYSGPLRSGR : 1551
PC0382    : QNTNSLWHSGDVWKKNEVKDLLRRLTGQAEGKLISVEYGTEEKIKIPVISVYSGPLRSGR : 1560

                  *      1580
XM_094949 : NIERVSFYLGFSIEGPLAYDIEVI : 1575
PC0382    : NIERVSFYLGFSIEGPLAYDIEVI : 1584
```

FIG. 10B

```
                   *        20         *        40         *        60
PCP0842   : [illegible]                                                  :   60
XM_050424 : ------------------------------------------------------------ :    -

                   *        80         *       100         *       120
PCP0842   : [illegible]                                                  :  120
XM_050424 : ------------------------------------------------------------ :    -

                   *       140         *       160         *       180
PCP0842   : [illegible]                                                  :  180
XM_050424 : ------------------------------------------------------------ :    -

                   *       200         *       220         *       240
PCP0842   : [illegible]                                                  :  240
XM_050424 : ------------------------------------------------------------ :    -

                   *       260         *       280         *       300
PCP0842   : [illegible]                                                  :  300
XM_050424 : ------------------------------------------------------------ :    -

                   *       320         *       340         *       360
PCP0842   : [illegible]                                                  :  360
XM_050424 : ------------------------------------------------------------ :    -

                   *       380         *       400         *       420
PCP0842   : [illegible]                                                  :  420
XM_050424 : ------------------------------------------------------------ :    -

                   *       440         *       460         *       480
PCP0842   : [illegible]                       MTEACIKGGIEACYAAVSCVCILLGA :  480
XM_050424 : ----------------------------------MTEACIKGGIEACYAAVSCVCILLGA :   26

                   *       500         *       520         *       540
PCP0842   : LDELSQGKGLSEGQVQLLLLRLEELKDGAEWSRDSMEINEADFRWQRRVLSSEHTPWESG :  540
XM_050424 : LDELSQGKGLSEGQVQLLLLRLEELKDGAEWSRDSMEINEADFRWQRRVLSSEHTPWESG :   86

                   *       560         *       580         *       600
PCP0842   : NERSLDISISVTTDIGQTTLEGELGQTTPEDHSGNHKNSLKSPAIPEGKETLSKVLETEA :  600
XM_050424 : NERSLDISISVTTDIGQTTLEGELGQTTPEDHSGNHKNSLKSPAIPEGKETLSKVLETEA :  146

                   *       620         *       640         *       660
PCP0842   : VDQPDVVQRSHTVPYPDITNFLSVDCRTRSYGSRYSESNFSVDDQDLSRTEFDSCDQYSM :  660
XM_050424 : VDQPDVVQRSHTVPYPDITNFLSVDCRTRSYGSRYSESNFSVDDQDLSRTEFDSCDQYSM :  206

                   *       680         *       700         *       720
PCP0842   : AAEKDSGRSDVSDIGSDNCSLADEEQTPRDCLGHRSLRTAALSLKLLKNQEADQHSARLF :  720
XM_050424 : AAEKDSGRSDVSDIGSDNCSLADEEQTPRDCLGHRSLRTAALSLKLLKNQEADQHSARLF :  266

                   *       740         *       760         *       780
PCP0842   : IQSLEGLLPRLLSLSNVEEVDTALQNFASTFCSCMMHSPGFDGNSSLSFQMLMNADSLYT :  780
XM_050424 : IQSLEGLLPRLLSLSNVEEVDTALQNFASTFCSCMMHSPGFDGNSSLSFQMLMNADSLYT :  326
```

FIG. 11A

```
                        *        800         *        820         *        840
PCP0842   : AAHCALLLNLKLSHGDYYRKRPTLAPGVMKDFMKQVQTSGVLMVFSQAWIEELYHQVLDR :  840
XM_050424 : AAHCALLLNLKLSHGDYYRKRPTLAPGVMKDFMKQVQTSGVLMVFSQAWIEELYHQVLDR :  386

                        *        860         *        880         *        900
PCP0842   : NMLGEAGYWGSPEDNSLPLITMLTDIDGLESSAIGGQLMASAATESPFAQSRRIDDSTVA :  900
XM_050424 : NMLGEAGYWGSPEDNSLPLITMLTDIDGLESSAIGGQLMASAATESPFAQSRRIDDSTVA :  446

                        *        920         *        940         *        960
PCP0842   : GVAFARYILVGCWKNLIDTLSTPLTGRMAGSSKGLAFILGAEGIKEQNQKERDAICMSLL :  960
XM_050424 : GVAFARYILVGCWKNLIDTLSTPLTGRMAGSSKGLAFILGAEGIKEQNQKERDAICMSLL :  506

                        *        980         *       1000         *       1020
PCP0842   : GLRKAARLSCALGVAAKCASALAQMAAASCVQEEKEEREAQEPSDAITQVKLKVEQKLEQ : 1020
XM_050424 : GLRKAARLSCALGVAAKCASALAQMAAASCVQEEKEEREAQEPSDAITQVKLKVEQKLEQ :  566

                        *       1040         *       1060         *       1080
PCP0842   : IGKVQGVWLHTAHVLCMEAILSVGLEMGSHNPDCWPHVFRVCEYVGTLEHNHFSDGASQP : 1080
XM_050424 : IGKVQGVWLHTAHVLCMEAILSVGLEMGSHNPDCWPHVFRVCEYVGTLEHNHFSDGASQP :  626

                        *       1100         *       1120         *       1140
PCP0842   : PLTISQPQKATGSAGLLGDPECEGSPPEHSPEQGRSLSTAPVVQPLSIQDLVREGSRGRA : 1140
XM_050424 : PLTISQPQKATGSAGLLGDPECEGSPPEHSPEQGRSLSTAPVVQPLSIQDLVREGSRGRA :  686

                        *       1160         *       1180         *       1200
PCP0842   : SDFRGGSLMSGSSAAKVVLTLSTQADRLFEDATDKLNLMALGGFLYQLKKASQSQLFHSV : 1200
XM_050424 : SDFRGGSLMSGSSAAKVVLTLSTQADRLFEDATDKLNLMALGGFLYQLKKASQSQLFHSV :  746

                        *       1220         *       1240         *       1260
PCP0842   : TDTVDYSLAMPGEVKSTQDRKSALHLFRLGNAMLRIVRSKARPLLHVMRCWSLVAPHLVE : 1260
XM_050424 : TDTVDYSLAMPGEVKSTQDRKSALHLFRLGNAMLRIVRSKARPLLHVMRCWSLVAPHLVE :  806

                        *       1280         *       1300         *       1320
PCP0842   : AACHKERHVSQKAVSFIHDILTEVLTDWNEPPHFHFNEALFRPFERIMQLELCDEDVQDQ : 1320
XM_050424 : AACHKERHVSQKAVSFIHDILTEVLTDWNEPPHFHFNEALFRPFERIMQLELCDEDVQDQ :  866

                        *       1340         *       1360         *       1380
PCP0842   : VVTSICELVEVCSTQIQSGWRPLFSALETVHCCNKSEMKEYLVGDYSMGKGQAPVFDVFE : 1380
XM_050424 : VVTSICELVEVCSTQIQSGWRPLFSALETVHCCNKSEMKEYLVGDYSMGKGQAPVFDVFE :  926

                        *       1400         *       1420         *       1440
PCP0842   : AFLNTDNIQVFANAATSYIMCLMKFVKGLGEVDCKEIGDCAPAPGAPSTDLCLPALDYLR : 1440
XM_050424 : AFLNTDNIQVFANAATSYIMCLMKFVKGLGEVDCKEIGDCAPAPGAPSTDLCLPALDYLR :  986

                        *       1460         *       1480         *       1500
PCP0842   : RCSQLLAKIYKMPLKPIFLSGRLAGLPRRLQEQSASSEDGIESVLSDFDDDTGLIEVWII : 1500
XM_050424 : RCSQLLAKIYKMPLKPIFLSGRLAGLPRRLQEQSASSEDGIESVLSDFDDDTGLIEVWII : 1046

                        *       1520         *       1540         *       1560
PCP0842   : LLEQLTAAVSNCPRQHQPPTLDLLFELLRDVTKTPGPGFGIYAVVHLLLPVMSVWLRRSH : 1560
XM_050424 : LLEQLTAAVSNCPRQHQPPTLDLLFELLRDVTKTPGPGFGIYAVVHLLLPVMSVWLRRSH : 1106
```

FIG. 11B

```
                     *        1580          *        1600          *        1620
PCP0842    : KDHSYWDMASANFKHAIGLSCELVVEHIQSFLHSDIRYESMINTMLKDLFELLVACVAKP : 1620
XM_050424  : KDHSYWDMASANFKHAIGLSCELVVEHIQSFLHSDIRYESMINTMLKDLFELLVACVAKP : 1166

                     *        1640          *        1660          *        1680
PCP0842    : TETISRVGCSCIRYVLVTAGPVFTEEMWRLACCALQDAFSATLKPVKDLLGCFHSGTESF : 1680
XM_050424  : TETISRVGCSCIRYVLVTAGPVFTEEMWRLACCALQDAFSATLKPVKDLLGCFHSGTESF : 1226

                     *        1700          *        1720          *        1740
PCP0842    : SGEGCQVRVAAPSSSPSAEAEYWRIRAMAQQVFMLDTQCSPKTPNNFDHAQSCQLIIELP : 1740
XM_050424  : SGEGCQVRVAAPSSSPSAEAEYWRIRAMAQQVFMLDTQCSPKTPNNFDHAQSCQLIIELP : 1286

                     *        1760          *        1780          *        1800
PCP0842    : PDEKPNGHTKKSVSFREIVVSLLSHQVLLQNLYDILLEEFVKGPSPGEEKTIQVPEAKLA : 1800
XM_050424  : PDEKPNGHTKKSVSFREIVVSLLSHQVLLQNLYDILLEEFVKGPSPGEEKTIQVPEAKLA : 1346

                     *        1820          *        1840          *        1860
PCP0842    : GFLRYISMQNLAVIFDLLLDSYRTAREFDTSPGLKCLLKKVSGIGGAANLYRQSAMSFNI : 1860
XM_050424  : GFLRYISMQNLAVIFDLLLDSYRTAREFDTSPGLKCLLKKVSGIGGAANLYRQSAMSFNI : 1406

                     *        1880          *        1900          *        1920
PCP0842    : YFHALVCAVLTNQETITAEQVKKVLFEDDERSTDSSQQCSSEDEDIFEETAQVSPPRGKE : 1920
XM_050424  : YFHALVCAVLTNQETITAEQVKKVLFEDDERSTDSSQQCSSEDEDIFEETAQVSPPRGKE : 1466

                     *        1940          *        1960          *        1980
PCP0842    : KRQWRARMPLLSVQPVSNADWVWLVKRLHKLCMELCNNYIQMHLDLENCMEEPPIFKGDP : 1980
XM_050424  : KRQWRARMPLLSVQPVSNADWVWLVKRLHKLCMELCNNYIQMHLDLENCMEEPPIFKGDP : 1526

                     *        2000          *        2020          *        2040
PCP0842    : FFILPSFQSESSTPSTGGFSGKETPSEDDRSQSREHMGESLSLKAGGGDLLLPPSPKVEK : 2040
XM_050424  : FFILPSFQSESSTPSTGGFSGKETPSEDDRSQSREHMGESLSLKAGGGDLLLPPSPKVEK : 1586

                     *        2060          *        2080          *        2100
PCP0842    : KDPSRKKEWWENAGNKIYTMAADKTISKLMTEYKKRKQQHNLSAFPKEVKVEKKGEPLGP : 2100
XM_050424  : KDPSRKKEWWENAGNKIYTMAADKTISKLMTEYKKRKQQHNLSAFPKEVKVEKKGEPLGP : 1646

                     *        2120          *        2140          *        2160
PCP0842    : RGQDSPLLQRPQHLMDQGQMRHSFSAGPELLRQDKRPRSGSTGSSLSVSVRDAEAQIQAW : 2160
XM_050424  : RGQDSPLLQRPQHLMDQGQMRHSFSAGPELLRQDKRPRSGSTGSSLSVSVRDAEAQIQAW : 1706

                     *        2180          *        2200          *        2220
PCP0842    : TNMVLTVLNQIQILPDQTFIALQPAVFPCISQLTCHVTDIRVRQAVREWLGRVGRVYDII : 2220
XM_050424  : TNMVLTVLNQIQILPDQTFIALQPAVFPCISQLTCHVTDIRVRQAVREWLGRVGRVYDII : 1766

PCP0842    : V : 2221
XM_050424  : V : 1767
```

FIG. 11C

REGULATED PROSTATE CANCER GENES

DESCRIPTION OF THE DRAWINGS

FIGS. 1–11 show amino acid sequence alignments between polypeptides of the present invention, and polypeptides listed in public databases. SEQ ID NOS for the polypeptides of the present invention are listed in Table 3. Others are as follows:

FIGS. 1A and 1B KIAA0803 (SEQ ID NO31);

FIG. 2 KIAA0408 (SEQ ID NO 32);

FIG. 3 NM_030817 (SEQ ID NO 33);

FIGS. 4A–4E NM_015384 (SEQ ID NO34);

FIGS. 4A–4E NM_133433 (SEQ ID NO 35);

FIGS. 5A–5B XM_033473 (SEQ ID NO 36);

FIG. 6 XM_059862 (SEQ ID NO 37);

FIGS. 7A–7B NM_012062 (SEQ ID NO 38);

FIGS. 7A–7B NM_012063 (SEQ ID NO 39);

FIGS. 7A–7B NM_005690 (SEQ ID NO 40);

FIGS. 8A–8B XM_042775 (SEQ ID NO 41);

FIG. 9 NM_000125 (SEQ ID NO 42);

FIGS. 10A–10B XM_094949 (SEQ ID NO 43);

FIGS. 11A–11C XM_050424 (SEQ ID NO 44).

DESCRIPTION OF THE INVENTION

The present invention relates to all facets of novel polynucleotides, the polypeptides they encode, antibodies and specific binding partners thereto, and their applications to research, diagnosis, drug discovery, therapy, clinical medicine, forensic science and medicine, etc. The polynucleotides are differentially regulated in prostate cancer and are therefore useful in variety of ways, including, but not limited to, as molecular markers, as drug targets, and for detecting, diagnosing, staging, monitoring, prognosticating, preventing or treating, determining predisposition to, etc., diseases and conditions, such as cancer, especially relating to prostate. The identification of specific genes, and groups of genes, expressed in pathways physiologically relevant to prostate permits the definition of functional and disease pathways, and the delineation of targets in these pathways which are useful in diagnostic, therapeutic, and clinical applications. The present invention also relates to methods of using the polynucleotides and related products (proteins, antibodies, etc.) in business and computer-related methods, e.g., advertising, displaying, offering, selling, etc., such products for sale, commercial use, licensing, etc.

Prostate cancer is the most common form of cancer diagnosed in the American male, occurring predominantly in males over age 50. The number of men diagnosed with prostate cancer has steadily increased as a result of the increasing population of older men. In the US, approximately 198,000 men were diagnosed with prostate cancer in 2001, and an estimated 31,500 men in the US died from the disease. In comparison, 1998 estimates for lung cancer in men were 171,500 cases and 160,100 deaths, and for colorectal cancer, the estimates were 131,600 cases and 56,000 deaths. Despite these high numbers, 89 percent of men diagnosed with the disease will survive at least five years and 63 percent will survive at least 10 years.

Patients having prostate cancer display a wide range of phenotypes. In some men, following detection, the tumor remains a latent histological tumor and does not become clinically significant. However, in other men, the tumor progresses rapidly, metastasizing and killing the patient in a relatively short time. Prostate cancer can be cured if the tumor is confined to a small region of the gland and is discovered at early stage. In such cases, radiation or surgical removal often results in complete elimination of the disease. Frequently, however, the prostate cancer has already spread to surrounding tissue and metastasized to remote locations. In these cases, radiation and other therapies, are less likely to effect a complete cure.

Androgen deprivation is a conventional therapy to treat prostate cancer. Androgen blockade can be achieved through several different routes. Androgen suppressive drugs include, e.g., Lupron (leuprolide acetate), Casodex (bicalutamide), Eulexin (flutamide), Nilandron (nilutamide), Zoladex (goserelin acetate implant), and Viadur (leuprolide acetate), which act through several different mechanisms. While these drugs may offer remission and tumor regression in many cases, often the therapeutic effects are only temporary. Prostate tumors lose their sensitivity to such treatments, and become androgen-independent. Thus, new therapies are clearly needed.

The first clinical symptoms of prostate cancer are typically urinary disturbances, including painful and more frequent urination. Diagnosis for prostate cancer is usually accomplished using a combination of different procedures. Since the prostate is located next to the rectum, rectal digital examination allows the prostate to be examined manually for the presence of hyperplasia and abnormal tissue masses. Usually, this is the first line of detection. If a palpable mass is observed, a blood specimen can be assayed for prostate-specific antigen (PSA). Very little PSA is present in the blood of a healthy individual, but BPH and prostate cancer can cause large amounts of PSA to be released into the blood, indicating the presence of diseased tissue. Definitive diagnosis is generally accomplished by biopsy of the prostate tissue.

No single gene or protein has been identified which is responsible for the etiology of all prostate cancers. Although PSA is widely used as a diagnostic reagent, it has limitations in its sensitivity and its ability to detect early cancers. It is estimated that approximately 20% to 30% of tumors will be missed when PSA is used alone. It is likely that diagnostic and prognostic markers for prostate cancer disease will involve the identification and use of many different genes and gene products to reflect its multifactorial origin.

A continuing goal is to characterize the gene expression patterns of the various prostate cancers to genetically differentiate them, providing important guidance in preventing and treating cancers. Molecular pictures of cancer, such as the pattern of differentially-regulated genes identified herein, provide an important tool for molecularly dissecting and classifying cancer, identifying drug targets, providing prognosis and therapeutic information, etc. For instance, an array of polynucleotides corresponding to genes differentially regulated in prostate cancer can be used to screen tissue samples for the existence of cancer, to categorize the cancer (e.g., by the particular pattern observed), to grade the cancer (e.g., by the number of differentially-regulated genes and their amounts of expression), to identify the source of a secondary tumor, to screen for metastatic cells, etc. These arrays can be used in combination with other markers, e.g., PSA, PMSA (prostate membrane specific antigen), or any of the grading systems used in clinical medicine.

As indicated by these studies, cancer is a highly diverse disease. Although all cancers share certain characteristics, the underlying cause and disease progression can differ significantly from patient to patient. So far, over a dozen distinct genes have been identified which, when mutant, result in a cancer. In breast cancer, alone, a handful of different genes have been isolated which either cause the cancer, or produce a predisposition to it. As a consequence, disease phenotypes for a particular cancer do not look all the same. In addition to the differences in the gene(s) responsible for the cancer, heterogeneity among individuals, e.g., in age, health, sex, and genetic background, can also influence the disease and its progression. Gene penetrance, in particular, can vary widely among population members. Recent studies have shown tremendous diversity in gene expression patterns among cancer patients. For these and other reasons, one gene/polypeptide target alone can be insufficient to diagnose or treat a cancer. Even a gene which is highly differentially-expressed and penetrant in cancer patients may not be so highly expressed in all patients and at all stages of the cancer. By selecting a set of genes and/or the polypeptides they encode, cancer diagnostics and therapeutics can be designed which effectively diagnose and treat a population of diseased individuals, rather than only a small handful when single genes are targeted.

Table 1 is a list of the genes, the cellular locations of the polypeptides coded for by the genes, and their corresponding functional and structural polypeptide domains. The polynucleotide and polypeptide sequences are shown in FIGS. 1–11 and SEQ ID NOS 1–30.

Membrane (i.e., cell-surface) proteins coded for by up-regulated genes (e.g., PCP0816) are useful targets for antibodies and other binding partners (e.g., ligands, aptamers, small peptides, etc.) to selectively target agents to a breast cancer tissue for any purpose, included, but not limited to, imaging, therapeutic, diagnostic, drug delivery, gene therapy, etc. For example, binding partners, such as antibodies, can be used to treat carcinomas in analogy to how c-erbB-2 antibodies are used to prostate cancer. Membrane (e.g., when shed into the blood and other fluid) and extracellular proteins (e.g., PCP0389) can also be used as diagnostic markers for cancer, and to assess the progress of the disease, e.g., in analogy to how PSA levels are used to diagnose prostate cancer. Useful antibodies or other binding partners include those that are specific for parts of the polypeptide which are exposed extracellularly as indicated in Table 1. Table 3 summarizes the expression profile of these genes.

Polynucleotides of the present invention can also be used to detect metastatic cells in the blood. For instance, PCP0389, PCP0814, PCP0424, PC0382, PCP0840, and PCP0842 are absent from peripheral blood cells, and can therefore be used in diagnostic tests to assess whether prostate cancer cells have metastasized from the primary site.

Polynucleotides of the present invention have been mapped to specific chromosomal bands. Different human disorders are associated with these chromosome locations. See, Table 2. The polynucleotides and polypeptides they encode can be used as linkage markers, diagnostic targets, therapeutic targets, for any of the mentioned disorders, as well as any disorders or genes mapping in proximity to them. Of particular interest are those genes which map to cancer loci, such as PCP0749, PCP0814 and PCP0816.

The present invention relates to the complete polynucleotide and polypeptide sequences disclosed herein, as well as fragments thereof. Useful fragments include those which are unique and which do not overlap any known gene (e.g., amino acid residues 1–394 of SEQ ID NO 2 of PCP0749), which overlap with a known sequence (e.g., amino acids residues 395–1564 of SEQ ID NO 2 of PCP0749, which span alternative splice junctions (e.g., comprising amino acid residues 585–586 of PCP0424A of SEQ ID NO 18), which are unique to a public sequence as indicated in the Figures (e.g., e.g., amino acids residues 2149–2265 of NM_133433 of SEQ ID NO 35), which span an alternative splice junction of a public sequence (e.g., 532–533 of NM_005690 of SEQ ID NO 40), etc. Unique sequences can also be described as being specific for a gene because they are characteristic of the gene, but not related genes. The unique or specific sequences included polypeptide sequences, coding nucleotide sequences (e.g., as illustrated in the figures), and non-coding nucleotide sequences.

Below, for illustration, are some examples of polypeptides (included are the polynucleotides which encode them); however, the present invention includes all fragments, especially of the categories mentioned above are exemplified below.

PCP0749 (SEQ ID NO 1–2):polypeptides comprising, consisting of, or consisting essentially of about amino acids 1–394, polypeptide fragments thereof, and polynucleotides encoding said polypeptides;

PCP0389 (SEQ ID NO 5–6): polypeptides comprising, consisting of, or consisting essentially of about amino acids 1–1–117, polypeptide fragments thereof, and polynucleotides encoding said polypeptides;

PCP0814 (SEQ ID NO 9–10): polypeptides comprising, consisting of, or consisting essentially of about amino acids 1–33, polypeptide fragments thereof, and polynucleotides encoding said polypeptides;

PCP0623 (SEQ ID NO 11–12): polypeptides comprising, consisting of, or consisting essentially of about amino acids 1–539, polypeptide fragments thereof, and polynucleotides encoding said polypeptides;

PCP0815 (SEQ ID NO 13–14): polypeptides comprising, consisting of, or consisting essentially of about amino acids 1–22, 964–1010, 1011–1041, polypeptide fragments thereof, and polynucleotides encoding said polypeptides;

PCP0840 (SEQ ID NO 15–16): polypeptides comprising, consisting of, or consisting essentially of about amino acids 1–129, polypeptide fragments thereof, and polynucleotides encoding said polypeptides;

PCP0424A (SEQ ID NO 17–18): polypeptides comprising, consisting of, or consisting essentially of about amino acids 1–53, 585–586, 586–611, polypeptide fragments thereof, and polynucleotides encoding said polypeptides;

PCP0424B (SEQ ID NO 19–20): polypeptides comprising, consisting of, or consisting essentially of about amino acids 1–53, 585–586, polypeptide fragments thereof, and polynucleotides encoding said polypeptides;

PCP0424C (SEQ ID NO 21–22): polypeptides comprising, consisting of, or consisting essentially of about amino acids 1–53, 585–586, polypeptide fragments thereof, and polynucleotides encoding said polypeptides;

PCP0816 (SEQ ID NO 25–26): polypeptides comprising, consisting of, or consisting essentially of about amino acids 268–317, 623, 992–1013, polypeptide fragments thereof, and polynucleotides encoding said polypeptides;

PCP0480 (SEQ ID NO 27–28): polypeptides comprising, consisting of, or consisting essentially of about amino acids 1–151, 152–171, polypeptide fragments thereof, and polynucleotides encoding said polypeptides;

PC0382 (SEQ ID NO 23–24): polypeptides comprising, consisting of, or consisting essentially of about amino acids 1–9, polypeptide fragments thereof, and polynucleotides encoding said polypeptides;

PCP0842 (SEQ ID NO 29–30): polypeptides comprising, consisting of, or consisting essentially of about amino acids 1–454, polypeptide fragments thereof, and polynucleotides encoding said polypeptides.

Nucleic Acids

In accordance with the present invention, genes have been identified which are differentially expressed in prostate cancer. These genes can be further divided into groups based on additional characteristics of their expression and the tissues in which they are expressed. For instance, genes can be further subdivided based on the stage and/or grade of the cancer in which they are expressed. Genes can also be grouped based on their penetrance in a prostate cancer, e.g., expressed in all prostate cancer examined, expressed in a certain percentage of prostate cancer examined, etc. These groupings do not restrict or limit the use such genes in therapeutic, diagnostic, prognostic, etc., applications. For instance, a gene which is expressed in only some cancers (e.g., incompletely penetrant) may be useful in therapeutic applications to treat a subset of cancers. Similarly, a co-penetrant gene, or a gene which is expressed in prostate cancer and other normal tissues, may be useful as a therapeutic or diagnostic, even if its expression pattern is not highly prostate specific. Thus, the uses of the genes or their products are not limited by their patterns of expression.

By the phrase "differential expression," it is meant that the levels of expression of a gene, as measured by its transcription or translation product, are different depending upon the specific cell-type or tissue (e.g., in an averaging assay that looks at a population of cells). There are no absolute amounts by which the gene expression levels must vary, as long as the differences are measurable.

The phrase "up-regulated" indicates that an mRNA transcript or other nucleic acid corresponding to a polynucleotide of the present invention is expressed in larger amounts in a cancer as compared to the same transcript expressed in normal cells from which the cancer was derived. In general, up-regulation can be assessed by any suitable method, including any of the nucleic acid detection and hybridization methods mentioned below, as well as polypeptide-based methods. Up-regulation also includes going from substantially no expression in a normal tissue, from detectable expression in a normal tissue, from significant expression in a normal tissue, to higher levels in the cancer.

The phrase "down-regulated" indicates that an mRNA transcript or other nucleic acid corresponding to a polynucleotide of the present invention is expressed in lower amounts in a cancer as compared to the same transcript expressed in normal cells from which the cancer was derived. A down-regulated gene can show no detectable expression, or any amount of expression which is less than the gene's expression in normal tissue.

Differential regulation can be determined by any suitable method, e.g., by comparing its abundance per gram of RNA (e.g., total RNA, polyadenylated mRNA, etc.) extracted from a prostate tissue in comparison to the corresponding normal tissue. The normal tissue can be from the same or different individual or source. For convenience, it can be supplied as a separate component or in a kit in combination with probes and other reagents for detecting genes. The quantity by which a nucleic acid is differentially-regulated can be any value, e.g., about 10% more or less of normal expression, about 50% more or less of normal expression, 2-fold more or less, 5-fold more or less, 10-fold more or less, etc.

The amount of transcript can also be compared to a different gene in the same sample, especially a gene whose abundance is known and substantially no different in its expression between normal and cancer cells (e.g., a "control" gene). If represented as a ratio, with the quantity of differentially-regulated gene transcript in the numerator and the control gene transcript in the denominator, the ratio would be larger, e.g., in breast cancer than in a sample from normal breast tissue.

Differential-regulation can arise through a number of different mechanisms. The present invention is not bound by any specific way through which it occurs. Differential-regulation of a polynucleotide can occur, e.g., by modulating (1) transcriptional rate of the gene (e.g., increasing its rate, inducing or stimulating its transcription from a basal, low-level rate, etc.), (2) the post-transcriptional processing of RNA transcripts, (3) the transport of RNA from the nucleus into the cytoplasm, (4) the RNA nuclear and cytoplasmic turnover (e.g., by virtue of having higher stability or resistance to degradation), and combinations thereof. See, e.g., Tollervey and Caceras, *Cell*, 103:703–709, 2000.

A differentially-regulated polynucleotide is useful in a variety of different applications as described in greater details below. Because it is more abundant in cancer, it and its expression products can be used in a diagnostic test to assay for the presence of cancer, e.g., in tissue sections, in a biopsy sample, in total RNA, in lymph, in blood, etc. Differentially-regulated polynucleotides and polypeptides can be used individually, or in groups, to assess the cancer, e.g., to determine the specific type of cancer, its stage of development, the nature of the genetic defect, etc., or to assess the efficacy of a treatment modality. How to use polynucleotides in diagnostic and prognostic assays is discussed below. In addition, the polynucleotides and the polypeptides they encode, can serve as a target for therapy or drug discovery. A polypeptide, coded for by a differentially-regulated polynucleotide, which is displayed on the cell-surface, can be a target for immunotherapy to destroy, inhibit, etc., the diseased tissue. Differentially-regulated transcripts can also be used in drug discovery schemes to identify pharmacological agents which suppress, inhibit, etc., their differential-regulation, thereby preventing the phenotype associated with their expression. Thus, a differentially-regulated polynucleotide and its expression products of the present invention have significant applications in diagnostic, therapeutic, prognostic, drug development, and related areas.

The expression patterns of the differentially expressed genes disclosed herein can be described as a "fingerprint" in that they are a distinctive pattern displayed by a cancer. Just as with a fingerprint, an expression pattern can be used as a unique identifier to characterize the status of a tissue sample. The list of genes represented by SEQ ID NOS 1–30 provides an example of a cell expression profile for a prostate cancer. It can be used as a point of reference to compare and characterize unknown samples and samples for which further information is sought. Tissue fingerprints can be used in many ways, e.g., to classify an unknown tissue as being a prostate cancer, to determine the origin of a particular cancer (e.g., the origin of metastatic cells), to determine the presence of a cancer in a biopsy sample, to assess the efficacy of a cancer therapy in a human patient or a non-human animal model, to detect circulating cancer cells in blood or a lymph node biopsy, etc. While the expression profile of the complete gene set represented by SEQ ID NOS 1–30 may be most informative, a fingerprint containing expression information from less than the full collection can be useful, as well. In the same way that an incomplete fingerprint may contain enough of the pattern of whorls, arches, loops, and ridges, to identify the individual, a cell expression fingerprint containing less than the full complement may be adequate to provide useful and unique identifying and other information about the sample. Moreover, cancer is a multi-factorial disease, involving genetic aberrations in more than gene locus. This multifaceted nature may be reflected in different cell expression profiles associated with breast cancers arising in different individuals, in different locations in the same individual, or even within the same cancer locus. As a result, a complete match with a particular cell expression profile, as shown herein, is not necessary to classify a cancer as being of the same type or stage. Similarity to one cell expression profile, e.g., as compared to another, can be adequate to classify cancer types, grades, and stages.

A mammalian polynucleotide, or fragment thereof, of the present invention is a polynucleotide having a nucleotide sequence obtainable from a natural source. When the species name is used, e.g., human, it indicates that the polynucleotide or polypeptide is obtainable from a natural source. It therefore includes naturally-occurring normal It therefore includes naturally-occurring normal, naturally-occurring mutant, and naturally-occurring polymorphic alleles (e.g., SNPs), differentially-spliced transcripts, splice-variants, etc. By the term "naturally-occurring," it is meant that the polynucleotide is obtainable from a natural source, e.g., animal tissue and cells, body fluids, tissue culture cells, forensic samples. Natural sources include, e.g., living cells obtained from tissues and whole organisms, tumors, cultured cell lines, including primary and immortalized cell lines. Naturally-occurring mutations can include deletions (e.g., a truncated amino- or carboxy-terminus), substitutions, inversions, or additions of nucleotide sequence. These genes can be detected and isolated by polynucleotide hybridization according to methods which one skilled in the art would know, e.g., as discussed below.

A polynucleotide according to the present invention can be obtained from a variety of different sources. It can be obtained from DNA or RNA, such as polyadenylated mRNA or total RNA, e.g., isolated from tissues, cells, or whole organism. The polynucleotide can be obtained directly from DNA or RNA, from a cDNA library, from a genomic library, etc. The polynucleotide can be obtained from a cell or tissue (e.g., from an embryonic or adult tissues) at a particular stage of development, having a desired genotype, phenotype, disease status, etc.

The polynucleotides described in SEQ ID NOS 1, 3, 5, 7, 9, 11, 13, 15, 17, 19, 21, 23, 25, 27, and 29 can be partial sequences that correspond to full-length, naturally-occurring transcripts. The present invention includes, as well, full-length polynucleotides that comprise these partial sequences, e.g., genomic DNAs and polynucleotides comprising a start and stop codon, a start codon and a polyA tail, a transcription start and a polyA tail, etc. These sequences can be obtained by any suitable method, e.g., using a partial sequence as a probe to select a full-length cDNA from a library containing full-length inserts. A polynucleotide which "codes without interruption" refers to a polynucleotide having a continuous open reading frame ("ORF") as compared to an ORF which is interrupted by introns or other noncoding sequences.

Polynucleotides and polypeptides (including any part of regulated prostate gene) can be excluded as compositions from the present invention if, e.g., listed in a publicly available databases on the day this application was filed and/or disclosed in a patent application having an earlier filing or priority date than this application and/or conceived and/or reduced to practice earlier than a polynucleotide in this application.

As described herein, the phrase "an isolated polynucleotide which is SEQ ID NO," or "an isolated polynucleotide which is selected from SEQ ID NO," refers to an isolated nucleic acid molecule from which the recited sequence was derived (e.g., a cDNA derived from mRNA; cDNA derived from genomic DNA). Because of sequencing errors, typographical errors, etc., the actual naturally-occurring sequence may differ from a SEQ ID listed herein. Thus, the phrase indicates the specific molecule from which the sequence was derived, rather than a molecule having that exact recited nucleotide sequence, analogously to how a culture depository number refers to a specific cloned fragment in a cryotube.

As explained in more detail below, a polynucleotide sequence of the invention can contain the complete sequence as shown in SEQ ID NOS 1, 3, 5, 7, 9, 11, 13, 15, 17,19, 21, 23, 25, 27, and 29, degenerate sequences thereof, anti-sense, muteins thereof, genes comprising said sequences, full-length cDNAs comprising said sequences, complete genomic sequences, fragments thereof, homologs, primers, nucleic acid molecules which hybridize thereto, derivatives thereof, etc.

Genomic

The present invention also relates genomic DNA from which the polynucleotides of the present invention can be derived. A genomic DNA coding for a human, mouse, or other mammalian polynucleotide, can be obtained routinely, for example, by screening a genomic library (e.g., a YAC library) with a polynucleotide of the present invention, or by searching nucleotide databases, such as GenBank and EMBL, for matches. Promoter and other regulatory regions (including both 5' and 3' regions, as well introns) can be identified upstream or downstream of coding and expressed RNAs, and assayed routinely for activity, e.g., by joining to a reporter gene (e.g., CAT, GFP, alkaline phosphatase, luciferase, galatosidase). A promoter obtained from a prostate selective gene can be used, e.g., in gene therapy to obtain tissue-specific expression of a heterologous gene (e.g., coding for a therapeutic product or cytotoxin). 5' and 3' sequences (including, UTRs and introns) can be used to modulate or regulate stability, transcription, and translation of nucleic acids, including the sequence to which is attached in nature, as well as heterologous nucleic acids.

Constructs

A polynucleotide of the present invention can comprise additional polynucleotide sequences, e.g., sequences to enhance expression, detection, uptake, cataloging, tagging, etc. A polynucleotide can include only coding sequence; a coding sequence and additional non-naturally occurring or heterologous coding sequence (e.g., sequences coding for leader, signal, secretory, targeting, enzymatic, fluorescent, antibiotic resistance, and other functional or diagnostic peptides); coding sequences and non-coding sequences, e.g., untranslated sequences at either a 5' or 3' end, or dispersed in the coding sequence, e.g., introns.

A polynucleotide according to the present invention also can comprise an expression control sequence operably linked to a polynucleotide as described above. The phrase "expression control sequence" means a polynucleotide sequence that regulates expression of a polypeptide coded for by a polynucleotide to which it is functionally ("operably") linked. Expression can be regulated at the level of the mRNA or polypeptide. Thus, the expression control sequence includes mRNA-related elements and protein-related elements. Such elements include promoters, enhancers (viral or cellular), ribosome binding sequences, transcriptional terminators, etc. An expression control sequence is operably linked to a nucleotide coding sequence when the expression control sequence is positioned in such a manner to effect or achieve expression of the coding sequence. For example, when a promoter is operably linked 5' to a coding sequence, expression of the coding sequence is driven by the promoter. Expression control sequences can include an initiation codon and additional nucleotides to place a partial nucleotide sequence of the present invention in-frame in order to produce a polypeptide (e.g., pET vectors from Promega have been designed to permit a molecule to be inserted into all three reading frames to identify the one that results in polypeptide expression). Expression control sequences can be heterologous or endogenous to the normal gene.

A polynucleotide of the present invention can also comprise nucleic acid vector sequences, e.g., for cloning, expression, amplification, selection, etc. Any effective vector can be used. A vector is, e.g., a polynucleotide molecule which can replicate autonomously in a host cell, e.g., containing an origin of replication. Vectors can be useful to perform manipulations, to propagate, and/or obtain large quantities of the recombinant molecule in a desired host. A skilled worker can select a vector depending on the purpose desired, e.g., to propagate the recombinant molecule in bacteria, yeast, insect, or mammalian cells. The following vectors are provided by way of example. Bacterial: pQE70, pQE60, pQE-9 (Qiagen), pBS, pD10, Phagescript, phiX174, pBK Phagemid, pNH8A, pNH16a, pNH18Z, pNH46A (Stratagene); Bluescript KS+II (Stratagene); ptrc99a, pKK223-3, pKK233-3, pDR54 0, pRIT5 (Pharmacia). Eukaryotic: PWLNEO, pSV2CAT, pOG44, pXT1, pSG (Stratagene), pSVK3, PBPV, PMSG, pSVL (Pharmacia), pCR2.1/TOPO, pCRII/TOPO, pCR4/TOPO, pTrcHisB, pCMV6-XL4, etc. However, any other vector, e.g., plasmids, viruses, or parts thereof, may be used as long as they are replicable and viable in the desired host. The vector can also comprise sequences which enable it to replicate in the host whose genome is to be modified.

Hybridization

Polynucleotide hybridization, as discussed in more detail below, is useful in a variety of applications, including, in gene detection methods, for identifying mutations, for making mutations, to identify homologs in the same and different species, to identify related members of the same gene family, in diagnostic and prognostic assays, in therapeutic applications (e.g., where an antisense polynucleotide is used to inhibit expression), etc.

The ability of two single-stranded polynucleotide preparations to hybridize together is a measure of their nucleotide sequence complementarity, e.g., base-pairing between nucleotides, such as A-T, G-C, etc. The invention thus also relates to polynucleotides, and their complements, which hybridize to a polynucleotide comprising a nucleotide sequence as set forth in SEQ ID NOS 1, 3, 5, 7, 9, 11, 13, 15, 17, 19, 21, 23, 25, 27, and 29 and genomic sequences thereof. A nucleotide sequence hybridizing to the latter sequence will have a complementary polynucleotide strand, or act as a template for one in the presence of a polymerase (i.e., an appropriate polynucleotide synthesizing enzyme). The present invention includes both strands of polynucleotide, e.g., a sense strand and an anti-sense strand.

Hybridization conditions can be chosen to select polynucleotides which have a desired amount of nucleotide complementarity with the nucleotide sequences set forth in SEQ ID NOS 1, 3, 5, 7, 9, 11, 13, 15, 17, 19, 21, 23, 25, 27, and 29 and genomic sequences thereof. A polynucleotide capable of hybridizing to such sequence, preferably, possesses, e.g., about 70%, 75%, 80%, 85%, 87%, 90%, 92%, 95%, 97%, 99%, or 100% complementarity, between the sequences. The present invention particularly relates to polynucleotide sequences which hybridize to the nucleotide sequences set forth in SEQ ID NOS 1, 3, 5, 7, 9, 11, 13, 15, 17, 19, 21, 23, 25, 27, and 29 or genomic sequences thereof, under low or high stringency conditions. These conditions can be used, e.g., to select corresponding homologs in non-human species.

Polynucleotides which hybridize to polynucleotides of the present invention can be selected in various ways. Filter-type blots (i.e., matrices containing polynucleotide, such as nitrocellulose), glass chips, and other matrices and substrates comprising polynucleotides (short or long) of interest, can be incubated in a prehybridization solution (e.g., 6×SSC, 0.5% SDS, 100 $\mu$g/ml denatured salmon sperm DNA, 5× Denhardt's solution, and 50% formamide), at 22–68° C., overnight, and then hybridized with a detectable polynucleotide probe under conditions appropriate to achieve the desired stringency. In general, when high homology or sequence identity is desired, a high temperature can be used (e.g., 65° C.). As the homology drops, lower washing temperatures are used. For salt concentrations, the lower the salt concentration, the higher the stringency. The length of the probe is another consideration. Very short probes (e.g., less than 100 base pairs) are washed at lower temperatures, even if the homology is high. With short probes, formamide can be omitted. See, e.g., *Current Protocols in Molecular Biology*, Chapter 6, Screening of Recombinant Libraries; Sambrook et al., *Molecular Cloning*, 1989, Chapter 9.

For instance, high stringency conditions can be achieved by incubating the blot overnight (e.g., at least 12 hours) with a long polynucleotide probe in a hybridization solution containing, e.g., about 5×SSC, 0.5% SDS, 100 $\mu$g/ml denatured salmon sperm DNA and 50% formamide, at 42° C. Blots can be washed at high stringency conditions that allow, e.g., for less than 5% bp mismatch (e.g., wash twice in 0.1% SSC and 0.1% SDS for 30 min at 65° C.), i.e., selecting sequences having 95% or greater sequence identity.

Other non-limiting examples of high stringency conditions includes a final wash at 65° C. in aqueous buffer containing 30 mM NaCl and 0.5% SDS. Another example of high stringent conditions is hybridization in 7% SDS, 0.5 M $NaPO_4$, pH 7, 1 mM EDTA at 50° C., e.g., overnight, followed by one or more washes with a 1% SDS solution at 42° C. Whereas high stringency washes can allow for less than 5% mismatch, reduced or low stringency conditions can permit up to 20% nucleotide mismatch. Hybridization at low stringency can be accomplished as above, but using lower formamide conditions, lower temperatures and/or lower salt concentrations, as well as longer periods of incubation time.

Hybridization can also be based on a calculation of melting temperature (Tm) of the hybrid formed between the probe and its target, as described in Sambrook et al. Generally, the temperature Tm at which a short oligonucleotide (containing 18 nucleotides or fewer) will melt from its target sequence is given by the following equation: Tm=(number of A's and T's)×2° C.+(number of C's and G's)×4° C. For longer molecules, Tm=81.5+16.6 $\log_{10}[Na^+]$+0.41(%

GC)−600/N where [$Na^+$] is the molar concentration of sodium ions, % GC is the percentage of GC base pairs in the probe, and N is the length. Hybridization can be carried out at several degrees below this temperature to ensure that the probe and target can hybridize. Mismatches can be allowed for by lowering the temperature even further.

Stringent conditions can be selected to isolate sequences, and their complements, which have, e.g., at least about 90%, 95%, or 97%, nucleotide complementarity between the probe (e.g., a short polynucleotide of SEQ ID NOS 1, 3, 5, 7, 9, 11, 13, 15, 17, 19, 21, 23, 25, 27, and 29 or genomic sequences thereof) and a target polynucleotide.

Other homologs of polynucleotides of the present invention can be obtained from mammalian and non-mammalian sources according to various methods. For example, hybridization with a polynucleotide can be employed to select homologs, e.g., as described in Sambrook et al., *Molecular Cloning*, Chapter 11, 1989. Such homologs can have varying amounts of nucleotide and amino acid sequence identity and similarity to such polynucleotides of the present invention. Mammalian organisms include, e.g., mice, rats, monkeys, pigs, cows, etc. Non-mammalian organisms include, e.g., vertebrates, invertebrates, zebra fish, chicken, *Drosophila, C. elegans, Xenopus*, yeast such as *S. pombe, S. cerevisiae*, roundworms, prokaryotes, plants, *Arabidopsis*, artemia, viruses, etc. The degree of nucleotide sequence identity between human and mouse can be about, e.g. 70% or more, 85% or more for open reading frames, etc.

Alignment

Alignments can be accomplished by using any effective algorithm. For pairwise alignments of DNA sequences, the methods described by Wilbur-Lipman (e.g., Wilbur and Lipman, *Proc. Natl. Acad. Sci.*, 80:726–730, 1983) or Martinez/Needleman-Wunsch (e.g., Martinez, *Nucleic Acid Res.*, 11:4629–4634, 1983) can be used. For instance, if the Martinez/Needleman-Wunsch DNA alignment is applied, the minimum match can be set at 9, gap penalty at 1.10, and gap length penalty at 0.33. The results can be calculated as a similarity index, equal to the sum of the matching residues divided by the sum of all residues and gap characters, and then multiplied by 100 to express as a percent. Similarity index for related genes at the nucleotide level in accordance with the present invention can be greater than 70%, 80%, 85%, 90%, 95%, 99%, or more. Pairs of protein sequences can be aligned by the Lipman-Pearson method (e.g., Lipman and Pearson, *Science*, 227:1435–1441, 1985) with k-tuple set at 2, gap penalty set at 4, and gap length penalty set at 12. Results can be expressed as percent similarity index, where related genes at the amino acid level in accordance with the present invention can be greater than 65%, 70%, 75%, 80%, 85%, 90%, 95%, 99%, or more. Various commercial and free sources of alignment programs are available, e.g., MegAlign by DNA Star, BLAST (National Center for Biotechnology Information), BCM (Baylor College of Medicine) Launcher, etc. BLAST can be used to calculate amino acid sequence identity, amino acid sequence homology, and nucleotide sequence identity. These calculations can be made along the entire length of each of the target sequences which are to be compared.

Percent sequence identity can also be determined by other conventional methods, e.g., as described in Altschul et al., *Bull. Math. Bio*, 48: 603–616, 1986 and Henikoff and Henikoff, *Proc. Natl. Acad. Sci.* USA 89:10915–10919, 1992.

Specific Polynucleotide Probes

A polynucleotide of the present invention can comprise any continuous nucleotide sequence of SEQ ID NOS 1, 3, 5, 7, 9, 11, 13, 15, 17, 19, 21, 23, 25, 27, and 29, sequences which share sequence identity thereto, or complements thereof. The term "probe" refers to any substance that can be used to detect, identify, isolate, etc., another substance. A polynucleotide probe is comprised of nucleic acid can be used to detect, identify, etc., other nucleic acids, such as DNA and RNA.

These polynucleotides can be of any desired size that is effective to achieve the specificity desired. For example, a probe can be from about 7 or 8 nucleotides to several thousand nucleotides, depending upon its use and purpose. For instance, a probe used as a primer PCR can be shorter than a probe used in an ordered array of polynucleotide probes. Probe sizes vary, and the invention is not limited in any way by their size, e.g., probes can be from about 7–2000 nucleotides, 7–1000, 8–700, 8–600, 8–500, 8–400, 8–300, 8–150, 8–100, 8–7–50, 10–25, 14–16, at least about 8, at least about 10, at least about 15, at least about 25, etc. The polynucleotides can have non-naturally-occurring nucleotides, e.g., inosine, AZT, 3TC, etc. The polynucleotides can have 100% sequence identity or complementarity to a sequence of SEQ ID NOS 1, 3, 5, 7, 9, 11, 13, 15, 17, 19, 21, 23, 25, 27, and 29, or it can have mismatches or nucleotide substitutions, e.g., 1, 2, 3, 4, or 5 substitutions. The probes can be single-stranded or double-stranded.

In accordance with the present invention, a polynucleotide can be present in a kit, where the kit includes, e.g., one or more polynucleotides, a desired buffer (e.g., phosphate, tris, etc.), detection compositions, RNA or cDNA from different tissues to be used as controls, libraries, etc. The polynucleotide can be labeled or unlabeled, with radioactive or non-radioactive labels as known in the art. Kits can comprise one or more pairs of polynucleotides for amplifying nucleic acids specific for differentially-regulated genes of the present invention, e.g., comprising a forward and reverse primer effective in PCR. These include both sense and anti-sense orientations. For instance, in PCR-based methods (such as RT-PCR), a pair of primers are typically used, one having a sense sequence and the other having an antisense sequence.

Another aspect of the present invention is a nucleotide sequence that is specific to, or for, a selective polynucleotide. The phrases "specific for" or "specific to" a polynucleotide have a functional meaning that the polynucleotide can be used to identify the presence of one or more target genes in a sample and distinguish them from non-target genes. It is specific in the sense that it can be used to detect polynucleotides above background noise ("non-specific binding"). A specific sequence is a defined order of nucleotides (or amino acid sequences, if it is a polypeptide sequence) which occurs in the polynucleotide, e.g., in the nucleotide sequences of SEQ ID NOS 1, 3, 5, 7, 9, 11, 13, 15, 17, 19, 21, 23, 25, 27, and 29, and which is characteristic of that target sequence, and substantially no non-target sequences. A probe or mixture of probes can comprise a sequence or sequences that are specific to a plurality of target sequences, e.g., where the sequence is a consensus sequence, a functional domain, etc., e.g., capable of recognizing a family of related genes. Such sequences can be used as probes in any of the methods described herein or incorporated by reference. Both sense and antisense nucleotide sequences are included. A specific polynucleotide according to the present invention can be determined routinely.

A polynucleotide comprising a specific sequence can be used as a hybridization probe to identify the presence of, e.g., human or mouse polynucleotide, in a sample comprising a mixture of polynucleotides, e.g., on a Northern blot.

Hybridization can be performed under high stringent conditions (see, above) to select polynucleotides (and their complements which can contain the coding sequence) having at least 90%, 95%, 99%, etc., identity (i.e., complementarity) to the probe, but less stringent conditions can also be used. A specific polynucleotide sequence can also be fused in-frame, at either its 5' or 3' end, to various nucleotide sequences as mentioned throughout the patent, including coding sequences for enzymes, detectable markers, GFP, etc, expression control sequences, etc.

A polynucleotide probe, especially one that is specific to a polynucleotide of the present invention, can be used in gene detection and hybridization methods as already described. In one embodiment, a specific polynucleotide probe can be used to detect whether a particular tissue or cell-type is present in a target sample. To carry out such a method, a selective polynucleotide can be chosen which is characteristic of the desired target tissue. Such polynucleotide is preferably chosen so that it is expressed or displayed in the target tissue, but not in other tissues which are present in the sample. For instance, if detection of prostate is desired, it may not matter whether the selective polynucleotide is expressed in other tissues, as long as it is not expressed in cells normally present in blood, e.g., peripheral blood mononuclear cells. Starting from the selective polynucleotide, a specific polynucleotide probe can be designed which hybridizes (if hybridization is the basis of the assay) under the hybridization conditions to the selective polynucleotide, whereby the presence of the selective polynucleotide can be determined.

Probes which are specific for polynucleotides of the present invention can also be prepared using involve transcription-based systems, e.g., incorporating an RNA polymerase promoter into a selective polynucleotide of the present invention, and then transcribing anti-sense RNA using the polynucleotide as a template. See, e.g., U.S. Pat. No. 5,545,522.

Polynucleotide Composition

A polynucleotide according to the present invention can comprise, e.g., DNA, RNA, synthetic polynucleotide, peptide polynucleotide, modified nucleotides, dsDNA, ssDNA, ssRNA, dsRNA, and mixtures thereof. A polynucleotide can be single- or double-stranded, triplex, DNA:RNA, duplexes, comprise hairpins, and other secondary structures, etc. Nucleotides comprising a polynucleotide can be joined via various known linkages, e.g., ester, sulfamate, sulfamide, phosphorothioate, phosphoramidate, methylphosphonate, carbamate, etc., depending on the desired purpose, e.g., resistance to nucleases, such as RNAse H, improved in vivo stability, etc. See, e.g., U.S. Pat. No. 5,378,825. Any desired nucleotide or nucleotide analog can be incorporated, e.g., 6-mercaptoguanine, 8-oxo-guanine, etc.

Various modifications can be made to the polynucleotides, such as attaching detectable markers (avidin, biotin, radioactive elements, fluorescent tags and dyes, energy transfer labels, energy-emitting labels, binding partners, etc.) or moieties which improve hybridization, detection, and/or stability. The polynucleotides can also be attached to solid supports, e.g., nitrocellulose, magnetic or paramagnetic microspheres (e.g., as described in U.S. Pat. Nos. 5,411,863; 5,543,289; for instance, comprising ferromagnetic, supermagnetic, paramagnetic, superparamagnetic, iron oxide and polysaccharide), nylon, agarose, diazotized cellulose, latex solid microspheres, polyacrylamides, etc., according to a desired method. See, e.g., U.S. Pat. Nos. 5,470,967, 5,476,925, and 5,478,893.

Polynucleotide according to the present invention can be labeled according to any desired method. The polynucleotide can be labeled using radioactive tracers such as $^{32}P$, $^{35}S$, $^{3}H$, or $^{14}C$, to mention some commonly used tracers. The radioactive labeling can be carried out according to any method, such as, for example, terminal labeling at the 3' or 5' end using a radiolabeled nueleotide, polynucleotide kinase (with or without dephosphorylation with a phosphatase) or a ligase (depending on the end to be labeled). A non-radioactive labeling can also be used, combining a polynucleotide of the present invention with residues having immunological properties (antigens, haptens), a specific affinity for certain reagents (ligands), properties enabling detectable enzyme reactions to be completed (enzymes or coenzymes, enzyme substrates, or other substances involved in an enzymatic reaction), or characteristic physical properties, such as fluorescence or the emission or absorption of light at a desired wavelength, etc.

Nucleic Acid Detection Methods

Another aspect of the present invention relates to methods and processes for detecting differentially-regulated genes of the present invention. Detection methods have a variety of applications, including for diagnostic, prognostic, forensic, and research applications. To accomplish gene detection, a polynucleotide in accordance with the present invention can be used as a "probe." The term "probe" or "polynucleotide probe" has its customary meaning in the art, e.g., a polynucleotide which is effective to identify (e.g., by hybridization), when used in an appropriate process, the presence of a target polynucleotide to which it is designed. Identification can involve simply determining presence or absence, or it can be quantitative, e.g., in assessing amounts of a gene or gene transcript present in a sample. Probes can be useful in a variety of ways, such as for diagnostic purposes, to identify homologs, and to detect, quantitate, or isolate a polynucleotide of the present invention in a test sample.

Assays can be utilized which permit quantification and/or presence/absence detection of a target nucleic acid in a sample. Assays can be performed at the single-cell level, or in a sample comprising many cells, where the assay is "averaging" expression over the entire collection of cells and tissue present in the sample. Any suitable assay format can be used, including, but not limited to, e.g., Southern blot analysis, Northern blot analysis, polymerase chain reaction ("PCR") (e.g., Saiki et al., *Science*, 241:53, 1988; U.S. Pat. Nos. 4,683,195, 4,683,202, and 6,040,166*; PCR Protocols: A Guide to Methods and Applications*, Innis et al., eds., Academic Press, New York, 1990), reverse transcriptase polymerase chain reaction ("RT-PCR"), anchored PCR, rapid amplification of cDNA ends ("RACE") (e.g., Schaefer in *Gene Cloning and Analysis: Current Innovations*, Pages 99–115, 1997), ligase chain reaction ("LCR") (EP 320 308), one-sided PCR (Ohara et al., *Proc. Natl. Acad. Sci.*, 86:5673–5677, 1989), indexing methods (e.g., U.S. Pat. No. 5,508,169), in situ hybridization, differential display (e.g., Liang et al., *Nucl. Acid. Res.*, 21:3269–3275, 1993; U.S. Pat. Nos. 5,262,311, 5,599,672 and 5,965,409; WO97/18454; Prashar and Weissman, *Proc. Natl. Acad. Sci.*, 93:659–663, and U.S. Pat. Nos. 6,010,850 and 5,712,126; Welsh et al., *Nucleic Acid Res.*, 20:4965–4970, 1992, and U.S. Pat. No. 5,487,985) and other RNA fingerprinting techniques, nucleic acid sequence based amplification ("NASBA") and other transcription based amplification systems (e.g., U.S. Pat. Nos. 5,409,818 and 5,554,527; WO 88/10315), polynucleotide arrays (e.g., U.S. Pat. Nos. 5,143,854, 5,424,186; 5,700,637, 5,874,219, and 6,054,270; PCT WO 92/10092; PCT WO 90/15070), Qbeta Replicase (PCT/US87/00880), Strand Displacement Amplification ("SDA"), Repair Chain Reaction ("RCR"), nuclease protection assays, subtraction-based methods, Rapid-Scan™, etc. Additional useful methods include, but are not limited to, e.g., template-based amplification methods, competitive PCR (e.g., U.S. Pat. No. 5,747,251), redox-based assays (e.g., U.S. Pat. No. 5,871,918), Taqman-based assays (e.g., Holland et al., *Proc. Natl. Acad, Sci.*, 88:7276–7280, 1991; U.S. Pat. Nos. 5,210,015 and 5,994,063), real-time fluorescence-based monitoring (e.g., U.S. Pat. No. 5,928,907), molecular energy transfer labels (e.g., U.S. Pat. Nos. 5,348,853, 5,532,129, 5,565,322, 6,030,787, and 6,117,635; Tyagi and Kramer, *Nature Biotech.*, 14:303–309, 1996). Any method suitable for single cell analysis of gene or protein expression can be used, including in situ hybridization, immunocytochemistry, MACS, FACS, flow cytometry, etc. For single cell assays, expression products can be measured using antibodies, PCR, or other types of nucleic acid amplification (e.g., Brady et al., *Methods Mol. & Cell. Biol.* 2, 17–25, 1990; Eberwine et al., 1992, *Proc. Natl. Acad. Sci.*, 89, 3010–3014, 1992; U.S. Pat. No. 5,723,290). These and other methods can be carried out conventionally, e.g., as described in the mentioned publications.

Many of such methods may require that the polynucleotide is labeled, or comprises a particular nucleotide type useful for detection. The present invention includes such modified polynucleotides that are necessary to carry out such methods. Thus, polynucleotides can be DNA, RNA, DNA:RNA hybrids, PNA, etc., and can comprise any modification or substituent which is effective to achieve detection.

Detection can be desirable for a variety of different purposes, including research, diagnostic, prognostic, and forensic. For diagnostic purposes, it may be desirable to identify the presence or quantity of a polynucleotide sequence in a sample, where the sample is obtained from tissue, cells, body fluids, etc. In a preferred method as described in more detail below, the present invention relates to a method of detecting a polynucleotide comprising, contacting a target polynucleotide in a test sample with a polynucleotide probe under conditions effective to achieve hybridization between the target and probe; and detecting hybridization.

Any test sample in which it is desired to identify a polynucleotide or polypeptide thereof can be used, including, e.g., blood, urine, saliva, stool (for extracting nucleic acid, see, e.g., U.S. Pat. No. 6,177,251), swabs comprising tissue, biopsied tissue, tissue sections, cultured cells, etc.

Detection can be accomplished in combination with polynucleotide probes for other genes, e.g., genes which are expressed in other disease states, tissues, cells, such as brain, heart, kidney, spleen, thymus, liver, stomach, small intestine, colon, muscle, lung, testis, placenta, pituitary, thyroid, skin, adrenal gland, pancreas, salivary gland, uterus, ovary, prostate gland, peripheral blood cells (T-cells, lymphocytes, etc.), embryo, normal breast fat, adult and embryonic stem cells, specific cell-types, such as endothelial, epithelial, myocytes, adipose, luminal epithelial, basoepithelial, myoepithelial, stromal cells, etc.

Polynucleotides can be used in wide range of methods and compositions, including for detecting, diagnosing, staging, grading, assessing, prognosticating, etc. diseases and disorders associated with differentially-regulated genes of the present invention, for monitoring or assessing therapeutic and/or preventative measures, in ordered arrays, etc. Any method of detecting genes and polynucleotides of SEQ ID NOS 1, 3, 5, 7, 9, 11, 13, 15, 17, 19, 21, 23, 25, 27, and 29 can be used; certainly, the present invention is not to be limited how such methods are implemented.

Along these lines, the present invention relates to methods of detecting differentially-regulated genes described herein in a sample comprising nucleic acid. Such methods can comprise one or more the following steps in any effective order, e.g., contacting said sample with a polynucleotide probe under conditions effective for said probe to hybridize specifically to nucleic acid in said sample, and detecting the presence or absence of probe hybridized to nucleic acid in said sample, wherein said probe is a polynucleotide which is SEQ ID NOS 1, 3, 5, 7, 9, 11, 13, 15, 17, 19, 21, 23, 25, 27, and 29, a polynucleotide having, e.g., about 70%, 80%, 85%, 90%, 95%, 99%, or more sequence identity thereto, effective or specific fragments thereof, or complements thereto. The detection method can be applied to any sample, e.g., cultured primary, secondary, or established cell lines, tissue biopsy, blood, urine, stool, cerebral spinal fluid, and other bodily fluids, for any purpose.

Contacting the sample with probe can be carried out by any effective means in any effective environment. It can be accomplished in a solid, liquid, frozen, gaseous, amorphous, solidified, coagulated, colloid, etc., mixtures thereof, matrix. For instance, a probe in an aqueous medium can be contacted with a sample which is also in an aqueous medium, or which is affixed to a solid matrix, or vice-versa.

Generally, as used throughout the specification, the term "effective conditions" means, e.g., the particular milieu in which the desired effect is achieved. Such a milieu, includes, e.g., appropriate buffers, oxidizing agents, reducing agents, pH, co-factors, temperature, ion concentrations, suitable age and/or stage of cell (such as, in particular part of the cell cycle, or at a particular stage where particular genes are being expressed) where cells are being used, culture conditions (including substrate, oxygen, carbon dioxide, etc.). When hybridization is the chosen means of achieving detection, the probe and sample can be combined such that the resulting conditions are functional for said probe to hybridize specifically to nucleic acid in said sample.

The phrase "hybridize specifically" indicates that the hybridization between single-stranded polynucleotides is based on nucleotide sequence complementarity. The effective conditions are selected such that the probe hybridizes to a preselected and/or definite target nucleic acid in the sample. For instance, if detection of a polynucleotide set forth in SEQ ID NOS 1,3,5,7,9, 11, 13, 15, 17, 19, 21, 23, 25, 27, and 29 is desired, aprobe can be selected which can hybridize to such target gene under high stringent conditions, without significant hybridization to other genes in the sample. To detect homologs of a polynucleotide set forth in SEQ ID NOS 1, 3, 5, 7, 9, 11, 13, 15, 17, 19, 21, 23, 25, 27, and 29, the effective hybridization conditions can be less stringent, and/or the probe can comprise codon degeneracy, such that a homolog is detected in the sample.

As already mentioned, the methods can be carried out by any effective process, e.g., by Northern blot analysis, polymerase chain reaction (PCR), reverse transcriptase PCR, RACE PCR, in situ hybridization, etc., as indicated above. When PCR based techniques are used, two or more probes are generally used. One probe can be specific for a defined sequence which is characteristic of a selective polynucleotide, but the other probe can be specific for the selective polynucleotide, or specific for a more general sequence, e.g., a sequence such as polyA which is characteristic of mRNA, a sequence which is specific for a promoter, ribosome binding site, or other transcriptional features, a consensus sequence (e.g., representing a functional domain). For the former aspects, 5' and 3' probes (e.g., polyA, Kozak, etc.) are preferred which are capable of specifically hybridizing to the ends of transcripts. When PCR is utilized, the probes can also be referred to as "primers" in that they can prime a DNA polymerase reaction.

In addition to testing for the presence or absence of polynucleotides, the present invention also relates to determining the amounts at which polynucleotides of the present invention are expressed in sample and determining the differential expression of such polynucleotides in samples. Such methods can involve substantially the same steps as described above for presence/absence detection, e.g., contacting with probe, hybridizing, and detecting hybridized probe, but using more quantitative methods and/or comparisons to standards.

The amount of hybridization between the probe and target can be determined by any suitable methods, e.g., PCR, RT-PCR, RACE PCR, Northern blot, polynucleotide microarrays, Rapid-Scan, etc., and includes both quantitative and qualitative measurements. For further details, see the hybridization methods described above and below. Determining by such hybridization whether the target is differentially expressed (e.g., up-regulated or down-regulated) in the sample can also be accomplished by any effective means. For instance, the target's expression pattern in the sample can be compared to its pattern in a known standard, such as in a normal tissue, or it can be compared to another gene in the same sample. When a second sample is utilized for the comparison, it can be a sample of normal tissue that is known not to contain diseased cells. The comparison can be performed on samples which contain the same amount of RNA (such as polyadenylated RNA or total RNA), or, on RNA extracted from the same amounts of starting tissue. Such a second sample can also be referred to as a control or standard. Hybridization can also be compared to a second target in the same tissue sample. Experiments can be performed that determine a ratio between the target nucleic acid and a second nucleic acid (a standard or control), e.g., in a normal tissue. When the ratio between the target and control are substantially the same in a normal and sample, the sample is determined or diagnosed not to contain cells. However, if the ratio is different between the normal and sample tissues, the sample is determined to contain cancer cells. The approaches can be combined, and one or more second samples, or second targets can be used. Any second target nucleic acid can be used as a comparison, including "housekeeping" genes, such as beta-actin, alcohol dehydrogenase, or any other gene whose expression does not vary depending upon the disease status of the cell.

Methods of Identifying Polymorphisms, Mutations, etc., of a Differentially-Regulated Gene Polynucleotides of the present invention can also be utilized to identify mutant alleles, SNPs, gene rearrangements and modifications, and other polymorphisms of the wild-type gene. Mutant alleles, polymorphisms, SNPs, etc., can be identified and isolated from cancers that are known, or suspected to have, a genetic component. Identification of such genes can be carried out routinely (see, above for more guidance), e.g., using PCR, hybridization techniques, direct sequencing, mismatch reactions (see, e.g., above), RFLP analysis, SSCP (e.g., Orita et al., *Proc. Natl. Acad. Sci.*, 86:2766, 1992), etc., where a polynucleotide having a sequence selected from SEQ ID NOS 1, 3, 5, 7, 9, 11, 13, 15, 17, 19, 21, 23, 25, 27, and 29 is used as a probe. The selected mutant alleles, SNPs, polymorphisms, etc., can be used diagnostically to determine whether a subject has, or is susceptible to a disorder associated with a differentially-regulated gene, as well as to design therapies and predict the outcome of the disorder. Methods involve, e.g., diagnosing a disorder associated with a differentially-regulated gene or determining susceptibility to a disorder, comprising, detecting the presence of a mutation in a gene represented by a polynucleotide selected from SEQ ID NOS 1, 3, 5, 7, 9, 11, 13, 15, 17, 19, 21, 23, 25, 27, and 29. The detecting can be carried out by any effective method, e.g., obtaining cells from a subject, determining the gene sequence or structure of a target gene (using, e.g., mRNA, cDNA, genomic DNA, etc), comparing the sequence or structure of the target gene to the structure of the normal gene, whereby a difference in sequence or structure indicates a mutation in the gene in the subject. Polynucleotides can also be used to test for mutations, SNPs, polymorphisms, etc., e.g., using mismatch DNA repair technology as described in U.S. Pat. No. 5,683,877; U.S. Pat. No. 5,656,430; Wu et al., *Proc. Natl. Acad. Sci.*, 89:8779–8783, 1992.

The present invention also relates to methods of detecting polymorphisms in a differentially-regulated gene, comprising, e.g., comparing the structure of: genomic DNA comprising all or part of said gene, mRNA comprising all or part of said gene, cDNA comprising all or part of said gene, or a polypeptide comprising all or part of said gene, with the structure of said gene as set forth herein. The methods can be carried out on a sample from any source, e.g., cells, tissues, body fluids, blood, urine, stool, hair, egg, sperm, etc.

These methods can be implemented in many different ways. For example, "comparing the structure" steps include, but are not limited to, comparing restriction maps, nucleotide sequences, amino acid sequences, RFLPs, DNAse sites, DNA methylation fingerprints (e.g., U.S. Pat. No. 6,214,556), protein cleavage sites, molecular weights, electrophoretic mobilities, charges, ion mobility, etc., between a standard gene and a test gene. The term "structure" can refer to any physical characteristics or configurations which can be used to distinguish between nucleic acids and polypeptides. The methods and instruments used to accomplish the comparing step depends upon the physical characteristics which are to be compared. Thus, various techniques are contemplated, including, e.g., sequencing machines (both amino acid and polynucleotide), electrophoresis, mass spectrometer (U.S. Pat. Nos. 6,093,541, 6,002,127), liquid chromatography, HPLC, etc.

To carry out such methods, "all or part" of the gene or polypeptide can be compared. For example, if nucleotide sequencing is utilized, the entire gene can be sequenced, including promoter, introns, and exons, or only parts of it can be sequenced and compared, e.g., exon 1, exon 2, etc.

Mutagenesis

Mutated polynucleotide sequences of the present invention are useful for various purposes, e.g., to create mutations of the polypeptides they encode, to identify functional regions of genomic DNA, to produce probes for screening libraries, etc. Mutagenesis can be carried out routinely according to any effective method, e.g., oligonucleotide-directed (Smith, M., *Ann. Rev. Genet.* 19:423–463, 1985), degenerate oligonucleotide-directed (Hill et al., *Method Enzymology*, 155:558–568, 1987), region-specific (Myers et al., *Science*, 229:242–246, 1985; Derbyshire et al., *Gene*, 46:145, 1986; Ner et al., DNA, 7:127, 1988), linker-scanning (McKnight and Kingsbury, *Science*, 217:316–324, 1982), directed using PCR, recursive ensemble mutagenesis (Arkin and Yourvan, *Proc. Natl. Acad. Sci.*, 89:7811–7815, 1992), random mutagenesis (e.g., U.S. Pat. Nos. 5,096,815; 5,198,346; and 5,223,409), site-directed mutagenesis (e.g., Walder et al., *Gene*, 42:133, 1986; Bauer et al., *Gene*, 37:73, 1985; Craik, *Bio Techniques*, Jan. 12–19, 1985; Smith et al., *Genetic Engineering: Principles and Methods*, Plenum Press, 1981), phage display (e.g., Lowman et al., *Biochem.* 30:10832–10837, 1991; Ladner et al., U.S. Pat. No. 5,223,409; Huse, WIPO Publication WO 92/06204), etc. Desired sequences can also be produced by the assembly of target sequences using mutually priming oligonucleotides (Uhlmann, *Gene*, 71:29–40, 1988). For directed mutagenesis methods, analysis of the three-dimensional structure of the polypeptide can be used to guide and facilitate making mutants which effect polypeptide activity. Sites of substrate-enzyme interaction or other biological activities can also be determined by analysis of crystal structure as determined by such techniques as nuclear magnetic resonance, crystallography or photoaffinity labeling. See, for example, de Vos et al., Science 255:306–312, 1992; Smith et al., J. Mol. Biol. 224:899–904, 1992; Wlodaver et al., FEBS Lett. 309:59–64, 1992.

In addition, libraries of differentially-regulated genes and fragments thereof can be used for screening and selection of gene variants. For instance, a library of coding sequences can be generated by treating a double-stranded DNA with a nuclease under conditions where the nicking occurs, e.g., only once per molecule, denaturing the double-stranded DNA, renaturing it to for double-stranded DNA that can include sense/antisense pairs from different nicked products, removing single-stranded portions from reformed duplexes by treatment with S1 nuclease, and ligating the resulting DNAs into an expression vecore. By this method, expression libraries can be made comprising "mutagenized" differentially-regulated genes. The entire coding sequence or parts thereof can be used.

Polynucleotide Expression, Polypeptides Produced thereby, and Specific-binding Partners Thereto A polynucleotide according to the present invention can be expressed in a variety of different systems, in vitro and in vivo, according to the desired purpose. For example, a polynucleotide can be inserted into an expression vector, introduced into a desired host, and cultured under conditions effective to achieve expression of a polypeptide coded for by the polynucleotide, to search for specific binding partners. Effective conditions include any culture conditions which are suitable for achieving production of the polypeptide by the host cell, including effective temperatures, pH, medium, additives to the media in which the host cell is cultured (e.g., additives which amplify or induce expression such as butyrate, or methotrexate if the coding polynucleotide is adjacent to a dhfr gene), cycloheximide, cell densities, culture dishes, etc. A polynucleotide can be introduced into the cell by any effective method including, e.g., naked DNA, calcium phosphate precipitation, electroporation, injection, DEAE-Dextran mediated transfection, fusion with liposomes, association with agents which enhance its uptake into cells, viral transfection. A cell into which a polynucleotide of the present invention has been introduced is a transformed host cell. The polynucleotide can be extrachromosomal or integrated into a chromosome(s) of the host cell. It can be stable or transient. An expression vector is selected for its compatibility with the host cell. Host cells include, mammalian cells, e.g., COS, CV1, BHK, CHO, HeLa, LTK, NIH 3T3, PC-3 (CRL-1435), LNCaP (CRL-1740), CA-HPV-10 (CRL-2220), PZ-HPV-7 (CRL-2221), MDA-PCa 2b (CRL-2422), 22Rvl (CRL2505), NCI-H660 (CRL-5813), HS 804.Sk (CRL-7535), LNCaP-FGF (CRL-10995), RWPE-1 (CRL-11609), RWPE-2 (CRL-11610), PWR-1E (CRL 11611), rat MAT-Ly-LuB-2 (CRL-2376), and other primary and established prostate and prostate cancer cell lines, insect cells, such as Sf9 (*S. frugipeda*) and *Drosophila*, bacteria, such as *E. coli, Streptococcus, bacillus*, yeast, such as *Sacharomyces, S. cerevisiae*, fungal cells, plant cells, embryonic or adult stem cells (e.g., mammalian, such as mouse or human).

Expression control sequences are similarly selected for host compatibility and a desired purpose, e.g., high copy number, high amounts, induction, amplification, controlled expression. Other sequences which can be employed include enhancers such as from SV40, CMV, RSV, inducible promoters, cell-type specific elements, or sequences which allow selective or specific cell expression. Promoters that can be used to drive its expression, include, e.g., the endogenous promoter, MMTV, SV40, trp, lac, tac, or T7 promoters for bacterial hosts; or alpha factor, alcohol oxidase, or PGH promoters for yeast. RNA promoters can be used to produced RNA transcripts, such as T7 or SP6. See, e.g., Melton et al., *Polynucleotide Res.*, 12(18):7035–7056, 1984; Dunn and Studier. *J Mol. Bio.*, 166:477–435, 1984; U.S. Pat. No. 5,891,636; Studier et al., *Gene Expression Technology, Methods in Enzymology*, 85:60–89, 1987. In addition, as discussed above, translational signals (including in-frame insertions) can be included.

When a polynucleotide is expressed as a heterologous gene in a transfected cell line, the gene is introduced into a cell as described above, under effective conditions in which the gene is expressed. The term "heterologous" means that the gene has been introduced into the cell line by the "hand-of-man." Introduction of a gene into a cell line is discussed above. The transfected (or transformed) cell expressing the gene can be lysed or the cell line can be used intact.

For expression and other purposes, a polynucleotide can contain codons found in a naturally-occurring gene, transcript, or cDNA, for example, e.g., as set forth in SEQ ID NOS 1, 3, 5, 7, 9, 11, 13, 15, 17, 19, 21, 23, 25, 27, and 29, or it can contain degenerate codons coding for the same amino acid sequences. For instance, it may be desirable to change the codons in the sequence to optimize the sequence for expression in a desired host. See, e.g., U.S. Pat. Nos. 5,567,600 and 5,567,862.

A polypeptide according to the present invention can be recovered from natural sources, transformed host cells (culture medium or cells) according to the usual methods, including, detergent extraction (e.g., non-ionic detergent, Triton X-100, CHAPS, octylglucoside, Igepal CA-630), ammonium sulfate or ethanol precipitation, acid extraction, anion or cation exchange chromatography, phosphocellulose chromatography, hydrophobic interaction chromatography, hydroxyapatite chromatography, lectin chromatography, gel electrophoresis. Protein refolding steps can be used, as necessary, in completing the configuration of the mature protein. Finally, high performance liquid chromatography (HPLC) can be employed for purification steps. Another approach is express the polypeptide recombinantly with an affinity tag (Flag epitope, HA epitope, myc epitope, 6×His, maltose binding protein, chitinase, etc) and then purify by anti-tag antibody-conjugated affinity chromatography.

The present invention also relates to antibodies, and other specific-binding partners, which are specific for polypeptides encoded by polynucleotides of the present invention. Antibodies, e.g., polyclonal, monoclonal, recombinant, chimeric, humanized, single-chain, Fab, and fragments thereof, can be prepared according to any desired method. See, also, screening recombinant immunoglobulin libraries (e.g., Orlandi et al., *Proc. Natl. Acad. Sci.*, 86:3833–3837, 1989; Huse et al., *Science*, 256:1275–1281, 1989); in vitro stimulation of lymphocyte populations; Winter and Milstein, *Nature*, 349: 293–299, 1991. The antibodies can be Ig, IgG, subtypes, IgG2a, IgG1, etc. Antibodies, and immune responses, can also be generated by administering naked DNA See, e.g., U.S. Pat. Nos. 5,703,055; 5,589,466; 5,580, 859. Antibodies can be used from any source, including, goat, rabbit, mouse, chicken (e.g., IgY; see, Duan, W0/029444 for methods of making antibodies in avian hosts, and harvesting the antibodies from the eggs). An antibody specific for a polypeptide means that the antibody recognizes a defined sequence of amino acids within or including the polypeptide. Other specific binding partners include, e.g., aptamers and PNA, can be prepared against specific epitopes or domains of differentially regulated genes.

The preparation of polyclonal antibodies is well-known to those skilled in the art. See, for example, Green et al., Production of Polyclonal Antisera, in IMMUNOCHEMICAL PROTOCOLS (Manson, ed.), pages 1–5 (Humana Press 1992); Coligan et al., Production of Polyclonal Antisera in Rabbits, Rats, Mice and Hamsters, in CURRENT PROTOCOLS IN IMMUNOLOGY, section 2.4.1 (1992). The preparation of monoclonal antibodies likewise is conventional. See, for example, Kohler & Milstein, Nature 256:495 (1975); Coligan et al., sections 2.5.1–2.6.7; and Harlow et al., ANTIBODIES: A LABORATORY MANUAL, page 726 (Cold Spring Harbor Pub. 1988).

Antibodies can also be humanized, e.g., where they are to be used therapeutically. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., Proc. Nat'l Acad. Sci. USA 86:3833 (1989), which is hereby incorporated in its entirety by reference. Techniques for producing humanized monoclonal antibodies are described, for example, in U.S. Pat. No. 6,054,297, Jones et al., Nature 321: 522 (1986); Riechmann et al., Nature 332: 323 (1988); Verhoeyen et al., Science 239: 1534 (1988); Carter et al., Proc. Nat'l Acad. Sci. USA 89: 4285 (1992); Sandhu, Crit. Rev. Biotech. 12: 437 (1992); and Singer et al., J. Immunol. 150: 2844 (1993).

Antibodies of the invention also may be derived from human antibody fragments isolated from a combinatorial immunoglobulin library. See, for example, Barbas et al., METHODS: A COMPANION TO METHODS IN ENZYMOLOGY, VOL. 2, page 119 (1991); Winter et al., Ann. Rev. Immunol. 12:433 (1994). Cloning and expression vectors that are useful for producing a human immunoglobulin phage library can be obtained commercially, for example, from STRATAGENE Cloning Systems (La Jolla, Calif.).

In addition, antibodies of the present invention may be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens and can be used to produce human antibody-secreting hybridomas. Methods for obtaining human antibodies from transgenic mice are described, e.g., in Green et al., Nature Genet. 7:13 (1994); Lonberg et al., Nature 368:856 (1994); and Taylor et al., Int. Immunol. 6:579 (1994).

Antibody fragments of the present invention can be prepared by proteolytic hydrolysis of the antibody or by expression in *E. coli* of nucleic acid encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab').sub.2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein. These patents are hereby incorporated in their entireties by reference. See also Nisoiihoff et al., Arch. Biochem. Biophys. 89:230 (1960); Porter, Biochem. J. 73:119 (1959); Edelman et al, METHODS IN ENZYMOLOGY, VOL. 1, page 422 (Academic Press 1967); and Coligan et al. at sections 2.8.1–2.8.10 and 2.10.1–2.10.4.

Other methods of cleaving antibodies, such as separation of heavy chains to form monovalent light-heavy chain fragments, further cleavage of fragments, or other enzymatic, chemical, or genetic techniques can also be used. For example, Fv fragments comprise an association of V.sub.H and V.sub.L chains. This association may be noncovalent, as described in Inbar et al., Proc. Nat'l Acad. Sci. USA 69:2659 (1972). Alternatively, the variable chains can be linked by an intermolecular disulfide bond or cross-linked by chemicals such as glutaraldehyde. See, e.g., Sandhu, supra. Preferably, the Fv fragments comprise V.sub.H and V.sub.L chains connected by a peptide linker. These single-chain antigen binding proteins (sFv) are prepared by constructing a structural gene comprising nucleic acid sequences encoding the V.sub.H and V.sub.L domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow et al., METHODS: A COMPANION TO METHODS IN ENZYMOLOGY, VOL. 2, page 97 (1991); Bird et al., Science 242:423–426 (1988); Ladneret al., U.S. Pat. No. 4,946,778; Pack et al., Bio/Technology 11:1271–77 (1993); and Sandhu, supra.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick et al., METHODS: A COMPANION TO METHODS IN ENZYMOLOGY, VOL. 2, page 106 (1991).

The term "antibody" as used herein includes intact molecules as well as fragments thereof, such as Fab, F(ab')2, and Fv which are capable of binding to an epitopic determinant present in Bin1 polypeptide. Such antibody fragments retain some ability to selectively bind with its antigen or receptor. The term "epitope" refers to an antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics. Antibodies can be prepared against specific epitopes or polypeptide domains.

Antibodies which bind to a differentially-regulated polypeptide of the present invention can be prepared using an intact polypeptide or fragments containing small peptides of interest as the immunizing antigen. For example, it may be desirable to produce antibodies that specifically bind to the N- or C-terminal domains of said polypeptide. The polypeptide or peptide used to immunize an animal which is derived from translated cDNA or chemically synthesized which can be conjugated to a carrier protein, if desired. Such commonly used carriers which are chemically coupled to the immunizing peptide include keyhole limpet hemocyanin (KLH), thyroglobulin, bovine serum albumin (BSA), and tetanus toxoid.

Polyclonal or monoclonal antibodies can be further purified, for example, by binding to and elution from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, *Current Protocols in Immunology*, Wiley Interscience, 1994, incorporated by reference).

Anti-idiotype technology can also be used to produce invention monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

Methods of Detecting Polypeptides

Polypeptides coded for by a differentially-regulated gene of the present invention can be detected, visualized, determined, quantitated, etc. according to any effective method. useful methods include, e.g., but are not limited to, immunoassays, RIA (radioimmunassay), ELISA, (enzyme-linked-immunosorbent assay), immunoflourescence, flow cytometry, histology, electron microscopy, light microscopy, in situ assays, immunoprecipitation, Western blot, etc.

Immunoassays may be carried in liquid or on biological support. For instance, a sample (e.g., blood, stool, urine, cells, tissue, body fluids, etc.) can be brought in contact with and immobilized onto a solid phase support or carrier such as nitrocellulose, or other solid support that is capable of immobilizing cells, cell particles or soluble proteins. The support may then be washed with suitable buffers followed by treatment with the detectably labeled differentially-regulated gene specific antibody. The solid phase support can then be washed with a buffer a second time to remove unbound antibody. The amount of bound label on solid support may then be detected by conventional means.

A "solid phase support or carrier" includes any support capable of binding an antigen, antibody, or other specific binding partner. Supports or carriers include glass, polystyrene, polypropylene, polyethylene, dextran, nylon, amylases, natural and modified celluloses, polyacrylamides, and magnetite. A support material can have any structural or physical configuration. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads One of the many ways in which gene peptide-specific antibody can be detectably labeled is by linking it to an enzyme and using it in an enzyme immunoassay (EIA). See, e.g., Voller, A., "The Enzyme Linked Immunosorbent Assay (ELISA)," 1978, Diagnostic Horizons 2, 1–7, Microbiological Associates Quarterly Publication, Walkersville, Md.); Voller, A. et al., 1978, J. Clin. Pathol. 31, 507–520; Butler, J. E., 1981, Meth. Enzymol. 73, 482–523; Maggio, E. (ed.), 1980, Enzyme Immunoassay, CRC Press, Boca Raton, Fla. The enzyme which is bound to the antibody will react with an appropriate substrate, preferably a chromogenic substrate, in such a manner as to produce a chemical moiety that can be detected, for example, by spectrophotometric, fluorimetric or by visual means. Enzymes that can be used to detectably label the antibody include, but are not limited to, malate dehydrogenase, staphylococcal nuclease, delta-5-steroid isomerase, yeast alcohol dehydrogenase, .alpha.-glycerophosphate, dehydrogenase, triose phosphate isomerase, horseradish peroxidase, alkaline phosphatase, asparaginase, glucose oxidase, .beta.-galactosidase, ribonuclease, urease, catalase, glucose-6-phosphate dehydrogenase, glucoamylase and acetylcholinesterase. The detection can be accomplished by calorimetric methods that employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect differentially-regulated peptides through the use of a radioimmunoassay (RIA). See, e.g., Weintraub, B., Principles of Radioimmunoassays, Seventh Training Course on Radioligand Assay Techniques, The Endocrine Society, March, 1986. The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine. The antibody can also be detectably labeled using fluorescence emitting metals such as those in the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Tissue and Disease

Tissue and Disease

The prostate is a secretory organ surrounding the neck of the bladder and urethra. Its primary function is to produce fluids and other materials necessary for sperm transport and maintenance. Structurally, it has both glandular and non-glandular components. The glandular component is predominantly comprised of ducts and acini responsible for the production and transport prostatic fluids. Epithelial cells are the main identifiable cell found in these regions, primarily of the basal and secretory types, but also endocrine-paracrine and transitional epithelial. The non-glandular component contains the capsular and muscle tissues, which, respectively, hold the organ together and function in fluid discharge. See, e.g., *Histology for Pathologists*, Sternberg, S. S., editor, Raven Press, NY, 1992, Chapter 40.

The major diseases of the prostate include, e.g., prostatic hyperplasia (BPH), prostatitis, and prostate cancer (e.g., prostatic adenocarcinoma). BPH is a benign, proliferative disease of the prostatic epithelial cells. While it may cause urinary tract obstruction in some patients, for the most part, it is generally asymptomatic. Prostate cancer, on the other hand, is the most common form of cancer in white males in the United States, occurring predominantly in males over age 50. The prevalence of prostate diseases, such as prostate cancer, has made the discovery of prostate selective markers and gene expression patterns of great importance.

The most common scale of assessing prostate pathology is the Gleason grading system. See, e.g., Bostwick, *Am. J. Clin. Path.*, 102: s38–s56, 1994. Once the cancer is identified, staging can assess the size, location, and extent of the cancer. Several different staging scales are commonly used, including stages A–D, and Tumor-Nodes-Metastases (TNM). For treatment, diagnosis, staging, etc., of prostate conditions, methods can be carried out analogously to, and in combination with, U.S. Pat. Nos. 6,107,090; 6,057,116; 6,034,218; 6,004,267; 5,919,638; 5,882,864; 5,763,202; 5,747,264; 5,688,649; 5,552,277.

In addition, the present invention relates to methods of assessing a therapeutic or preventative intervention in a subject having a prostate cancer, comprising, e.g., detecting the expression levels of differentially-regulated target genes, wherein the target genes comprise a gene which is represented by a sequence selected from Tables 1 and 2, or, a gene represented by a sequence having 95% sequence identity or more to a sequence selected from Tables 1 and 2. By "therapeutic or preventative intervention," it is meant, e.g., a drug administered a patient, surgery, radiation, chemotherapy, and other measures taken to prevent a cancer or treat a cancer.

Grading, Staging, Comparing, Assessing, Methods and Compositions

The present invention also relates to methods and compositions for staging and grading cancers. As already defined, staging relates to determining the extent of a cancer's spread, including its size and the degree to which other tissues, such as lymph nodes are involved in the cancer. Grading refers to the degree of a cell's retention of the characteristics of the tissue of its origin. A lower grade cancer comprises tumor cells that more closely resemble normal cells than a medium or higher grade cancer. Grading can be a useful diagnostic and prognostic tool. Higher grade cancers usually behave more aggressively than lower grade cancers. Thus, knowledge of the cancer grade, as well as its stage, can be a significant factor in the choice of the appropriate therapeutic intervention for the particular patient, e.g., surgery, radiation, chemotherapy, etc. Staging and grading can also be used in conjunction with a therapy to assess its efficacy, to determine prognosis, to determine effective dosages, etc.

Various methods of staging and grading cancers can be employed in accordance with the present invention. A "cell expression profile" or "cell expression fingerprint" is a representation of the expression of various different genes in a given cell or sample comprising cells. These cell expression profiles can be useful as reference standards. The cell expression fingerprints can be used alone for grading, or in combination with other grading methods.

The present invention also relates to methods and compositions for diagnosing a prostate cancer, or determining susceptibility to a prostate cancer, using polynucleotides, polypeptides, and specific-binding partners of the present invention to detect, assess, determine, etc., differentially-regulated genes of the present invention. In such methods, the gene can serve as a marker for prostate cancer, e.g., where the gene, when mutant, is a direct cause of the prostate cancer; where the gene is affected by another gene(s) which is directly responsible for the prostate cancer, e.g., when the gene is part of the same signaling pathway as the directly responsible gene; and, where the gene is chromosomally linked to the gene(s) directly responsible for the prostate cancer, and segregates with it. Many other situations are possible. To detect, assess, determine, etc., a probe specific for the gene can be employed as described above and below. Any method of detecting and/or assessing the gene can be used, including detecting expression of the gene using polynucleotides, antibodies, or other specific-binding partners.

The present invention relates to methods of diagnosing a disorder associated with prostate cancer, or determining a subject's susceptibility to such prostate cancer, comprising, e.g., assessing the expression of a differentially-regulated gene in a tissue sample comprising tissue or cells suspected of having a prostate cancer (e.g., where the sample comprises prostate). The phrase "diagnosing" indicates that it is determined whether the sample has prostate cancer. "Determining a subject's susceptibility to a prostate cancer" indicates that the subject is assessed for whether s/he is predisposed to get such a disease or disorder, where the predisposition is indicated by abnormal expression of the gene (e.g., gene mutation, gene expression pattern is not normal, etc.). Predisposition or susceptibility to a disease may result when a such disease is influenced by epigenetic, environmental, etc., factors. This includes prenatal screening where samples from the fetus or embryo (e.g., via amniocentesis or CV sampling) are analyzed for the expression of the genes.

By the phrase "assessing expression of a differentially-regulated gene," it is meant that the functional status of the gene is evaluated. This includes, but is not limited to, measuring expression levels of said gene, determining the genomic structure of said gene, determining the mRNA structure of transcripts from said gene, or measuring the expression levels of polypeptide coded for by said gene. Thus, the term "assessing expression" includes evaluating the all aspects of the transcriptional and translational machinery of the gene. For instance, if a promoter defect causes, or is suspected of causing, the disorder, then a sample can be evaluated (i.e., "assessed") by looking (e.g., sequencing or restriction mapping) at the promoter sequence in the gene, by detecting transcription products (e.g., RNA), by detecting translation product (e.g., polypeptide). Any measure of whether the gene is functional can be used, including, polypeptide, polynucleotide, and functional assays for the gene's biological activity.

In making the assessment, it can be useful to compare the results to a normal gene, e.g., a gene which is not associated with the disorder. The nature of the comparison can be determined routinely, depending upon how the assessing is accomplished. If, for example, the mRNA levels of a sample is detected, then the mRNA levels of a normal can serve as a comparison, or a gene which is known not to be affected by the disorder. Methods of detecting mRNA are well known, and discussed above, e.g., but not limited to, Northern blot analysis, polymerase chain reaction (PCR), reverse transcriptase PCR, RACE PCR, etc. Similarly, if polypeptide production is used to evaluate the gene, then the polypeptide in a normal tissue sample can be used as a comparison, or, polypeptide from a different gene whose expression is known not to be affected by the disorder. These are only examples of how such a method could be carried out.

Assessing the effects of therapeutic and preventative interventions (e.g., administration of a drug, chemotherapy, radiation, etc.) on prostate cancer is a major effort in drug discovery, clinical medicine, and pharmacogenomics. The evaluation of therapeutic and preventative measures, whether experimental or already in clinical use, has broad applicability, e.g., in clinical trials, for monitoring the status of a patient, for analyzing and assessing animal models, and in any scenario involving cancer treatment and prevention. Analyzing the expression profiles of polynucleotides of the present invention can be utilized as a parameter by which interventions are judged and measured. Treatment of a disorder can change the expression profile in some manner which is prognostic or indicative of the drug's effect on it. Changes in the profile can indicate, e.g., drug toxicity, return to a normal level, etc. Accordingly, the present invention also relates to methods of monitoring or assessing a therapeutic or preventative measure (e.g., chemotherapy, radiation, anti-neoplastic drugs, antibodies, etc.) in a subject having prostate cancer, or, susceptible to such a disorder, comprising, e.g., detecting the expression levels of one or more differentially-regulated genes of the present invention. A subject can be a cell-based assay system, non-human animal model, human patient, etc. Detecting can be accomplished as described for the methods above and below. By "therapeutic or preventative intervention," it is meant, e.g., a drug administered to a patient, surgery, radiation, chemotherapy, and other measures taken to prevent, treat, or diagnose prostate cancer.

Expression can be assessed in any sample comprising any tissue or cell type, body fluid, etc., as discussed for other methods of the present invention, including cells from prostate can be used, or cells derived from prostate. By the phrase "cells derived from prostate," it is meant that the derived cells originate from prostate, e.g., when metastasis from a primary tumor site has occurred, when a progenitor-type or pluripotent cell gives rise to other cells, etc.

The present invention also relates to methods of using binding partners for differentially-regulated genes, such as antibodies, to deliver active agents to the prostate for a variety of different purposes, including, e.g., for diagnostic, therapeutic (e.g., to treat cancer), and research purposes. Methods can involve delivering or administering an active agent to the prostate, comprising, e.g., administering to a subject in need thereof, an effective amount of an active agent coupled to a binding partner specific for a idfferentially-regulated gene polypeptide, wherein said binding partner is effective to deliver said active agent specifically to prostate.

Any type of active agent can be used in combination with the binding partner, including, therapeutic, cytotoxic, cytostatic, chemotherapeutic, anti-neoplastic, anti-proliferative, anti-biotic, etc., agents. A chemotherapeutic agent can be, e.g., DNA-interactive agent, alkylating agent, antimetabolite, tubulin-interactive agent, hormonal agent, hydroxyurea, Cisplatin, Cyclophosphamide, Altretamine, Bleomycin, Dactinomycin, Doxorubicin, Etoposide, Teniposide, paclitaxel, cytoxan, 2-methoxycarbonylaminobenzimidazole, Plicamycin, Methotrexate, Fluorouracil, Fluorodeoxyuridin, CB3717, Azacitidine, Floxuridine, Mercapyopurine, 6-Thioguanine, Pentostatin, Cytarabine, Fludarabine, etc. Agents can also be contrast agents useful in imaging technology, e.g., X-ray, CT, CAT, MRI, ultrasound, PET, SPECT, and scintographic.

An active agent can be associated in any manner with a binding partner which is effective to achieve its delivery specifically to the target. Specific delivery or targeting indicates that the agent is provided to the prostate, without being substantially provided to other tissues. This is useful especially where an agent is toxic, and specific targeting to the prostate enables the majority of the toxicity to be aimed at the prostate, with as small as possible effect on other tissues in the body. The association of the active agent and the binding partner ("coupling) can be direct, e.g., through chemical bonds between the binding partner and the agent, or, via a linking agent, or the association can be less direct, e.g., where the active agent is in a liposome, or other carrier, and the binding partner is associated with the liposome surface. In such case, the binding partner can be oriented in such a way that it is able to bind to the gene product on prostate cell surface. Methods for delivery of DNA via a cell-surface receptor is described, e.g., in U.S. Pat. No. 6,339,139.

Identifying Agent Methods

The present invention also relates to methods of identifying agents, and the agents themselves, which modulate differentially regulated genes and gene products of the present invention. These agents can be used to modulate the biological activity of the polypeptide encoded for the gene, or the gene, itself. Agents which regulate the gene or its product are useful in variety of different environments, including as medicinal agents to treat or prevent disorders associated with differentially regulated genes and as research reagents to modify the function of tissues and cell.

Methods of identifying agents generally comprise steps in which an agent is placed in contact with the gene, transcription product, translation product, or other target, and then a determination is performed to assess whether the agent "modulates" the target. The specific method utilized will depend upon a number of factors, including, e.g., the target (i.e., is it the gene or polypeptide encoded by it), the environment (e.g., in vitro or in vivo), the composition of the agent, etc.

For modulating the expression of differentially-regulated genes of the present invention, a method can comprise, in any effective order, one or more of the following steps, e.g., contacting a differentially-regulated gene (e.g., in a cell population) with a test agent under conditions effective for said test agent to modulate the expression of said gene, and determining whether said test agent modulates said gene. An agent can modulate expression of a differentially-regulated gene at any level, including transcription, translation, and/or perdurance of the nucleic acid (e.g., degradation, stability, etc.) in the cell. For modulating the biological activity of polypeptides coded for by differentially-regulated genes, a method can comprise, in any effective order, one or more of the following steps, e.g., contacting a polypeptide (e.g., in a cell, lysate, or isolated) with a test agent under conditions effective for said test agent to modulate the biological activity of said polypeptide, and determining whether said test agent modulates said biological activity.

Contacting a differentially-regulated gene or polypeptide with the test agent can be accomplished by any suitable method and/or means that places the agent in a position to functionally control expression or biological activity of said gene or polypeptide present in the sample. Functional control indicates that the agent can exert its physiological effect on the gene or polypeptide through whatever mechanism it works. The choice of the method and/or means can depend upon the nature of the agent and the condition and type of environment in which the gene or polypeptide is presented, e.g., lysate, isolated, or in a cell population (such as, in vivo, in vitro, organ explants, etc.). For instance, if the cell population is an in vitro cell culture, the agent can be contacted with the cells by adding it directly into the culture medium. If the agent cannot dissolve readily in an aqueous medium, it can be incorporated into liposomes, or another lipophilic carrier, and then administered to the cell culture. Contact can also be facilitated by incorporation of agent with carriers and delivery molecules and complexes, by injection, by infusion, etc.

After the agent has been administered in such a way that it can gain access to the gene or polypeptide, it can be determined whether the test agent modulates their expression or biological activity. Modulation can be of any type, quality, or quantity, e.g., increase, facilitate, enhance, up-regulate, stimulate, activate, amplify, augment, induce, decrease, down-regulate, diminish, lessen, reduce, etc. The modulatory quantity can also encompass any value, e.g., 1%, 5%, 10%, 50%, 75%, 1-fold, 2-fold, 5-fold, 10-fold, 100-fold, etc. To modulate gene expression means, e.g., that the test agent has an effect on its expression, e.g., to effect the amount of transcription, to effect RNA splicing, to effect translation of the RNA into polypeptide, to effect RNA or polypeptide stability, to effect polyadenylation or other processing of the RNA, to effect post-transcriptional or post-translational processing, etc. To modulate biological activity means, e.g., that a functional activity of the polypeptide is changed in comparison to its normal activity in the absence of the agent. This effect includes, increase, decrease, block, inhibit, enhance, etc.

A test agent can be of any molecular composition, e.g., chemical compounds, biomolecules, such as polypeptides, lipids, nucleic acids (e.g., antisense to a polynucleotide sequence selected from SEQ ID NOS 1, 3, 5, 7, 9, 11, 13, 15, 17, 19, 21, 23, 25, 27, and 29), carbohydrates, antibodies, ribozymes, double-stranded RNA, aptamers, etc. For example, if a polypeptide to be modulated is a cell-surface molecule, a test agent can be an antibody that specifically recognizes it and, e.g., causes the polypeptide to be internalized, leading to its down regulation on the surface of the cell. Such an effect does not have to be permanent, but can require the presence of the antibody to continue the down-regulatory effect. Antibodies can also be used to modulate the biological activity a polypeptide in a lysate or other cell-free form. Antisense can also be used as test agents to modulate gene expression.

Markers

The polynucleotides of the present invention can be used with other markers, especially prostate and prostate cancer markers to identity, detect, stage, diagnosis, determine, prognosticate, treat, etc., tissue, diseases and conditions, etc, of the prostate. Markers can be polynucleotides, polypeptides, antibodies, ligands, specific binding partners, etc.

A number of genes and gene products have been identified which are associated with prostate cancer metastasis and/or progression, e.g., PSA, KAI1 (shows decreased expression in metastatic cells; Dong et al., *Science*, 268:884–6, 1995), D44 isoforms (differentially-regulated during carcinoma progression; Noordzij et al., *Clin. Cancer Res.*, 3:805–15, 1997), p53 (Effert et al., *J Urol.*, 150:257–61, 1993), Rb, CDKN2, E-cadherin, PTEN (Hamilton et al., *Br. J. Cancer*, 82:1671–6, 2000; Dong et al., *Clin. Cancer Res.*, 7:304–308, 2001), bcl-2, prostatic acid phosphatase (PAP), prostate specific membrane antigen (e.g., U.S. Pat. Nos. 5,538,866 and 6,107,090), Smad3 (e.g., Kang et al., *Proc. Natl. Acad. Sci.*, 98:3018–3023, 2001), TGF-beta, and other oncogenes and tumor suppressor genes. See, also, Myers and Grizzle, *Eur. Urol.*, 30:153–166, 1996, for other biomarkers associated with prostatic carcinoma, such as PCNA, p185-erbB-2, p180erbB-3, TAG-72, nm23-H1 and FASE. Such markers can be used in combination with the methods of the present invention to facilitate identifying, grading, staging, prognostication, etc, of conditions and diseases of the prostate.

Therapeutics

Selective polynucleotides, polypeptides, and specific-binding partners thereto, can be utilized in therapeutic applications, especially to treat prostate cancer. Useful methods include, but are not limited to, immunotherapy (e.g., using specific-binding partners to polypeptides), vaccination (e.g., using a selective polypeptide or a naked DNA encoding such polypeptide), protein or polypeptide replacement therapy, gene therapy (e.g., germ-line correction, antisense), etc.

Various immunotherapeutic approaches can be used. For instance, unlabeled antibody that specifically recognizes a tissue-specific antigen can be used to stimulate the body to destroy or attack the cancer, to cause down-regulation, to produce complement-mediated lysis, to inhibit cell growth, etc., of target cells which display the antigen, e.g., analogously to how c-erbB-2 antibodies are used to treat breast cancer. In addition, antibody can be labeled or conjugated to enhance its deleterious effect, e.g., with radionuclides and other energy emitting entitities, toxins, such as ricin, exotoxin A (ETA), and diphtheria, cytotoxic or cytostatic agents, immunomodulators, chemotherapeutic agents, etc. See, e.g., U.S. Pat. No. 6,107,090.

An antibody or other specific-binding partner can be conjugated to a second molecule, such as a cytotoxic agent, and used for targeting the second molecule to a tissue-antigen positive cell (Vitetta, E. S. et al., 1993, Immunotoxin therapy, in DeVita, Jr., V. T. et al., eds, Cancer: Principles and Practice of Oncology, 4th ed., J. B. Lippincott Co., Philadelphia, 2624–2636). Examples of cytotoxic agents include, but are not limited to, antimetabolites, alkylating agents, anthracyclines, antibiotics, anti-mitotic agents, radioisotopes and chemotherapeutic agents. Further examples of cytotoxic agents include, but are not limited to ricin, doxorubicin, daunorubicin, taxol, ethidium bromide, mitomycin, etoposide, tenoposide, vincristine, vinblastine, colchicine, dihydroxy anthracin dione, actinomycin D, 1-dehydrotestosterone, diptheria toxin, Pseudomonas exotoxin (PE) A, PE40, abrin, elongation factor-2 and glucocorticoid. Techniques for conjugating therapeutic agents to antibodies are well.

In addition to immunotherapy, polynucleotides and polypeptides can be used as targets for non-immunotherapeutic applications, e.g., using compounds which interfere with function, expression (e.g., antisense as a therapeutic agent), assembly, etc. RNA interference can be used in vivtro and in vivo to silence differentially-expressed genes when its expression contributes to a disease (but also for other purposes, e.g., to identify the gene's function to change a developmental pathway of a cell, etc.). See, e.g., Sharp and Zamore, *Science*, 287:2431–2433, 2001; Grishok et al., *Science*, 287:2494, 2001.

Delivery of therapeutic agents can be achieved according to any effective method, including, liposomes, viruses, plasmid vectors, bacterial delivery systems, orally, systemically, etc. Therapeutic agents of the present invention can be administered in any form by any effective route, including, e.g., oral, parenteral, enteral, intraperitoneal, topical, transdermal (e.g., using any standard patch), ophthalmic, nasally, local, non-oral, such as aerosal, inhalation, subcutaneous, intramuscular, buccal, sublingual, rectal, vaginal, intraarterial, and intrathecal, etc. They can be administered alone, or in combination with any ingredient(s), active or inactive.

In addition to therapeutics, per se, the present invention also relates to methods of treating prostate cancer showing altered expression of differentially-regulated genes, such as SEQ ID NOS 1–30, comprising, e.g., administering to a subject in need thereof a therapeutic agent which is effective for regulating expression of said genes and/or which is effective in treating said disease. The term "treating" is used conventionally, e.g., the management or care of a subject for the purpose of combating, alleviating, reducing, relieving, improving the condition of, etc., of a disease or disorder. By the phrase "altered expression," it is meant that the disease is associated with a mutation in the gene, or any modification to the gene (or corresponding product) which affects its normal function. Thus, expression of a differentially-regulated gene refers to, e.g., transcription, translation, splicing, stability of the mRNA or protein product, activity of the gene product, differential expression, etc.

Any agent which "treats" the disease can be used. Such an agent can be one which regulates the expression of the gene. Expression refers to the same acts already mentioned, e.g. transcription, translation, splicing, stability of the mRNA or protein product, activity of the gene product, differential expression, etc. For instance, if the condition was a result of a complete deficiency of the gene product, administration of gene product to a patient would be said to treat the disease and regulate the gene's expression. Many other possible situations are possible, e.g., where the gene is aberrantly expressed, and the therapeutic agent regulates the aberrant expression by restoring its normal expression pattern.

Antisense

Antisense polynucleotide (e.g., RNA) can also be prepared from a polynucleotide according to the present invention, preferably an anti-sense to a sequence of SEQ ID NOS 1, 3, 5, 7, 9, 11, 13, 15, 17, 19, 21, 23, 25, 27, and 29. Antisense polynucleotide can be used in various ways, such as to regulate or modulate expression of the polypeptides they encode, e.g., inhibit their expression, for in situ hybridization, for therapeutic purposes, for making targeted mutations (in vivo, triplex, etc.) etc. For guidance on administering and designing anti-sense, see, e.g., U.S. Pat. Nos. 6,200,960, 6,200,807, 6,197,584, 6,190,869, 6,190,661, 6,187,587, 6,168,950, 6,153,595, 6,150,162, 6,133,246, 6,117,847, 6,096,722, 6,087,343, 6,040,296, 6,005,095, 5,998,383, 5,994,230, 5,891,725, 5,885,970, and 5,840,708. An antisense polynucleotides can be operably linked to an expression control sequence. A total length of about 35 bp can be used in cell culture with cationic liposomes to facilitate cellular uptake, but for in vivo use, preferably shorter oligonucleotides are administered, e.g. 25 nucleotides.

Antisense polynucleotides can comprise modified, nonnaturally-occurring nucleotides and linkages between the nucleotides (e.g., modification of the phosphate-sugar backbone; methyl phosphonate, phosphorothioate, or phosphorodithioate linkages; and 2'-O-methyl ribose sugar units), e.g., to enhance in vivo or in vitro stability, to confer nuclease resistance, to modulate uptake, to modulate cellular distribution and compartmentalization, etc. Any effective nucleotide or modification can be used, including those already mentioned, as known in the art, etc., e.g., disclosed in U.S. Pat. Nos. 6,133,438; 6,127,533; 6,124,445; 6,121,437; 5,218,103 (e.g., nucleoside thiophosphoramidites); 4,973,679; Sproat et al., "2'-O-Methyloligoribonucleotides: synthesis and applications," Oligonucleotides and Analogs A Practical Approach, Eckstein (ed.), IRL Press, Oxford, 1991, 49–86; Iribarren et al., "2'O-Alkyl Oligoribonucleotides as Antisense Probes," Proc. Natl. Acad. Sci. USA, 1990, 87, 7747–775 1; Cotton et al., "2'-O-methyl, 2'-O-ethyl oligoribonucleotides and phosphorothioate oligodeoxyribonucleotides as inhibitors of the in vitro U7 snRNP-dependent mRNA processing event," Nucl. Acids Res., 1991, 19, 2629–2635.

Arrays

The present invention also relates to an ordered array of polynucleotide probes and specific-binding partners (e.g., antibodies) for detecting the expression of differentially-regulated genes in a sample, comprising, one or more polynucleotide probes or specific binding partners associated with a solid support, wherein each probe is specific for said genes, and the probes comprise a nucleotide sequence of SEQ ID NOS 1, 3, 5, 7, 9, 11, 13, 15, 17, 19, 21, 23, 25, 27, and 29 which is specific for said gene, a nucleotide sequence having sequence identity to SEQ ID NOS 1, 3, 5, 7, 9, 11, 13, 15, 17, 19, 21, 23, 25, 27, and 29 which is specific for said gene or polynucleotide, or complements thereto, or a specific-binding partner which is specific for said genes.

The phrase "ordered array" indicates that the probes are arranged in an identifiable or position-addressable pattern, e.g., such as the arrays disclosed in U.S. Pat. Nos. 6,156,501, 6,077,673, 6,054,270, 5,723,320, 5,700,637, WO09919711, WO00023803. The probes are associated with the solid support in any effective way. For instance, the probes can be bound to the solid support, either by polymerizing the probes on the substrate, or by attaching a probe to the substrate. Association can be, covalent, electrostatic, noncovalent, hydrophobic, hydrophilic, noncovalent, coordination, adsorbed, absorbed, polar, etc. When fibers or hollow filaments are utilized for the array, the probes can fill the hollow orifice, be absorbed into the solid filament, be attached to the surface of the orifice, etc. Probes can be of any effective size, sequence identity, composition, etc., as already discussed.

Ordered arrays can further comprise polynucleotide probes or specific-binding partners which are specific for other genes, including genes specific for prostate or disorders associated with prostate.

Transgenic Animals

The present invention also relates to transgenic animals comprising differentially-regulated genes of the present invention. Such genes, as discussed in more detail below, include, but are not limited to, functionally-disrupted genes, mutated genes, ectopically or selectively-expressed genes, inducible or regulatable genes, etc. These transgenic animals can be produced according to any suitable technique or method, including homologous recombination, mutagenesis (e.g., ENU, Rathkolb et al., *Exp. Physiol.*, 85(6):635–644, 2000), and the tetracycline-regulated gene expression system (e.g., U.S. Pat. No. 6,242,667). The term "gene" as used herein includes any part of a gene, i.e., regulatory sequences, promoters, enhancers, exons, introns, coding sequences, etc. The nucleic acid present in the construct or transgene can be naturally-occurring wild-type, polymorphic, or mutated. When a mouse or other mammal is used, the appropriate homolog can be used in place of a human gene of the present invention.

Along these lines, polynucleotides of the present invention can be used to create transgenic animals, e.g. a non-human animal, comprising at least one cell whose genome comprises a functional disruption of a differentially-regulated gene. By the phrases "functional disruption" or "functionally disrupted," it is meant that the gene does not express a biologically-active product. It can be substantially deficient in at least one functional activity coded for by the gene. Expression of a polypeptide can be substantially absent, i.e., essentially undetectable amounts are made. However, polypeptide can also be made, but which is deficient in activity, e.g., where only an amino-terminal portion of the gene product is produced.

The transgenic animal can comprise one or more cells. When substantially all its cells contain the engineered gene, it can be referred to as a transgenic animal "whose genome comprises" the engineered gene. This indicates that the endogenous gene loci of the animal has been modified and substantially all cells contain such modification.

Functional disruption of the gene can be accomplished in any effective way, including, e.g., introduction of a stop codon into any part of the coding sequence such that the resulting polypeptide is biologically inactive (e.g., because it lacks a catalytic domain, a ligand binding domain, etc.), introduction of a mutation into a promoter or other regulatory sequence that is effective to turn it off, or reduce transcription of the gene, insertion of an exogenous sequence into the gene which inactivates it (e.g., which disrupts the production of a biologically-active polypeptide or which disrupts the promoter or other transcriptional machinery), deletion of sequences from the a differentially-regulated gene, etc. Examples of transgenic animals having functionally disrupted genes are well known, e.g., as described in U.S. Pat. Nos. 6,239,326, 6,225,525, 6,207,878, 6,194,633, 6,187,992, 6,180,849, 6,177,610, 6,100,445, 6,087,555, 6,080,910, 6,069,297, 6,060,642, 6,028,244, 6,013,858, 5,981,830, 5,866,760, 5,859,314, 5,850,004, 5,817,912, 5,789,654, 5,777,195, and 5,569,824. A transgenic animal which comprises the functional disruption can also be referred to as a "knock-out" animal, since the biological activity of its a differentially-regulated gene has been "knocked-out." Knock-outs can be homozygous or heterozygous.

For creating functional disrupted genes, and other gene mutations, homologous recombination technology is of special interest since it allows specific regions of the genome to be targeted. Using homologous recombination methods, genes can be specifically-inactivated, specific mutations can be introduced, and exogenous sequences can be introduced at specific sites. These methods are well known in the art, e.g., as described in the patents above. See, also, Robertson, *Biol. Reproduc.*, 44(2):238–245, 1991. Generally, the genetic engineering is performed in an embryonic stem (ES) cell, or other pluripotent cell line (e.g., adult stem cells, EG cells), and that genetically-modified cell (or nucleus) is used to create a whole organism. Nuclear transfer can be used in combination with homologous recombination technologies.

For example, a differentially-regulated gene locus can be disrupted in mouse ES cells using a positive-negative selection method (e.g., Mansour et al., *Nature*, 336:348–352, 1988). In this method, a targeting vector can be constructed which comprises a part of the gene to be targeted. A selectable marker, such as neomycin resistance genes, can be inserted into a a differentially-regulated gene exon present in the targeting vector, disrupting it. When the vector recombines with the ES cell genome, it disrupts the function of the gene. The presence in the cell of the vector can be determined by expression of neomycin resistance. See, e.g., U.S. Pat. No. 6,239,326. Cells having at least one functionally disrupted gene can be used to make chimeric and germline animals, e.g., animals having somatic and/or germ cells comprising the engineered gene. Homozygous knock-out animals can be obtained from breeding heterozygous knock-out animals. See, e.g., U.S. Pat. No. 6,225,525.

A transgenic animal, or animal cell, lacking one or more functional differentially-regulated genes can be useful in a variety of applications, including, as an animal model for cancer, for drug screening assays, as a source of tissues deficient in said gene activity, and any of the utilities mentioned in any issued U.S. Patent on transgenic animals, including, U.S. Pat. Nos. 6,239,326, 6,225,525, 6,207,878, 6,194,633, 6,187,992, 6,180,849, 6,177,610, 6,100,445, 6,087,555, 6,080,910, 6,069,297, 6,060,642, 6,028,244, 6,013,858, 5,981,830, 5,866,760, 5,859,314, 5,850,004, 5,817,912, 5,789,654, 5,777,195, and 5,569,824.

The present invention also relates to non-human, transgenic animal whose genome comprises recombinant a differentially-regulated gene nucleic acid operatively linked to an expression control sequence effective to express said coding sequence, e.g., in prostate. such a transgenic animal can also be referred to as a "knock-in" animal since an exogenous gene has been introduced, stably, into its genome.

A recombinant a differentially-regulated gene nucleic acid refers to a gene which has been introduced into a target host cell and optionally modified, such as cells derived from animals, plants, bacteria, yeast, etc. A recombinant a differentially-regulated gene includes completely synthetic nucleic acid sequences, semi-synthetic nucleic acid sequences, sequences derived from natural sources, and chimeras thereof. "Operable linkage" has the meaning used through the specification, i.e., placed in a functional relationship with another nucleic acid. When a gene is operably linked to an expression control sequence, as explained above, it indicates that the gene (e.g., coding sequence) is joined to the expression control sequence (e.g., promoter) in such a way that facilitates transcription and translation of the coding sequence. As described above, the phrase "genome" indicates that the genome of the cell has been modified. In this case, the recombinant a differentially-regulated gene has been stably integrated into the genome of the animal. The a differentially-regulated gene nucleic acid in operable linkage with the expression control sequence can also be referred to as a construct or transgene.

Any expression control sequence can be used depending on the purpose. For instance, if selective expression is desired, then expression control sequences which limit its expression can be selected. These include, e.g., tissue or cell-specific promoters, introns, enhancers, etc. For various methods of cell and tissue-specific expression, see, e.g., U.S. Pat. Nos. 6,215,040, 6,210,736, and 6,153,427. These also include the endogenous promoter, i.e., the coding sequence can be operably linked to its own promoter. Inducible and regulatable promoters can also be utilized.

The present invention also relates to a transgenic animal which contains a functionally disrupted and a transgene stably integrated into the animals genome. Such an animal can be constructed using combinations any of the above- and below-mentioned methods. Such animals have any of the aforementioned uses, including permitting the knock-out of the normal gene and its replacement with a mutated gene. Such a transgene can be integrated at the endogenous gene locus so that the functional disruption and "knock-in" are carried out in the same step.

In addition to the methods mentioned above, transgenic animals can be prepared according to known methods, including, e.g., by pronuclear injection of recombinant genes into pronuclei of 1-cell embryos, incorporating an artificial yeast chromosome into embryonic stem cells, gene targeting methods, embryonic stem cell methodology, cloning methods, nuclear transfer methods. See, also, e.g., U.S. Pat. Nos. 4,736,866; 4,873,191; 4,873,316; 5,082,779; 5,304,489; 5,174,986; 5,175,384; 5,175,385; 5,221,778; Gordon et al., Proc. Natl. Acad. Sci., 77:7380–7384, 1980; Palmiter et al., Cell, 41:343–345, 1985; Palmiter et al., Ann. Rev. Genet., 20:465–499, 1986; Askew et al., Mol. Cell. Bio., 13:4115–4124, 1993; Games et al. Nature, 373:523–527, 1995; Valancius and Smithies, Mol. Cell. Bio., 11:1402–1408, 1991; Stacey et al., Mol. Cell. Bio., 14:1009–1016, 1994; Hasty et al., Nature, 350:243–246, 1995; Rubinstein et al., Nucl. Acid Res., 21:2613–2617, 1993; Cibelli et al., Science, 280:1256–1258, 1998. For guidance on recombinase excision systems, see, e.g., U.S. Pat. Nos. 5,626,159, 5,527,695, and 5,434,066. See also, Orban, P. C., et al., "Tissue- and Site-Specific DNA Recombination in Transgenic Mice," Proc. Natl. Acad. Sci. USA, 89:6861–6865 (1992); O'Gorman, S., et al., "Recombinase-Mediated Gene Activation and Site-Specific Integration in Mammalian Cells," Science, 251:1351–1355 (1991); Sauer, B., et al., "Cre-stimulated recombination at loxP-Containing DNA sequences placed into the mammalian genome," Polynucleotides Research, 17(1):147–161 (1989); Gagneten, S. et al. (1997) Nucl. Acids Res. 25:3326–3331; Xiao and Weaver (1997) Nucl. Acids Res. 25:2985–2991; Agah, R. et al. (1997) J. Clin. Invest. 100:169–179; Barlow, C. et. al. (1997) Nucl. Acids Res. 25:2543–2545; Araki, K. et al. (1997) Nucl. Acids Res. 25:868–872; Mortensen, R. N. et al. (1992) Mol. Cell. Biol. 12:2391–2395 (G418 escalation method); Lakhlani, P. P. et al. (1997) Proc. Natl. Acad. Sci. USA 94:9950–9955 ("hit and run"); Westphal and Leder (1997) Curr. Biol. 7:530–533 (transposon-generated "knock-out" and "knock-in"); Templeton, N. S. et al. (1997) Gene Ther. 4:700–709 (methods for efficient gene targeting, allowing for a high frequency of homologous recombination events, e.g., without selectable markers); PCT International Publication WO 93/22443 (functionally-disrupted).

A polynucleotide according to the present invention can be introduced into any non-human animal, including a non-human mammal, mouse (Hogan et al., *Manipulating the Mouse Embryo: A Laboratory Manual, Cold Spring Harbor Laboratory*, Cold Spring Harbor, New York, 1986), pig (Hammer et al., Nature, 315:343–345, 1985), sheep (Hammer et al., Nature, 315:343–345, 1985), cattle, rat, or primate. See also, e.g., Church, 1987, Trends in Biotech. 5:13–19; Clark et al., Trends in Biotech. 5:20–24, 1987); and DePamphilis et al., BioTechniques, 6:662–680, 1988. Transgenic animals can be produced by the methods described in U.S. Pat. No. 5,994,618, and utilized for any of the utilities described therein.

Database

The present invention also relates to electronic forms of polynucleotides, polypeptides, etc., of the present invention, including computer-readable medium (e.g., magnetic, optical, etc., stored in any suitable format, such as flat files or hierarchical files) which comprise such sequences, or fragments thereof, e-commerce-related means, etc. Along these lines, the present invention relates to methods of retrieving gene sequences from a computer-readable medium, comprising, one or more of the following steps in any effective order, e.g., selecting a cell or gene expression profile, e.g., a profile that specifies that said gene is differentially expressed in prostate cancer, and retrieving said differentially expressed gene sequences, where the gene sequences consist of the genes represented by SEQ ID NOS 1–30.

A "gene expression profile" means the list of tissues, cells, etc., in which a defined gene is expressed (i.e, transcribed and/or translated). A "cell expression profile" means the genes which are expressed in the particular cell type. The profile can be a list of the tissues in which the gene is expressed, but can include additional information as well, including level of expression (e.g., a quantity as compared or normalized to a control gene), and information on temporal (e.g., at what point in the cell-cycle or developmental program) and spatial expression. By the phrase "selecting a gene or cell expression profile," it is meant that a user decides what type of gene or cell expression pattern he is interested in retrieving, e.g., he may require that the gene is differentially expressed in a tissue, or he may require that the gene is not expressed in blood, but must be expressed in prostate cancer. Any pattern of expression preferences may be selected. The selecting can be performed by any effective method. In general, "selecting" refers to the process in which a user forms a query that is used to search a database of gene expression profiles. The step of retrieving involves searching for results in a database that correspond to the query set forth in the selecting step. Any suitable algorithm can be utilized to perform the search query, including algorithms that look for matches, or that perform optimization between query and data. The database is information that has been stored in an appropriate storage medium, having a suitable computer-readable format. Once results are retrieved, they can be displayed in any suitable format, such as HTML.

For instance, the user may be interested in identifying genes that are differentially expressed in a prostate cancer. He may not care whether small amounts of expression occur in other tissues, as long as such genes are not expressed in peripheral blood lymphocytes. A query is formed by the user to retrieve the set of genes from the database having the desired gene or cell expression profile. Once the query is inputted into the system, a search algorithm is used to interrogate the database, and retrieve results.

Advertising, Licensing, etc., Methods

The present invention also relates to methods of advertising, licensing, selling, purchasing, brokering, etc., genes, polynucleotides, specific-binding partners, antibodies, etc., of the present invention. Methods can comprises, e.g., displaying a differentially-regulated gene , a differentially-regulated gene polypeptide, or antibody specific for a differentially-regulated gene in a printed or computer-readable medium (e.g., on the Web or Internet), accepting an offer to purchase said gene, polypeptide, or antibody.

Other

A polynucleotide, probe, polypeptide, antibody, specific-binding partner, etc., according to the present invention can be isolated. The term "isolate" means that the material is in a form in which it is not found in its original environment or in nature, e.g., more concentrated, more purified, separated from component, etc. An isolated polynucleotide includes, e.g., a polynucleotide having the sequenced separated from the chromosomal DNA found in a living animal, e.g., as the complete gene, a transcript, or a cDNA. This polynucleotide can be part of a vector or inserted into a chromosome (by specific gene-targeting or by random integration at a position other than its normal position) and still be isolated in that it is not in a form that is found in its natural environment. A polynucleotide, polypeptide, etc., of the present invention can also be substantially purified. By substantially purified, it is meant that polynucleotide or polypeptide is separated and is essentially free from other polynucleotides or polypeptides, i.e., the polynucleotide or polypeptide is the primary and active constituent. A polynucleotide can also be a recombinant molecule. By "recombinant," it is meant that the polynucleotide is an arrangement or form which does not occur in nature. For instance, a recombinant molecule comprising a promoter sequence would not encompass the naturally-occurring gene, but would include the promoter operably linked to a coding sequence not associated with it in nature, e.g., a reporter gene, or a truncation of the normal coding sequence.

The term "marker" is used herein to indicate a means for detecting or labeling a target. A marker can be a polynucleotide (usually referred to as a "probe"), polypeptide (e.g., an antibody conjugated to a detectable label), PNA, or any effective material.

The topic headings set forth above are meant as guidance where certain information can be found in the application, but are not intended to be the only source in the application where information on such topic can be found.

Reference Materials

For other aspects of the polynucleotides, reference is made to standard textbooks of molecular biology. See, e.g., Hames et al., *Polynucleotide Hybridization*, IL Press, 1985; Davis et al., *Basic Methods in Molecular Biology*, Elsevir Sciences Publishing, Inc., New York, 1986; Sambrook et al., *Molecular Cloning*, CSH Press, 1989; Howe, *Gene Cloning and Manipulation*, Cambridge University Press, 1995; Ausubel et al., *Current Protocols in Molecular Biology*, John Wiley & Sons, Inc., 1994–1998.

The preceding preferred specific embodiments are, therefore, to be construed as merely illustrative, and not limiting the remainder of the disclosure in any way whatsoever. The entire disclosure of all applications, patents and publications, cited above and in the figures are hereby incorporated by reference in their entirety.

TABLE 1

| Clone ID | Protein-L* | Location | Domains Names |
|---|---|---|---|
| 1. Pcp0749-2z | 1564aa | Nuclear | 1. ZnF_C3H1 domain: 36–63aa;<br>2. Caldesmon domain: 423–1027aa;<br>3. Coiled coil: 162–197aa;<br>4. Coiled coil: 645–789aa;<br>5. Coiled coil: 1339–1366aa. |
| 2. Pcp0389Az | 694aa | Extracellular | 1. Coiled coil: 17–51aa;<br>2. Methyl-accepting chemotaxis-like domain (MA): 101–200aa. |
| 3. Pcp0814z | 279aa | Membrane | 1. Transmembrane domain: 83–105aa;<br>2. Transmembrane domain: 120–142aa;<br>3. Transmembrane domain: 192–211aa;<br>4. MotA/TolQ/ExbB proton channel domain: 34–156aa;<br>5. Coiled coil: 226–253aa. |
| 4. Pcp0623 | 2697aa | Nuclear | 1. Caldesmon domain: 590–884aa. |
| 5. Pcp0815 | 1041aa | Nuclear | 1. ZF_C2H2: 371–393aa;<br>2. ZF_C2H2: 399–421aa;<br>3. ZF_C2H2: 621–651aa;<br>4. ZF_C2H2: 657–679aa;<br>5. ZF_C2H2: 689–711aa;<br>6. ZF_C2H2: 909–931aa;<br>7. ZF_C2H2: 938–961aa;<br>8. PP_M1 Phosphoprotein domain: 754–923aa. |
| 6. Pcp0840z | 243aa | Nuclear | 1. ZnF_C2H2 domains: 12–37aa;<br>2. ZnF_C2H2 domains: 173–198aa;<br>3. ZnF_C2H2 domains: 208–230aa. |
| 7. Pcp0424Az | 789aa | Cytoplasm | 1. Dynamin, large GTPase domain: 54–308aa. (GTP-binding);<br>2. Dynamin GTPase effector domain: 692–783aa. |
| 7. Pcp0424Bz | 763aa | Cytoplasm | 1. Dynamin, large GTPase domain: 54–308aa. (GTP-binding);<br>2. Dynamin GTPase effector domain: 692783aa; |
| 7. Pcp0424Cz | 752aa | Cytoplasm | 1. Dynamin, large GTPase domain: 54–308aa. (GTP-binding);<br>2. Dynamin GTPase effector domain: 692–783aa. |
| 8. Pc0382 | 1584aa | Nuclear | 1. SAM domain: 11–78aa;<br>2. Kinesin domain: 1079–1103aa. |
| 9. Pcp0816 | 1013aa | Membrane | 1. Signal peptide: 1–38aa;<br>2. EGF-like domain: 274–308aa;<br>3. Transmembrane domain: 908–930aa. |
| 10. Pcp0480 | 171aa | Nuclear | 1. Estrogen receptor: 1–169aa. |
| 11. Pcp0842x | 2221aa | Cytoplasm | 1. SET7 domain: 630–842aa |

L* stands for protein length in amino acids

TABLE 2

| Clone ID | Locus | Associated diseases |
|---|---|---|
| 1. Pcp0749-2z | 13q14.11 | 1. Rieger syndrome type 2 at 13q14;<br>2. Low grade B-cell malignancy at 13q14. |
| 2. Pcp0389Az | 6q22.33 | 1. IgA Nephropathy at 6q22–q23;<br>2. Autosomal recessive craniometaphyseal dysplasia at 6q21–q22;<br>3. Heterocellular hereditary persistence of fetal hemoglobin at 6q22.3–q23.1;<br>4. Oculodentodigital dysplasia at 6q22–q24;<br>5. Susceptibility to severe hepatic fibrosis due to Schistosoma mansoni infection at 6q22–q23. |
| 3. Pcp0814z | 12p13.3 | 1. Chromosomal abnormalities associated with breast and ovary cancer. |
| 4. Pcp0623 | 5p13.2 | |
| 5. Pcp0815 | 14q11.1 | 1. Respiratory allergies (asthma) at 14q11.1 |
| 6. Pcp0840z | 7p15.1 | 1. JAZF1 gene at 7p15 [The gene has not yet been discovered except EST (Hs.346818). It creates a fusion protein by t (7;17) (p15; q21 and causes all type endometrial stromal tumors]. |
| 7. Pcp0424Az | 12p12.23 | 1. Alzheimer disease familial type 5 at 12p11.23–q13.l2;<br>2. Fibrosis of extraocular muscles congenital lat 12p11.2–q12;<br>3. Hypertension with brachydactyly at 12p12.2–p11.2. |
| 7. Pcp0424Bz | 12p12.3 | same as Bcu0424Az. |
| 7. Pcp0424Cz | 12p12.3 | same as Bcu0424Az. |
| 8. Pc0382 | 7q21.3 | 1. Split-hand/foot malformation type-1 (SHFM1) at 7q21.2–q21.3;<br>2. SHFM with sensorineural hearing loss (SHFM1D at 7q21.2–21.3.);<br>4. Malignant hyperthermia susceptibility 3 at 7q21–q22;<br>5. Myoclonic dystonia-11 at 7q21. |
| 9. Pcp0816 | 1p13.1 | 1. Vesicoureteral reflux (VUR) at 1p13;<br>2. Trisomy and Monosomy at 1p13 cause cancers in prostate, ovary and breast. |
| 10. Pcp0480 | 6q25.1 | 1. Estrogen receptor-1 at 6q25.1 (Alternative isoforms are related to breast cancer);<br>2. Schizophrenia-5 at 6q26–q13;<br>3. Insulin-dependent diabetes mellitus-8 at 6q25–q27. |
| 11. Pcp0842x | 6q23.3 | 1. Dilated cardiomyopathy 1J (CMD1J) at 6q23–q24;<br>2. Dilated cardiomyopathy 1F (CMD1F) at 6q23;<br>3. Oculodentodigital dysplasia (ODDD) at 6q22–q24;<br>4. Susceptibility to severe hepatic fibrosis due to Schistosoma mansoni infection at 6q22–q23;<br>5. IgA nephropathy at 6q22–q23. |

TABLE 3

| Gene Name | SEQ ID NO | Expression | |
|---|---|---|---|
| PCP0749 | 1–4 | UP | |
| PCP0389 | 5–8 | UP | |
| PCP0814 | 9–10 | DOWN | |
| PCP0623 | 11–12 | DOWN | |
| PCP0815 | 13–14 | UP | |
| PCP0840 | 15–16 | DOWN | |
| PCP0424 | 17–18 (A); 19–20 (B); 21–22 (C) | UP | |
| PC0382 | 23–24 | UP | |
| PCP0816 | 25–26 | UP | |
| PCP0480 | 27–28 | UP | normal expression restricted to muscle and uterus |
| PCP0842 | 29–30 | UP | |

What is claimed is:

1. An in vitro method of detecting expression of a human prostate cancer gene of SEQ ID NO 29 in a sample from prostate tissue, comprising, contacting a sample comprising nucleic acid from prostate tissue with a polynucleotide probe specific for a sequence selected from nucleotides 1–1456 of a human prostate cancer gene of SEQ ID NO 29, under high stringency conditions effective for said probe to hybridize specifically with said gene, and detecting hybridization between said probe and said nucleic acid, wherein said probe hybridizes under high stringency conditions to said nucleotides 1–1456 of a human prostate cancer gene of SEQ ID NO 29, or a complement thereto, and the presence or absence of expression of said gene is determined by a comparison between a control or standard.

2. A method of claim 1, wherein said high stringency conditions comprise hybridizing at 42° C. in 5×SSC, 0.5% SDS, and 50% formamide, and washing at 65° C. in 0.1% SSC and 0.1% SDS.

3. A method of claim 1, wherein said sample is obtained from a prostate cancer.

4. A method of claim 1, wherein said detecting is performed by:

Northern blot analysis, polymerase chain reaction (PCR), reverse transcriptase PCR, RACE PCR, or in situ hybridization.

5. A method of claim 1, wherein the expression of said gene is up-regulated in said sample.

6. A method of claim 1, wherein said probe consists of nucleotides 1–1456 of SEQ ID NO:29.

7. A method of claim 1, wherein said probe is at least 25 nucleotides.

8. An in vitro method of detecting expression of a human prostate cancer gene of SEQ ID NO 29 in a sample from prostate tissue, comprising, contacting a sample comprising nucleic acid from prostate tissue with a polynucleotide probe specific for a human prostate cancer gene of SEQ ID NO 29 under conditions effective for said probe to hybridize specifically with said gene, and detecting hybridization between said probe and said nucleic acid, wherein said probe comprises a sequence selected from nucleotides 1–1456 of SEQ ID NO 29, or a complement thereto, and hybridizes specifically to said gene, and the presence or absence of expression of said gene is determined by a comparison between a control or standard.

9. A method of claim 8, wherein said conditions comprise hybridizing at 42° C. in 5×SSC, 0.5% SDS, and 50% formamide, and washing at 65° C. in 0.1% SSC and 0.1% SDS.

10. A method of claim 8, wherein said sample is obtained from a prostate cancer.

11. A method of claim 8, wherein said detecting is performed by:

Northern blot analysis, polymerase chain reaction (PCR), reverse transcriptase PCR, RACE PCR, or in situ hybridization.

12. A method of claim 8, wherein the expression of said gene is up-regulated in said sample.

13. A method of claim 8, wherein said probe consists of nucleotides 1–1456 of SEQ ID NO:29.

14. A method of claim 8, wherein said probe is at least 25 nucleotides.

* * * * *

SEQUENCE LISTING

<160> NUMBER OF SEQ ID NOS: 44

<210> SEQ ID NO 1
<211> LENGTH: 6726
<212> TYPE: DNA
<213> ORGANISM: Homo sapiens
<220> FEATURE:

-continued

```
<221> NAME/KEY: CDS
<222> LOCATION: (367)..(5061)

<400> SEQUENCE: 1

gagaggaaca gggcaaacct ctgacttccg gcggcatttt gaggcggtcc tcctagcggc     60

ctggtagtgt ttttgttgcc ttttcttaat ctacaatctc ttcgttattt ttcttcctgc    120

gacccagttt cgcttgaccc tggagaggcg gcgggcgggt tggttctgct tctcagccat    180

cccgggggct cctcgctagc caagagccgg ttcccgggag ccgcgcgcgc atcgctttct    240

cctcgtcgtc gtcctcctgg gtccaggcgc ggggacagag tcgcctcccc cgctcctcgg    300

agcggcggcg gcggtggtgc ctccggactg cacttgcgaa gggagcttgg ggaggaatag    360

tacaaa atg tca aaa att aga agg aag gtc aca gtg gaa aat acc aag       408
       Met Ser Lys Ile Arg Arg Lys Val Thr Val Glu Asn Thr Lys
       1               5                   10

act ata tct gat agc aca tcc cga aga ccc agt gta ttt gag agg ctt      456
Thr Ile Ser Asp Ser Thr Ser Arg Arg Pro Ser Val Phe Glu Arg Leu
15                  20                  25                  30

gga ccc agc act ggc agt aca gca gag aca cag tgc cgt aac tgg ctg      504
Gly Pro Ser Thr Gly Ser Thr Ala Glu Thr Gln Cys Arg Asn Trp Leu
                35                  40                  45

aag act ggc aac tgc ctc tat gga aac aca tgt aga ttc gta cat ggc      552
Lys Thr Gly Asn Cys Leu Tyr Gly Asn Thr Cys Arg Phe Val His Gly
            50                  55                  60

cct tca cct cgt ggt aaa ggt tat agc agc aat tat aga agg tca cca      600
Pro Ser Pro Arg Gly Lys Gly Tyr Ser Ser Asn Tyr Arg Arg Ser Pro
        65                  70                  75

gaa aga cct aca ggg gat ctt aga gaa aga atg aag aac aag cgc caa      648
Glu Arg Pro Thr Gly Asp Leu Arg Glu Arg Met Lys Asn Lys Arg Gln
    80                  85                  90

gac gtg gac act gag ccc cag aaa cga aat aca gag gag tca tcc tca      696
Asp Val Asp Thr Glu Pro Gln Lys Arg Asn Thr Glu Glu Ser Ser Ser
95                  100                 105                 110

cct gtt agg aaa gaa tct tca aga ggg aga cat agg gaa aag gaa gac      744
Pro Val Arg Lys Glu Ser Ser Arg Gly Arg His Arg Glu Lys Glu Asp
                115                 120                 125

ata aaa atc act aag gaa aga act cca gaa agt gaa gaa gaa aat gta      792
Ile Lys Ile Thr Lys Glu Arg Thr Pro Glu Ser Glu Glu Glu Asn Val
            130                 135                 140

gaa tgg gaa act aat aga gat gat tct gac aat gga gat att aat tat      840
Glu Trp Glu Thr Asn Arg Asp Asp Ser Asp Asn Gly Asp Ile Asn Tyr
        145                 150                 155

gat tat gtt cat gaa ttg tca ttg gaa atg aag cgt cag aag ata cag      888
Asp Tyr Val His Glu Leu Ser Leu Glu Met Lys Arg Gln Lys Ile Gln
    160                 165                 170

agg gaa tta atg aag ctg gaa caa gaa aac atg gag aag aga gaa gaa      936
Arg Glu Leu Met Lys Leu Glu Gln Glu Asn Met Glu Lys Arg Glu Glu
175                 180                 185                 190

att atc att aaa aag gag gtt tca cca gaa gtg gtt aga tca aaa ttg      984
Ile Ile Ile Lys Lys Glu Val Ser Pro Glu Val Val Arg Ser Lys Leu
                195                 200                 205

tcc ccg tca cct tct cta aga aag tct agc aaa tct ccg aag cga aaa     1032
Ser Pro Ser Pro Ser Leu Arg Lys Ser Ser Lys Ser Pro Lys Arg Lys
            210                 215                 220

tca agc ccg aag tcg tct tca gct agc aag aaa gat agg aag aca tct     1080
Ser Ser Pro Lys Ser Ser Ser Ala Ser Lys Lys Asp Arg Lys Thr Ser
        225                 230                 235

gca gta tct tct ccc ctg ttg gac cag cag aga aat tca aaa acc aac     1128
Ala Val Ser Ser Pro Leu Leu Asp Gln Gln Arg Asn Ser Lys Thr Asn
```

-continued

```
    240                 245                 250

caa agt aaa aag aaa gga cca cgt act cct agt cca ccc cct cct ata     1176
Gln Ser Lys Lys Lys Gly Pro Arg Thr Pro Ser Pro Pro Pro Pro Ile
255                 260                 265                 270

cca gaa gat atc gct ctg ggg aaa aaa tac aaa gaa aaa tat aaa gta     1224
Pro Glu Asp Ile Ala Leu Gly Lys Lys Tyr Lys Glu Lys Tyr Lys Val
                275                 280                 285

aaa gac agg ata gaa gaa aaa aca aga gat gga aag gac aga gga cga     1272
Lys Asp Arg Ile Glu Glu Lys Thr Arg Asp Gly Lys Asp Arg Gly Arg
            290                 295                 300

gat ttt gaa cga caa aga gaa aag aga gac aag cca agg tct act tcc     1320
Asp Phe Glu Arg Gln Arg Glu Lys Arg Asp Lys Pro Arg Ser Thr Ser
        305                 310                 315

cca gca gga cag cat cat tct cct ata tct tct aga cat cac tca tct     1368
Pro Ala Gly Gln His His Ser Pro Ile Ser Ser Arg His His Ser Ser
    320                 325                 330

tcc tca caa tca gga tca tct att caa aga cat tct cct tct cct cgt     1416
Ser Ser Gln Ser Gly Ser Ser Ile Gln Arg His Ser Pro Ser Pro Arg
335                 340                 345                 350

cga aaa aga act cct tca cca tct tat cag cgg aca cta act cca cct     1464
Arg Lys Arg Thr Pro Ser Pro Ser Tyr Gln Arg Thr Leu Thr Pro Pro
                355                 360                 365

tta cga cgc tct gcc tct cct tat cct tca cat tct ttg tcg tct ccc     1512
Leu Arg Arg Ser Ala Ser Pro Tyr Pro Ser His Ser Leu Ser Ser Pro
            370                 375                 380

cag aga aag cag agt cct cca aga cat cgc tct cca atg cga gag aaa     1560
Gln Arg Lys Gln Ser Pro Pro Arg His Arg Ser Pro Met Arg Glu Lys
        385                 390                 395

ggg aga cat gat cat gaa cga act tca cag tct cat gat cga cgc cac     1608
Gly Arg His Asp His Glu Arg Thr Ser Gln Ser His Asp Arg Arg His
    400                 405                 410

gaa agg agg gaa gat act agg ggc aaa cga gac aga gaa aag gac tca     1656
Glu Arg Arg Glu Asp Thr Arg Gly Lys Arg Asp Arg Glu Lys Asp Ser
415                 420                 425                 430

aga gaa gaa cga gaa tat gaa cag gat cag agc tct tct aga gac cac     1704
Arg Glu Glu Arg Glu Tyr Glu Gln Asp Gln Ser Ser Ser Arg Asp His
                435                 440                 445

aga gat gac aga gaa cct cga gat ggt cgg gat cgg aga gat gcc aga     1752
Arg Asp Asp Arg Glu Pro Arg Asp Gly Arg Asp Arg Arg Asp Ala Arg
            450                 455                 460

gat act agg gac cga agg gaa cta aga gac tcc aga gac atg cgg gac     1800
Asp Thr Arg Asp Arg Arg Glu Leu Arg Asp Ser Arg Asp Met Arg Asp
        465                 470                 475

tca agg gag atg aga gat tat agc aga gat acc aaa gag agc cgt gat     1848
Ser Arg Glu Met Arg Asp Tyr Ser Arg Asp Thr Lys Glu Ser Arg Asp
    480                 485                 490

ccc aga gat tct cgg tcc act cgt gat gcc cat gac tac agg gac cgt     1896
Pro Arg Asp Ser Arg Ser Thr Arg Asp Ala His Asp Tyr Arg Asp Arg
495                 500                 505                 510

gaa ggt cga gat act cat cga aag gag gat aca tat cca gaa gaa tcc     1944
Glu Gly Arg Asp Thr His Arg Lys Glu Asp Thr Tyr Pro Glu Glu Ser
                515                 520                 525

cgg agt tat ggc cga aac cat ttg aga gaa gaa agt tct cgt acg gaa     1992
Arg Ser Tyr Gly Arg Asn His Leu Arg Glu Glu Ser Ser Arg Thr Glu
            530                 535                 540

ata agg aat gag tcc aga aat gag tct cga agt gaa att aga aat gac     2040
Ile Arg Asn Glu Ser Arg Asn Glu Ser Arg Ser Glu Ile Arg Asn Asp
        545                 550                 555

cga atg ggc cga agt agg ggg agg gtt cct gag tta cct gaa aag gga     2088
```

-continued

```
Arg Met Gly Arg Ser Arg Gly Arg Val Pro Glu Leu Pro Glu Lys Gly
    560                 565                 570

agt cga ggc tca aga ggt tct caa att gat agt cac agt agt aat agc     2136
Ser Arg Gly Ser Arg Gly Ser Gln Ile Asp Ser His Ser Ser Asn Ser
575                 580                 585                 590

aac tat cat gac agc tgg gaa act cga agt agc tat cct gaa aga gat     2184
Asn Tyr His Asp Ser Trp Glu Thr Arg Ser Ser Tyr Pro Glu Arg Asp
                595                 600                 605

aga tat cct gaa aga gac aac aga gat caa gca agg gat tct tcc ttt     2232
Arg Tyr Pro Glu Arg Asp Asn Arg Asp Gln Ala Arg Asp Ser Ser Phe
            610                 615                 620

gag aga aga cat gga gag cga gac cgt cgt gac aac aga gag aga gat     2280
Glu Arg Arg His Gly Glu Arg Asp Arg Arg Asp Asn Arg Glu Arg Asp
        625                 630                 635

caa aga cca agc tca cca att cga cat cag gga agg aat gac gag ctt     2328
Gln Arg Pro Ser Ser Pro Ile Arg His Gln Gly Arg Asn Asp Glu Leu
    640                 645                 650

gag cgt gat gaa aga aga gag gaa cga aga gta gac aga gtg gat gat     2376
Glu Arg Asp Glu Arg Arg Glu Glu Arg Arg Val Asp Arg Val Asp Asp
655                 660                 665                 670

agg aga gat gaa agg gct aga gag aga gat cgg gaa cga gaa cga gac     2424
Arg Arg Asp Glu Arg Ala Arg Glu Arg Asp Arg Glu Arg Glu Arg Asp
                675                 680                 685

agg gag cgg gag aga gag agg gaa cgt gaa cgg gat cgg gaa aga gaa     2472
Arg Glu Arg Glu Arg Glu Arg Glu Arg Glu Arg Asp Arg Glu Arg Glu
            690                 695                 700

aaa gag aga gaa cta gaa aga gag cgt gct agg gaa cgg gag aga gaa     2520
Lys Glu Arg Glu Leu Glu Arg Glu Arg Ala Arg Glu Arg Glu Arg Glu
        705                 710                 715

aga gaa aaa gag aga gat cgt gaa agg gat aga gac cga gac cac gat     2568
Arg Glu Lys Glu Arg Asp Arg Glu Arg Asp Arg Asp Arg Asp His Asp
    720                 725                 730

cga gag cgg gaa aga gag agg gaa cga gac agg gaa aaa gaa cgg gaa     2616
Arg Glu Arg Glu Arg Glu Arg Glu Arg Asp Arg Glu Lys Glu Arg Glu
735                 740                 745                 750

cga gaa aga gaa gag aga gag agg gag aga gag cga gaa cgg gag aga     2664
Arg Glu Arg Glu Glu Arg Glu Arg Glu Arg Glu Arg Glu Arg Glu Arg
                755                 760                 765

gag cga gag cga gaa cgg gaa cga gaa aga gcg aga gaa agg gat aaa     2712
Glu Arg Glu Arg Glu Arg Glu Arg Glu Arg Ala Arg Glu Arg Asp Lys
            770                 775                 780

gaa cga gaa cgc caa agg gat tgg gaa gac aaa gac aaa gga cga gat     2760
Glu Arg Glu Arg Gln Arg Asp Trp Glu Asp Lys Asp Lys Gly Arg Asp
        785                 790                 795

gac cgc aga gaa aag cga gaa gag atc cga gaa gat agg aat cca aga     2808
Asp Arg Arg Glu Lys Arg Glu Glu Ile Arg Glu Asp Arg Asn Pro Arg
    800                 805                 810

gat gga cat gat gaa aga aaa tca aag aag cgc tat aga aat gaa ggg     2856
Asp Gly His Asp Glu Arg Lys Ser Lys Lys Arg Tyr Arg Asn Glu Gly
815                 820                 825                 830

agt ccc agc cct aga cag tcc ccg aag cgc cgg cgt gaa cat tct ccg     2904
Ser Pro Ser Pro Arg Gln Ser Pro Lys Arg Arg Arg Glu His Ser Pro
                835                 840                 845

gac agt gat gcc tac aac agt gga gat gat aaa aat gaa aaa cac aga     2952
Asp Ser Asp Ala Tyr Asn Ser Gly Asp Asp Lys Asn Glu Lys His Arg
            850                 855                 860

ctc ttg agc caa gtt gta cga cct caa gaa tct cgt tct ctt agt ccc     3000
Leu Leu Ser Gln Val Val Arg Pro Gln Glu Ser Arg Ser Leu Ser Pro
        865                 870                 875
```

-continued

```
tcg cac ctc aca gaa gac aga cag ggt aga tgg aaa gag gag gat cgt      3048
Ser His Leu Thr Glu Asp Arg Gln Gly Arg Trp Lys Glu Glu Asp Arg
    880                 885                 890

aaa cca gaa agg aaa gag agt tca agg cgc tac gaa gaa cag gaa ctc      3096
Lys Pro Glu Arg Lys Glu Ser Ser Arg Arg Tyr Glu Glu Gln Glu Leu
895                 900                 905                 910

aag gag aaa gtt tct tct gta gat aaa cag aga gaa cag aca gaa atc      3144
Lys Glu Lys Val Ser Ser Val Asp Lys Gln Arg Glu Gln Thr Glu Ile
            915                 920                 925

ctg gaa agc tca aga atg cgt gca cag gac att ata gga cac cac cag      3192
Leu Glu Ser Ser Arg Met Arg Ala Gln Asp Ile Ile Gly His His Gln
            930                 935                 940

tct gaa gat cga gag aca tct gat cga gct cat gat gaa aac aag aag      3240
Ser Glu Asp Arg Glu Thr Ser Asp Arg Ala His Asp Glu Asn Lys Lys
        945                 950                 955

aaa gca aaa att caa aag aaa cca att aag aaa aag aaa gag gat gat      3288
Lys Ala Lys Ile Gln Lys Lys Pro Ile Lys Lys Lys Lys Glu Asp Asp
    960                 965                 970

gtt gga ata gag agg ggt aac ata gag aca aca tct gaa gat ggt caa      3336
Val Gly Ile Glu Arg Gly Asn Ile Glu Thr Thr Ser Glu Asp Gly Gln
975                 980                 985                 990

gta ttt tca cca aaa aaa gga cag aaa aag  aaa agc att gaa aaa  aaa    3384
Val Phe Ser Pro Lys Lys Gly Gln Lys Lys  Lys Ser Ile Glu Lys  Lys
                995                 1000                1005

cgt aaa aaa tcc  aaa ggt gat tct gat  att tct gat gaa gaa  gca      3429
Arg Lys Lys Ser  Lys Gly Asp Ser Asp  Ile Ser Asp Glu Glu  Ala
            1010                 1015                 1020

gcc cag caa agt  aag aag aaa aga ggc  cca cgg act ccc cct  ata      3474
Ala Gln Gln Ser  Lys Lys Lys Arg Gly  Pro Arg Thr Pro Pro  Ile
            1025                 1030                 1035

aca act aaa gag  gaa ttg gtt gaa atg  tgc aat ggt aag aat  ggt      3519
Thr Thr Lys Glu  Glu Leu Val Glu Met  Cys Asn Gly Lys Asn  Gly
            1040                 1045                 1050

att cta gag gac  tcc cag aaa aaa gaa  gat aca gca ttc agt  gac      3564
Ile Leu Glu Asp  Ser Gln Lys Lys Glu  Asp Thr Ala Phe Ser  Asp
            1055                 1060                 1065

tgg tct gat gag  gat gtc cct gac cgt  aca gag gtg aca gaa  gca      3609
Trp Ser Asp Glu  Asp Val Pro Asp Arg  Thr Glu Val Thr Glu  Ala
            1070                 1075                 1080

gag cat act gcc  acc gcc acg act cct  ggt agt acc cct tct  cct      3654
Glu His Thr Ala  Thr Ala Thr Thr Pro  Gly Ser Thr Pro Ser  Pro
            1085                 1090                 1095

cta tct tct ctt  ctt cct cct cca ccg  cct gtg gct act gcc  act      3699
Leu Ser Ser Leu  Leu Pro Pro Pro Pro  Pro Val Ala Thr Ala  Thr
            1100                 1105                 1110

gct aca act gtg  cct gca act ctt gct  gcc act act gct gct  gcc      3744
Ala Thr Thr Val  Pro Ala Thr Leu Ala  Ala Thr Thr Ala Ala  Ala
            1115                 1120                 1125

gcc acc tct ttc  agc aca tct gcc atc  act att tcc acc tct  gcc      3789
Ala Thr Ser Phe  Ser Thr Ser Ala Ile  Thr Ile Ser Thr Ser  Ala
            1130                 1135                 1140

acc ccc acc aat  acc acc aat aat act  ttt gcc aat gaa gac  tca      3834
Thr Pro Thr Asn  Thr Thr Asn Asn Thr  Phe Ala Asn Glu Asp  Ser
            1145                 1150                 1155

cac aga aaa tgc  cac aga aca cga gta  gaa aaa gta gag acg  cct      3879
His Arg Lys Cys  His Arg Thr Arg Val  Glu Lys Val Glu Thr  Pro
            1160                 1165                 1170

cac gtg act ata  gaa gat gca cag cat  cgc aag cct atg gat  caa      3924
His Val Thr Ile  Glu Asp Ala Gln His  Arg Lys Pro Met Asp  Gln
            1175                 1180                 1185
```

-continued

```
aag agg agc agc  agc ctc ggg agc aat  cgg agt aac cgt agt  cat      3969
Lys Arg Ser Ser  Ser Leu Gly Ser Asn  Arg Ser Asn Arg Ser  His
            1190                 1195                 1200

acg tct ggt cgt  ctt cgc tcc cca tcc  aat gat tca gcc cat  cga      4014
Thr Ser Gly Arg  Leu Arg Ser Pro Ser  Asn Asp Ser Ala His  Arg
            1205                 1210                 1215

agt gga gat gac  caa agt ggt cga aag  aga gta ctg cac agt  ggc      4059
Ser Gly Asp Asp  Gln Ser Gly Arg Lys  Arg Val Leu His Ser  Gly
            1220                 1225                 1230

tca aga gat aga  gaa aaa aca aaa agc  ctg gaa atc aca gga  gag      4104
Ser Arg Asp Arg  Glu Lys Thr Lys Ser  Leu Glu Ile Thr Gly  Glu
            1235                 1240                 1245

aga aaa tct agg  att gat cag tta aag  cgt gga gaa ccc agt  cga      4149
Arg Lys Ser Arg  Ile Asp Gln Leu Lys  Arg Gly Glu Pro Ser  Arg
            1250                 1255                 1260

agt act tct tca  gat cgc cag gat tca  aga agc cat agt tca  aga      4194
Ser Thr Ser Ser  Asp Arg Gln Asp Ser  Arg Ser His Ser Ser  Arg
            1265                 1270                 1275

aga agt tct cca  gag tca gat cga cag  gtc cat tca aga tct  ggg      4239
Arg Ser Ser Pro  Glu Ser Asp Arg Gln  Val His Ser Arg Ser  Gly
            1280                 1285                 1290

tca ttt gat agc  aga gac agg ctt caa  gaa cga gat cga tat  gaa      4284
Ser Phe Asp Ser  Arg Asp Arg Leu Gln  Glu Arg Asp Arg Tyr  Glu
            1295                 1300                 1305

cac gac aga gag  cgc gag aga gag agg  aga gat acg agg cag  aga      4329
His Asp Arg Glu  Arg Glu Arg Glu Arg  Arg Asp Thr Arg Gln  Arg
            1310                 1315                 1320

gaa tgg gac cga  gat gct gat aaa gat  tgg cca cgc aac agg  gat      4374
Glu Trp Asp Arg  Asp Ala Asp Lys Asp  Trp Pro Arg Asn Arg  Asp
            1325                 1330                 1335

cga gat aga ttg  cga gaa cga gaa cga  gag aga gaa cga gac  aaa      4419
Arg Asp Arg Leu  Arg Glu Arg Glu Arg  Glu Arg Glu Arg Asp  Lys
            1340                 1345                 1350

agg aga gac ttg  gat agg gaa aga gag  aga cta att tct gat  tct      4464
Arg Arg Asp Leu  Asp Arg Glu Arg Glu  Arg Leu Ile Ser Asp  Ser
            1355                 1360                 1365

gtt gaa agg gac  agg gac aga gac aga  gac aga act ttt gag  agt      4509
Val Glu Arg Asp  Arg Asp Arg Asp Arg  Asp Arg Thr Phe Glu  Ser
            1370                 1375                 1380

tct caa ata gag  tct gtg aaa cgc tgt  gaa gca aaa ctg gaa  ggt      4554
Ser Gln Ile Glu  Ser Val Lys Arg Cys  Glu Ala Lys Leu Glu  Gly
            1385                 1390                 1395

gaa cat gaa agg  gat cta gaa agc act  tcc cga gac tct cta  gcc      4599
Glu His Glu Arg  Asp Leu Glu Ser Thr  Ser Arg Asp Ser Leu  Ala
            1400                 1405                 1410

ttg gat aaa gag  aga atg gat aaa gat  ctg gga tct gtg cag  gga      4644
Leu Asp Lys Glu  Arg Met Asp Lys Asp  Leu Gly Ser Val Gln  Gly
            1415                 1420                 1425

ttt gaa gat aca  aat aaa tcc gag aga  act gag agt ctg gaa  gca      4689
Phe Glu Asp Thr  Asn Lys Ser Glu Arg  Thr Glu Ser Leu Glu  Ala
            1430                 1435                 1440

gga gat gac gag  tcc aag tta gat gat  gca cat tca tta ggc  tct      4734
Gly Asp Asp Glu  Ser Lys Leu Asp Asp  Ala His Ser Leu Gly  Ser
            1445                 1450                 1455

ggt gct gga gaa  gga tac gag cca atc  agt gat gac gaa cta  gat      4779
Gly Ala Gly Glu  Gly Tyr Glu Pro Ile  Ser Asp Asp Glu Leu  Asp
            1460                 1465                 1470

gaa att ctg gca  ggt gat gca gaa aag  agg gag gac caa cag  gat      4824
Glu Ile Leu Ala  Gly Asp Ala Glu Lys  Arg Glu Asp Gln Gln  Asp
```

-continued

```
            1475                1480                1485

gag gag aag atg  cca gat ccc tta gat  gtg ata gat gtg gat  tgg      4869
Glu Glu Lys Met  Pro Asp Pro Leu Asp  Val Ile Asp Val Asp  Trp
            1490                1495                1500

tct ggt ctt atg  cca aag cat cca aaa  gaa cca cga gag cct  ggg      4914
Ser Gly Leu Met  Pro Lys His Pro Lys  Glu Pro Arg Glu Pro  Gly
            1505                1510                1515

gct gca ctc tta  aaa ttc aca cct gga  gct gtt atg cta aga  gtt      4959
Ala Ala Leu Leu  Lys Phe Thr Pro Gly  Ala Val Met Leu Arg  Val
            1520                1525                1530

ggg att tct aaa  aag ttg gca ggt tct  gaa ctc ttt gcc aaa  gtc      5004
Gly Ile Ser Lys  Lys Leu Ala Gly Ser  Glu Leu Phe Ala Lys  Val
            1535                1540                1545

aaa gaa aca tgt  cag aga ctt tta gaa  aaa ccc aaa ggt agt  ttc      5049
Lys Glu Thr Cys  Gln Arg Leu Leu Glu  Lys Pro Lys Gly Ser  Phe
            1550                1555                1560

att tta ctt taa ctatataatg tctgttaacc atttaagatg ccatctgaag         5101
Ile Leu Leu

gggattctga tctgttctta tgtagcactt aacactgtgt agaaactatt ttttgagaaa   5161

tcattttata atcattattt aaccctcatg gtcaaagttt ctctttaaaa tttattttga   5221

gaagaagagt tatcccacag aaaagttggg aaaagagtac aatgaccttt ttgtatgaaa   5281

attacttatt aacaggccag gcgtggtgtt gcatgtctgt agtcacagct actcagggag   5341

gttgaggcag caggattgct ggagcccagg aaattgaggc tgcagtgagc catgattgag   5401

ccaccacact ccaacctagg tgacagagca agaccctgtc tcaaaaaaaa aaaaacaaat   5461

taaccaataa gttctaatat caaagtgctc agtggtttgc ccttggctaa atgaagcaga   5521

gccaggaaaa acagactaca tatttttcat gtctaaagaa attgggtatt ttggcagccc   5581

tttcccctag acatctaccc aaatgcaggt gtgtaggttg agtctttaac aaagtgatta   5641

agagcttggt ctgtaaggcc ggatgatctg gatttcagta ggcacaccac ttactggcta   5701

ttacttaatc tgtgtgttag tgtcatcatc tgtaagtcag gaataatcat accaccaact   5761

tcctatggta attaggagca aatgagttat tacaggcaaa acacttagaa cagttcctgg   5821

catatagtaa tacccaataa atattaactg ctactttgaa aatatcctat cacgctgatt   5881

tttgacctca ctgcagcaat tttcagttat tccagattat ctagcttatg gattctggtg   5941

gtaggggttg tttggttttg gttttcactg tctctgtctc atctagtacc taccttagtt   6001

tattttgcaa cttactaata ctttattaat ggggagggac gagtagatgg taaaaagaag   6061

gaaaaggagg taaaaggtga aaggaacaac attaattaac aattttacgt catgtccctg   6121

gacataaaag tttagttagt attaaatttt tcactaatac aaaataaaaa aatattgttt   6181

tatgagtttt atgaattcat gcccttcctt tactctatta gcataagcag taaatttttt   6241

tattttaata tagcccaata aacctagagt atacatgtac aaaatacata taattgttaa   6301

cgtgtattaa ccgaaaaatg acccaagact tagttcttgc cctactgtat ctgccttgtt   6361

tggttggttc tgtgacctta agcaaataac tcctgtgagc ctcaatttta tttgtaaagt   6421

gatggaataa aacccctaaa atcttaccca cctctaaaga tatttgtttc tgtgaccttt   6481

tgctagtagc atttcaagtt aaaatctggt ttgattttgc tacccatgaa atacagttcg   6541

gcccttactt attgatgact taacctaaac agtgaaaata tgcactgtaa agggtggggt   6601

gatgtggctt aacaatcaga cttcttctat ttttgctgct atggtggttg tattagagaa   6661

ctgatgtatt atcttgaata aagactttgt cttgtttact gccctaaaaa aaaaaaaaaa   6721
```

-continued

```
aaaaa                                                                     6726

<210> SEQ ID NO 2
<211> LENGTH: 1564
<212> TYPE: PRT
<213> ORGANISM: Homo sapiens

<400> SEQUENCE: 2

Met Ser Lys Ile Arg Arg Lys Val Thr Val Glu Asn Thr Lys Thr Ile
1               5                   10                  15

Ser Asp Ser Thr Ser Arg Arg Pro Ser Val Phe Glu Arg Leu Gly Pro
            20                  25                  30

Ser Thr Gly Ser Thr Ala Glu Thr Gln Cys Arg Asn Trp Leu Lys Thr
        35                  40                  45

Gly Asn Cys Leu Tyr Gly Asn Thr Cys Arg Phe Val His Gly Pro Ser
    50                  55                  60

Pro Arg Gly Lys Gly Tyr Ser Ser Asn Tyr Arg Arg Ser Pro Glu Arg
65                  70                  75                  80

Pro Thr Gly Asp Leu Arg Glu Arg Met Lys Asn Lys Arg Gln Asp Val
                85                  90                  95

Asp Thr Glu Pro Gln Lys Arg Asn Thr Glu Glu Ser Ser Ser Pro Val
            100                 105                 110

Arg Lys Glu Ser Ser Arg Gly Arg His Arg Glu Lys Glu Asp Ile Lys
        115                 120                 125

Ile Thr Lys Glu Arg Thr Pro Glu Ser Glu Glu Glu Asn Val Glu Trp
    130                 135                 140

Glu Thr Asn Arg Asp Asp Ser Asp Asn Gly Asp Ile Asn Tyr Asp Tyr
145                 150                 155                 160

Val His Glu Leu Ser Leu Glu Met Lys Arg Gln Lys Ile Gln Arg Glu
                165                 170                 175

Leu Met Lys Leu Glu Gln Glu Asn Met Glu Lys Arg Glu Glu Ile Ile
            180                 185                 190

Ile Lys Lys Glu Val Ser Pro Glu Val Val Arg Ser Lys Leu Ser Pro
        195                 200                 205

Ser Pro Ser Leu Arg Lys Ser Ser Lys Ser Pro Lys Arg Lys Ser Ser
    210                 215                 220

Pro Lys Ser Ser Ser Ala Ser Lys Lys Asp Arg Lys Thr Ser Ala Val
225                 230                 235                 240

Ser Ser Pro Leu Leu Asp Gln Gln Arg Asn Ser Lys Thr Asn Gln Ser
                245                 250                 255

Lys Lys Lys Gly Pro Arg Thr Pro Ser Pro Pro Pro Pro Ile Pro Glu
            260                 265                 270

Asp Ile Ala Leu Gly Lys Lys Tyr Lys Glu Lys Tyr Lys Val Lys Asp
        275                 280                 285

Arg Ile Glu Glu Lys Thr Arg Asp Gly Lys Asp Arg Gly Arg Asp Phe
    290                 295                 300

Glu Arg Gln Arg Glu Lys Arg Asp Lys Pro Arg Ser Thr Ser Pro Ala
305                 310                 315                 320

Gly Gln His His Ser Pro Ile Ser Ser Arg His His Ser Ser Ser Ser
                325                 330                 335

Gln Ser Gly Ser Ser Ile Gln Arg His Ser Pro Ser Pro Arg Arg Lys
            340                 345                 350

Arg Thr Pro Ser Pro Ser Tyr Gln Arg Thr Leu Thr Pro Pro Leu Arg
        355                 360                 365
```

-continued

```
Arg Ser Ala Ser Pro Tyr Pro Ser His Ser Leu Ser Ser Pro Gln Arg
    370                 375                 380

Lys Gln Ser Pro Pro Arg His Arg Ser Pro Met Arg Glu Lys Gly Arg
385                 390                 395                 400

His Asp His Glu Arg Thr Ser Gln Ser His Asp Arg Arg His Glu Arg
                405                 410                 415

Arg Glu Asp Thr Arg Gly Lys Arg Asp Arg Glu Lys Asp Ser Arg Glu
            420                 425                 430

Glu Arg Glu Tyr Glu Gln Asp Gln Ser Ser Ser Arg Asp His Arg Asp
        435                 440                 445

Asp Arg Glu Pro Arg Asp Gly Arg Asp Arg Arg Asp Ala Arg Asp Thr
    450                 455                 460

Arg Asp Arg Arg Glu Leu Arg Asp Ser Arg Asp Met Arg Asp Ser Arg
465                 470                 475                 480

Glu Met Arg Asp Tyr Ser Arg Asp Thr Lys Glu Ser Arg Asp Pro Arg
                485                 490                 495

Asp Ser Arg Ser Thr Arg Asp Ala His Asp Tyr Arg Asp Arg Glu Gly
            500                 505                 510

Arg Asp Thr His Arg Lys Glu Asp Thr Tyr Pro Glu Glu Ser Arg Ser
        515                 520                 525

Tyr Gly Arg Asn His Leu Arg Glu Glu Ser Ser Arg Thr Glu Ile Arg
    530                 535                 540

Asn Glu Ser Arg Asn Glu Ser Arg Ser Glu Ile Arg Asn Asp Arg Met
545                 550                 555                 560

Gly Arg Ser Arg Gly Arg Val Pro Glu Leu Pro Glu Lys Gly Ser Arg
                565                 570                 575

Gly Ser Arg Gly Ser Gln Ile Asp Ser His Ser Ser Asn Ser Asn Tyr
            580                 585                 590

His Asp Ser Trp Glu Thr Arg Ser Ser Tyr Pro Glu Arg Asp Arg Tyr
        595                 600                 605

Pro Glu Arg Asp Asn Arg Asp Gln Ala Arg Asp Ser Ser Phe Glu Arg
    610                 615                 620

Arg His Gly Glu Arg Asp Arg Arg Asp Asn Arg Glu Arg Asp Gln Arg
625                 630                 635                 640

Pro Ser Ser Pro Ile Arg His Gln Gly Arg Asn Asp Glu Leu Glu Arg
                645                 650                 655

Asp Glu Arg Arg Glu Glu Arg Arg Val Asp Arg Val Asp Asp Arg Arg
            660                 665                 670

Asp Glu Arg Ala Arg Glu Arg Asp Arg Glu Arg Glu Arg Asp Arg Glu
        675                 680                 685

Arg Glu Arg Glu Arg Glu Arg Glu Arg Asp Arg Glu Arg Glu Lys Glu
    690                 695                 700

Arg Glu Leu Glu Arg Glu Arg Ala Arg Glu Arg Glu Arg Glu Arg Glu
705                 710                 715                 720

Lys Glu Arg Asp Arg Glu Arg Asp Arg Asp Arg Asp His Asp Arg Glu
                725                 730                 735

Arg Glu Arg Glu Arg Glu Arg Asp Arg Glu Lys Glu Arg Glu Arg Glu
            740                 745                 750

Arg Glu Glu Arg Glu Arg Glu Arg Glu Arg Glu Arg Glu Arg Glu Arg
        755                 760                 765

Glu Arg Glu Arg Glu Arg Glu Arg Ala Arg Glu Arg Asp Lys Glu Arg
    770                 775                 780

Glu Arg Gln Arg Asp Trp Glu Asp Lys Asp Lys Gly Arg Asp Asp Arg
```

-continued

```
785                 790                 795                 800

Arg Glu Lys Arg Glu Glu Ile Arg Glu Asp Arg Asn Pro Arg Asp Gly
                805                 810                 815

His Asp Glu Arg Lys Ser Lys Lys Arg Tyr Arg Asn Glu Gly Ser Pro
            820                 825                 830

Ser Pro Arg Gln Ser Pro Lys Arg Arg Arg Glu His Ser Pro Asp Ser
        835                 840                 845

Asp Ala Tyr Asn Ser Gly Asp Asp Lys Asn Glu Lys His Arg Leu Leu
    850                 855                 860

Ser Gln Val Val Arg Pro Gln Glu Ser Arg Ser Leu Ser Pro Ser His
865                 870                 875                 880

Leu Thr Glu Asp Arg Gln Gly Arg Trp Lys Glu Glu Asp Arg Lys Pro
                885                 890                 895

Glu Arg Lys Glu Ser Ser Arg Arg Tyr Glu Glu Gln Glu Leu Lys Glu
            900                 905                 910

Lys Val Ser Ser Val Asp Lys Gln Arg Glu Gln Thr Glu Ile Leu Glu
        915                 920                 925

Ser Ser Arg Met Arg Ala Gln Asp Ile Ile Gly His His Gln Ser Glu
    930                 935                 940

Asp Arg Glu Thr Ser Asp Arg Ala His Asp Glu Asn Lys Lys Lys Ala
945                 950                 955                 960

Lys Ile Gln Lys Lys Pro Ile Lys Lys Lys Lys Glu Asp Asp Val Gly
                965                 970                 975

Ile Glu Arg Gly Asn Ile Glu Thr Thr Ser Glu Asp Gly Gln Val Phe
            980                 985                 990

Ser Pro Lys Lys Gly Gln Lys Lys  Lys Ser Ile Glu Lys  Lys Arg Lys
        995                 1000                1005

Lys Ser  Lys Gly Asp Ser Asp  Ile Ser Asp Glu Glu  Ala Ala Gln
    1010                1015                1020

Gln Ser  Lys Lys Lys Arg Gly  Pro Arg Thr Pro Pro  Ile Thr Thr
    1025                1030                1035

Lys Glu  Glu Leu Val Glu Met  Cys Asn Gly Lys Asn  Gly Ile Leu
    1040                1045                1050

Glu Asp  Ser Gln Lys Lys Glu  Asp Thr Ala Phe Ser  Asp Trp Ser
    1055                1060                1065

Asp Glu  Asp Val Pro Asp Arg  Thr Glu Val Thr Glu  Ala Glu His
    1070                1075                1080

Thr Ala  Thr Ala Thr Thr Pro  Gly Ser Thr Pro Ser  Pro Leu Ser
    1085                1090                1095

Ser Leu  Leu Pro Pro Pro Pro  Pro Val Ala Thr Ala  Thr Ala Thr
    1100                1105                1110

Thr Val  Pro Ala Thr Leu Ala  Ala Thr Thr Ala Ala  Ala Ala Thr
    1115                1120                1125

Ser Phe  Ser Thr Ser Ala Ile  Thr Ile Ser Thr Ser  Ala Thr Pro
    1130                1135                1140

Thr Asn  Thr Thr Asn Asn Thr  Phe Ala Asn Glu Asp  Ser His Arg
    1145                1150                1155

Lys Cys  His Arg Thr Arg Val  Glu Lys Val Glu Thr  Pro His Val
    1160                1165                1170

Thr Ile  Glu Asp Ala Gln His  Arg Lys Pro Met Asp  Gln Lys Arg
    1175                1180                1185

Ser Ser  Ser Leu Gly Ser Asn  Arg Ser Asn Arg Ser  His Thr Ser
    1190                1195                1200
```

-continued

```
Gly Arg Leu Arg Ser Pro Ser Asn Asp Ser Ala His Arg Ser Gly
    1205                1210                1215

Asp Asp Gln Ser Gly Arg Lys Arg Val Leu His Ser Gly Ser Arg
    1220                1225                1230

Asp Arg Glu Lys Thr Lys Ser Leu Glu Ile Thr Gly Glu Arg Lys
    1235                1240                1245

Ser Arg Ile Asp Gln Leu Lys Arg Gly Glu Pro Ser Arg Ser Thr
    1250                1255                1260

Ser Ser Asp Arg Gln Asp Ser Arg Ser His Ser Ser Arg Arg Ser
    1265                1270                1275

Ser Pro Glu Ser Asp Arg Gln Val His Ser Arg Ser Gly Ser Phe
    1280                1285                1290

Asp Ser Arg Asp Arg Leu Gln Glu Arg Asp Arg Tyr Glu His Asp
    1295                1300                1305

Arg Glu Arg Glu Arg Glu Arg Arg Asp Thr Arg Gln Arg Glu Trp
    1310                1315                1320

Asp Arg Asp Ala Asp Lys Asp Trp Pro Arg Asn Arg Asp Arg Asp
    1325                1330                1335

Arg Leu Arg Glu Arg Glu Arg Glu Arg Glu Arg Asp Lys Arg Arg
    1340                1345                1350

Asp Leu Asp Arg Glu Arg Glu Arg Leu Ile Ser Asp Ser Val Glu
    1355                1360                1365

Arg Asp Arg Asp Arg Asp Arg Asp Arg Thr Phe Glu Ser Ser Gln
    1370                1375                1380

Ile Glu Ser Val Lys Arg Cys Glu Ala Lys Leu Glu Gly Glu His
    1385                1390                1395

Glu Arg Asp Leu Glu Ser Thr Ser Arg Asp Ser Leu Ala Leu Asp
    1400                1405                1410

Lys Glu Arg Met Asp Lys Asp Leu Gly Ser Val Gln Gly Phe Glu
    1415                1420                1425

Asp Thr Asn Lys Ser Glu Arg Thr Glu Ser Leu Glu Ala Gly Asp
    1430                1435                1440

Asp Glu Ser Lys Leu Asp Asp Ala His Ser Leu Gly Ser Gly Ala
    1445                1450                1455

Gly Glu Gly Tyr Glu Pro Ile Ser Asp Asp Glu Leu Asp Glu Ile
    1460                1465                1470

Leu Ala Gly Asp Ala Glu Lys Arg Glu Asp Gln Gln Asp Glu Glu
    1475                1480                1485

Lys Met Pro Asp Pro Leu Asp Val Ile Asp Val Asp Trp Ser Gly
    1490                1495                1500

Leu Met Pro Lys His Pro Lys Glu Pro Arg Glu Pro Gly Ala Ala
    1505                1510                1515

Leu Leu Lys Phe Thr Pro Gly Ala Val Met Leu Arg Val Gly Ile
    1520                1525                1530

Ser Lys Lys Leu Ala Gly Ser Glu Leu Phe Ala Lys Val Lys Glu
    1535                1540                1545

Thr Cys Gln Arg Leu Leu Glu Lys Pro Lys Gly Ser Phe Ile Leu
    1550                1555                1560

Leu
```

<210> SEQ ID NO 3
<211> LENGTH: 6429
<212> TYPE: DNA

-continued

```
<213> ORGANISM: Homo sapiens
<220> FEATURE:
<221> NAME/KEY: CDS
<222> LOCATION: (70)..(4764)

<400> SEQUENCE: 3

gagaggaaca gggcaaacct ctgacttccg gcggcatttt gaggcggtcc tcctagcggc      60

ctgtacaaa atg tca aaa att aga agg aag gtc aca gtg gaa aat acc aag     111
          Met Ser Lys Ile Arg Arg Lys Val Thr Val Glu Asn Thr Lys
          1               5                   10

act ata tct gat agc aca tcc cga aga ccc agt gta ttt gag agg ctt       159
Thr Ile Ser Asp Ser Thr Ser Arg Arg Pro Ser Val Phe Glu Arg Leu
15                  20                  25                  30

gga ccc agc act ggc agt aca gca gag aca cag tgc cgt aac tgg ctg       207
Gly Pro Ser Thr Gly Ser Thr Ala Glu Thr Gln Cys Arg Asn Trp Leu
                35                  40                  45

aag act ggc aac tgc ctc tat gga aac aca tgt aga ttc gta cat ggc       255
Lys Thr Gly Asn Cys Leu Tyr Gly Asn Thr Cys Arg Phe Val His Gly
            50                  55                  60

cct tca cct cgt ggt aaa ggt tat agc agc aat tat aga agg tca cca       303
Pro Ser Pro Arg Gly Lys Gly Tyr Ser Ser Asn Tyr Arg Arg Ser Pro
        65                  70                  75

gaa aga cct aca ggg gat ctt aga gaa aga atg aag aac aag cgc caa       351
Glu Arg Pro Thr Gly Asp Leu Arg Glu Arg Met Lys Asn Lys Arg Gln
    80                  85                  90

gac gtg gac act gag ccc cag aaa cga aat aca gag gag tca tcc tca       399
Asp Val Asp Thr Glu Pro Gln Lys Arg Asn Thr Glu Glu Ser Ser Ser
95                  100                 105                 110

cct gtt agg aaa gaa tct tca aga ggg aga cat agg gaa aag gaa gac       447
Pro Val Arg Lys Glu Ser Ser Arg Gly Arg His Arg Glu Lys Glu Asp
                115                 120                 125

ata aaa atc act aag gaa aga act cca gaa agt gaa gaa gaa aat gta       495
Ile Lys Ile Thr Lys Glu Arg Thr Pro Glu Ser Glu Glu Glu Asn Val
            130                 135                 140

gaa tgg gaa act aat aga gat gat tct gac aat gga gat att aat tat       543
Glu Trp Glu Thr Asn Arg Asp Asp Ser Asp Asn Gly Asp Ile Asn Tyr
        145                 150                 155

gat tat gtt cat gaa ttg tca ttg gaa atg aag cgt cag aag ata cag       591
Asp Tyr Val His Glu Leu Ser Leu Glu Met Lys Arg Gln Lys Ile Gln
    160                 165                 170

agg gaa tta atg aag ctg gaa caa gaa aac atg gag aag aga gaa gaa       639
Arg Glu Leu Met Lys Leu Glu Gln Glu Asn Met Glu Lys Arg Glu Glu
175                 180                 185                 190

att atc att aaa aag gag gtt tca cca gaa gtg gtt aga tca aaa ttg       687
Ile Ile Ile Lys Lys Glu Val Ser Pro Glu Val Val Arg Ser Lys Leu
                195                 200                 205

tcc ccg tca cct tct cta aga aag tct agc aaa tct ccg aag cga aaa       735
Ser Pro Ser Pro Ser Leu Arg Lys Ser Ser Lys Ser Pro Lys Arg Lys
            210                 215                 220

tca agc ccg aag tcg tct tca gct agc aag aaa gat agg aag aca tct       783
Ser Ser Pro Lys Ser Ser Ser Ala Ser Lys Lys Asp Arg Lys Thr Ser
        225                 230                 235

gca gta tct tct ccc ctg ttg gac cag cag aga aat tca aaa acc aac       831
Ala Val Ser Ser Pro Leu Leu Asp Gln Gln Arg Asn Ser Lys Thr Asn
    240                 245                 250

caa agt aaa aag aaa gga cca cgt act cct agt cca ccc cct cct ata       879
Gln Ser Lys Lys Lys Gly Pro Arg Thr Pro Ser Pro Pro Pro Pro Ile
255                 260                 265                 270

cca gaa gat atc gct ctg ggg aaa aaa tac aaa gaa aaa tat aaa gta       927
Pro Glu Asp Ile Ala Leu Gly Lys Lys Tyr Lys Glu Lys Tyr Lys Val
```

-continued

```
                275                 280                 285

aaa gac agg ata gaa gaa aaa aca aga gat gga aag gac aga gga cga      975
Lys Asp Arg Ile Glu Glu Lys Thr Arg Asp Gly Lys Asp Arg Gly Arg
            290                 295                 300

gat ttt gaa cga caa aga gaa aag aga gac aag cca agg tct act tcc     1023
Asp Phe Glu Arg Gln Arg Glu Lys Arg Asp Lys Pro Arg Ser Thr Ser
        305                 310                 315

cca gca gga cag cat cat tct cct ata tct tct aga cat cac tca tct     1071
Pro Ala Gly Gln His His Ser Pro Ile Ser Ser Arg His His Ser Ser
    320                 325                 330

tcc tca caa tca gga tca tct att caa aga cat tct cct tct cct cgt     1119
Ser Ser Gln Ser Gly Ser Ser Ile Gln Arg His Ser Pro Ser Pro Arg
335                 340                 345                 350

cga aaa aga act cct tca cca tct tat cag cgg aca cta act cca cct     1167
Arg Lys Arg Thr Pro Ser Pro Ser Tyr Gln Arg Thr Leu Thr Pro Pro
                355                 360                 365

tta cga cgc tct gcc tct cct tat cct tca cat tct ttg tcg tct ccc     1215
Leu Arg Arg Ser Ala Ser Pro Tyr Pro Ser His Ser Leu Ser Ser Pro
            370                 375                 380

cag aga aag cag agt cct cca aga cat cgc tct cca atg cga gag aaa     1263
Gln Arg Lys Gln Ser Pro Pro Arg His Arg Ser Pro Met Arg Glu Lys
        385                 390                 395

ggg aga cat gat cat gaa cga act tca cag tct cat gat cga cgc cac     1311
Gly Arg His Asp His Glu Arg Thr Ser Gln Ser His Asp Arg Arg His
    400                 405                 410

gaa agg agg gaa gat act agg ggc aaa cga gac aga gaa aag gac tca     1359
Glu Arg Arg Glu Asp Thr Arg Gly Lys Arg Asp Arg Glu Lys Asp Ser
415                 420                 425                 430

aga gaa gaa cga gaa tat gaa cag gat cag agc tct tct aga gac cac     1407
Arg Glu Glu Arg Glu Tyr Glu Gln Asp Gln Ser Ser Ser Arg Asp His
                435                 440                 445

aga gat gac aga gaa cct cga gat ggt cgg gat cgg aga gat gcc aga     1455
Arg Asp Asp Arg Glu Pro Arg Asp Gly Arg Asp Arg Arg Asp Ala Arg
            450                 455                 460

gat act agg gac cga agg gaa cta aga gac tcc aga gac atg cgg gac     1503
Asp Thr Arg Asp Arg Arg Glu Leu Arg Asp Ser Arg Asp Met Arg Asp
        465                 470                 475

tca agg gag atg aga gat tat agc aga gat acc aaa gag agc cgt gat     1551
Ser Arg Glu Met Arg Asp Tyr Ser Arg Asp Thr Lys Glu Ser Arg Asp
    480                 485                 490

ccc aga gat tct cgg tcc act cgt gat gcc cat gac tac agg gac cgt     1599
Pro Arg Asp Ser Arg Ser Thr Arg Asp Ala His Asp Tyr Arg Asp Arg
495                 500                 505                 510

gaa ggt cga gat act cat cga aag gag gat aca tat cca gaa gaa tcc     1647
Glu Gly Arg Asp Thr His Arg Lys Glu Asp Thr Tyr Pro Glu Glu Ser
                515                 520                 525

cgg agt tat ggc cga aac cat ttg aga gaa gaa agt tct cgt acg gaa     1695
Arg Ser Tyr Gly Arg Asn His Leu Arg Glu Glu Ser Ser Arg Thr Glu
            530                 535                 540

ata agg aat gag tcc aga aat gag tct cga agt gaa att aga aat gac     1743
Ile Arg Asn Glu Ser Arg Asn Glu Ser Arg Ser Glu Ile Arg Asn Asp
        545                 550                 555

cga atg ggc cga agt agg ggg agg gtt cct gag tta cct gaa aag gga     1791
Arg Met Gly Arg Ser Arg Gly Arg Val Pro Glu Leu Pro Glu Lys Gly
    560                 565                 570

agt cga ggc tca aga ggt tct caa att gat agt cac agt agt aat agc     1839
Ser Arg Gly Ser Arg Gly Ser Gln Ile Asp Ser His Ser Ser Asn Ser
575                 580                 585                 590

aac tat cat gac agc tgg gaa act cga agt agc tat cct gaa aga gat     1887
```

-continued

```
Asn Tyr His Asp Ser Trp Glu Thr Arg Ser Ser Tyr Pro Glu Arg Asp
                595                 600                 605

aga tat cct gaa aga gac aac aga gat caa gca agg gat tct tcc ttt      1935
Arg Tyr Pro Glu Arg Asp Asn Arg Asp Gln Ala Arg Asp Ser Ser Phe
            610                 615                 620

gag aga aga cat gga gag cga gac cgt cgt gac aac aga gag aga gat      1983
Glu Arg Arg His Gly Glu Arg Asp Arg Arg Asp Asn Arg Glu Arg Asp
        625                 630                 635

caa aga cca agc tca cca att cga cat cag gga agg aat gac gag ctt      2031
Gln Arg Pro Ser Ser Pro Ile Arg His Gln Gly Arg Asn Asp Glu Leu
    640                 645                 650

gag cgt gat gaa aga aga gag gaa cga aga gta gac aga gtg gat gat      2079
Glu Arg Asp Glu Arg Arg Glu Glu Arg Arg Val Asp Arg Val Asp Asp
655                 660                 665                 670

agg aga gat gaa agg gct aga gag aga gat cgg gaa cga gaa cga gac      2127
Arg Arg Asp Glu Arg Ala Arg Glu Arg Asp Arg Glu Arg Glu Arg Asp
                675                 680                 685

agg gag cgg gag aga gag agg gaa cgt gaa cgg gat cgg gaa aga gaa      2175
Arg Glu Arg Glu Arg Glu Arg Glu Arg Glu Arg Asp Arg Glu Arg Glu
            690                 695                 700

aaa gag aga gaa cta gaa aga gag cgt gct agg gaa cgg gag aga gaa      2223
Lys Glu Arg Glu Leu Glu Arg Glu Arg Ala Arg Glu Arg Glu Arg Glu
        705                 710                 715

aga gaa aaa gag aga gat cgt gaa agg gat aga gac cga gac cac gat      2271
Arg Glu Lys Glu Arg Asp Arg Glu Arg Asp Arg Asp Arg Asp His Asp
    720                 725                 730

cga gag cgg gaa aga gag agg gaa cga gac agg gaa aaa gaa cgg gaa      2319
Arg Glu Arg Glu Arg Glu Arg Glu Arg Asp Arg Glu Lys Glu Arg Glu
735                 740                 745                 750

cga gaa aga gaa gag aga gag agg gag aga gag cga gaa cgg gag aga      2367
Arg Glu Arg Glu Glu Arg Glu Arg Glu Arg Glu Arg Glu Arg Glu Arg
                755                 760                 765

gag cga gag cga gaa cgg gaa cga gaa aga gcg aga gaa agg gat aaa      2415
Glu Arg Glu Arg Glu Arg Glu Arg Glu Arg Ala Arg Glu Arg Asp Lys
            770                 775                 780

gaa cga gaa cgc caa agg gat tgg gaa gac aaa gac aaa gga cga gat      2463
Glu Arg Glu Arg Gln Arg Asp Trp Glu Asp Lys Asp Lys Gly Arg Asp
        785                 790                 795

gac cgc aga gaa aag cga gaa gag atc cga gaa gat agg aat cca aga      2511
Asp Arg Arg Glu Lys Arg Glu Glu Ile Arg Glu Asp Arg Asn Pro Arg
    800                 805                 810

gat gga cat gat gaa aga aaa tca aag aag cgc tat aga aat gaa ggg      2559
Asp Gly His Asp Glu Arg Lys Ser Lys Lys Arg Tyr Arg Asn Glu Gly
815                 820                 825                 830

agt ccc agc cct aga cag tcc ccg aag cgc cgg cgt gaa cat tct ccg      2607
Ser Pro Ser Pro Arg Gln Ser Pro Lys Arg Arg Arg Glu His Ser Pro
                835                 840                 845

gac agt gat gcc tac aac agt gga gat gat aaa aat gaa aaa cac aga      2655
Asp Ser Asp Ala Tyr Asn Ser Gly Asp Asp Lys Asn Glu Lys His Arg
            850                 855                 860

ctc ttg agc caa gtt gta cga cct caa gaa tct cgt tct ctt agt ccc      2703
Leu Leu Ser Gln Val Val Arg Pro Gln Glu Ser Arg Ser Leu Ser Pro
        865                 870                 875

tcg cac ctc aca gaa gac aga cag ggt aga tgg aaa gag gag gat cgt      2751
Ser His Leu Thr Glu Asp Arg Gln Gly Arg Trp Lys Glu Glu Asp Arg
    880                 885                 890

aaa cca gaa agg aaa gag agt tca agg cgc tac gaa gaa cag gaa ctc      2799
Lys Pro Glu Arg Lys Glu Ser Ser Arg Arg Tyr Glu Glu Gln Glu Leu
895                 900                 905                 910
```

-continued

```
aag gag aaa gtt tct tct gta gat aaa cag aga gaa cag aca gaa atc      2847
Lys Glu Lys Val Ser Ser Val Asp Lys Gln Arg Glu Gln Thr Glu Ile
                915                 920                 925

ctg gaa agc tca aga atg cgt gca cag gac att ata gga cac cac cag      2895
Leu Glu Ser Ser Arg Met Arg Ala Gln Asp Ile Ile Gly His His Gln
            930                 935                 940

tct gaa gat cga gag aca tct gat cga gct cat gat gaa aac aag aag      2943
Ser Glu Asp Arg Glu Thr Ser Asp Arg Ala His Asp Glu Asn Lys Lys
        945                 950                 955

aaa gca aaa att caa aag aaa cca att aag aaa aag aaa gag gat gat      2991
Lys Ala Lys Ile Gln Lys Lys Pro Ile Lys Lys Lys Lys Glu Asp Asp
    960                 965                 970

gtt gga ata gag agg ggt aac ata gag aca aca tct gaa gat ggt caa      3039
Val Gly Ile Glu Arg Gly Asn Ile Glu Thr Thr Ser Glu Asp Gly Gln
975                 980                 985                 990

gta ttt tca cca aaa aaa gga cag aaa aag  aaa agc att gaa aaa  aaa    3087
Val Phe Ser Pro Lys Lys Gly Gln Lys Lys  Lys Ser Ile Glu Lys  Lys
                995                 1000                1005

cgt aaa aaa tcc  aaa ggt gat tct gat  att tct gat gaa gaa  gca       3132
Arg Lys Lys Ser  Lys Gly Asp Ser Asp  Ile Ser Asp Glu Glu  Ala
            1010                 1015                 1020

gcc cag caa agt  aag aag aaa aga ggc  cca cgg act ccc cct  ata       3177
Ala Gln Gln Ser  Lys Lys Lys Arg Gly  Pro Arg Thr Pro Pro  Ile
            1025                 1030                 1035

aca act aaa gag  gaa ttg gtt gaa atg  tgc aat ggt aag aat  ggt       3222
Thr Thr Lys Glu  Glu Leu Val Glu Met  Cys Asn Gly Lys Asn  Gly
            1040                 1045                 1050

att cta gag gac  tcc cag aaa aaa gaa  gat aca gca ttc agt  gac       3267
Ile Leu Glu Asp  Ser Gln Lys Lys Glu  Asp Thr Ala Phe Ser  Asp
            1055                 1060                 1065

tgg tct gat gag  gat gtc cct gac cgt  aca gag gtg aca gaa  gca       3312
Trp Ser Asp Glu  Asp Val Pro Asp Arg  Thr Glu Val Thr Glu  Ala
            1070                 1075                 1080

gag cat act gcc  acc gcc acg act cct  ggt agt acc cct tct  cct       3357
Glu His Thr Ala  Thr Ala Thr Thr Pro  Gly Ser Thr Pro Ser  Pro
            1085                 1090                 1095

cta tct tct ctt  ctt cct cct cca ccg  cct gtg gct act gcc  act       3402
Leu Ser Ser Leu  Leu Pro Pro Pro Pro  Pro Val Ala Thr Ala  Thr
            1100                 1105                 1110

gct aca act gtg  cct gca act ctt gct  gcc act act gct gct  gcc       3447
Ala Thr Thr Val  Pro Ala Thr Leu Ala  Ala Thr Thr Ala Ala  Ala
            1115                 1120                 1125

gcc acc tct ttc  agc aca tct gcc atc  act att tcc acc tct  gcc       3492
Ala Thr Ser Phe  Ser Thr Ser Ala Ile  Thr Ile Ser Thr Ser  Ala
            1130                 1135                 1140

acc ccc acc aat  acc acc aat aat act  ttt gcc aat gaa gac  tca       3537
Thr Pro Thr Asn  Thr Thr Asn Asn Thr  Phe Ala Asn Glu Asp  Ser
            1145                 1150                 1155

cac aga aaa tgc  cac aga aca cga gta  gaa aaa gta gag acg  cct       3582
His Arg Lys Cys  His Arg Thr Arg Val  Glu Lys Val Glu Thr  Pro
            1160                 1165                 1170

cac gtg act ata  gaa gat gca cag cat  cgc aag cct atg gat  caa       3627
His Val Thr Ile  Glu Asp Ala Gln His  Arg Lys Pro Met Asp  Gln
            1175                 1180                 1185

aag agg agc agc  agc ctc ggg agc aat  cgg agt aac cgt agt  cat       3672
Lys Arg Ser Ser  Ser Leu Gly Ser Asn  Arg Ser Asn Arg Ser  His
            1190                 1195                 1200

acg tct ggt cgt  ctt cgc tcc cca tcc  aat gat tca gcc cat  cga       3717
Thr Ser Gly Arg  Leu Arg Ser Pro Ser  Asn Asp Ser Ala His  Arg
            1205                 1210                 1215
```

-continued

```
agt gga gat gac  caa agt ggt cga aag  aga gta ctg cac agt  ggc      3762
Ser Gly Asp Asp  Gln Ser Gly Arg Lys  Arg Val Leu His Ser  Gly
            1220                 1225                 1230

tca aga gat aga  gaa aaa aca aaa agc  ctg gaa atc aca gga  gag      3807
Ser Arg Asp Arg  Glu Lys Thr Lys Ser  Leu Glu Ile Thr Gly  Glu
            1235                 1240                 1245

aga aaa tct agg  att gat cag tta aag  cgt gga gaa ccc agt  cga      3852
Arg Lys Ser Arg  Ile Asp Gln Leu Lys  Arg Gly Glu Pro Ser  Arg
            1250                 1255                 1260

agt act tct tca  gat cgc cag gat tca  aga agc cat agt tca  aga      3897
Ser Thr Ser Ser  Asp Arg Gln Asp Ser  Arg Ser His Ser Ser  Arg
            1265                 1270                 1275

aga agt tct cca  gag tca gat cga cag  gtc cat tca aga tct  ggg      3942
Arg Ser Ser Pro  Glu Ser Asp Arg Gln  Val His Ser Arg Ser  Gly
            1280                 1285                 1290

tca ttt gat agc  aga gac agg ctt caa  gaa cga gat cga tat  gaa      3987
Ser Phe Asp Ser  Arg Asp Arg Leu Gln  Glu Arg Asp Arg Tyr  Glu
            1295                 1300                 1305

cac gac aga gag  cgc gag aga gag agg  aga gat acg agg cag  aga      4032
His Asp Arg Glu  Arg Glu Arg Glu Arg  Arg Asp Thr Arg Gln  Arg
            1310                 1315                 1320

gaa tgg gac cga  gat gct gat aaa gat  tgg cca cgc aac agg  gat      4077
Glu Trp Asp Arg  Asp Ala Asp Lys Asp  Trp Pro Arg Asn Arg  Asp
            1325                 1330                 1335

cga gat aga ttg  cga gaa cga gaa cga  gag aga gaa cga gac  aaa      4122
Arg Asp Arg Leu  Arg Glu Arg Glu Arg  Glu Arg Glu Arg Asp  Lys
            1340                 1345                 1350

agg aga gac ttg  gat agg gaa aga gag  aga cta att tct gat  tct      4167
Arg Arg Asp Leu  Asp Arg Glu Arg Glu  Arg Leu Ile Ser Asp  Ser
            1355                 1360                 1365

gtt gaa agg gac  agg gac aga gac aga  gac aga act ttt gag  agt      4212
Val Glu Arg Asp  Arg Asp Arg Asp Arg  Asp Arg Thr Phe Glu  Ser
            1370                 1375                 1380

tct caa ata gag  tct gtg aaa cgc tgt  gaa gca aaa ctg gaa  ggt      4257
Ser Gln Ile Glu  Ser Val Lys Arg Cys  Glu Ala Lys Leu Glu  Gly
            1385                 1390                 1395

gaa cat gaa agg  gat cta gaa agc act  tcc cga gac tct cta  gcc      4302
Glu His Glu Arg  Asp Leu Glu Ser Thr  Ser Arg Asp Ser Leu  Ala
            1400                 1405                 1410

ttg gat aaa gag  aga atg gat aaa gat  ctg gga tct gtg cag  gga      4347
Leu Asp Lys Glu  Arg Met Asp Lys Asp  Leu Gly Ser Val Gln  Gly
            1415                 1420                 1425

ttt gaa gat aca  aat aaa tcc gag aga  act gag agt ctg gaa  gca      4392
Phe Glu Asp Thr  Asn Lys Ser Glu Arg  Thr Glu Ser Leu Glu  Ala
            1430                 1435                 1440

gga gat gac gag  tcc aag tta gat gat  gca cat tca tta ggc  tct      4437
Gly Asp Asp Glu  Ser Lys Leu Asp Asp  Ala His Ser Leu Gly  Ser
            1445                 1450                 1455

ggt gct gga gaa  gga tac gag cca atc  agt gat gac gaa cta  gat      4482
Gly Ala Gly Glu  Gly Tyr Glu Pro Ile  Ser Asp Asp Glu Leu  Asp
            1460                 1465                 1470

gaa att ctg gca  ggt gat gca gaa aag  agg gag gac caa cag  gat      4527
Glu Ile Leu Ala  Gly Asp Ala Glu Lys  Arg Glu Asp Gln Gln  Asp
            1475                 1480                 1485

gag gag aag atg  cca gat ccc tta gat  gtg ata gat gtg gat  tgg      4572
Glu Glu Lys Met  Pro Asp Pro Leu Asp  Val Ile Asp Val Asp  Trp
            1490                 1495                 1500

tct ggt ctt atg  cca aag cat cca aaa  gaa cca cga gag cct  ggg      4617
Ser Gly Leu Met  Pro Lys His Pro Lys  Glu Pro Arg Glu Pro  Gly
```

-continued

```
            1505                1510                1515

gct gca ctc tta  aaa ttc aca cct gga  gct gtt atg cta aga  gtt      4662
Ala Ala Leu Leu  Lys Phe Thr Pro Gly  Ala Val Met Leu Arg  Val
            1520                1525                1530

ggg att tct aaa  aag ttg gca ggt tct  gaa ctc ttt gcc aaa  gtc      4707
Gly Ile Ser Lys  Lys Leu Ala Gly Ser  Glu Leu Phe Ala Lys  Val
            1535                1540                1545

aaa gaa aca tgt  cag aga ctt tta gaa  aaa ccc aaa ggt agt  ttc      4752
Lys Glu Thr Cys  Gln Arg Leu Leu Glu  Lys Pro Lys Gly Ser  Phe
            1550                1555                1560

att tta ctt taa ctatataatg tctgttaacc atttaagatg ccatctgaag         4804
Ile Leu Leu

gggattctga tctgttctta tgtagcactt aacactgtgt agaaactatt ttttgagaaa   4864

tcattttata atcattattt aaccctcatg gtcaaagttt ctctttaaaa tttattttga   4924

gaagaagagt tatcccacag aaaagttggg aaaagagtac aatgaccttt ttgtatgaaa   4984

attacttatt aacaggccag gcgtggtgtt gcatgtctgt agtcacagct actcagggag   5044

gttgaggcag caggattgct ggagcccagg aaattgaggc tgcagtgagc catgattgag   5104

ccaccacact ccaacctagg tgacagagca agaccctgtc tcaaaaaaaa aaaaacaaat   5164

taaccaataa gttctaatat caaagtgctc agtggtttgc ccttggctaa atgaagcaga   5224

gccaggaaaa acagactaca tatttttcat gtctaaagaa attgggtatt ttggcagccc   5284

tttcccctag acatctaccc aaatgcaggt gtgtaggttg agtctttaac aaagtgatta   5344

agagcttggt ctgtaaggcc ggatgatctg gatttcagta ggcacaccac ttactggcta   5404

ttacttaatc tgtgtgttag tgtcatcatc tgtaagtcag gaataatcat accaccaact   5464

tcctatggta attaggagca aatgagttat tacaggcaaa acacttagaa cagttcctgg   5524

catatagtaa tacccaataa atattaactg ctactttgaa aatatcctat cacgctgatt   5584

tttgacctca ctgcagcaat tttcagttat tccagattat ctagcttatg gattctggtg   5644

gtaggggttg tttggttttg gttttcactg tctctgtctc atctagtacc taccttagtt   5704

tattttgcaa cttactaata ctttattaat ggggagggac gagtagatgg taaaaagaag   5764

gaaaaggagg taaaaggtga aaggaacaac attaattaac aattttacgt catgtccctg   5824

gacataaaag tttagttagt attaaatttt tcactaatac aaaataaaaa aatattgttt   5884

tatgagtttt atgaattcat gcccttcctt tactctatta gcataagcag taaatttttt   5944

tattttaata tagcccaata aacctagagt atacatgtac aaaatacata taattgttaa   6004

cgtgtattaa ccgaaaaatg acccaagact tagttcttgc cctactgtat ctgccttgtt   6064

tggttggttc tgtgacctta agcaaataac tcctgtgagc ctcaatttta tttgtaaagt   6124

gatggaataa aacccctaaa atcttaccca cctctaaaga tatttgtttc tgtgaccttt   6184

tgctagtagc atttcaagtt aaaatctggt ttgattttgc tacccatgaa atacagttcg   6244

gcccttactt attgatgact taacctaaac agtgaaaata tgcactgtaa agggtggggt   6304

gatgtggctt aacaatcaga cttcttctat ttttgctgct atggtggttg tattagagaa   6364

ctgatgtatt atcttgaata aagactttgt cttgtttact gccctaaaaa aaaaaaaaaa   6424

aaaaa                                                               6429
```

<210> SEQ ID NO 4
<211> LENGTH: 1564
<212> TYPE: PRT
<213> ORGANISM: Homo sapiens -continued

<400> SEQUENCE: 4

Met Ser Lys Ile Arg Arg Lys Val Thr Val Glu Asn Thr Lys Thr Ile
1               5                   10                  15

Ser Asp Ser Thr Ser Arg Arg Pro Ser Val Phe Glu Arg Leu Gly Pro
            20                  25                  30

Ser Thr Gly Ser Thr Ala Glu Thr Gln Cys Arg Asn Trp Leu Lys Thr
        35                  40                  45

Gly Asn Cys Leu Tyr Gly Asn Thr Cys Arg Phe Val His Gly Pro Ser
    50                  55                  60

Pro Arg Gly Lys Gly Tyr Ser Ser Asn Tyr Arg Arg Ser Pro Glu Arg
65                  70                  75                  80

Pro Thr Gly Asp Leu Arg Glu Arg Met Lys Asn Lys Arg Gln Asp Val
                85                  90                  95

Asp Thr Glu Pro Gln Lys Arg Asn Thr Glu Glu Ser Ser Ser Pro Val
            100                 105                 110

Arg Lys Glu Ser Ser Arg Gly Arg His Arg Glu Lys Glu Asp Ile Lys
        115                 120                 125

Ile Thr Lys Glu Arg Thr Pro Glu Ser Glu Glu Glu Asn Val Glu Trp
    130                 135                 140

Glu Thr Asn Arg Asp Asp Ser Asp Asn Gly Asp Ile Asn Tyr Asp Tyr
145                 150                 155                 160

Val His Glu Leu Ser Leu Glu Met Lys Arg Gln Lys Ile Gln Arg Glu
                165                 170                 175

Leu Met Lys Leu Glu Gln Glu Asn Met Glu Lys Arg Glu Glu Ile Ile
            180                 185                 190

Ile Lys Lys Glu Val Ser Pro Glu Val Val Arg Ser Lys Leu Ser Pro
        195                 200                 205

Ser Pro Ser Leu Arg Lys Ser Ser Lys Ser Pro Lys Arg Lys Ser Ser
    210                 215                 220

Pro Lys Ser Ser Ser Ala Ser Lys Lys Asp Arg Lys Thr Ser Ala Val
225                 230                 235                 240

Ser Ser Pro Leu Leu Asp Gln Gln Arg Asn Ser Lys Thr Asn Gln Ser
                245                 250                 255

Lys Lys Lys Gly Pro Arg Thr Pro Ser Pro Pro Pro Pro Ile Pro Glu
            260                 265                 270

Asp Ile Ala Leu Gly Lys Lys Tyr Lys Glu Lys Tyr Lys Val Lys Asp
        275                 280                 285

Arg Ile Glu Glu Lys Thr Arg Asp Gly Lys Asp Arg Gly Arg Asp Phe
    290                 295                 300

Glu Arg Gln Arg Glu Lys Arg Asp Lys Pro Arg Ser Thr Ser Pro Ala
305                 310                 315                 320

Gly Gln His His Ser Pro Ile Ser Ser Arg His His Ser Ser Ser Ser
                325                 330                 335

Gln Ser Gly Ser Ser Ile Gln Arg His Ser Pro Ser Pro Arg Arg Lys
            340                 345                 350

Arg Thr Pro Ser Pro Ser Tyr Gln Arg Thr Leu Thr Pro Pro Leu Arg
        355                 360                 365

Arg Ser Ala Ser Pro Tyr Pro Ser His Ser Leu Ser Ser Pro Gln Arg
    370                 375                 380

Lys Gln Ser Pro Pro Arg His Arg Ser Pro Met Arg Glu Lys Gly Arg
385                 390                 395                 400

His Asp His Glu Arg Thr Ser Gln Ser His Asp Arg Arg His Glu Arg
                405                 410                 415

-continued

```
Arg Glu Asp Thr Arg Gly Lys Arg Asp Arg Glu Lys Asp Ser Arg Glu
            420                 425                 430

Glu Arg Glu Tyr Glu Gln Asp Gln Ser Ser Ser Arg Asp His Arg Asp
        435                 440                 445

Asp Arg Glu Pro Arg Asp Gly Arg Asp Arg Arg Asp Ala Arg Asp Thr
    450                 455                 460

Arg Asp Arg Arg Glu Leu Arg Asp Ser Arg Asp Met Arg Asp Ser Arg
465                 470                 475                 480

Glu Met Arg Asp Tyr Ser Arg Asp Thr Lys Glu Ser Arg Asp Pro Arg
                485                 490                 495

Asp Ser Arg Ser Thr Arg Asp Ala His Asp Tyr Arg Asp Arg Glu Gly
            500                 505                 510

Arg Asp Thr His Arg Lys Glu Asp Thr Tyr Pro Glu Glu Ser Arg Ser
        515                 520                 525

Tyr Gly Arg Asn His Leu Arg Glu Glu Ser Ser Arg Thr Glu Ile Arg
    530                 535                 540

Asn Glu Ser Arg Asn Glu Ser Arg Ser Glu Ile Arg Asn Asp Arg Met
545                 550                 555                 560

Gly Arg Ser Arg Gly Arg Val Pro Glu Leu Pro Glu Lys Gly Ser Arg
                565                 570                 575

Gly Ser Arg Gly Ser Gln Ile Asp Ser His Ser Ser Asn Ser Asn Tyr
            580                 585                 590

His Asp Ser Trp Glu Thr Arg Ser Ser Tyr Pro Glu Arg Asp Arg Tyr
        595                 600                 605

Pro Glu Arg Asp Asn Arg Asp Gln Ala Arg Asp Ser Ser Phe Glu Arg
    610                 615                 620

Arg His Gly Glu Arg Asp Arg Arg Asp Asn Arg Glu Arg Asp Gln Arg
625                 630                 635                 640

Pro Ser Ser Pro Ile Arg His Gln Gly Arg Asn Asp Glu Leu Glu Arg
                645                 650                 655

Asp Glu Arg Arg Glu Glu Arg Arg Val Asp Arg Val Asp Asp Arg Arg
            660                 665                 670

Asp Glu Arg Ala Arg Glu Arg Asp Arg Glu Arg Glu Arg Asp Arg Glu
        675                 680                 685

Arg Glu Arg Glu Arg Glu Arg Glu Arg Asp Arg Glu Arg Glu Lys Glu
    690                 695                 700

Arg Glu Leu Glu Arg Glu Arg Ala Arg Glu Arg Glu Arg Glu Arg Glu
705                 710                 715                 720

Lys Glu Arg Asp Arg Glu Arg Asp Arg Asp Arg Asp His Asp Arg Glu
                725                 730                 735

Arg Glu Arg Glu Arg Glu Arg Asp Arg Glu Lys Glu Arg Glu Arg Glu
            740                 745                 750

Arg Glu Glu Arg Glu Arg Glu Arg Glu Arg Glu Arg Glu Arg Glu Arg
        755                 760                 765

Glu Arg Glu Arg Glu Arg Glu Arg Ala Arg Glu Arg Asp Lys Glu Arg
    770                 775                 780

Glu Arg Gln Arg Asp Trp Glu Asp Lys Asp Lys Gly Arg Asp Asp Arg
785                 790                 795                 800

Arg Glu Lys Arg Glu Glu Ile Arg Glu Asp Arg Asn Pro Arg Asp Gly
                805                 810                 815

His Asp Glu Arg Lys Ser Lys Lys Arg Tyr Arg Asn Glu Gly Ser Pro
            820                 825                 830
```

-continued

```
Ser Pro Arg Gln Ser Pro Lys Arg Arg Arg Glu His Ser Pro Asp Ser
        835                 840                 845

Asp Ala Tyr Asn Ser Gly Asp Asp Lys Asn Glu Lys His Arg Leu Leu
    850                 855                 860

Ser Gln Val Val Arg Pro Gln Glu Ser Arg Ser Leu Ser Pro Ser His
865                 870                 875                 880

Leu Thr Glu Asp Arg Gln Gly Arg Trp Lys Glu Glu Asp Arg Lys Pro
                885                 890                 895

Glu Arg Lys Glu Ser Ser Arg Arg Tyr Glu Glu Gln Glu Leu Lys Glu
            900                 905                 910

Lys Val Ser Ser Val Asp Lys Gln Arg Glu Gln Thr Glu Ile Leu Glu
        915                 920                 925

Ser Ser Arg Met Arg Ala Gln Asp Ile Ile Gly His His Gln Ser Glu
    930                 935                 940

Asp Arg Glu Thr Ser Asp Arg Ala His Asp Glu Asn Lys Lys Lys Ala
945                 950                 955                 960

Lys Ile Gln Lys Lys Pro Ile Lys Lys Lys Lys Glu Asp Asp Val Gly
                965                 970                 975

Ile Glu Arg Gly Asn Ile Glu Thr Thr Ser Glu Asp Gly Gln Val Phe
            980                 985                 990

Ser Pro Lys Lys Gly Gln Lys Lys  Lys Ser Ile Glu Lys  Lys Arg Lys
        995                 1000                1005

Lys Ser  Lys Gly Asp Ser Asp  Ile Ser Asp Glu Glu  Ala Ala Gln
    1010                 1015                 1020

Gln Ser  Lys Lys Lys Arg Gly  Pro Arg Thr Pro Pro  Ile Thr Thr
    1025                 1030                 1035

Lys Glu  Glu Leu Val Glu Met  Cys Asn Gly Lys Asn  Gly Ile Leu
    1040                 1045                 1050

Glu Asp  Ser Gln Lys Lys Glu  Asp Thr Ala Phe Ser  Asp Trp Ser
    1055                 1060                 1065

Asp Glu  Asp Val Pro Asp Arg  Thr Glu Val Thr Glu  Ala Glu His
    1070                 1075                 1080

Thr Ala  Thr Ala Thr Thr Pro  Gly Ser Thr Pro Ser  Pro Leu Ser
    1085                 1090                 1095

Ser Leu  Leu Pro Pro Pro Pro  Pro Val Ala Thr Ala  Thr Ala Thr
    1100                 1105                 1110

Thr Val  Pro Ala Thr Leu Ala  Ala Thr Thr Ala Ala  Ala Ala Thr
    1115                 1120                 1125

Ser Phe  Ser Thr Ser Ala Ile  Thr Ile Ser Thr Ser  Ala Thr Pro
    1130                 1135                 1140

Thr Asn  Thr Thr Asn Asn Thr  Phe Ala Asn Glu Asp  Ser His Arg
    1145                 1150                 1155

Lys Cys  His Arg Thr Arg Val  Glu Lys Val Glu Thr  Pro His Val
    1160                 1165                 1170

Thr Ile  Glu Asp Ala Gln His  Arg Lys Pro Met Asp  Gln Lys Arg
    1175                 1180                 1185

Ser Ser  Ser Leu Gly Ser Asn  Arg Ser Asn Arg Ser  His Thr Ser
    1190                 1195                 1200

Gly Arg  Leu Arg Ser Pro Ser  Asn Asp Ser Ala His  Arg Ser Gly
    1205                 1210                 1215

Asp Asp  Gln Ser Gly Arg Lys  Arg Val Leu His Ser  Gly Ser Arg
    1220                 1225                 1230

Asp Arg  Glu Lys Thr Lys Ser  Leu Glu Ile Thr Gly  Glu Arg Lys
```

-continued

```
    1235                1240                1245

Ser Arg  Ile Asp Gln Leu Lys  Arg Gly Glu Pro Ser  Arg Ser Thr
    1250                1255                1260

Ser Ser  Asp Arg Gln Asp Ser  Arg Ser His Ser Ser  Arg Arg Ser
    1265                1270                1275

Ser Pro  Glu Ser Asp Arg Gln  Val His Ser Arg Ser  Gly Ser Phe
    1280                1285                1290

Asp Ser  Arg Asp Arg Leu Gln  Glu Arg Asp Arg Tyr  Glu His Asp
    1295                1300                1305

Arg Glu  Arg Glu Arg Glu Arg  Arg Asp Thr Arg Gln  Arg Glu Trp
    1310                1315                1320

Asp Arg  Asp Ala Asp Lys Asp  Trp Pro Arg Asn Arg  Asp Arg Asp
    1325                1330                1335

Arg Leu  Arg Glu Arg Glu Arg  Glu Arg Glu Arg Asp  Lys Arg Arg
    1340                1345                1350

Asp Leu  Asp Arg Glu Arg Glu  Arg Leu Ile Ser Asp  Ser Val Glu
    1355                1360                1365

Arg Asp  Arg Asp Arg Asp Arg  Asp Arg Thr Phe Glu  Ser Ser Gln
    1370                1375                1380

Ile Glu  Ser Val Lys Arg Cys  Glu Ala Lys Leu Glu  Gly Glu His
    1385                1390                1395

Glu Arg  Asp Leu Glu Ser Thr  Ser Arg Asp Ser Leu  Ala Leu Asp
    1400                1405                1410

Lys Glu  Arg Met Asp Lys Asp  Leu Gly Ser Val Gln  Gly Phe Glu
    1415                1420                1425

Asp Thr  Asn Lys Ser Glu Arg  Thr Glu Ser Leu Glu  Ala Gly Asp
    1430                1435                1440

Asp Glu  Ser Lys Leu Asp Asp  Ala His Ser Leu Gly  Ser Gly Ala
    1445                1450                1455

Gly Glu  Gly Tyr Glu Pro Ile  Ser Asp Asp Glu Leu  Asp Glu Ile
    1460                1465                1470

Leu Ala  Gly Asp Ala Glu Lys  Arg Glu Asp Gln Gln  Asp Glu Glu
    1475                1480                1485

Lys Met  Pro Asp Pro Leu Asp  Val Ile Asp Val Asp  Trp Ser Gly
    1490                1495                1500

Leu Met  Pro Lys His Pro Lys  Glu Pro Arg Glu Pro  Gly Ala Ala
    1505                1510                1515

Leu Leu  Lys Phe Thr Pro Gly  Ala Val Met Leu Arg  Val Gly Ile
    1520                1525                1530

Ser Lys  Lys Leu Ala Gly Ser  Glu Leu Phe Ala Lys  Val Lys Glu
    1535                1540                1545

Thr Cys  Gln Arg Leu Leu Glu  Lys Pro Lys Gly Ser  Phe Ile Leu
    1550                1555                1560

Leu
```

```
<210> SEQ ID NO 5
<211> LENGTH: 6164
<212> TYPE: DNA
<213> ORGANISM: Homo sapiens
<220> FEATURE:
<221> NAME/KEY: CDS
<222> LOCATION: (314)..(2398)

<400> SEQUENCE: 5

gtaaaacttt ggacaatact tattacttta ttgactgtgt tagtttcttc ttcttaagta     60
```

-continued

```
gactgttgtc atctcttttc ttttgagtcc aattttccta tagtttgttt atgtcaatgg    120

ctcgacaaaa tgataaaata tatttccaga aagcacatgg atttggaact ctctcttgtt    180

atgtttatat taggctttat tttaaaggca agtgagactg cttcaaataa aacaacttca    240

agcttccaag aaacagttaa gaggaggcag agaggagcag aaacacttct ttgctgacac    300

ttacactgtt gcc atg gac cta cat aag cag tgg gag aac aca gag act       349
               Met Asp Leu His Lys Gln Trp Glu Asn Thr Glu Thr
               1               5                   10

aac tgg cat aag gaa aag atg gaa tta ctg gac cag ttt gac aat gaa      397
Asn Trp His Lys Glu Lys Met Glu Leu Leu Asp Gln Phe Asp Asn Glu
        15                  20                  25

aga aag gaa tgg gaa agt caa tgg aag att atg cag aag aaa ata gaa      445
Arg Lys Glu Trp Glu Ser Gln Trp Lys Ile Met Gln Lys Lys Ile Glu
    30                  35                  40

gag ctt tgc cgg gaa gta aag ctt tgg agg aaa atc aat atc aat gaa      493
Glu Leu Cys Arg Glu Val Lys Leu Trp Arg Lys Ile Asn Ile Asn Glu
45                  50                  55                  60

agt gct aag atc att gat ctt tac cat gag aag acc att cca gag aaa      541
Ser Ala Lys Ile Ile Asp Leu Tyr His Glu Lys Thr Ile Pro Glu Lys
                65                  70                  75

gtg ata gaa tct tcc cca aat tac ccc gat tta gga caa agt gaa ttt      589
Val Ile Glu Ser Ser Pro Asn Tyr Pro Asp Leu Gly Gln Ser Glu Phe
            80                  85                  90

ata agg acg aat cac aaa gat ggt ctg aga aaa gaa aat aaa aga gag      637
Ile Arg Thr Asn His Lys Asp Gly Leu Arg Lys Glu Asn Lys Arg Glu
        95                  100                 105

cag agc tta gtc agt gga gga aat caa atg tgt aag gaa caa aaa gca      685
Gln Ser Leu Val Ser Gly Gly Asn Gln Met Cys Lys Glu Gln Lys Ala
    110                 115                 120

aca aaa aaa tca aaa gta ggg ttt ttg gat cct ttg gct aca gac aac      733
Thr Lys Lys Ser Lys Val Gly Phe Leu Asp Pro Leu Ala Thr Asp Asn
125                 130                 135                 140

caa aag gaa tgt gag gcc tgg cct gac ctg agg act tct gag gaa gac      781
Gln Lys Glu Cys Glu Ala Trp Pro Asp Leu Arg Thr Ser Glu Glu Asp
                145                 150                 155

agc aag agc tgt tct ggc gcc ctc agt aca gct ctt gaa gaa ctt gcg      829
Ser Lys Ser Cys Ser Gly Ala Leu Ser Thr Ala Leu Glu Glu Leu Ala
            160                 165                 170

aag gtg agt gaa gaa tta tgc agc ttt caa gag gaa att cga aag cgg      877
Lys Val Ser Glu Glu Leu Cys Ser Phe Gln Glu Glu Ile Arg Lys Arg
        175                 180                 185

tct aac cat aga agg atg aag tca gat tct ttt ctc cag gaa atg cca      925
Ser Asn His Arg Arg Met Lys Ser Asp Ser Phe Leu Gln Glu Met Pro
    190                 195                 200

aat gta act aat ata cct cat ggg gac ccc atg atc aac aat gac cag      973
Asn Val Thr Asn Ile Pro His Gly Asp Pro Met Ile Asn Asn Asp Gln
205                 210                 215                 220

tgc att ctt cca atc agt tta gaa aaa gaa aaa cag aaa aac agg aag     1021
Cys Ile Leu Pro Ile Ser Leu Glu Lys Glu Lys Gln Lys Asn Arg Lys
                225                 230                 235

aat ctg agc tgt acc aat gtg ctc cag agc aat tct acg aaa aaa tgt     1069
Asn Leu Ser Cys Thr Asn Val Leu Gln Ser Asn Ser Thr Lys Lys Cys
            240                 245                 250

gga att gat aca atc gat tta aaa aga aat gaa act cca cca gtt cct     1117
Gly Ile Asp Thr Ile Asp Leu Lys Arg Asn Glu Thr Pro Pro Val Pro
        255                 260                 265

cct cca aga agc acc tct cga aat ttt ccc agc tcg gat tct gaa caa     1165
Pro Pro Arg Ser Thr Ser Arg Asn Phe Pro Ser Ser Asp Ser Glu Gln
```

-continued

```
    270                 275                 280

gcc tat gaa aga tgg aag gaa agg tta gac cac aac agc tgg gtg ccc      1213
Ala Tyr Glu Arg Trp Lys Glu Arg Leu Asp His Asn Ser Trp Val Pro
285                 290                 295                 300

cat gag ggt cga agt aaa agg aat tac aac cct cac ttc cct ttg aga      1261
His Glu Gly Arg Ser Lys Arg Asn Tyr Asn Pro His Phe Pro Leu Arg
                305                 310                 315

caa caa gag atg tct atg ttg tat cca aat gaa ggg aaa act tcg aaa      1309
Gln Gln Glu Met Ser Met Leu Tyr Pro Asn Glu Gly Lys Thr Ser Lys
            320                 325                 330

gat ggt atc atc ttt tcc tct ttg gta cca gaa gtc aaa ata gat agc      1357
Asp Gly Ile Ile Phe Ser Ser Leu Val Pro Glu Val Lys Ile Asp Ser
        335                 340                 345

aag cct cca agt aat gaa gat gtt gga ctt agc atg tgg tca tgt gac      1405
Lys Pro Pro Ser Asn Glu Asp Val Gly Leu Ser Met Trp Ser Cys Asp
    350                 355                 360

att ggg ata ggt gca aaa agg agc ccc tct act tcg tgg ttt cag aaa      1453
Ile Gly Ile Gly Ala Lys Arg Ser Pro Ser Thr Ser Trp Phe Gln Lys
365                 370                 375                 380

acc tgc tct acc ccc agt aat cca aaa tat gaa atg gtg atc cca gat      1501
Thr Cys Ser Thr Pro Ser Asn Pro Lys Tyr Glu Met Val Ile Pro Asp
                385                 390                 395

cac cct gct aaa tct cat cct gat ctt cat gta agt aat gac tgt agc      1549
His Pro Ala Lys Ser His Pro Asp Leu His Val Ser Asn Asp Cys Ser
            400                 405                 410

tcc tca gta gca gag agc agt agc cca ctt aga aat ttc agt tgt ggc      1597
Ser Ser Val Ala Glu Ser Ser Ser Pro Leu Arg Asn Phe Ser Cys Gly
        415                 420                 425

ttt gaa agg act aca agg aat gag aag ctg gca gca aag act gat gaa      1645
Phe Glu Arg Thr Thr Arg Asn Glu Lys Leu Ala Ala Lys Thr Asp Glu
    430                 435                 440

ttt aac aga act gta ttt aga aca gat aga aat tgt cag gca ata cag      1693
Phe Asn Arg Thr Val Phe Arg Thr Asp Arg Asn Cys Gln Ala Ile Gln
445                 450                 455                 460

caa aat cac agc tgc tca aaa tca tcg gag gat ctc aag ccc tgt gat      1741
Gln Asn His Ser Cys Ser Lys Ser Ser Glu Asp Leu Lys Pro Cys Asp
                465                 470                 475

acc tca tct act cac aca ggt agc ata tca caa agt aac gat gtg tcc      1789
Thr Ser Ser Thr His Thr Gly Ser Ile Ser Gln Ser Asn Asp Val Ser
            480                 485                 490

ggt att tgg aaa acc aat gcc cac atg cct gtg ccc atg gaa aat gtg      1837
Gly Ile Trp Lys Thr Asn Ala His Met Pro Val Pro Met Glu Asn Val
        495                 500                 505

cct gat aat ccc acc aag aaa tcc aca aca ggc cta gta aga caa atg      1885
Pro Asp Asn Pro Thr Lys Lys Ser Thr Thr Gly Leu Val Arg Gln Met
    510                 515                 520

cag gga cac cta agt cct cgc agt tat cga aat atg ctc cac gag cat      1933
Gln Gly His Leu Ser Pro Arg Ser Tyr Arg Asn Met Leu His Glu His
525                 530                 535                 540

gac tgg aga ccg agt aat ttg tct ggc cgt ccg agg tca gct gat ccc      1981
Asp Trp Arg Pro Ser Asn Leu Ser Gly Arg Pro Arg Ser Ala Asp Pro
                545                 550                 555

agg tca aat tat ggt gtt gtg gaa aag ctg ctg aaa acc tat gag aca      2029
Arg Ser Asn Tyr Gly Val Val Glu Lys Leu Leu Lys Thr Tyr Glu Thr
            560                 565                 570

gca aca gag tct gca ttg caa aat tct aag tgc ttc cag gat aat tgg      2077
Ala Thr Glu Ser Ala Leu Gln Asn Ser Lys Cys Phe Gln Asp Asn Trp
        575                 580                 585

acc aaa tgt aat tct gat gtc agt ggt ggt gcc aca tta agt cag cat      2125
```

-continued

```
Thr Lys Cys Asn Ser Asp Val Ser Gly Gly Ala Thr Leu Ser Gln His
    590                 595                 600

tta gaa atg ctc caa atg gaa caa cag ttt cag caa aag aca gct gtg     2173
Leu Glu Met Leu Gln Met Glu Gln Gln Phe Gln Gln Lys Thr Ala Val
605                 610                 615                 620

tgg ggg gga cag gaa gtg aag caa gga ata gat ccg aaa aag ata aca     2221
Trp Gly Gly Gln Glu Val Lys Gln Gly Ile Asp Pro Lys Lys Ile Thr
                625                 630                 635

gag gaa tcc atg tca gtg aac gcc tca cat gga aaa gga ttt tcc cga     2269
Glu Glu Ser Met Ser Val Asn Ala Ser His Gly Lys Gly Phe Ser Arg
            640                 645                 650

cct gct aga cca gca aat cgt cgt ctc ccc tcc aga tgg gca tcc aga     2317
Pro Ala Arg Pro Ala Asn Arg Arg Leu Pro Ser Arg Trp Ala Ser Arg
        655                 660                 665

tct cca tct gca ccc cct gcc ttg cgg aga act acc cac aac tat acc     2365
Ser Pro Ser Ala Pro Pro Ala Leu Arg Arg Thr Thr His Asn Tyr Thr
    670                 675                 680

att tct ctg cga tcc gaa gca ttg atg gtt taa gtctttggcc tggattgcta   2418
Ile Ser Leu Arg Ser Glu Ala Leu Met Val
685                 690

tattacagaa gttctagtcc cacttgtcaa acagagcatt ctgagtgttt acaggcggac   2478

ctgttctctt ccgacaagca atttgaatct taactttcca tcagtcttca gtgtttttaa   2538

tctaaggaat aattatcttc ctgcattttg atttcttaga tcagaatttt ttaatgccat   2598

cctcattagt tttccaatac aatataagtt gaaacaatgt acaatattgt atattctttg   2658

ttgcaagtgg cagaaagtaa ggttatgtgc atggccatgt gtttgtaggt gcatgtgttg   2718

aaataggaag tatcctagta tgtatttaga tatgaaaaac ttatgtgcta gtgttgactt   2778

tgaaattata acatgtatac ctatatattc tttgtgttta tttaaaagtt ttgaaaatat   2838

gcagtactgt ttatattttg tataccttttt aataggtatc cacttaaggc atttgcagta   2898

caaatattaa ttgaccactt ccttggcccc cagctacaat gaaaaagaag aattatgcac   2958

acatctaaca ttggtagatt tctaaagaca actcataaat aatttcttaa cccatataag   3018

gataaaataa taccattgat attcttgttt attcttttta aataaaaatg tcacaagttt   3078

aatagatcag ccttgtaaag caagcataaa atgttcataa atgttttata tattatttgg   3138

tagtctagta tggctttaac tgaatatttg atcctcagag acagtatcat gagactgcat   3198

tataaatgac atgattaaat gatgaattta ttttgtcagc ctcagcaaca aacatttcct   3258

aaatgggatg caaaaagaaa ctgaatgatg ttgaatttta gtttttcttt aagttgtggt   3318

aagcttttag tttagctgct ttaacatgga gtcatacata cttagaggta agtcatttat   3378

tattttttc ctttttctaa tcttttcctt aaaattaata gataacaaac taagttactt   3438

ttttactaac aaggaagatc aggaataata tttctttgaa agctgaaatt atacttctca   3498

cagtttgcta ccgaaaaaag gcttaaacta aaccttgaca tccacagtag catcaggaat   3558

agaaatgtgt attttggcta cagtttgcat acagtgaaca cataaaatct atattgaaaa   3618

ctgacagaaa tatgaatgtc gaggggcttg gaattctaaa tggaagattt tagaaggaac   3678

tttgctctct actgtcacta tataaaacca attatgttat gttattagat attaactcta   3738

tttaagcttt tcttttacta agaaattctt atgccaaatg tattccaaga gccatctcct   3798

tatgatgtat ttgaaccatt tagagaaatt cacttcattg taccccatga cctgaggtaa   3858

agaaaataat tttcaaattg cagacttcct tgaaaggctc aagactgtag catggtgatg   3918

tctagattca tactttactg taaggacagt ttcggtagtt aagtggaatt aaaggtctag   3978
```

-continued

```
agtgatttgt attggatggt aactaaggtc tatacatcta ctcttttaat tcttatttcc   4038

ttcaggaaga tccttttcca caggaagcta tcaaagaaaa gtaaactaga caccaagtaa   4098

tatcactctc ataatatgct ttccagctag aggggagaaa acaccaggaa agaggaaccc   4158

tgggtcataa aatgacggac ctgttaggaa aatgctgttg tgtgacaatg gagagcctgc   4218

ccaaggactg tgcaacctat ctgttcctct ccaccagtgt atcccaagta gtctggtatg   4278

atctgtggtt ccttagaata ttgaggatct ctttaaaaaa tgaaatttct gatctcaccc   4338

catattacta aagcaaaatt tccaggggta gggactggga ctccagaacc attaataaaa   4398

caaaacaaaa caaagcaaaa tattgatgat caggcagatt tgaaaacagt gacattgctt   4458

gatctctgaa tggatggatg cccttgggtg gtcacttttc ttcctaggac ttgcctttgt   4518

tatctgtaaa ttagaatggc tatactttca gacttcacaa ttttaagcca cttttttcta   4578

ttaacagttg aatgaaccag tgggacacat tttaacgtct tcttatgttg actaaaatta   4638

tagttagagc tgagaaaaaa aaaatagcat ctagtccaac tccttgattg taaaactgaa   4698

aaactaaggt tatttgaatg ttctgttttc tctttttaaa tattttataa cttttaaatg   4758

gaaaaaccta ttaggtaaat ggaaataatc cttgaaaata gtttttgatg ttttgtgatt   4818

tttaactggt aaatttctac tttaggtggg cattttcttc cctagaatat gccctttatt   4878

atgctatcat tgctagattt aaagggactt gtaagcattt ctggaaatat ttgatttaaa   4938

aacatatatt aatagatgtt ttccctagca gacttttgga gcaaaaatat tattttagtt   4998

cagcagagga ttactgatat tatgggctga tctcagaaag gaataaggat gaggcagaga   5058

ggagtacttg agtttgtgtg tgtgtgtgtg tgtgtgtgtt tgtgtcagtg tcacataagt   5118

tctccatatt gccttatgtc ccaaagccaa atataaaaat ataaatgatg ctttgtataa   5178

ttcattttat caaaaattac ccataacttt catttgtttt tatatcgaca atgaagatga   5238

tcatatttca ttttgcagat gtggccataa aatattattt acttctatat aggtgatttt   5298

accaggttta gttatcctga gaaaacatct ggacttaaga gtttctgctt ccctacaaag   5358

atctttaaag ttatttttag gcacatttgt gacaaacaac tacttgatat tgaaatctcc   5418

ttcagccatt agaagctatc aaataaagta ggtgtaaaaa caactgtctg tggcatttgt   5478

atacatcgag aacatttttc tttccctcat tttctgcagt gaactccagt aaagctaagt   5538

gtcttatgaa atctaaactc atatatgtac acagttcact ctagcttctt ccaaaatatc   5598

tctaggtagt acaactgaag ccaaacctgc ctgacttcct gctcctggcc acccaaaact   5658

ccatatggct tctcgtacac tgacatcctc tctctaccca tttaactgct aattgagtct   5718

gataaaagtc ttctttgaaa aaagttttta cttctaagat ttgcatttac atcataaaat   5778

taaaccattt tcaggaaaat cagatttttt tattacagta ctatttgctt taaattcggc   5838

atgtttttct taagtagcaa gtacatgtat cggaacttag aactggtggg cgcggtggct   5898

cttgcctgta atcccagcac tttgggaggc caaggtgggg ggatcacgag gtcaggagat   5958

ggagaccatc ctggtttcat cacggtgaaa ccccctctct gctaaaaata caaaaaatta   6018

gccaggcatt gtggtggtca cctgtagtcc cagctgctcg ggaggctgag gcaggagaat   6078

ggcatgaacc cgggaggcag agcttgcagt gagcagagat cgcgccactg cactccagcc   6138

tgggtgacag agtgagactc tgtctc                                        6164
```

<210> SEQ ID NO 6
<211> LENGTH: 694
<212> TYPE: PRT
<213> ORGANISM: Homo sapiens -continued

<400> SEQUENCE: 6

Met Asp Leu His Lys Gln Trp Glu Asn Thr Glu Thr Asn Trp His Lys
1 5 10 15

Glu Lys Met Glu Leu Leu Asp Gln Phe Asp Asn Glu Arg Lys Glu Trp
20 25 30

Glu Ser Gln Trp Lys Ile Met Gln Lys Lys Ile Glu Glu Leu Cys Arg
35 40 45

Glu Val Lys Leu Trp Arg Lys Ile Asn Ile Asn Glu Ser Ala Lys Ile
50 55 60

Ile Asp Leu Tyr His Glu Lys Thr Ile Pro Glu Lys Val Ile Glu Ser
65 70 75 80

Ser Pro Asn Tyr Pro Asp Leu Gly Gln Ser Glu Phe Ile Arg Thr Asn
85 90 95

His Lys Asp Gly Leu Arg Lys Glu Asn Lys Arg Glu Gln Ser Leu Val
100 105 110

Ser Gly Gly Asn Gln Met Cys Lys Glu Gln Lys Ala Thr Lys Lys Ser
115 120 125

Lys Val Gly Phe Leu Asp Pro Leu Ala Thr Asp Asn Gln Lys Glu Cys
130 135 140

Glu Ala Trp Pro Asp Leu Arg Thr Ser Glu Glu Asp Ser Lys Ser Cys
145 150 155 160

Ser Gly Ala Leu Ser Thr Ala Leu Glu Glu Leu Ala Lys Val Ser Glu
165 170 175

Glu Leu Cys Ser Phe Gln Glu Glu Ile Arg Lys Arg Ser Asn His Arg
180 185 190

Arg Met Lys Ser Asp Ser Phe Leu Gln Glu Met Pro Asn Val Thr Asn
195 200 205

Ile Pro His Gly Asp Pro Met Ile Asn Asn Asp Gln Cys Ile Leu Pro
210 215 220

Ile Ser Leu Glu Lys Glu Lys Gln Lys Asn Arg Lys Asn Leu Ser Cys
225 230 235 240

Thr Asn Val Leu Gln Ser Asn Ser Thr Lys Lys Cys Gly Ile Asp Thr
245 250 255

Ile Asp Leu Lys Arg Asn Glu Thr Pro Pro Val Pro Pro Pro Arg Ser
260 265 270

Thr Ser Arg Asn Phe Pro Ser Ser Asp Ser Glu Gln Ala Tyr Glu Arg
275 280 285

Trp Lys Glu Arg Leu Asp His Asn Ser Trp Val Pro His Glu Gly Arg
290 295 300

Ser Lys Arg Asn Tyr Asn Pro His Phe Pro Leu Arg Gln Gln Glu Met
305 310 315 320

Ser Met Leu Tyr Pro Asn Glu Gly Lys Thr Ser Lys Asp Gly Ile Ile
325 330 335

Phe Ser Ser Leu Val Pro Glu Val Lys Ile Asp Ser Lys Pro Pro Ser
340 345 350

Asn Glu Asp Val Gly Leu Ser Met Trp Ser Cys Asp Ile Gly Ile Gly
355 360 365

Ala Lys Arg Ser Pro Ser Thr Ser Trp Phe Gln Lys Thr Cys Ser Thr
370 375 380

Pro Ser Asn Pro Lys Tyr Glu Met Val Ile Pro Asp His Pro Ala Lys
385 390 395 400

Ser His Pro Asp Leu His Val Ser Asn Asp Cys Ser Ser Ser Val Ala

-continued

```
            405                 410                 415

Glu Ser Ser Ser Pro Leu Arg Asn Phe Ser Cys Gly Phe Glu Arg Thr
        420                 425                 430

Thr Arg Asn Glu Lys Leu Ala Ala Lys Thr Asp Glu Phe Asn Arg Thr
    435                 440                 445

Val Phe Arg Thr Asp Arg Asn Cys Gln Ala Ile Gln Gln Asn His Ser
450                 455                 460

Cys Ser Lys Ser Ser Glu Asp Leu Lys Pro Cys Asp Thr Ser Ser Thr
465                 470                 475                 480

His Thr Gly Ser Ile Ser Gln Ser Asn Asp Val Ser Gly Ile Trp Lys
                485                 490                 495

Thr Asn Ala His Met Pro Val Pro Met Glu Asn Val Pro Asp Asn Pro
            500                 505                 510

Thr Lys Lys Ser Thr Thr Gly Leu Val Arg Gln Met Gln Gly His Leu
        515                 520                 525

Ser Pro Arg Ser Tyr Arg Asn Met Leu His Glu His Asp Trp Arg Pro
    530                 535                 540

Ser Asn Leu Ser Gly Arg Pro Arg Ser Ala Asp Pro Arg Ser Asn Tyr
545                 550                 555                 560

Gly Val Val Glu Lys Leu Leu Lys Thr Tyr Glu Thr Ala Thr Glu Ser
                565                 570                 575

Ala Leu Gln Asn Ser Lys Cys Phe Gln Asp Asn Trp Thr Lys Cys Asn
            580                 585                 590

Ser Asp Val Ser Gly Gly Ala Thr Leu Ser Gln His Leu Glu Met Leu
        595                 600                 605

Gln Met Glu Gln Gln Phe Gln Gln Lys Thr Ala Val Trp Gly Gly Gln
    610                 615                 620

Glu Val Lys Gln Gly Ile Asp Pro Lys Lys Ile Thr Glu Glu Ser Met
625                 630                 635                 640

Ser Val Asn Ala Ser His Gly Lys Gly Phe Ser Arg Pro Ala Arg Pro
                645                 650                 655

Ala Asn Arg Arg Leu Pro Ser Arg Trp Ala Ser Arg Ser Pro Ser Ala
            660                 665                 670

Pro Pro Ala Leu Arg Arg Thr Thr His Asn Tyr Thr Ile Ser Leu Arg
        675                 680                 685

Ser Glu Ala Leu Met Val
    690


<210> SEQ ID NO 7
<211> LENGTH: 7014
<212> TYPE: DNA
<213> ORGANISM: Homo sapiens
<220> FEATURE:
<221> NAME/KEY: CDS
<222> LOCATION: (1164)..(3248)

<400> SEQUENCE: 7

agcagaacaa gcgcatcacg gcggagctca acaagtacaa gtacaagtcc ggcggccacg      60

acagcgcgcg gcaccacgac aacgccaaga ccgaggccct gcaggaggag ctgaaggcgg     120

cgcgcctgca gatcaacgag ctcagcggca aggtcatgca gctgcagtac gagaaccgcg     180

tgcttatgtc caacatgcag cgctacgacc tggcctcgca cctgggcatc cgcggcagcc     240

cccgcgacag cgacgccgag agcgacgcgg gcaagaagga gagcgacgac gactcgcggc     300

ctccgcaccg caagcgcgaa gggcccatcg gcggcgagag cgactcggag gaggtgcgca     360
```

-continued

```
acatccgctg cctcacgccc actcgctcct tctacccggc gcccgggccc tggcccaaga    420

gcttctccga tcggcagcag atgaaggaca tccgctcgga ggccgagcgc ctgggcaaga    480

ccatcgaccg gctcatcgcc gacacgagca ccatcatcac cgaggcgcgc atctacgtgg    540

ccaacgggga cctgttcgga ctcatggacg aggaggacga cggcagccgc atccgggagc    600

acgagctgct ctaccgcatc aacgctcaga tgaaggcctt ccgcaaggag ctgcagacct    660

tcatcgaccg cctcgaggtg cccaagtctg cggacgaccg cggcgccgag gagcccattt    720

ccgtgagtca gatgttccag cctatcattt tacttattct cattcttgta ttattttcat    780

cactttctta cacaacaata tttaaacttg tcttcctttt tacactgttt tttgtactgt    840

aaatctttca tcatttacca ttcattgtag tattttcagt ttgtttattt tgttcaccct    900

tcaagacaag aagtaaaaga agtataattt ctgtagtaac caatgctata aaaacactga    960

agactgctta tttctttaaa aagatacaac tcatcttacc aagaccaaat tcaataagaa   1020

gcccaaacac taaaatattt caggctttat tttaaaggca agtgagactg cttcaaataa   1080

aacaacttca agcttccaag aaacagttaa gaggaggcag agaggagcag aaacacttct   1140

ttgctgacac ttacactgtt gcc atg gac cta cat aag cag tgg gag aac aca   1193
                          Met Asp Leu His Lys Gln Trp Glu Asn Thr
                          1               5                   10

gag act aac tgg cat aag gaa aag atg gaa tta ctg gac cag ttt gac     1241
Glu Thr Asn Trp His Lys Glu Lys Met Glu Leu Leu Asp Gln Phe Asp
                15                  20                  25

aat gaa aga aag gaa tgg gaa agt caa tgg aag att atg cag aag aaa     1289
Asn Glu Arg Lys Glu Trp Glu Ser Gln Trp Lys Ile Met Gln Lys Lys
            30                  35                  40

ata gaa gag ctt tgc cgg gaa gta aag ctt tgg agg aaa atc aat atc     1337
Ile Glu Glu Leu Cys Arg Glu Val Lys Leu Trp Arg Lys Ile Asn Ile
        45                  50                  55

aat gaa agt gct aag atc att gat ctt tac cat gag aag acc att cca     1385
Asn Glu Ser Ala Lys Ile Ile Asp Leu Tyr His Glu Lys Thr Ile Pro
    60                  65                  70

gag aaa gtg ata gaa tct tcc cca aat tac ccc gat tta gga caa agt     1433
Glu Lys Val Ile Glu Ser Ser Pro Asn Tyr Pro Asp Leu Gly Gln Ser
75                  80                  85                  90

gaa ttt ata agg acg aat cac aaa gat ggt ctg aga aaa gaa aat aaa     1481
Glu Phe Ile Arg Thr Asn His Lys Asp Gly Leu Arg Lys Glu Asn Lys
                95                  100                 105

aga gag cag agc tta gtc agt gga gga aat caa atg tgt aag gaa caa     1529
Arg Glu Gln Ser Leu Val Ser Gly Gly Asn Gln Met Cys Lys Glu Gln
            110                 115                 120

aaa gca aca aaa aaa tca aaa gta ggg ttt ttg gat cct ttg gct aca     1577
Lys Ala Thr Lys Lys Ser Lys Val Gly Phe Leu Asp Pro Leu Ala Thr
        125                 130                 135

gac aac caa aag gaa tgt gag gcc tgg cct gac ctg agg act tct gag     1625
Asp Asn Gln Lys Glu Cys Glu Ala Trp Pro Asp Leu Arg Thr Ser Glu
    140                 145                 150

gaa gac agc aag agc tgt tct ggc gcc ctc agt aca gct ctt gaa gaa     1673
Glu Asp Ser Lys Ser Cys Ser Gly Ala Leu Ser Thr Ala Leu Glu Glu
155                 160                 165                 170

ctt gcg aag gtg agt gaa gaa tta tgc agc ttt caa gag gaa att cga     1721
Leu Ala Lys Val Ser Glu Glu Leu Cys Ser Phe Gln Glu Glu Ile Arg
                175                 180                 185

aag cgg tct aac cat aga agg atg aag tca gat tct ttt ctc cag gaa     1769
Lys Arg Ser Asn His Arg Arg Met Lys Ser Asp Ser Phe Leu Gln Glu
            190                 195                 200

atg cca aat gta act aat ata cct cat ggg gac ccc atg atc aac aat     1817
```

-continued

```
Met Pro Asn Val Thr Asn Ile Pro His Gly Asp Pro Met Ile Asn Asn
        205                 210                 215

gac cag tgc att ctt cca atc agt tta gaa aaa gaa aaa cag aaa aac      1865
Asp Gln Cys Ile Leu Pro Ile Ser Leu Glu Lys Glu Lys Gln Lys Asn
    220                 225                 230

agg aag aat ctg agc tgt acc aat gtg ctc cag agc aat tct acg aaa      1913
Arg Lys Asn Leu Ser Cys Thr Asn Val Leu Gln Ser Asn Ser Thr Lys
235                 240                 245                 250

aaa tgt gga att gat aca atc gat tta aaa aga aat gaa act cca cca      1961
Lys Cys Gly Ile Asp Thr Ile Asp Leu Lys Arg Asn Glu Thr Pro Pro
                255                 260                 265

gtt cct cct cca aga agc acc tct cga aat ttt ccc agc tcg gat tct      2009
Val Pro Pro Pro Arg Ser Thr Ser Arg Asn Phe Pro Ser Ser Asp Ser
            270                 275                 280

gaa caa gcc tat gaa aga tgg aag gaa agg tta gac cac aac agc tgg      2057
Glu Gln Ala Tyr Glu Arg Trp Lys Glu Arg Leu Asp His Asn Ser Trp
        285                 290                 295

gtg ccc cat gag ggt cga agt aaa agg aat tac aac cct cac ttc cct      2105
Val Pro His Glu Gly Arg Ser Lys Arg Asn Tyr Asn Pro His Phe Pro
    300                 305                 310

ttg aga caa caa gag atg tct atg ttg tat cca aat gaa ggg aaa act      2153
Leu Arg Gln Gln Glu Met Ser Met Leu Tyr Pro Asn Glu Gly Lys Thr
315                 320                 325                 330

tcg aaa gat ggt atc atc ttt tcc tct ttg gta cca gaa gtc aaa ata      2201
Ser Lys Asp Gly Ile Ile Phe Ser Ser Leu Val Pro Glu Val Lys Ile
                335                 340                 345

gat agc aag cct cca agt aat gaa gat gtt gga ctt agc atg tgg tca      2249
Asp Ser Lys Pro Pro Ser Asn Glu Asp Val Gly Leu Ser Met Trp Ser
            350                 355                 360

tgt gac att ggg ata ggt gca aaa agg agc ccc tct act tcg tgg ttt      2297
Cys Asp Ile Gly Ile Gly Ala Lys Arg Ser Pro Ser Thr Ser Trp Phe
        365                 370                 375

cag aaa acc tgc tct acc ccc agt aat cca aaa tat gaa atg gtg atc      2345
Gln Lys Thr Cys Ser Thr Pro Ser Asn Pro Lys Tyr Glu Met Val Ile
    380                 385                 390

cca gat cac cct gct aaa tct cat cct gat ctt cat gta agt aat gac      2393
Pro Asp His Pro Ala Lys Ser His Pro Asp Leu His Val Ser Asn Asp
395                 400                 405                 410

tgt agc tcc tca gta gca gag agc agt agc cca ctt aga aat ttc agt      2441
Cys Ser Ser Ser Val Ala Glu Ser Ser Ser Pro Leu Arg Asn Phe Ser
                415                 420                 425

tgt ggc ttt gaa agg act aca agg aat gag aag ctg gca gca aag act      2489
Cys Gly Phe Glu Arg Thr Thr Arg Asn Glu Lys Leu Ala Ala Lys Thr
            430                 435                 440

gat gaa ttt aac aga act gta ttt aga aca gat aga aat tgt cag gca      2537
Asp Glu Phe Asn Arg Thr Val Phe Arg Thr Asp Arg Asn Cys Gln Ala
        445                 450                 455

ata cag caa aat cac agc tgc tca aaa tca tcg gag gat ctc aag ccc      2585
Ile Gln Gln Asn His Ser Cys Ser Lys Ser Ser Glu Asp Leu Lys Pro
    460                 465                 470

tgt gat acc tca tct act cac aca ggt agc ata tca caa agt aac gat      2633
Cys Asp Thr Ser Ser Thr His Thr Gly Ser Ile Ser Gln Ser Asn Asp
475                 480                 485                 490

gtg tcc ggt att tgg aaa acc aat gcc cac atg cct gtg ccc atg gaa      2681
Val Ser Gly Ile Trp Lys Thr Asn Ala His Met Pro Val Pro Met Glu
                495                 500                 505

aat gtg cct gat aat ccc acc aag aaa tcc aca aca ggc cta gta aga      2729
Asn Val Pro Asp Asn Pro Thr Lys Lys Ser Thr Thr Gly Leu Val Arg
            510                 515                 520
```

-continued

```
caa atg cag gga cac cta agt cct cgc agt tat cga aat atg ctc cac     2777
Gln Met Gln Gly His Leu Ser Pro Arg Ser Tyr Arg Asn Met Leu His
        525                 530                 535

gag cat gac tgg aga ccg agt aat ttg tct ggc cgt ccg agg tca gct     2825
Glu His Asp Trp Arg Pro Ser Asn Leu Ser Gly Arg Pro Arg Ser Ala
    540                 545                 550

gat ccc agg tca aat tat ggt gtt gtg gaa aag ctg ctg aaa acc tat     2873
Asp Pro Arg Ser Asn Tyr Gly Val Val Glu Lys Leu Leu Lys Thr Tyr
555                 560                 565                 570

gag aca gca aca gag tct gca ttg caa aat tct aag tgc ttc cag gat     2921
Glu Thr Ala Thr Glu Ser Ala Leu Gln Asn Ser Lys Cys Phe Gln Asp
                575                 580                 585

aat tgg acc aaa tgt aat tct gat gtc agt ggt ggt gcc aca tta agt     2969
Asn Trp Thr Lys Cys Asn Ser Asp Val Ser Gly Gly Ala Thr Leu Ser
            590                 595                 600

cag cat tta gaa atg ctc caa atg gaa caa cag ttt cag caa aag aca     3017
Gln His Leu Glu Met Leu Gln Met Glu Gln Gln Phe Gln Gln Lys Thr
        605                 610                 615

gct gtg tgg ggg gga cag gaa gtg aag caa gga ata gat ccg aaa aag     3065
Ala Val Trp Gly Gly Gln Glu Val Lys Gln Gly Ile Asp Pro Lys Lys
    620                 625                 630

ata aca gag gaa tcc atg tca gtg aac gcc tca cat gga aaa gga ttt     3113
Ile Thr Glu Glu Ser Met Ser Val Asn Ala Ser His Gly Lys Gly Phe
635                 640                 645                 650

tcc cga cct gct aga cca gca aat cgt cgt ctc ccc tcc aga tgg gca     3161
Ser Arg Pro Ala Arg Pro Ala Asn Arg Arg Leu Pro Ser Arg Trp Ala
                655                 660                 665

tcc aga tct cca tct gca ccc cct gcc ttg cgg aga act acc cac aac     3209
Ser Arg Ser Pro Ser Ala Pro Pro Ala Leu Arg Arg Thr Thr His Asn
            670                 675                 680

tat acc att tct ctg cga tcc gaa gca ttg atg gtt taa gtctttggcc     3258
Tyr Thr Ile Ser Leu Arg Ser Glu Ala Leu Met Val
        685                 690

tggattgcta tattacagaa gttctagtcc cacttgtcaa acagagcatt ctgagtgttt   3318

acaggcggac ctgttctctt ccgacaagca atttgaatct taactttcca tcagtcttca   3378

gtgtttttaa tctaaggaat aattatcttc ctgcattttg atttcttaga tcagaatttt   3438

ttaatgccat cctcattagt tttccaatac aatataagtt gaaacaatgt acaatattgt   3498

atattctttg ttgcaagtgg cagaaagtaa ggttatgtgc atggccatgt gtttgtaggt   3558

gcatgtgttg aaataggaag tatcctagta tgtatttaga tatgaaaaac ttatgtgcta   3618

gtgttgactt tgaaattata acatgtatac ctatatattc tttgtgttta tttaaaagtt   3678

ttgaaaatat gcagtactgt ttatattttg tatacctttt aataggtatc cacttaaggc   3738

atttgcagta caaatattaa ttgaccactt ccttggcccc cagctacaat gaaaaagaag   3798

aattatgcac acatctaaca ttggtagatt tctaaagaca actcataaat aatttcttaa   3858

cccatataag gataaaataa taccattgat attcttgttt attcttttta aataaaaatg   3918

tcacaagttt aatagatcag ccttgtaaag caagcataaa atgttcataa atgttttata   3978

tattatttgg tagtctagta tggctttaac tgaatatttg atcctcagag acagtatcat   4038

gagactgcat tataaatgac atgattaaat gatgaattta ttttgtcagc ctcagcaaca   4098

aacatttcct aaatgggatg caaaaagaaa ctgaatgatg ttgaatttta gtttttcttt   4158

aagttgtggt aagcttttag tttagctgct ttaacatgga gtcatacata cttagaggta   4218

agtcatttat tattttttc ctttttctaa tcttttcctt aaaattaata gataacaaac   4278

taagttactt ttttactaac aaggaagatc aggaataata tttctttgaa agctgaaatt   4338
```

-continued

```
atacttctca cagtttgcta ccgaaaaaag gcttaaacta aaccttgaca tccacagtag   4398
catcaggaat agaaatgtgt attttggcta cagtttgcat acagtgaaca cataaaatct   4458
atattgaaaa ctgacagaaa tatgaatgtc gaggggcttg gaattctaaa tggaagattt   4518
tagaaggaac tttgctctct actgtcacta tataaaacca attatgttat gttattagat   4578
attaactcta tttaagcttt tcttttacta agaaattctt atgccaaatg tattccaaga   4638
gccatctcct tatgatgtat ttgaaccatt tagagaaatt cacttcattg taccccatga   4698
cctgaggtaa agaaaataat tttcaaattg cagacttcct tgaaaggctc aagactgtag   4758
catggtgatg tctagattca tactttactg taaggacagt ttcggtagtt aagtggaatt   4818
aaaggtctag agtgatttgt attggatggt aactaaggtc tatacatcta ctcttttaat   4878
tcttatttcc ttcaggaaga tccttttcca caggaagcta tcaaagaaaa gtaaactaga   4938
caccaagtaa tatcactctc ataatatgct ttccagctag aggggagaaa acaccaggaa   4998
agaggaaccc tgggtcataa aatgacggac ctgttaggaa aatgctgttg tgtgacaatg   5058
gagagcctgc ccaaggactg tgcaacctat ctgttcctct ccaccagtgt atcccaagta   5118
gtctggtatg atctgtggtt ccttagaata ttgaggatct ctttaaaaaa tgaaatttct   5178
gatctcaccc catattacta aagcaaaatt tccaggggta gggactggga ctccagaacc   5238
attaataaaa caaaacaaaa caaagcaaaa tattgatgat caggcagatt tgaaaacagt   5298
gacattgctt gatctctgaa tggatggatg cccttgggtg gtcacttttc ttcctaggac   5358
ttgcctttgt tatctgtaaa ttagaatggc tatactttca gacttcacaa ttttaagcca   5418
ctttttteta ttaacagttg aatgaaccag tgggacacat tttaacgtct tcttatgttg   5478
actaaaatta tagttagagc tgagaaaaaa aaaatagcat ctagtccaac tccttgattg   5538
taaaactgaa aaactaaggt tatttgaatg ttctgttttc tctttttaaa tattttataa   5598
cttttaaatg gaaaaaccta ttaggtaaat ggaaataatc cttgaaaata gtttttgatg   5658
ttttgtgatt tttaactggt aaatttctac tttaggtggg cattttcttc cctagaatat   5718
gccctttatt atgctatcat tgctagattt aaagggactt gtaagcattt ctggaaatat   5778
ttgatttaaa aacatatatt aatagatgtt ttccctagca gacttttgga gcaaaaatat   5838
tattttagtt cagcagagga ttactgatat tatgggctga tctcagaaag gaataaggat   5898
gaggcagaga ggagtacttg agtttgtgtg tgtgtgtgtg tgtgtgtgtt tgtgtcagtg   5958
tcacataagt tctccatatt gccttatgtc ccaaagccaa atataaaaat ataaatgatg   6018
ctttgtataa ttcattttat caaaaattac ccataacttt catttgtttt tatatcgaca   6078
atgaagatga tcatatttca ttttgcagat gtggccataa aatattattt acttctatat   6138
aggtgatttt accaggttta gttatcctga gaaaacatct ggacttaaga gtttctgctt   6198
ccctacaaag atctttaaag ttatttttag gcacatttgt gacaaacaac tacttgatat   6258
tgaaatctcc ttcagccatt agaagctatc aaataaagta ggtgtaaaaa caactgtctg   6318
tggcatttgt atacatcgag aacatttttc tttccctcat tttctgcagt gaactccagt   6378
aaagctaagt gtcttatgaa atctaaactc atatatgtac acagttcact ctagcttctt   6438
ccaaaatatc tctaggtagt acaactgaag ccaaacctgc ctgacttcct gctcctggcc   6498
acccaaaact ccatatggct tctcgtacac tgacatcctc tctctaccca tttaactgct   6558
aattgagtct gataaaagtc ttctttgaaa aaagttttta cttctaagat ttgcatttac   6618
atcataaaat taaaccattt tcaggaaaat cagattttt tattacagta ctatttgctt   6678
```

-continued

```
taaattcggc atgtttttct taagtagcaa gtacatgtat cggaacttag aactggtggg   6738

cgcggtggct cttgcctgta atcccagcac tttgggaggc caaggtgggg ggatcacgag   6798

gtcaggagat ggagaccatc ctggtttcat cacggtgaaa ccccctctct gctaaaaata   6858

caaaaaatta gccaggcatt gtggtggtca cctgtagtcc cagctgctcg ggaggctgag   6918

gcaggagaat ggcatgaacc cgggaggcag agcttgcagt gagcagagat cgcgccactg   6978

cactccagcc tgggtgacag agtgagactc tgtctc                              7014


<210> SEQ ID NO 8
<211> LENGTH: 694
<212> TYPE: PRT
<213> ORGANISM: Homo sapiens

<400> SEQUENCE: 8

Met Asp Leu His Lys Gln Trp Glu Asn Thr Glu Thr Asn Trp His Lys
1               5                   10                  15

Glu Lys Met Glu Leu Leu Asp Gln Phe Asp Asn Glu Arg Lys Glu Trp
            20                  25                  30

Glu Ser Gln Trp Lys Ile Met Gln Lys Lys Ile Glu Glu Leu Cys Arg
        35                  40                  45

Glu Val Lys Leu Trp Arg Lys Ile Asn Ile Asn Glu Ser Ala Lys Ile
    50                  55                  60

Ile Asp Leu Tyr His Glu Lys Thr Ile Pro Glu Lys Val Ile Glu Ser
65                  70                  75                  80

Ser Pro Asn Tyr Pro Asp Leu Gly Gln Ser Glu Phe Ile Arg Thr Asn
                85                  90                  95

His Lys Asp Gly Leu Arg Lys Glu Asn Lys Arg Glu Gln Ser Leu Val
            100                 105                 110

Ser Gly Gly Asn Gln Met Cys Lys Glu Gln Lys Ala Thr Lys Lys Ser
        115                 120                 125

Lys Val Gly Phe Leu Asp Pro Leu Ala Thr Asp Asn Gln Lys Glu Cys
    130                 135                 140

Glu Ala Trp Pro Asp Leu Arg Thr Ser Glu Glu Asp Ser Lys Ser Cys
145                 150                 155                 160

Ser Gly Ala Leu Ser Thr Ala Leu Glu Glu Leu Ala Lys Val Ser Glu
                165                 170                 175

Glu Leu Cys Ser Phe Gln Glu Glu Ile Arg Lys Arg Ser Asn His Arg
            180                 185                 190

Arg Met Lys Ser Asp Ser Phe Leu Gln Glu Met Pro Asn Val Thr Asn
        195                 200                 205

Ile Pro His Gly Asp Pro Met Ile Asn Asn Asp Gln Cys Ile Leu Pro
    210                 215                 220

Ile Ser Leu Glu Lys Glu Lys Gln Lys Asn Arg Lys Asn Leu Ser Cys
225                 230                 235                 240

Thr Asn Val Leu Gln Ser Asn Ser Thr Lys Lys Cys Gly Ile Asp Thr
                245                 250                 255

Ile Asp Leu Lys Arg Asn Glu Thr Pro Pro Val Pro Pro Pro Arg Ser
            260                 265                 270

Thr Ser Arg Asn Phe Pro Ser Ser Asp Ser Glu Gln Ala Tyr Glu Arg
        275                 280                 285

Trp Lys Glu Arg Leu Asp His Asn Ser Trp Val Pro His Glu Gly Arg
    290                 295                 300

Ser Lys Arg Asn Tyr Asn Pro His Phe Pro Leu Arg Gln Gln Glu Met
305                 310                 315                 320
```

-continued

```
Ser Met Leu Tyr Pro Asn Glu Gly Lys Thr Ser Lys Asp Gly Ile Ile
                325                 330                 335

Phe Ser Ser Leu Val Pro Glu Val Lys Ile Asp Ser Lys Pro Pro Ser
            340                 345                 350

Asn Glu Asp Val Gly Leu Ser Met Trp Ser Cys Asp Ile Gly Ile Gly
        355                 360                 365

Ala Lys Arg Ser Pro Ser Thr Ser Trp Phe Gln Lys Thr Cys Ser Thr
    370                 375                 380

Pro Ser Asn Pro Lys Tyr Glu Met Val Ile Pro Asp His Pro Ala Lys
385                 390                 395                 400

Ser His Pro Asp Leu His Val Ser Asn Asp Cys Ser Ser Ser Val Ala
                405                 410                 415

Glu Ser Ser Ser Pro Leu Arg Asn Phe Ser Cys Gly Phe Glu Arg Thr
            420                 425                 430

Thr Arg Asn Glu Lys Leu Ala Ala Lys Thr Asp Glu Phe Asn Arg Thr
        435                 440                 445

Val Phe Arg Thr Asp Arg Asn Cys Gln Ala Ile Gln Gln Asn His Ser
    450                 455                 460

Cys Ser Lys Ser Ser Glu Asp Leu Lys Pro Cys Asp Thr Ser Ser Thr
465                 470                 475                 480

His Thr Gly Ser Ile Ser Gln Ser Asn Asp Val Ser Gly Ile Trp Lys
                485                 490                 495

Thr Asn Ala His Met Pro Val Pro Met Glu Asn Val Pro Asp Asn Pro
            500                 505                 510

Thr Lys Lys Ser Thr Thr Gly Leu Val Arg Gln Met Gln Gly His Leu
        515                 520                 525

Ser Pro Arg Ser Tyr Arg Asn Met Leu His Glu His Asp Trp Arg Pro
    530                 535                 540

Ser Asn Leu Ser Gly Arg Pro Arg Ser Ala Asp Pro Arg Ser Asn Tyr
545                 550                 555                 560

Gly Val Val Glu Lys Leu Leu Lys Thr Tyr Glu Thr Ala Thr Glu Ser
                565                 570                 575

Ala Leu Gln Asn Ser Lys Cys Phe Gln Asp Asn Trp Thr Lys Cys Asn
            580                 585                 590

Ser Asp Val Ser Gly Gly Ala Thr Leu Ser Gln His Leu Glu Met Leu
        595                 600                 605

Gln Met Glu Gln Gln Phe Gln Gln Lys Thr Ala Val Trp Gly Gly Gln
    610                 615                 620

Glu Val Lys Gln Gly Ile Asp Pro Lys Lys Ile Thr Glu Glu Ser Met
625                 630                 635                 640

Ser Val Asn Ala Ser His Gly Lys Gly Phe Ser Arg Pro Ala Arg Pro
                645                 650                 655

Ala Asn Arg Arg Leu Pro Ser Arg Trp Ala Ser Arg Ser Pro Ser Ala
            660                 665                 670

Pro Pro Ala Leu Arg Arg Thr Thr His Asn Tyr Thr Ile Ser Leu Arg
        675                 680                 685

Ser Glu Ala Leu Met Val
    690

<210> SEQ ID NO 9
<211> LENGTH: 4891
<212> TYPE: DNA
<213> ORGANISM: Homo sapiens
<220> FEATURE:
```

-continued

```
<221> NAME/KEY: CDS
<222> LOCATION: (202)..(1041)

<400> SEQUENCE: 9

gtgtgacgaa acctgcttcg gcggcccgag gtgggggttt tgagtcggtt agtggaggca      60

gtgggagcag gatgggcgga gcttctgttc caaaaatttc ccctaagtgc ggttgacagt     120

gtgcaggcag gcgggggtgc gcggggcggt cagcgatctg cagcttcgcg gggacagaga     180

tgtaacccaa ctcgttcacg g atg ttc cgc gcg ccg tgt cac cgg ctg cgg      231
                        Met Phe Arg Ala Pro Cys His Arg Leu Arg
                        1               5                   10

gcc agg ggt act cgg aag gcg cgg gca gga gcc tgg cga gga tgc acc      279
Ala Arg Gly Thr Arg Lys Ala Arg Ala Gly Ala Trp Arg Gly Cys Thr
                15                  20                  25

ttc ccc tgc ctt gga aag gga atg gag agg ccg gcg gcc cgg gag ccg      327
Phe Pro Cys Leu Gly Lys Gly Met Glu Arg Pro Ala Ala Arg Glu Pro
            30                  35                  40

cat ggg ccc gac gcg ctg cgg cgc ttc cag gga ctg ctg ctg gac cgc      375
His Gly Pro Asp Ala Leu Arg Arg Phe Gln Gly Leu Leu Leu Asp Arg
        45                  50                  55

cga ggc cgg ctg cac cgc cag gtg ctg cgc ctg cgc gag gtg gcc cgg      423
Arg Gly Arg Leu His Arg Gln Val Leu Arg Leu Arg Glu Val Ala Arg
    60                  65                  70

cgc ctg gag cgc ctg cgc agg cgc tcc ctc gta gcc aac gtg gcc ggc      471
Arg Leu Glu Arg Leu Arg Arg Arg Ser Leu Val Ala Asn Val Ala Gly
75                  80                  85                  90

agc tcg ctg agc gca acg ggc gcc ctc gcc gcc atc gtg ggg ctc tcg      519
Ser Ser Leu Ser Ala Thr Gly Ala Leu Ala Ala Ile Val Gly Leu Ser
                95                  100                 105

ctc agc ccg gtc acc ctg ggg acc tcg ctg ctg gtg tcg gcc gtg ggg      567
Leu Ser Pro Val Thr Leu Gly Thr Ser Leu Leu Val Ser Ala Val Gly
            110                 115                 120

ctg ggg gtg gcc aca gcc gga ggg gcc gtc acc atc acg tcc gat ctc      615
Leu Gly Val Ala Thr Ala Gly Gly Ala Val Thr Ile Thr Ser Asp Leu
        125                 130                 135

tcg ctg atc ttc tgc aac tcc cgg gag ctg cgg agg gtg cag gag atc      663
Ser Leu Ile Phe Cys Asn Ser Arg Glu Leu Arg Arg Val Gln Glu Ile
    140                 145                 150

gcg gcc acc tgc cag gac cag atg cga gag atc ctg agc tgc ctc gag      711
Ala Ala Thr Cys Gln Asp Gln Met Arg Glu Ile Leu Ser Cys Leu Glu
155                 160                 165                 170

ttt ttc tgc cgc tgg cag ggc tgc ggg gac cgc cag ctg ctg cag tgc      759
Phe Phe Cys Arg Trp Gln Gly Cys Gly Asp Arg Gln Leu Leu Gln Cys
                175                 180                 185

ggg agg aac gcc tcc atc gcc ctg tac aat tct gtc tac ttc atc gtc      807
Gly Arg Asn Ala Ser Ile Ala Leu Tyr Asn Ser Val Tyr Phe Ile Val
            190                 195                 200

ttc ttt ggc tca cgt ggc ttc ctc atc ccc agg cgg gcg gag ggg gac      855
Phe Phe Gly Ser Arg Gly Phe Leu Ile Pro Arg Arg Ala Glu Gly Asp
        205                 210                 215

acc aag gtt agc cag gcc gtg ctg aag gcc aag att cag aaa ctg gcc      903
Thr Lys Val Ser Gln Ala Val Leu Lys Ala Lys Ile Gln Lys Leu Ala
    220                 225                 230

gag agc ctg gag tcc tgc acc ggg gct ctg gac gaa ctc agc gag cag      951
Glu Ser Leu Glu Ser Cys Thr Gly Ala Leu Asp Glu Leu Ser Glu Gln
235                 240                 245                 250

ctg gag tct cgg gtt cag ctc tgc acc aag tcc agt cgt ggc cac gac      999
Leu Glu Ser Arg Val Gln Leu Cys Thr Lys Ser Ser Arg Gly His Asp
                255                 260                 265
```

-continued

```
ctc aag atc tct gct gac cag cgt gca ggg ctg ttt ttc tga           1041
Leu Lys Ile Ser Ala Asp Gln Arg Ala Gly Leu Phe Phe
            270                 275

gaacatcctt tccccctaat gaccgaggcc agcaaatcat cctcatggga tgctccagaa   1101

tttgtagctc ccttaggaaa acaccaagct gggttaggag ccgaaggcaa aggatgagaa   1161

aaactgtttt tgaagtgggc aggtccccaa agcccttctt ttcccatcac tgtgacatct   1221

gcctgggctt gagtgctacg gacttttcag tcttcctagt ggaaaaatgt gacccaaaaa   1281

ctccttttcc tttatcaaaa actttctgtc taaacacagc tgggcaggca ctcctgtttt   1341

aaagttattt cggggtccct gaccctgccc tggtggcttg gcctgagact ggagagagtg   1401

ccatcctctg ggtcctctcc aagtcctact agtctttgaa gtcctcaaaa tgtgcgtgag   1461

gaaggcattt gcctctattc cagaatttct gatacaaaga actccagaat ccagagcaaa   1521

tcagcccttc tctgaacgtt gtaggatggt tcagaaccca gagaggaccc tggtgctgat   1581

atctcctcct cttccctttc ccctcagctt acttactccc agatgcggcc tgggtatgaa   1641

gtaggccttt cctgagtggc tcccaatcca gtcctccaag tactcagagg ggaagcccgt   1701

gaagccgtca tctaagtcct gctccctcac atgaagctga gggccagata gatggagcga   1761

ctgccaactt catttcccga catcattgtg ttcagaagag agtgatgggt tttgagttag   1821

acagtcctgg gcttgagaca ggctttgtca ctactgtgtg agtgtagcca cctaatctct   1881

ctgagactgt gtaaaacaaa gatgataaaa tctcaccctg ttgtgagata ttaaatgagc   1941

caaagtgcct agcatgatgg tgctggctca tatagtgtag tccctggaat ggcaaattaa   2001

catcacccag gaacttgtta gaaaggcaaa ttcttggaca caaccctcct gatttatgga   2061

atcagaaact ctggctgtgg ggcccagcaa cctgagttta aacaatttct ctgggtggtt   2121

ctgcggcaca ctaaggtttg aaaatcacta caacaaatgc taacttctaa tccccttgat   2181

gagctttcac gaagtctcac ggcttctcta gggactccat ggtcttcaga gtcgttcaca   2241

gatgaccaag gacagactgt gtcccagaag ccaaaatgag agagagagag agagcacgcg   2301

tacgtgcacc ctggggcagt gtctcaccgt atgaataagg gatgtaacac taaaagccca   2361

ttagggggca gtgtttcccg cctgttgtag aaactggtac agaaaggatc ctatatgaag   2421

ttcctgaaac tgacctttgt ctattattac cttctctgaa aagtgccagt ccatgtattt   2481

tttatttatt ttaagtttgt aatttaattt ttaattattg tttagtgttt gcatttaatt   2541

ttatttaatc accacattta gaaaataata agagcaagtt tctaaatggg agactgctga   2601

ggctctttgc aagagatgag attaagtttg agtttctaag gcagggcatg agctggaaat   2661

agcattgctt tccttgattg tctctctcct tcagggagat tctttttctc tagtgtttta   2721

agtgatcctt tgaagtaagt gtggagagtc ttgaatggca agaccaggag ctgagtttaa   2781

gcttgtaatg gaagcttgca ttgtgggata tataactgag gaagcatatt tatcctgaag   2841

gtattttgcc agaaggtatc acttgacctg gaaaaggaat ctatttagtt caggaaagat   2901

aaaaagttta gaggtatgtg aaggaagcac ttagaacttg caagcctgat gtcctatcaa   2961

gttatgtctt ctgggtgaca gacaaaatag cttgtcttat ggtggtgatg tgttgcattt   3021

tcactttggg gtctgtaaga aactgtcagt gaaaatatgt acaattcctt caatttccat   3081

tcttaacaac tgtaatgttg aaaaataagt tgaaaagtct ttgggaccat acatgcaaaa   3141

acggtgcctc tgttacttaa ttatttaata ttctataaat gtacccaatc tgtccgcacc   3201

cttcccagtg atggggcagt atgtctgagg aagtataatt tcagtactgg ggtcggggag   3261

aggaggtgat gtttctacat ttttattttt tctataaatt gcaattggtc tgtatgctgg   3321
```

-continued

```
tttattttga aatttatatt ggtttctttt caagctggtg tcatctccta gactgtttca   3381

cccagatgct agcatttttt ttttttttga gacagagtct cactctgtca cctaggctgg   3441

agttgcagtg gtttgatctc ggctcactgc aacctccgac tcctgggttc aagcaattct   3501

tctgcctcag cctcctgagt agctgggatt acagatgtgc accagcacac ccggctaatt   3561

ttttgtattt ttagtagaga cagggtttcg ccatgttggc caggctggtc ttgaactcct   3621

ggccttatgt gatccgccca ccttggcttc ccaaagtgct gggattacag gcatgagcca   3681

cctcgcctgg ccagatgcta gcattttaga tcaaacaatt cattttagat gaattgtttt   3741

gtttcacaat cattttaaat cattttagaa tgtacttcac attattagtt gtgttatggc   3801

ataaaggtac aaccattccc taactccatc ttttattaat gcttaagttt aaattatatt   3861

cttccaatgc ctaagctatt ccctagaatt aaactgggca cttttggaag cagcaacagt   3921

aacagcagca gcaaactttt cctctcatat tttgggtgta tcaaaagttc tagacttttg   3981

aagttatgat ttcagtggcc cactttattt ctaaggaaga gtgtctactt tggaacgata   4041

ctttgcacat agtaggaact caagaaatac atttgaataa ttataattaa ctgtttagct   4101

atcttaatga gaatttgttg acaacaaaag atcatccatc gccttatgtg tgagtaagat   4161

tggagcctct atcaagattt agtcaagttc agttagattg attctagaaa caaatattta   4221

tttctttctt ttacggggat gtgaataagg cttttcctta aggccttcat tctttaaaca   4281

aacaggttga aatggtatgt tgtaaaagag aagacgggag agaggtattt agatgataag   4341

tgtacttcac aaaaatgcca aagtttgaaa aataggtatg tttgttctaa atgtttaagt   4401

gcttctctgt taggttctgg ggcttgcaat catttgaatt gttctgtttc acaataaagg   4461

agattcactg ggttctgcat tttcaggatt caatagaact gctccattaa aaaaataatc   4521

cttagcaagc attcgaatcc taactgcttt gatgcacttg ccctcgggca cctgtcattt   4581

ccaatatggt aggtgtcaaa gtcaaaagta tttactggga gaaaaaagag aggagtggtt   4641

gtagaagtct ccctaaatca gacatgtcaa gcaatcagcc aacgtggtgt atttctcatt   4701

caatatttta gtgtgaattg agacactgag ataaagacat cgtgcagaga taaatgggga   4761

tacagttaaa tgtagcaact cttgagttca ttttttccca ctgtagcaaa attaatgctt   4821

tctctttatt gaaataaatt gctcattcct ccaaaaaaaa aaaaaaaaaa aaaaaaaaaa   4881

aaaaaaaagg                                                          4891
```

```
<210> SEQ ID NO 10
<211> LENGTH: 279
<212> TYPE: PRT
<213> ORGANISM: Homo sapiens

<400> SEQUENCE: 10

Met Phe Arg Ala Pro Cys His Arg Leu Arg Ala Arg Gly Thr Arg Lys
1               5                   10                  15

Ala Arg Ala Gly Ala Trp Arg Gly Cys Thr Phe Pro Cys Leu Gly Lys
            20                  25                  30

Gly Met Glu Arg Pro Ala Ala Arg Glu Pro His Gly Pro Asp Ala Leu
        35                  40                  45

Arg Arg Phe Gln Gly Leu Leu Leu Asp Arg Arg Gly Arg Leu His Arg
    50                  55                  60

Gln Val Leu Arg Leu Arg Glu Val Ala Arg Arg Leu Glu Arg Leu Arg
65                  70                  75                  80

Arg Arg Ser Leu Val Ala Asn Val Ala Gly Ser Ser Leu Ser Ala Thr
```

85                  90                  95
Gly Ala Leu Ala Ala Ile Val Gly Leu Ser Leu Ser Pro Val Thr Leu
            100                 105                 110
Gly Thr Ser Leu Leu Val Ser Ala Val Gly Leu Gly Val Ala Thr Ala
        115                 120                 125
Gly Gly Ala Val Thr Ile Thr Ser Asp Leu Ser Leu Ile Phe Cys Asn
    130                 135                 140
Ser Arg Glu Leu Arg Arg Val Gln Glu Ile Ala Ala Thr Cys Gln Asp
145                 150                 155                 160
Gln Met Arg Glu Ile Leu Ser Cys Leu Glu Phe Phe Cys Arg Trp Gln
                165                 170                 175
Gly Cys Gly Asp Arg Gln Leu Leu Gln Cys Gly Arg Asn Ala Ser Ile
            180                 185                 190
Ala Leu Tyr Asn Ser Val Tyr Phe Ile Val Phe Phe Gly Ser Arg Gly
        195                 200                 205
Phe Leu Ile Pro Arg Arg Ala Glu Gly Asp Thr Lys Val Ser Gln Ala
    210                 215                 220
Val Leu Lys Ala Lys Ile Gln Lys Leu Ala Glu Ser Leu Glu Ser Cys
225                 230                 235                 240
Thr Gly Ala Leu Asp Glu Leu Ser Glu Gln Leu Glu Ser Arg Val Gln
                245                 250                 255
Leu Cys Thr Lys Ser Ser Arg Gly His Asp Leu Lys Ile Ser Ala Asp
            260                 265                 270
Gln Arg Ala Gly Leu Phe Phe
        275

<210> SEQ ID NO 11
<211> LENGTH: 8733
<212> TYPE: DNA
<213> ORGANISM: Homo sapiens
<220> FEATURE:
<221> NAME/KEY: CDS
<222> LOCATION: (473)..(8566)

<400> SEQUENCE: 11
agagacggaa cgagagagag acacacacag ggctccttcc ccccgccctc ccccccctcc    60
ctccgtcggt accgactcac ccgacaccac caagccgcag ggaggacgc ccccgccgac   120 aggagaattg gttcccgggt ccgcggcgat gcccccccgg tagctcgggc ccgtggtcgg   180
gtgtttgtga gtgtttctat gtgggagaag gaggaggagg aggaagaaga agcaacgatt   240
tgtcttctcg gctggtctcc ccccggctct acatgttccc cgcactgagg agacggaaga   300
ggagccgtag ccaccccccc tcccggcccg gattatagtc tctcgccaca gcggcctcgg   360 cctcccccttg gattcagacg ccgattcgcc cagtgtttgg gaaatgggaa gtaatgacag   420
ctggcacctg aactaagtac ttttataggc aacaccattc cagaaattca gg atg aat   478
                                                            Met Asn
                                                              1 ggg gat atg ccc cat gtc ccc att act act ctt gcg ggg att gct agt    526
Gly Asp Met Pro His Val Pro Ile Thr Thr Leu Ala Gly Ile Ala Ser
        5                   10                  15 ctc aca gac ctc ctg aac cag ctg cct ctt cca tct cct tta cct gct    574
Leu Thr Asp Leu Leu Asn Gln Leu Pro Leu Pro Ser Pro Leu Pro Ala
    20                  25                  30 aca act aca aag agc ctt ctc ttt aat gca cga ata gca gaa gag gtg    622
Thr Thr Thr Lys Ser Leu Leu Phe Asn Ala Arg Ile Ala Glu Glu Val
35                  40                  45                  50

-continued

```
aac tgc ctt ttg gct tgt agg gat gac aat ttg gtt tca cag ctt gtc      670
Asn Cys Leu Leu Ala Cys Arg Asp Asp Asn Leu Val Ser Gln Leu Val
                55                  60                  65

cat agc ctc aac cag gta tca aca gat cac ata gag ttg aaa gat aac      718
His Ser Leu Asn Gln Val Ser Thr Asp His Ile Glu Leu Lys Asp Asn
            70                  75                  80

ctt ggc agt gat gac cca gaa ggt gac ata cca gtc ttg ttg cag gcc      766
Leu Gly Ser Asp Asp Pro Glu Gly Asp Ile Pro Val Leu Leu Gln Ala
        85                  90                  95

gtc ctg gca agg agt cct aat gtt ttc agg gag aaa agc atg cag aac      814
Val Leu Ala Arg Ser Pro Asn Val Phe Arg Glu Lys Ser Met Gln Asn
    100                 105                 110

aga tat gta caa agt gga atg atg atg tct cag tat aaa ctt tct cag      862
Arg Tyr Val Gln Ser Gly Met Met Met Ser Gln Tyr Lys Leu Ser Gln
115                 120                 125                 130

aat tcc atg cac agt agt cct gca tct tcc aat tat caa caa acc act      910
Asn Ser Met His Ser Ser Pro Ala Ser Ser Asn Tyr Gln Gln Thr Thr
                135                 140                 145

atc tca cat agc ccc tcc agc cgg ttt gtg cca cca cag aca agc tct      958
Ile Ser His Ser Pro Ser Ser Arg Phe Val Pro Pro Gln Thr Ser Ser
            150                 155                 160

ggg aac aga ttt atg cca cag caa aat agc cca gtg cct agt cca tac     1006
Gly Asn Arg Phe Met Pro Gln Gln Asn Ser Pro Val Pro Ser Pro Tyr
        165                 170                 175

gcc cca caa agc cct gca gga tac atg cca tat tcc cat cct tca agt     1054
Ala Pro Gln Ser Pro Ala Gly Tyr Met Pro Tyr Ser His Pro Ser Ser
    180                 185                 190

tac aca aca cat cca cag atg caa caa gca tcg gta tca agt ccc att     1102
Tyr Thr Thr His Pro Gln Met Gln Gln Ala Ser Val Ser Ser Pro Ile
195                 200                 205                 210

gtt gca ggt ggt ttg aga aac ata cat gat aat aaa gtt tct ggt ccg     1150
Val Ala Gly Gly Leu Arg Asn Ile His Asp Asn Lys Val Ser Gly Pro
                215                 220                 225

ttg tct ggc aat tca gct aat cat cat gct gat aat cct aga cat ggt     1198
Leu Ser Gly Asn Ser Ala Asn His His Ala Asp Asn Pro Arg His Gly
            230                 235                 240

tca agt gag gac tac cta cac atg gtg cac agg cta agt agt gac gat     1246
Ser Ser Glu Asp Tyr Leu His Met Val His Arg Leu Ser Ser Asp Asp
        245                 250                 255

gga gat tct tca aca atg agg aat gct gca tct ttt ccc ttg aga tct     1294
Gly Asp Ser Ser Thr Met Arg Asn Ala Ala Ser Phe Pro Leu Arg Ser
    260                 265                 270

cca cag cca gta tgc tcc cct gct gga agt gaa gga act cct aaa ggc     1342
Pro Gln Pro Val Cys Ser Pro Ala Gly Ser Glu Gly Thr Pro Lys Gly
275                 280                 285                 290

tca aga cca cct tta atc cta caa tct cag tct cta cct tgt tca tca     1390
Ser Arg Pro Pro Leu Ile Leu Gln Ser Gln Ser Leu Pro Cys Ser Ser
                295                 300                 305

cct cga gat gtt cca cca gat atc ttg cta gat tct cca gaa aga aaa     1438
Pro Arg Asp Val Pro Pro Asp Ile Leu Leu Asp Ser Pro Glu Arg Lys
            310                 315                 320

caa aag aag cag aag aaa atg aaa tta ggc aag gat gaa aaa gag cag     1486
Gln Lys Lys Gln Lys Lys Met Lys Leu Gly Lys Asp Glu Lys Glu Gln
        325                 330                 335

agt gag aaa gcg gca atg tat gat ata att agt tct cca tcc aag gac     1534
Ser Glu Lys Ala Ala Met Tyr Asp Ile Ile Ser Ser Pro Ser Lys Asp
    340                 345                 350

tct act aaa ctt aca tta aga ctt tct cgt gta agg tct tca gac atg     1582
Ser Thr Lys Leu Thr Leu Arg Leu Ser Arg Val Arg Ser Ser Asp Met
355                 360                 365                 370
```

-continued

```
gac cag caa gag gat atg att tct ggt gtg gaa aat agc aat gtt tca      1630
Asp Gln Gln Glu Asp Met Ile Ser Gly Val Glu Asn Ser Asn Val Ser
                375                 380                 385

gaa aat gat att cct ttt aat gtg cag tac cca gga cag act tca aaa      1678
Glu Asn Asp Ile Pro Phe Asn Val Gln Tyr Pro Gly Gln Thr Ser Lys
            390                 395                 400

aca ccc att act cca caa gat ata aac cgc cca cta aat gct gct caa      1726
Thr Pro Ile Thr Pro Gln Asp Ile Asn Arg Pro Leu Asn Ala Ala Gln
        405                 410                 415

tgt ttg tcg cag caa gaa caa aca gca ttc ctt cca gca aat caa gtg      1774
Cys Leu Ser Gln Gln Glu Gln Thr Ala Phe Leu Pro Ala Asn Gln Val
    420                 425                 430

cct gtt tta caa cag aac act tca gtt gct gca aaa caa ccc cag act      1822
Pro Val Leu Gln Gln Asn Thr Ser Val Ala Ala Lys Gln Pro Gln Thr
435                 440                 445                 450

tct gtg gta cag aat caa caa cag ata tca caa cag gga cct ata tat      1870
Ser Val Val Gln Asn Gln Gln Gln Ile Ser Gln Gln Gly Pro Ile Tyr
                455                 460                 465

gat gaa gtg gaa ttg gat gca ttg gct gaa att gag cga ata gag aga      1918
Asp Glu Val Glu Leu Asp Ala Leu Ala Glu Ile Glu Arg Ile Glu Arg
            470                 475                 480

gaa tca gct att gaa agg gag cgc ttc tca aaa gaa gtt caa gat aaa      1966
Glu Ser Ala Ile Glu Arg Glu Arg Phe Ser Lys Glu Val Gln Asp Lys
        485                 490                 495

gat aag cct ttg aaa aaa aga aaa caa gat tct tac cca cag gag gct      2014
Asp Lys Pro Leu Lys Lys Arg Lys Gln Asp Ser Tyr Pro Gln Glu Ala
    500                 505                 510

ggg ggt gct aca gga ggt aat aga cca gct tct cag gag acg ggt tct      2062
Gly Gly Ala Thr Gly Gly Asn Arg Pro Ala Ser Gln Glu Thr Gly Ser
515                 520                 525                 530

acg gga aat ggg tca agg cca gca tta atg gtt agc att gat ctt cat      2110
Thr Gly Asn Gly Ser Arg Pro Ala Leu Met Val Ser Ile Asp Leu His
                535                 540                 545

cag gca gga aga gtg gac tct cag gct tct ata act cag gat tca gac      2158
Gln Ala Gly Arg Val Asp Ser Gln Ala Ser Ile Thr Gln Asp Ser Asp
            550                 555                 560

tcc ata aaa aag cct gaa gaa atc aaa caa tgt aat gat gca cct gtt      2206
Ser Ile Lys Lys Pro Glu Glu Ile Lys Gln Cys Asn Asp Ala Pro Val
        565                 570                 575

tct gtt ctt cag gaa gat att gtt gga agt ctt aaa tct aca cca gaa      2254
Ser Val Leu Gln Glu Asp Ile Val Gly Ser Leu Lys Ser Thr Pro Glu
    580                 585                 590

aac cat cct gag aca cct aaa aaa aag tct gat cct gag ctt tca aag      2302
Asn His Pro Glu Thr Pro Lys Lys Lys Ser Asp Pro Glu Leu Ser Lys
595                 600                 605                 610

agt gaa atg aaa caa agt gaa agt aga tta gca gaa tct aaa cca aat      2350
Ser Glu Met Lys Gln Ser Glu Ser Arg Leu Ala Glu Ser Lys Pro Asn
                615                 620                 625

gaa aac cga ttg gtg gag aca aaa tca agt gaa aat aag tta gaa act      2398
Glu Asn Arg Leu Val Glu Thr Lys Ser Ser Glu Asn Lys Leu Glu Thr
            630                 635                 640

aaa gtt gag acc caa aca gaa gaa ctt aaa cag aat gag agc aga aca      2446
Lys Val Glu Thr Gln Thr Glu Glu Leu Lys Gln Asn Glu Ser Arg Thr
        645                 650                 655

act gaa tgc aaa caa aac gag agc acc ata gtt gag cct aaa caa aat      2494
Thr Glu Cys Lys Gln Asn Glu Ser Thr Ile Val Glu Pro Lys Gln Asn
    660                 665                 670

gaa aat aga ctg tct gac aca aaa cca aat gac aac aaa caa aat aat      2542
Glu Asn Arg Leu Ser Asp Thr Lys Pro Asn Asp Asn Lys Gln Asn Asn
```

-continued

```
675                 680                 685                 690

ggc aga tca gaa aca aca aaa tca agg cct gaa acc cca aag caa aag      2590
Gly Arg Ser Glu Thr Thr Lys Ser Arg Pro Glu Thr Pro Lys Gln Lys
                695                 700                 705

ggt gaa agc cgg cct gag act cca aaa caa aag agt gat ggg cat cct      2638
Gly Glu Ser Arg Pro Glu Thr Pro Lys Gln Lys Ser Asp Gly His Pro
            710                 715                 720

gaa acc cca aaa cag aag ggt gat gga agg cct gaa act cca aag caa      2686
Glu Thr Pro Lys Gln Lys Gly Asp Gly Arg Pro Glu Thr Pro Lys Gln
        725                 730                 735

aaa ggt gag agc cgc cct gaa act cca aag caa aaa aat gaa ggg cga      2734
Lys Gly Glu Ser Arg Pro Glu Thr Pro Lys Gln Lys Asn Glu Gly Arg
    740                 745                 750

cct gaa aca cca aaa cac agg cat gac aat agg agg gat tct gga aag      2782
Pro Glu Thr Pro Lys His Arg His Asp Asn Arg Arg Asp Ser Gly Lys
755                 760                 765                 770

cca tct aca gag aaa aaa cct gaa gtg tct aaa cat aaa caa gat act      2830
Pro Ser Thr Glu Lys Lys Pro Glu Val Ser Lys His Lys Gln Asp Thr
                775                 780                 785

aaa tct gac tca cct cgg tta aaa tca gaa cga gct gaa gcc tta aag      2878
Lys Ser Asp Ser Pro Arg Leu Lys Ser Glu Arg Ala Glu Ala Leu Lys
            790                 795                 800

cag aga cct gat ggg cga tct gtt tct gag tca cta aga cgt gac cat      2926
Gln Arg Pro Asp Gly Arg Ser Val Ser Glu Ser Leu Arg Arg Asp His
        805                 810                 815

gat aat aaa caa aaa tca gat gac agg ggt gaa tca gag cga cat cga      2974
Asp Asn Lys Gln Lys Ser Asp Asp Arg Gly Glu Ser Glu Arg His Arg
    820                 825                 830

ggg gat cag tct agg gtt cga aga cca gaa aca ttg aga tcc tct agt      3022
Gly Asp Gln Ser Arg Val Arg Arg Pro Glu Thr Leu Arg Ser Ser Ser
835                 840                 845                 850

aga aat gaa cat ggc att aaa tct gat agt tca aaa act gat aaa cta      3070
Arg Asn Glu His Gly Ile Lys Ser Asp Ser Ser Lys Thr Asp Lys Leu
                855                 860                 865

gaa cga aaa cac agg cat gaa tca ggg gac tca agg gaa aga cca tct      3118
Glu Arg Lys His Arg His Glu Ser Gly Asp Ser Arg Glu Arg Pro Ser
            870                 875                 880

tct ggg gaa caa aaa tca aga cct gac agt cct cgt gtt aaa caa gga      3166
Ser Gly Glu Gln Lys Ser Arg Pro Asp Ser Pro Arg Val Lys Gln Gly
        885                 890                 895

gat tct aat aaa tca aga tct gat aaa ctt ggt ttt aaa tca cca act      3214
Asp Ser Asn Lys Ser Arg Ser Asp Lys Leu Gly Phe Lys Ser Pro Thr
    900                 905                 910

agt aaa gat gac aaa agg aca gag ggt aac aag agt aaa gta gac act      3262
Ser Lys Asp Asp Lys Arg Thr Glu Gly Asn Lys Ser Lys Val Asp Thr
915                 920                 925                 930

aat aaa gca cac cct gac aat aag gca gaa ttt cca agt tat ttg ttg      3310
Asn Lys Ala His Pro Asp Asn Lys Ala Glu Phe Pro Ser Tyr Leu Leu
                935                 940                 945

ggg ggc agg tct ggt gcg ttg aaa aat ttt gtc att ccg aaa atc aag      3358
Gly Gly Arg Ser Gly Ala Leu Lys Asn Phe Val Ile Pro Lys Ile Lys
            950                 955                 960

agg gat aaa gat ggc aat gtt act cag gag aca aag aaa atg gaa atg      3406
Arg Asp Lys Asp Gly Asn Val Thr Gln Glu Thr Lys Lys Met Glu Met
        965                 970                 975

aaa gga gag ccg aaa gac aaa gta gaa aaa ata gga tta gtt gaa gat      3454
Lys Gly Glu Pro Lys Asp Lys Val Glu Lys Ile Gly Leu Val Glu Asp
    980                 985                 990

cta aat aaa gga gct aag  cct gta gtt gtg cta  caa aaa ctg tct      3499
```

-continued

```
Leu Asn Lys Gly Ala Lys  Pro Val Val Val Leu  Gln Lys Leu Ser
995                 1000                 1005

ttg  gat gat gtt cag aaa  ctt att aaa gat aga  gag gac aaa tca      3544
Leu  Asp Asp Val Gln Lys  Leu Ile Lys Asp Arg  Glu Asp Lys Ser
1010                1015                 1020

aga  agt tcc ctt aaa cct  atc aag aat aaa cca  tca aag tca aat      3589
Arg  Ser Ser Leu Lys Pro  Ile Lys Asn Lys Pro  Ser Lys Ser Asn
1025                1030                 1035

aaa  ggt agt ata gat caa  tca gtg tta aaa gaa  tta ccc cct gaa      3634
Lys  Gly Ser Ile Asp Gln  Ser Val Leu Lys Glu  Leu Pro Pro Glu
1040                1045                 1050

ctc  ctg gca gaa att gag  tcc acc atg cca ctt  tgt gaa cgt gtg      3679
Leu  Leu Ala Glu Ile Glu  Ser Thr Met Pro Leu  Cys Glu Arg Val
1055                1060                 1065

aaa  atg aac aaa cgc aag  cgt agc aca gtt aat  gaa aag cca aaa      3724
Lys  Met Asn Lys Arg Lys  Arg Ser Thr Val Asn  Glu Lys Pro Lys
1070                1075                 1080

tat  gct gaa atc agt tca  gat gaa gat aat gat  agt gat gaa gct      3769
Tyr  Ala Glu Ile Ser Ser  Asp Glu Asp Asn Asp  Ser Asp Glu Ala
1085                1090                 1095

ttt  gaa tcc tct agg aaa  cga cat aaa aaa gat  gat gat aaa gct      3814
Phe  Glu Ser Ser Arg Lys  Arg His Lys Lys Asp  Asp Asp Lys Ala
1100                1105                 1110

tgg  gaa tat gaa gag cgt  gac aga aga agc tct  ggg gat cat agg      3859
Trp  Glu Tyr Glu Glu Arg  Asp Arg Arg Ser Ser  Gly Asp His Arg
1115                1120                 1125

aga  agt ggc cac tct cat  gaa gga aga agg agt  tca ggt ggt ggt      3904
Arg  Ser Gly His Ser His  Glu Gly Arg Arg Ser  Ser Gly Gly Gly
1130                1135                 1140

cgt  tat cga aac cga agt  ccg tca gat tct gac  atg gaa gat tat      3949
Arg  Tyr Arg Asn Arg Ser  Pro Ser Asp Ser Asp  Met Glu Asp Tyr
1145                1150                 1155

tct  cct cct ccc agc ctt  agt gag gtt gct agg  aaa atg aag aaa      3994
Ser  Pro Pro Pro Ser Leu  Ser Glu Val Ala Arg  Lys Met Lys Lys
1160                1165                 1170

aaa  gaa aaa cag aag aaa  agg aaa gca tat gaa  cca aaa cta aca      4039
Lys  Glu Lys Gln Lys Lys  Arg Lys Ala Tyr Glu  Pro Lys Leu Thr
1175                1180                 1185

cct  gaa gaa atg atg gac  tct tca act ttt aag  aga ttc aca gcc      4084
Pro  Glu Glu Met Met Asp  Ser Ser Thr Phe Lys  Arg Phe Thr Ala
1190                1195                 1200

tca  ata gag aat att ttg  gat aat ttg gaa gat  atg gat ttt act      4129
Ser  Ile Glu Asn Ile Leu  Asp Asn Leu Glu Asp  Met Asp Phe Thr
1205                1210                 1215

gcg  ttt ggt gat gat gat  gaa att cct cag gaa  ctg ctc tta gga      4174
Ala  Phe Gly Asp Asp Asp  Glu Ile Pro Gln Glu  Leu Leu Leu Gly
1220                1225                 1230

aaa  cat cag ctt aat gaa  ctt ggc agt gaa tct  gct aaa ata aaa      4219
Lys  His Gln Leu Asn Glu  Leu Gly Ser Glu Ser  Ala Lys Ile Lys
1235                1240                 1245

gca  atg ggt ata atg gat  aag ctt tca act gac  aaa act gtg aaa      4264
Ala  Met Gly Ile Met Asp  Lys Leu Ser Thr Asp  Lys Thr Val Lys
1250                1255                 1260

gtc  tta aat atc ttg gag  aag aat att cag gat  ggg tca aag ctt      4309
Val  Leu Asn Ile Leu Glu  Lys Asn Ile Gln Asp  Gly Ser Lys Leu
1265                1270                 1275

tcc  act ttg tta aat cat  aat aac gat act gaa  gaa gaa gaa agg      4354
Ser  Thr Leu Leu Asn His  Asn Asn Asp Thr Glu  Glu Glu Glu Arg
1280                1285                 1290
```

-continued

```
tta  tgg aga gac ctt att  atg gag aga gtt aca  aaa tca gcg gat      4399
Leu  Trp Arg Asp Leu Ile  Met Glu Arg Val Thr  Lys Ser Ala Asp
1295                 1300                 1305

gct  tgt ctt aca act atc  aac att atg aca tcc  cct aac atg cca      4444
Ala  Cys Leu Thr Thr Ile  Asn Ile Met Thr Ser  Pro Asn Met Pro
1310                 1315                 1320

aaa  gct gtg tac att gag  gat gta att gaa aga  gtt ata cag tac      4489
Lys  Ala Val Tyr Ile Glu  Asp Val Ile Glu Arg  Val Ile Gln Tyr
1325                 1330                 1335

act  aaa ttt cat ttg cag  aat aca ctt tat cct  cag tat gat cct      4534
Thr  Lys Phe His Leu Gln  Asn Thr Leu Tyr Pro  Gln Tyr Asp Pro
1340                 1345                 1350

gtt  tac aga tta gat cct  cat gga gga ggc tta  tta agt tca aaa      4579
Val  Tyr Arg Leu Asp Pro  His Gly Gly Gly Leu  Leu Ser Ser Lys
1355                 1360                 1365

gca  aaa cgg gct aaa tgt  tct acc cat aag cag  aga gta ata gta      4624
Ala  Lys Arg Ala Lys Cys  Ser Thr His Lys Gln  Arg Val Ile Val
1370                 1375                 1380

atg  ctt tat aac aaa gtt  tgt gac att gtt agc  agc tta tca gaa      4669
Met  Leu Tyr Asn Lys Val  Cys Asp Ile Val Ser  Ser Leu Ser Glu
1385                 1390                 1395

ttg  cta gag ata caa ctt  ctt aca gac aca aca  att ctt cag gtt      4714
Leu  Leu Glu Ile Gln Leu  Leu Thr Asp Thr Thr  Ile Leu Gln Val
1400                 1405                 1410

tca  tct atg gga ata aca  cca ttt ttt gtg gaa  aat gtc agt gaa      4759
Ser  Ser Met Gly Ile Thr  Pro Phe Phe Val Glu  Asn Val Ser Glu
1415                 1420                 1425

cta  cag ttg tgt gcc att  aag tta gtc act gca  gta ttc tca aga      4804
Leu  Gln Leu Cys Ala Ile  Lys Leu Val Thr Ala  Val Phe Ser Arg
1430                 1435                 1440

tat  gaa aaa cat agg cag  tta att ttg gaa gaa  att ttt act tca      4849
Tyr  Glu Lys His Arg Gln  Leu Ile Leu Glu Glu  Ile Phe Thr Ser
1445                 1450                 1455

ctt  gca aga tta cca acc  agc aag agg agt tta  agg aac ttc agg      4894
Leu  Ala Arg Leu Pro Thr  Ser Lys Arg Ser Leu  Arg Asn Phe Arg
1460                 1465                 1470

tta  aac agt agt gat atg  gat gga gaa cct atg  tat att cag atg      4939
Leu  Asn Ser Ser Asp Met  Asp Gly Glu Pro Met  Tyr Ile Gln Met
1475                 1480                 1485

gtt  aca gca ctg gtt tta  caa ctt att cag tgt  gtg gta cac tta      4984
Val  Thr Ala Leu Val Leu  Gln Leu Ile Gln Cys  Val Val His Leu
1490                 1495                 1500

cca  tca tca gag aag gac  tct aat gca gaa gaa  gat tca aat aaa      5029
Pro  Ser Ser Glu Lys Asp  Ser Asn Ala Glu Glu  Asp Ser Asn Lys
1505                 1510                 1515

aaa  att gac cag gat gtt  gtc att act aac tct  tat gaa aca gct      5074
Lys  Ile Asp Gln Asp Val  Val Ile Thr Asn Ser  Tyr Glu Thr Ala
1520                 1525                 1530

atg  cga aca gcc caa aac  ttc ctc tcc atc ttc  ctt aaa aaa tgt      5119
Met  Arg Thr Ala Gln Asn  Phe Leu Ser Ile Phe  Leu Lys Lys Cys
1535                 1540                 1545

ggt  agt aag caa ggt gaa  gaa gat tac aga cca  ctg ttt gaa aat      5164
Gly  Ser Lys Gln Gly Glu  Glu Asp Tyr Arg Pro  Leu Phe Glu Asn
1550                 1555                 1560

ttt  gtt caa gac ctt ctt  tca aca gtc aat aag  cct gaa tgg cca      5209
Phe  Val Gln Asp Leu Leu  Ser Thr Val Asn Lys  Pro Glu Trp Pro
1565                 1570                 1575

gct  gct gaa cta ctc ctt  agt ttg tta ggg aga  ctg ttg gtt cat      5254
Ala  Ala Glu Leu Leu Leu  Ser Leu Leu Gly Arg  Leu Leu Val His
1580                 1585                 1590
```

-continued

```
cag  ttc agt aac aag tca  aca gag atg gct tta  aga gtg gca tct      5299
Gln  Phe Ser Asn Lys Ser  Thr Glu Met Ala Leu  Arg Val Ala Ser
1595                 1600                 1605

ctt  gat tac ctt gga act  gtt gct gca cgg cta  aga aaa gat gct      5344
Leu  Asp Tyr Leu Gly Thr  Val Ala Ala Arg Leu  Arg Lys Asp Ala
1610                 1615                 1620

gtt  aca agc aaa atg gat  caa gga tct ata gaa  cgc att tta aaa      5389
Val  Thr Ser Lys Met Asp  Gln Gly Ser Ile Glu  Arg Ile Leu Lys
1625                 1630                 1635

cag  gtt tca gga ggg gaa  gat gaa atc caa caa  tta caa aaa gca      5434
Gln  Val Ser Gly Gly Glu  Asp Glu Ile Gln Gln  Leu Gln Lys Ala
1640                 1645                 1650

ttg  ctt gat tac ttg gat  gaa aac act gag act  gat cct tca cta      5479
Leu  Leu Asp Tyr Leu Asp  Glu Asn Thr Glu Thr  Asp Pro Ser Leu
1655                 1660                 1665

gtg  ttt tct cgt aaa ttc  tat ata gcc cag tgg  ttt cga gac aca      5524
Val  Phe Ser Arg Lys Phe  Tyr Ile Ala Gln Trp  Phe Arg Asp Thr
1670                 1675                 1680

act  ctg gaa aca gaa aaa  gca atg aaa tca caa  aaa gat gaa gaa      5569
Thr  Leu Glu Thr Glu Lys  Ala Met Lys Ser Gln  Lys Asp Glu Glu
1685                 1690                 1695

tca  tct gaa gga aca cat  cat gca aag gaa att  gag aca act ggc      5614
Ser  Ser Glu Gly Thr His  His Ala Lys Glu Ile  Glu Thr Thr Gly
1700                 1705                 1710

caa  att atg cat cga gct  gaa aac cga aaa aag  ttt ctt aga agc      5659
Gln  Ile Met His Arg Ala  Glu Asn Arg Lys Lys  Phe Leu Arg Ser
1715                 1720                 1725

att  atc aaa acc aca cct  tct cag ttt agc aca  tta aag atg aac      5704
Ile  Ile Lys Thr Thr Pro  Ser Gln Phe Ser Thr  Leu Lys Met Asn
1730                 1735                 1740

tct  gat act gtg gac tat  gat gat gct tgc ttg  att gtt cga tac      5749
Ser  Asp Thr Val Asp Tyr  Asp Asp Ala Cys Leu  Ile Val Arg Tyr
1745                 1750                 1755

ttg  gcc tcc atg agg ccg  ttt gcc cag agc ttt  gat att tat ttg      5794
Leu  Ala Ser Met Arg Pro  Phe Ala Gln Ser Phe  Asp Ile Tyr Leu
1760                 1765                 1770

aca  cag atc cta cga gtt  ctt ggt gaa aat gca  att gct gtt cga      5839
Thr  Gln Ile Leu Arg Val  Leu Gly Glu Asn Ala  Ile Ala Val Arg
1775                 1780                 1785

aca  aaa gcc atg aag tgt  ttg tct gag gtt gtt  gct gta gac ccc      5884
Thr  Lys Ala Met Lys Cys  Leu Ser Glu Val Val  Ala Val Asp Pro
1790                 1795                 1800

agt  att cta gca agg ctt  gat atg caa cga ggt  gtt cat gga cga      5929
Ser  Ile Leu Ala Arg Leu  Asp Met Gln Arg Gly  Val His Gly Arg
1805                 1810                 1815

ttg  atg gat aat tcg act  agt gtc cga gaa gca  gca gta gaa tta      5974
Leu  Met Asp Asn Ser Thr  Ser Val Arg Glu Ala  Ala Val Glu Leu
1820                 1825                 1830

cta  ggt cga ttt gtc ctt  tgt cga cct cag ctt  gct gaa cag tat      6019
Leu  Gly Arg Phe Val Leu  Cys Arg Pro Gln Leu  Ala Glu Gln Tyr
1835                 1840                 1845

tat  gat atg ctg att gaa  aga ata ttg gat act  ggt atc agt gtc      6064
Tyr  Asp Met Leu Ile Glu  Arg Ile Leu Asp Thr  Gly Ile Ser Val
1850                 1855                 1860

agg  aaa aga gta ata aag  att ctc aga gac att  tgt att gaa caa      6109
Arg  Lys Arg Val Ile Lys  Ile Leu Arg Asp Ile  Cys Ile Glu Gln
1865                 1870                 1875

cca  aca ttt cca aaa atc  aca gaa atg tgt gta  aaa atg att cgc      6154
Pro  Thr Phe Pro Lys Ile  Thr Glu Met Cys Val  Lys Met Ile Arg
```

-continued

```
1880                1885                1890

aga  gtc aat gat gaa gag  ggc att aag aaa tta  gta aat gaa aca      6199
Arg  Val Asn Asp Glu Glu  Gly Ile Lys Lys Leu  Val Asn Glu Thr
1895                1900                1905

ttc  cag aaa ctc tgg ttt  act cca act cca cac  aat gac aaa gaa      6244
Phe  Gln Lys Leu Trp Phe  Thr Pro Thr Pro His  Asn Asp Lys Glu
1910                1915                1920

gca  atg aca agg aaa att  tta aac att acc gat  gtg gtt gca gca      6289
Ala  Met Thr Arg Lys Ile  Leu Asn Ile Thr Asp  Val Val Ala Ala
1925                1930                1935

tgc  aga gat act gga tat  gac tgg ttt gag caa  ctg ctt caa aac      6334
Cys  Arg Asp Thr Gly Tyr  Asp Trp Phe Glu Gln  Leu Leu Gln Asn
1940                1945                1950

ttg  ttg aag tcc gaa gag  gat tcc tca tat aaa  cct gtg aag aaa      6379
Leu  Leu Lys Ser Glu Glu  Asp Ser Ser Tyr Lys  Pro Val Lys Lys
1955                1960                1965

gct  tgt act caa ctt gtt  gat aac cta gtt gag  cac att ctt aaa      6424
Ala  Cys Thr Gln Leu Val  Asp Asn Leu Val Glu  His Ile Leu Lys
1970                1975                1980

tat  gag gaa tct cta gct  gac tct gac aat aaa  ggt gtg aat tct      6469
Tyr  Glu Glu Ser Leu Ala  Asp Ser Asp Asn Lys  Gly Val Asn Ser
1985                1990                1995

gga  aga ttg gta gct tgc  ata acc act ttg ttc  tta ttc agc aaa      6514
Gly  Arg Leu Val Ala Cys  Ile Thr Thr Leu Phe  Leu Phe Ser Lys
2000                2005                2010

ata  aga ccc cag ctc atg  gtt aaa cat gca atg  act atg caa cca      6559
Ile  Arg Pro Gln Leu Met  Val Lys His Ala Met  Thr Met Gln Pro
2015                2020                2025

tac  ctt acc act aaa tgt  agt acg caa aat gat  ttc atg gtt atc      6604
Tyr  Leu Thr Thr Lys Cys  Ser Thr Gln Asn Asp  Phe Met Val Ile
2030                2035                2040

tgc  aat gtt gca aaa atc  cta gag cta gtt gta  cca ctg atg gag      6649
Cys  Asn Val Ala Lys Ile  Leu Glu Leu Val Val  Pro Leu Met Glu
2045                2050                2055

cat  cca agt gaa act ttt  ctt gcc act att gag  gaa gat cta atg      6694
His  Pro Ser Glu Thr Phe  Leu Ala Thr Ile Glu  Glu Asp Leu Met
2060                2065                2070

aag  ctc atc atc aaa tat  ggc atg act gta gtg  caa cat tgt gtg      6739
Lys  Leu Ile Ile Lys Tyr  Gly Met Thr Val Val  Gln His Cys Val
2075                2080                2085

agc  tgt ctt gga gct gtt  gta aat aaa gtg aca  caa aat ttt aaa      6784
Ser  Cys Leu Gly Ala Val  Val Asn Lys Val Thr  Gln Asn Phe Lys
2090                2095                2100

ttt  gtg tgg gct tgt ttc  aat aga tac tat ggt  gcc att tca aaa      6829
Phe  Val Trp Ala Cys Phe  Asn Arg Tyr Tyr Gly  Ala Ile Ser Lys
2105                2110                2115

tta  aaa agt caa cac caa  gag gac cca aat aac  act tca ctt cta      6874
Leu  Lys Ser Gln His Gln  Glu Asp Pro Asn Asn  Thr Ser Leu Leu
2120                2125                2130

aca  aac aaa cca gca ctt  ctt aga tcc ctt ttc  acc gtt gga gca      6919
Thr  Asn Lys Pro Ala Leu  Leu Arg Ser Leu Phe  Thr Val Gly Ala
2135                2140                2145

cta  tgt cgg cat ttt gat  ttt gat ctg gaa gat  ttt aaa ggc aac      6964
Leu  Cys Arg His Phe Asp  Phe Asp Leu Glu Asp  Phe Lys Gly Asn
2150                2155                2160

agc  aag gtt aac ata aaa  gat aaa gta ctt gaa  cta ttg atg tat      7009
Ser  Lys Val Asn Ile Lys  Asp Lys Val Leu Glu  Leu Leu Met Tyr
2165                2170                2175

ttt  aca aaa cac tca gat  gaa gaa gta caa aca  aaa gct atc att      7054
```

-continued

```
Phe  Thr Lys His Ser Asp  Glu Glu Val Gln Thr  Lys Ala Ile Ile
2180                 2185                 2190

ggt  cta gga ttt gcc ttt  att cag cat cca agt  cta atg ttc gag      7099
Gly  Leu Gly Phe Ala Phe  Ile Gln His Pro Ser  Leu Met Phe Glu
2195                 2200                 2205

caa  gaa gtg aag aat cta  tat aat aat att tta  tct gat aag aac      7144
Gln  Glu Val Lys Asn Leu  Tyr Asn Asn Ile Leu  Ser Asp Lys Asn
2210                 2215                 2220

tcc  tca gtc aat tta aaa  ata caa gtg tta aaa  aac ctc cag acc      7189
Ser  Ser Val Asn Leu Lys  Ile Gln Val Leu Lys  Asn Leu Gln Thr
2225                 2230                 2235

tac  cta caa gaa gaa gat  aca cgt atg cag cag  gca gat aga gac      7234
Tyr  Leu Gln Glu Glu Asp  Thr Arg Met Gln Gln  Ala Asp Arg Asp
2240                 2245                 2250

tgg  aag aaa gtt gca aaa  cag gaa gac tta aaa  gaa atg ggt gat      7279
Trp  Lys Lys Val Ala Lys  Gln Glu Asp Leu Lys  Glu Met Gly Asp
2255                 2260                 2265

gtt  tcc tca ggg atg agt  agt tcc atc atg cag  ctt tat ctc aaa      7324
Val  Ser Ser Gly Met Ser  Ser Ser Ile Met Gln  Leu Tyr Leu Lys
2270                 2275                 2280

cag  gtg ctt gag gca ttt  ttt cac acc cag tca  agt gta cgc cac      7369
Gln  Val Leu Glu Ala Phe  Phe His Thr Gln Ser  Ser Val Arg His
2285                 2290                 2295

ttt  gcc cta aat gtc att  gca ttg act cta aat  caa ggt ctt att      7414
Phe  Ala Leu Asn Val Ile  Ala Leu Thr Leu Asn  Gln Gly Leu Ile
2300                 2305                 2310

cat  cca gtt cag tgt gtg  cca tat tta att gct  atg ggc aca gac      7459
His  Pro Val Gln Cys Val  Pro Tyr Leu Ile Ala  Met Gly Thr Asp
2315                 2320                 2325

cca  gaa cct gct atg cgg  aac aag gct gat cag  caa ctt gtg gaa      7504
Pro  Glu Pro Ala Met Arg  Asn Lys Ala Asp Gln  Gln Leu Val Glu
2330                 2335                 2340

ata  gac aaa aaa tat gct  gga ttc att cat atg  aaa gca gtg gct      7549
Ile  Asp Lys Lys Tyr Ala  Gly Phe Ile His Met  Lys Ala Val Ala
2345                 2350                 2355

ggt  atg aag atg tct tac  cag gta caa cag gca  atc aac aca tgc      7594
Gly  Met Lys Met Ser Tyr  Gln Val Gln Gln Ala  Ile Asn Thr Cys
2360                 2365                 2370

cta  aaa gat cct gta agg  ggt ttc aga caa gac  gag tcc tct agc      7639
Leu  Lys Asp Pro Val Arg  Gly Phe Arg Gln Asp  Glu Ser Ser Ser
2375                 2380                 2385

gct  ttg tgt tca cac ctt  tac tcc atg atc cgt  gga aac cgc caa      7684
Ala  Leu Cys Ser His Leu  Tyr Ser Met Ile Arg  Gly Asn Arg Gln
2390                 2395                 2400

cac  aga cga gcc ttt ctt  att tct tta ctc aac  ctc ttt gat gac      7729
His  Arg Arg Ala Phe Leu  Ile Ser Leu Leu Asn  Leu Phe Asp Asp
2405                 2410                 2415

aca  gca aaa aca gac gtg  act atg ctc ttg tat  ata gca gac aat      7774
Thr  Ala Lys Thr Asp Val  Thr Met Leu Leu Tyr  Ile Ala Asp Asn
2420                 2425                 2430

cta  gcc tgt ttt cca tac  cag aca cag gaa gag  ccg ttg ttt ata      7819
Leu  Ala Cys Phe Pro Tyr  Gln Thr Gln Glu Glu  Pro Leu Phe Ile
2435                 2440                 2445

atg  cat cat ata gac att  aca ctc tca gtt tct  ggt agt aac cta      7864
Met  His His Ile Asp Ile  Thr Leu Ser Val Ser  Gly Ser Asn Leu
2450                 2455                 2460

ctg  cag tca ttc aag gag  tct atg gta aag gac  aaa agg aaa gag      7909
Leu  Gln Ser Phe Lys Glu  Ser Met Val Lys Asp  Lys Arg Lys Glu
2465                 2470                 2475
```

-continued

```
aga  aaa tca tca cct agt  aag gaa aat gag tca  agc gac agt gaa      7954
Arg  Lys Ser Ser Pro Ser  Lys Glu Asn Glu Ser  Ser Asp Ser Glu
2480                 2485                 2490

gaa  gaa gtt tcc agg cct  cgg aag tca cgg aaa  cgt gta gat tca      7999
Glu  Glu Val Ser Arg Pro  Arg Lys Ser Arg Lys  Arg Val Asp Ser
2495                 2500                 2505

gat  tca gat tca gat tca  gaa gac gat ata aat  tca gtg atg aaa      8044
Asp  Ser Asp Ser Asp Ser  Glu Asp Asp Ile Asn  Ser Val Met Lys
2510                 2515                 2520

tgt  ttg cca gaa aat tca  gct cct tta atc gaa  ttt gca aat gtg      8089
Cys  Leu Pro Glu Asn Ser  Ala Pro Leu Ile Glu  Phe Ala Asn Val
2525                 2530                 2535

tcc  cag ggt att tta tta  ctt ctc atg tta aaa  caa cat ttg aag      8134
Ser  Gln Gly Ile Leu Leu  Leu Leu Met Leu Lys  Gln His Leu Lys
2540                 2545                 2550

aat  ctt tgt gga ttt tct  gat agt aaa att cag  aag tac tct cca      8179
Asn  Leu Cys Gly Phe Ser  Asp Ser Lys Ile Gln  Lys Tyr Ser Pro
2555                 2560                 2565

tct  gaa tct gca aaa gta  tat gat aaa gcg ata  aac cga aaa aca      8224
Ser  Glu Ser Ala Lys Val  Tyr Asp Lys Ala Ile  Asn Arg Lys Thr
2570                 2575                 2580

gga  gtt cat ttt cat cca  aaa caa aca ctg gac  ttc ctg cgg agt      8269
Gly  Val His Phe His Pro  Lys Gln Thr Leu Asp  Phe Leu Arg Ser
2585                 2590                 2595

gac  atg gct aat tcc aaa  atc aca gaa gag gtg  aaa agg agt ata      8314
Asp  Met Ala Asn Ser Lys  Ile Thr Glu Glu Val  Lys Arg Ser Ile
2600                 2605                 2610

gta  aaa cag tat cta gat  ttc aaa ctt ctc atg  gaa cat ctg gac      8359
Val  Lys Gln Tyr Leu Asp  Phe Lys Leu Leu Met  Glu His Leu Asp
2615                 2620                 2625

cct  gat gaa gaa gaa gaa  gaa ggg gag gtt tca  gct agc aca aat      8404
Pro  Asp Glu Glu Glu Glu  Glu Gly Glu Val Ser  Ala Ser Thr Asn
2630                 2635                 2640

gct  cgg aac aaa gca att  acc tca ctg ctt gga  gga ggc agc cct      8449
Ala  Arg Asn Lys Ala Ile  Thr Ser Leu Leu Gly  Gly Gly Ser Pro
2645                 2650                 2655

aaa  aat aat aca gca gca  gag aca gaa gat gat  gaa agt gat ggg      8494
Lys  Asn Asn Thr Ala Ala  Glu Thr Glu Asp Asp  Glu Ser Asp Gly
2660                 2665                 2670

gag  gat aga gga gga ggc  act tca ggg gtg agg  cgg agg agg agt      8539
Glu  Asp Arg Gly Gly Gly  Thr Ser Gly Val Arg  Arg Arg Arg Ser
2675                 2680                 2685

caa  cgt att tcg cag cgt  att acg taa aatgattttt atgtgcttat        8586
Gln  Arg Ile Ser Gln Arg  Ile Thr
2690                 2695

atatgtcagt ctattaaatg tacaccaagt aatgtaatac ttaaaagaga aaacattttg   8646

tagatagaga ttctctactt acccgtttat acatcctttt gtagaaagtt taacataaaa   8706

gacaataaaa aaacagaaat gagattt                                       8733


<210> SEQ ID NO 12
<211> LENGTH: 2697
<212> TYPE: PRT
<213> ORGANISM: Homo sapiens

<400> SEQUENCE: 12

Met Asn Gly Asp Met Pro His Val Pro Ile Thr Thr Leu Ala Gly Ile
1               5                   10                  15

Ala Ser Leu Thr Asp Leu Leu Asn Gln Leu Pro Leu Pro Ser Pro Leu
            20                  25                  30
```

-continued

```
Pro Ala Thr Thr Thr Lys Ser Leu Leu Phe Asn Ala Arg Ile Ala Glu
        35                  40                  45

Glu Val Asn Cys Leu Leu Ala Cys Arg Asp Asp Asn Leu Val Ser Gln
    50                  55                  60

Leu Val His Ser Leu Asn Gln Val Ser Thr Asp His Ile Glu Leu Lys
65                  70                  75                  80

Asp Asn Leu Gly Ser Asp Asp Pro Glu Gly Asp Ile Pro Val Leu Leu
                85                  90                  95

Gln Ala Val Leu Ala Arg Ser Pro Asn Val Phe Arg Glu Lys Ser Met
            100                 105                 110

Gln Asn Arg Tyr Val Gln Ser Gly Met Met Met Ser Gln Tyr Lys Leu
        115                 120                 125

Ser Gln Asn Ser Met His Ser Ser Pro Ala Ser Ser Asn Tyr Gln Gln
    130                 135                 140

Thr Thr Ile Ser His Ser Pro Ser Ser Arg Phe Val Pro Pro Gln Thr
145                 150                 155                 160

Ser Ser Gly Asn Arg Phe Met Pro Gln Gln Asn Ser Pro Val Pro Ser
                165                 170                 175

Pro Tyr Ala Pro Gln Ser Pro Ala Gly Tyr Met Pro Tyr Ser His Pro
            180                 185                 190

Ser Ser Tyr Thr Thr His Pro Gln Met Gln Gln Ala Ser Val Ser Ser
        195                 200                 205

Pro Ile Val Ala Gly Gly Leu Arg Asn Ile His Asp Asn Lys Val Ser
    210                 215                 220

Gly Pro Leu Ser Gly Asn Ser Ala Asn His His Ala Asp Asn Pro Arg
225                 230                 235                 240

His Gly Ser Ser Glu Asp Tyr Leu His Met Val His Arg Leu Ser Ser
                245                 250                 255

Asp Asp Gly Asp Ser Ser Thr Met Arg Asn Ala Ala Ser Phe Pro Leu
            260                 265                 270

Arg Ser Pro Gln Pro Val Cys Ser Pro Ala Gly Ser Glu Gly Thr Pro
        275                 280                 285

Lys Gly Ser Arg Pro Pro Leu Ile Leu Gln Ser Gln Ser Leu Pro Cys
    290                 295                 300

Ser Ser Pro Arg Asp Val Pro Pro Asp Ile Leu Leu Asp Ser Pro Glu
305                 310                 315                 320

Arg Lys Gln Lys Lys Gln Lys Lys Met Lys Leu Gly Lys Asp Glu Lys
                325                 330                 335

Glu Gln Ser Glu Lys Ala Ala Met Tyr Asp Ile Ile Ser Ser Pro Ser
            340                 345                 350

Lys Asp Ser Thr Lys Leu Thr Leu Arg Leu Ser Arg Val Arg Ser Ser
        355                 360                 365

Asp Met Asp Gln Gln Glu Asp Met Ile Ser Gly Val Glu Asn Ser Asn
    370                 375                 380

Val Ser Glu Asn Asp Ile Pro Phe Asn Val Gln Tyr Pro Gly Gln Thr
385                 390                 395                 400

Ser Lys Thr Pro Ile Thr Pro Gln Asp Ile Asn Arg Pro Leu Asn Ala
                405                 410                 415

Ala Gln Cys Leu Ser Gln Gln Glu Gln Thr Ala Phe Leu Pro Ala Asn
            420                 425                 430

Gln Val Pro Val Leu Gln Gln Asn Thr Ser Val Ala Ala Lys Gln Pro
        435                 440                 445
```

-continued

```
Gln Thr Ser Val Val Gln Asn Gln Gln Gln Ile Ser Gln Gln Gly Pro
    450                 455                 460

Ile Tyr Asp Glu Val Glu Leu Asp Ala Leu Ala Glu Ile Glu Arg Ile
465                 470                 475                 480

Glu Arg Glu Ser Ala Ile Glu Arg Glu Arg Phe Ser Lys Glu Val Gln
                485                 490                 495

Asp Lys Asp Lys Pro Leu Lys Lys Arg Lys Gln Asp Ser Tyr Pro Gln
            500                 505                 510

Glu Ala Gly Gly Ala Thr Gly Gly Asn Arg Pro Ala Ser Gln Glu Thr
        515                 520                 525

Gly Ser Thr Gly Asn Gly Ser Arg Pro Ala Leu Met Val Ser Ile Asp
    530                 535                 540

Leu His Gln Ala Gly Arg Val Asp Ser Gln Ala Ser Ile Thr Gln Asp
545                 550                 555                 560

Ser Asp Ser Ile Lys Lys Pro Glu Glu Ile Lys Gln Cys Asn Asp Ala
                565                 570                 575

Pro Val Ser Val Leu Gln Glu Asp Ile Val Gly Ser Leu Lys Ser Thr
            580                 585                 590

Pro Glu Asn His Pro Glu Thr Pro Lys Lys Lys Ser Asp Pro Glu Leu
        595                 600                 605

Ser Lys Ser Glu Met Lys Gln Ser Glu Ser Arg Leu Ala Glu Ser Lys
    610                 615                 620

Pro Asn Glu Asn Arg Leu Val Glu Thr Lys Ser Ser Glu Asn Lys Leu
625                 630                 635                 640

Glu Thr Lys Val Glu Thr Gln Thr Glu Glu Leu Lys Gln Asn Glu Ser
                645                 650                 655

Arg Thr Thr Glu Cys Lys Gln Asn Glu Ser Thr Ile Val Glu Pro Lys
            660                 665                 670

Gln Asn Glu Asn Arg Leu Ser Asp Thr Lys Pro Asn Asp Asn Lys Gln
        675                 680                 685

Asn Asn Gly Arg Ser Glu Thr Thr Lys Ser Arg Pro Glu Thr Pro Lys
    690                 695                 700

Gln Lys Gly Glu Ser Arg Pro Glu Thr Pro Lys Gln Lys Ser Asp Gly
705                 710                 715                 720

His Pro Glu Thr Pro Lys Gln Lys Gly Asp Gly Arg Pro Glu Thr Pro
                725                 730                 735

Lys Gln Lys Gly Glu Ser Arg Pro Glu Thr Pro Lys Gln Lys Asn Glu
            740                 745                 750

Gly Arg Pro Glu Thr Pro Lys His Arg His Asp Asn Arg Arg Asp Ser
        755                 760                 765

Gly Lys Pro Ser Thr Glu Lys Lys Pro Glu Val Ser Lys His Lys Gln
    770                 775                 780

Asp Thr Lys Ser Asp Ser Pro Arg Leu Lys Ser Glu Arg Ala Glu Ala
785                 790                 795                 800

Leu Lys Gln Arg Pro Asp Gly Arg Ser Val Ser Glu Ser Leu Arg Arg
                805                 810                 815

Asp His Asp Asn Lys Gln Lys Ser Asp Asp Arg Gly Glu Ser Glu Arg
            820                 825                 830

His Arg Gly Asp Gln Ser Arg Val Arg Arg Pro Glu Thr Leu Arg Ser
        835                 840                 845

Ser Ser Arg Asn Glu His Gly Ile Lys Ser Asp Ser Ser Lys Thr Asp
    850                 855                 860

Lys Leu Glu Arg Lys His Arg His Glu Ser Gly Asp Ser Arg Glu Arg
```

-continued

```
865                 870                 875                 880

Pro Ser Ser Gly Glu Gln Lys Ser Arg Pro Asp Ser Pro Arg Val Lys
                885                 890                 895

Gln Gly Asp Ser Asn Lys Ser Arg Ser Asp Lys Leu Gly Phe Lys Ser
            900                 905                 910

Pro Thr Ser Lys Asp Asp Lys Arg Thr Glu Gly Asn Lys Ser Lys Val
        915                 920                 925

Asp Thr Asn Lys Ala His Pro Asp Asn Lys Ala Glu Phe Pro Ser Tyr
    930                 935                 940

Leu Leu Gly Gly Arg Ser Gly Ala Leu Lys Asn Phe Val Ile Pro Lys
945                 950                 955                 960

Ile Lys Arg Asp Lys Asp Gly Asn Val Thr Gln Glu Thr Lys Lys Met
                965                 970                 975

Glu Met Lys Gly Glu Pro Lys Asp Lys Val Glu Lys Ile Gly Leu Val
            980                 985                 990

Glu Asp Leu Asn Lys Gly Ala Lys  Pro Val Val Val Leu  Gln Lys Leu
        995                 1000                 1005

Ser Leu  Asp Asp Val Gln Lys  Leu Ile Lys Asp Arg  Glu Asp Lys
    1010                 1015                 1020

Ser Arg  Ser Ser Leu Lys Pro  Ile Lys Asn Lys Pro  Ser Lys Ser
    1025                 1030                 1035

Asn Lys  Gly Ser Ile Asp Gln  Ser Val Leu Lys Glu  Leu Pro Pro
    1040                 1045                 1050

Glu Leu  Leu Ala Glu Ile Glu  Ser Thr Met Pro Leu  Cys Glu Arg
    1055                 1060                 1065

Val Lys  Met Asn Lys Arg Lys  Arg Ser Thr Val Asn  Glu Lys Pro
    1070                 1075                 1080

Lys Tyr  Ala Glu Ile Ser Ser  Asp Glu Asp Asn Asp  Ser Asp Glu
    1085                 1090                 1095

Ala Phe  Glu Ser Ser Arg Lys  Arg His Lys Lys Asp  Asp Asp Lys
    1100                 1105                 1110

Ala Trp  Glu Tyr Glu Glu Arg  Asp Arg Arg Ser Ser  Gly Asp His
    1115                 1120                 1125

Arg Arg  Ser Gly His Ser His  Glu Gly Arg Arg Ser  Ser Gly Gly
    1130                 1135                 1140

Gly Arg  Tyr Arg Asn Arg Ser  Pro Ser Asp Ser Asp  Met Glu Asp
    1145                 1150                 1155

Tyr Ser  Pro Pro Pro Ser Leu  Ser Glu Val Ala Arg  Lys Met Lys
    1160                 1165                 1170

Lys Lys  Glu Lys Gln Lys Lys  Arg Lys Ala Tyr Glu  Pro Lys Leu
    1175                 1180                 1185

Thr Pro  Glu Glu Met Met Asp  Ser Ser Thr Phe Lys  Arg Phe Thr
    1190                 1195                 1200

Ala Ser  Ile Glu Asn Ile Leu  Asp Asn Leu Glu Asp  Met Asp Phe
    1205                 1210                 1215

Thr Ala  Phe Gly Asp Asp Asp  Glu Ile Pro Gln Glu  Leu Leu Leu
    1220                 1225                 1230

Gly Lys  His Gln Leu Asn Glu  Leu Gly Ser Glu Ser  Ala Lys Ile
    1235                 1240                 1245

Lys Ala  Met Gly Ile Met Asp  Lys Leu Ser Thr Asp  Lys Thr Val
    1250                 1255                 1260

Lys Val  Leu Asn Ile Leu Glu  Lys Asn Ile Gln Asp  Gly Ser Lys
    1265                 1270                 1275
```

-continued

```
Leu Ser Thr Leu Leu Asn His Asn Asn Asp Thr Glu Glu Glu Glu
    1280                1285                1290

Arg Leu Trp Arg Asp Leu Ile Met Glu Arg Val Thr Lys Ser Ala
    1295                1300                1305

Asp Ala Cys Leu Thr Thr Ile Asn Ile Met Thr Ser Pro Asn Met
    1310                1315                1320

Pro Lys Ala Val Tyr Ile Glu Asp Val Ile Glu Arg Val Ile Gln
    1325                1330                1335

Tyr Thr Lys Phe His Leu Gln Asn Thr Leu Tyr Pro Gln Tyr Asp
    1340                1345                1350

Pro Val Tyr Arg Leu Asp Pro His Gly Gly Gly Leu Leu Ser Ser
    1355                1360                1365

Lys Ala Lys Arg Ala Lys Cys Ser Thr His Lys Gln Arg Val Ile
    1370                1375                1380

Val Met Leu Tyr Asn Lys Val Cys Asp Ile Val Ser Ser Leu Ser
    1385                1390                1395

Glu Leu Leu Glu Ile Gln Leu Leu Thr Asp Thr Thr Ile Leu Gln
    1400                1405                1410

Val Ser Ser Met Gly Ile Thr Pro Phe Phe Val Glu Asn Val Ser
    1415                1420                1425

Glu Leu Gln Leu Cys Ala Ile Lys Leu Val Thr Ala Val Phe Ser
    1430                1435                1440

Arg Tyr Glu Lys His Arg Gln Leu Ile Leu Glu Glu Ile Phe Thr
    1445                1450                1455

Ser Leu Ala Arg Leu Pro Thr Ser Lys Arg Ser Leu Arg Asn Phe
    1460                1465                1470

Arg Leu Asn Ser Ser Asp Met Asp Gly Glu Pro Met Tyr Ile Gln
    1475                1480                1485

Met Val Thr Ala Leu Val Leu Gln Leu Ile Gln Cys Val Val His
    1490                1495                1500

Leu Pro Ser Ser Glu Lys Asp Ser Asn Ala Glu Glu Asp Ser Asn
    1505                1510                1515

Lys Lys Ile Asp Gln Asp Val Val Ile Thr Asn Ser Tyr Glu Thr
    1520                1525                1530

Ala Met Arg Thr Ala Gln Asn Phe Leu Ser Ile Phe Leu Lys Lys
    1535                1540                1545

Cys Gly Ser Lys Gln Gly Glu Glu Asp Tyr Arg Pro Leu Phe Glu
    1550                1555                1560

Asn Phe Val Gln Asp Leu Leu Ser Thr Val Asn Lys Pro Glu Trp
    1565                1570                1575

Pro Ala Ala Glu Leu Leu Leu Ser Leu Leu Gly Arg Leu Leu Val
    1580                1585                1590

His Gln Phe Ser Asn Lys Ser Thr Glu Met Ala Leu Arg Val Ala
    1595                1600                1605

Ser Leu Asp Tyr Leu Gly Thr Val Ala Ala Arg Leu Arg Lys Asp
    1610                1615                1620

Ala Val Thr Ser Lys Met Asp Gln Gly Ser Ile Glu Arg Ile Leu
    1625                1630                1635

Lys Gln Val Ser Gly Gly Glu Asp Glu Ile Gln Gln Leu Gln Lys
    1640                1645                1650

Ala Leu Leu Asp Tyr Leu Asp Glu Asn Thr Glu Thr Asp Pro Ser
    1655                1660                1665
```

-continued

```
Leu Val  Phe Ser Arg Lys Phe  Tyr Ile Ala Gln Trp  Phe Arg Asp
    1670                 1675                 1680

Thr Thr  Leu Glu Thr Glu Lys  Ala Met Lys Ser Gln  Lys Asp Glu
    1685                 1690                 1695

Glu Ser  Ser Glu Gly Thr His  His Ala Lys Glu Ile  Glu Thr Thr
    1700                 1705                 1710

Gly Gln  Ile Met His Arg Ala  Glu Asn Arg Lys Lys  Phe Leu Arg
    1715                 1720                 1725

Ser Ile  Ile Lys Thr Thr Pro  Ser Gln Phe Ser Thr  Leu Lys Met
    1730                 1735                 1740

Asn Ser  Asp Thr Val Asp Tyr  Asp Asp Ala Cys Leu  Ile Val Arg
    1745                 1750                 1755

Tyr Leu  Ala Ser Met Arg Pro  Phe Ala Gln Ser Phe  Asp Ile Tyr
    1760                 1765                 1770

Leu Thr  Gln Ile Leu Arg Val  Leu Gly Glu Asn Ala  Ile Ala Val
    1775                 1780                 1785

Arg Thr  Lys Ala Met Lys Cys  Leu Ser Glu Val Val  Ala Val Asp
    1790                 1795                 1800

Pro Ser  Ile Leu Ala Arg Leu  Asp Met Gln Arg Gly  Val His Gly
    1805                 1810                 1815

Arg Leu  Met Asp Asn Ser Thr  Ser Val Arg Glu Ala  Ala Val Glu
    1820                 1825                 1830

Leu Leu  Gly Arg Phe Val Leu  Cys Arg Pro Gln Leu  Ala Glu Gln
    1835                 1840                 1845

Tyr Tyr  Asp Met Leu Ile Glu  Arg Ile Leu Asp Thr  Gly Ile Ser
    1850                 1855                 1860

Val Arg  Lys Arg Val Ile Lys  Ile Leu Arg Asp Ile  Cys Ile Glu
    1865                 1870                 1875

Gln Pro  Thr Phe Pro Lys Ile  Thr Glu Met Cys Val  Lys Met Ile
    1880                 1885                 1890

Arg Arg  Val Asn Asp Glu Glu  Gly Ile Lys Lys Leu  Val Asn Glu
    1895                 1900                 1905

Thr Phe  Gln Lys Leu Trp Phe  Thr Pro Thr Pro His  Asn Asp Lys
    1910                 1915                 1920

Glu Ala  Met Thr Arg Lys Ile  Leu Asn Ile Thr Asp  Val Val Ala
    1925                 1930                 1935

Ala Cys  Arg Asp Thr Gly Tyr  Asp Trp Phe Glu Gln  Leu Leu Gln
    1940                 1945                 1950

Asn Leu  Leu Lys Ser Glu Glu  Asp Ser Ser Tyr Lys  Pro Val Lys
    1955                 1960                 1965

Lys Ala  Cys Thr Gln Leu Val  Asp Asn Leu Val Glu  His Ile Leu
    1970                 1975                 1980

Lys Tyr  Glu Glu Ser Leu Ala  Asp Ser Asp Asn Lys  Gly Val Asn
    1985                 1990                 1995

Ser Gly  Arg Leu Val Ala Cys  Ile Thr Thr Leu Phe  Leu Phe Ser
    2000                 2005                 2010

Lys Ile  Arg Pro Gln Leu Met  Val Lys His Ala Met  Thr Met Gln
    2015                 2020                 2025

Pro Tyr  Leu Thr Thr Lys Cys  Ser Thr Gln Asn Asp  Phe Met Val
    2030                 2035                 2040

Ile Cys  Asn Val Ala Lys Ile  Leu Glu Leu Val Val  Pro Leu Met
    2045                 2050                 2055

Glu His  Pro Ser Glu Thr Phe  Leu Ala Thr Ile Glu  Glu Asp Leu
```

-continued

```
    2060                2065                2070

Met Lys  Leu Ile Ile Lys Tyr  Gly Met Thr Val Val  Gln His Cys
    2075                2080                2085

Val Ser  Cys Leu Gly Ala Val  Val Asn Lys Val Thr  Gln Asn Phe
    2090                2095                2100

Lys Phe  Val Trp Ala Cys Phe  Asn Arg Tyr Tyr Gly  Ala Ile Ser
    2105                2110                2115

Lys Leu  Lys Ser Gln His Gln  Glu Asp Pro Asn Asn  Thr Ser Leu
    2120                2125                2130

Leu Thr  Asn Lys Pro Ala Leu  Leu Arg Ser Leu Phe  Thr Val Gly
    2135                2140                2145

Ala Leu  Cys Arg His Phe Asp  Phe Asp Leu Glu Asp  Phe Lys Gly
    2150                2155                2160

Asn Ser  Lys Val Asn Ile Lys  Asp Lys Val Leu Glu  Leu Leu Met
    2165                2170                2175

Tyr Phe  Thr Lys His Ser Asp  Glu Glu Val Gln Thr  Lys Ala Ile
    2180                2185                2190

Ile Gly  Leu Gly Phe Ala Phe  Ile Gln His Pro Ser  Leu Met Phe
    2195                2200                2205

Glu Gln  Glu Val Lys Asn Leu  Tyr Asn Asn Ile Leu  Ser Asp Lys
    2210                2215                2220

Asn Ser  Ser Val Asn Leu Lys  Ile Gln Val Leu Lys  Asn Leu Gln
    2225                2230                2235

Thr Tyr  Leu Gln Glu Glu Asp  Thr Arg Met Gln Gln  Ala Asp Arg
    2240                2245                2250

Asp Trp  Lys Lys Val Ala Lys  Gln Glu Asp Leu Lys  Glu Met Gly
    2255                2260                2265

Asp Val  Ser Ser Gly Met Ser  Ser Ser Ile Met Gln  Leu Tyr Leu
    2270                2275                2280

Lys Gln  Val Leu Glu Ala Phe  Phe His Thr Gln Ser  Ser Val Arg
    2285                2290                2295

His Phe  Ala Leu Asn Val Ile  Ala Leu Thr Leu Asn  Gln Gly Leu
    2300                2305                2310

Ile His  Pro Val Gln Cys Val  Pro Tyr Leu Ile Ala  Met Gly Thr
    2315                2320                2325

Asp Pro  Glu Pro Ala Met Arg  Asn Lys Ala Asp Gln  Gln Leu Val
    2330                2335                2340

Glu Ile  Asp Lys Lys Tyr Ala  Gly Phe Ile His Met  Lys Ala Val
    2345                2350                2355

Ala Gly  Met Lys Met Ser Tyr  Gln Val Gln Gln Ala  Ile Asn Thr
    2360                2365                2370

Cys Leu  Lys Asp Pro Val Arg  Gly Phe Arg Gln Asp  Glu Ser Ser
    2375                2380                2385

Ser Ala  Leu Cys Ser His Leu  Tyr Ser Met Ile Arg  Gly Asn Arg
    2390                2395                2400

Gln His  Arg Arg Ala Phe Leu  Ile Ser Leu Leu Asn  Leu Phe Asp
    2405                2410                2415

Asp Thr  Ala Lys Thr Asp Val  Thr Met Leu Leu Tyr  Ile Ala Asp
    2420                2425                2430

Asn Leu  Ala Cys Phe Pro Tyr  Gln Thr Gln Glu Glu  Pro Leu Phe
    2435                2440                2445

Ile Met  His His Ile Asp Ile  Thr Leu Ser Val Ser  Gly Ser Asn
    2450                2455                2460
```

-continued

```
Leu Leu Gln Ser Phe Lys Glu Ser Met Val Lys Asp Lys Arg Lys
    2465                2470                2475

Glu Arg Lys Ser Ser Pro Ser Lys Glu Asn Glu Ser Ser Asp Ser
    2480                2485                2490

Glu Glu Glu Val Ser Arg Pro Arg Lys Ser Arg Lys Arg Val Asp
    2495                2500                2505

Ser Asp Ser Asp Ser Asp Ser Glu Asp Asp Ile Asn Ser Val Met
    2510                2515                2520

Lys Cys Leu Pro Glu Asn Ser Ala Pro Leu Ile Glu Phe Ala Asn
    2525                2530                2535

Val Ser Gln Gly Ile Leu Leu Leu Leu Met Leu Lys Gln His Leu
    2540                2545                2550

Lys Asn Leu Cys Gly Phe Ser Asp Ser Lys Ile Gln Lys Tyr Ser
    2555                2560                2565

Pro Ser Glu Ser Ala Lys Val Tyr Asp Lys Ala Ile Asn Arg Lys
    2570                2575                2580

Thr Gly Val His Phe His Pro Lys Gln Thr Leu Asp Phe Leu Arg
    2585                2590                2595

Ser Asp Met Ala Asn Ser Lys Ile Thr Glu Glu Val Lys Arg Ser
    2600                2605                2610

Ile Val Lys Gln Tyr Leu Asp Phe Lys Leu Leu Met Glu His Leu
    2615                2620                2625

Asp Pro Asp Glu Glu Glu Glu Glu Gly Glu Val Ser Ala Ser Thr
    2630                2635                2640

Asn Ala Arg Asn Lys Ala Ile Thr Ser Leu Leu Gly Gly Gly Ser
    2645                2650                2655

Pro Lys Asn Asn Thr Ala Ala Glu Thr Glu Asp Asp Glu Ser Asp
    2660                2665                2670

Gly Glu Asp Arg Gly Gly Gly Thr Ser Gly Val Arg Arg Arg Arg
    2675                2680                2685

Ser Gln Arg Ile Ser Gln Arg Ile Thr
    2690                2695
```

<210> SEQ ID NO 13
<211> LENGTH: 4191
<212> TYPE: DNA
<213> ORGANISM: Homo sapiens
<220> FEATURE:
<221> NAME/KEY: CDS
<222> LOCATION: (121)..(3246)

<400> SEQUENCE: 13

```
catctccgca gtctgggccg ctgggtgcag aggctgccgc agacccagcg gccatcgcct      60

ccctcaatcc caatatccat tgtctcccac cccacctggc cctccacttc ccccacaacc     120

atg gcg cac gaa tcc gag agg agc tct cgt ctc ggg gtg ccc tgc ggg       168
Met Ala His Glu Ser Glu Arg Ser Ser Arg Leu Gly Val Pro Cys Gly
1               5                   10                  15

gag ccg gca gag ctc gga ggt gat gct agc gag gag gat cac ccc caa       216
Glu Pro Ala Glu Leu Gly Gly Asp Ala Ser Glu Glu Asp His Pro Gln
            20                  25                  30

gtc tgt gcc aag tgc tgc gca caa ttc act gac cca act gaa ttc ctc       264
Val Cys Ala Lys Cys Cys Ala Gln Phe Thr Asp Pro Thr Glu Phe Leu
        35                  40                  45

gcc cac cag aac gca tgt tct act gac cct cct gta atg gtg ata att       312
Ala His Gln Asn Ala Cys Ser Thr Asp Pro Pro Val Met Val Ile Ile
    50                  55                  60
```

-continued

```
ggg ggc cag gag aac ccc aac aac tct tcg gcc tcc tct gaa ccc cgg      360
Gly Gly Gln Glu Asn Pro Asn Asn Ser Ser Ala Ser Ser Glu Pro Arg
65                  70                  75                  80

cct gag ggt cac aat aat cct cag gtc atg gac aca gag cat agc aac      408
Pro Glu Gly His Asn Asn Pro Gln Val Met Asp Thr Glu His Ser Asn
                85                  90                  95

ccc cca gat tct ggg tcc tcc gtg ccc acg gat ccc acc tgg ggc cca      456
Pro Pro Asp Ser Gly Ser Ser Val Pro Thr Asp Pro Thr Trp Gly Pro
            100                 105                 110

gag agg aga gga gag gag tct tca ggg cat ttc ctg gtc gct gcc aca      504
Glu Arg Arg Gly Glu Glu Ser Ser Gly His Phe Leu Val Ala Ala Thr
        115                 120                 125

ggt aca gcg gct ggg gga ggc ggg ggc ctg atc ttg gcc agt ccc aag      552
Gly Thr Ala Ala Gly Gly Gly Gly Gly Leu Ile Leu Ala Ser Pro Lys
    130                 135                 140

ctg gga gca acc cca tta cct cca gaa tcg acc cct gca ccc cct cct      600
Leu Gly Ala Thr Pro Leu Pro Pro Glu Ser Thr Pro Ala Pro Pro Pro
145                 150                 155                 160

cct cca cca ccc cct ccg ccc cca ggg gta ggc agt ggc cac ttg aat      648
Pro Pro Pro Pro Pro Pro Pro Pro Gly Val Gly Ser Gly His Leu Asn
                165                 170                 175

atc ccc ctg atc ttg gaa gag cta cgg gtg ctg cag cag cgg cag atc      696
Ile Pro Leu Ile Leu Glu Glu Leu Arg Val Leu Gln Gln Arg Gln Ile
            180                 185                 190

cat cag atg cag atg act gag caa atc tgc agg cag gtg ctg ttg ctt      744
His Gln Met Gln Met Thr Glu Gln Ile Cys Arg Gln Val Leu Leu Leu
        195                 200                 205

ggc tcc tta ggc cag acg gtg ggt gcc cct gcc agt ccc tca gag cta      792
Gly Ser Leu Gly Gln Thr Val Gly Ala Pro Ala Ser Pro Ser Glu Leu
    210                 215                 220

cct ggg aca ggg act gcc tct tcc acc aag ccc cta cta ccc ctc ttc      840
Pro Gly Thr Gly Thr Ala Ser Ser Thr Lys Pro Leu Leu Pro Leu Phe
225                 230                 235                 240

agc ccc atc aag cct gtc caa acc agc aag aca ctg gca tct tcc tcc      888
Ser Pro Ile Lys Pro Val Gln Thr Ser Lys Thr Leu Ala Ser Ser Ser
                245                 250                 255

tcc tcc tcc tct tcc tct tca ggg gca gaa acg ccc aag cag gcc ttc      936
Ser Ser Ser Ser Ser Ser Ser Gly Ala Glu Thr Pro Lys Gln Ala Phe
            260                 265                 270

ttc cac ctt tac cac cca ctg ggg tca cag cat cct ttc tct gct gga      984
Phe His Leu Tyr His Pro Leu Gly Ser Gln His Pro Phe Ser Ala Gly
        275                 280                 285

ggg gtt ggg cga agc cac aaa ccc acc cct gcc cct tcc cca gcc ttg     1032
Gly Val Gly Arg Ser His Lys Pro Thr Pro Ala Pro Ser Pro Ala Leu
    290                 295                 300

cca ggc agc aca gat cag ctg att gcc tcg cct cat ctg gca ttc cca     1080
Pro Gly Ser Thr Asp Gln Leu Ile Ala Ser Pro His Leu Ala Phe Pro
305                 310                 315                 320

agc acc acg gga cta ctg gca gca cag tgt ctt ggg gca gcc cga ggc     1128
Ser Thr Thr Gly Leu Leu Ala Ala Gln Cys Leu Gly Ala Ala Arg Gly
                325                 330                 335

ctt gag gcc act gcc tcc cca ggg ctc ctg aag cca aag aat gga agt     1176
Leu Glu Ala Thr Ala Ser Pro Gly Leu Leu Lys Pro Lys Asn Gly Ser
            340                 345                 350

ggt gag ctg agc tac gga gaa gtg atg ggt ccc ttg gag aag cct ggt     1224
Gly Glu Leu Ser Tyr Gly Glu Val Met Gly Pro Leu Glu Lys Pro Gly
        355                 360                 365

gga agg cac aaa tgc cgc ttc tgt gcc aaa gta ttt ggc agt gac agt     1272
Gly Arg His Lys Cys Arg Phe Cys Ala Lys Val Phe Gly Ser Asp Ser
```

-continued

```
    370                 375                 380

gcc ctg cag atc cac ctt cgt tcc cac acg ggt gag agg ccc tat aag     1320
Ala Leu Gln Ile His Leu Arg Ser His Thr Gly Glu Arg Pro Tyr Lys
385                 390                 395                 400

tgc aat gtc tgt gga aac cgt ttt acc acc cgt ggc aac ctc aaa gtg     1368
Cys Asn Val Cys Gly Asn Arg Phe Thr Thr Arg Gly Asn Leu Lys Val
                405                 410                 415

cat ttc cac cgg cat cgt gag aag tac cca cat gtg cag atg aac cca     1416
His Phe His Arg His Arg Glu Lys Tyr Pro His Val Gln Met Asn Pro
            420                 425                 430

cac cca gta cca gag cac cta gac tat gtc att acc agc agt ggc ttg     1464
His Pro Val Pro Glu His Leu Asp Tyr Val Ile Thr Ser Ser Gly Leu
        435                 440                 445

cct tat ggt atg tcc gtg cca cca gag aag gcc gag gag gag gca gcc     1512
Pro Tyr Gly Met Ser Val Pro Pro Glu Lys Ala Glu Glu Glu Ala Ala
    450                 455                 460

act cca ggt gga ggg gtt gag cgc aag cct ctg gtg gcc tcc aca aca     1560
Thr Pro Gly Gly Gly Val Glu Arg Lys Pro Leu Val Ala Ser Thr Thr
465                 470                 475                 480

gca ctc agt gcc aca gag agc ctg act ctg ctc tcc acc agt gca ggc     1608
Ala Leu Ser Ala Thr Glu Ser Leu Thr Leu Leu Ser Thr Ser Ala Gly
                485                 490                 495

aca gcc acg gct cca gga ctc cct gct ttc aat aag ttt gtg ctc atg     1656
Thr Ala Thr Ala Pro Gly Leu Pro Ala Phe Asn Lys Phe Val Leu Met
            500                 505                 510

aaa gca gtg gaa ccc aag aat aaa gct gat gaa aac acc ccc cca ggg     1704
Lys Ala Val Glu Pro Lys Asn Lys Ala Asp Glu Asn Thr Pro Pro Gly
        515                 520                 525

agt gag ggc tca gcc atc agt gga gtg gca gaa agt agc acg gca act     1752
Ser Glu Gly Ser Ala Ile Ser Gly Val Ala Glu Ser Ser Thr Ala Thr
    530                 535                 540

cgc atg caa cta agt aag ttg gtg act tca cta cca agc tgg gca ctg     1800
Arg Met Gln Leu Ser Lys Leu Val Thr Ser Leu Pro Ser Trp Ala Leu
545                 550                 555                 560

ctt acc aac cac ttc aag tcc act ggc agc ttc ccc ttc ccc tat gtg     1848
Leu Thr Asn His Phe Lys Ser Thr Gly Ser Phe Pro Phe Pro Tyr Val
                565                 570                 575

cta gag ccc ttg ggg gcc tca ccc tct gag aca tca aag ctg cag caa     1896
Leu Glu Pro Leu Gly Ala Ser Pro Ser Glu Thr Ser Lys Leu Gln Gln
            580                 585                 590

ctg gta gaa aag att gac cgg caa gga gct gtg gcg gtg acc tca gct     1944
Leu Val Glu Lys Ile Asp Arg Gln Gly Ala Val Ala Val Thr Ser Ala
        595                 600                 605

gcc tca gga gcc ccc acc acc tct gcc cct gca cct tca tcc tca gcc     1992
Ala Ser Gly Ala Pro Thr Thr Ser Ala Pro Ala Pro Ser Ser Ser Ala
    610                 615                 620

tct tct gga cct aac cag tgt gtc atc tgt ctc cga gtg ctt agc tgt     2040
Ser Ser Gly Pro Asn Gln Cys Val Ile Cys Leu Arg Val Leu Ser Cys
625                 630                 635                 640

cct cgg gcc cta cgc ctt cat tat ggc caa cat gga ggt gag agg ccc     2088
Pro Arg Ala Leu Arg Leu His Tyr Gly Gln His Gly Gly Glu Arg Pro
                645                 650                 655

ttc aaa tgc aaa gtg tgt ggc aga gcc ttc tcc acc agg ggt aat ctg     2136
Phe Lys Cys Lys Val Cys Gly Arg Ala Phe Ser Thr Arg Gly Asn Leu
            660                 665                 670

cgt gca cat ttc gtg ggc cac aag gcc agt cca gct gcc cgg gca cag     2184
Arg Ala His Phe Val Gly His Lys Ala Ser Pro Ala Ala Arg Ala Gln
        675                 680                 685

aat tcc tgc ccc atc tgc cag aag aag ttc acc aat gct gtc act ctg     2232
```

-continued

```
Asn Ser Cys Pro Ile Cys Gln Lys Lys Phe Thr Asn Ala Val Thr Leu
    690                 695                 700

cag cag cat gtc cgg atg cac ctg ggg ggc cag atc ccc aac ggt ggt     2280
Gln Gln His Val Arg Met His Leu Gly Gly Gln Ile Pro Asn Gly Gly
705                 710                 715                 720

act gca ctc cct gaa ggt gga gga gct gct cag gag aat ggc tcc gag     2328
Thr Ala Leu Pro Glu Gly Gly Gly Ala Ala Gln Glu Asn Gly Ser Glu
                725                 730                 735

caa tct aca gtc tcc ggg gca ggg agt ttc ccc cag cag cag tcc cag     2376
Gln Ser Thr Val Ser Gly Ala Gly Ser Phe Pro Gln Gln Gln Ser Gln
            740                 745                 750

cag cca tca ccg gaa gag gag ttg tct gag gag gag gaa gag gag gat     2424
Gln Pro Ser Pro Glu Glu Glu Leu Ser Glu Glu Glu Glu Glu Glu Asp
        755                 760                 765

gag gaa gaa gag gaa gat gtg act gat gaa gat tcc ctg gca ggg aga     2472
Glu Glu Glu Glu Glu Asp Val Thr Asp Glu Asp Ser Leu Ala Gly Arg
    770                 775                 780

ggc tca gag agt gga ggt gag aag gca ata tca gtg aga ggt gat tca     2520
Gly Ser Glu Ser Gly Gly Glu Lys Ala Ile Ser Val Arg Gly Asp Ser
785                 790                 795                 800

gaa gag gca tct ggg gca gag gag gag gtg ggg aca gtg gcg gca gca     2568
Glu Glu Ala Ser Gly Ala Glu Glu Glu Val Gly Thr Val Ala Ala Ala
                805                 810                 815

gcc aca gct ggg aag gag atg gac agt aat gag aaa act act caa cag     2616
Ala Thr Ala Gly Lys Glu Met Asp Ser Asn Glu Lys Thr Thr Gln Gln
            820                 825                 830

tct tct ttg cca cca cca cca cca cct gac agc ctg gat cag cct cag     2664
Ser Ser Leu Pro Pro Pro Pro Pro Pro Asp Ser Leu Asp Gln Pro Gln
        835                 840                 845

cca atg gag cag gga agc agt ggt gtt tta gga ggc aag gaa gag ggg     2712
Pro Met Glu Gln Gly Ser Ser Gly Val Leu Gly Gly Lys Glu Glu Gly
    850                 855                 860

ggc aaa ccg gag aga agc tca agt ccg gca tca gca ctc acc cca gaa     2760
Gly Lys Pro Glu Arg Ser Ser Ser Pro Ala Ser Ala Leu Thr Pro Glu
865                 870                 875                 880

ggg gaa gcc acc agc gtg acc ttg gta gag gag ctg agc ctg cag gag     2808
Gly Glu Ala Thr Ser Val Thr Leu Val Glu Glu Leu Ser Leu Gln Glu
                885                 890                 895

gca atg aga aag gag cca gga gag agc agc agc aga aag gcc tgc gaa     2856
Ala Met Arg Lys Glu Pro Gly Glu Ser Ser Ser Arg Lys Ala Cys Glu
            900                 905                 910

gtg tgt ggc cag gcc ttt ccc tcc cag gca gct ctg gag gag cat cag     2904
Val Cys Gly Gln Ala Phe Pro Ser Gln Ala Ala Leu Glu Glu His Gln
        915                 920                 925

aag acc cac ccc aag gag ggg ccg ctc ttc act tgt gtt ttc tgc agg     2952
Lys Thr His Pro Lys Glu Gly Pro Leu Phe Thr Cys Val Phe Cys Arg
    930                 935                 940

cag ggc ttt ctt gag cgg gct acc ctc aag aag cat atg ctc ctg gca     3000
Gln Gly Phe Leu Glu Arg Ala Thr Leu Lys Lys His Met Leu Leu Ala
945                 950                 955                 960

cac cac cag aac cag tat gtg gca ttc ctg tca aat ggc ctg ccc atg     3048
His His Gln Asn Gln Tyr Val Ala Phe Leu Ser Asn Gly Leu Pro Met
                965                 970                 975

aag ccc tgg aat tcc agc tcc acc tcc act acc act cca agc ctg gcc     3096
Lys Pro Trp Asn Ser Ser Ser Thr Ser Thr Thr Thr Pro Ser Leu Ala
            980                 985                 990

cca cca gtg ctg ttt ggc cta gga  act gtg gct ggg aag  gtg cct cca   3144
Pro Pro Val Leu Phe Gly Leu Gly  Thr Val Ala Gly Lys  Val Pro Pro
        995                 1000                1005
```

-continued

```
aca atg  gga tcc agg gaa gcc  aag gag aag aca gcc  ccc ctc cta      3189
Thr Met  Gly Ser Arg Glu Ala  Lys Glu Lys Thr Ala  Pro Leu Leu
    1010                 1015                 1020

ttt cag  cct cct gca ccc aag  gca gtg cct gag aag  ccc atc ata      3234
Phe Gln  Pro Pro Ala Pro Lys  Ala Val Pro Glu Lys  Pro Ile Ile
    1025                 1030                 1035

gac aag  aag tag caaactgtac attccttctt cctccccctg ctccagaagg       3286
Asp Lys  Lys
    1040

tgccggtact gaagatgctc cagtaattgg tgacccaacc ctaggaagta gggagaaatg   3346

aaggaagggc ataggaaaat tttcccagta aatcccctga tggtcacatt aaggtaaagg   3406

ttttggctgg tcagtgtgcc aagacctctc cagcttctca ttcatgatga cctctcaaag   3466

ttgggaaaca agctgatttc ttgccaagag gtctcccagg agatatttgg gaaatgtgaa   3526

gttcgtatct ttaaggagca tttttggtca gcatggttga tgaactaatg atgagagagt   3586

taaggaatgt tgctagaaca tagggcttgc tggtacctat gtgactaaga aagggacatg   3646

atgtaaggga aaaggcctca aattcttgtg aatgtctgga cattctcgtt aatattcttt   3706

tgggctaata gtgacatagt gtgcagaggt gtaccaggga tcatggggga tttcctagca   3766

ctagtatgct tctagtttta gataactccc tcctttattc cctggcccct tgtattttcc   3826

ttatcttcct ctttcaagac ccctacccat tttgcctatc cgtaggctgg ggcttgtgtc   3886

tttgtcattg tctggttctt aagagtccca gactttggga gaccagctcc aggtggcgtc   3946

ctccctgcct ctccgtcttg taatgagttg tagtatttac tcttaacata ggatcatttg   4006

gaacaggagt tctgaggagg agagagtgag ggttttgcta ttgactgact tgaacgatgg   4066

cttctcctca agctgtaggc tccagagctt cctaacctag taaaatgtca agaacagacg   4126

ggagatatta gtgtctttcc ctctatcatt aaaggtgttt taaccaaaaa aaaaaaaaaa   4186

aaaaa                                                               4191


<210> SEQ ID NO 14
<211> LENGTH: 1041
<212> TYPE: PRT
<213> ORGANISM: Homo sapiens

<400> SEQUENCE: 14

Met Ala His Glu Ser Glu Arg Ser Ser Arg Leu Gly Val Pro Cys Gly
1               5                   10                  15

Glu Pro Ala Glu Leu Gly Gly Asp Ala Ser Glu Glu Asp His Pro Gln
            20                  25                  30

Val Cys Ala Lys Cys Cys Ala Gln Phe Thr Asp Pro Thr Glu Phe Leu
        35                  40                  45

Ala His Gln Asn Ala Cys Ser Thr Asp Pro Pro Val Met Val Ile Ile
    50                  55                  60

Gly Gly Gln Glu Asn Pro Asn Asn Ser Ser Ala Ser Ser Glu Pro Arg
65                  70                  75                  80

Pro Glu Gly His Asn Asn Pro Gln Val Met Asp Thr Glu His Ser Asn
                85                  90                  95

Pro Pro Asp Ser Gly Ser Ser Val Pro Thr Asp Pro Thr Trp Gly Pro
            100                 105                 110

Glu Arg Arg Gly Glu Glu Ser Ser Gly His Phe Leu Val Ala Ala Thr
        115                 120                 125

Gly Thr Ala Ala Gly Gly Gly Gly Gly Leu Ile Leu Ala Ser Pro Lys
    130                 135                 140
```

-continued

```
Leu Gly Ala Thr Pro Leu Pro Pro Glu Ser Thr Pro Ala Pro Pro Pro
145                 150                 155                 160

Pro Pro Pro Pro Pro Pro Pro Pro Gly Val Gly Ser Gly His Leu Asn
                165                 170                 175

Ile Pro Leu Ile Leu Glu Glu Leu Arg Val Leu Gln Gln Arg Gln Ile
            180                 185                 190

His Gln Met Gln Met Thr Glu Gln Ile Cys Arg Gln Val Leu Leu Leu
        195                 200                 205

Gly Ser Leu Gly Gln Thr Val Gly Ala Pro Ala Ser Pro Ser Glu Leu
    210                 215                 220

Pro Gly Thr Gly Thr Ala Ser Ser Thr Lys Pro Leu Leu Pro Leu Phe
225                 230                 235                 240

Ser Pro Ile Lys Pro Val Gln Thr Ser Lys Thr Leu Ala Ser Ser Ser
                245                 250                 255

Ser Ser Ser Ser Ser Ser Ser Gly Ala Glu Thr Pro Lys Gln Ala Phe
            260                 265                 270

Phe His Leu Tyr His Pro Leu Gly Ser Gln His Pro Phe Ser Ala Gly
        275                 280                 285

Gly Val Gly Arg Ser His Lys Pro Thr Pro Ala Pro Ser Pro Ala Leu
    290                 295                 300

Pro Gly Ser Thr Asp Gln Leu Ile Ala Ser Pro His Leu Ala Phe Pro
305                 310                 315                 320

Ser Thr Thr Gly Leu Leu Ala Ala Gln Cys Leu Gly Ala Ala Arg Gly
                325                 330                 335

Leu Glu Ala Thr Ala Ser Pro Gly Leu Leu Lys Pro Lys Asn Gly Ser
            340                 345                 350

Gly Glu Leu Ser Tyr Gly Glu Val Met Gly Pro Leu Glu Lys Pro Gly
        355                 360                 365

Gly Arg His Lys Cys Arg Phe Cys Ala Lys Val Phe Gly Ser Asp Ser
    370                 375                 380

Ala Leu Gln Ile His Leu Arg Ser His Thr Gly Glu Arg Pro Tyr Lys
385                 390                 395                 400

Cys Asn Val Cys Gly Asn Arg Phe Thr Thr Arg Gly Asn Leu Lys Val
                405                 410                 415

His Phe His Arg His Arg Glu Lys Tyr Pro His Val Gln Met Asn Pro
            420                 425                 430

His Pro Val Pro Glu His Leu Asp Tyr Val Ile Thr Ser Ser Gly Leu
        435                 440                 445

Pro Tyr Gly Met Ser Val Pro Pro Glu Lys Ala Glu Glu Glu Ala Ala
    450                 455                 460

Thr Pro Gly Gly Gly Val Glu Arg Lys Pro Leu Val Ala Ser Thr Thr
465                 470                 475                 480

Ala Leu Ser Ala Thr Glu Ser Leu Thr Leu Leu Ser Thr Ser Ala Gly
                485                 490                 495

Thr Ala Thr Ala Pro Gly Leu Pro Ala Phe Asn Lys Phe Val Leu Met
            500                 505                 510

Lys Ala Val Glu Pro Lys Asn Lys Ala Asp Glu Asn Thr Pro Pro Gly
        515                 520                 525

Ser Glu Gly Ser Ala Ile Ser Gly Val Ala Glu Ser Ser Thr Ala Thr
    530                 535                 540

Arg Met Gln Leu Ser Lys Leu Val Thr Ser Leu Pro Ser Trp Ala Leu
545                 550                 555                 560

Leu Thr Asn His Phe Lys Ser Thr Gly Ser Phe Pro Phe Pro Tyr Val
```

-continued 565 570 575

Leu Glu Pro Leu Gly Ala Ser Pro Ser Glu Thr Ser Lys Leu Gln Gln
580 585 590

Leu Val Glu Lys Ile Asp Arg Gln Gly Ala Val Ala Val Thr Ser Ala
595 600 605

Ala Ser Gly Ala Pro Thr Thr Ser Ala Pro Ala Pro Ser Ser Ser Ala
610 615 620

Ser Ser Gly Pro Asn Gln Cys Val Ile Cys Leu Arg Val Leu Ser Cys
625 630 635 640

Pro Arg Ala Leu Arg Leu His Tyr Gly Gln His Gly Gly Glu Arg Pro
645 650 655

Phe Lys Cys Lys Val Cys Gly Arg Ala Phe Ser Thr Arg Gly Asn Leu
660 665 670

Arg Ala His Phe Val Gly His Lys Ala Ser Pro Ala Ala Arg Ala Gln
675 680 685

Asn Ser Cys Pro Ile Cys Gln Lys Lys Phe Thr Asn Ala Val Thr Leu
690 695 700

Gln Gln His Val Arg Met His Leu Gly Gly Gln Ile Pro Asn Gly Gly
705 710 715 720

Thr Ala Leu Pro Glu Gly Gly Gly Ala Ala Gln Glu Asn Gly Ser Glu
725 730 735

Gln Ser Thr Val Ser Gly Ala Gly Ser Phe Pro Gln Gln Gln Ser Gln
740 745 750

Gln Pro Ser Pro Glu Glu Glu Leu Ser Glu Glu Glu Glu Glu Glu Asp
755 760 765

Glu Glu Glu Glu Glu Asp Val Thr Asp Glu Asp Ser Leu Ala Gly Arg
770 775 780

Gly Ser Glu Ser Gly Gly Glu Lys Ala Ile Ser Val Arg Gly Asp Ser
785 790 795 800

Glu Glu Ala Ser Gly Ala Glu Glu Glu Val Gly Thr Val Ala Ala Ala
805 810 815

Ala Thr Ala Gly Lys Glu Met Asp Ser Asn Glu Lys Thr Thr Gln Gln
820 825 830

Ser Ser Leu Pro Pro Pro Pro Pro Pro Asp Ser Leu Asp Gln Pro Gln
835 840 845

Pro Met Glu Gln Gly Ser Ser Gly Val Leu Gly Gly Lys Glu Glu Gly
850 855 860

Gly Lys Pro Glu Arg Ser Ser Ser Pro Ala Ser Ala Leu Thr Pro Glu
865 870 875 880

Gly Glu Ala Thr Ser Val Thr Leu Val Glu Glu Leu Ser Leu Gln Glu
885 890 895

Ala Met Arg Lys Glu Pro Gly Glu Ser Ser Ser Arg Lys Ala Cys Glu
900 905 910

Val Cys Gly Gln Ala Phe Pro Ser Gln Ala Ala Leu Glu Glu His Gln
915 920 925

Lys Thr His Pro Lys Glu Gly Pro Leu Phe Thr Cys Val Phe Cys Arg
930 935 940

Gln Gly Phe Leu Glu Arg Ala Thr Leu Lys Lys His Met Leu Leu Ala
945 950 955 960

His His Gln Asn Gln Tyr Val Ala Phe Leu Ser Asn Gly Leu Pro Met
965 970 975

Lys Pro Trp Asn Ser Ser Ser Thr Ser Thr Thr Thr Pro Ser Leu Ala
980 985 990

-continued

```
Pro Pro Val Leu Phe Gly Leu Gly  Thr Val Ala Gly Lys  Val Pro Pro
        995                 1000                1005

Thr Met  Gly Ser Arg Glu Ala  Lys Glu Lys Thr Ala  Pro Leu Leu
    1010                 1015                 1020

Phe Gln  Pro Pro Ala Pro Lys  Ala Val Pro Glu Lys  Pro Ile Ile
    1025                 1030                 1035

Asp Lys  Lys
    1040


<210> SEQ ID NO 15
<211> LENGTH: 3138
<212> TYPE: DNA
<213> ORGANISM: Homo sapiens
<220> FEATURE:
<221> NAME/KEY: CDS
<222> LOCATION: (182)..(913)

<400> SEQUENCE: 15

cctcgctctc cttccatctc tctcgccccc tctccctccg tcccgtcctc gccgctcccc      60

tcaccccgcc tctctccccc tcccccagcc cctcctctcc tcaccccacc cggcctccct     120

ccctccctcg cccgcccggc gctcgcagaa ccgacaccag gggggctctc gatgtagcac     180

c atg aca ggc atc gcc gcc gcc tcc ttc ttc tcc aat acc tgc cga ttc     229
  Met Thr Gly Ile Ala Ala Ala Ser Phe Phe Ser Asn Thr Cys Arg Phe
  1               5                   10                  15

ggg ggc tgc gga ctc cac ttc ccc acc ctg gcc gac ctc atc gag cac       277
Gly Gly Cys Gly Leu His Phe Pro Thr Leu Ala Asp Leu Ile Glu His
            20                  25                  30

atc gag gac aac cac atc gat aca gat cca cgg gtt tta gaa aaa caa       325
Ile Glu Asp Asn His Ile Asp Thr Asp Pro Arg Val Leu Glu Lys Gln
        35                  40                  45

gaa tta cag cag cca acc tat gtt gcc ctg agt tac ata aat aga ttc       373
Glu Leu Gln Gln Pro Thr Tyr Val Ala Leu Ser Tyr Ile Asn Arg Phe
    50                  55                  60

atg aca gat gct gcc cgc cga gag cag gag tcc cta aag aag aag att       421
Met Thr Asp Ala Ala Arg Arg Glu Gln Glu Ser Leu Lys Lys Lys Ile
65                  70                  75                  80

cag ccg aag ctc tcg ctg act ctg tcc agc tca gtg tct cga ggg aat       469
Gln Pro Lys Leu Ser Leu Thr Leu Ser Ser Ser Val Ser Arg Gly Asn
                85                  90                  95

gtg tcc act ccc cca cgc cac agc agt gga agc ctt act ccc ccc gtg       517
Val Ser Thr Pro Pro Arg His Ser Ser Gly Ser Leu Thr Pro Pro Val
            100                 105                 110

acc cca ccc atc acc ccc tcc tct tca ttc cgc agc agc act ccg aca       565
Thr Pro Pro Ile Thr Pro Ser Ser Ser Phe Arg Ser Ser Thr Pro Thr
        115                 120                 125

ggc agc gag tat gac gag gag gag gtg gac tat gag gag tcg gac agc       613
Gly Ser Glu Tyr Asp Glu Glu Glu Val Asp Tyr Glu Glu Ser Asp Ser
    130                 135                 140

gat gag tcc tgg acc aca gag agt gcc atc agc tcc gaa gcc atc ctc       661
Asp Glu Ser Trp Thr Thr Glu Ser Ala Ile Ser Ser Glu Ala Ile Leu
145                 150                 155                 160

agc tcc atg tgc atg aat gga ggg gaa gag aag cct ttt gcc tgc cca       709
Ser Ser Met Cys Met Asn Gly Gly Glu Glu Lys Pro Phe Ala Cys Pro
                165                 170                 175

gtt cct gga tgt aaa aag aga tac aag aat gtg aat ggc ata aag tat       757
Val Pro Gly Cys Lys Lys Arg Tyr Lys Asn Val Asn Gly Ile Lys Tyr
            180                 185                 190

cac gct aag aat ggt cac aga aca cag att cgt gtc cgc aaa cca ttc       805
```

-continued

```
His Ala Lys Asn Gly His Arg Thr Gln Ile Arg Val Arg Lys Pro Phe
        195                 200                 205

aag tgt cgc tgt ggg aag agt tac aag aca gct cag ggc ctg cgg cac      853
Lys Cys Arg Cys Gly Lys Ser Tyr Lys Thr Ala Gln Gly Leu Arg His
    210                 215                 220

cac aca atc aat ttc cat ccc ccg gtg tcg gct gag att atc agg aag      901
His Thr Ile Asn Phe His Pro Pro Val Ser Ala Glu Ile Ile Arg Lys
225                 230                 235                 240

atg cag caa taa catgctggtc ataactgtgc caagaaatcc tcaccagcag          953
Met Gln Gln

ttgctgattt tgaaaacagc caccttttt cagggggaagc attcagcaac cctttaaaga   1013

aaaagaatta aatgcatgct ttaaattttt tctgtaattt tggaatgatg tatctttgta   1073

gagttaatga ttttgtacat ttgcacatgt aatcatcata cccattttca ttactttgat   1133

ataaggtgct aaacaaaaaa agctctaggt tcttcagcac atttccccca aaacaaaata   1193

aaattgaggg catgttgcat attgttgaat tgtattgcgg tggtatcaac ctgggggggag   1253

gaggggctgg cactgagatt tttttttcaa gattgtaatg tgattgaagt tttcaacaca   1313

tcaactcaca tatgttcaaa accaaaataa taccttcatt atcaaactgg ttaccatgcc   1373

ttacataatg gagttagtat ttgtgagtag aaagacttta ggtaatggaa atataaataa   1433

gaaagaatgt ttaacataat atgctaaaaa tattttcata tttaaataac atacgtaaag   1493

gtgtgctttc tgtgttttat attatcttgc aaatcctttt gccctttaaa aagctgaaaa   1553

tcttgccatc tgacttacta gtcattttag tgttataaat ggcattttgt acaaaatagt   1613

ctattcagtt cgttcattca tttaacacac attgattgag tgcctgctgg gtacaaggga   1673

ttcaatttat gcctattgat atctgcggac caagataccc ayttagtgaa atactttttt   1733

ccctgaaatc tgttagaaaa gactttgaaa tacttcagtg caaagtgtgt gtgtgtgaag   1793

tttagttata tcttcatctt cagatgaagt tttaaagcac tttgtagttc tctattgcca   1853

acaatttaat gtttatgtgt tgccaattct tgcaaccact gccctaccaa acctgtgggt   1913

tgcaaatcag aactaaaatt ctaagcacgt ttcaaagatg aacacttttg ttaagacccc   1973

tattgcctct tcttcatgct catttttttac tttttttaaa aggtactttt ctcatcacat   2033

tgtagagagg tctgcattct cattggaaat gtctgtttag ctttataaaa caaacacttt   2093

gctgaaatag gaaaatgagc cttattgaca attaagtgct tcttgcagca ggtggtcaaa   2153

gaaaagcatg actaatacga cctattagag taatctacat ctggaccatt ccttaagttt   2213

ttcctcaccg acagtaccat catgccttga gtgttctttt ctcccaagtg ctattcctta   2273

aacacgagag tttaccagtt gcctaataat gcaataaaaa atgctttgag atagctaact   2333

gcccataaaa caaactcaaa ttgcttataa agtttcttcc catgttccca tttgatgaaa   2393

agtcttacat cacatataac tgggaagcag gggtccctcc tcaattttca gacattttga   2453

aaggatgaca gttctgtttg ttagatgagt aaacctctat attcataagt tctaaaatcc   2513

ttcattatga gggattcaaa gtatttataa aaacactgcc ctctaaaaat ttcctcagat   2573

ctgaagtatg gtcttggtcc tgaatataca gtgttatcct atgtttaaaa gggtgatcca   2633

gacatgagac gcaactagtt ggtgcataag aaggccccac ttggctattt catatctacc   2693

tacaattgac caaaaaaaat tttttaggcc agcaattatt atttagcttc gctctttcta   2753

gtgcaagaaa ctgcaggctg gatcagtagt tcaacagcta aacagtcata aaatagtcat   2813

tgtgcatgtt aaatttcttt cratgctttc aaagataaat tccaatttct atttacttat   2873

tcattgtgac agtattacta aacaggtaag gatgggaata ttttgttata ctgtgtatag   2933
```

-continued

```
tgaatgtatt gtactgtgtc tgtgaaaact gtgctttaaa ttatattttc atatgttttg   2993

ttggggacag agcacattaa gtctgaaagc aacagaggtt tgttttagaa ctgaaggcaa   3053

tttaatcaaa attcctgtca agaaaagctg cttataaatg taaatgaaat cacatttaaa   3113

ataaactgcc tctgacccaa aaaaa                                          3138
```

<210> SEQ ID NO 16
<211> LENGTH: 243
<212> TYPE: PRT
<213> ORGANISM: Homo sapiens

<400> SEQUENCE: 16

```
Met Thr Gly Ile Ala Ala Ala Ser Phe Phe Ser Asn Thr Cys Arg Phe
1               5                   10                  15

Gly Gly Cys Gly Leu His Phe Pro Thr Leu Ala Asp Leu Ile Glu His
            20                  25                  30

Ile Glu Asp Asn His Ile Asp Thr Asp Pro Arg Val Leu Glu Lys Gln
        35                  40                  45

Glu Leu Gln Gln Pro Thr Tyr Val Ala Leu Ser Tyr Ile Asn Arg Phe
    50                  55                  60

Met Thr Asp Ala Ala Arg Arg Glu Gln Glu Ser Leu Lys Lys Lys Ile
65                  70                  75                  80

Gln Pro Lys Leu Ser Leu Thr Leu Ser Ser Ser Val Ser Arg Gly Asn
                85                  90                  95

Val Ser Thr Pro Pro Arg His Ser Ser Gly Ser Leu Thr Pro Pro Val
            100                 105                 110

Thr Pro Pro Ile Thr Pro Ser Ser Ser Phe Arg Ser Ser Thr Pro Thr
        115                 120                 125

Gly Ser Glu Tyr Asp Glu Glu Glu Val Asp Tyr Glu Glu Ser Asp Ser
    130                 135                 140

Asp Glu Ser Trp Thr Thr Glu Ser Ala Ile Ser Ser Glu Ala Ile Leu
145                 150                 155                 160

Ser Ser Met Cys Met Asn Gly Gly Glu Glu Lys Pro Phe Ala Cys Pro
                165                 170                 175

Val Pro Gly Cys Lys Lys Arg Tyr Lys Asn Val Asn Gly Ile Lys Tyr
            180                 185                 190

His Ala Lys Asn Gly His Arg Thr Gln Ile Arg Val Arg Lys Pro Phe
        195                 200                 205

Lys Cys Arg Cys Gly Lys Ser Tyr Lys Thr Ala Gln Gly Leu Arg His
    210                 215                 220

His Thr Ile Asn Phe His Pro Pro Val Ser Ala Glu Ile Ile Arg Lys
225                 230                 235                 240

Met Gln Gln
```

<210> SEQ ID NO 17
<211> LENGTH: 3387
<212> TYPE: DNA
<213> ORGANISM: Homo sapiens
<220> FEATURE:
<221> NAME/KEY: CDS
<222> LOCATION: (8)..(2377)

<400> SEQUENCE: 17

```
agcgggc atg gcc tgc cgg gag ggg gca ggt agc cgg cgg gcc cgg tcc       49
        Met Ala Cys Arg Glu Gly Ala Gly Ser Arg Arg Ala Arg Ser
        1               5                   10
```

-continued

```
aat ggg tgc cgg ctt ccg agg aga ggg cgg agg aga gga gga agg agg        97
Asn Gly Cys Arg Leu Pro Arg Arg Gly Arg Arg Arg Gly Gly Arg Arg
15                  20                  25                  30

cga act gtg ggc ccc ggc ccc att cat tgc cgt ggc cgg cgg gca ctg       145
Arg Thr Val Gly Pro Gly Pro Ile His Cys Arg Gly Arg Arg Ala Leu
                35                  40                  45

ggg ccc cgt gtt ttc aga gtc atg gag gcg cta att cct gtc ata aac       193
Gly Pro Arg Val Phe Arg Val Met Glu Ala Leu Ile Pro Val Ile Asn
            50                  55                  60

aag ctc cag gac gtc ttc aac acg gtg ggc gcc gac atc atc cag ctg       241
Lys Leu Gln Asp Val Phe Asn Thr Val Gly Ala Asp Ile Ile Gln Leu
        65                  70                  75

cct caa atc gtc gta gtg gga acg cag agc agc gga aag agc tca gtg       289
Pro Gln Ile Val Val Val Gly Thr Gln Ser Ser Gly Lys Ser Ser Val
    80                  85                  90

cta gaa agc ctg gtg ggg agg gac ctg ctt ccc aga ggt act gga att       337
Leu Glu Ser Leu Val Gly Arg Asp Leu Leu Pro Arg Gly Thr Gly Ile
95                  100                 105                 110

gtc acc cgg aga cct ctc att ctg caa ctg gtc cat gtg aca caa gaa       385
Val Thr Arg Arg Pro Leu Ile Leu Gln Leu Val His Val Thr Gln Glu
                115                 120                 125

gat aaa cgg aaa aca aca gga gaa gaa aat ggg gtg gaa gca gaa gaa       433
Asp Lys Arg Lys Thr Thr Gly Glu Glu Asn Gly Val Glu Ala Glu Glu
            130                 135                 140

tgg ggt aaa ttt ctt cac acc aaa aat aag ctt tac acg gat ttt gat       481
Trp Gly Lys Phe Leu His Thr Lys Asn Lys Leu Tyr Thr Asp Phe Asp
        145                 150                 155

gaa att cga caa gaa att gaa aat gaa aca gaa aga att tca gga aat       529
Glu Ile Arg Gln Glu Ile Glu Asn Glu Thr Glu Arg Ile Ser Gly Asn
    160                 165                 170

aat aag gga gta agc cct gaa cca att cat ctt aag att ttt tca ccc       577
Asn Lys Gly Val Ser Pro Glu Pro Ile His Leu Lys Ile Phe Ser Pro
175                 180                 185                 190

aac gtt gtc aat ttg aca ctt gtg gat ttg cca gga atg acc aag gtg       625
Asn Val Val Asn Leu Thr Leu Val Asp Leu Pro Gly Met Thr Lys Val
                195                 200                 205

cct gta ggt gat caa cct aag gat att gag ctt caa atc aga gag ctc       673
Pro Val Gly Asp Gln Pro Lys Asp Ile Glu Leu Gln Ile Arg Glu Leu
            210                 215                 220

att ctt cgg ttc atc agt aat cct aat tcc att atc ctc gct gtc act       721
Ile Leu Arg Phe Ile Ser Asn Pro Asn Ser Ile Ile Leu Ala Val Thr
        225                 230                 235

gct gct aat aca gat atg gca aca tca gag gca ctt aaa att tca aga       769
Ala Ala Asn Thr Asp Met Ala Thr Ser Glu Ala Leu Lys Ile Ser Arg
    240                 245                 250

gag gta gat cca gat ggt cgc aga acc cta gct gta atc act aaa ctt       817
Glu Val Asp Pro Asp Gly Arg Arg Thr Leu Ala Val Ile Thr Lys Leu
255                 260                 265                 270

gat ctc atg gat gcg ggt act gat gcc atg gat gta ttg atg gga agg       865
Asp Leu Met Asp Ala Gly Thr Asp Ala Met Asp Val Leu Met Gly Arg
                275                 280                 285

gtt att cca gtc aaa ctt gga ata att gga gta gtt aac agg agc cag       913
Val Ile Pro Val Lys Leu Gly Ile Ile Gly Val Val Asn Arg Ser Gln
            290                 295                 300

cta gat att aac aac aag aag agt gta act gat tca atc cgt gat gag       961
Leu Asp Ile Asn Asn Lys Lys Ser Val Thr Asp Ser Ile Arg Asp Glu
        305                 310                 315

tat gct ttt ctt caa aag aaa tat cca tct ctg gcc aat aga aat gga      1009
Tyr Ala Phe Leu Gln Lys Lys Tyr Pro Ser Leu Ala Asn Arg Asn Gly
    320                 325                 330
```

-continued

```
aca aag tat ctt gct agg act cta aac agg tta ctg atg cat cac atc      1057
Thr Lys Tyr Leu Ala Arg Thr Leu Asn Arg Leu Leu Met His His Ile
335                 340                 345                 350

aga gat tgt tta cca gag ttg aaa aca aga ata aat gtt cta gct gct      1105
Arg Asp Cys Leu Pro Glu Leu Lys Thr Arg Ile Asn Val Leu Ala Ala
                355                 360                 365

cag tat cag tct ctt cta aat agc tac ggt gaa ccc gtg gat gat aaa      1153
Gln Tyr Gln Ser Leu Leu Asn Ser Tyr Gly Glu Pro Val Asp Asp Lys
            370                 375                 380

agt gct act tta ctc caa ctt att acc aaa ttt gcc aca gaa tat tgt      1201
Ser Ala Thr Leu Leu Gln Leu Ile Thr Lys Phe Ala Thr Glu Tyr Cys
        385                 390                 395

aac act att gaa gga act gca aaa tat att gaa act tcg gag cta tgc      1249
Asn Thr Ile Glu Gly Thr Ala Lys Tyr Ile Glu Thr Ser Glu Leu Cys
    400                 405                 410

ggt ggt gct aga att tgt tat att ttc cat gag act ttt ggg cga acc      1297
Gly Gly Ala Arg Ile Cys Tyr Ile Phe His Glu Thr Phe Gly Arg Thr
415                 420                 425                 430

tta gaa tct gtt gat cca ctt ggt ggc ctt aac act att gac att ttg      1345
Leu Glu Ser Val Asp Pro Leu Gly Gly Leu Asn Thr Ile Asp Ile Leu
                435                 440                 445

act gcc att aga aat gct act ggt cct cgt cct gct tta ttt gtg cct      1393
Thr Ala Ile Arg Asn Ala Thr Gly Pro Arg Pro Ala Leu Phe Val Pro
            450                 455                 460

gag gtt tca ttt gag tta ctg gtg aag cgg caa atc aaa cgt cta gaa      1441
Glu Val Ser Phe Glu Leu Leu Val Lys Arg Gln Ile Lys Arg Leu Glu
        465                 470                 475

gag ccc agc ctc cgc tgt gtg gaa ctg gtt cat gag gaa atg caa agg      1489
Glu Pro Ser Leu Arg Cys Val Glu Leu Val His Glu Glu Met Gln Arg
    480                 485                 490

atc att cag cac tgt agc aat tac agt aca cag gaa ttg tta cga ttt      1537
Ile Ile Gln His Cys Ser Asn Tyr Ser Thr Gln Glu Leu Leu Arg Phe
495                 500                 505                 510

cct aaa ctt cat gat gcc ata gtt gaa gtg gtg act tgt ctt ctt cgt      1585
Pro Lys Leu His Asp Ala Ile Val Glu Val Val Thr Cys Leu Leu Arg
                515                 520                 525

aaa agg ttg cct gtt aca aat gaa atg gtc cat aac tta gtg gca att      1633
Lys Arg Leu Pro Val Thr Asn Glu Met Val His Asn Leu Val Ala Ile
            530                 535                 540

gaa ctg gct tat atc aac aca aaa cat cca gac ttt gct gat gct tgt      1681
Glu Leu Ala Tyr Ile Asn Thr Lys His Pro Asp Phe Ala Asp Ala Cys
        545                 550                 555

ggg cta atg aac aat aat ata gag gaa caa agg aga aac agg cta gcc      1729
Gly Leu Met Asn Asn Asn Ile Glu Glu Gln Arg Arg Asn Arg Leu Ala
    560                 565                 570

aga gaa tta cct tca gct gta tca cga gac aag tct tct aaa gtt cca      1777
Arg Glu Leu Pro Ser Ala Val Ser Arg Asp Lys Ser Ser Lys Val Pro
575                 580                 585                 590

agt gct ttg gca cct gcc tcc cag gag ccc tcc ccc gct gct tct gct      1825
Ser Ala Leu Ala Pro Ala Ser Gln Glu Pro Ser Pro Ala Ala Ser Ala
                595                 600                 605

gag gct gat ggc aag tta att cag gac agc aga aga gaa act aaa aat      1873
Glu Ala Asp Gly Lys Leu Ile Gln Asp Ser Arg Arg Glu Thr Lys Asn
            610                 615                 620

gtt gca tct gga ggt ggt ggg gtt gga gat ggt gtt caa gaa cca acc      1921
Val Ala Ser Gly Gly Gly Gly Val Gly Asp Gly Val Gln Glu Pro Thr
        625                 630                 635

aca ggc aac tgg aga gga atg ctg aaa act tca aaa gct gaa gag tta      1969
Thr Gly Asn Trp Arg Gly Met Leu Lys Thr Ser Lys Ala Glu Glu Leu
```

-continued

```
    640                 645                 650

tta gca gaa gaa aaa tca aaa ccc att cca att atg cca gcc agt cca     2017
Leu Ala Glu Glu Lys Ser Lys Pro Ile Pro Ile Met Pro Ala Ser Pro
655                 660                 665                 670

caa aaa ggt cat gcc gtg aac ctg cta gat gtg cca gtt cct gtt gca     2065
Gln Lys Gly His Ala Val Asn Leu Leu Asp Val Pro Val Pro Val Ala
                675                 680                 685

cga aaa cta tct gct cgg gaa cag cga gat tgt gag gtt att gaa cga     2113
Arg Lys Leu Ser Ala Arg Glu Gln Arg Asp Cys Glu Val Ile Glu Arg
            690                 695                 700

ctc att aaa tca tat ttt ctc att gtc aga aag aat att caa gac agt     2161
Leu Ile Lys Ser Tyr Phe Leu Ile Val Arg Lys Asn Ile Gln Asp Ser
        705                 710                 715

gtg cca aag gca gta atg cat ttt ttg gtt aat cat gtg aaa gac act     2209
Val Pro Lys Ala Val Met His Phe Leu Val Asn His Val Lys Asp Thr
    720                 725                 730

ctt cag agt gag cta gta ggc cag ctg tat aaa tca tcc tta ttg gat     2257
Leu Gln Ser Glu Leu Val Gly Gln Leu Tyr Lys Ser Ser Leu Leu Asp
735                 740                 745                 750

gat ctt ctg aca gaa tct gag gac atg gca cag cgc agg aaa gaa gca     2305
Asp Leu Leu Thr Glu Ser Glu Asp Met Ala Gln Arg Arg Lys Glu Ala
                755                 760                 765

gct gat atg cta aag gca tta caa gga gcc agt caa att att gct gaa     2353
Ala Asp Met Leu Lys Ala Leu Gln Gly Ala Ser Gln Ile Ile Ala Glu
            770                 775                 780

atc cgg gag act cat ctt tgg tga agagaactat gtaatactga gactttgttg    2407
Ile Arg Glu Thr His Leu Trp
        785

actcaaaact tgctagttac tgcctacctg agtagaatct tatttatgaa ctcctgtgta   2467

ttgcaatggt atgaatctgc tcatgtggag actggctata aactgaaaag tgtattccaa   2527

attgcagaac acatcacaca tttaatccaa ataataaatg gctgtttcta aagtttccca   2587

gtatatataa aatacatcaa gtctgtcttg tgacagtttc atctgaactt aacttaaaaa   2647

caactgttaa tgttctagtt gtgcaaagca gtttgcctgt ggataagatg acctgtgtaa   2707

taatctttgt tagtagtctt aaagctgctg ccatagtcct ccaagaagaa agcaccaaga   2767

caacatttca tatgactata atgcatgtac tatataagct gatctggctt tgaaagatgt   2827

gagttggcaa gttcctcaca tagagtcatt gtattccacc tgtccttcaa tttagttttt   2887

tctgagcttc tttgcagcct ttgatgtgtt tttaagaaag ctgaatgcac aagaggatct   2947

gtgacactga catggctgtg gtgtgcatac tgtgtagtta catagccctt ccaattctgg   3007

gtccatttgc actagcaaat taaaatatgc tttgattcat acttaaacct gaaagcagga   3067

atgcctacat taattcctac attaaaaaca gccatctacc cttgattatc tagaaagact   3127

tggtaatgat ggtcagttcc ttttagattt cagaaaatca aatgatgacc taaatttccc   3187

ttaatttgca aatacagtag taattaaggt acatctctaa agtggagcac ttacaccagg   3247

ctctaagatt cactttgagg tggaacttaa aaccagtgta ctgtatgtat gcattggtaa   3307

tagctacttt tgcttcatag cttcatacca acaaaatata tttattagaa tagtatgaaa   3367

gtactgaagg agttgaaaga                                               3387
```

<210> SEQ ID NO 18
<211> LENGTH: 789
<212> TYPE: PRT
<213> ORGANISM: Homo sapiens

<400> SEQUENCE: 18

-continued

```
Met Ala Cys Arg Glu Gly Ala Gly Ser Arg Arg Ala Arg Ser Asn Gly
1               5                   10                  15

Cys Arg Leu Pro Arg Arg Gly Arg Arg Arg Gly Gly Arg Arg Arg Thr
            20                  25                  30

Val Gly Pro Gly Pro Ile His Cys Arg Gly Arg Arg Ala Leu Gly Pro
        35                  40                  45

Arg Val Phe Arg Val Met Glu Ala Leu Ile Pro Val Ile Asn Lys Leu
    50                  55                  60

Gln Asp Val Phe Asn Thr Val Gly Ala Asp Ile Ile Gln Leu Pro Gln
65                  70                  75                  80

Ile Val Val Val Gly Thr Gln Ser Ser Gly Lys Ser Ser Val Leu Glu
                85                  90                  95

Ser Leu Val Gly Arg Asp Leu Leu Pro Arg Gly Thr Gly Ile Val Thr
            100                 105                 110

Arg Arg Pro Leu Ile Leu Gln Leu Val His Val Thr Gln Glu Asp Lys
        115                 120                 125

Arg Lys Thr Thr Gly Glu Glu Asn Gly Val Glu Ala Glu Glu Trp Gly
    130                 135                 140

Lys Phe Leu His Thr Lys Asn Lys Leu Tyr Thr Asp Phe Asp Glu Ile
145                 150                 155                 160

Arg Gln Glu Ile Glu Asn Glu Thr Glu Arg Ile Ser Gly Asn Asn Lys
                165                 170                 175

Gly Val Ser Pro Glu Pro Ile His Leu Lys Ile Phe Ser Pro Asn Val
            180                 185                 190

Val Asn Leu Thr Leu Val Asp Leu Pro Gly Met Thr Lys Val Pro Val
        195                 200                 205

Gly Asp Gln Pro Lys Asp Ile Glu Leu Gln Ile Arg Glu Leu Ile Leu
    210                 215                 220

Arg Phe Ile Ser Asn Pro Asn Ser Ile Ile Leu Ala Val Thr Ala Ala
225                 230                 235                 240

Asn Thr Asp Met Ala Thr Ser Glu Ala Leu Lys Ile Ser Arg Glu Val
                245                 250                 255

Asp Pro Asp Gly Arg Arg Thr Leu Ala Val Ile Thr Lys Leu Asp Leu
            260                 265                 270

Met Asp Ala Gly Thr Asp Ala Met Asp Val Leu Met Gly Arg Val Ile
        275                 280                 285

Pro Val Lys Leu Gly Ile Ile Gly Val Val Asn Arg Ser Gln Leu Asp
    290                 295                 300

Ile Asn Asn Lys Lys Ser Val Thr Asp Ser Ile Arg Asp Glu Tyr Ala
305                 310                 315                 320

Phe Leu Gln Lys Lys Tyr Pro Ser Leu Ala Asn Arg Asn Gly Thr Lys
                325                 330                 335

Tyr Leu Ala Arg Thr Leu Asn Arg Leu Leu Met His His Ile Arg Asp
            340                 345                 350

Cys Leu Pro Glu Leu Lys Thr Arg Ile Asn Val Leu Ala Ala Gln Tyr
        355                 360                 365

Gln Ser Leu Leu Asn Ser Tyr Gly Glu Pro Val Asp Asp Lys Ser Ala
    370                 375                 380

Thr Leu Leu Gln Leu Ile Thr Lys Phe Ala Thr Glu Tyr Cys Asn Thr
385                 390                 395                 400

Ile Glu Gly Thr Ala Lys Tyr Ile Glu Thr Ser Glu Leu Cys Gly Gly
                405                 410                 415
```

-continued

```
Ala Arg Ile Cys Tyr Ile Phe His Glu Thr Phe Gly Arg Thr Leu Glu
            420                 425                 430

Ser Val Asp Pro Leu Gly Gly Leu Asn Thr Ile Asp Ile Leu Thr Ala
        435                 440                 445

Ile Arg Asn Ala Thr Gly Pro Arg Pro Ala Leu Phe Val Pro Glu Val
    450                 455                 460

Ser Phe Glu Leu Leu Val Lys Arg Gln Ile Lys Arg Leu Glu Glu Pro
465                 470                 475                 480

Ser Leu Arg Cys Val Glu Leu Val His Glu Glu Met Gln Arg Ile Ile
                485                 490                 495

Gln His Cys Ser Asn Tyr Ser Thr Gln Glu Leu Leu Arg Phe Pro Lys
            500                 505                 510

Leu His Asp Ala Ile Val Glu Val Val Thr Cys Leu Leu Arg Lys Arg
        515                 520                 525

Leu Pro Val Thr Asn Glu Met Val His Asn Leu Val Ala Ile Glu Leu
    530                 535                 540

Ala Tyr Ile Asn Thr Lys His Pro Asp Phe Ala Asp Ala Cys Gly Leu
545                 550                 555                 560

Met Asn Asn Asn Ile Glu Glu Gln Arg Arg Asn Arg Leu Ala Arg Glu
                565                 570                 575

Leu Pro Ser Ala Val Ser Arg Asp Lys Ser Ser Lys Val Pro Ser Ala
            580                 585                 590

Leu Ala Pro Ala Ser Gln Glu Pro Ser Pro Ala Ala Ser Ala Glu Ala
        595                 600                 605

Asp Gly Lys Leu Ile Gln Asp Ser Arg Arg Glu Thr Lys Asn Val Ala
    610                 615                 620

Ser Gly Gly Gly Gly Val Gly Asp Gly Val Gln Glu Pro Thr Thr Gly
625                 630                 635                 640

Asn Trp Arg Gly Met Leu Lys Thr Ser Lys Ala Glu Glu Leu Leu Ala
                645                 650                 655

Glu Glu Lys Ser Lys Pro Ile Pro Ile Met Pro Ala Ser Pro Gln Lys
            660                 665                 670

Gly His Ala Val Asn Leu Leu Asp Val Pro Val Pro Val Ala Arg Lys
        675                 680                 685

Leu Ser Ala Arg Glu Gln Arg Asp Cys Glu Val Ile Glu Arg Leu Ile
    690                 695                 700

Lys Ser Tyr Phe Leu Ile Val Arg Lys Asn Ile Gln Asp Ser Val Pro
705                 710                 715                 720

Lys Ala Val Met His Phe Leu Val Asn His Val Lys Asp Thr Leu Gln
                725                 730                 735

Ser Glu Leu Val Gly Gln Leu Tyr Lys Ser Ser Leu Leu Asp Asp Leu
            740                 745                 750

Leu Thr Glu Ser Glu Asp Met Ala Gln Arg Arg Lys Glu Ala Ala Asp
        755                 760                 765

Met Leu Lys Ala Leu Gln Gly Ala Ser Gln Ile Ile Ala Glu Ile Arg
    770                 775                 780

Glu Thr His Leu Trp
785
```

```
<210> SEQ ID NO 19
<211> LENGTH: 2509
<212> TYPE: DNA
<213> ORGANISM: Homo sapiens
<220> FEATURE:
<221> NAME/KEY: CDS
```

-continued

```
<222> LOCATION: (8)..(2299)

<400> SEQUENCE: 19

agcgggc atg gcc tgc cgg gag ggg gca ggt agc cgg cgg gcc cgg tcc        49
        Met Ala Cys Arg Glu Gly Ala Gly Ser Arg Arg Ala Arg Ser
        1               5                   10

aat ggg tgc cgg ctt ccg agg aga ggg cgg agg aga gga gga agg agg        97
Asn Gly Cys Arg Leu Pro Arg Arg Gly Arg Arg Arg Gly Gly Arg Arg
15                  20                  25                  30

cga act gtg ggc ccc ggc ccc att cat tgc cgt ggc cgg cgg gca ctg       145
Arg Thr Val Gly Pro Gly Pro Ile His Cys Arg Gly Arg Arg Ala Leu
                35                  40                  45

ggg ccc cgt gtt ttc aga gtc atg gag gcg cta att cct gtc ata aac       193
Gly Pro Arg Val Phe Arg Val Met Glu Ala Leu Ile Pro Val Ile Asn
            50                  55                  60

aag ctc cag gac gtc ttc aac acg gtg ggc gcc gac atc atc cag ctg       241
Lys Leu Gln Asp Val Phe Asn Thr Val Gly Ala Asp Ile Ile Gln Leu
        65                  70                  75

cct caa atc gtc gta gtg gga acg cag agc agc gga aag agc tca gtg       289
Pro Gln Ile Val Val Val Gly Thr Gln Ser Ser Gly Lys Ser Ser Val
    80                  85                  90

cta gaa agc ctg gtg ggg agg gac ctg ctt ccc aga ggt act gga att       337
Leu Glu Ser Leu Val Gly Arg Asp Leu Leu Pro Arg Gly Thr Gly Ile
95                  100                 105                 110

gtc acc cgg aga cct ctc att ctg caa ctg gtc cat gtg aca caa gaa       385
Val Thr Arg Arg Pro Leu Ile Leu Gln Leu Val His Val Thr Gln Glu
                115                 120                 125

gat aaa cgg aaa aca aca gga gaa gaa aat ggg gtg gaa gca gaa gaa       433
Asp Lys Arg Lys Thr Thr Gly Glu Glu Asn Gly Val Glu Ala Glu Glu
            130                 135                 140

tgg ggt aaa ttt ctt cac acc aaa aat aag ctt tac acg gat ttt gat       481
Trp Gly Lys Phe Leu His Thr Lys Asn Lys Leu Tyr Thr Asp Phe Asp
        145                 150                 155

gaa att cga caa gaa att gaa aat gaa aca gaa aga att tca gga aat       529
Glu Ile Arg Gln Glu Ile Glu Asn Glu Thr Glu Arg Ile Ser Gly Asn
    160                 165                 170

aat aag gga gta agc cct gaa cca att cat ctt aag att ttt tca ccc       577
Asn Lys Gly Val Ser Pro Glu Pro Ile His Leu Lys Ile Phe Ser Pro
175                 180                 185                 190

aac gtt gtc aat ttg aca ctt gtg gat ttg cca gga atg acc aag gtg       625
Asn Val Val Asn Leu Thr Leu Val Asp Leu Pro Gly Met Thr Lys Val
                195                 200                 205

cct gta ggt gat caa cct aag gat att gag ctt caa atc aga gag ctc       673
Pro Val Gly Asp Gln Pro Lys Asp Ile Glu Leu Gln Ile Arg Glu Leu
            210                 215                 220

att ctt cgg ttc atc agt aat cct aat tcc att atc ctc gct gtc act       721
Ile Leu Arg Phe Ile Ser Asn Pro Asn Ser Ile Ile Leu Ala Val Thr
        225                 230                 235

gct gct aat aca gat atg gca aca tca gag gca ctt aaa att tca aga       769
Ala Ala Asn Thr Asp Met Ala Thr Ser Glu Ala Leu Lys Ile Ser Arg
    240                 245                 250

gag gta gat cca gat ggt cgc aga acc cta gct gta atc act aaa ctt       817
Glu Val Asp Pro Asp Gly Arg Arg Thr Leu Ala Val Ile Thr Lys Leu
255                 260                 265                 270

gat ctc atg gat gcg ggt act gat gcc atg gat gta ttg atg gga agg       865
Asp Leu Met Asp Ala Gly Thr Asp Ala Met Asp Val Leu Met Gly Arg
                275                 280                 285

gtt att cca gtc aaa ctt gga ata att gga gta gtt aac agg agc cag       913
Val Ile Pro Val Lys Leu Gly Ile Ile Gly Val Val Asn Arg Ser Gln
            290                 295                 300
```

-continued

```
cta gat att aac aac aag aag agt gta act gat tca atc cgt gat gag      961
Leu Asp Ile Asn Asn Lys Lys Ser Val Thr Asp Ser Ile Arg Asp Glu
        305                 310                 315

tat gct ttt ctt caa aag aaa tat cca tct ctg gcc aat aga aat gga     1009
Tyr Ala Phe Leu Gln Lys Lys Tyr Pro Ser Leu Ala Asn Arg Asn Gly
    320                 325                 330

aca aag tat ctt gct agg act cta aac agg tta ctg atg cat cac atc     1057
Thr Lys Tyr Leu Ala Arg Thr Leu Asn Arg Leu Leu Met His His Ile
335                 340                 345                 350

aga gat tgt tta cca gag ttg aaa aca aga ata aat gtt cta gct gct     1105
Arg Asp Cys Leu Pro Glu Leu Lys Thr Arg Ile Asn Val Leu Ala Ala
                355                 360                 365

cag tat cag tct ctt cta aat agc tac ggt gaa ccc gtg gat gat aaa     1153
Gln Tyr Gln Ser Leu Leu Asn Ser Tyr Gly Glu Pro Val Asp Asp Lys
            370                 375                 380

agt gct act tta ctc caa ctt att acc aaa ttt gcc aca gaa tat tgt     1201
Ser Ala Thr Leu Leu Gln Leu Ile Thr Lys Phe Ala Thr Glu Tyr Cys
        385                 390                 395

aac act att gaa gga act gca aaa tat att gaa act tcg gag cta tgc     1249
Asn Thr Ile Glu Gly Thr Ala Lys Tyr Ile Glu Thr Ser Glu Leu Cys
    400                 405                 410

ggt ggt gct aga att tgt tat att ttc cat gag act ttt ggg cga acc     1297
Gly Gly Ala Arg Ile Cys Tyr Ile Phe His Glu Thr Phe Gly Arg Thr
415                 420                 425                 430

tta gaa tct gtt gat cca ctt ggt ggc ctt aac act att gac att ttg     1345
Leu Glu Ser Val Asp Pro Leu Gly Gly Leu Asn Thr Ile Asp Ile Leu
                435                 440                 445

act gcc att aga aat gct act ggt cct cgt cct gct tta ttt gtg cct     1393
Thr Ala Ile Arg Asn Ala Thr Gly Pro Arg Pro Ala Leu Phe Val Pro
            450                 455                 460

gag gtt tca ttt gag tta ctg gtg aag cgg caa atc aaa cgt cta gaa     1441
Glu Val Ser Phe Glu Leu Leu Val Lys Arg Gln Ile Lys Arg Leu Glu
        465                 470                 475

gag ccc agc ctc cgc tgt gtg gaa ctg gtt cat gag gaa atg caa agg     1489
Glu Pro Ser Leu Arg Cys Val Glu Leu Val His Glu Glu Met Gln Arg
    480                 485                 490

atc att cag cac tgt agc aat tac agt aca cag gaa ttg tta cga ttt     1537
Ile Ile Gln His Cys Ser Asn Tyr Ser Thr Gln Glu Leu Leu Arg Phe
495                 500                 505                 510

cct aaa ctt cat gat gcc ata gtt gaa gtg gtg act tgt ctt ctt cgt     1585
Pro Lys Leu His Asp Ala Ile Val Glu Val Val Thr Cys Leu Leu Arg
                515                 520                 525

aaa agg ttg cct gtt aca aat gaa atg gtc cat aac tta gtg gca att     1633
Lys Arg Leu Pro Val Thr Asn Glu Met Val His Asn Leu Val Ala Ile
            530                 535                 540

gaa ctg gct tat atc aac aca aaa cat cca gac ttt gct gat gct tgt     1681
Glu Leu Ala Tyr Ile Asn Thr Lys His Pro Asp Phe Ala Asp Ala Cys
        545                 550                 555

ggg cta atg aac aat aat ata gag gaa caa agg aga aac agg cta gcc     1729
Gly Leu Met Asn Asn Asn Ile Glu Glu Gln Arg Arg Asn Arg Leu Ala
    560                 565                 570

aga gaa tta cct tca gct gta tca cga gac aag tta att cag gac agc     1777
Arg Glu Leu Pro Ser Ala Val Ser Arg Asp Lys Leu Ile Gln Asp Ser
575                 580                 585                 590

aga aga gaa act aaa aat gtt gca tct gga ggt ggt ggg gtt gga gat     1825
Arg Arg Glu Thr Lys Asn Val Ala Ser Gly Gly Gly Gly Val Gly Asp
                595                 600                 605

ggt gtt caa gaa cca acc aca ggc aac tgg aga gga atg ctg aaa act     1873
Gly Val Gln Glu Pro Thr Thr Gly Asn Trp Arg Gly Met Leu Lys Thr
```

-continued

```
            610                 615                 620

tca aaa gct gaa gag tta tta gca gaa gaa aaa tca aaa ccc att cca     1921
Ser Lys Ala Glu Glu Leu Leu Ala Glu Glu Lys Ser Lys Pro Ile Pro
        625                 630                 635

att atg cca gcc agt cca caa aaa ggt cat gcc gtg aac ctg cta gat     1969
Ile Met Pro Ala Ser Pro Gln Lys Gly His Ala Val Asn Leu Leu Asp
    640                 645                 650

gtg cca gtt cct gtt gca cga aaa cta tct gct cgg gaa cag cga gat     2017
Val Pro Val Pro Val Ala Arg Lys Leu Ser Ala Arg Glu Gln Arg Asp
655                 660                 665                 670

tgt gag gtt att gaa cga ctc att aaa tca tat ttt ctc att gtc aga     2065
Cys Glu Val Ile Glu Arg Leu Ile Lys Ser Tyr Phe Leu Ile Val Arg
            675                 680                 685

aag aat att caa gac agt gtg cca aag gca gta atg cat ttt ttg gtt     2113
Lys Asn Ile Gln Asp Ser Val Pro Lys Ala Val Met His Phe Leu Val
            690                 695                 700

aat cat gtg aaa gac act ctt cag agt gag cta gta ggc cag ctg tat     2161
Asn His Val Lys Asp Thr Leu Gln Ser Glu Leu Val Gly Gln Leu Tyr
        705                 710                 715

aaa tca tcc tta ttg gat gat ctt ctg aca gaa tct gag gac atg gca     2209
Lys Ser Ser Leu Leu Asp Asp Leu Leu Thr Glu Ser Glu Asp Met Ala
    720                 725                 730

cag cgc agg aaa gaa gca gct gat atg cta aag gca tta caa gga gcc     2257
Gln Arg Arg Lys Glu Ala Ala Asp Met Leu Lys Ala Leu Gln Gly Ala
735                 740                 745                 750

agt caa att att gct gaa atc cgg gag act cat ctt tgg tga             2299
Ser Gln Ile Ile Ala Glu Ile Arg Glu Thr His Leu Trp
            755                 760

agagaactat gtaatactga gactttgttg actcaaaact tgctagttac tgcctacctg   2359

agtagaatct tatttatgaa ctcctgtgta ttgcaatggt atgaatctgc tcatgtggag   2419

actggctata aactgaaaag tgtattccaa attgcagaac acatcacaca tttaatccaa   2479

ataataaatg gctgtttcta aaaaaaaaaa                                    2509


<210> SEQ ID NO 20
<211> LENGTH: 763
<212> TYPE: PRT
<213> ORGANISM: Homo sapiens

<400> SEQUENCE: 20

Met Ala Cys Arg Glu Gly Ala Gly Ser Arg Arg Ala Arg Ser Asn Gly
1               5                   10                  15

Cys Arg Leu Pro Arg Arg Gly Arg Arg Arg Gly Gly Arg Arg Arg Thr
            20                  25                  30

Val Gly Pro Gly Pro Ile His Cys Arg Gly Arg Arg Ala Leu Gly Pro
        35                  40                  45

Arg Val Phe Arg Val Met Glu Ala Leu Ile Pro Val Ile Asn Lys Leu
    50                  55                  60

Gln Asp Val Phe Asn Thr Val Gly Ala Asp Ile Ile Gln Leu Pro Gln
65                  70                  75                  80

Ile Val Val Val Gly Thr Gln Ser Ser Gly Lys Ser Ser Val Leu Glu
                85                  90                  95

Ser Leu Val Gly Arg Asp Leu Leu Pro Arg Gly Thr Gly Ile Val Thr
            100                 105                 110

Arg Arg Pro Leu Ile Leu Gln Leu Val His Val Thr Gln Glu Asp Lys
        115                 120                 125

Arg Lys Thr Thr Gly Glu Glu Asn Gly Val Glu Ala Glu Glu Trp Gly
```

-continued

```
    130                 135                 140

Lys Phe Leu His Thr Lys Asn Lys Leu Tyr Thr Asp Phe Asp Glu Ile
145                 150                 155                 160

Arg Gln Glu Ile Glu Asn Glu Thr Glu Arg Ile Ser Gly Asn Asn Lys
                165                 170                 175

Gly Val Ser Pro Glu Pro Ile His Leu Lys Ile Phe Ser Pro Asn Val
            180                 185                 190

Val Asn Leu Thr Leu Val Asp Leu Pro Gly Met Thr Lys Val Pro Val
        195                 200                 205

Gly Asp Gln Pro Lys Asp Ile Glu Leu Gln Ile Arg Glu Leu Ile Leu
    210                 215                 220

Arg Phe Ile Ser Asn Pro Asn Ser Ile Ile Leu Ala Val Thr Ala Ala
225                 230                 235                 240

Asn Thr Asp Met Ala Thr Ser Glu Ala Leu Lys Ile Ser Arg Glu Val
                245                 250                 255

Asp Pro Asp Gly Arg Arg Thr Leu Ala Val Ile Thr Lys Leu Asp Leu
            260                 265                 270

Met Asp Ala Gly Thr Asp Ala Met Asp Val Leu Met Gly Arg Val Ile
        275                 280                 285

Pro Val Lys Leu Gly Ile Ile Gly Val Val Asn Arg Ser Gln Leu Asp
    290                 295                 300

Ile Asn Asn Lys Lys Ser Val Thr Asp Ser Ile Arg Asp Glu Tyr Ala
305                 310                 315                 320

Phe Leu Gln Lys Lys Tyr Pro Ser Leu Ala Asn Arg Asn Gly Thr Lys
                325                 330                 335

Tyr Leu Ala Arg Thr Leu Asn Arg Leu Leu Met His His Ile Arg Asp
            340                 345                 350

Cys Leu Pro Glu Leu Lys Thr Arg Ile Asn Val Leu Ala Ala Gln Tyr
        355                 360                 365

Gln Ser Leu Leu Asn Ser Tyr Gly Glu Pro Val Asp Asp Lys Ser Ala
    370                 375                 380

Thr Leu Leu Gln Leu Ile Thr Lys Phe Ala Thr Glu Tyr Cys Asn Thr
385                 390                 395                 400

Ile Glu Gly Thr Ala Lys Tyr Ile Glu Thr Ser Glu Leu Cys Gly Gly
                405                 410                 415

Ala Arg Ile Cys Tyr Ile Phe His Glu Thr Phe Gly Arg Thr Leu Glu
            420                 425                 430

Ser Val Asp Pro Leu Gly Gly Leu Asn Thr Ile Asp Ile Leu Thr Ala
        435                 440                 445

Ile Arg Asn Ala Thr Gly Pro Arg Pro Ala Leu Phe Val Pro Glu Val
    450                 455                 460

Ser Phe Glu Leu Leu Val Lys Arg Gln Ile Lys Arg Leu Glu Glu Pro
465                 470                 475                 480

Ser Leu Arg Cys Val Glu Leu Val His Glu Glu Met Gln Arg Ile Ile
                485                 490                 495

Gln His Cys Ser Asn Tyr Ser Thr Gln Glu Leu Leu Arg Phe Pro Lys
            500                 505                 510

Leu His Asp Ala Ile Val Glu Val Val Thr Cys Leu Leu Arg Lys Arg
        515                 520                 525

Leu Pro Val Thr Asn Glu Met Val His Asn Leu Val Ala Ile Glu Leu
    530                 535                 540

Ala Tyr Ile Asn Thr Lys His Pro Asp Phe Ala Asp Ala Cys Gly Leu
545                 550                 555                 560
```

-continued

```
Met Asn Asn Asn Ile Glu Glu Gln Arg Arg Asn Arg Leu Ala Arg Glu
                565                 570                 575

Leu Pro Ser Ala Val Ser Arg Asp Lys Leu Ile Gln Asp Ser Arg Arg
            580                 585                 590

Glu Thr Lys Asn Val Ala Ser Gly Gly Gly Gly Val Gly Asp Gly Val
        595                 600                 605

Gln Glu Pro Thr Thr Gly Asn Trp Arg Gly Met Leu Lys Thr Ser Lys
    610                 615                 620

Ala Glu Glu Leu Leu Ala Glu Glu Lys Ser Lys Pro Ile Pro Ile Met
625                 630                 635                 640

Pro Ala Ser Pro Gln Lys Gly His Ala Val Asn Leu Leu Asp Val Pro
                645                 650                 655

Val Pro Val Ala Arg Lys Leu Ser Ala Arg Glu Gln Arg Asp Cys Glu
            660                 665                 670

Val Ile Glu Arg Leu Ile Lys Ser Tyr Phe Leu Ile Val Arg Lys Asn
        675                 680                 685

Ile Gln Asp Ser Val Pro Lys Ala Val Met His Phe Leu Val Asn His
    690                 695                 700

Val Lys Asp Thr Leu Gln Ser Glu Leu Val Gly Gln Leu Tyr Lys Ser
705                 710                 715                 720

Ser Leu Leu Asp Asp Leu Leu Thr Glu Ser Glu Asp Met Ala Gln Arg
                725                 730                 735

Arg Lys Glu Ala Ala Asp Met Leu Lys Ala Leu Gln Gly Ala Ser Gln
            740                 745                 750

Ile Ile Ala Glu Ile Arg Glu Thr His Leu Trp
        755                 760


<210> SEQ ID NO 21
<211> LENGTH: 2539
<212> TYPE: DNA
<213> ORGANISM: Homo sapiens
<220> FEATURE:
<221> NAME/KEY: CDS
<222> LOCATION: (8)..(2266)

<400> SEQUENCE: 21

agcgggc atg gcc tgc cgg gag ggg gca ggt agc cgg cgg gcc cgg tcc       49
        Met Ala Cys Arg Glu Gly Ala Gly Ser Arg Arg Ala Arg Ser
        1               5                   10

aat ggg tgc cgg ctt ccg agg aga ggg cgg agg aga gga gga agg agg       97
Asn Gly Cys Arg Leu Pro Arg Arg Gly Arg Arg Arg Gly Gly Arg Arg
15                  20                  25                  30

cga act gtg ggc ccc ggc ccc att cat tgc cgt ggc cgg cgg gca ctg      145
Arg Thr Val Gly Pro Gly Pro Ile His Cys Arg Gly Arg Arg Ala Leu
                35                  40                  45

ggg ccc cgt gtt ttc aga gtc atg gag gcg cta att cct gtc ata aac      193
Gly Pro Arg Val Phe Arg Val Met Glu Ala Leu Ile Pro Val Ile Asn
            50                  55                  60

aag ctc cag gac gtc ttc aac acg gtg ggc gcc gac atc atc cag ctg      241
Lys Leu Gln Asp Val Phe Asn Thr Val Gly Ala Asp Ile Ile Gln Leu
        65                  70                  75

cct caa atc gtc gta gtg gga acg cag agc agc gga aag agc tca gtg      289
Pro Gln Ile Val Val Val Gly Thr Gln Ser Ser Gly Lys Ser Ser Val
    80                  85                  90

cta gaa agc ctg gtg ggg agg gac ctg ctt ccc aga ggt act gga att      337
Leu Glu Ser Leu Val Gly Arg Asp Leu Leu Pro Arg Gly Thr Gly Ile
95                  100                 105                 110
```

-continued

```
gtc acc cgg aga cct ctc att ctg caa ctg gtc cat gtg aca caa gaa      385
Val Thr Arg Arg Pro Leu Ile Leu Gln Leu Val His Val Thr Gln Glu
                115                 120                 125

gat aaa cgg aaa aca aca gga gaa gaa aat ggg gtg gaa gca gaa gaa      433
Asp Lys Arg Lys Thr Thr Gly Glu Glu Asn Gly Val Glu Ala Glu Glu
            130                 135                 140

tgg ggt aaa ttt ctt cac acc aaa aat aag ctt tac acg gat ttt gat      481
Trp Gly Lys Phe Leu His Thr Lys Asn Lys Leu Tyr Thr Asp Phe Asp
        145                 150                 155

gaa att cga caa gaa att gaa aat gaa aca gaa aga att tca gga aat      529
Glu Ile Arg Gln Glu Ile Glu Asn Glu Thr Glu Arg Ile Ser Gly Asn
    160                 165                 170

aat aag gga gta agc cct gaa cca att cat ctt aag att ttt tca ccc      577
Asn Lys Gly Val Ser Pro Glu Pro Ile His Leu Lys Ile Phe Ser Pro
175                 180                 185                 190

aac gtt gtc aat ttg aca ctt gtg gat ttg cca gga atg acc aag gtg      625
Asn Val Val Asn Leu Thr Leu Val Asp Leu Pro Gly Met Thr Lys Val
                195                 200                 205

cct gta ggt gat caa cct aag gat att gag ctt caa atc aga gag ctc      673
Pro Val Gly Asp Gln Pro Lys Asp Ile Glu Leu Gln Ile Arg Glu Leu
            210                 215                 220

att ctt cgg ttc atc agt aat cct aat tcc att atc ctc gct gtc act      721
Ile Leu Arg Phe Ile Ser Asn Pro Asn Ser Ile Ile Leu Ala Val Thr
        225                 230                 235

gct gct aat aca gat atg gca aca tca gag gca ctt aaa att tca aga      769
Ala Ala Asn Thr Asp Met Ala Thr Ser Glu Ala Leu Lys Ile Ser Arg
    240                 245                 250

gag gta gat cca gat ggc tgc aga acc cta gct gta atc act aaa ctt      817
Glu Val Asp Pro Asp Gly Cys Arg Thr Leu Ala Val Ile Thr Lys Leu
255                 260                 265                 270

gat ctc atg gat gcg ggt act gat gcc atg gat gta ttg atg gga agg      865
Asp Leu Met Asp Ala Gly Thr Asp Ala Met Asp Val Leu Met Gly Arg
                275                 280                 285

gtt att cca gtc aaa ctt gga ata att gga gta gtt aac agg agc cag      913
Val Ile Pro Val Lys Leu Gly Ile Ile Gly Val Val Asn Arg Ser Gln
            290                 295                 300

cta gat att aac aac aag aag agt gta act gat tca atc cgt gat gag      961
Leu Asp Ile Asn Asn Lys Lys Ser Val Thr Asp Ser Ile Arg Asp Glu
        305                 310                 315

tat gct ttt ctt caa aag aaa tat cca tct ctg gcc aat aga aat gga     1009
Tyr Ala Phe Leu Gln Lys Lys Tyr Pro Ser Leu Ala Asn Arg Asn Gly
    320                 325                 330

aca aag tat ctt gct agg act cta aac agg tta ctg atg cat cac atc     1057
Thr Lys Tyr Leu Ala Arg Thr Leu Asn Arg Leu Leu Met His His Ile
335                 340                 345                 350

aga gat tgt tta cca gag ttg aaa aca aga ata aat gtt cta gct gct     1105
Arg Asp Cys Leu Pro Glu Leu Lys Thr Arg Ile Asn Val Leu Ala Ala
                355                 360                 365

cag tat cag tct ctt cta aat agc tac ggt gaa ccc gtg gat gat aaa     1153
Gln Tyr Gln Ser Leu Leu Asn Ser Tyr Gly Glu Pro Val Asp Asp Lys
            370                 375                 380

agt gct act tta ctc caa ctt att acc aaa ttt gcc aca gaa tat tgt     1201
Ser Ala Thr Leu Leu Gln Leu Ile Thr Lys Phe Ala Thr Glu Tyr Cys
        385                 390                 395

aac act att gaa gga act gca aaa tat att gaa act tcg gag cta tgc     1249
Asn Thr Ile Glu Gly Thr Ala Lys Tyr Ile Glu Thr Ser Glu Leu Cys
    400                 405                 410

ggt ggt gct aga att tgt tat att ttc cat gag act ttt ggg cga acc     1297
Gly Gly Ala Arg Ile Cys Tyr Ile Phe His Glu Thr Phe Gly Arg Thr
415                 420                 425                 430
```

-continued

```
tta gaa tct gtt gat cca ctt ggt ggc ctt aac act att gac att ttg      1345
Leu Glu Ser Val Asp Pro Leu Gly Gly Leu Asn Thr Ile Asp Ile Leu
                435                 440                 445

act gcc att aga aat gct act ggt cct cgt cct gct tta ttt gtg cct      1393
Thr Ala Ile Arg Asn Ala Thr Gly Pro Arg Pro Ala Leu Phe Val Pro
            450                 455                 460

gag gtt tca ttt gag tta ctg gtg aag cgg caa atc aaa cgt cta gaa      1441
Glu Val Ser Phe Glu Leu Leu Val Lys Arg Gln Ile Lys Arg Leu Glu
        465                 470                 475

gag ccc agc ctc cgc tgt gtg gaa ctg gtt cat gag gaa atg caa agg      1489
Glu Pro Ser Leu Arg Cys Val Glu Leu Val His Glu Glu Met Gln Arg
    480                 485                 490

atc att cag cac tgt agc aat tac agt aca cag gaa ttg tta cga ttt      1537
Ile Ile Gln His Cys Ser Asn Tyr Ser Thr Gln Glu Leu Leu Arg Phe
495                 500                 505                 510

cct aaa ctt cat gat gcc ata gtt gaa gtg gtg act tgt ctt ctt cgt      1585
Pro Lys Leu His Asp Ala Ile Val Glu Val Val Thr Cys Leu Leu Arg
                515                 520                 525

aaa agg ttg cct gtt aca aat gaa atg gtc cat aac tta gtg gca att      1633
Lys Arg Leu Pro Val Thr Asn Glu Met Val His Asn Leu Val Ala Ile
            530                 535                 540

gaa ctg gct tat atc aac aca aaa cat cca gac ttt gct gat gct tgt      1681
Glu Leu Ala Tyr Ile Asn Thr Lys His Pro Asp Phe Ala Asp Ala Cys
        545                 550                 555

ggg cta atg aac aat aat ata gag gaa caa agg aga aac agg cta gcc      1729
Gly Leu Met Asn Asn Asn Ile Glu Glu Gln Arg Arg Asn Arg Leu Ala
    560                 565                 570

aga gaa tta cct tca gct gta tca cga gac aag gtt gca tct gga ggt      1777
Arg Glu Leu Pro Ser Ala Val Ser Arg Asp Lys Val Ala Ser Gly Gly
575                 580                 585                 590

ggt ggg gtt gga gat ggt gtt caa gaa cca acc aca ggc aac tgg aga      1825
Gly Gly Val Gly Asp Gly Val Gln Glu Pro Thr Thr Gly Asn Trp Arg
                595                 600                 605

gga atg ctg aaa act tca aaa gct gaa gag tta tta gca gaa gaa aaa      1873
Gly Met Leu Lys Thr Ser Lys Ala Glu Glu Leu Leu Ala Glu Glu Lys
            610                 615                 620

tca aaa ccc att cca att atg cca gcc agt cca caa aaa ggt cat gcc      1921
Ser Lys Pro Ile Pro Ile Met Pro Ala Ser Pro Gln Lys Gly His Ala
        625                 630                 635

gtg aac ctg cta gat gtg cca gtt cct gtt gca cga aaa cta tct gct      1969
Val Asn Leu Leu Asp Val Pro Val Pro Val Ala Arg Lys Leu Ser Ala
    640                 645                 650

cgg gaa cag cga gat tgt gag gtt att gaa cga ctc att aaa tca tat      2017
Arg Glu Gln Arg Asp Cys Glu Val Ile Glu Arg Leu Ile Lys Ser Tyr
655                 660                 665                 670

ttt ctc att gtc aga aag aat att caa gac agt gtg cca aag gca gta      2065
Phe Leu Ile Val Arg Lys Asn Ile Gln Asp Ser Val Pro Lys Ala Val
                675                 680                 685

atg cat ttt ttg gtt aat cat gtg aaa gac act ctt cag agt gag cta      2113
Met His Phe Leu Val Asn His Val Lys Asp Thr Leu Gln Ser Glu Leu
            690                 695                 700

gta ggc cag ctg tat aaa tca tcc tta ttg gat gat ctt ctg aca gaa      2161
Val Gly Gln Leu Tyr Lys Ser Ser Leu Leu Asp Asp Leu Leu Thr Glu
        705                 710                 715

tct gag gac atg gca cag cgc agg aaa gaa gca gct gat atg cta aag      2209
Ser Glu Asp Met Ala Gln Arg Arg Lys Glu Ala Ala Asp Met Leu Lys
    720                 725                 730

gca tta caa gga gcc agt caa att att gct gaa atc cgg gag act cat      2257
Ala Leu Gln Gly Ala Ser Gln Ile Ile Ala Glu Ile Arg Glu Thr His
```

-continued

```
735                 740                 745                 750

ctt tgg tga agagaactat gtaatactga gactttgttg actcaaaact             2306
Leu Trp

tgctagttac tgcctacctg agtagaatct tatttatgaa ctcctgtgta ttgcaatggt   2366

atgaatctgc tcatgtggag actggctata aactgaaaag tgtattctaa attgcagaac   2426

acatcacaca tttaatccaa ataataaatg gctgtttcaa aaaaaaaaaa aaaaaaaaaa   2486

aaaaaaaaaa aaaaaaaaaa aaaaaaaaaa aaaaaaaaaa aaaaaaaaaa aaa          2539


<210> SEQ ID NO 22
<211> LENGTH: 752
<212> TYPE: PRT
<213> ORGANISM: Homo sapiens

<400> SEQUENCE: 22

Met Ala Cys Arg Glu Gly Ala Gly Ser Arg Arg Ala Arg Ser Asn Gly
1               5                   10                  15

Cys Arg Leu Pro Arg Arg Gly Arg Arg Arg Gly Gly Arg Arg Arg Thr
            20                  25                  30

Val Gly Pro Gly Pro Ile His Cys Arg Gly Arg Arg Ala Leu Gly Pro
        35                  40                  45

Arg Val Phe Arg Val Met Glu Ala Leu Ile Pro Val Ile Asn Lys Leu
    50                  55                  60

Gln Asp Val Phe Asn Thr Val Gly Ala Asp Ile Ile Gln Leu Pro Gln
65                  70                  75                  80

Ile Val Val Val Gly Thr Gln Ser Ser Gly Lys Ser Ser Val Leu Glu
                85                  90                  95

Ser Leu Val Gly Arg Asp Leu Leu Pro Arg Gly Thr Gly Ile Val Thr
            100                 105                 110

Arg Arg Pro Leu Ile Leu Gln Leu Val His Val Thr Gln Glu Asp Lys
        115                 120                 125

Arg Lys Thr Thr Gly Glu Glu Asn Gly Val Glu Ala Glu Glu Trp Gly
    130                 135                 140

Lys Phe Leu His Thr Lys Asn Lys Leu Tyr Thr Asp Phe Asp Glu Ile
145                 150                 155                 160

Arg Gln Glu Ile Glu Asn Glu Thr Glu Arg Ile Ser Gly Asn Asn Lys
                165                 170                 175

Gly Val Ser Pro Glu Pro Ile His Leu Lys Ile Phe Ser Pro Asn Val
            180                 185                 190

Val Asn Leu Thr Leu Val Asp Leu Pro Gly Met Thr Lys Val Pro Val
        195                 200                 205

Gly Asp Gln Pro Lys Asp Ile Glu Leu Gln Ile Arg Glu Leu Ile Leu
    210                 215                 220

Arg Phe Ile Ser Asn Pro Asn Ser Ile Ile Leu Ala Val Thr Ala Ala
225                 230                 235                 240

Asn Thr Asp Met Ala Thr Ser Glu Ala Leu Lys Ile Ser Arg Glu Val
                245                 250                 255

Asp Pro Asp Gly Cys Arg Thr Leu Ala Val Ile Thr Lys Leu Asp Leu
            260                 265                 270

Met Asp Ala Gly Thr Asp Ala Met Asp Val Leu Met Gly Arg Val Ile
        275                 280                 285

Pro Val Lys Leu Gly Ile Ile Gly Val Val Asn Arg Ser Gln Leu Asp
    290                 295                 300

Ile Asn Asn Lys Lys Ser Val Thr Asp Ser Ile Arg Asp Glu Tyr Ala
```

-continued

```
305                 310                 315                 320

Phe Leu Gln Lys Lys Tyr Pro Ser Leu Ala Asn Arg Asn Gly Thr Lys
                325                 330                 335

Tyr Leu Ala Arg Thr Leu Asn Arg Leu Leu Met His His Ile Arg Asp
            340                 345                 350

Cys Leu Pro Glu Leu Lys Thr Arg Ile Asn Val Leu Ala Ala Gln Tyr
        355                 360                 365

Gln Ser Leu Leu Asn Ser Tyr Gly Glu Pro Val Asp Asp Lys Ser Ala
    370                 375                 380

Thr Leu Leu Gln Leu Ile Thr Lys Phe Ala Thr Glu Tyr Cys Asn Thr
385                 390                 395                 400

Ile Glu Gly Thr Ala Lys Tyr Ile Glu Thr Ser Glu Leu Cys Gly Gly
                405                 410                 415

Ala Arg Ile Cys Tyr Ile Phe His Glu Thr Phe Gly Arg Thr Leu Glu
            420                 425                 430

Ser Val Asp Pro Leu Gly Gly Leu Asn Thr Ile Asp Ile Leu Thr Ala
        435                 440                 445

Ile Arg Asn Ala Thr Gly Pro Arg Pro Ala Leu Phe Val Pro Glu Val
    450                 455                 460

Ser Phe Glu Leu Leu Val Lys Arg Gln Ile Lys Arg Leu Glu Glu Pro
465                 470                 475                 480

Ser Leu Arg Cys Val Glu Leu Val His Glu Glu Met Gln Arg Ile Ile
                485                 490                 495

Gln His Cys Ser Asn Tyr Ser Thr Gln Glu Leu Leu Arg Phe Pro Lys
            500                 505                 510

Leu His Asp Ala Ile Val Glu Val Val Thr Cys Leu Leu Arg Lys Arg
        515                 520                 525

Leu Pro Val Thr Asn Glu Met Val His Asn Leu Val Ala Ile Glu Leu
    530                 535                 540

Ala Tyr Ile Asn Thr Lys His Pro Asp Phe Ala Asp Ala Cys Gly Leu
545                 550                 555                 560

Met Asn Asn Asn Ile Glu Glu Gln Arg Arg Asn Arg Leu Ala Arg Glu
                565                 570                 575

Leu Pro Ser Ala Val Ser Arg Asp Lys Val Ala Ser Gly Gly Gly Gly
            580                 585                 590

Val Gly Asp Gly Val Gln Glu Pro Thr Thr Gly Asn Trp Arg Gly Met
        595                 600                 605

Leu Lys Thr Ser Lys Ala Glu Glu Leu Leu Ala Glu Glu Lys Ser Lys
    610                 615                 620

Pro Ile Pro Ile Met Pro Ala Ser Pro Gln Lys Gly His Ala Val Asn
625                 630                 635                 640

Leu Leu Asp Val Pro Val Pro Val Ala Arg Lys Leu Ser Ala Arg Glu
                645                 650                 655

Gln Arg Asp Cys Glu Val Ile Glu Arg Leu Ile Lys Ser Tyr Phe Leu
            660                 665                 670

Ile Val Arg Lys Asn Ile Gln Asp Ser Val Pro Lys Ala Val Met His
        675                 680                 685

Phe Leu Val Asn His Val Lys Asp Thr Leu Gln Ser Glu Leu Val Gly
    690                 695                 700

Gln Leu Tyr Lys Ser Ser Leu Leu Asp Asp Leu Leu Thr Glu Ser Glu
705                 710                 715                 720

Asp Met Ala Gln Arg Arg Lys Glu Ala Ala Asp Met Leu Lys Ala Leu
                725                 730                 735
```

-continued

```
Gln Gly Ala Ser Gln Ile Ile Ala Glu Ile Arg Glu Thr His Leu Trp
            740                 745                 750


<210> SEQ ID NO 23
<211> LENGTH: 6289
<212> TYPE: DNA
<213> ORGANISM: Homo sapiens
<220> FEATURE:
<221> NAME/KEY: CDS
<222> LOCATION: (1177)..(5931)

<400> SEQUENCE: 23

atgcctcagt ttttaaaaaa ggatccttac acttcatgtc tcctagccat cagaagagga     60

atgagacagc aaaagttcaa atggcctgtt tcaagtttct gatataaaac gatgacattt    120

tcaggaaaat cctgcatttc cagagagaga ctggctggtt aaatttctga aagaggacac    180

cagctaaaag aaggtattgc atctcacccg agcagactgt gtctgtggaa agtgtaagcc    240

ccttgccaga agagcagctt cccagcaaag gcagagggtg aaaacagcaa aggtcttaag    300

acactgggga cctagagtca aaagggacct cctccaggga aaacgctgtg tgagaaatgg    360

cctcattcgg tgactgtgag tgacacagca gaaagttggg tcattccggc tgctttttttg    420

agaagtccct gaagagatca ataacagcaa gagggaacct ggcaaggaag ctattcctat    480

aatccaggaa agagatgagg aaggcttgga ccaggtggta gtggtgtcag gtagtcaaat    540

gctgggtata ttttgaagat acaccccata ggatttgctc cacattgaat gtggaatgct    600

ggaagagaga taaagtgtac ctgtcacata ctttttgagt tttatttatt ttcttagaag    660

taagtacaca aagagatgct acctaggaga agggtattct tttcactatt ctttcaaatt    720

ttctgtatgt tcgaacattt tcatagtaga aagttggggg gaaaatctgt ttcataaaca    780

tttcctcagc agcagtccag tctattgcat tttaattggt tgtgatatca ttgttttatg    840

caatacgttc tcaacaagta tatcctccgg caaactgaac aaggaccaag tctgttctgc    900

ctacagctct gcttcctcat agctgctttc cagaacgtga ctcttgcaaa ttatcaagaa    960

aggggaacta atctaaggga tccagatcaa acagcctcat gaagacttat tttatgtttc   1020

taatataaag atagaagttt tcagaaaagc cctgctacac agaggatcag agcaggggtg   1080

ggcctgctgg gctgcagctg ggattctgag catcctttcc cggaggcacg gaaagtgagt   1140

gagtgagccc agtgaggaag aagttgaagc tttgat atg agt aaa caa gta tct     1194
                                        Met Ser Lys Gln Val Ser
                                        1               5

cta cct gaa atg att aaa gac tgg acc aaa gag cat gtg aaa aaa tgg     1242
Leu Pro Glu Met Ile Lys Asp Trp Thr Lys Glu His Val Lys Lys Trp
            10                  15                  20

gta aat gaa gac ctt aag att aat gag caa tac ggg caa att ctg ctc     1290
Val Asn Glu Asp Leu Lys Ile Asn Glu Gln Tyr Gly Gln Ile Leu Leu
        25                  30                  35

agt gaa gaa gta aca gga tta gtc ctg cag gaa tta act gag aag gac     1338
Ser Glu Glu Val Thr Gly Leu Val Leu Gln Glu Leu Thr Glu Lys Asp
    40                  45                  50

ctt gta gaa atg ggg cta cca tgg ggt cca gca ctt ttg ata aaa cgt     1386
Leu Val Glu Met Gly Leu Pro Trp Gly Pro Ala Leu Leu Ile Lys Arg
55                  60                  65                  70

tca tac aac aaa ttg aat agt aag tcc cct gaa agt gac aat cat gat     1434
Ser Tyr Asn Lys Leu Asn Ser Lys Ser Pro Glu Ser Asp Asn His Asp
                75                  80                  85

ccg gga caa tta gat aat tca aaa ccg tcc aaa aca gaa cac caa aaa     1482
Pro Gly Gln Leu Asp Asn Ser Lys Pro Ser Lys Thr Glu His Gln Lys
```

-continued

```
            90                  95                  100

aat cca aaa cac acc aaa aag gaa gaa gaa aat tca atg tca tct aat      1530
Asn Pro Lys His Thr Lys Lys Glu Glu Glu Asn Ser Met Ser Ser Asn
        105                 110                 115

att gat tat gat ccc aga gag atc aga gat atc aaa caa gaa gaa tca      1578
Ile Asp Tyr Asp Pro Arg Glu Ile Arg Asp Ile Lys Gln Glu Glu Ser
    120                 125                 130

att ctt atg aaa gaa aat gtg tta gat gaa gta gca aat gct aaa cac      1626
Ile Leu Met Lys Glu Asn Val Leu Asp Glu Val Ala Asn Ala Lys His
135                 140                 145                 150

aag aaa aag ggt aag cta aaa cct gaa caa ttg act tgt atg cca tat      1674
Lys Lys Lys Gly Lys Leu Lys Pro Glu Gln Leu Thr Cys Met Pro Tyr
                155                 160                 165

cct ttt gat cag ttc cat gac agc cat cgc tac ata gaa cat tat act      1722
Pro Phe Asp Gln Phe His Asp Ser His Arg Tyr Ile Glu His Tyr Thr
            170                 175                 180

cta caa cct gaa aca gga gca ctc aat ctc att gat cca ata cat gag      1770
Leu Gln Pro Glu Thr Gly Ala Leu Asn Leu Ile Asp Pro Ile His Glu
        185                 190                 195

ttc aaa gct ctc aca aac aca gaa aca gcc acg gaa gtg gac att aag      1818
Phe Lys Ala Leu Thr Asn Thr Glu Thr Ala Thr Glu Val Asp Ile Lys
    200                 205                 210

atg aaa ttc agc aat gaa gtc ttc cga ttt gca tca gct tgt atg aat      1866
Met Lys Phe Ser Asn Glu Val Phe Arg Phe Ala Ser Ala Cys Met Asn
215                 220                 225                 230

tca cgc acc aat ggc acc atc cat ttt gga gtc aag gac aaa ccc cat      1914
Ser Arg Thr Asn Gly Thr Ile His Phe Gly Val Lys Asp Lys Pro His
                235                 240                 245

gga gaa att gtt ggt gtg aaa atc acc agt aag gct gcc ttc att gac      1962
Gly Glu Ile Val Gly Val Lys Ile Thr Ser Lys Ala Ala Phe Ile Asp
            250                 255                 260

cac ttc aat gta atg atc aaa aag tat ttt gaa gaa agt gag atc aat      2010
His Phe Asn Val Met Ile Lys Lys Tyr Phe Glu Glu Ser Glu Ile Asn
        265                 270                 275

gaa gcc aag aag tgt att cgg gag cca agg ttt gtg gaa gtc ctt ctg      2058
Glu Ala Lys Lys Cys Ile Arg Glu Pro Arg Phe Val Glu Val Leu Leu
    280                 285                 290

cag aac aat aca cca tct gac aga ttt gtc att gaa gtt gat act att      2106
Gln Asn Asn Thr Pro Ser Asp Arg Phe Val Ile Glu Val Asp Thr Ile
295                 300                 305                 310

cca aaa cac tct ata tgt aat gat aag tat ttc tac att cag atg caa      2154
Pro Lys His Ser Ile Cys Asn Asp Lys Tyr Phe Tyr Ile Gln Met Gln
                315                 320                 325

att tgt aaa gat aaa ata tgg aaa caa aac caa aat ctt tca ctg ttt      2202
Ile Cys Lys Asp Lys Ile Trp Lys Gln Asn Gln Asn Leu Ser Leu Phe
            330                 335                 340

gta aga gaa ggg gct agc tct agg gat atc ctg gcc aat tcc aag caa      2250
Val Arg Glu Gly Ala Ser Ser Arg Asp Ile Leu Ala Asn Ser Lys Gln
        345                 350                 355

cgg gat gta gat ttc aag gca ttt tta caa aat tta aag tca ctg gta      2298
Arg Asp Val Asp Phe Lys Ala Phe Leu Gln Asn Leu Lys Ser Leu Val
    360                 365                 370

gca tct aga aaa gag gct gaa gaa gag tat gga atg aag gca atg aag      2346
Ala Ser Arg Lys Glu Ala Glu Glu Glu Tyr Gly Met Lys Ala Met Lys
375                 380                 385                 390

aag gag agt gaa gga cta aag ctg gtt aaa ctt ctc ata gga aac cga      2394
Lys Glu Ser Glu Gly Leu Lys Leu Val Lys Leu Leu Ile Gly Asn Arg
                395                 400                 405

gac tca ctg gat aat tca tac tat gac tgg tac att ctt gta aca aat      2442
```

-continued

```
Asp Ser Leu Asp Asn Ser Tyr Tyr Asp Trp Tyr Ile Leu Val Thr Asn
            410                 415                 420

aaa tgc cat cca aac caa ata aag cac tta gat ttt tta aaa gaa att      2490
Lys Cys His Pro Asn Gln Ile Lys His Leu Asp Phe Leu Lys Glu Ile
        425                 430                 435

aaa tgg ttt gct gtg ttg gag ttt gat cct gaa tct atg atc aat gga      2538
Lys Trp Phe Ala Val Leu Glu Phe Asp Pro Glu Ser Met Ile Asn Gly
    440                 445                 450

gtg gtc aaa gct tac aaa gaa agt cgg gtg gca aac ctt cac ttt cca      2586
Val Val Lys Ala Tyr Lys Glu Ser Arg Val Ala Asn Leu His Phe Pro
455                 460                 465                 470

aat caa tat gaa gac aag aca act aac atg tgg gag aag att tct act      2634
Asn Gln Tyr Glu Asp Lys Thr Thr Asn Met Trp Glu Lys Ile Ser Thr
            475                 480                 485

ctt aat ctt tac caa cag ccc agc tgg att ttc tgc aac ggc aga tca      2682
Leu Asn Leu Tyr Gln Gln Pro Ser Trp Ile Phe Cys Asn Gly Arg Ser
            490                 495                 500

gac ctg aaa agc gag aca tat aaa cct cta gaa cca cat tta tgg cag      2730
Asp Leu Lys Ser Glu Thr Tyr Lys Pro Leu Glu Pro His Leu Trp Gln
        505                 510                 515

aga gaa aga gct tca gaa gtc agg aaa cta att tta ttt ctc aca gat      2778
Arg Glu Arg Ala Ser Glu Val Arg Lys Leu Ile Leu Phe Leu Thr Asp
    520                 525                 530

gaa aat ata atg aca aga gga aaa ttt ttg gta gtg ttt cta tta ctc      2826
Glu Asn Ile Met Thr Arg Gly Lys Phe Leu Val Val Phe Leu Leu Leu
535                 540                 545                 550

tct tca gtg gaa agc cca gga gat cca ctc att gaa act ttc tgg gct      2874
Ser Ser Val Glu Ser Pro Gly Asp Pro Leu Ile Glu Thr Phe Trp Ala
            555                 560                 565

ttc tat caa gct ctc aaa gga atg gaa aat atg ttg tgt atc tct gta      2922
Phe Tyr Gln Ala Leu Lys Gly Met Glu Asn Met Leu Cys Ile Ser Val
            570                 575                 580

aac tca cat att tat caa cga tgg aaa gat cta cta caa aca aga acg      2970
Asn Ser His Ile Tyr Gln Arg Trp Lys Asp Leu Leu Gln Thr Arg Thr
        585                 590                 595

aag atg gaa gat gaa cta aca aac cac agt att tcc act tta aat ata      3018
Lys Met Glu Asp Glu Leu Thr Asn His Ser Ile Ser Thr Leu Asn Ile
    600                 605                 610

gaa ctg gta aac agc act atc ctt aaa cta aaa tcg gtg act cgg tca      3066
Glu Leu Val Asn Ser Thr Ile Leu Lys Leu Lys Ser Val Thr Arg Ser
615                 620                 625                 630

tca aga agg ttt ttg ccc gcc cgt gga tct tct tca gtt atc cta gag      3114
Ser Arg Arg Phe Leu Pro Ala Arg Gly Ser Ser Ser Val Ile Leu Glu
            635                 640                 645

aaa aag aaa gag gat gtc ttg act gca ctg gaa atc ctc tgt gaa aat      3162
Lys Lys Lys Glu Asp Val Leu Thr Ala Leu Glu Ile Leu Cys Glu Asn
            650                 655                 660

gag tgt aca gag aca gac atc gag aaa gac aaa tct aaa ttc ctg gag      3210
Glu Cys Thr Glu Thr Asp Ile Glu Lys Asp Lys Ser Lys Phe Leu Glu
        665                 670                 675

ttt aag aaa tca aaa gaa gaa cac ttt tat cga ggt ggc aaa gta tcc      3258
Phe Lys Lys Ser Lys Glu Glu His Phe Tyr Arg Gly Gly Lys Val Ser
    680                 685                 690

tgg tgg aac ttc tat ttt tct tct gaa aac tat tct tca gat ttt gtt      3306
Trp Trp Asn Phe Tyr Phe Ser Ser Glu Asn Tyr Ser Ser Asp Phe Val
695                 700                 705                 710

aaa agg gac agt tat gaa aag ctt aaa gat tta ata cac tgc tgg gca      3354
Lys Arg Asp Ser Tyr Glu Lys Leu Lys Asp Leu Ile His Cys Trp Ala
            715                 720                 725
```

-continued

```
gag tct cct aaa cca ata ttt gca aaa atc atc aat ctt tat cat cat     3402
Glu Ser Pro Lys Pro Ile Phe Ala Lys Ile Ile Asn Leu Tyr His His
            730                 735                 740

cca ggc tgt gga ggt acc aca ctg gct atg cat gtt ctc tgg gac tta     3450
Pro Gly Cys Gly Gly Thr Thr Leu Ala Met His Val Leu Trp Asp Leu
        745                 750                 755

aag aaa aac ttc aga tgt gct gtg tta aaa aac aag aca act gat ttt     3498
Lys Lys Asn Phe Arg Cys Ala Val Leu Lys Asn Lys Thr Thr Asp Phe
    760                 765                 770

gca gaa att gca gag caa gtg atc aat ctg gtc acc tat agg gca aag     3546
Ala Glu Ile Ala Glu Gln Val Ile Asn Leu Val Thr Tyr Arg Ala Lys
775                 780                 785                 790

agc cat cag gat tac att cct gtg ctt ctc ctt gtg gat gat ttt gaa     3594
Ser His Gln Asp Tyr Ile Pro Val Leu Leu Leu Val Asp Asp Phe Glu
                795                 800                 805

gaa caa gaa aat gtc tac ttt cta caa aat gcc atc cat tcc gtt tta     3642
Glu Gln Glu Asn Val Tyr Phe Leu Gln Asn Ala Ile His Ser Val Leu
            810                 815                 820

gca gaa aag gat ttg cga tat gaa aaa aca ttg gta att atc tta aac     3690
Ala Glu Lys Asp Leu Arg Tyr Glu Lys Thr Leu Val Ile Ile Leu Asn
        825                 830                 835

tgc atg aga tcc cgg aat cca gat gaa agt gca aaa ttg gca gac agt     3738
Cys Met Arg Ser Arg Asn Pro Asp Glu Ser Ala Lys Leu Ala Asp Ser
    840                 845                 850

att gca cta aat tac caa ctt tct tcc aag gaa caa aga gcc ttt ggt     3786
Ile Ala Leu Asn Tyr Gln Leu Ser Ser Lys Glu Gln Arg Ala Phe Gly
855                 860                 865                 870

gcc aaa ctg aag gaa att gaa aag cag cac aag aac tgt gaa aac ttt     3834
Ala Lys Leu Lys Glu Ile Glu Lys Gln His Lys Asn Cys Glu Asn Phe
                875                 880                 885

tat tcc ttc atg atc atg aaa agc aat ttt gat gaa aca tat ata gaa     3882
Tyr Ser Phe Met Ile Met Lys Ser Asn Phe Asp Glu Thr Tyr Ile Glu
            890                 895                 900

aat gta gtc agg aat atc cta aaa gga cag gat gtt gac agc aag gaa     3930
Asn Val Val Arg Asn Ile Leu Lys Gly Gln Asp Val Asp Ser Lys Glu
        905                 910                 915

gca caa ctc att tcc ttc ctg gct tta ctc agc tct tat gtt act gac     3978
Ala Gln Leu Ile Ser Phe Leu Ala Leu Leu Ser Ser Tyr Val Thr Asp
    920                 925                 930

tct aca att tca gtt tca cag tgt gaa ata ttt ttg gga atc ata tac     4026
Ser Thr Ile Ser Val Ser Gln Cys Glu Ile Phe Leu Gly Ile Ile Tyr
935                 940                 945                 950

act agt aca ccc tgg gaa cct gaa agc tta gaa gac aag atg gga act     4074
Thr Ser Thr Pro Trp Glu Pro Glu Ser Leu Glu Asp Lys Met Gly Thr
                955                 960                 965

tat tct aca ctt cta ata aaa aca gaa gtt gca gaa tat ggg aga tac     4122
Tyr Ser Thr Leu Leu Ile Lys Thr Glu Val Ala Glu Tyr Gly Arg Tyr
            970                 975                 980

aca ggt gtg cgt atc att cac cct ctg att gcc ctg tac tgt cta aaa     4170
Thr Gly Val Arg Ile Ile His Pro Leu Ile Ala Leu Tyr Cys Leu Lys
        985                 990                 995

gaa ctg  gaa aga agc tat cac  ttg gat aaa tgt caa  att gca ttg      4215
Glu Leu  Glu Arg Ser Tyr His  Leu Asp Lys Cys Gln  Ile Ala Leu
    1000                 1005                 1010

aat ata  tta gaa gag aat tta  ttc tat gat tct gga  ata gga aga      4260
Asn Ile  Leu Glu Glu Asn Leu  Phe Tyr Asp Ser Gly  Ile Gly Arg
    1015                 1020                 1025

gac aaa  ttt caa cat gat gtt  caa act ctt ctg ctt  aca aga cag      4305
Asp Lys  Phe Gln His Asp Val  Gln Thr Leu Leu Leu  Thr Arg Gln
    1030                 1035                 1040
```

-continued

```
cgc aag  gtg tat gga gat gaa  aca gac act ctg ttt  tcc cca tta      4350
Arg Lys  Val Tyr Gly Asp Glu  Thr Asp Thr Leu Phe  Ser Pro Leu
    1045                1050                1055

atg gaa  gct tta cag aat aaa  gac att gaa aag gtc  ttg agt gca      4395
Met Glu  Ala Leu Gln Asn Lys  Asp Ile Glu Lys Val  Leu Ser Ala
    1060                1065                1070

gga agt  aga cga ttc cca caa  aat gca ttc att tgt  caa gcc tta      4440
Gly Ser  Arg Arg Phe Pro Gln  Asn Ala Phe Ile Cys  Gln Ala Leu
    1075                1080                1085

gca aga  cat ttc tac att aaa  gag aag gac ttt aac  aca gct ctg      4485
Ala Arg  His Phe Tyr Ile Lys  Glu Lys Asp Phe Asn  Thr Ala Leu
    1090                1095                1100

gac tgg  gca cgt cag gcc aaa  atg aaa gca cct aaa  aat tcc tat      4530
Asp Trp  Ala Arg Gln Ala Lys  Met Lys Ala Pro Lys  Asn Ser Tyr
    1105                1110                1115

att tca  gat aca cta ggt caa  gtc tac aaa agt gaa  atc aaa tgg      4575
Ile Ser  Asp Thr Leu Gly Gln  Val Tyr Lys Ser Glu  Ile Lys Trp
    1120                1125                1130

tgg ttg  gat ggg aac aaa aac  tgt agg agc att act  gtt aat gac      4620
Trp Leu  Asp Gly Asn Lys Asn  Cys Arg Ser Ile Thr  Val Asn Asp
    1135                1140                1145

cta aca  cat ctc cta gaa gct  gcg gaa aaa gcc tca  aga gct ttc      4665
Leu Thr  His Leu Leu Glu Ala  Ala Glu Lys Ala Ser  Arg Ala Phe
    1150                1155                1160

aaa gaa  tcc caa agg caa act  gat agt aaa aac tat  gaa acc gag      4710
Lys Glu  Ser Gln Arg Gln Thr  Asp Ser Lys Asn Tyr  Glu Thr Glu
    1165                1170                1175

aac tgg  tca cca cag aag tcc  cag aga cga tat gac  atg tat aac      4755
Asn Trp  Ser Pro Gln Lys Ser  Gln Arg Arg Tyr Asp  Met Tyr Asn
    1180                1185                1190

aca gct  tgt ttc ttg ggt gaa  ata gaa gtt ggt ctt  tac act atc      4800
Thr Ala  Cys Phe Leu Gly Glu  Ile Glu Val Gly Leu  Tyr Thr Ile
    1195                1200                1205

cag att  ctt cag ctc act ccc  ttt ttc cac aaa gaa  aat gaa tta      4845
Gln Ile  Leu Gln Leu Thr Pro  Phe Phe His Lys Glu  Asn Glu Leu
    1210                1215                1220

tcc aaa  aaa cat atg gtg caa  ttt tta tca gga aag  tgg acc att      4890
Ser Lys  Lys His Met Val Gln  Phe Leu Ser Gly Lys  Trp Thr Ile
    1225                1230                1235

cct cct  gat ccc aga aat gaa  tgt tat ttg gct ctt  agc aag ttc      4935
Pro Pro  Asp Pro Arg Asn Glu  Cys Tyr Leu Ala Leu  Ser Lys Phe
    1240                1245                1250

aca tcc  cac cta aaa aat tta  caa tca gat ctg aaa  agg tgc ttt      4980
Thr Ser  His Leu Lys Asn Leu  Gln Ser Asp Leu Lys  Arg Cys Phe
    1255                1260                1265

gac ttt  ttt att gat tat atg  gtt ctt ctg aaa atg  agg tat acc      5025
Asp Phe  Phe Ile Asp Tyr Met  Val Leu Leu Lys Met  Arg Tyr Thr
    1270                1275                1280

caa aaa  gaa att gca gaa atc  atg tta agc aag aaa  gtc agt cgt      5070
Gln Lys  Glu Ile Ala Glu Ile  Met Leu Ser Lys Lys  Val Ser Arg
    1285                1290                1295

tgt ttc  agg aaa tac aca gaa  ctt ttc tgt cat ttg  gat cca tgt      5115
Cys Phe  Arg Lys Tyr Thr Glu  Leu Phe Cys His Leu  Asp Pro Cys
    1300                1305                1310

cta tta  caa agt aaa gag agt  caa tta ctc cag gag  gag aat tgc      5160
Leu Leu  Gln Ser Lys Glu Ser  Gln Leu Leu Gln Glu  Glu Asn Cys
    1315                1320                1325

agg aaa  aag cta gaa gct ctg  aga gca gat agg ttt  gct gga ctc      5205
Arg Lys  Lys Leu Glu Ala Leu  Arg Ala Asp Arg Phe  Ala Gly Leu
```

-continued

```
    1330                1335                1340

ttg gaa  tat ctt aat cca aac  tac aaa gat gct acc  acc atg gaa      5250
Leu Glu  Tyr Leu Asn Pro Asn  Tyr Lys Asp Ala Thr  Thr Met Glu
    1345                1350                1355

agt ata  gtg aat gaa tat gcc  ttc cta ctg cag caa  aac tca aaa      5295
Ser Ile  Val Asn Glu Tyr Ala  Phe Leu Leu Gln Gln  Asn Ser Lys
    1360                1365                1370

aag ccc  atg aca aat gag aaa  caa aat tcc att ttg  gcc aac att      5340
Lys Pro  Met Thr Asn Glu Lys  Gln Asn Ser Ile Leu  Ala Asn Ile
    1375                1380                1385

att ctg  agt tgt cta aag ccc  aac tcc aag tta att  caa cca ctt      5385
Ile Leu  Ser Cys Leu Lys Pro  Asn Ser Lys Leu Ile  Gln Pro Leu
    1390                1395                1400

acc acg  cta aaa aaa caa ctc  cga gag gtc ttg caa  ttt gta gga      5430
Thr Thr  Leu Lys Lys Gln Leu  Arg Glu Val Leu Gln  Phe Val Gly
    1405                1410                1415

cta agt  cat caa tat cca ggt  cct tat ttc ttg gcc  tgc ctc ctg      5475
Leu Ser  His Gln Tyr Pro Gly  Pro Tyr Phe Leu Ala  Cys Leu Leu
    1420                1425                1430

ttc tgg  cca gaa aat caa gag  cta gat caa gat tcc  aaa cta ata      5520
Phe Trp  Pro Glu Asn Gln Glu  Leu Asp Gln Asp Ser  Lys Leu Ile
    1435                1440                1445

gaa aag  tat gtt tca tcc tta  aat aga tcc ttc agg  gga cag tac      5565
Glu Lys  Tyr Val Ser Ser Leu  Asn Arg Ser Phe Arg  Gly Gln Tyr
    1450                1455                1460

aag cgc  atg tgc agg tcc aag  cag gca agc aca ctt  ttc tat ctg      5610
Lys Arg  Met Cys Arg Ser Lys  Gln Ala Ser Thr Leu  Phe Tyr Leu
    1465                1470                1475

ggc aaa  agg aag ggt cta aac  agt att gtt cac aag  gcc aaa ata      5655
Gly Lys  Arg Lys Gly Leu Asn  Ser Ile Val His Lys  Ala Lys Ile
    1480                1485                1490

gag cag  tac ttt gat aaa gca  caa aat aca aat tcc  ctc tgg cac      5700
Glu Gln  Tyr Phe Asp Lys Ala  Gln Asn Thr Asn Ser  Leu Trp His
    1495                1500                1505

agt ggg  gat gtg tgg aaa aaa  aat gaa gtc aaa gac  ctc ctg cgt      5745
Ser Gly  Asp Val Trp Lys Lys  Asn Glu Val Lys Asp  Leu Leu Arg
    1510                1515                1520

cgt cta  act ggt cag gct gaa  ggc aag cta atc tct  gta gaa tat      5790
Arg Leu  Thr Gly Gln Ala Glu  Gly Lys Leu Ile Ser  Val Glu Tyr
    1525                1530                1535

gga aca  gag gaa aaa ata aaa  ata cca gta ata tct  gtt tat tca      5835
Gly Thr  Glu Glu Lys Ile Lys  Ile Pro Val Ile Ser  Val Tyr Ser
    1540                1545                1550

ggt cca  ctc aga agt ggt agg  aac ata gaa aga gtg  tct ttc tac      5880
Gly Pro  Leu Arg Ser Gly Arg  Asn Ile Glu Arg Val  Ser Phe Tyr
    1555                1560                1565

cta gga  ttt tcc att gaa ggc  cct ctg gca tat gat  ata gaa gta      5925
Leu Gly  Phe Ser Ile Glu Gly  Pro Leu Ala Tyr Asp  Ile Glu Val
    1570                1575                1580

att taa gacaatacat cacctgtagt tcaaatatgt ttatttatat ctttatgatt      5981
Ile

ttattctctc tctctattct catggcactt tcataacatt atggctaacc tctaattaca   6041

gattttgctt ttgcctccct gaatgaatta caagcctttt taagatatga aatatgccta   6101

cccgcagagc ttggcacaaa gtggagtcaa tcttttaatg ttttaaatat gcattttcag   6161

actcaaataa ttaagaagtt tcattgatat ccactggtca catcataact gtctataggg   6221

caataaaatc tgtgttaaac tcaaaaaaaa aaaaaaaaaa aaaaaaaaaa aaaaaaaaaa   6281
```

-continued aaaaaaaa 6289

<210> SEQ ID NO 24
<211> LENGTH: 1584
<212> TYPE: PRT
<213> ORGANISM: Homo sapiens

<400> SEQUENCE: 24

```
Met Ser Lys Gln Val Ser Leu Pro Glu Met Ile Lys Asp Trp Thr Lys
1               5                   10                  15

Glu His Val Lys Lys Trp Val Asn Glu Asp Leu Lys Ile Asn Glu Gln
            20                  25                  30

Tyr Gly Gln Ile Leu Leu Ser Glu Glu Val Thr Gly Leu Val Leu Gln
        35                  40                  45

Glu Leu Thr Glu Lys Asp Leu Val Glu Met Gly Leu Pro Trp Gly Pro
    50                  55                  60

Ala Leu Leu Ile Lys Arg Ser Tyr Asn Lys Leu Asn Ser Lys Ser Pro
65                  70                  75                  80

Glu Ser Asp Asn His Asp Pro Gly Gln Leu Asp Asn Ser Lys Pro Ser
                85                  90                  95

Lys Thr Glu His Gln Lys Asn Pro Lys His Thr Lys Lys Glu Glu Glu
            100                 105                 110

Asn Ser Met Ser Ser Asn Ile Asp Tyr Asp Pro Arg Glu Ile Arg Asp
        115                 120                 125

Ile Lys Gln Glu Glu Ser Ile Leu Met Lys Glu Asn Val Leu Asp Glu
    130                 135                 140

Val Ala Asn Ala Lys His Lys Lys Lys Gly Lys Leu Lys Pro Glu Gln
145                 150                 155                 160

Leu Thr Cys Met Pro Tyr Pro Phe Asp Gln Phe His Asp Ser His Arg
                165                 170                 175

Tyr Ile Glu His Tyr Thr Leu Gln Pro Glu Thr Gly Ala Leu Asn Leu
            180                 185                 190

Ile Asp Pro Ile His Glu Phe Lys Ala Leu Thr Asn Thr Glu Thr Ala
        195                 200                 205

Thr Glu Val Asp Ile Lys Met Lys Phe Ser Asn Glu Val Phe Arg Phe
    210                 215                 220

Ala Ser Ala Cys Met Asn Ser Arg Thr Asn Gly Thr Ile His Phe Gly
225                 230                 235                 240

Val Lys Asp Lys Pro His Gly Glu Ile Val Gly Val Lys Ile Thr Ser
                245                 250                 255

Lys Ala Ala Phe Ile Asp His Phe Asn Val Met Ile Lys Lys Tyr Phe
            260                 265                 270

Glu Glu Ser Glu Ile Asn Glu Ala Lys Lys Cys Ile Arg Glu Pro Arg
        275                 280                 285

Phe Val Glu Val Leu Leu Gln Asn Asn Thr Pro Ser Asp Arg Phe Val
    290                 295                 300

Ile Glu Val Asp Thr Ile Pro Lys His Ser Ile Cys Asn Asp Lys Tyr
305                 310                 315                 320

Phe Tyr Ile Gln Met Gln Ile Cys Lys Asp Lys Ile Trp Lys Gln Asn
                325                 330                 335

Gln Asn Leu Ser Leu Phe Val Arg Glu Gly Ala Ser Ser Arg Asp Ile
            340                 345                 350

Leu Ala Asn Ser Lys Gln Arg Asp Val Asp Phe Lys Ala Phe Leu Gln
        355                 360                 365
```

-continued

```
Asn Leu Lys Ser Leu Val Ala Ser Arg Lys Glu Ala Glu Glu Glu Tyr
    370                 375                 380

Gly Met Lys Ala Met Lys Lys Glu Ser Glu Gly Leu Lys Leu Val Lys
385                 390                 395                 400

Leu Leu Ile Gly Asn Arg Asp Ser Leu Asp Asn Ser Tyr Tyr Asp Trp
                405                 410                 415

Tyr Ile Leu Val Thr Asn Lys Cys His Pro Asn Gln Ile Lys His Leu
            420                 425                 430

Asp Phe Leu Lys Glu Ile Lys Trp Phe Ala Val Leu Glu Phe Asp Pro
        435                 440                 445

Glu Ser Met Ile Asn Gly Val Val Lys Ala Tyr Lys Glu Ser Arg Val
    450                 455                 460

Ala Asn Leu His Phe Pro Asn Gln Tyr Glu Asp Lys Thr Thr Asn Met
465                 470                 475                 480

Trp Glu Lys Ile Ser Thr Leu Asn Leu Tyr Gln Gln Pro Ser Trp Ile
                485                 490                 495

Phe Cys Asn Gly Arg Ser Asp Leu Lys Ser Glu Thr Tyr Lys Pro Leu
            500                 505                 510

Glu Pro His Leu Trp Gln Arg Glu Arg Ala Ser Glu Val Arg Lys Leu
        515                 520                 525

Ile Leu Phe Leu Thr Asp Glu Asn Ile Met Thr Arg Gly Lys Phe Leu
    530                 535                 540

Val Val Phe Leu Leu Leu Ser Ser Val Glu Ser Pro Gly Asp Pro Leu
545                 550                 555                 560

Ile Glu Thr Phe Trp Ala Phe Tyr Gln Ala Leu Lys Gly Met Glu Asn
                565                 570                 575

Met Leu Cys Ile Ser Val Asn Ser His Ile Tyr Gln Arg Trp Lys Asp
            580                 585                 590

Leu Leu Gln Thr Arg Thr Lys Met Glu Asp Glu Leu Thr Asn His Ser
        595                 600                 605

Ile Ser Thr Leu Asn Ile Glu Leu Val Asn Ser Thr Ile Leu Lys Leu
    610                 615                 620

Lys Ser Val Thr Arg Ser Ser Arg Arg Phe Leu Pro Ala Arg Gly Ser
625                 630                 635                 640

Ser Ser Val Ile Leu Glu Lys Lys Lys Glu Asp Val Leu Thr Ala Leu
                645                 650                 655

Glu Ile Leu Cys Glu Asn Glu Cys Thr Glu Thr Asp Ile Glu Lys Asp
            660                 665                 670

Lys Ser Lys Phe Leu Glu Phe Lys Lys Ser Lys Glu Glu His Phe Tyr
        675                 680                 685

Arg Gly Gly Lys Val Ser Trp Trp Asn Phe Tyr Phe Ser Ser Glu Asn
    690                 695                 700

Tyr Ser Ser Asp Phe Val Lys Arg Asp Ser Tyr Glu Lys Leu Lys Asp
705                 710                 715                 720

Leu Ile His Cys Trp Ala Glu Ser Pro Lys Pro Ile Phe Ala Lys Ile
                725                 730                 735

Ile Asn Leu Tyr His His Pro Gly Cys Gly Gly Thr Thr Leu Ala Met
            740                 745                 750

His Val Leu Trp Asp Leu Lys Lys Asn Phe Arg Cys Ala Val Leu Lys
        755                 760                 765

Asn Lys Thr Thr Asp Phe Ala Glu Ile Ala Glu Gln Val Ile Asn Leu
    770                 775                 780

Val Thr Tyr Arg Ala Lys Ser His Gln Asp Tyr Ile Pro Val Leu Leu
```

-continued

```
785                 790                 795                 800

Leu Val Asp Asp Phe Glu Glu Gln Glu Asn Val Tyr Phe Leu Gln Asn
                805                 810                 815

Ala Ile His Ser Val Leu Ala Glu Lys Asp Leu Arg Tyr Glu Lys Thr
            820                 825                 830

Leu Val Ile Ile Leu Asn Cys Met Arg Ser Arg Asn Pro Asp Glu Ser
        835                 840                 845

Ala Lys Leu Ala Asp Ser Ile Ala Leu Asn Tyr Gln Leu Ser Ser Lys
    850                 855                 860

Glu Gln Arg Ala Phe Gly Ala Lys Leu Lys Glu Ile Glu Lys Gln His
865                 870                 875                 880

Lys Asn Cys Glu Asn Phe Tyr Ser Phe Met Ile Met Lys Ser Asn Phe
                885                 890                 895

Asp Glu Thr Tyr Ile Glu Asn Val Val Arg Asn Ile Leu Lys Gly Gln
            900                 905                 910

Asp Val Asp Ser Lys Glu Ala Gln Leu Ile Ser Phe Leu Ala Leu Leu
        915                 920                 925

Ser Ser Tyr Val Thr Asp Ser Thr Ile Ser Val Ser Gln Cys Glu Ile
    930                 935                 940

Phe Leu Gly Ile Ile Tyr Thr Ser Thr Pro Trp Glu Pro Glu Ser Leu
945                 950                 955                 960

Glu Asp Lys Met Gly Thr Tyr Ser Thr Leu Leu Ile Lys Thr Glu Val
                965                 970                 975

Ala Glu Tyr Gly Arg Tyr Thr Gly Val Arg Ile Ile His Pro Leu Ile
            980                 985                 990

Ala Leu Tyr Cys Leu Lys Glu Leu  Glu Arg Ser Tyr His  Leu Asp Lys
        995                 1000                1005

Cys Gln  Ile Ala Leu Asn Ile  Leu Glu Glu Asn Leu  Phe Tyr Asp
    1010                1015                1020

Ser Gly  Ile Gly Arg Asp Lys  Phe Gln His Asp Val  Gln Thr Leu
    1025                1030                1035

Leu Leu  Thr Arg Gln Arg Lys  Val Tyr Gly Asp Glu  Thr Asp Thr
    1040                1045                1050

Leu Phe  Ser Pro Leu Met Glu  Ala Leu Gln Asn Lys  Asp Ile Glu
    1055                1060                1065

Lys Val  Leu Ser Ala Gly Ser  Arg Arg Phe Pro Gln  Asn Ala Phe
    1070                1075                1080

Ile Cys  Gln Ala Leu Ala Arg  His Phe Tyr Ile Lys  Glu Lys Asp
    1085                1090                1095

Phe Asn  Thr Ala Leu Asp Trp  Ala Arg Gln Ala Lys  Met Lys Ala
    1100                1105                1110

Pro Lys  Asn Ser Tyr Ile Ser  Asp Thr Leu Gly Gln  Val Tyr Lys
    1115                1120                1125

Ser Glu  Ile Lys Trp Trp Leu  Asp Gly Asn Lys Asn  Cys Arg Ser
    1130                1135                1140

Ile Thr  Val Asn Asp Leu Thr  His Leu Leu Glu Ala  Ala Glu Lys
    1145                1150                1155

Ala Ser  Arg Ala Phe Lys Glu  Ser Gln Arg Gln Thr  Asp Ser Lys
    1160                1165                1170

Asn Tyr  Glu Thr Glu Asn Trp  Ser Pro Gln Lys Ser  Gln Arg Arg
    1175                1180                1185

Tyr Asp  Met Tyr Asn Thr Ala  Cys Phe Leu Gly Glu  Ile Glu Val
    1190                1195                1200
```

-continued

```
Gly Leu  Tyr Thr Ile Gln Ile  Leu Gln Leu Thr Pro  Phe Phe His
    1205                 1210                 1215

Lys Glu  Asn Glu Leu Ser Lys  Lys His Met Val Gln  Phe Leu Ser
    1220                 1225                 1230

Gly Lys  Trp Thr Ile Pro Pro  Asp Pro Arg Asn Glu  Cys Tyr Leu
    1235                 1240                 1245

Ala Leu  Ser Lys Phe Thr Ser  His Leu Lys Asn Leu  Gln Ser Asp
    1250                 1255                 1260

Leu Lys  Arg Cys Phe Asp Phe  Phe Ile Asp Tyr Met  Val Leu Leu
    1265                 1270                 1275

Lys Met  Arg Tyr Thr Gln Lys  Glu Ile Ala Glu Ile  Met Leu Ser
    1280                 1285                 1290

Lys Lys  Val Ser Arg Cys Phe  Arg Lys Tyr Thr Glu  Leu Phe Cys
    1295                 1300                 1305

His Leu  Asp Pro Cys Leu Leu  Gln Ser Lys Glu Ser  Gln Leu Leu
    1310                 1315                 1320

Gln Glu  Glu Asn Cys Arg Lys  Lys Leu Glu Ala Leu  Arg Ala Asp
    1325                 1330                 1335

Arg Phe  Ala Gly Leu Leu Glu  Tyr Leu Asn Pro Asn  Tyr Lys Asp
    1340                 1345                 1350

Ala Thr  Thr Met Glu Ser Ile  Val Asn Glu Tyr Ala  Phe Leu Leu
    1355                 1360                 1365

Gln Gln  Asn Ser Lys Lys Pro  Met Thr Asn Glu Lys  Gln Asn Ser
    1370                 1375                 1380

Ile Leu  Ala Asn Ile Ile Leu  Ser Cys Leu Lys Pro  Asn Ser Lys
    1385                 1390                 1395

Leu Ile  Gln Pro Leu Thr Thr  Leu Lys Lys Gln Leu  Arg Glu Val
    1400                 1405                 1410

Leu Gln  Phe Val Gly Leu Ser  His Gln Tyr Pro Gly  Pro Tyr Phe
    1415                 1420                 1425

Leu Ala  Cys Leu Leu Phe Trp  Pro Glu Asn Gln Glu  Leu Asp Gln
    1430                 1435                 1440

Asp Ser  Lys Leu Ile Glu Lys  Tyr Val Ser Ser Leu  Asn Arg Ser
    1445                 1450                 1455

Phe Arg  Gly Gln Tyr Lys Arg  Met Cys Arg Ser Lys  Gln Ala Ser
    1460                 1465                 1470

Thr Leu  Phe Tyr Leu Gly Lys  Arg Lys Gly Leu Asn  Ser Ile Val
    1475                 1480                 1485

His Lys  Ala Lys Ile Glu Gln  Tyr Phe Asp Lys Ala  Gln Asn Thr
    1490                 1495                 1500

Asn Ser  Leu Trp His Ser Gly  Asp Val Trp Lys Lys  Asn Glu Val
    1505                 1510                 1515

Lys Asp  Leu Leu Arg Arg Leu  Thr Gly Gln Ala Glu  Gly Lys Leu
    1520                 1525                 1530

Ile Ser  Val Glu Tyr Gly Thr  Glu Glu Lys Ile Lys  Ile Pro Val
    1535                 1540                 1545

Ile Ser  Val Tyr Ser Gly Pro  Leu Arg Ser Gly Arg  Asn Ile Glu
    1550                 1555                 1560

Arg Val  Ser Phe Tyr Leu Gly  Phe Ser Ile Glu Gly  Pro Leu Ala
    1565                 1570                 1575

Tyr Asp  Ile Glu Val Ile
    1580
```

-continued

<210> SEQ ID NO 25
<211> LENGTH: 3345
<212> TYPE: DNA
<213> ORGANISM: Homo sapiens
<220> FEATURE:
<221> NAME/KEY: CDS
<222> LOCATION: (67)..(3108)

<400> SEQUENCE: 25

```
cttctgccag cagaagcagc agccgcagca cctgagccgc tactgccgct cactcaggac     60

aacgct atg gct gag cct ggg cac agc cac cat ctc tcc gcc aga gtc       108
       Met Ala Glu Pro Gly His Ser His His Leu Ser Ala Arg Val
       1               5                   10

agg gga aga act gag agg cgc ata ccc cgg ctg tgg cgg ctg ctg ctc       156
Arg Gly Arg Thr Glu Arg Arg Ile Pro Arg Leu Trp Arg Leu Leu Leu
15                  20                  25                  30

tgg gct ggg acc gcc ttc cag gtg acc cag gga acg gga ccg gag ctt       204
Trp Ala Gly Thr Ala Phe Gln Val Thr Gln Gly Thr Gly Pro Glu Leu
                35                  40                  45

cac gcc tgc aaa gag tct gag tac cac tat gag tac acg gcg tgt gac       252
His Ala Cys Lys Glu Ser Glu Tyr His Tyr Glu Tyr Thr Ala Cys Asp
            50                  55                  60

agc acg ggt tcc agg tgg agg gtc gcc gtg ccg cat acc ccg ggc ctg       300
Ser Thr Gly Ser Arg Trp Arg Val Ala Val Pro His Thr Pro Gly Leu
        65                  70                  75

tgc acc agc ctg cct gac ccc gtc aag ggc acc gag tgc tcc ttc tcc       348
Cys Thr Ser Leu Pro Asp Pro Val Lys Gly Thr Glu Cys Ser Phe Ser
    80                  85                  90

tgc aac gcc ggg gag ttt ctg gat atg aag gac cag tca tgt aag cca       396
Cys Asn Ala Gly Glu Phe Leu Asp Met Lys Asp Gln Ser Cys Lys Pro
95                  100                 105                 110

tgc gct gag ggc cgc tac tcc ctc ggc aca ggc att cgg ttt gat gag       444
Cys Ala Glu Gly Arg Tyr Ser Leu Gly Thr Gly Ile Arg Phe Asp Glu
                115                 120                 125

tgg gat gag ctg ccc cat ggc ttt gcc agc ctc tca gcc aac atg gag       492
Trp Asp Glu Leu Pro His Gly Phe Ala Ser Leu Ser Ala Asn Met Glu
            130                 135                 140

ctg gat gac agt gct gct gag tcc acc ggg aac tgt act tcg tcc aag       540
Leu Asp Asp Ser Ala Ala Glu Ser Thr Gly Asn Cys Thr Ser Ser Lys
        145                 150                 155

tgg gtt ccc cgg ggc gac tac atc gcc tcc aac acg gac gaa tgc aca       588
Trp Val Pro Arg Gly Asp Tyr Ile Ala Ser Asn Thr Asp Glu Cys Thr
    160                 165                 170

gcc aca ctg atg tac gcc gtc aac ctg aag caa tct ggc acc gtt aac       636
Ala Thr Leu Met Tyr Ala Val Asn Leu Lys Gln Ser Gly Thr Val Asn
175                 180                 185                 190

ttc gaa tac tac tat cca gac tcc agc atc atc ttt gag ttt ttc gtt       684
Phe Glu Tyr Tyr Tyr Pro Asp Ser Ser Ile Ile Phe Glu Phe Phe Val
                195                 200                 205

cag aat gac cag tgc cag ccc aat gca gat gac tcc agg tgg atg aag       732
Gln Asn Asp Gln Cys Gln Pro Asn Ala Asp Asp Ser Arg Trp Met Lys
            210                 215                 220

acc aca gag aaa gga tgg gaa ttc cac agt gtg gag cta aat cga ggc       780
Thr Thr Glu Lys Gly Trp Glu Phe His Ser Val Glu Leu Asn Arg Gly
        225                 230                 235

aat aat gtc ctc tat tgg aga acc aca gcc ttc tca gta tgg acc aaa       828
Asn Asn Val Leu Tyr Trp Arg Thr Thr Ala Phe Ser Val Trp Thr Lys
    240                 245                 250

gta ccc aag cct gtg ctg gtg aga aac att gcc ata aca ggg gtg gcc       876
Val Pro Lys Pro Val Leu Val Arg Asn Ile Ala Ile Thr Gly Val Ala
```

-continued

```
255                 260                 265                 270

tac act tca gaa tgc ttc ccc tgc aaa cct ggc acg tat gca gac aag      924
Tyr Thr Ser Glu Cys Phe Pro Cys Lys Pro Gly Thr Tyr Ala Asp Lys
                275                 280                 285

cag ggc tcc tct ttc tgc aaa ctt tgc cca gcc aac tct tat tca aat      972
Gln Gly Ser Ser Phe Cys Lys Leu Cys Pro Ala Asn Ser Tyr Ser Asn
            290                 295                 300

aaa gga gaa act tct tgc cac cag tgt gac cct gac aaa tac tca gag     1020
Lys Gly Glu Thr Ser Cys His Gln Cys Asp Pro Asp Lys Tyr Ser Glu
        305                 310                 315

aaa gga tct tct tcc tgt aac gtg cgc cca gct tgc aca gac aaa gat     1068
Lys Gly Ser Ser Ser Cys Asn Val Arg Pro Ala Cys Thr Asp Lys Asp
    320                 325                 330

tat ttc tac aca cac acg gcc tgc gat gcc aac gga gag aca caa ctc     1116
Tyr Phe Tyr Thr His Thr Ala Cys Asp Ala Asn Gly Glu Thr Gln Leu
335                 340                 345                 350

atg tac aaa tgg gcc aag ccg aaa atc tgt agc gag gac ctt gag ggg     1164
Met Tyr Lys Trp Ala Lys Pro Lys Ile Cys Ser Glu Asp Leu Glu Gly
                355                 360                 365

gca gtg aag ctg cct gcc tct ggt gtg aag acc cac tgc cca ccc tgc     1212
Ala Val Lys Leu Pro Ala Ser Gly Val Lys Thr His Cys Pro Pro Cys
            370                 375                 380

aac cca ggc ttc ttc aaa acc aac aac agc acc tgc cag ccc tgc cca     1260
Asn Pro Gly Phe Phe Lys Thr Asn Asn Ser Thr Cys Gln Pro Cys Pro
        385                 390                 395

tat ggt tcc tac tcc aat ggc tca gac tgt acc cgc tgc cct gca ggg     1308
Tyr Gly Ser Tyr Ser Asn Gly Ser Asp Cys Thr Arg Cys Pro Ala Gly
    400                 405                 410

act gaa cct gct gtg gga ttt gaa tac aaa tgg tgg aac acg ctg ccc     1356
Thr Glu Pro Ala Val Gly Phe Glu Tyr Lys Trp Trp Asn Thr Leu Pro
415                 420                 425                 430

aca aac atg gaa acg acc gtt ctc agt ggg atc aac ttc gag tac aag     1404
Thr Asn Met Glu Thr Thr Val Leu Ser Gly Ile Asn Phe Glu Tyr Lys
                435                 440                 445

ggc atg aca ggc tgg gag gtg gct ggt gat cac att tac aca gct gct     1452
Gly Met Thr Gly Trp Glu Val Ala Gly Asp His Ile Tyr Thr Ala Ala
            450                 455                 460

gga gcc tca gac aat gac ttc atg att ctc act ctg gtt gtg cca gga     1500
Gly Ala Ser Asp Asn Asp Phe Met Ile Leu Thr Leu Val Val Pro Gly
        465                 470                 475

ttt aga cct ccg cag tcg gtg atg gca gac aca gag aat aaa gag gtg     1548
Phe Arg Pro Pro Gln Ser Val Met Ala Asp Thr Glu Asn Lys Glu Val
    480                 485                 490

gcc aga atc aca ttt gtc ttt gag acc ctc tgt tct gtg aac tgt gag     1596
Ala Arg Ile Thr Phe Val Phe Glu Thr Leu Cys Ser Val Asn Cys Glu
495                 500                 505                 510

ctc tac ttc atg gtg ggt gtg aat tct agg acc aac act cct gtg gag     1644
Leu Tyr Phe Met Val Gly Val Asn Ser Arg Thr Asn Thr Pro Val Glu
                515                 520                 525

acg tgg aaa ggt tcc aaa ggc aaa cag tcc tat acc tac atc att gag     1692
Thr Trp Lys Gly Ser Lys Gly Lys Gln Ser Tyr Thr Tyr Ile Ile Glu
            530                 535                 540

gag aac act acc acg agc ttc acc tgg gcc ttc cag agg acc act ttt     1740
Glu Asn Thr Thr Thr Ser Phe Thr Trp Ala Phe Gln Arg Thr Thr Phe
        545                 550                 555

cat gag gca agc agg aag tac acc aat gac gtt gcc aag atc tac tcc     1788
His Glu Ala Ser Arg Lys Tyr Thr Asn Asp Val Ala Lys Ile Tyr Ser
    560                 565                 570

atc aat gtc acc aat gtt atg aat ggc gtg gcc tcc tac tgc cgt ccc     1836
```

-continued

```
Ile Asn Val Thr Asn Val Met Asn Gly Val Ala Ser Tyr Cys Arg Pro
575                 580                 585                 590

tgt gcc cta gaa gcc tct gat gtg ggc tcc tcc tgc acc tct tgt cct      1884
Cys Ala Leu Glu Ala Ser Asp Val Gly Ser Ser Cys Thr Ser Cys Pro
                595                 600                 605

gct ggt tac tat att gac cga gat tca gga acc tgc cac tcc tgc ccc      1932
Ala Gly Tyr Tyr Ile Asp Arg Asp Ser Gly Thr Cys His Ser Cys Pro
            610                 615                 620

cct aac aca att ctg aaa gcc cac cag cct tat ggt gtc cag gcc tgt      1980
Pro Asn Thr Ile Leu Lys Ala His Gln Pro Tyr Gly Val Gln Ala Cys
        625                 630                 635

gtg ccc tgt ggt cca ggg acc aag aac aac aag atc cac tct ctg tgc      2028
Val Pro Cys Gly Pro Gly Thr Lys Asn Asn Lys Ile His Ser Leu Cys
    640                 645                 650

tac aat gat tgc acc ttc tca cgc aac act cca acc agg act ttc aac      2076
Tyr Asn Asp Cys Thr Phe Ser Arg Asn Thr Pro Thr Arg Thr Phe Asn
655                 660                 665                 670

tac aac ttc tcc gct ttg gca aac acc gtc act ctt gct gga ggg cca      2124
Tyr Asn Phe Ser Ala Leu Ala Asn Thr Val Thr Leu Ala Gly Gly Pro
                675                 680                 685

agc ttc act tcc aaa ggg ttg aaa tac ttc cat cac ttt acc ctc agt      2172
Ser Phe Thr Ser Lys Gly Leu Lys Tyr Phe His His Phe Thr Leu Ser
            690                 695                 700

ctc tgt gga aac cag ggt agg aaa atg tct gtg tgc acc gac aat gtc      2220
Leu Cys Gly Asn Gln Gly Arg Lys Met Ser Val Cys Thr Asp Asn Val
        705                 710                 715

act gac ctc cgg att cct gag ggt gag tca ggg ttc tcc aaa tct atc      2268
Thr Asp Leu Arg Ile Pro Glu Gly Glu Ser Gly Phe Ser Lys Ser Ile
    720                 725                 730

aca gcc tac gtc tgc cag gca gtc atc atc ccc cca gag gtg aca ggc      2316
Thr Ala Tyr Val Cys Gln Ala Val Ile Ile Pro Pro Glu Val Thr Gly
735                 740                 745                 750

tac aag gcc ggg gtt tcc tca cag cct gtc agc ctt gct gat cga ctt      2364
Tyr Lys Ala Gly Val Ser Ser Gln Pro Val Ser Leu Ala Asp Arg Leu
                755                 760                 765

att ggg gtg aca aca gat atg act ctg gat gga atc acc tcc cca gct      2412
Ile Gly Val Thr Thr Asp Met Thr Leu Asp Gly Ile Thr Ser Pro Ala
            770                 775                 780

gaa ctt ttc cac ctg gag tcc ttg gga ata ccg gac gtg atc ttc ttt      2460
Glu Leu Phe His Leu Glu Ser Leu Gly Ile Pro Asp Val Ile Phe Phe
        785                 790                 795

tat agg tcc aat gat gtg acc cag tcc tgc agt tct ggg aga tca acc      2508
Tyr Arg Ser Asn Asp Val Thr Gln Ser Cys Ser Ser Gly Arg Ser Thr
    800                 805                 810

acc atc cgc gtc agg tgc agt cca cag aaa act gtc cct gga agt ttg      2556
Thr Ile Arg Val Arg Cys Ser Pro Gln Lys Thr Val Pro Gly Ser Leu
815                 820                 825                 830

ctg ctg cca gga acg tgc tca gat ggg acc tgt gat ggc tgc aac ttc      2604
Leu Leu Pro Gly Thr Cys Ser Asp Gly Thr Cys Asp Gly Cys Asn Phe
                835                 840                 845

cac ttc ctg tgg gag agc gcg gct gct tgc ccg ctc tgc tca gtg gct      2652
His Phe Leu Trp Glu Ser Ala Ala Ala Cys Pro Leu Cys Ser Val Ala
            850                 855                 860

gac tac cat gct atc gtc agc agc tgt gtg gct ggg atc cag aag act      2700
Asp Tyr His Ala Ile Val Ser Ser Cys Val Ala Gly Ile Gln Lys Thr
        865                 870                 875

act tac gtg tgg cga gaa ccc aag cta tgc tct ggt ggc att tct ctg      2748
Thr Tyr Val Trp Arg Glu Pro Lys Leu Cys Ser Gly Gly Ile Ser Leu
    880                 885                 890
```

-continued

```
cct gag cag aga gtc acc atc tgc aaa acc ata gat ttc tgg ctg aaa     2796
Pro Glu Gln Arg Val Thr Ile Cys Lys Thr Ile Asp Phe Trp Leu Lys
895                 900                 905                 910

gtg ggc atc tct gca ggc acc tgt act gcc atc ctg ctc acc gtc ttg     2844
Val Gly Ile Ser Ala Gly Thr Cys Thr Ala Ile Leu Leu Thr Val Leu
                915                 920                 925

acc tgc tac ttt tgg aaa aag aat caa aaa cta gag tac aag tac tcc     2892
Thr Cys Tyr Phe Trp Lys Lys Asn Gln Lys Leu Glu Tyr Lys Tyr Ser
            930                 935                 940

aag ctg gtg atg aat gct act ctc aag gac tgt gac ctg cca gca gct     2940
Lys Leu Val Met Asn Ala Thr Leu Lys Asp Cys Asp Leu Pro Ala Ala
        945                 950                 955

gac agc tgc gcc atc atg gaa ggc gag gat gta gag gac gac ctc atc     2988
Asp Ser Cys Ala Ile Met Glu Gly Glu Asp Val Glu Asp Asp Leu Ile
    960                 965                 970

ttt acc agc aag aag tca ctc ttt ggg aag atc aaa tca ttt acc tcc     3036
Phe Thr Ser Lys Lys Ser Leu Phe Gly Lys Ile Lys Ser Phe Thr Ser
975                 980                 985                 990

aag agg act cct gat gga ttt gac tca gtg  ccg ctg aag aca tcc  tca   3084
Lys Arg Thr Pro Asp Gly Phe Asp Ser Val  Pro Leu Lys Thr Ser  Ser
                995                 1000                1005

gga ggc cca gac  atg gac ctg tga gaggcactgc ctgcctcacc tgcctcctca   3138
Gly Gly Pro Asp  Met Asp Leu
            1010

ccttgcatag cacctttgca agcctgcggc gatttgggtg ccagcatcct gcaacaccca   3198

ctgctggaaa tctcttcatt gtggccttat cagatgtttg aatttcagat ctttttttat   3258

agagtaccca aaccctcctt tctgcttgcc tcaaacctgc caaatatacc cacactttgt   3318

ttgtaaatta aaaaaaaaaa aaaaaaa                                       3345


<210> SEQ ID NO 26
<211> LENGTH: 1013
<212> TYPE: PRT
<213> ORGANISM: Homo sapiens

<400> SEQUENCE: 26

Met Ala Glu Pro Gly His Ser His His Leu Ser Ala Arg Val Arg Gly
1               5                   10                  15

Arg Thr Glu Arg Arg Ile Pro Arg Leu Trp Arg Leu Leu Leu Trp Ala
            20                  25                  30

Gly Thr Ala Phe Gln Val Thr Gln Gly Thr Gly Pro Glu Leu His Ala
        35                  40                  45

Cys Lys Glu Ser Glu Tyr His Tyr Glu Tyr Thr Ala Cys Asp Ser Thr
    50                  55                  60

Gly Ser Arg Trp Arg Val Ala Val Pro His Thr Pro Gly Leu Cys Thr
65                  70                  75                  80

Ser Leu Pro Asp Pro Val Lys Gly Thr Glu Cys Ser Phe Ser Cys Asn
                85                  90                  95

Ala Gly Glu Phe Leu Asp Met Lys Asp Gln Ser Cys Lys Pro Cys Ala
            100                 105                 110

Glu Gly Arg Tyr Ser Leu Gly Thr Gly Ile Arg Phe Asp Glu Trp Asp
        115                 120                 125

Glu Leu Pro His Gly Phe Ala Ser Leu Ser Ala Asn Met Glu Leu Asp
    130                 135                 140

Asp Ser Ala Ala Glu Ser Thr Gly Asn Cys Thr Ser Ser Lys Trp Val
145                 150                 155                 160

Pro Arg Gly Asp Tyr Ile Ala Ser Asn Thr Asp Glu Cys Thr Ala Thr
```

-continued

```
                165                 170                 175

Leu Met Tyr Ala Val Asn Leu Lys Gln Ser Gly Thr Val Asn Phe Glu
            180                 185                 190

Tyr Tyr Tyr Pro Asp Ser Ser Ile Ile Phe Glu Phe Phe Val Gln Asn
        195                 200                 205

Asp Gln Cys Gln Pro Asn Ala Asp Asp Ser Arg Trp Met Lys Thr Thr
    210                 215                 220

Glu Lys Gly Trp Glu Phe His Ser Val Glu Leu Asn Arg Gly Asn Asn
225                 230                 235                 240

Val Leu Tyr Trp Arg Thr Thr Ala Phe Ser Val Trp Thr Lys Val Pro
                245                 250                 255

Lys Pro Val Leu Val Arg Asn Ile Ala Ile Thr Gly Val Ala Tyr Thr
            260                 265                 270

Ser Glu Cys Phe Pro Cys Lys Pro Gly Thr Tyr Ala Asp Lys Gln Gly
        275                 280                 285

Ser Ser Phe Cys Lys Leu Cys Pro Ala Asn Ser Tyr Ser Asn Lys Gly
    290                 295                 300

Glu Thr Ser Cys His Gln Cys Asp Pro Asp Lys Tyr Ser Glu Lys Gly
305                 310                 315                 320

Ser Ser Ser Cys Asn Val Arg Pro Ala Cys Thr Asp Lys Asp Tyr Phe
                325                 330                 335

Tyr Thr His Thr Ala Cys Asp Ala Asn Gly Glu Thr Gln Leu Met Tyr
            340                 345                 350

Lys Trp Ala Lys Pro Lys Ile Cys Ser Glu Asp Leu Glu Gly Ala Val
        355                 360                 365

Lys Leu Pro Ala Ser Gly Val Lys Thr His Cys Pro Pro Cys Asn Pro
    370                 375                 380

Gly Phe Phe Lys Thr Asn Asn Ser Thr Cys Gln Pro Cys Pro Tyr Gly
385                 390                 395                 400

Ser Tyr Ser Asn Gly Ser Asp Cys Thr Arg Cys Pro Ala Gly Thr Glu
                405                 410                 415

Pro Ala Val Gly Phe Glu Tyr Lys Trp Trp Asn Thr Leu Pro Thr Asn
            420                 425                 430

Met Glu Thr Thr Val Leu Ser Gly Ile Asn Phe Glu Tyr Lys Gly Met
        435                 440                 445

Thr Gly Trp Glu Val Ala Gly Asp His Ile Tyr Thr Ala Ala Gly Ala
    450                 455                 460

Ser Asp Asn Asp Phe Met Ile Leu Thr Leu Val Val Pro Gly Phe Arg
465                 470                 475                 480

Pro Pro Gln Ser Val Met Ala Asp Thr Glu Asn Lys Glu Val Ala Arg
                485                 490                 495

Ile Thr Phe Val Phe Glu Thr Leu Cys Ser Val Asn Cys Glu Leu Tyr
            500                 505                 510

Phe Met Val Gly Val Asn Ser Arg Thr Asn Thr Pro Val Glu Thr Trp
        515                 520                 525

Lys Gly Ser Lys Gly Lys Gln Ser Tyr Thr Tyr Ile Ile Glu Glu Asn
    530                 535                 540

Thr Thr Thr Ser Phe Thr Trp Ala Phe Gln Arg Thr Thr Phe His Glu
545                 550                 555                 560

Ala Ser Arg Lys Tyr Thr Asn Asp Val Ala Lys Ile Tyr Ser Ile Asn
                565                 570                 575

Val Thr Asn Val Met Asn Gly Val Ala Ser Tyr Cys Arg Pro Cys Ala
            580                 585                 590
```

-continued

```
Leu Glu Ala Ser Asp Val Gly Ser Ser Cys Thr Ser Cys Pro Ala Gly
        595                 600                 605

Tyr Tyr Ile Asp Arg Asp Ser Gly Thr Cys His Ser Cys Pro Pro Asn
    610                 615                 620

Thr Ile Leu Lys Ala His Gln Pro Tyr Gly Val Gln Ala Cys Val Pro
625                 630                 635                 640

Cys Gly Pro Gly Thr Lys Asn Asn Lys Ile His Ser Leu Cys Tyr Asn
                645                 650                 655

Asp Cys Thr Phe Ser Arg Asn Thr Pro Thr Arg Thr Phe Asn Tyr Asn
            660                 665                 670

Phe Ser Ala Leu Ala Asn Thr Val Thr Leu Ala Gly Gly Pro Ser Phe
        675                 680                 685

Thr Ser Lys Gly Leu Lys Tyr Phe His His Phe Thr Leu Ser Leu Cys
    690                 695                 700

Gly Asn Gln Gly Arg Lys Met Ser Val Cys Thr Asp Asn Val Thr Asp
705                 710                 715                 720

Leu Arg Ile Pro Glu Gly Glu Ser Gly Phe Ser Lys Ser Ile Thr Ala
                725                 730                 735

Tyr Val Cys Gln Ala Val Ile Ile Pro Pro Glu Val Thr Gly Tyr Lys
            740                 745                 750

Ala Gly Val Ser Ser Gln Pro Val Ser Leu Ala Asp Arg Leu Ile Gly
        755                 760                 765

Val Thr Thr Asp Met Thr Leu Asp Gly Ile Thr Ser Pro Ala Glu Leu
    770                 775                 780

Phe His Leu Glu Ser Leu Gly Ile Pro Asp Val Ile Phe Phe Tyr Arg
785                 790                 795                 800

Ser Asn Asp Val Thr Gln Ser Cys Ser Ser Gly Arg Ser Thr Thr Ile
                805                 810                 815

Arg Val Arg Cys Ser Pro Gln Lys Thr Val Pro Gly Ser Leu Leu Leu
            820                 825                 830

Pro Gly Thr Cys Ser Asp Gly Thr Cys Asp Gly Cys Asn Phe His Phe
        835                 840                 845

Leu Trp Glu Ser Ala Ala Ala Cys Pro Leu Cys Ser Val Ala Asp Tyr
    850                 855                 860

His Ala Ile Val Ser Ser Cys Val Ala Gly Ile Gln Lys Thr Thr Tyr
865                 870                 875                 880

Val Trp Arg Glu Pro Lys Leu Cys Ser Gly Gly Ile Ser Leu Pro Glu
                885                 890                 895

Gln Arg Val Thr Ile Cys Lys Thr Ile Asp Phe Trp Leu Lys Val Gly
            900                 905                 910

Ile Ser Ala Gly Thr Cys Thr Ala Ile Leu Leu Thr Val Leu Thr Cys
        915                 920                 925

Tyr Phe Trp Lys Lys Asn Gln Lys Leu Glu Tyr Lys Tyr Ser Lys Leu
    930                 935                 940

Val Met Asn Ala Thr Leu Lys Asp Cys Asp Leu Pro Ala Ala Asp Ser
945                 950                 955                 960

Cys Ala Ile Met Glu Gly Glu Asp Val Glu Asp Asp Leu Ile Phe Thr
                965                 970                 975

Ser Lys Lys Ser Leu Phe Gly Lys Ile Lys Ser Phe Thr Ser Lys Arg
            980                 985                 990

Thr Pro Asp Gly Phe Asp Ser Val  Pro Leu Lys Thr Ser  Ser Gly Gly
        995                 1000                1005
```

-continued

```
Pro Asp  Met Asp Leu
    1010


<210> SEQ ID NO 27
<211> LENGTH: 2998
<212> TYPE: DNA
<213> ORGANISM: Homo sapiens
<220> FEATURE:
<221> NAME/KEY: CDS
<222> LOCATION: (218)..(733)

<400> SEQUENCE: 27

gttcgtcctg ggactgcact tgctcccgtc gggtcgcccg gcttcaccgg acccgcaggc     60

tcccggggca gggccggggc cagagctcgc gtgtcggcgg gacatgcgct gcgtcgcctc    120

taacctcggg ctgtgctctt tttccaggtg gcccgccggt ttctgagcct tctgccctgc    180

ggggacacgg tctgcaccct gcccgcggcc acggacc atg acc atg acc ctc cac     235
                                        Met Thr Met Thr Leu His
                                        1               5

acc aaa gca tct ggg atg gcc cta ctg cat cag atc caa ggg aac gag      283
Thr Lys Ala Ser Gly Met Ala Leu Leu His Gln Ile Gln Gly Asn Glu
            10                  15                  20

ctg gag ccc ctg aac cgt ccg cag ctc aag atc ccc ctg gag cgg ccc      331
Leu Glu Pro Leu Asn Arg Pro Gln Leu Lys Ile Pro Leu Glu Arg Pro
        25                  30                  35

ctg ggc gag gtg tac ctg gac agc agc aag ccc gcc gtg tac aac tac      379
Leu Gly Glu Val Tyr Leu Asp Ser Ser Lys Pro Ala Val Tyr Asn Tyr
    40                  45                  50

ccc gag ggc gcc gcc tac gag ttc aac gcc gcg gcc gcc gcc aac gcg      427
Pro Glu Gly Ala Ala Tyr Glu Phe Asn Ala Ala Ala Ala Ala Asn Ala
55                  60                  65                  70

cag gtc tac ggt cag acc ggc ctc ccc tac ggc ccc ggg tct gag gct      475
Gln Val Tyr Gly Gln Thr Gly Leu Pro Tyr Gly Pro Gly Ser Glu Ala
                75                  80                  85

gcg gcg ttc ggc tcc aac ggc ctg ggg ggt ttc ccc cca ctc aac agc      523
Ala Ala Phe Gly Ser Asn Gly Leu Gly Gly Phe Pro Pro Leu Asn Ser
            90                  95                  100

gtg tct ccg agc ccg ctg atg cta ctg cac ccg ccg ccg cag ctg tcg      571
Val Ser Pro Ser Pro Leu Met Leu Leu His Pro Pro Pro Gln Leu Ser
        105                 110                 115

cct ttc ctg cag ccc cac ggc cag cag gtg ccc tac tac ctg gag aac      619
Pro Phe Leu Gln Pro His Gly Gln Gln Val Pro Tyr Tyr Leu Glu Asn
    120                 125                 130

gag ccc agc ggc tac acg gtg cgc gag gcc ggc ccg ccg gca ttc tac      667
Glu Pro Ser Gly Tyr Thr Val Arg Glu Ala Gly Pro Pro Ala Phe Tyr
135                 140                 145                 150

aga atg gtg ctg tca tgt gga ctg tcc tcc cga gtg tcc cac tgg atg      715
Arg Met Val Leu Ser Cys Gly Leu Ser Ser Arg Val Ser His Trp Met
                155                 160                 165

ttc aga gaa ttt atg tga aggtcacgtc atttagcatt gagatgctgt             763
Phe Arg Glu Phe Met
            170

ggttaccttc ttccatttct tccataatat gcagccacat ctatgtgtga agaaatgtaa    823

tagataaaat ttctctggac gcataataat gtgagaaaga ttgtcacatg tcccagcaaa    883

ttgttattaa tataaatttg ttacttggca agctgagatt ttgcaagatg ttactcaaaa    943

tttcacaatg aaggaaacag ggagtcatct tatcctgggt tcctttttta gatttcaaac   1003

aacttaggaa ctttgaataa aactaaagat gaagcttaac tatatcaact atccttttta   1063

aagttctaat taggaattta atgctgcatg cttatttcag ttttattact cagtattctt   1123
```

-continued

```
aaaagttaga catctctcac ttctccaaaa aacttggcaa atgtataaat cttttgcatc   1183

aaaatcaatg ccctgctaat ttgtatcctg gccatctgca tattttggac aactaatttt   1243

tccactggtg atcatttgaa actctttctc aactttgaat agagactgat ttccaaagtg   1303

agatttaagt gactaagttt caagtttccg atacattttt ccttttactt agataacatt   1363

tcagcccccct tcctttctga tcttactttt ttattaattt aaattgttac tgattacgtg   1423

acactttgtg ctggtctaag aatagtccag agtcacatat tccctggtga atgagcatat   1483

tttcggatga aaacggaatc acatcttcaa tccccatttc attttcacct cctccatgtg   1543

gcttgtacct gtttggaaga aagctcctga aggataattg ccacttattc taatctttct   1603

cacactcatt taatttggat ccctggctaa agttgttatt tacttttgtg attatactta   1663

gtctatgaca ttcataattt gggaaaattc tcaggtttga gaattttggc ggcttgggat   1723

ttcttttagt ttcttatagt tttaaggata tgtaagacag gtgtaagaaa ctgccaaggg   1783

gaggaaccat agatatcagg aaaaactaga aaagatgcca gacttaccat taatgaatga   1843

tgagacaata gtaactttgt taagtgagat tgtatatgtg aaagtggtat agaaactaaa   1903

caaacattag gtgtttttat tattttactc acatgttaat atttgttttg gtgctttcat   1963

aggctaaaaa gctgggaaat aacagattta agtggtcagg aattttgtta taaatataga   2023

atgatgatta tatgaaatct tttcctgtga aagtcaaatt taagtaaaat ctttatcacc   2083

atctgcaaca tttgtctgca gcctggctta ccaggttatc ataaagaaca tttattttac   2143

agatacatta aagaaagtca aaaccctgat tatgtgtaaa caattttaca taaggaaata   2203

tatgaatttt aattatattt ttctaaaatc cgtactcagc atgaaattaa tacatcttaa   2263

cccctccctg tgacttcatt attattttta atgtaacttt agaagaaccc agtagagaga   2323

gcagcgtgct aagtgtgttt ctttcttttc cagacaactt tgaatggaga ggagcaaatt   2383

agtcttttgg tttaattctg tctcagtttg cttatctaaa gaaaggaaaa cagagtggct   2443

acacttgttt agaaccatat gcatactcca gagaaagatg ctctattaat ccaaaaaata   2503

cagccacttg aaaccagcca aagcgaaagt gtaagggact tcatggaaag gaggcagttc   2563

accaaagtta ttgaggggtt ttatatttta aactccgcca gtgaattgac gtgtaatgtc   2623

acttacaaaa aaaaaaaaaa gtatgtctga gctgttcgct acttcgtctc taaaatatac   2683

tcatactgat ctctgaaatc ccagaattta agtgggctgg aggttacggg aagcaccttt   2743

ataaatatcct taatctcatg agggaagaaa ccataattgc tgaattctct gccttggata   2803

atatcaggag ggactctgaa gaaagttttg cagtaatcaa caatgtttta aattatgtgt   2863

atatttttag atcacctcaa aaaatatagg aagcacagaa tgacaactat tctggtctca   2923

actgacacaa ttttatgtag tttaataaag taataatttc aagaaacgtg ggcaaataaa   2983

aaaaaaaaaa aaaaa                                                      2998
```

<210> SEQ ID NO 28
<211> LENGTH: 171
<212> TYPE: PRT
<213> ORGANISM: Homo sapiens

<400> SEQUENCE: 28

```
Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30
```

-continued

```
Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80

Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
    130                 135                 140

Gly Pro Pro Ala Phe Tyr Arg Met Val Leu Ser Cys Gly Leu Ser Ser
145                 150                 155                 160

Arg Val Ser His Trp Met Phe Arg Glu Phe Met
                165                 170


<210> SEQ ID NO 29
<211> LENGTH: 14955
<212> TYPE: DNA
<213> ORGANISM: Homo sapiens
<220> FEATURE:
<221> NAME/KEY: CDS
<222> LOCATION: (95)..(6760)

<400> SEQUENCE: 29

taggcgccca gggccaggca gcggttgctt ccccggcccg gctcgcccgc gcttctctcc      60

ctgtgggcgg cggcccggcg cctggaaggt caag atg gaa gaa atc ctg agg aag     115
                                      Met Glu Glu Ile Leu Arg Lys
                                      1               5

ctg cag aag gag gcg tcc ggg agc aag tac aaa gcc atc aag gag agc       163
Leu Gln Lys Glu Ala Ser Gly Ser Lys Tyr Lys Ala Ile Lys Glu Ser
        10                  15                  20

tgc acc tgg gcc ctg gaa act cta ggt ggt ctg gat acc att gcc aag       211
Cys Thr Trp Ala Leu Glu Thr Leu Gly Gly Leu Asp Thr Ile Ala Lys
    25                  30                  35

atc cct cca cat gta ctg agg gag aaa tgc ctg ctg cct ctc cag ttg       259
Ile Pro Pro His Val Leu Arg Glu Lys Cys Leu Leu Pro Leu Gln Leu
40                  45                  50                  55

gct ttg gaa tcc aag aat gtg aag ctg gcc caa cat gct ttg gca ggg       307
Ala Leu Glu Ser Lys Asn Val Lys Leu Ala Gln His Ala Leu Ala Gly
                60                  65                  70

atg cag aag ctt ctg tcg gaa gag agg ttt gta tcc atg gaa aca gat       355
Met Gln Lys Leu Leu Ser Glu Glu Arg Phe Val Ser Met Glu Thr Asp
            75                  80                  85

tct gat gag aag cag ctg ctc aat cag ata ctg aat gcc gtg aaa gtg       403
Ser Asp Glu Lys Gln Leu Leu Asn Gln Ile Leu Asn Ala Val Lys Val
        90                  95                  100

acg cct tcg ctc aac gag gac ctg cag gtg gaa gtg atg aag gtt tta       451
Thr Pro Ser Leu Asn Glu Asp Leu Gln Val Glu Val Met Lys Val Leu
    105                 110                 115

cta tgc atc acc tac acg cca aca ttt gat ctg aat ggg agt gcc gtg       499
Leu Cys Ile Thr Tyr Thr Pro Thr Phe Asp Leu Asn Gly Ser Ala Val
120                 125                 130                 135

ctg aag atc gcg gag gtg tgc att gag acg tac ata agc agc tgt cac       547
Leu Lys Ile Ala Glu Val Cys Ile Glu Thr Tyr Ile Ser Ser Cys His
                140                 145                 150
```

-continued

```
cag cgt agc ata aac act gct gtg cgg gca act ctc agt caa atg ctg      595
Gln Arg Ser Ile Asn Thr Ala Val Arg Ala Thr Leu Ser Gln Met Leu
            155                 160                 165

agt gac ttg act tta cag tta cga cag agg cag gag aat acg ata att      643
Ser Asp Leu Thr Leu Gln Leu Arg Gln Arg Gln Glu Asn Thr Ile Ile
        170                 175                 180

gaa aac cca gat gtc cca cag gat ttc ggg aat caa ggg tca aca gta      691
Glu Asn Pro Asp Val Pro Gln Asp Phe Gly Asn Gln Gly Ser Thr Val
    185                 190                 195

gag tcc ctc tgt gat gat gtt gtc tct gta ctc acc gtc ctg tgt gag      739
Glu Ser Leu Cys Asp Asp Val Val Ser Val Leu Thr Val Leu Cys Glu
200                 205                 210                 215

aag ctg caa gcc gcc ata aag tgc cca tct ttc ctg acc atg gcg tgt      787
Lys Leu Gln Ala Ala Ile Lys Cys Pro Ser Phe Leu Thr Met Ala Cys
                220                 225                 230

tgg aac agt gga gct ggc act cag att acc atc cta act gag ggc tct      835
Trp Asn Ser Gly Ala Gly Thr Gln Ile Thr Ile Leu Thr Glu Gly Ser
            235                 240                 245

agc acc aac tgc agc gac ccc atc tgg gac acc aca gcc tcg ccg gtg      883
Ser Thr Asn Cys Ser Asp Pro Ile Trp Asp Thr Thr Ala Ser Pro Val
        250                 255                 260

gca gcc agt gac agc cag cag ctg cag ctt ctc tac ctg gag tgc atc      931
Ala Ala Ser Asp Ser Gln Gln Leu Gln Leu Leu Tyr Leu Glu Cys Ile
    265                 270                 275

ctg tct gtg ctc agc agc tcc tcc tcc tcc atg cac ctg cac agg cgc      979
Leu Ser Val Leu Ser Ser Ser Ser Ser Ser Met His Leu His Arg Arg
280                 285                 290                 295

ttc acg gac ctg atc tgg aaa aac ctc tgc cct gct ctc atc gtg atc     1027
Phe Thr Asp Leu Ile Trp Lys Asn Leu Cys Pro Ala Leu Ile Val Ile
                300                 305                 310

ttg ggg aat cca att cat gac aaa acc atc acc tct gct cac acc agc     1075
Leu Gly Asn Pro Ile His Asp Lys Thr Ile Thr Ser Ala His Thr Ser
            315                 320                 325

agc acc agt acc agc ctg gag tcg gac tct gcg tct ccg gga gtg tct     1123
Ser Thr Ser Thr Ser Leu Glu Ser Asp Ser Ala Ser Pro Gly Val Ser
        330                 335                 340

gac cac ggc cga gga tca ggc tgc tcc tgc act gcg ccg gcc ctg agc     1171
Asp His Gly Arg Gly Ser Gly Cys Ser Cys Thr Ala Pro Ala Leu Ser
    345                 350                 355

gga cct gtg gct cgg act atc tat tac atc gca gcc gag ctg gtc cgg     1219
Gly Pro Val Ala Arg Thr Ile Tyr Tyr Ile Ala Ala Glu Leu Val Arg
360                 365                 370                 375

ctg gtg ggg tct gtg gac tcc atg aag ccc gtg ctc cag tcc ctc tac     1267
Leu Val Gly Ser Val Asp Ser Met Lys Pro Val Leu Gln Ser Leu Tyr
                380                 385                 390

cac cga gtg ctg ctc tac ccc cca ccc cag cac cgg gtg gaa gcc atc     1315
His Arg Val Leu Leu Tyr Pro Pro Pro Gln His Arg Val Glu Ala Ile
            395                 400                 405

aaa ata atg aaa gag ata ctt ggg agc cca cag cgt ctc tgt gac ttg     1363
Lys Ile Met Lys Glu Ile Leu Gly Ser Pro Gln Arg Leu Cys Asp Leu
        410                 415                 420

gca gga ccc agc tcc act gaa tca gag tcc aga aaa aga tca att tca     1411
Ala Gly Pro Ser Ser Thr Glu Ser Glu Ser Arg Lys Arg Ser Ile Ser
    425                 430                 435

aaa aga aag tct cat ctg gat ctc ctc aaa ctc atc atg gat ggc atg     1459
Lys Arg Lys Ser His Leu Asp Leu Leu Lys Leu Ile Met Asp Gly Met
440                 445                 450                 455

acc gaa gca tgc atc aag ggt ggc atc gaa gct tgc tat gca gcc gtg     1507
Thr Glu Ala Cys Ile Lys Gly Gly Ile Glu Ala Cys Tyr Ala Ala Val
```

-continued

```
            460                 465                 470

tcc tgt gtc tgc acc ttg ctg ggt gcc ctg gat gag ctc agc cag ggg     1555
Ser Cys Val Cys Thr Leu Leu Gly Ala Leu Asp Glu Leu Ser Gln Gly
        475                 480                 485

aag ggc ttg agc gaa ggt cag gtg caa ctg ctg ctt ctg cgc ctt gag     1603
Lys Gly Leu Ser Glu Gly Gln Val Gln Leu Leu Leu Leu Arg Leu Glu
    490                 495                 500

gag ctg aag gat ggg gct gag tgg agc cga gat tcc atg gag atc aat     1651
Glu Leu Lys Asp Gly Ala Glu Trp Ser Arg Asp Ser Met Glu Ile Asn
    505                 510                 515

gag gct gac ttc cgc tgg cag cgg cga gtg ctg tcc tca gaa cac acg     1699
Glu Ala Asp Phe Arg Trp Gln Arg Arg Val Leu Ser Ser Glu His Thr
520                 525                 530                 535

ccg tgg gag tca ggg aac gag agg agc ctt gac atc agc atc agt gtc     1747
Pro Trp Glu Ser Gly Asn Glu Arg Ser Leu Asp Ile Ser Ile Ser Val
            540                 545                 550

acc aca gac aca ggc cag acc act ctc gag gga gag ttg ggt cag act     1795
Thr Thr Asp Thr Gly Gln Thr Thr Leu Glu Gly Glu Leu Gly Gln Thr
        555                 560                 565

aca ccc gag gac cat tcg gga aac cac aag aac agt ctc aag tcg cca     1843
Thr Pro Glu Asp His Ser Gly Asn His Lys Asn Ser Leu Lys Ser Pro
        570                 575                 580

gcc atc cca gag ggt aag gag acg ctg agc aaa gta ttg gaa aca gag     1891
Ala Ile Pro Glu Gly Lys Glu Thr Leu Ser Lys Val Leu Glu Thr Glu
    585                 590                 595

gcg gta gac cag cca gat gtc gtg cag aga agc cac acg gtc cct tac     1939
Ala Val Asp Gln Pro Asp Val Val Gln Arg Ser His Thr Val Pro Tyr
600                 605                 610                 615

cct gac ata act aac ttc ctg tca gta gac tgc agg aca agg tcc tat     1987
Pro Asp Ile Thr Asn Phe Leu Ser Val Asp Cys Arg Thr Arg Ser Tyr
            620                 625                 630

gga tct agg tat agt gag agc aat ttt agc gtt gat gac caa gac ctt     2035
Gly Ser Arg Tyr Ser Glu Ser Asn Phe Ser Val Asp Asp Gln Asp Leu
        635                 640                 645

tct agg aca gag ttt gat tcc tgt gat cag tac tct atg gca gca gaa     2083
Ser Arg Thr Glu Phe Asp Ser Cys Asp Gln Tyr Ser Met Ala Ala Glu
        650                 655                 660

aag gac tcg ggc agg tcc gac gtg tca gac att ggg tcg gac aac tgt     2131
Lys Asp Ser Gly Arg Ser Asp Val Ser Asp Ile Gly Ser Asp Asn Cys
    665                 670                 675

tca cta gcc gat gaa gag cag aca ccc cgg gac tgc cta ggc cac cgg     2179
Ser Leu Ala Asp Glu Glu Gln Thr Pro Arg Asp Cys Leu Gly His Arg
680                 685                 690                 695

tcc ctg cga act gcc gcc ctg tct cta aaa ctg ctg aag aac cag gag     2227
Ser Leu Arg Thr Ala Ala Leu Ser Leu Lys Leu Leu Lys Asn Gln Glu
            700                 705                 710

gcg gat cag cac agc gcc agg ctg ttc ata cag tcc ctg gaa ggc ctc     2275
Ala Asp Gln His Ser Ala Arg Leu Phe Ile Gln Ser Leu Glu Gly Leu
        715                 720                 725

ctc cct cgg ctc ctg tct ctc tcc aat gta gag gag gtg gac acc gct     2323
Leu Pro Arg Leu Leu Ser Leu Ser Asn Val Glu Glu Val Asp Thr Ala
        730                 735                 740

ctg cag aac ttt gcc tct act ttc tgc tca ggc atg atg cac tct cct     2371
Leu Gln Asn Phe Ala Ser Thr Phe Cys Ser Gly Met Met His Ser Pro
    745                 750                 755

ggc ttt gac ggg aat agc agc ctc agc ttc cag atg ctg atg aac gca     2419
Gly Phe Asp Gly Asn Ser Ser Leu Ser Phe Gln Met Leu Met Asn Ala
760                 765                 770                 775

gac agc ctc tac aca gct gca cac tgc gcc ctg ctc ctc aac ctg aag     2467
```

-continued

```
Asp Ser Leu Tyr Thr Ala Ala His Cys Ala Leu Leu Leu Asn Leu Lys
                780                 785                 790

ctc tcc cac ggt gac tac tac agg aag cgg ccg acc ctg gcg cca ggc      2515
Leu Ser His Gly Asp Tyr Tyr Arg Lys Arg Pro Thr Leu Ala Pro Gly
            795                 800                 805

gtg atg aag gac ttc atg aag cag gtg cag acc agc ggc gtg ctg atg      2563
Val Met Lys Asp Phe Met Lys Gln Val Gln Thr Ser Gly Val Leu Met
        810                 815                 820

gtc ttc tct cag gcc tgg att gag gag ctc tac cat cag gtg ctc gac      2611
Val Phe Ser Gln Ala Trp Ile Glu Glu Leu Tyr His Gln Val Leu Asp
    825                 830                 835

agg aac atg ctt gga gag gct ggc tat tgg ggc agc cca gaa gat aac      2659
Arg Asn Met Leu Gly Glu Ala Gly Tyr Trp Gly Ser Pro Glu Asp Asn
840                 845                 850                 855

agc ctt ccc ctc atc aca atg ctg acc gat att gac ggc tta gag agc      2707
Ser Leu Pro Leu Ile Thr Met Leu Thr Asp Ile Asp Gly Leu Glu Ser
                860                 865                 870

agt gcc att ggt ggc cag ctg atg gcc tcg gct gct aca gag tct cct      2755
Ser Ala Ile Gly Gly Gln Leu Met Ala Ser Ala Ala Thr Glu Ser Pro
            875                 880                 885

ttc gcc cag agc agg aga att gat gac tcc aca gtg gca ggc gtg gca      2803
Phe Ala Gln Ser Arg Arg Ile Asp Asp Ser Thr Val Ala Gly Val Ala
        890                 895                 900

ttt gct cgc tat att ctg gtg ggc tgc tgg aag aac ttg atc gat act      2851
Phe Ala Arg Tyr Ile Leu Val Gly Cys Trp Lys Asn Leu Ile Asp Thr
    905                 910                 915

tta tca acc cca ctg act ggt cga atg gcg ggg agc tcc aaa ggg ctg      2899
Leu Ser Thr Pro Leu Thr Gly Arg Met Ala Gly Ser Ser Lys Gly Leu
920                 925                 930                 935

gcc ttc att ctg gga gct gaa ggc atc aaa gag cag aac cag aag gag      2947
Ala Phe Ile Leu Gly Ala Glu Gly Ile Lys Glu Gln Asn Gln Lys Glu
                940                 945                 950

cgg gac gcc atc tgc atg agc ctc gac ggg ctg cgg aaa gcc gca cgg      2995
Arg Asp Ala Ile Cys Met Ser Leu Asp Gly Leu Arg Lys Ala Ala Arg
            955                 960                 965

ctg agc tgc gct cta ggc gtt gct gct aac tgc gcc tca gcc ctt gcc      3043
Leu Ser Cys Ala Leu Gly Val Ala Ala Asn Cys Ala Ser Ala Leu Ala
        970                 975                 980

cag atg gca gct gcc tcc tgt gtc caa gaa gaa aaa gaa gag agg gag      3091
Gln Met Ala Ala Ala Ser Cys Val Gln Glu Glu Lys Glu Glu Arg Glu
    985                 990                 995

gcc  caa gaa ccc agt gat  gcc atc aca caa gtg  aaa cta aaa gtg      3136
Ala  Gln Glu Pro Ser Asp  Ala Ile Thr Gln Val  Lys Leu Lys Val
1000                 1005                 1010

gag  cag aaa ctg gag cag  att ggg aag gtg cag  ggg gtg tgg ctg      3181
Glu  Gln Lys Leu Glu Gln  Ile Gly Lys Val Gln  Gly Val Trp Leu
1015                 1020                 1025

cac  act gcc cac gtc ttg  tgc atg gag gcc atc  ctc agc gta ggc      3226
His  Thr Ala His Val Leu  Cys Met Glu Ala Ile  Leu Ser Val Gly
1030                 1035                 1040

ctg  gag atg gga agc cac  aac ccg gac tgc tgg  cca cac gtg ttc      3271
Leu  Glu Met Gly Ser His  Asn Pro Asp Cys Trp  Pro His Val Phe
1045                 1050                 1055

agg  gtg tgt gaa tac gtg  ggc acc ctg gag cac  aac cac ttc agc      3316
Arg  Val Cys Glu Tyr Val  Gly Thr Leu Glu His  Asn His Phe Ser
1060                 1065                 1070

gat  ggt gcc tcg cag ccc  cct ctg acc atc agc  cag ccc cag aag      3361
Asp  Gly Ala Ser Gln Pro  Pro Leu Thr Ile Ser  Gln Pro Gln Lys
1075                 1080                 1085
```

-continued

```
gcc  act gga agc gct ggc  ctc ctt ggg gac ccc  gag tgt gag ggc      3406
Ala  Thr Gly Ser Ala Gly  Leu Leu Gly Asp Pro  Glu Cys Glu Gly
1090                 1095                 1100

tcg  ccc ccc gag cac agc  ccg gag cag ggg cgc  tcc ctg agc acg      3451
Ser  Pro Pro Glu His Ser  Pro Glu Gln Gly Arg  Ser Leu Ser Thr
1105                 1110                 1115

gcc  cct gtc gtc cag ccc  ctg tcc atc cag gac  ctc gtc cgg gaa      3496
Ala  Pro Val Val Gln Pro  Leu Ser Ile Gln Asp  Leu Val Arg Glu
1120                 1125                 1130

ggc  agc cgg ggt cgg gcc  tcc gac ttc cgc ggc  ggg agc ctc atg      3541
Gly  Ser Arg Gly Arg Ala  Ser Asp Phe Arg Gly  Gly Ser Leu Met
1135                 1140                 1145

agc  ggg agc agc gcg gcc  aag gtg gtg ctc acc  ctc tcc acg caa      3586
Ser  Gly Ser Ser Ala Ala  Lys Val Val Leu Thr  Leu Ser Thr Gln
1150                 1155                 1160

gcc  gac agg ctc ttt gaa  gat gct acg gat aag  ttg aac ctc atg      3631
Ala  Asp Arg Leu Phe Glu  Asp Ala Thr Asp Lys  Leu Asn Leu Met
1165                 1170                 1175

gcc  ttg gga ggt ttt ctt  tac cag ctg aag aaa  gca tcg cag tct      3676
Ala  Leu Gly Gly Phe Leu  Tyr Gln Leu Lys Lys  Ala Ser Gln Ser
1180                 1185                 1190

cag  ctt ttc cat tct gtt  aca gat aca gtt gat  tac tct ctg gca      3721
Gln  Leu Phe His Ser Val  Thr Asp Thr Val Asp  Tyr Ser Leu Ala
1195                 1200                 1205

atg  cca gga gaa gtt aaa  tcc act caa gac cga  aaa agc gcc ctc      3766
Met  Pro Gly Glu Val Lys  Ser Thr Gln Asp Arg  Lys Ser Ala Leu
1210                 1215                 1220

cac  ctg ttc cgc ctg ggg  aat gcc atg ctg agg  att gtg cgg agc      3811
His  Leu Phe Arg Leu Gly  Asn Ala Met Leu Arg  Ile Val Arg Ser
1225                 1230                 1235

aaa  gca cgg ccc ctg ctc  cac gtg atg cgc tgc  tgg agc ctt gtg      3856
Lys  Ala Arg Pro Leu Leu  His Val Met Arg Cys  Trp Ser Leu Val
1240                 1245                 1250

gcc  cca cac ctg gtg gag  gct gct tgc cat aag  gaa aga cat gtg      3901
Ala  Pro His Leu Val Glu  Ala Ala Cys His Lys  Glu Arg His Val
1255                 1260                 1265

tct  cag aag gct gtt tcc  ttc atc cat gac ata  ctg aca gaa gtc      3946
Ser  Gln Lys Ala Val Ser  Phe Ile His Asp Ile  Leu Thr Glu Val
1270                 1275                 1280

ctc  act gac tgg aat gag  cca cct cat ttt cac  ttc aat gaa gca      3991
Leu  Thr Asp Trp Asn Glu  Pro Pro His Phe His  Phe Asn Glu Ala
1285                 1290                 1295

ctc  ttc cga cct ttc gag  cgc att atg cag ctg  gaa ttg tgt gat      4036
Leu  Phe Arg Pro Phe Glu  Arg Ile Met Gln Leu  Glu Leu Cys Asp
1300                 1305                 1310

gag  gac gtc caa gac cag  gtt gtc aca tcc att  ggt gag ctg gtt      4081
Glu  Asp Val Gln Asp Gln  Val Val Thr Ser Ile  Gly Glu Leu Val
1315                 1320                 1325

gaa  gtg tgt tcc acg cag  atc cag tcg gga tgg  aga ccc ttg ttc      4126
Glu  Val Cys Ser Thr Gln  Ile Gln Ser Gly Trp  Arg Pro Leu Phe
1330                 1335                 1340

agt  gcc ctg gaa aca gtg  cat ggc ggg aac aag  tca gag atg aag      4171
Ser  Ala Leu Glu Thr Val  His Gly Gly Asn Lys  Ser Glu Met Lys
1345                 1350                 1355

gag  tac ctg gtt ggt gac  tac tcc atg gga aaa  ggc caa gct cca      4216
Glu  Tyr Leu Val Gly Asp  Tyr Ser Met Gly Lys  Gly Gln Ala Pro
1360                 1365                 1370

gtg  ttt gat gta ttt gaa  gct ttt ctc aat act  gac aac atc cag      4261
Val  Phe Asp Val Phe Glu  Ala Phe Leu Asn Thr  Asp Asn Ile Gln
1375                 1380                 1385
```

-continued

```
gtc  ttt gct aat gca gcc  act agc tac atc atg  tgc ctt atg aag      4306
Val  Phe Ala Asn Ala Ala  Thr Ser Tyr Ile Met  Cys Leu Met Lys
1390                1395                1400

ttt  gtc aaa gga ctg ggg  gag gtg gac tgt aaa  gag att gga gac      4351
Phe  Val Lys Gly Leu Gly  Glu Val Asp Cys Lys  Glu Ile Gly Asp
1405                1410                1415

tgt  gcc cca gca ccc gga  gcc ccg tcc aca gac  ctg tgc ctc ccg      4396
Cys  Ala Pro Ala Pro Gly  Ala Pro Ser Thr Asp  Leu Cys Leu Pro
1420                1425                1430

gcc  ctg gat tac ctc agg  cgc tgc tct cag tta  ttg gcc aaa atc      4441
Ala  Leu Asp Tyr Leu Arg  Arg Cys Ser Gln Leu  Leu Ala Lys Ile
1435                1440                1445

tac  aaa atg ccc ttg aag  cca ata ttc ctt agt  ggg aga ctt gcc      4486
Tyr  Lys Met Pro Leu Lys  Pro Ile Phe Leu Ser  Gly Arg Leu Ala
1450                1455                1460

ggc  ttg cct cga aga ctt  cag gaa cag tca gcc  agc agt gag gat      4531
Gly  Leu Pro Arg Arg Leu  Gln Glu Gln Ser Ala  Ser Ser Glu Asp
1465                1470                1475

gga  att gaa tca gtc ctg  tct gat ttt gat gat  gac acc ggt ctg      4576
Gly  Ile Glu Ser Val Leu  Ser Asp Phe Asp Asp  Asp Thr Gly Leu
1480                1485                1490

ata  gaa gtc tgg ata atc  ctg ctg gag cag ctg  aca gcg gct gtg      4621
Ile  Glu Val Trp Ile Ile  Leu Leu Glu Gln Leu  Thr Ala Ala Val
1495                1500                1505

tcc  aat tgt cca cgg cag  cac caa cca cca act  ctg gat tta ctc      4666
Ser  Asn Cys Pro Arg Gln  His Gln Pro Pro Thr  Leu Asp Leu Leu
1510                1515                1520

ttt  gag ctg ttg aga gat  gtg acg aaa aca cca  gga cca ggg ttt      4711
Phe  Glu Leu Leu Arg Asp  Val Thr Lys Thr Pro  Gly Pro Gly Phe
1525                1530                1535

ggt  atc tat gca gtg gtt  cac ctc ctc ctt cct  gtg atg tcc gtt      4756
Gly  Ile Tyr Ala Val Val  His Leu Leu Leu Pro  Val Met Ser Val
1540                1545                1550

tgg  ctc cgc cgg agc cat  aaa gac cat tcc tac  tgg gat atg gcc      4801
Trp  Leu Arg Arg Ser His  Lys Asp His Ser Tyr  Trp Asp Met Ala
1555                1560                1565

tct  gcc aat ttc aag cac  gct att ggt ctg tcc  tgt gag ctg gtg      4846
Ser  Ala Asn Phe Lys His  Ala Ile Gly Leu Ser  Cys Glu Leu Val
1570                1575                1580

gtg  gag cac att caa agc  ttt cta cat tca gat  atc agg tac gag      4891
Val  Glu His Ile Gln Ser  Phe Leu His Ser Asp  Ile Arg Tyr Glu
1585                1590                1595

agc  atg atc aat acc atg  ctg aag gac ctc ttt  gag ttg ctg gtc      4936
Ser  Met Ile Asn Thr Met  Leu Lys Asp Leu Phe  Glu Leu Leu Val
1600                1605                1610

gcc  tgt gtg gcc aag ccc  act gaa acc atc tcc  aga gtg ggc tgc      4981
Ala  Cys Val Ala Lys Pro  Thr Glu Thr Ile Ser  Arg Val Gly Cys
1615                1620                1625

tcc  tgt att aga tac gtc  ctt gtg aca gcg ggc  cct gtg ttc act      5026
Ser  Cys Ile Arg Tyr Val  Leu Val Thr Ala Gly  Pro Val Phe Thr
1630                1635                1640

gag  gag atg tgg agg ctt  gcc tgc tgt gcc ctg  caa gat gcg ttc      5071
Glu  Glu Met Trp Arg Leu  Ala Cys Cys Ala Leu  Gln Asp Ala Phe
1645                1650                1655

tct  gcc aca ctc aag cca  gtg aag gac ctg ctg  ggc tgc ttc cac      5116
Ser  Ala Thr Leu Lys Pro  Val Lys Asp Leu Leu  Gly Cys Phe His
1660                1665                1670

agc  ggc acg gag agc ttc  agc ggg gaa ggc tgc  cag gtg cga gtg      5161
Ser  Gly Thr Glu Ser Phe  Ser Gly Glu Gly Cys  Gln Val Arg Val
```

-continued

```
1675                1680                1685

gcg  gcc ccg tcc tcc tcc  cca agt gcc gag gcc  gag tac tgg cgc      5206
Ala  Ala Pro Ser Ser Ser  Pro Ser Ala Glu Ala  Glu Tyr Trp Arg
1690                1695                1700

atc  cga gcc atg gcc cag  cag gtg ttt atg ctg  gac acc cag tgc      5251
Ile  Arg Ala Met Ala Gln  Gln Val Phe Met Leu  Asp Thr Gln Cys
1705                1710                1715

tca  cca aag aca cca aac  aac ttt gac cac gct  cag tcc tgc cag      5296
Ser  Pro Lys Thr Pro Asn  Asn Phe Asp His Ala  Gln Ser Cys Gln
1720                1725                1730

ctc  att att gag ctg cct  cct gat gaa aaa cca  aat gga cac acc      5341
Leu  Ile Ile Glu Leu Pro  Pro Asp Glu Lys Pro  Asn Gly His Thr
1735                1740                1745

aag  aaa agc gtg tct ttc  agg gaa att gtg gtg  agc ctg ctg tct      5386
Lys  Lys Ser Val Ser Phe  Arg Glu Ile Val Val  Ser Leu Leu Ser
1750                1755                1760

cat  cag gtg tta ctc cag  aac tta tat gac atc  ttg tta gaa gag      5431
His  Gln Val Leu Leu Gln  Asn Leu Tyr Asp Ile  Leu Leu Glu Glu
1765                1770                1775

ttt  gtc aaa ggc ccc tct  cct gga gag gaa aag  acg ata caa gtg      5476
Phe  Val Lys Gly Pro Ser  Pro Gly Glu Glu Lys  Thr Ile Gln Val
1780                1785                1790

cca  gaa gcc aag ctg gct  ggc ttc ctc aga tac  atc tct atg cag      5521
Pro  Glu Ala Lys Leu Ala  Gly Phe Leu Arg Tyr  Ile Ser Met Gln
1795                1800                1805

aac  ttg gca gtc ata ttc  gac ctg ctg ctg gac  tct tat agg act      5566
Asn  Leu Ala Val Ile Phe  Asp Leu Leu Leu Asp  Ser Tyr Arg Thr
1810                1815                1820

gcc  agg gag ttt gac acc  agc ccc ggg ctg aag  tgc ctg ctg aag      5611
Ala  Arg Glu Phe Asp Thr  Ser Pro Gly Leu Lys  Cys Leu Leu Lys
1825                1830                1835

aaa  gtg tct ggc atc ggg  ggc gcc gcc aac ctc  tac cgc cag tct      5656
Lys  Val Ser Gly Ile Gly  Gly Ala Ala Asn Leu  Tyr Arg Gln Ser
1840                1845                1850

gcg  atg agc ttt aac att  tat ttc cac gcc ctg  gtg tgt gct gtt      5701
Ala  Met Ser Phe Asn Ile  Tyr Phe His Ala Leu  Val Cys Ala Val
1855                1860                1865

ctc  acc aat caa gaa acc  atc acg gcc gag caa  gtg aag aag gtc      5746
Leu  Thr Asn Gln Glu Thr  Ile Thr Ala Glu Gln  Val Lys Lys Val
1870                1875                1880

ctt  ttt gag gac gac gag  aga agc acg gat tct  tcc cag cag tgt      5791
Leu  Phe Glu Asp Asp Glu  Arg Ser Thr Asp Ser  Ser Gln Gln Cys
1885                1890                1895

tca  tct gag gat gaa gac  atc ttt gag gaa acc  gcc cag gtc agc      5836
Ser  Ser Glu Asp Glu Asp  Ile Phe Glu Glu Thr  Ala Gln Val Ser
1900                1905                1910

ccc  ccg aga ggc aag gag  aag aga cag tgg cgg  gca cgg atg ccc      5881
Pro  Pro Arg Gly Lys Glu  Lys Arg Gln Trp Arg  Ala Arg Met Pro
1915                1920                1925

ttg  ctc agc gtc cag cct  gtc agc aac gca gat  tgg gtg tgg ctg      5926
Leu  Leu Ser Val Gln Pro  Val Ser Asn Ala Asp  Trp Val Trp Leu
1930                1935                1940

gtc  aag agg ctg cac aag  ctg tgc atg gaa ctg  tgc aac aac tac      5971
Val  Lys Arg Leu His Lys  Leu Cys Met Glu Leu  Cys Asn Asn Tyr
1945                1950                1955

atc  cag atg cac ttg gac  ctg gag aac tgt atg  gag gag cct ccc      6016
Ile  Gln Met His Leu Asp  Leu Glu Asn Cys Met  Glu Glu Pro Pro
1960                1965                1970

atc  ttc aag ggc gac ccg  ttc ttc atc ctg ccc  tcc ttc cag tcc      6061
```

-continued

```
Ile  Phe Lys Gly Asp Pro  Phe Phe Ile Leu Pro  Ser Phe Gln Ser
1975                 1980                 1985

gag  tca tcc acc cca tcc  acc ggg ggc ttc tct  ggg aaa gaa acc      6106
Glu  Ser Ser Thr Pro Ser  Thr Gly Gly Phe Ser  Gly Lys Glu Thr
1990                 1995                 2000

cct  tcc gag gat gac aga  agc cag tcc cgg gag  cac atg ggc gag      6151
Pro  Ser Glu Asp Asp Arg  Ser Gln Ser Arg Glu  His Met Gly Glu
2005                 2010                 2015

tcc  ctg agc ctg aag gcc  ggt ggt ggg gac ctg  ctg ctg ccc ccc      6196
Ser  Leu Ser Leu Lys Ala  Gly Gly Gly Asp Leu  Leu Leu Pro Pro
2020                 2025                 2030

agc  ccc aaa gtg gag aag  aag gat ccc agc cgg  aag aag gag tgg      6241
Ser  Pro Lys Val Glu Lys  Lys Asp Pro Ser Arg  Lys Lys Glu Trp
2035                 2040                 2045

tgg  gag aat gcg ggg aac  aaa atc tac acc atg  gca gcc gac aag      6286
Trp  Glu Asn Ala Gly Asn  Lys Ile Tyr Thr Met  Ala Ala Asp Lys
2050                 2055                 2060

acc  att tca aag ttg atg  acc gaa tac aaa aag  agg aaa cag cag      6331
Thr  Ile Ser Lys Leu Met  Thr Glu Tyr Lys Lys  Arg Lys Gln Gln
2065                 2070                 2075

cac  aac ctg tcc gcg ttc  ccc aaa gag gtc aaa  gtg gag aag aaa      6376
His  Asn Leu Ser Ala Phe  Pro Lys Glu Val Lys  Val Glu Lys Lys
2080                 2085                 2090

gga  gag cca ctg ggt ccc  agg ggc cag gac tcc  ccg ctg ctt cag      6421
Gly  Glu Pro Leu Gly Pro  Arg Gly Gln Asp Ser  Pro Leu Leu Gln
2095                 2100                 2105

cgt  ccc cag cac ttg atg  gac caa ggg caa atg  cgg cat tcc ttc      6466
Arg  Pro Gln His Leu Met  Asp Gln Gly Gln Met  Arg His Ser Phe
2110                 2115                 2120

agc  gca ggc ccc gag ctg  ctg cga cag gac aag  agg ccc cgc tca      6511
Ser  Ala Gly Pro Glu Leu  Leu Arg Gln Asp Lys  Arg Pro Arg Ser
2125                 2130                 2135

ggc  tcc acc ggg agc tcc  ctc agt gtc tcg gtg  aga gac gca gaa      6556
Gly  Ser Thr Gly Ser Ser  Leu Ser Val Ser Val  Arg Asp Ala Glu
2140                 2145                 2150

gca  cag atc cag gca tgg  acc aac atg gtg cta  aca gtt ctc aat      6601
Ala  Gln Ile Gln Ala Trp  Thr Asn Met Val Leu  Thr Val Leu Asn
2155                 2160                 2165

cag  att cag att ctc cca  gac cag acc ttc acg  gcc ctc cag ccc      6646
Gln  Ile Gln Ile Leu Pro  Asp Gln Thr Phe Thr  Ala Leu Gln Pro
2170                 2175                 2180

gca  gtg ttc ccg tgc atc  agt cag ctg acc tgt  cac gtg acc gac      6691
Ala  Val Phe Pro Cys Ile  Ser Gln Leu Thr Cys  His Val Thr Asp
2185                 2190                 2195

atc  aga gtt cgc cag gct  gtg agg gag tgg ctg  ggc agg gtg ggc      6736
Ile  Arg Val Arg Gln Ala  Val Arg Glu Trp Leu  Gly Arg Val Gly
2200                 2205                 2210

cgt  gtc tat gac atc att  gtg tag ccgactcctg ttctactctc            6780
Arg  Val Tyr Asp Ile Ile  Val
2215                 2220

ccaccaaata acagtagtga gggttagagt cctgccaata cagctgttgc attttcccca   6840

ccactagccc cacttaaact actactactg tctcagagaa cagtgtttcc taatgtaaaa   6900

agcctttcca accactgatc agcattgggg ccatactaag gtttgtatct agatgacaca   6960

aacgatattc tgattttgca cattattata gaagaatcta taatccttga tatgtttcta   7020

actcttgaag tatatttccc agtgcttttg cttacagtgt tgtccccaaa tgggtcattt   7080

tcaaggatta ctcatttgaa aacactatat tgatccattt gatccatcat ttaaaaaata   7140
```

-continued

```
aatacaattc ctaaggcaat atctgctggt aagtcaagct gataaacact cagacatcta   7200
gtaccaggga ttattaattg gaggaagatt tatggttatg ggtctggctg ggaagaagac   7260
aactataaat acatattctt gggtgtcata atcaagaaag aggtgacttc tgttgtaaaa   7320
taatccagaa cacttcaaaa ttattcctaa atcattaaga ttttcaggta ttcaccaatt   7380
tccccatgta aggtactgtg ttgtaccttt atttctgtat ttctaaaaga agaaagttct   7440
ttcctagcag ggtttgaagt ctgtggctta tcagcctgtg acacagagta cccagtgaaa   7500
gtggctggta cgtagattgt caagagacat aagaccgacc agccaccctg gctgttcttg   7560
tggtgtttgt ttccatcccc aaggcaaaca aggaaaggaa aggaaagaag aaaaggtgcc   7620
ttagtccttt gttgcacttc catttccatg ccccacaatt gtctgaacat aaggtatagc   7680
atttggtttt taagaaaaca aaacattaag acgcaactca ttttatatca acacgcttgg   7740
aggaaaggga ctcagggaag ggagcaggga gtgtggggtg gggatggatt atgatgaaat   7800
cattttcaat cttaaaatat aatacaacaa tcttgcaaaa ttatggtgtc agttacacaa   7860
gctctagtct caaaatgaaa gtaatggaga aagacactga aatttagaaa attttgtcga   7920
tttaaaatat ttctcctatc taccaagtaa agttacccta tgtttgatgt ctttgcattc   7980
agaccaatat ttcaggtgga tatttctaag tattactaga aaatacgttt gaaagcttta   8040
tcttattatt tacagtattt ttatatttct tacattatcc taatgattga aaactcctca   8100
atcaagctta cttacacaca ttctacagag ttatttaagg catacattat aatctcccag   8160
ccccattcat aatgaataag tcacccttta aatataagac acaaattcta cagtattgaa   8220
ataaggattt aaaggggtat ttgtaaactt tgccctcctt gagaaatatg gaactacctt   8280
agaggttaag aggaaggcag tgttctgact tctttaggtg atctgaaaaa aacaccctta   8340
tcatccagtg taccatctag agatcaccac agaatccatt tttttcccag ttccacaaaa   8400
cactctgttt gccttcagtt tttactcact agacaataat tcaagtttag aaacaggtaa   8460
tcagctattt gatcttaaaa ggcaatgaat tgttgggata tcagtgaact atgttgtata   8520
cttttgaatt tttacatttt ataaatggaa ttgaaagttg gataactgct ttttttaaat   8580
tttccaacag aagtaacacc acagttgctt tgtttctttt tatagcttac ctgaggttca   8640
gttcttcttt gtgaacctgt gagtactcca cagtttactg ggggaaaagg cttcagtaaa   8700
gcagaggcta gaattacagt atttatacat agcaactttt cataaagtag aaaaattcaa   8760
aggaagctgt ctcaatttga gaataccagc tgggcacggt ggctcacgcc tgtaatccca   8820
gcacttactt tgggaggcca aggtgggcag ataacctgcg gtcaggagtt tgagaccagg   8880
ctggacaaca tggtgaaacc tcgtctctac taaaaataca aaaattagcc aggtgtggta   8940
ggatgcacct gtaatcccag ctacttagga ggccgagaca ggagaatcgc tcgaacccag   9000
gaggcggacg ttgcagtgag ccaagattgc accattgcac tccagactgg gtgacaagag   9060
tgaaactcca tctaaaaaaa aaaaaaaaaa aaagtgaata ctgtatccca aagtatgtta   9120
gttgtttgtt tggaaatcag cattctcccc gatgctctat tatgggatcc aaaattcttg   9180
aacataagtt taccctgtac tgtgtccaaa cactgttcta gttctagcct gattatgggt   9240
cccaagaata aaaggatgag taggtgtaca gagctcttga cctacaattt tttaagagtg   9300
ttttggtacc ttcccattgt cttctctata actcagtcct aacatactct gcactcgagt   9360
taccagccat ccacactgac atcagatttc aaccagaacc atcactgagt gacagcagta   9420
cttctcagag gtatttgcag cttgatgcaa agtagtctct aatgagtagg cattcaggtg   9480
gttcttccca gcaggtggag aagaaaggga ggagatgaag aacactgaga ggggagtggc   9540
```

-continued

```
accttcccag gctgcccagc tcagtctctt gccctgttcc tgtgactcag ctgcccactc   9600
ccccaacttt gtttccctcc ctcccagtct ctgaaagtgt caggtgtttc tctcctcaca   9660
gtctcttttg cagcaacagt aagacaaaat tcaaggcagc cttttaaagt tacgaacagt   9720
tattagcatg tatttacaga cctaagcaga atgagagttt atacattgtt tttagttgcc   9780
tgtatttata gccaaaagta tattacctta aagttgagat ctttctcttc ttttcctaaa   9840
ttttggtaaa gtgtgcttca tgaaacaaac atctggaaaa ctccaagtat aagagaccct   9900
ggactgatga tggcccagcc aagtatatgg agggacagag ttctctctgt cattaatgag   9960
gacatcggtt ttcacaattg aacctcatgc actgtccaca gcatctcacc tagctcctgt  10020
atctcctgat ctgcttttaa aaatagttag ttaggctgcc tttttacacc accttctctc  10080
tctccccttg tggtaatttt ccagccttcc ccatagatat aaaactagaa cacctttatg  10140
atttggggtc tatgtaatga ctgaccgata agaacccagg cagatgctaa catacttaac  10200
agctcgcatt aaaatacttt aaatcaggcg tgatggctca ttcctgtaat ctcaagcact  10260
ttgggaggct aaggtgggtg gatctcttga ggtcaggagt tcgagaccaa cctggccaac  10320
gtggtgaaac cccgtctcta ctaaaaatac aaaattagcc gggcatggtg gcagctgcct  10380
gtaatcccag ctactcggga agctgaggca ggagaattgc ttgaacctgg gaggtgggga  10440
ttgcagtcag ccaagattgt tctgcagcat gggtgacaaa gtgagacttc gtctcaagta  10500
aataaaacta aaatttttaa atcaaacatg acaaaaatgt taatataatt cagaagtacc  10560
ttgaaattga aacatatttg tgcaatgatc attaggcttt ttgtccttgt tgttttaaaa  10620
tgaggcttat acagagtgag ttgagagtca agtagccttc gctgtgagac ggtaatgcag  10680
ttatataata gataccottg actttgccag attcatcaca atactgctta tacaggaaag  10740
ttttctcaga aaggaaaatc cattagtatc agtcccatca agccaaacag aatgaagacc  10800
tttgatagta atagcaagag gttacaaata gcagggagga ggcgagtagt gaatgtcact  10860
gtgattgcaa acccttacct gtattatcac acgtagtcct cacaacaacc ttgtgagaca  10920
agtgttgtgt tcctcatttt ttcagagggg aacacagacc cagagaggtt aagaaatttg  10980
cccaagataa caagtaaaag gcaaagttgg ttgcaaaaga ggtgtttctg aattcaaggg  11040
ccatactctc tctctgacaa catgctctaa gtccatagag taagcactct agtatgaaaa  11100
aaagtttcaa ggaacgaggc catgaaaatg agactatttg acatctcaga tctgtctggg  11160
atgttatgga ggtttttaaa aataaagttg aaaaaagaaa atgaatcatg tttatacata  11220
aaaaaatcac atgtaacaca tttcaagtgt ttgaaaataa aaccaaaatc taaactttag  11280
tcttcaagca gacattcagt gttactttag aaaactcact gaattaggtg gaaatgatgg  11340
aataatacta ttcatggcca gctattaaca cagaagaaca tggcagtgtg tgtctggaac  11400
ggcatgcaca atttgtaaac ctttttcaaa tatcatttaa tcaactcaga ataaagtgcc  11460
ctgtagccaa cagtgcctct ttacttgctt ctctgggaaa tacatggtac taaattagta  11520
gcacaaagtt tgggaatatg caaaataatg gataaccatt tttcaaaatg tacattctct  11580
gaagaggaag cagctggttg gacaggattt cttgaagagc caggtgctaa gggcatcagg  11640
tcgacatcca tagtaaccat gtgccataac atctacacat ttccacttgt tttacagaca  11700
aggtaacagg cagaaggaaa atccagagtc ttgcagtaag cagatgacaa aacttcaata  11760
tgcttgggca ccacttaggt gaccccaggg agatttagtg tggccttagg aaagcaaaag  11820
agcacttttt attggaaata tgagcttgtc actgggaaag atttgtaaaa ttgatcaaga  11880
```

-continued

```
acttgattta taattatgcc tcaaaaaaaa aagttctcat ttagtagtgg agcaatctag  11940
aaaacatacc tttttgttt gtttggaaga tcctctttcc ctggctgtat tgtagtgttt  12000
gctatttgat gtggaaataa ctaataactt aagattttgg aacagaacac cctttagatt  12060
tccaaaacac aattcttatt tcagggaaga cagaccaaaa atatctcctg agatcattgg  12120
tttctttata aattgtggta ccactccatc attgaagaga aaccactacc acaccactag  12180
caccatacag aacctttttct ctgtatcttt gtacaatact acaaaggggt accagggagg  12240
agagagtggc tgaccacttt agtgacaaaa cagcactcca ctgctggtga atcccatcta  12300
attatggtcc ttccaccctt ttcaaccacc aacaactgtt cgtactgtta attcctatcc  12360
tgaaggttta accagtggtt gtctagtatc ttctgtcttt agaacagtgg ttctcaaact  12420
ttagtacaca tcagcatcac ctggagggcc tttttttaaa ataagacaca gattgctggg  12480
ctcatggtca gagttcccag ttaagtaaat caggaaattt gtatttctaa caagtttata  12540
ggtgaggcca atactgctgt tttgggaact atgctttgag aaccactgcc ttgaaaaaat  12600
ttccaacttc tacctttaag atcagcctga cttatcaaac gctagagaaa aactgaatct  12660
acccttgggc agatgacttg ggattggatt ctatacagca gtcttgctca atcttcccag  12720
tttccagttt tattatacca acaattggtt tttacaagct agaagacaat gaatgtataa  12780
gttctatgga acagtgagat aaatctaagc ttcttgtctt tgtatttaga aacattgatt  12840
ctatggatga tcatttgtat catgttgacc ctttgacttg tactgaaggt gattttaaat  12900
ttaagtatgt agtgtttgaa tttcttccat ccatgtcgtt ttaatgagat gtttccatgt  12960
cagctccttt acagccttgg ctcctggctt acagattttt gaatagttgt ttgcttgcca  13020
gttgttttac atctttcatt ggccaccaaa atattagcca tttgagatga gatgagacta  13080
cttgttgtac cttcatcttt catttaattt tctggcgtaa attaacattt taatttcata  13140
tatatctgta aagagtctac ccaaaggctt cacggaaatt tgcaaaatga actaattccc  13200
ttttaagcag caggtgtgcc tgttttttgac ttttcagtaa atatgttgtt tgtgcacata  13260
tctacatggt ggagaccata ttcattattt catcttccaa ataatgggaa aaatataaaa  13320
gtgaatcagt gtgctttggg aattcagtga aatcatgtta actcatatag agggggcctt  13380
agtttatctc ttctttactg aattaattag ttttggaaat tcttttacca ttaaaaaaaa  13440
ttaaggacca tacagagaat gatttaagaa aaaacaagtc acttaaaaat catcacctat  13500
ttataaactg tattaattac acataatgct tattgattca atgaggtttc tctaaagact  13560
tctgcttaat aaatatgctg acttcattta aattagttta gactattgta ggaatggaag  13620
gaaatgatta tatttactag aattagtgag atcagaaagc atatcagaat gttgatgata  13680
tcaaggagac aatctacaga gtttttgcct ctgtggatgg aaataagggt gttttttttt  13740
ggtttttttt ttactttagt ttcccataat ttttggaaat tatgtgtgca tttagttctt  13800
ttagtaacac tgattttaaa attaaatttc aaaagtcaat ctctaagagt aatttatttt  13860
tgttttacca accagtgcca aaaaggagag gagggaatcc aaaagccaat cttttgaacc  13920
aatgtgtaaa agattatgtt ttttcttaaa gttagggagg ctcgggccct gacactgcca  13980
gccccagtga gcatccctgg ctacctcggg attatgtgca agctgctttg tcctacattt  14040
ctttcatctg gttcttattg ggagtgcttc tctctaataa aaattgattt cccacaaaat  14100
aggcaaagct gaacaaagat gaatgctttt gataagttgg gtttcacttc agttgaaaca  14160
atgtgataga atatccaggt gtggcatgat ggggcaggag gaggtgccta gagggaaaag  14220
ttatttttgt ttcttagtgt tgtgttgtgg ggatgggaca gataagaata agatgtttat  14280
```

-continued

```
tgccctaatc atgctaagag actattattc aatatgcttt tcccgctttt ctaagaggaa  14340

taaacttaga caaattacat tataaacagt tcccctacta ctatctccca ctctagataa  14400

agccagtggg tggtatgggt ccttttattc cttatagtat tatgccaaag aatcaactta  14460

ttttcattga agattataaa taaatgaagc ttgttatagc cataatgatt tgagtcagta  14520

taccatttta cctataaaat gcaaaattca tccttgcaac cccattcacc aggagccttg  14580

aagcattttg tttactccaa aggccttgtc aaggaagcat aattttttgt tttgccttct  14640

tatttagtca gtttggtcat atttacttaa aaaaacaaac tgaaaatcac actcctttat  14700

atgttgatat aactgatttt atagaatctg tctgttcttt gtttaacagg tctctgtaag  14760

caagcttgca agtgtatttt gtgtacattt tatctgaggt ggaaatgaaa attctaaaga  14820

gaaaatattt taaaagatat tgtatttatg ttgcttgtgt tgtagaataa agattcaaat  14880

gcattaaaaa tctggtacat gaaacaattg tgtttactga ataaatatat ataaatatca  14940

aaaaagcact aaaaa                                                   14955
```

```
<210> SEQ ID NO 30
<211> LENGTH: 2221
<212> TYPE: PRT
<213> ORGANISM: Homo sapiens

<400> SEQUENCE: 30

Met Glu Glu Ile Leu Arg Lys Leu Gln Lys Glu Ala Ser Gly Ser Lys
1               5                   10                  15

Tyr Lys Ala Ile Lys Glu Ser Cys Thr Trp Ala Leu Glu Thr Leu Gly
            20                  25                  30

Gly Leu Asp Thr Ile Ala Lys Ile Pro Pro His Val Leu Arg Glu Lys
        35                  40                  45

Cys Leu Leu Pro Leu Gln Leu Ala Leu Glu Ser Lys Asn Val Lys Leu
    50                  55                  60

Ala Gln His Ala Leu Ala Gly Met Gln Lys Leu Leu Ser Glu Glu Arg
65                  70                  75                  80

Phe Val Ser Met Glu Thr Asp Ser Asp Glu Lys Gln Leu Leu Asn Gln
                85                  90                  95

Ile Leu Asn Ala Val Lys Val Thr Pro Ser Leu Asn Glu Asp Leu Gln
            100                 105                 110

Val Glu Val Met Lys Val Leu Leu Cys Ile Thr Tyr Thr Pro Thr Phe
        115                 120                 125

Asp Leu Asn Gly Ser Ala Val Leu Lys Ile Ala Glu Val Cys Ile Glu
    130                 135                 140

Thr Tyr Ile Ser Ser Cys His Gln Arg Ser Ile Asn Thr Ala Val Arg
145                 150                 155                 160

Ala Thr Leu Ser Gln Met Leu Ser Asp Leu Thr Leu Gln Leu Arg Gln
                165                 170                 175

Arg Gln Glu Asn Thr Ile Ile Glu Asn Pro Asp Val Pro Gln Asp Phe
            180                 185                 190

Gly Asn Gln Gly Ser Thr Val Glu Ser Leu Cys Asp Asp Val Val Ser
        195                 200                 205

Val Leu Thr Val Leu Cys Glu Lys Leu Gln Ala Ala Ile Lys Cys Pro
    210                 215                 220

Ser Phe Leu Thr Met Ala Cys Trp Asn Ser Gly Ala Gly Thr Gln Ile
225                 230                 235                 240

Thr Ile Leu Thr Glu Gly Ser Ser Thr Asn Cys Ser Asp Pro Ile Trp
```

-continued

```
                245                 250                 255

Asp Thr Thr Ala Ser Pro Val Ala Ala Ser Asp Ser Gln Gln Leu Gln
            260                 265                 270

Leu Leu Tyr Leu Glu Cys Ile Leu Ser Val Leu Ser Ser Ser Ser Ser
        275                 280                 285

Ser Met His Leu His Arg Arg Phe Thr Asp Leu Ile Trp Lys Asn Leu
    290                 295                 300

Cys Pro Ala Leu Ile Val Ile Leu Gly Asn Pro Ile His Asp Lys Thr
305                 310                 315                 320

Ile Thr Ser Ala His Thr Ser Ser Thr Ser Thr Ser Leu Glu Ser Asp
                325                 330                 335

Ser Ala Ser Pro Gly Val Ser Asp His Gly Arg Gly Ser Gly Cys Ser
            340                 345                 350

Cys Thr Ala Pro Ala Leu Ser Gly Pro Val Ala Arg Thr Ile Tyr Tyr
        355                 360                 365

Ile Ala Ala Glu Leu Val Arg Leu Val Gly Ser Val Asp Ser Met Lys
    370                 375                 380

Pro Val Leu Gln Ser Leu Tyr His Arg Val Leu Leu Tyr Pro Pro Pro
385                 390                 395                 400

Gln His Arg Val Glu Ala Ile Lys Ile Met Lys Glu Ile Leu Gly Ser
                405                 410                 415

Pro Gln Arg Leu Cys Asp Leu Ala Gly Pro Ser Ser Thr Glu Ser Glu
            420                 425                 430

Ser Arg Lys Arg Ser Ile Ser Lys Arg Lys Ser His Leu Asp Leu Leu
        435                 440                 445

Lys Leu Ile Met Asp Gly Met Thr Glu Ala Cys Ile Lys Gly Gly Ile
    450                 455                 460

Glu Ala Cys Tyr Ala Ala Val Ser Cys Val Cys Thr Leu Leu Gly Ala
465                 470                 475                 480

Leu Asp Glu Leu Ser Gln Gly Lys Gly Leu Ser Glu Gly Gln Val Gln
                485                 490                 495

Leu Leu Leu Leu Arg Leu Glu Glu Leu Lys Asp Gly Ala Glu Trp Ser
            500                 505                 510

Arg Asp Ser Met Glu Ile Asn Glu Ala Asp Phe Arg Trp Gln Arg Arg
        515                 520                 525

Val Leu Ser Ser Glu His Thr Pro Trp Glu Ser Gly Asn Glu Arg Ser
    530                 535                 540

Leu Asp Ile Ser Ile Ser Val Thr Thr Asp Thr Gly Gln Thr Thr Leu
545                 550                 555                 560

Glu Gly Glu Leu Gly Gln Thr Thr Pro Glu Asp His Ser Gly Asn His
                565                 570                 575

Lys Asn Ser Leu Lys Ser Pro Ala Ile Pro Glu Gly Lys Glu Thr Leu
            580                 585                 590

Ser Lys Val Leu Glu Thr Glu Ala Val Asp Gln Pro Asp Val Val Gln
        595                 600                 605

Arg Ser His Thr Val Pro Tyr Pro Asp Ile Thr Asn Phe Leu Ser Val
    610                 615                 620

Asp Cys Arg Thr Arg Ser Tyr Gly Ser Arg Tyr Ser Glu Ser Asn Phe
625                 630                 635                 640

Ser Val Asp Asp Gln Asp Leu Ser Arg Thr Glu Phe Asp Ser Cys Asp
                645                 650                 655

Gln Tyr Ser Met Ala Ala Glu Lys Asp Ser Gly Arg Ser Asp Val Ser
            660                 665                 670
```

-continued

```
Asp Ile Gly Ser Asp Asn Cys Ser Leu Ala Asp Glu Glu Gln Thr Pro
        675                 680                 685

Arg Asp Cys Leu Gly His Arg Ser Leu Arg Thr Ala Ala Leu Ser Leu
    690                 695                 700

Lys Leu Leu Lys Asn Gln Glu Ala Asp Gln His Ser Ala Arg Leu Phe
705                 710                 715                 720

Ile Gln Ser Leu Glu Gly Leu Leu Pro Arg Leu Leu Ser Leu Ser Asn
                725                 730                 735

Val Glu Glu Val Asp Thr Ala Leu Gln Asn Phe Ala Ser Thr Phe Cys
            740                 745                 750

Ser Gly Met Met His Ser Pro Gly Phe Asp Gly Asn Ser Ser Leu Ser
        755                 760                 765

Phe Gln Met Leu Met Asn Ala Asp Ser Leu Tyr Thr Ala Ala His Cys
    770                 775                 780

Ala Leu Leu Leu Asn Leu Lys Leu Ser His Gly Asp Tyr Tyr Arg Lys
785                 790                 795                 800

Arg Pro Thr Leu Ala Pro Gly Val Met Lys Asp Phe Met Lys Gln Val
                805                 810                 815

Gln Thr Ser Gly Val Leu Met Val Phe Ser Gln Ala Trp Ile Glu Glu
            820                 825                 830

Leu Tyr His Gln Val Leu Asp Arg Asn Met Leu Gly Glu Ala Gly Tyr
        835                 840                 845

Trp Gly Ser Pro Glu Asp Asn Ser Leu Pro Leu Ile Thr Met Leu Thr
    850                 855                 860

Asp Ile Asp Gly Leu Glu Ser Ser Ala Ile Gly Gly Gln Leu Met Ala
865                 870                 875                 880

Ser Ala Ala Thr Glu Ser Pro Phe Ala Gln Ser Arg Arg Ile Asp Asp
                885                 890                 895

Ser Thr Val Ala Gly Val Ala Phe Ala Arg Tyr Ile Leu Val Gly Cys
            900                 905                 910

Trp Lys Asn Leu Ile Asp Thr Leu Ser Thr Pro Leu Thr Gly Arg Met
        915                 920                 925

Ala Gly Ser Ser Lys Gly Leu Ala Phe Ile Leu Gly Ala Glu Gly Ile
    930                 935                 940

Lys Glu Gln Asn Gln Lys Glu Arg Asp Ala Ile Cys Met Ser Leu Asp
945                 950                 955                 960

Gly Leu Arg Lys Ala Ala Arg Leu Ser Cys Ala Leu Gly Val Ala Ala
                965                 970                 975

Asn Cys Ala Ser Ala Leu Ala Gln Met Ala Ala Ala Ser Cys Val Gln
            980                 985                 990

Glu Glu Lys Glu Glu Arg Glu Ala  Gln Glu Pro Ser Asp  Ala Ile Thr
        995                 1000                1005

Gln Val  Lys Leu Lys Val Glu  Gln Lys Leu Glu Gln  Ile Gly Lys
    1010                1015                1020

Val Gln  Gly Val Trp Leu His  Thr Ala His Val Leu  Cys Met Glu
    1025                1030                1035

Ala Ile  Leu Ser Val Gly Leu  Glu Met Gly Ser His  Asn Pro Asp
    1040                1045                1050

Cys Trp  Pro His Val Phe Arg  Val Cys Glu Tyr Val  Gly Thr Leu
    1055                1060                1065

Glu His  Asn His Phe Ser Asp  Gly Ala Ser Gln Pro  Pro Leu Thr
    1070                1075                1080
```

-continued

```
Ile Ser  Gln Pro Gln Lys Ala  Thr Gly Ser Ala Gly  Leu Leu Gly
    1085                 1090                 1095

Asp Pro  Glu Cys Glu Gly Ser  Pro Pro Glu His Ser  Pro Glu Gln
    1100                 1105                 1110

Gly Arg  Ser Leu Ser Thr Ala  Pro Val Val Gln Pro  Leu Ser Ile
    1115                 1120                 1125

Gln Asp  Leu Val Arg Glu Gly  Ser Arg Gly Arg Ala  Ser Asp Phe
    1130                 1135                 1140

Arg Gly  Gly Ser Leu Met Ser  Gly Ser Ser Ala Ala  Lys Val Val
    1145                 1150                 1155

Leu Thr  Leu Ser Thr Gln Ala  Asp Arg Leu Phe Glu  Asp Ala Thr
    1160                 1165                 1170

Asp Lys  Leu Asn Leu Met Ala  Leu Gly Gly Phe Leu  Tyr Gln Leu
    1175                 1180                 1185

Lys Lys  Ala Ser Gln Ser Gln  Leu Phe His Ser Val  Thr Asp Thr
    1190                 1195                 1200

Val Asp  Tyr Ser Leu Ala Met  Pro Gly Glu Val Lys  Ser Thr Gln
    1205                 1210                 1215

Asp Arg  Lys Ser Ala Leu His  Leu Phe Arg Leu Gly  Asn Ala Met
    1220                 1225                 1230

Leu Arg  Ile Val Arg Ser Lys  Ala Arg Pro Leu Leu  His Val Met
    1235                 1240                 1245

Arg Cys  Trp Ser Leu Val Ala  Pro His Leu Val Glu  Ala Ala Cys
    1250                 1255                 1260

His Lys  Glu Arg His Val Ser  Gln Lys Ala Val Ser  Phe Ile His
    1265                 1270                 1275

Asp Ile  Leu Thr Glu Val Leu  Thr Asp Trp Asn Glu  Pro Pro His
    1280                 1285                 1290

Phe His  Phe Asn Glu Ala Leu  Phe Arg Pro Phe Glu  Arg Ile Met
    1295                 1300                 1305

Gln Leu  Glu Leu Cys Asp Glu  Asp Val Gln Asp Gln  Val Val Thr
    1310                 1315                 1320

Ser Ile  Gly Glu Leu Val Glu  Val Cys Ser Thr Gln  Ile Gln Ser
    1325                 1330                 1335

Gly Trp  Arg Pro Leu Phe Ser  Ala Leu Glu Thr Val  His Gly Gly
    1340                 1345                 1350

Asn Lys  Ser Glu Met Lys Glu  Tyr Leu Val Gly Asp  Tyr Ser Met
    1355                 1360                 1365

Gly Lys  Gly Gln Ala Pro Val  Phe Asp Val Phe Glu  Ala Phe Leu
    1370                 1375                 1380

Asn Thr  Asp Asn Ile Gln Val  Phe Ala Asn Ala Ala  Thr Ser Tyr
    1385                 1390                 1395

Ile Met  Cys Leu Met Lys Phe  Val Lys Gly Leu Gly  Glu Val Asp
    1400                 1405                 1410

Cys Lys  Glu Ile Gly Asp Cys  Ala Pro Ala Pro Gly  Ala Pro Ser
    1415                 1420                 1425

Thr Asp  Leu Cys Leu Pro Ala  Leu Asp Tyr Leu Arg  Arg Cys Ser
    1430                 1435                 1440

Gln Leu  Leu Ala Lys Ile Tyr  Lys Met Pro Leu Lys  Pro Ile Phe
    1445                 1450                 1455

Leu Ser  Gly Arg Leu Ala Gly  Leu Pro Arg Arg Leu  Gln Glu Gln
    1460                 1465                 1470

Ser Ala  Ser Ser Glu Asp Gly  Ile Glu Ser Val Leu  Ser Asp Phe
```

-continued

```
    1475                1480                1485

Asp Asp  Asp Thr Gly Leu Ile  Glu Val Trp Ile Ile  Leu Leu Glu
    1490                1495                1500

Gln Leu  Thr Ala Ala Val Ser  Asn Cys Pro Arg Gln  His Gln Pro
    1505                1510                1515

Pro Thr  Leu Asp Leu Leu Phe  Glu Leu Leu Arg Asp  Val Thr Lys
    1520                1525                1530

Thr Pro  Gly Pro Gly Phe Gly  Ile Tyr Ala Val Val  His Leu Leu
    1535                1540                1545

Leu Pro  Val Met Ser Val Trp  Leu Arg Arg Ser His  Lys Asp His
    1550                1555                1560

Ser Tyr  Trp Asp Met Ala Ser  Ala Asn Phe Lys His  Ala Ile Gly
    1565                1570                1575

Leu Ser  Cys Glu Leu Val Val  Glu His Ile Gln Ser  Phe Leu His
    1580                1585                1590

Ser Asp  Ile Arg Tyr Glu Ser  Met Ile Asn Thr Met  Leu Lys Asp
    1595                1600                1605

Leu Phe  Glu Leu Leu Val Ala  Cys Val Ala Lys Pro  Thr Glu Thr
    1610                1615                1620

Ile Ser  Arg Val Gly Cys Ser  Cys Ile Arg Tyr Val  Leu Val Thr
    1625                1630                1635

Ala Gly  Pro Val Phe Thr Glu  Glu Met Trp Arg Leu  Ala Cys Cys
    1640                1645                1650

Ala Leu  Gln Asp Ala Phe Ser  Ala Thr Leu Lys Pro  Val Lys Asp
    1655                1660                1665

Leu Leu  Gly Cys Phe His Ser  Gly Thr Glu Ser Phe  Ser Gly Glu
    1670                1675                1680

Gly Cys  Gln Val Arg Val Ala  Ala Pro Ser Ser Ser  Pro Ser Ala
    1685                1690                1695

Glu Ala  Glu Tyr Trp Arg Ile  Arg Ala Met Ala Gln  Gln Val Phe
    1700                1705                1710

Met Leu  Asp Thr Gln Cys Ser  Pro Lys Thr Pro Asn  Asn Phe Asp
    1715                1720                1725

His Ala  Gln Ser Cys Gln Leu  Ile Ile Glu Leu Pro  Pro Asp Glu
    1730                1735                1740

Lys Pro  Asn Gly His Thr Lys  Lys Ser Val Ser Phe  Arg Glu Ile
    1745                1750                1755

Val Val  Ser Leu Leu Ser His  Gln Val Leu Leu Gln  Asn Leu Tyr
    1760                1765                1770

Asp Ile  Leu Leu Glu Glu Phe  Val Lys Gly Pro Ser  Pro Gly Glu
    1775                1780                1785

Glu Lys  Thr Ile Gln Val Pro  Glu Ala Lys Leu Ala  Gly Phe Leu
    1790                1795                1800

Arg Tyr  Ile Ser Met Gln Asn  Leu Ala Val Ile Phe  Asp Leu Leu
    1805                1810                1815

Leu Asp  Ser Tyr Arg Thr Ala  Arg Glu Phe Asp Thr  Ser Pro Gly
    1820                1825                1830

Leu Lys  Cys Leu Leu Lys Lys  Val Ser Gly Ile Gly  Gly Ala Ala
    1835                1840                1845

Asn Leu  Tyr Arg Gln Ser Ala  Met Ser Phe Asn Ile  Tyr Phe His
    1850                1855                1860

Ala Leu  Val Cys Ala Val Leu  Thr Asn Gln Glu Thr  Ile Thr Ala
    1865                1870                1875
```

-continued

Glu Gln Val Lys Lys Val Leu Phe Glu Asp Asp Glu Arg Ser Thr
1880 1885 1890

Asp Ser Ser Gln Gln Cys Ser Ser Glu Asp Glu Asp Ile Phe Glu
1895 1900 1905

Glu Thr Ala Gln Val Ser Pro Pro Arg Gly Lys Glu Lys Arg Gln
1910 1915 1920

Trp Arg Ala Arg Met Pro Leu Leu Ser Val Gln Pro Val Ser Asn
1925 1930 1935

Ala Asp Trp Val Trp Leu Val Lys Arg Leu His Lys Leu Cys Met
1940 1945 1950

Glu Leu Cys Asn Asn Tyr Ile Gln Met His Leu Asp Leu Glu Asn
1955 1960 1965

Cys Met Glu Glu Pro Pro Ile Phe Lys Gly Asp Pro Phe Phe Ile
1970 1975 1980

Leu Pro Ser Phe Gln Ser Glu Ser Ser Thr Pro Ser Thr Gly Gly
1985 1990 1995

Phe Ser Gly Lys Glu Thr Pro Ser Glu Asp Asp Arg Ser Gln Ser
2000 2005 2010

Arg Glu His Met Gly Glu Ser Leu Ser Leu Lys Ala Gly Gly Gly
2015 2020 2025

Asp Leu Leu Leu Pro Pro Ser Pro Lys Val Glu Lys Lys Asp Pro
2030 2035 2040

Ser Arg Lys Lys Glu Trp Trp Glu Asn Ala Gly Asn Lys Ile Tyr
2045 2050 2055

Thr Met Ala Ala Asp Lys Thr Ile Ser Lys Leu Met Thr Glu Tyr
2060 2065 2070

Lys Lys Arg Lys Gln Gln His Asn Leu Ser Ala Phe Pro Lys Glu
2075 2080 2085

Val Lys Val Glu Lys Lys Gly Glu Pro Leu Gly Pro Arg Gly Gln
2090 2095 2100

Asp Ser Pro Leu Leu Gln Arg Pro Gln His Leu Met Asp Gln Gly
2105 2110 2115

Gln Met Arg His Ser Phe Ser Ala Gly Pro Glu Leu Leu Arg Gln
2120 2125 2130

Asp Lys Arg Pro Arg Ser Gly Ser Thr Gly Ser Ser Leu Ser Val
2135 2140 2145

Ser Val Arg Asp Ala Glu Ala Gln Ile Gln Ala Trp Thr Asn Met
2150 2155 2160

Val Leu Thr Val Leu Asn Gln Ile Gln Ile Leu Pro Asp Gln Thr
2165 2170 2175

Phe Thr Ala Leu Gln Pro Ala Val Phe Pro Cys Ile Ser Gln Leu
2180 2185 2190

Thr Cys His Val Thr Asp Ile Arg Val Arg Gln Ala Val Arg Glu
2195 2200 2205

Trp Leu Gly Arg Val Gly Arg Val Tyr Asp Ile Ile Val
2210 2215 2220

<210> SEQ ID NO 31
<211> LENGTH: 1522
<212> TYPE: PRT
<213> ORGANISM: Homo sapiens

<400> SEQUENCE: 31

Met Ser Val Arg Leu Pro Gln Ser Ile Asp Arg Leu Ser Ser Leu Ser

-continued

```
1               5                   10                  15

Ser Leu Gly Asp Ser Ala Pro Glu Arg Lys Ser Pro Ser His His Arg
            20                  25                  30

Gln Pro Ser Asp Ala Ser Glu Thr Thr Gly Leu Val Gln Arg Cys Val
        35                  40                  45

Ile Ile Gln Lys Asp Gln His Gly Phe Gly Phe Thr Val Ser Gly Asp
    50                  55                  60

Arg Ile Val Leu Val Gln Ser Val Arg Pro Gly Gly Ala Ala Met Lys
65                  70                  75                  80

Ala Gly Val Lys Glu Gly Asp Arg Ile Ile Lys Val Asn Gly Thr Met
                85                  90                  95

Val Thr Asn Ser Ser His Leu Glu Val Val Lys Leu Ile Lys Ser Gly
            100                 105                 110

Ala Tyr Val Ala Leu Thr Leu Leu Gly Ser Ser Pro Ser Ser Met Gly
        115                 120                 125

Ile Ser Gly Leu Gln Gln Asp Pro Ser Pro Ala Gly Ala Pro Arg Ile
    130                 135                 140

Thr Ser Val Ile Pro Ser Pro Pro Pro Pro Pro Pro Leu Pro Pro Pro
145                 150                 155                 160

Gln Arg Ile Thr Gly Pro Lys Pro Leu Gln Asp Pro Glu Val Gln Lys
                165                 170                 175

His Ala Thr Gln Ile Leu Arg Asn Met Leu Arg Gln Glu Glu Lys Glu
            180                 185                 190

Leu Gln Asp Ile Leu Pro Leu Tyr Gly Asp Thr Ser Gln Arg Pro Ser
        195                 200                 205

Glu Gly Arg Leu Ser Leu Asp Ser Gln Glu Gly Asp Ser Gly Leu Asp
    210                 215                 220

Ser Gly Thr Glu Arg Phe Pro Ser Leu Ser Glu Ser Leu Met Asn Arg
225                 230                 235                 240

Asn Ser Val Leu Ser Asp Pro Gly Leu Asp Ser Pro Arg Thr Ser Pro
                245                 250                 255

Val Ile Met Ala Arg Val Ala Gln His His Arg Arg Gln Gly Ser Asp
            260                 265                 270

Ala Ala Val Pro Ser Thr Gly Asp Gln Gly Val Asp Gln Ser Pro Lys
        275                 280                 285

Pro Leu Ile Ile Gly Pro Glu Glu Asp Tyr Asp Pro Gly Tyr Phe Asn
    290                 295                 300

Asn Glu Ser Asp Ile Ile Phe Gln Asp Leu Glu Lys Leu Lys Ser Arg
305                 310                 315                 320

Pro Ala His Leu Gly Val Phe Leu Arg Tyr Ile Phe Ser Gln Ala Asp
                325                 330                 335

Pro Ser Pro Leu Leu Phe Tyr Leu Cys Ala Glu Val Tyr Gln Gln Ala
            340                 345                 350

Ser Pro Lys Asp Ser Arg Ser Leu Gly Lys Asp Ile Trp Asn Ile Phe
        355                 360                 365

Leu Glu Lys Asn Ala Pro Leu Arg Val Lys Ile Pro Glu Met Leu Gln
    370                 375                 380

Ala Glu Ile Asp Ser Arg Leu Arg Asn Ser Glu Asp Ala Arg Gly Val
385                 390                 395                 400

Leu Cys Glu Ala Gln Glu Ala Ala Met Pro Glu Ile Gln Glu Gln Ile
                405                 410                 415

His Asp Tyr Arg Thr Lys Arg Thr Leu Gly Leu Gly Ser Leu Tyr Gly
            420                 425                 430
```

-continued

```
Glu Asn Asp Leu Leu Asp Leu Asp Gly Asp Pro Leu Arg Glu Arg Gln
        435                 440                 445

Val Ala Glu Lys Gln Leu Ala Ala Leu Gly Asp Ile Leu Ser Lys Tyr
    450                 455                 460

Glu Glu Asp Arg Ser Ala Pro Met Asp Phe Ala Leu Asn Thr Tyr Met
465                 470                 475                 480

Ser His Ala Gly Ile Arg Leu Arg Glu Ala Arg Pro Ser Asn Thr Ala
                485                 490                 495

Glu Lys Ala Gln Ser Ala Pro Asp Lys Asp Lys Trp Leu Pro Phe Phe
            500                 505                 510

Pro Lys Thr Lys Lys Ser Ser Asn Ser Lys Lys Glu Lys Asp Ala Leu
        515                 520                 525

Glu Asp Lys Lys Arg Asn Pro Ile Leu Lys Tyr Ile Gly Lys Pro Lys
    530                 535                 540

Ser Ser Ser Gln Ser Thr Phe His Ile Pro Leu Ser Pro Val Glu Val
545                 550                 555                 560

Lys Pro Gly Asn Val Arg Asn Ile Ile Gln His Phe Glu Asn Asn Gln
                565                 570                 575

Gln Tyr Asp Ala Pro Glu Pro Gly Thr Gln Arg Leu Ser Thr Gly Ser
            580                 585                 590

Phe Pro Glu Asp Leu Leu Glu Ser Asp Ser Ser Arg Ser Glu Ile Arg
        595                 600                 605

Leu Gly Arg Ser Glu Ser Leu Lys Gly Arg Glu Glu Met Lys Arg Ser
    610                 615                 620

Arg Lys Ala Glu Asn Val Pro Arg Ser Arg Ser Asp Val Asp Met Asp
625                 630                 635                 640

Ala Ala Ala Glu Ala Thr Arg Leu His Gln Ser Ala Ser Ser Ser Thr
                645                 650                 655

Ser Ser Leu Ser Thr Arg Ser Leu Glu Asn Pro Thr Pro Pro Phe Thr
            660                 665                 670

Pro Lys Met Gly Arg Arg Ser Ile Glu Ser Pro Ser Leu Gly Phe Cys
        675                 680                 685

Thr Asp Thr Leu Leu Pro His Leu Leu Glu Asp Asp Leu Gly Gln Leu
    690                 695                 700

Ser Asp Leu Glu Pro Glu Pro Asp Ala Gln Asn Trp Gln His Thr Val
705                 710                 715                 720

Gly Lys Asp Val Val Ala Gly Leu Thr Gln Arg Glu Ile Asp Arg Gln
                725                 730                 735

Glu Val Ile Asn Glu Leu Phe Val Thr Glu Ala Ser His Leu Arg Thr
            740                 745                 750

Leu Arg Val Leu Asp Leu Ile Phe Tyr Gln Arg Met Lys Lys Glu Asn
        755                 760                 765

Leu Met Pro Arg Glu Glu Leu Ala Arg Leu Phe Pro Asn Leu Pro Glu
    770                 775                 780

Leu Ile Glu Ile His Asn Ser Trp Cys Glu Ala Met Lys Lys Leu Arg
785                 790                 795                 800

Glu Glu Gly Pro Ile Ile Lys Glu Ile Ser Asp Leu Met Leu Ala Arg
                805                 810                 815

Phe Asp Gly Pro Ala Arg Glu Glu Leu Gln Gln Val Ala Ala Gln Phe
            820                 825                 830

Cys Ser Tyr Gln Ser Ile Ala Leu Glu Leu Ile Lys Thr Lys Gln Arg
        835                 840                 845
```

-continued

```
Lys Glu Ser Arg Phe Gln Leu Phe Met Gln Glu Ala Glu Ser His Pro
    850                 855                 860

Gln Cys Arg Arg Leu Gln Leu Arg Asp Leu Ile Ile Ser Glu Met Gln
865                 870                 875                 880

Arg Leu Thr Lys Tyr Pro Leu Leu Leu Glu Ser Ile Ile Lys His Thr
                885                 890                 895

Glu Gly Gly Thr Ser Glu His Glu Lys Leu Cys Arg Ala Arg Asp Gln
            900                 905                 910

Cys Arg Glu Ile Leu Lys Tyr Val Asn Glu Ala Val Lys Gln Thr Glu
        915                 920                 925

Asn Arg His Arg Leu Glu Gly Tyr Gln Lys Arg Leu Asp Ala Thr Ala
    930                 935                 940

Leu Glu Arg Ala Ser Asn Pro Leu Ala Ala Glu Phe Lys Ser Leu Asp
945                 950                 955                 960

Leu Thr Thr Arg Lys Met Ile His Glu Gly Pro Leu Thr Trp Arg Ile
                965                 970                 975

Ser Lys Asp Lys Thr Leu Asp Leu His Val Leu Leu Leu Glu Asp Leu
            980                 985                 990

Leu Val Leu Leu Gln Lys Gln Asp  Glu Lys Leu Leu Leu  Lys Cys His
        995                 1000                1005

Ser Lys  Thr Ala Val Gly Ser  Ser Asp Ser Lys Gln  Thr Phe Ser
    1010                1015                1020

Pro Val  Leu Lys Leu Asn Ala  Val Leu Ile Arg Ser  Val Ala Thr
    1025                1030                1035

Asp Lys  Arg Ala Phe Phe Ile  Ile Cys Thr Ser Lys  Leu Gly Pro
    1040                1045                1050

Pro Gln  Ile Tyr Glu Leu Val  Ala Leu Thr Ser Ser  Asp Lys Asn
    1055                1060                1065

Thr Trp  Met Glu Leu Leu Glu  Glu Ala Val Arg Asn  Ala Thr Arg
    1070                1075                1080

His Pro  Gly Ala Ala Pro Met  Pro Val His Pro Pro  Pro Pro Gly
    1085                1090                1095

Pro Arg  Glu Pro Ala Gln Gln  Gly Pro Thr Pro Ser  Arg Val Glu
    1100                1105                1110

Leu Asp  Asp Ser Asp Val Phe  His Gly Glu Pro Glu  Pro Glu Glu
    1115                1120                1125

Leu Pro  Gly Gly Thr Gly Ser  Gln Gln Arg Val Gln  Gly Lys His
    1130                1135                1140

Gln Val  Leu Leu Glu Asp Pro  Glu Gln Glu Gly Ser  Ala Glu Glu
    1145                1150                1155

Glu Glu  Leu Gly Val Leu Pro  Cys Pro Ser Thr Ser  Leu Asp Gly
    1160                1165                1170

Glu Asn  Arg Gly Ile Arg Thr  Arg Asn Pro Ile His  Leu Ala Phe
    1175                1180                1185

Pro Gly  Pro Leu Phe Met Glu  Gly Leu Ala Asp Ser  Ala Leu Glu
    1190                1195                1200

Asp Val  Glu Asn Leu Arg His  Leu Ile Leu Trp Ser  Leu Leu Pro
    1205                1210                1215

Gly His  Thr Met Glu Thr Gln  Ala Ala Gln Glu Pro  Glu Asp Asp
    1220                1225                1230

Leu Thr  Pro Thr Pro Ser Val  Ile Ser Val Thr Ser  His Pro Trp
    1235                1240                1245

Asp Pro  Gly Ser Pro Gly Gln  Ala Pro Pro Gly Gly  Glu Gly Asp
```

-continued

```
    1250                1255                1260

Asn Thr  Gln Leu Ala Gly Leu  Glu Gly Glu Arg Pro  Glu Gln Glu
    1265                1270                1275

Asp Met  Gly Leu Cys Ser Leu  Glu His Leu Pro Pro  Arg Thr Arg
    1280                1285                1290

Asn Ser  Gly Ile Trp Glu Ser  Pro Glu Leu Asp Arg  Asn Leu Ala
    1295                1300                1305

Glu Asp  Ala Ser Ser Thr Glu  Ala Ala Gly Gly Tyr  Lys Val Val
    1310                1315                1320

Arg Lys  Ala Glu Val Ala Gly  Ser Lys Val Val Pro  Ala Leu Pro
    1325                1330                1335

Glu Ser  Gly Gln Ser Glu Pro  Gly Pro Pro Glu Val  Glu Gly Gly
    1340                1345                1350

Thr Lys  Ala Thr Gly Asn Cys  Phe Tyr Val Ser Met  Pro Ser Gly
    1355                1360                1365

Pro Pro  Asp Ser Ser Thr Asp  His Ser Glu Ala Pro  Met Ser Pro
    1370                1375                1380

Pro Gln  Pro Asp Ser Leu Pro  Ala Gly Gln Thr Glu  Pro Gln Pro
    1385                1390                1395

Gln Leu  Gln Gly Gly Asn Asp  Asp Pro Arg Arg Pro  Ser Arg Ser
    1400                1405                1410

Pro Pro  Ser Leu Ala Leu Arg  Asp Val Gly Met Ile  Phe His Thr
    1415                1420                1425

Ile Glu  Gln Leu Thr Leu Lys  Leu Asn Arg Leu Lys  Asp Met Glu
    1430                1435                1440

Leu Ala  His Arg Glu Leu Leu  Lys Ser Leu Gly Gly  Glu Ser Ser
    1445                1450                1455

Gly Gly  Thr Thr Pro Val Gly  Ser Phe His Thr Glu  Ala Ala Arg
    1460                1465                1470

Trp Thr  Asp Gly Ser Leu Ser  Pro Pro Ala Lys Glu  Pro Leu Ala
    1475                1480                1485

Ser Asp  Ser Arg Asn Ser His  Glu Leu Gly Pro Cys  Pro Glu Asp
    1490                1495                1500

Gly Ser  Asp Ala Pro Leu Glu  Asp Ser Thr Ala Asp  Ala Ala Ala
    1505                1510                1515

Ser Pro  Gly Pro
    1520


<210> SEQ ID NO 32
<211> LENGTH: 577
<212> TYPE: PRT
<213> ORGANISM: Homo sapiens

<400> SEQUENCE: 32

Met Cys Lys Glu Gln Lys Ala Thr Lys Lys Ser Lys Val Gly Phe Leu
1               5                   10                  15

Asp Pro Leu Ala Thr Asp Asn Gln Lys Glu Cys Glu Ala Trp Pro Asp
            20                  25                  30

Leu Arg Thr Ser Glu Glu Asp Ser Lys Ser Cys Ser Gly Ala Leu Ser
        35                  40                  45

Thr Ala Leu Glu Glu Leu Ala Lys Val Ser Glu Glu Leu Cys Ser Phe
    50                  55                  60

Gln Glu Glu Ile Arg Lys Arg Ser Asn His Arg Arg Met Lys Ser Asp
65                  70                  75                  80
```

-continued

```
Ser Phe Leu Gln Glu Met Pro Asn Val Thr Asn Ile Pro His Gly Asp
                85                  90                  95

Pro Met Ile Asn Asn Asp Gln Cys Ile Leu Pro Ile Ser Leu Glu Lys
            100                 105                 110

Glu Lys Gln Lys Asn Arg Lys Asn Leu Ser Cys Thr Asn Val Leu Gln
        115                 120                 125

Ser Asn Ser Thr Lys Lys Cys Gly Ile Asp Thr Ile Asp Leu Lys Arg
    130                 135                 140

Asn Glu Thr Pro Pro Val Pro Pro Pro Arg Ser Thr Ser Arg Asn Phe
145                 150                 155                 160

Pro Ser Ser Asp Ser Glu Gln Ala Tyr Glu Arg Trp Lys Glu Arg Leu
                165                 170                 175

Asp His Asn Ser Trp Val Pro His Glu Gly Arg Ser Lys Arg Asn Tyr
            180                 185                 190

Asn Pro His Phe Pro Leu Arg Gln Gln Glu Met Ser Met Leu Tyr Pro
        195                 200                 205

Asn Glu Gly Lys Thr Ser Lys Asp Gly Ile Ile Phe Ser Ser Leu Val
    210                 215                 220

Pro Glu Val Lys Ile Asp Ser Lys Pro Pro Ser Asn Glu Asp Val Gly
225                 230                 235                 240

Leu Ser Met Trp Ser Cys Asp Ile Gly Ile Gly Ala Lys Arg Ser Pro
                245                 250                 255

Ser Thr Ser Trp Phe Gln Lys Thr Cys Ser Thr Pro Ser Asn Pro Lys
            260                 265                 270

Tyr Glu Met Val Ile Pro Asp His Pro Ala Lys Ser His Pro Asp Leu
        275                 280                 285

His Val Ser Asn Asp Cys Ser Ser Ser Val Ala Glu Ser Ser Ser Pro
    290                 295                 300

Leu Arg Asn Phe Ser Cys Gly Phe Glu Arg Thr Thr Arg Asn Glu Lys
305                 310                 315                 320

Leu Ala Ala Lys Thr Asp Glu Phe Asn Arg Thr Val Phe Arg Thr Asp
                325                 330                 335

Arg Asn Cys Gln Ala Ile Gln Gln Asn His Ser Cys Ser Lys Ser Ser
            340                 345                 350

Glu Asp Leu Lys Pro Cys Asp Thr Ser Ser Thr His Thr Gly Ser Ile
        355                 360                 365

Ser Gln Ser Asn Asp Val Ser Gly Ile Trp Lys Thr Asn Ala His Met
    370                 375                 380

Pro Val Pro Met Glu Asn Val Pro Asp Asn Pro Thr Lys Lys Ser Thr
385                 390                 395                 400

Thr Gly Leu Val Arg Gln Met Gln Gly His Leu Ser Pro Arg Ser Tyr
                405                 410                 415

Arg Asn Met Leu His Glu His Asp Trp Arg Pro Ser Asn Leu Ser Gly
            420                 425                 430

Arg Pro Arg Ser Ala Asp Pro Arg Ser Asn Tyr Gly Val Val Glu Lys
        435                 440                 445

Leu Leu Lys Thr Tyr Glu Thr Ala Thr Glu Ser Ala Leu Gln Asn Ser
    450                 455                 460

Lys Cys Phe Gln Asp Asn Trp Thr Lys Cys Asn Ser Asp Val Ser Gly
465                 470                 475                 480

Gly Ala Thr Leu Ser Gln His Leu Glu Met Leu Gln Met Glu Gln Gln
                485                 490                 495

Phe Gln Gln Lys Thr Ala Val Trp Gly Gly Gln Glu Val Lys Gln Gly
```

-continued

```
            500                 505                 510

Ile Asp Pro Lys Lys Ile Thr Glu Glu Ser Met Ser Val Asn Ala Ser
        515                 520                 525

His Gly Lys Gly Phe Ser Arg Pro Ala Arg Pro Ala Asn Arg Arg Leu
    530                 535                 540

Pro Ser Arg Trp Ala Ser Arg Ser Pro Ser Ala Pro Pro Ala Leu Arg
545                 550                 555                 560

Arg Thr Thr His Asn Tyr Thr Ile Ser Leu Arg Ser Glu Ala Leu Met
                565                 570                 575

Val


<210> SEQ ID NO 33
<211> LENGTH: 248
<212> TYPE: PRT
<213> ORGANISM: Homo sapiens

<400> SEQUENCE: 33

Met Gly Met Glu Arg Pro Ala Ala Arg Glu Pro His Gly Pro Asp Ala
1               5                   10                  15

Leu Arg Arg Phe Gln Gly Leu Leu Leu Asp Arg Arg Gly Arg Leu His
            20                  25                  30

Arg Gln Val Leu Arg Leu Arg Glu Val Ala Arg Arg Leu Glu Arg Leu
        35                  40                  45

Arg Arg Arg Ser Leu Val Ala Asn Val Ala Gly Ser Ser Leu Ser Ala
    50                  55                  60

Thr Gly Ala Leu Ala Ala Ile Val Gly Leu Ser Leu Ser Pro Val Thr
65                  70                  75                  80

Leu Gly Thr Ser Leu Leu Val Ser Ala Val Gly Leu Gly Val Ala Thr
                85                  90                  95

Ala Gly Gly Ala Val Thr Ile Thr Ser Asp Leu Ser Leu Ile Phe Cys
            100                 105                 110

Asn Ser Arg Glu Leu Arg Arg Val Gln Glu Ile Ala Ala Thr Cys Gln
        115                 120                 125

Asp Gln Met Arg Glu Ile Leu Ser Cys Leu Glu Phe Phe Cys Arg Trp
    130                 135                 140

Gln Gly Cys Gly Asp Arg Gln Leu Leu Gln Cys Gly Arg Asn Ala Ser
145                 150                 155                 160

Ile Ala Leu Tyr Asn Ser Val Tyr Phe Ile Val Phe Phe Gly Ser Arg
                165                 170                 175

Gly Phe Leu Ile Pro Arg Arg Ala Glu Gly Asp Thr Lys Val Ser Gln
            180                 185                 190

Ala Val Leu Lys Ala Lys Ile Gln Lys Leu Ala Glu Ser Leu Glu Ser
        195                 200                 205

Cys Thr Gly Ala Leu Asp Glu Leu Ser Glu Gln Leu Glu Ser Arg Val
    210                 215                 220

Gln Leu Cys Thr Lys Ser Ser Arg Gly His Asp Leu Lys Ile Ser Ala
225                 230                 235                 240

Asp Gln Arg Ala Gly Leu Phe Phe
                245


<210> SEQ ID NO 34
<211> LENGTH: 2158
<212> TYPE: PRT
<213> ORGANISM: Homo sapiens

<400> SEQUENCE: 34
```

-continued

```
Met Val Ser Ile Asp Leu His Gln Ala Gly Arg Val Asp Ser Gln Ala
1               5                   10                  15

Ser Ile Thr Gln Asp Ser Asp Ser Ile Lys Lys Pro Glu Glu Ile Lys
            20                  25                  30

Gln Cys Asn Asp Ala Pro Val Ser Val Leu Gln Glu Asp Ile Val Gly
        35                  40                  45

Ser Leu Lys Ser Thr Pro Glu Asn His Pro Glu Thr Pro Lys Lys Lys
    50                  55                  60

Ser Asp Pro Glu Leu Ser Lys Ser Glu Met Lys Gln Ser Glu Ser Arg
65                  70                  75                  80

Leu Ala Glu Ser Lys Pro Asn Glu Asn Arg Leu Val Glu Thr Lys Ser
                85                  90                  95

Ser Glu Asn Lys Leu Glu Thr Lys Val Glu Thr Gln Thr Glu Glu Leu
            100                 105                 110

Lys Gln Asn Glu Ser Arg Thr Thr Glu Cys Lys Gln Asn Glu Ser Thr
        115                 120                 125

Ile Val Glu Pro Lys Gln Asn Glu Asn Arg Leu Ser Asp Thr Lys Pro
    130                 135                 140

Asn Asp Asn Lys Gln Asn Asn Gly Arg Ser Glu Thr Thr Lys Ser Arg
145                 150                 155                 160

Pro Glu Thr Pro Lys Gln Lys Gly Glu Ser Arg Pro Glu Thr Pro Lys
                165                 170                 175

Gln Lys Ser Asp Gly His Pro Glu Thr Pro Lys Gln Lys Gly Asp Gly
            180                 185                 190

Arg Pro Glu Thr Pro Lys Gln Lys Gly Glu Ser Arg Pro Glu Thr Pro
        195                 200                 205

Lys Gln Lys Asn Glu Gly Arg Pro Glu Thr Pro Lys His Arg His Asp
    210                 215                 220

Asn Arg Arg Asp Ser Gly Lys Pro Ser Thr Glu Lys Lys Pro Glu Val
225                 230                 235                 240

Ser Lys His Lys Gln Asp Thr Lys Ser Asp Ser Pro Arg Leu Lys Ser
                245                 250                 255

Glu Arg Ala Glu Ala Leu Lys Gln Arg Pro Asp Gly Arg Ser Val Ser
            260                 265                 270

Glu Ser Leu Arg Arg Asp His Asp Asn Lys Gln Lys Ser Asp Asp Arg
        275                 280                 285

Gly Glu Ser Glu Arg His Arg Gly Asp Gln Ser Arg Val Arg Arg Pro
    290                 295                 300

Glu Thr Leu Arg Ser Ser Ser Arg Asn Glu His Gly Ile Lys Ser Asp
305                 310                 315                 320

Ser Ser Lys Thr Asp Lys Leu Glu Arg Lys His Arg His Glu Ser Gly
                325                 330                 335

Asp Ser Arg Glu Arg Pro Ser Ser Gly Glu Gln Lys Ser Arg Pro Asp
            340                 345                 350

Ser Pro Arg Val Lys Gln Gly Asp Ser Asn Lys Ser Arg Ser Asp Lys
        355                 360                 365

Leu Gly Phe Lys Ser Pro Thr Ser Lys Asp Asp Lys Arg Thr Glu Gly
    370                 375                 380

Asn Lys Ser Lys Val Asp Thr Asn Lys Ala His Pro Asp Asn Lys Ala
385                 390                 395                 400

Glu Phe Pro Ser Tyr Leu Leu Gly Gly Arg Ser Gly Ala Leu Lys Asn
                405                 410                 415
```

-continued

```
Phe Val Ile Pro Lys Ile Lys Arg Asp Lys Asp Gly Asn Val Thr Gln
            420                 425                 430

Glu Thr Lys Lys Met Glu Met Lys Gly Glu Pro Lys Asp Lys Val Glu
        435                 440                 445

Lys Ile Gly Leu Val Glu Asp Leu Asn Lys Gly Ala Lys Pro Val Val
    450                 455                 460

Val Leu Gln Lys Leu Ser Leu Asp Asp Val Gln Lys Leu Ile Lys Asp
465                 470                 475                 480

Arg Glu Asp Lys Ser Arg Ser Ser Leu Lys Pro Ile Lys Asn Lys Pro
                485                 490                 495

Ser Lys Ser Asn Lys Gly Ser Ile Asp Gln Ser Val Leu Lys Glu Leu
            500                 505                 510

Pro Pro Glu Leu Leu Ala Glu Ile Glu Ser Thr Met Pro Leu Cys Glu
        515                 520                 525

Arg Val Lys Met Asn Lys Arg Lys Arg Ser Thr Val Asn Glu Lys Pro
    530                 535                 540

Lys Tyr Ala Glu Ile Ser Ser Asp Glu Asp Asn Asp Ser Asp Glu Ala
545                 550                 555                 560

Phe Glu Ser Ser Arg Lys Arg His Lys Lys Asp Asp Asp Lys Ala Trp
                565                 570                 575

Glu Tyr Glu Glu Arg Asp Arg Arg Ser Ser Gly Asp His Arg Arg Ser
            580                 585                 590

Gly His Ser His Glu Gly Arg Arg Ser Ser Gly Gly Gly Arg Tyr Arg
        595                 600                 605

Asn Arg Ser Pro Ser Asp Ser Asp Met Glu Asp Tyr Ser Pro Pro Pro
    610                 615                 620

Ser Leu Ser Glu Val Ala Arg Lys Met Lys Lys Lys Glu Lys Gln Lys
625                 630                 635                 640

Lys Arg Lys Ala Tyr Glu Pro Lys Leu Thr Pro Glu Glu Met Met Asp
                645                 650                 655

Ser Ser Thr Phe Lys Arg Phe Thr Ala Ser Ile Glu Asn Ile Leu Asp
            660                 665                 670

Asn Leu Glu Asp Met Asp Phe Thr Ala Phe Gly Asp Asp Asp Glu Ile
        675                 680                 685

Pro Gln Glu Leu Leu Leu Gly Lys His Gln Leu Asn Glu Leu Gly Ser
    690                 695                 700

Glu Ser Ala Lys Ile Lys Ala Met Gly Ile Met Asp Lys Leu Ser Thr
705                 710                 715                 720

Asp Lys Thr Val Lys Val Leu Asn Ile Leu Glu Lys Asn Ile Gln Asp
                725                 730                 735

Gly Ser Lys Leu Ser Thr Leu Leu Asn His Asn Asn Asp Thr Glu Glu
            740                 745                 750

Glu Glu Arg Leu Trp Arg Asp Leu Ile Met Glu Arg Val Thr Lys Ser
        755                 760                 765

Ala Asp Ala Cys Leu Thr Thr Ile Asn Ile Met Thr Ser Pro Asn Met
    770                 775                 780

Pro Lys Ala Val Tyr Ile Glu Asp Val Ile Glu Arg Val Ile Gln Tyr
785                 790                 795                 800

Thr Lys Phe His Leu Gln Asn Thr Leu Tyr Pro Gln Tyr Asp Pro Val
                805                 810                 815

Tyr Arg Leu Asp Pro His Gly Gly Gly Leu Leu Ser Ser Lys Ala Lys
            820                 825                 830

Arg Ala Lys Cys Ser Thr His Lys Gln Arg Val Ile Val Met Leu Tyr
```

-continued

```
        835                 840                 845

Asn Lys Val Cys Asp Ile Val Ser Ser Leu Ser Glu Leu Leu Glu Ile
    850                 855                 860

Gln Leu Leu Thr Asp Thr Thr Ile Leu Gln Val Ser Ser Met Gly Ile
865                 870                 875                 880

Thr Pro Phe Phe Val Glu Asn Val Ser Glu Leu Gln Leu Cys Ala Ile
                885                 890                 895

Lys Leu Val Thr Ala Val Phe Ser Arg Tyr Glu Lys His Arg Gln Leu
            900                 905                 910

Ile Leu Glu Glu Ile Phe Thr Ser Leu Ala Arg Leu Pro Thr Ser Lys
        915                 920                 925

Arg Ser Leu Arg Asn Phe Arg Leu Asn Ser Ser Asp Met Asp Gly Glu
    930                 935                 940

Pro Met Tyr Ile Gln Met Val Thr Ala Leu Val Leu Gln Leu Ile Gln
945                 950                 955                 960

Cys Val Val His Leu Pro Ser Ser Glu Lys Asp Ser Asn Ala Glu Glu
                965                 970                 975

Asp Ser Asn Lys Lys Ile Asp Gln Asp Val Val Ile Thr Asn Ser Tyr
            980                 985                 990

Glu Thr Ala Met Arg Thr Ala Gln  Asn Phe Leu Ser Ile  Phe Leu Lys
        995                 1000                1005

Lys Cys  Gly Ser Lys Gln Gly  Glu Glu Asp Tyr Arg  Pro Leu Phe
    1010                 1015                 1020

Glu Asn  Phe Val Gln Asp Leu  Leu Ser Thr Val Asn  Lys Pro Glu
    1025                 1030                 1035

Trp Pro  Ala Ala Glu Leu Leu  Leu Ser Leu Leu Gly  Arg Leu Leu
    1040                 1045                 1050

Val His  Gln Phe Ser Asn Lys  Ser Thr Glu Met Ala  Leu Arg Val
    1055                 1060                 1065

Ala Ser  Leu Asp Tyr Leu Gly  Thr Val Ala Ala Arg  Leu Arg Lys
    1070                 1075                 1080

Asp Ala  Val Thr Ser Lys Met  Asp Gln Gly Ser Ile  Glu Arg Ile
    1085                 1090                 1095

Leu Lys  Gln Val Ser Gly Gly  Glu Asp Glu Ile Gln  Gln Leu Gln
    1100                 1105                 1110

Lys Ala  Leu Leu Asp Tyr Leu  Asp Glu Asn Thr Glu  Thr Asp Pro
    1115                 1120                 1125

Ser Leu  Val Phe Ser Arg Lys  Phe Tyr Ile Ala Gln  Trp Phe Arg
    1130                 1135                 1140

Asp Thr  Thr Leu Glu Thr Glu  Lys Ala Met Lys Ser  Gln Lys Asp
    1145                 1150                 1155

Glu Glu  Ser Ser Glu Gly Thr  His His Ala Lys Glu  Ile Glu Thr
    1160                 1165                 1170

Thr Gly  Gln Ile Met His Arg  Ala Glu Asn Arg Lys  Lys Phe Leu
    1175                 1180                 1185

Arg Ser  Ile Ile Lys Thr Thr  Pro Ser Gln Phe Ser  Thr Leu Lys
    1190                 1195                 1200

Met Asn  Ser Asp Thr Val Asp  Tyr Asp Asp Ala Cys  Leu Ile Val
    1205                 1210                 1215

Arg Tyr  Leu Ala Ser Met Arg  Pro Phe Ala Gln Ser  Phe Asp Ile
    1220                 1225                 1230

Tyr Leu  Thr Gln Ile Leu Arg  Val Leu Gly Glu Asn  Ala Ile Ala
    1235                 1240                 1245
```

-continued

Val Arg Thr Lys Ala Met Lys Cys Leu Ser Glu Val Val Ala Val
1250 1255 1260

Asp Pro Ser Ile Leu Ala Arg Leu Asp Met Gln Arg Gly Val His
1265 1270 1275

Gly Arg Leu Met Asp Asn Ser Thr Ser Val Arg Glu Ala Ala Val
1280 1285 1290

Glu Leu Leu Gly Arg Phe Val Leu Cys Arg Pro Gln Leu Ala Glu
1295 1300 1305

Gln Tyr Tyr Asp Met Leu Ile Glu Arg Ile Leu Asp Thr Gly Ile
1310 1315 1320

Ser Val Arg Lys Arg Val Ile Lys Ile Leu Arg Asp Ile Cys Ile
1325 1330 1335

Glu Gln Pro Thr Phe Pro Lys Ile Thr Glu Met Cys Val Lys Met
1340 1345 1350

Ile Arg Arg Val Asn Asp Glu Glu Gly Ile Lys Lys Leu Val Asn
1355 1360 1365

Glu Thr Phe Gln Lys Leu Trp Phe Thr Pro Thr Pro His Asn Asp
1370 1375 1380

Lys Glu Ala Met Thr Arg Lys Ile Leu Asn Ile Thr Asp Val Val
1385 1390 1395

Ala Ala Cys Arg Asp Thr Gly Tyr Asp Trp Phe Glu Gln Leu Leu
1400 1405 1410

Gln Asn Leu Leu Lys Ser Glu Glu Asp Ser Ser Tyr Lys Pro Val
1415 1420 1425

Lys Lys Ala Cys Thr Gln Leu Val Asp Asn Leu Val Glu His Ile
1430 1435 1440

Leu Lys Tyr Glu Glu Ser Leu Ala Asp Ser Asp Asn Lys Gly Val
1445 1450 1455

Asn Ser Gly Arg Leu Val Ala Cys Ile Thr Thr Leu Phe Leu Phe
1460 1465 1470

Ser Lys Ile Arg Pro Gln Leu Met Val Lys His Ala Met Thr Met
1475 1480 1485

Gln Pro Tyr Leu Thr Thr Lys Cys Ser Thr Gln Asn Asp Phe Met
1490 1495 1500

Val Ile Cys Asn Val Ala Lys Ile Leu Glu Leu Val Val Pro Leu
1505 1510 1515

Met Glu His Pro Ser Glu Thr Phe Leu Ala Thr Ile Glu Glu Asp
1520 1525 1530

Leu Met Lys Leu Ile Ile Lys Tyr Gly Met Thr Val Val Gln His
1535 1540 1545

Cys Val Ser Cys Leu Gly Ala Val Val Asn Lys Val Thr Gln Asn
1550 1555 1560

Phe Lys Phe Val Trp Ala Cys Phe Asn Arg Tyr Tyr Gly Ala Ile
1565 1570 1575

Ser Lys Leu Lys Ser Gln His Gln Glu Asp Pro Asn Asn Thr Ser
1580 1585 1590

Leu Leu Thr Asn Lys Pro Ala Leu Leu Arg Ser Leu Phe Thr Val
1595 1600 1605

Gly Ala Leu Cys Arg His Phe Asp Phe Asp Leu Glu Asp Phe Lys
1610 1615 1620

Gly Asn Ser Lys Val Asn Ile Lys Asp Lys Val Leu Glu Leu Leu
1625 1630 1635

-continued

```
Met Tyr  Phe Thr Lys His Ser  Asp Glu Glu Val Gln  Thr Lys Ala
    1640                 1645                 1650

Ile Ile  Gly Leu Gly Phe Ala  Phe Ile Gln His Pro  Ser Leu Met
    1655                 1660                 1665

Phe Glu  Gln Glu Val Lys Asn  Leu Tyr Asn Asn Ile  Leu Ser Asp
    1670                 1675                 1680

Lys Asn  Ser Ser Val Asn Leu  Lys Ile Gln Val Leu  Lys Asn Leu
    1685                 1690                 1695

Gln Thr  Tyr Leu Gln Glu Glu  Asp Thr Arg Met Gln  Gln Ala Asp
    1700                 1705                 1710

Arg Asp  Trp Lys Lys Val Ala  Lys Gln Glu Asp Leu  Lys Glu Met
    1715                 1720                 1725

Gly Asp  Val Ser Ser Gly Met  Ser Ser Ser Ile Met  Gln Leu Tyr
    1730                 1735                 1740

Leu Lys  Gln Val Leu Glu Ala  Phe Phe His Thr Gln  Ser Ser Val
    1745                 1750                 1755

Arg His  Phe Ala Leu Asn Val  Ile Ala Leu Thr Leu  Asn Gln Gly
    1760                 1765                 1770

Leu Ile  His Pro Val Gln Cys  Val Pro Tyr Leu Ile  Ala Met Gly
    1775                 1780                 1785

Thr Asp  Pro Glu Pro Ala Met  Arg Asn Lys Ala Asp  Gln Gln Leu
    1790                 1795                 1800

Val Glu  Ile Asp Lys Lys Tyr  Ala Gly Phe Ile His  Met Lys Ala
    1805                 1810                 1815

Val Ala  Gly Met Lys Met Ser  Tyr Gln Val Gln Gln  Ala Ile Asn
    1820                 1825                 1830

Thr Cys  Leu Lys Asp Pro Val  Arg Gly Phe Arg Gln  Asp Glu Ser
    1835                 1840                 1845

Ser Ser  Ala Leu Cys Ser His  Leu Tyr Ser Met Ile  Arg Gly Asn
    1850                 1855                 1860

Arg Gln  His Arg Arg Ala Phe  Leu Ile Ser Leu Leu  Asn Leu Phe
    1865                 1870                 1875

Asp Asp  Thr Ala Lys Thr Asp  Val Thr Met Leu Leu  Tyr Ile Ala
    1880                 1885                 1890

Asp Asn  Leu Ala Cys Phe Pro  Tyr Gln Thr Gln Glu  Glu Pro Leu
    1895                 1900                 1905

Phe Ile  Met His His Ile Asp  Ile Thr Leu Ser Val  Ser Gly Ser
    1910                 1915                 1920

Asn Leu  Leu Gln Ser Phe Lys  Glu Ser Met Val Lys  Asp Lys Arg
    1925                 1930                 1935

Lys Glu  Arg Lys Ser Ser Pro  Ser Lys Glu Asn Glu  Ser Ser Asp
    1940                 1945                 1950

Ser Glu  Glu Glu Val Ser Arg  Pro Arg Lys Ser Arg  Lys Arg Val
    1955                 1960                 1965

Asp Ser  Asp Ser Asp Ser Asp  Ser Glu Asp Asp Ile  Asn Ser Val
    1970                 1975                 1980

Met Lys  Cys Leu Pro Glu Asn  Ser Ala Pro Leu Ile  Glu Phe Ala
    1985                 1990                 1995

Asn Val  Ser Gln Gly Ile Leu  Leu Leu Leu Met Leu  Lys Gln His
    2000                 2005                 2010

Leu Lys  Asn Leu Cys Gly Phe  Ser Asp Ser Lys Ile  Gln Lys Tyr
    2015                 2020                 2025

Ser Pro  Ser Glu Ser Ala Lys  Val Tyr Asp Lys Ala  Ile Asn Arg
```

-continued

```
    2030                2035                2040

Lys Thr  Gly Val His Phe His  Pro Lys Gln Thr Leu  Asp Phe Leu
    2045                2050                2055

Arg Ser  Asp Met Ala Asn Ser  Lys Ile Thr Glu Glu  Val Lys Arg
    2060                2065                2070

Ser Ile  Val Lys Gln Tyr Leu  Asp Phe Lys Leu Leu  Met Glu His
    2075                2080                2085

Leu Asp  Pro Asp Glu Glu Glu  Glu Glu Gly Glu Val  Ser Ala Ser
    2090                2095                2100

Thr Asn  Ala Arg Asn Lys Ala  Ile Thr Ser Leu Leu  Gly Gly Gly
    2105                2110                2115

Ser Pro  Lys Asn Asn Thr Ala  Ala Glu Thr Glu Asp  Asp Glu Ser
    2120                2125                2130

Asp Gly  Glu Asp Arg Gly Gly  Gly Thr Ser Gly Val  Arg Arg Arg
    2135                2140                2145

Arg Ser  Gln Arg Ile Ser Gln  Arg Ile Thr
    2150                2155


<210> SEQ ID NO 35
<211> LENGTH: 2265
<212> TYPE: PRT
<213> ORGANISM: Homo sapiens

<400> SEQUENCE: 35

Met Val Ser Ile Asp Leu His Gln Ala Gly Arg Val Asp Ser Gln Ala
1               5                   10                  15

Ser Ile Thr Gln Asp Ser Asp Ser Ile Lys Lys Pro Glu Glu Ile Lys
            20                  25                  30

Gln Cys Asn Asp Ala Pro Val Ser Val Leu Gln Glu Asp Ile Val Gly
        35                  40                  45

Ser Leu Lys Ser Thr Pro Glu Asn His Pro Glu Thr Pro Lys Lys Lys
    50                  55                  60

Ser Asp Pro Glu Leu Ser Lys Ser Glu Met Lys Gln Ser Glu Ser Arg
65                  70                  75                  80

Leu Ala Glu Ser Lys Pro Asn Glu Asn Arg Leu Val Glu Thr Lys Ser
                85                  90                  95

Ser Glu Asn Lys Leu Glu Thr Lys Val Glu Thr Gln Thr Glu Glu Leu
            100                 105                 110

Lys Gln Asn Glu Ser Arg Thr Thr Glu Cys Lys Gln Asn Glu Ser Thr
        115                 120                 125

Ile Val Glu Pro Lys Gln Asn Glu Asn Arg Leu Ser Asp Thr Lys Pro
    130                 135                 140

Asn Asp Asn Lys Gln Asn Asn Gly Arg Ser Glu Thr Thr Lys Ser Arg
145                 150                 155                 160

Pro Glu Thr Pro Lys Gln Lys Gly Glu Ser Arg Pro Glu Thr Pro Lys
                165                 170                 175

Gln Lys Ser Asp Gly His Pro Glu Thr Pro Lys Gln Lys Gly Asp Gly
            180                 185                 190

Arg Pro Glu Thr Pro Lys Gln Lys Gly Glu Ser Arg Pro Glu Thr Pro
        195                 200                 205

Lys Gln Lys Asn Glu Gly Arg Pro Glu Thr Pro Lys His Arg His Asp
    210                 215                 220

Asn Arg Arg Asp Ser Gly Lys Pro Ser Thr Glu Lys Lys Pro Glu Val
225                 230                 235                 240
```

-continued

```
Ser Lys His Lys Gln Asp Thr Lys Ser Asp Ser Pro Arg Leu Lys Ser
                245                 250                 255

Glu Arg Ala Glu Ala Leu Lys Gln Arg Pro Asp Gly Arg Ser Val Ser
            260                 265                 270

Glu Ser Leu Arg Arg Asp His Asp Asn Lys Gln Lys Ser Asp Asp Arg
        275                 280                 285

Gly Glu Ser Glu Arg His Arg Gly Asp Gln Ser Arg Val Arg Arg Pro
    290                 295                 300

Glu Thr Leu Arg Ser Ser Ser Arg Asn Glu His Gly Ile Lys Ser Asp
305                 310                 315                 320

Ser Ser Lys Thr Asp Lys Leu Glu Arg Lys His Arg His Glu Ser Gly
                325                 330                 335

Asp Ser Arg Glu Arg Pro Ser Ser Gly Glu Gln Lys Ser Arg Pro Asp
            340                 345                 350

Ser Pro Arg Val Lys Gln Gly Asp Ser Asn Lys Ser Arg Ser Asp Lys
        355                 360                 365

Leu Gly Phe Lys Ser Pro Thr Ser Lys Asp Asp Lys Arg Thr Glu Gly
    370                 375                 380

Asn Lys Ser Lys Val Asp Thr Asn Lys Ala His Pro Asp Asn Lys Ala
385                 390                 395                 400

Glu Phe Pro Ser Tyr Leu Leu Gly Gly Arg Ser Gly Ala Leu Lys Asn
                405                 410                 415

Phe Val Ile Pro Lys Ile Lys Arg Asp Lys Asp Gly Asn Val Thr Gln
            420                 425                 430

Glu Thr Lys Lys Met Glu Met Lys Gly Glu Pro Lys Asp Lys Val Glu
        435                 440                 445

Lys Ile Gly Leu Val Glu Asp Leu Asn Lys Gly Ala Lys Pro Val Val
    450                 455                 460

Val Leu Gln Lys Leu Ser Leu Asp Asp Val Gln Lys Leu Ile Lys Asp
465                 470                 475                 480

Arg Glu Asp Lys Ser Arg Ser Ser Leu Lys Pro Ile Lys Asn Lys Pro
                485                 490                 495

Ser Lys Ser Asn Lys Gly Ser Ile Asp Gln Ser Val Leu Lys Glu Leu
            500                 505                 510

Pro Pro Glu Leu Leu Ala Glu Ile Glu Ser Thr Met Pro Leu Cys Glu
        515                 520                 525

Arg Val Lys Met Asn Lys Arg Lys Arg Ser Thr Val Asn Glu Lys Pro
    530                 535                 540

Lys Tyr Ala Glu Ile Ser Ser Asp Glu Asp Asn Asp Ser Asp Glu Ala
545                 550                 555                 560

Phe Glu Ser Ser Arg Lys Arg His Lys Lys Asp Asp Asp Lys Ala Trp
                565                 570                 575

Glu Tyr Glu Glu Arg Asp Arg Arg Ser Ser Gly Asp His Arg Arg Ser
            580                 585                 590

Gly His Ser His Glu Gly Arg Arg Ser Ser Gly Gly Gly Arg Tyr Arg
        595                 600                 605

Asn Arg Ser Pro Ser Asp Ser Asp Met Glu Asp Tyr Ser Pro Pro Pro
    610                 615                 620

Ser Leu Ser Glu Val Ala Arg Lys Met Lys Lys Lys Glu Lys Gln Lys
625                 630                 635                 640

Lys Arg Lys Ala Tyr Glu Pro Lys Leu Thr Pro Glu Glu Met Met Asp
                645                 650                 655

Ser Ser Thr Phe Lys Arg Phe Thr Ala Ser Ile Glu Asn Ile Leu Asp
```

-continued

```
            660                 665                 670

Asn Leu Glu Asp Met Asp Phe Thr Ala Phe Gly Asp Asp Asp Glu Ile
        675                 680                 685

Pro Gln Glu Leu Leu Leu Gly Lys His Gln Leu Asn Glu Leu Gly Ser
    690                 695                 700

Glu Ser Ala Lys Ile Lys Ala Met Gly Ile Met Asp Lys Leu Ser Thr
705                 710                 715                 720

Asp Lys Thr Val Lys Val Leu Asn Ile Leu Glu Lys Asn Ile Gln Asp
                725                 730                 735

Gly Ser Lys Leu Ser Thr Leu Leu Asn His Asn Asn Asp Thr Glu Glu
            740                 745                 750

Glu Glu Arg Leu Trp Arg Asp Leu Ile Met Glu Arg Val Thr Lys Ser
        755                 760                 765

Ala Asp Ala Cys Leu Thr Thr Ile Asn Ile Met Thr Ser Pro Asn Met
    770                 775                 780

Pro Lys Ala Val Tyr Ile Glu Asp Val Ile Glu Arg Val Ile Gln Tyr
785                 790                 795                 800

Thr Lys Phe His Leu Gln Asn Thr Leu Tyr Pro Gln Tyr Asp Pro Val
                805                 810                 815

Tyr Arg Leu Asp Pro His Gly Gly Gly Leu Leu Ser Ser Lys Ala Lys
            820                 825                 830

Arg Ala Lys Cys Ser Thr His Lys Gln Arg Val Ile Val Met Leu Tyr
        835                 840                 845

Asn Lys Val Cys Asp Ile Val Ser Ser Leu Ser Glu Leu Leu Glu Ile
    850                 855                 860

Gln Leu Leu Thr Asp Thr Thr Ile Leu Gln Val Ser Ser Met Gly Ile
865                 870                 875                 880

Thr Pro Phe Phe Val Glu Asn Val Ser Glu Leu Gln Leu Cys Ala Ile
                885                 890                 895

Lys Leu Val Thr Ala Val Phe Ser Arg Tyr Glu Lys His Arg Gln Leu
            900                 905                 910

Ile Leu Glu Glu Ile Phe Thr Ser Leu Ala Arg Leu Pro Thr Ser Lys
        915                 920                 925

Arg Ser Leu Arg Asn Phe Arg Leu Asn Ser Ser Asp Met Asp Gly Glu
    930                 935                 940

Pro Met Tyr Ile Gln Met Val Thr Ala Leu Val Leu Gln Leu Ile Gln
945                 950                 955                 960

Cys Val Val His Leu Pro Ser Ser Glu Lys Asp Ser Asn Ala Glu Glu
                965                 970                 975

Asp Ser Asn Lys Lys Ile Asp Gln Asp Val Val Ile Thr Asn Ser Tyr
            980                 985                 990

Glu Thr Ala Met Arg Thr Ala Gln  Asn Phe Leu Ser Ile  Phe Leu Lys
        995                 1000                1005

Lys Cys  Gly Ser Lys Gln Gly  Glu Glu Asp Tyr Arg  Pro Leu Phe
    1010                1015                1020

Glu Asn  Phe Val Gln Asp Leu  Leu Ser Thr Val Asn  Lys Pro Glu
    1025                1030                1035

Trp Pro  Ala Ala Glu Leu Leu  Leu Ser Leu Leu Gly  Arg Leu Leu
    1040                1045                1050

Val His  Gln Phe Ser Asn Lys  Ser Thr Glu Met Ala  Leu Arg Val
    1055                1060                1065

Ala Ser  Leu Asp Tyr Leu Gly  Thr Val Ala Ala Arg  Leu Arg Lys
    1070                1075                1080
```

-continued

```
Asp Ala  Val Thr Ser Lys Met  Asp Gln Gly Ser Ile  Glu Arg Ile
    1085                 1090                 1095

Leu Lys  Gln Val Ser Gly Gly  Glu Asp Glu Ile Gln  Gln Leu Gln
    1100                 1105                 1110

Lys Ala  Leu Leu Asp Tyr Leu  Asp Glu Asn Thr Glu  Thr Asp Pro
    1115                 1120                 1125

Ser Leu  Val Phe Ser Arg Lys  Phe Tyr Ile Ala Gln  Trp Phe Arg
    1130                 1135                 1140

Asp Thr  Thr Leu Glu Thr Glu  Lys Ala Met Lys Ser  Gln Lys Asp
    1145                 1150                 1155

Glu Glu  Ser Ser Glu Gly Thr  His His Ala Lys Glu  Ile Glu Thr
    1160                 1165                 1170

Thr Gly  Gln Ile Met His Arg  Ala Glu Asn Arg Lys  Lys Phe Leu
    1175                 1180                 1185

Arg Ser  Ile Ile Lys Thr Thr  Pro Ser Gln Phe Ser  Thr Leu Lys
    1190                 1195                 1200

Met Asn  Ser Asp Thr Val Asp  Tyr Asp Asp Ala Cys  Leu Ile Val
    1205                 1210                 1215

Arg Tyr  Leu Ala Ser Met Arg  Pro Phe Ala Gln Ser  Phe Asp Ile
    1220                 1225                 1230

Tyr Leu  Thr Gln Ile Leu Arg  Val Leu Gly Glu Asn  Ala Ile Ala
    1235                 1240                 1245

Val Arg  Thr Lys Ala Met Lys  Cys Leu Ser Glu Val  Val Ala Val
    1250                 1255                 1260

Asp Pro  Ser Ile Leu Ala Arg  Leu Asp Met Gln Arg  Gly Val His
    1265                 1270                 1275

Gly Arg  Leu Met Asp Asn Ser  Thr Ser Val Arg Glu  Ala Ala Val
    1280                 1285                 1290

Glu Leu  Leu Gly Arg Phe Val  Leu Cys Arg Pro Gln  Leu Ala Glu
    1295                 1300                 1305

Gln Tyr  Tyr Asp Met Leu Ile  Glu Arg Ile Leu Asp  Thr Gly Ile
    1310                 1315                 1320

Ser Val  Arg Lys Arg Val Ile  Lys Ile Leu Arg Asp  Ile Cys Ile
    1325                 1330                 1335

Glu Gln  Pro Thr Phe Pro Lys  Ile Thr Glu Met Cys  Val Lys Met
    1340                 1345                 1350

Ile Arg  Arg Val Asn Asp Glu  Glu Gly Ile Lys Lys  Leu Val Asn
    1355                 1360                 1365

Glu Thr  Phe Gln Lys Leu Trp  Phe Thr Pro Thr Pro  His Asn Asp
    1370                 1375                 1380

Lys Glu  Ala Met Thr Arg Lys  Ile Leu Asn Ile Thr  Asp Val Val
    1385                 1390                 1395

Ala Ala  Cys Arg Asp Thr Gly  Tyr Asp Trp Phe Glu  Gln Leu Leu
    1400                 1405                 1410

Gln Asn  Leu Leu Lys Ser Glu  Glu Asp Ser Ser Tyr  Lys Pro Val
    1415                 1420                 1425

Lys Lys  Ala Cys Thr Gln Leu  Val Asp Asn Leu Val  Glu His Ile
    1430                 1435                 1440

Leu Lys  Tyr Glu Glu Ser Leu  Ala Asp Ser Asp Asn  Lys Gly Val
    1445                 1450                 1455

Asn Ser  Gly Arg Leu Val Ala  Cys Ile Thr Thr Leu  Phe Leu Phe
    1460                 1465                 1470
```

-continued

```
Ser Lys  Ile Arg Pro Gln Leu  Met Val Lys His Ala  Met Thr Met
    1475                 1480                 1485

Gln Pro  Tyr Leu Thr Thr Lys  Cys Ser Thr Gln Asn  Asp Phe Met
    1490                 1495                 1500

Val Ile  Cys Asn Val Ala Lys  Ile Leu Glu Leu Val  Val Pro Leu
    1505                 1510                 1515

Met Glu  His Pro Ser Glu Thr  Phe Leu Ala Thr Ile  Glu Glu Asp
    1520                 1525                 1530

Leu Met  Lys Leu Ile Ile Lys  Tyr Gly Met Thr Val  Val Gln His
    1535                 1540                 1545

Cys Val  Ser Cys Leu Gly Ala  Val Val Asn Lys Val  Thr Gln Asn
    1550                 1555                 1560

Phe Lys  Phe Val Trp Ala Cys  Phe Asn Arg Tyr Tyr  Gly Ala Ile
    1565                 1570                 1575

Ser Lys  Leu Lys Ser Gln His  Gln Glu Asp Pro Asn  Asn Thr Ser
    1580                 1585                 1590

Leu Leu  Thr Asn Lys Pro Ala  Leu Leu Arg Ser Leu  Phe Thr Val
    1595                 1600                 1605

Gly Ala  Leu Cys Arg His Phe  Asp Phe Asp Leu Glu  Asp Phe Lys
    1610                 1615                 1620

Gly Asn  Ser Lys Val Asn Ile  Lys Asp Lys Val Leu  Glu Leu Leu
    1625                 1630                 1635

Met Tyr  Phe Thr Lys His Ser  Asp Glu Glu Val Gln  Thr Lys Ala
    1640                 1645                 1650

Ile Ile  Gly Leu Gly Phe Ala  Phe Ile Gln His Pro  Ser Leu Met
    1655                 1660                 1665

Phe Glu  Gln Glu Val Lys Asn  Leu Tyr Asn Asn Ile  Leu Ser Asp
    1670                 1675                 1680

Lys Asn  Ser Ser Val Asn Leu  Lys Ile Gln Val Leu  Lys Asn Leu
    1685                 1690                 1695

Gln Thr  Tyr Leu Gln Glu Glu  Asp Thr Arg Met Gln  Gln Ala Asp
    1700                 1705                 1710

Arg Asp  Trp Lys Lys Val Ala  Lys Gln Glu Asp Leu  Lys Glu Met
    1715                 1720                 1725

Gly Asp  Val Ser Ser Gly Met  Ser Ser Ser Ile Met  Gln Leu Tyr
    1730                 1735                 1740

Leu Lys  Gln Val Leu Glu Ala  Phe Phe His Thr Gln  Ser Ser Val
    1745                 1750                 1755

Arg His  Phe Ala Leu Asn Val  Ile Ala Leu Thr Leu  Asn Gln Gly
    1760                 1765                 1770

Leu Ile  His Pro Val Gln Cys  Val Pro Tyr Leu Ile  Ala Met Gly
    1775                 1780                 1785

Thr Asp  Pro Glu Pro Ala Met  Arg Asn Lys Ala Asp  Gln Gln Leu
    1790                 1795                 1800

Val Glu  Ile Asp Lys Lys Tyr  Ala Gly Phe Ile His  Met Lys Ala
    1805                 1810                 1815

Val Ala  Gly Met Lys Met Ser  Tyr Gln Val Gln Gln  Ala Ile Asn
    1820                 1825                 1830

Thr Cys  Leu Lys Asp Pro Val  Arg Gly Phe Arg Gln  Asp Glu Ser
    1835                 1840                 1845

Ser Ser  Ala Leu Cys Ser His  Leu Tyr Ser Met Ile  Arg Gly Asn
    1850                 1855                 1860

Arg Gln  His Arg Arg Ala Phe  Leu Ile Ser Leu Leu  Asn Leu Phe
```

-continued

```
    1865                1870                1875

Asp Asp  Thr Ala Lys Thr Asp  Val Thr Met Leu Leu  Tyr Ile Ala
    1880                1885                1890

Asp Asn  Leu Ala Cys Phe Pro  Tyr Gln Thr Gln Glu  Glu Pro Leu
    1895                1900                1905

Phe Ile  Met His His Ile Asp  Ile Thr Leu Ser Val  Ser Gly Ser
    1910                1915                1920

Asn Leu  Leu Gln Ser Phe Lys  Glu Ser Met Val Lys  Asp Lys Arg
    1925                1930                1935

Lys Glu  Arg Lys Ser Ser Pro  Ser Lys Glu Asn Glu  Ser Ser Asp
    1940                1945                1950

Ser Glu  Glu Glu Val Ser Arg  Pro Arg Lys Ser Arg  Lys Arg Val
    1955                1960                1965

Asp Ser  Asp Ser Asp Ser Asp  Ser Glu Asp Asp Ile  Asn Ser Val
    1970                1975                1980

Met Lys  Cys Leu Pro Glu Asn  Ser Ala Pro Leu Ile  Glu Phe Ala
    1985                1990                1995

Asn Val  Ser Gln Gly Ile Leu  Leu Leu Leu Met Leu  Lys Gln His
    2000                2005                2010

Leu Lys  Asn Leu Cys Gly Phe  Ser Asp Ser Lys Ile  Gln Lys Tyr
    2015                2020                2025

Ser Pro  Ser Glu Ser Ala Lys  Val Tyr Asp Lys Ala  Ile Asn Arg
    2030                2035                2040

Lys Thr  Gly Val His Phe His  Pro Lys Gln Thr Leu  Asp Phe Leu
    2045                2050                2055

Arg Ser  Asp Met Ala Asn Ser  Lys Ile Thr Glu Glu  Val Lys Arg
    2060                2065                2070

Ser Ile  Val Lys Gln Tyr Leu  Asp Phe Lys Leu Leu  Met Glu His
    2075                2080                2085

Leu Asp  Pro Asp Glu Glu Glu  Glu Glu Gly Glu Val  Ser Ala Ser
    2090                2095                2100

Thr Asn  Ala Arg Asn Lys Ala  Ile Thr Ser Leu Leu  Gly Gly Gly
    2105                2110                2115

Ser Pro  Lys Asn Asn Thr Ala  Ala Glu Thr Glu Asp  Asp Glu Ser
    2120                2125                2130

Asp Gly  Glu Asp Arg Gly Gly  Gly Thr Ser Gly Ser  Leu Arg Arg
    2135                2140                2145

Ser Lys  Arg Asn Ser Asp Ser  Thr Glu Leu Ala Ala  Gln Met Asn
    2150                2155                2160

Glu Ser  Val Asp Val Met Asp  Val Ile Ala Ile Cys  Cys Pro Lys
    2165                2170                2175

Tyr Lys  Asp Arg Pro Gln Ile  Ala Arg Val Val Gln  Lys Thr Ser
    2180                2185                2190

Ser Gly  Phe Ser Val Gln Trp  Met Ala Gly Ser Tyr  Ser Gly Ser
    2195                2200                2205

Trp Thr  Glu Ala Lys Arg Arg  Asp Gly Arg Lys Leu  Val Pro Trp
    2210                2215                2220

Val Asp  Thr Ile Lys Glu Ser  Asp Ile Ile Tyr Lys  Lys Ile Ala
    2225                2230                2235

Leu Thr  Ser Ala Asn Lys Leu  Thr Asn Lys Val Val  Gln Thr Leu
    2240                2245                2250

Arg Ser  Leu Tyr Ala Ala Lys  Asp Gly Thr Ser Ser
    2255                2260                2265
```

-continued

<210> SEQ ID NO 36
<211> LENGTH: 1007
<212> TYPE: PRT
<213> ORGANISM: Homo sapiens

<400> SEQUENCE: 36

```
Met Ser Arg Arg Lys Gln Arg Lys Pro Gln Gln Leu Ile Ser Asp Cys
1               5                   10                  15

Glu Gly Pro Ser Ala Ser Glu Asn Gly Asp Ala Ser Glu Glu Asp His
            20                  25                  30

Pro Gln Val Cys Ala Lys Cys Cys Ala Gln Phe Thr Asp Pro Thr Glu
        35                  40                  45

Phe Leu Ala His Gln Asn Ala Cys Ser Thr Asp Pro Pro Val Met Val
    50                  55                  60

Ile Ile Gly Gly Gln Glu Asn Pro Asn Asn Ser Ser Ala Ser Ser Glu
65                  70                  75                  80

Pro Arg Pro Glu Gly His Asn Asn Pro Gln Val Met Asp Thr Glu His
                85                  90                  95

Ser Asn Pro Pro Asp Ser Gly Ser Ser Val Pro Thr Asp Pro Thr Trp
            100                 105                 110

Gly Pro Glu Arg Arg Gly Glu Glu Ser Pro Gly His Phe Leu Val Ala
        115                 120                 125

Ala Thr Gly Thr Ala Ala Gly Gly Gly Gly Gly Leu Ile Leu Ala Ser
    130                 135                 140

Pro Lys Leu Gly Ala Thr Pro Leu Pro Pro Glu Ser Thr Pro Ala Pro
145                 150                 155                 160

Pro Pro Pro Pro Pro Pro Pro Pro Pro Pro Gly Val Gly Ser Gly His
                165                 170                 175

Leu Asn Ile Pro Leu Ile Leu Glu Glu Leu Arg Val Leu Gln Gln Arg
            180                 185                 190

Gln Ile His Gln Met Gln Met Thr Glu Gln Ile Cys Arg Gln Val Leu
        195                 200                 205

Leu Leu Gly Ser Leu Gly Gln Thr Val Gly Ala Pro Ala Ser Pro Ser
    210                 215                 220

Glu Leu Pro Gly Thr Gly Thr Ala Ser Ser Thr Lys Pro Leu Leu Pro
225                 230                 235                 240

Leu Phe Ser Pro Ile Lys Pro Val Gln Thr Ser Lys Thr Leu Ala Ser
                245                 250                 255

Ser Ser Ser Ser Ser Ser Ser Ser Ser Gly Ala Glu Thr Pro Lys Gln
            260                 265                 270

Ala Phe Phe His Leu Tyr His Pro Leu Gly Ser Gln His Pro Phe Ser
        275                 280                 285

Ala Gly Gly Val Gly Arg Ser His Lys Pro Thr Pro Ala Pro Ser Pro
    290                 295                 300

Ala Leu Pro Gly Ser Thr Asp Gln Leu Ile Ala Ser Pro His Leu Ala
305                 310                 315                 320

Phe Pro Ser Thr Thr Gly Leu Leu Ala Ala Gln Cys Leu Gly Ala Ala
                325                 330                 335

Arg Gly Leu Glu Ala Thr Ala Ser Pro Gly Leu Leu Lys Pro Lys Asn
            340                 345                 350

Gly Ser Gly Glu Leu Ser Tyr Gly Glu Val Met Gly Pro Leu Glu Lys
        355                 360                 365

Pro Gly Gly Arg His Lys Cys Arg Phe Cys Ala Lys Val Phe Gly Ser
```

-continued

```
    370                 375                 380

Asp Ser Ala Leu Gln Ile His Leu Arg Ser His Thr Gly Glu Arg Pro
385                 390                 395                 400

Tyr Lys Cys Asn Val Cys Gly Asn Arg Phe Thr Thr Arg Gly Asn Leu
                405                 410                 415

Lys Val His Phe His Arg His Arg Glu Lys Tyr Pro His Val Gln Met
            420                 425                 430

Asn Pro His Pro Val Pro Glu His Leu Asp Tyr Val Ile Thr Ser Ser
        435                 440                 445

Gly Leu Pro Tyr Gly Met Ser Val Pro Pro Glu Lys Ala Glu Glu Glu
    450                 455                 460

Ala Ala Thr Pro Gly Gly Gly Val Glu Arg Lys Pro Leu Val Ala Ser
465                 470                 475                 480

Thr Thr Ala Leu Ser Ala Thr Glu Ser Leu Thr Leu Leu Ser Thr Ser
                485                 490                 495

Ala Gly Thr Ala Thr Ala Pro Gly Leu Pro Ala Phe Asn Lys Phe Val
            500                 505                 510

Leu Met Lys Ala Val Glu Pro Lys Asn Lys Ala Asp Glu Asn Thr Pro
        515                 520                 525

Pro Gly Ser Glu Gly Ser Ala Ile Ser Gly Val Ala Glu Ser Ser Thr
    530                 535                 540

Ala Thr Arg Met Gln Leu Ser Lys Leu Val Thr Ser Leu Pro Ser Trp
545                 550                 555                 560

Ala Leu Leu Thr Asn His Phe Lys Ser Thr Gly Ser Phe Pro Phe Pro
                565                 570                 575

Tyr Val Leu Glu Pro Leu Gly Ala Ser Pro Ser Glu Thr Ser Lys Leu
            580                 585                 590

Gln Gln Leu Val Glu Lys Ile Asp Arg Gln Gly Ala Val Ala Val Thr
        595                 600                 605

Ser Ala Ala Ser Gly Ala Pro Thr Thr Ser Ala Pro Ala Pro Ser Ser
    610                 615                 620

Ser Ala Ser Ser Gly Pro Asn Gln Cys Val Ile Cys Leu Arg Val Leu
625                 630                 635                 640

Ser Cys Pro Arg Ala Leu Arg Leu His Tyr Gly Gln His Gly Gly Glu
                645                 650                 655

Arg Pro Phe Lys Cys Lys Val Cys Gly Arg Ala Phe Ser Thr Arg Gly
            660                 665                 670

Asn Leu Arg Ala His Phe Val Gly His Lys Ala Ser Pro Ala Ala Arg
        675                 680                 685

Ala Gln Asn Ser Cys Pro Ile Cys Gln Lys Lys Phe Thr Asn Ala Val
    690                 695                 700

Thr Leu Gln Gln His Val Arg Met His Leu Gly Gly Gln Ile Pro Asn
705                 710                 715                 720

Gly Gly Thr Ala Leu Pro Glu Gly Gly Gly Ala Ala Gln Glu Asn Gly
                725                 730                 735

Ser Glu Gln Ser Thr Val Ser Gly Ala Gly Ser Phe Pro Gln Gln Gln
            740                 745                 750

Ser Gln Gln Pro Ser Pro Glu Glu Glu Leu Ser Glu Glu Glu Glu Glu
        755                 760                 765

Glu Asp Glu Glu Glu Glu Glu Asp Val Thr Asp Glu Asp Ser Leu Ala
    770                 775                 780

Gly Arg Gly Ser Glu Ser Gly Gly Glu Lys Ala Ile Ser Val Arg Gly
785                 790                 795                 800
```

-continued

```
Asp Ser Glu Glu Ala Ser Gly Ala Glu Glu Glu Val Gly Thr Val Ala
                805                 810                 815

Ala Ala Ala Thr Ala Gly Lys Glu Met Asp Ser Asn Glu Lys Thr Thr
            820                 825                 830

Gln Gln Ser Ser Leu Pro Pro Pro Pro Pro Pro Asp Ser Leu Asp Gln
        835                 840                 845

Pro Gln Pro Met Glu Gln Gly Ser Ser Gly Val Leu Gly Gly Lys Glu
    850                 855                 860

Glu Gly Gly Lys Pro Glu Arg Ser Ser Ser Pro Ala Ser Ala Leu Thr
865                 870                 875                 880

Pro Glu Gly Glu Ala Thr Ser Val Thr Leu Val Glu Glu Leu Ser Leu
                885                 890                 895

Gln Glu Ala Met Arg Lys Glu Pro Gly Glu Ser Ser Ser Arg Lys Ala
            900                 905                 910

Cys Glu Val Cys Gly Gln Ala Phe Pro Ser Gln Ala Ala Leu Glu Glu
        915                 920                 925

His Gln Lys Thr His Pro Lys Glu Gly Pro Leu Phe Thr Cys Val Phe
    930                 935                 940

Cys Arg Gln Gly Phe Leu Glu Arg Ala Thr Leu Lys Lys His Met Leu
945                 950                 955                 960

Leu Ala His His Gln Val Gln Pro Phe Ala Pro His Gly Pro Gln Asn
                965                 970                 975

Ile Ala Ala Leu Ser Leu Val Pro Gly Cys Ser Pro Ser Ile Thr Ser
            980                 985                 990

Thr Gly Leu Ser Pro Phe Pro Arg  Lys Asp Asp Pro Thr  Ile Pro
        995                 1000                1005


<210> SEQ ID NO 37
<211> LENGTH: 121
<212> TYPE: PRT
<213> ORGANISM: Homo sapiens

<400> SEQUENCE: 37

Met Asn Ala Pro Arg Ile Cys Ser Glu Tyr Asp Glu Glu Glu Val Asp
1               5                   10                  15

Tyr Glu Glu Ser Asp Ser Asp Glu Ser Trp Thr Thr Glu Ser Ala Ile
            20                  25                  30

Ser Ser Glu Ala Ile Leu Ser Ser Met Cys Met Asn Gly Gly Glu Glu
        35                  40                  45

Lys Pro Phe Ala Cys Pro Val Pro Gly Cys Lys Lys Arg Tyr Lys Asn
    50                  55                  60

Val Asn Gly Ile Lys Tyr His Ala Lys Asn Gly His Arg Thr Gln Ile
65                  70                  75                  80

Arg Val Arg Lys Pro Phe Lys Cys Arg Cys Gly Lys Ser Tyr Lys Thr
                85                  90                  95

Ala Gln Gly Leu Arg His His Thr Ile Asn Phe His Pro Pro Val Ser
            100                 105                 110

Ala Glu Ile Ile Arg Lys Met Gln Gln
        115                 120


<210> SEQ ID NO 38
<211> LENGTH: 736
<212> TYPE: PRT
<213> ORGANISM: Homo sapiens

<400> SEQUENCE: 38
```

-continued

```
Met Glu Ala Leu Ile Pro Val Ile Asn Lys Leu Gln Asp Val Phe Asn
1               5                   10                  15

Thr Val Gly Ala Asp Ile Ile Gln Leu Pro Gln Ile Val Val Val Gly
            20                  25                  30

Thr Gln Ser Ser Gly Lys Ser Ser Val Leu Glu Ser Leu Val Gly Arg
        35                  40                  45

Asp Leu Leu Pro Arg Gly Thr Gly Ile Val Thr Arg Arg Pro Leu Ile
    50                  55                  60

Leu Gln Leu Val His Val Thr Gln Glu Asp Lys Arg Lys Thr Thr Gly
65                  70                  75                  80

Glu Glu Asn Gly Val Glu Ala Glu Glu Trp Gly Lys Phe Leu His Thr
                85                  90                  95

Lys Asn Lys Leu Tyr Thr Asp Phe Asp Glu Ile Arg Gln Glu Ile Glu
            100                 105                 110

Asn Glu Thr Glu Arg Ile Ser Gly Asn Asn Lys Gly Val Ser Pro Glu
        115                 120                 125

Pro Ile His Leu Lys Ile Phe Ser Pro Asn Val Val Asn Leu Thr Leu
    130                 135                 140

Val Asp Leu Pro Gly Met Thr Lys Val Pro Val Gly Asp Gln Pro Lys
145                 150                 155                 160

Asp Ile Glu Leu Gln Ile Arg Glu Leu Ile Leu Arg Phe Ile Ser Asn
                165                 170                 175

Pro Asn Ser Ile Ile Leu Ala Val Thr Ala Ala Asn Thr Asp Met Ala
            180                 185                 190

Thr Ser Glu Ala Leu Lys Ile Ser Arg Glu Val Asp Pro Asp Gly Arg
        195                 200                 205

Arg Thr Leu Ala Val Ile Thr Lys Leu Asp Leu Met Asp Ala Gly Thr
    210                 215                 220

Asp Ala Met Asp Val Leu Met Gly Arg Val Ile Pro Val Lys Leu Gly
225                 230                 235                 240

Ile Ile Gly Val Val Asn Arg Ser Gln Leu Asp Ile Asn Asn Lys Lys
                245                 250                 255

Ser Val Thr Asp Ser Ile Arg Asp Glu Tyr Ala Phe Leu Gln Lys Lys
            260                 265                 270

Tyr Pro Ser Leu Ala Asn Arg Asn Gly Thr Lys Tyr Leu Ala Arg Thr
        275                 280                 285

Leu Asn Arg Leu Leu Met His His Ile Arg Asp Cys Leu Pro Glu Leu
    290                 295                 300

Lys Thr Arg Ile Asn Val Leu Ala Ala Gln Tyr Gln Ser Leu Leu Asn
305                 310                 315                 320

Ser Tyr Gly Glu Pro Val Asp Asp Lys Ser Ala Thr Leu Leu Gln Leu
                325                 330                 335

Ile Thr Lys Phe Ala Thr Glu Tyr Cys Asn Thr Ile Glu Gly Thr Ala
            340                 345                 350

Lys Tyr Ile Glu Thr Ser Glu Leu Cys Gly Gly Ala Arg Ile Cys Tyr
        355                 360                 365

Ile Phe His Glu Thr Phe Gly Arg Thr Leu Glu Ser Val Asp Pro Leu
    370                 375                 380

Gly Gly Leu Asn Thr Ile Asp Ile Leu Thr Ala Ile Arg Asn Ala Thr
385                 390                 395                 400

Gly Pro Arg Pro Ala Leu Phe Val Pro Glu Val Ser Phe Glu Leu Leu
                405                 410                 415
```

-continued

```
Val Lys Arg Gln Ile Lys Arg Leu Glu Glu Pro Ser Leu Arg Cys Val
            420                 425                 430

Glu Leu Val His Glu Glu Met Gln Arg Ile Ile Gln His Cys Ser Asn
        435                 440                 445

Tyr Ser Thr Gln Glu Leu Leu Arg Phe Pro Lys Leu His Asp Ala Ile
    450                 455                 460

Val Glu Val Val Thr Cys Leu Leu Arg Lys Arg Leu Pro Val Thr Asn
465                 470                 475                 480

Glu Met Val His Asn Leu Val Ala Ile Glu Leu Ala Tyr Ile Asn Thr
                485                 490                 495

Lys His Pro Asp Phe Ala Asp Ala Cys Gly Leu Met Asn Asn Asn Ile
            500                 505                 510

Glu Glu Gln Arg Arg Asn Arg Leu Ala Arg Glu Leu Pro Ser Ala Val
        515                 520                 525

Ser Arg Asp Lys Ser Ser Lys Val Pro Ser Ala Leu Ala Pro Ala Ser
    530                 535                 540

Gln Glu Pro Ser Pro Ala Ala Ser Ala Glu Ala Asp Gly Lys Leu Ile
545                 550                 555                 560

Gln Asp Ser Arg Arg Glu Thr Lys Asn Val Ala Ser Gly Gly Gly Gly
                565                 570                 575

Val Gly Asp Gly Val Gln Glu Pro Thr Thr Gly Asn Trp Arg Gly Met
            580                 585                 590

Leu Lys Thr Ser Lys Ala Glu Glu Leu Leu Ala Glu Glu Lys Ser Lys
        595                 600                 605

Pro Ile Pro Ile Met Pro Ala Ser Pro Gln Lys Gly His Ala Val Asn
    610                 615                 620

Leu Leu Asp Val Pro Val Pro Val Ala Arg Lys Leu Ser Ala Arg Glu
625                 630                 635                 640

Gln Arg Asp Cys Glu Val Ile Glu Arg Leu Ile Lys Ser Tyr Phe Leu
                645                 650                 655

Ile Val Arg Lys Asn Ile Gln Asp Ser Val Pro Lys Ala Val Met His
            660                 665                 670

Phe Leu Val Asn His Val Lys Asp Thr Leu Gln Ser Glu Leu Val Gly
        675                 680                 685

Gln Leu Tyr Lys Ser Ser Leu Leu Asp Asp Leu Leu Thr Glu Ser Glu
    690                 695                 700

Asp Met Ala Gln Arg Arg Lys Glu Ala Ala Asp Met Leu Lys Ala Leu
705                 710                 715                 720

Gln Gly Ala Ser Gln Ile Ile Ala Glu Ile Arg Glu Thr His Leu Trp
                725                 730                 735


<210> SEQ ID NO 39
<211> LENGTH: 710
<212> TYPE: PRT
<213> ORGANISM: Homo sapiens

<400> SEQUENCE: 39

Met Glu Ala Leu Ile Pro Val Ile Asn Lys Leu Gln Asp Val Phe Asn
1               5                   10                  15

Thr Val Gly Ala Asp Ile Ile Gln Leu Pro Gln Ile Val Val Val Gly
            20                  25                  30

Thr Gln Ser Ser Gly Lys Ser Ser Val Leu Glu Ser Leu Val Gly Arg
        35                  40                  45

Asp Leu Leu Pro Arg Gly Thr Gly Ile Val Thr Arg Arg Pro Leu Ile
    50                  55                  60
```

-continued

```
Leu Gln Leu Val His Val Thr Gln Glu Asp Lys Arg Lys Thr Thr Gly
65                  70                  75                  80

Glu Glu Asn Gly Val Glu Ala Glu Glu Trp Gly Lys Phe Leu His Thr
                85                  90                  95

Lys Asn Lys Leu Tyr Thr Asp Phe Asp Glu Ile Arg Gln Glu Ile Glu
            100                 105                 110

Asn Glu Thr Glu Arg Ile Ser Gly Asn Asn Lys Gly Val Ser Pro Glu
        115                 120                 125

Pro Ile His Leu Lys Ile Phe Ser Pro Asn Val Val Asn Leu Thr Leu
    130                 135                 140

Val Asp Leu Pro Gly Met Thr Lys Val Pro Val Gly Asp Gln Pro Lys
145                 150                 155                 160

Asp Ile Glu Leu Gln Ile Arg Glu Leu Ile Leu Arg Phe Ile Ser Asn
                165                 170                 175

Pro Asn Ser Ile Ile Leu Ala Val Thr Ala Ala Asn Thr Asp Met Ala
            180                 185                 190

Thr Ser Glu Ala Leu Lys Ile Ser Arg Glu Val Asp Pro Asp Gly Arg
        195                 200                 205

Arg Thr Leu Ala Val Ile Thr Lys Leu Asp Leu Met Asp Ala Gly Thr
    210                 215                 220

Asp Ala Met Asp Val Leu Met Gly Arg Val Ile Pro Val Lys Leu Gly
225                 230                 235                 240

Ile Ile Gly Val Val Asn Arg Ser Gln Leu Asp Ile Asn Asn Lys Lys
                245                 250                 255

Ser Val Thr Asp Ser Ile Arg Asp Glu Tyr Ala Phe Leu Gln Lys Lys
            260                 265                 270

Tyr Pro Ser Leu Ala Asn Arg Asn Gly Thr Lys Tyr Leu Ala Arg Thr
        275                 280                 285

Leu Asn Arg Leu Leu Met His His Ile Arg Asp Cys Leu Pro Glu Leu
    290                 295                 300

Lys Thr Arg Ile Asn Val Leu Ala Ala Gln Tyr Gln Ser Leu Leu Asn
305                 310                 315                 320

Ser Tyr Gly Glu Pro Val Asp Asp Lys Ser Ala Thr Leu Leu Gln Leu
                325                 330                 335

Ile Thr Lys Phe Ala Thr Glu Tyr Cys Asn Thr Ile Glu Gly Thr Ala
            340                 345                 350

Lys Tyr Ile Glu Thr Ser Glu Leu Cys Gly Gly Ala Arg Ile Cys Tyr
        355                 360                 365

Ile Phe His Glu Thr Phe Gly Arg Thr Leu Glu Ser Val Asp Pro Leu
    370                 375                 380

Gly Gly Leu Asn Thr Ile Asp Ile Leu Thr Ala Ile Arg Asn Ala Thr
385                 390                 395                 400

Gly Pro Arg Pro Ala Leu Phe Val Pro Glu Val Ser Phe Glu Leu Leu
                405                 410                 415

Val Lys Arg Gln Ile Lys Arg Leu Glu Glu Pro Ser Leu Arg Cys Val
            420                 425                 430

Glu Leu Val His Glu Glu Met Gln Arg Ile Ile Gln His Cys Ser Asn
        435                 440                 445

Tyr Ser Thr Gln Glu Leu Leu Arg Phe Pro Lys Leu His Asp Ala Ile
    450                 455                 460

Val Glu Val Val Thr Cys Leu Leu Arg Lys Arg Leu Pro Val Thr Asn
465                 470                 475                 480
```

-continued

```
Glu Met Val His Asn Leu Val Ala Ile Glu Leu Ala Tyr Ile Asn Thr
            485                 490                 495

Lys His Pro Asp Phe Ala Asp Ala Cys Gly Leu Met Asn Asn Asn Ile
            500                 505                 510

Glu Glu Gln Arg Arg Asn Arg Leu Ala Arg Glu Leu Pro Ser Ala Val
        515                 520                 525

Ser Arg Asp Lys Leu Ile Gln Asp Ser Arg Arg Glu Thr Lys Asn Val
    530                 535                 540

Ala Ser Gly Gly Gly Gly Val Gly Asp Gly Val Gln Glu Pro Thr Thr
545                 550                 555                 560

Gly Asn Trp Arg Gly Met Leu Lys Thr Ser Lys Ala Glu Glu Leu Leu
            565                 570                 575

Ala Glu Glu Lys Ser Lys Pro Ile Pro Ile Met Pro Ala Ser Pro Gln
            580                 585                 590

Lys Gly His Ala Val Asn Leu Leu Asp Val Pro Val Pro Val Ala Arg
        595                 600                 605

Lys Leu Ser Ala Arg Glu Gln Arg Asp Cys Glu Val Ile Glu Arg Leu
    610                 615                 620

Ile Lys Ser Tyr Phe Leu Ile Val Arg Lys Asn Ile Gln Asp Ser Val
625                 630                 635                 640

Pro Lys Ala Val Met His Phe Leu Val Asn His Val Lys Asp Thr Leu
            645                 650                 655

Gln Ser Glu Leu Val Gly Gln Leu Tyr Lys Ser Ser Leu Leu Asp Asp
            660                 665                 670

Leu Leu Thr Glu Ser Glu Asp Met Ala Gln Arg Arg Lys Glu Ala Ala
        675                 680                 685

Asp Met Leu Lys Ala Leu Gln Gly Ala Ser Gln Ile Ile Ala Glu Ile
    690                 695                 700

Arg Glu Thr His Leu Trp
705                 710


<210> SEQ ID NO 40
<211> LENGTH: 699
<212> TYPE: PRT
<213> ORGANISM: Homo sapiens

<400> SEQUENCE: 40

Met Glu Ala Leu Ile Pro Val Ile Asn Lys Leu Gln Asp Val Phe Asn
1               5                   10                  15

Thr Val Gly Ala Asp Ile Ile Gln Leu Pro Gln Ile Val Val Val Gly
            20                  25                  30

Thr Gln Ser Ser Gly Lys Ser Ser Val Leu Glu Ser Leu Val Gly Arg
        35                  40                  45

Asp Leu Leu Pro Arg Gly Thr Gly Ile Val Thr Arg Arg Pro Leu Ile
    50                  55                  60

Leu Gln Leu Val His Val Thr Gln Glu Asp Lys Arg Lys Thr Thr Gly
65                  70                  75                  80

Glu Glu Asn Gly Val Glu Ala Glu Glu Trp Gly Lys Phe Leu His Thr
            85                  90                  95

Lys Asn Lys Leu Tyr Thr Asp Phe Asp Glu Ile Arg Gln Glu Ile Glu
            100                 105                 110

Asn Glu Thr Glu Arg Ile Ser Gly Asn Asn Lys Gly Val Ser Pro Glu
        115                 120                 125

Pro Ile His Leu Lys Ile Phe Ser Pro Asn Val Val Asn Leu Thr Leu
    130                 135                 140
```

-continued

```
Val Asp Leu Pro Gly Met Thr Lys Val Pro Val Gly Asp Gln Pro Lys
145                 150                 155                 160

Asp Ile Glu Leu Gln Ile Arg Glu Leu Ile Leu Arg Phe Ile Ser Asn
                165                 170                 175

Pro Asn Ser Ile Ile Leu Ala Val Thr Ala Ala Asn Thr Asp Met Ala
            180                 185                 190

Thr Ser Glu Ala Leu Lys Ile Ser Arg Glu Val Asp Pro Asp Gly Cys
        195                 200                 205

Arg Thr Leu Ala Val Ile Thr Lys Leu Asp Leu Met Asp Ala Gly Thr
    210                 215                 220

Asp Ala Met Asp Val Leu Met Gly Arg Val Ile Pro Val Lys Leu Gly
225                 230                 235                 240

Ile Ile Gly Val Val Asn Arg Ser Gln Leu Asp Ile Asn Asn Lys Lys
                245                 250                 255

Ser Val Thr Asp Ser Ile Arg Asp Glu Tyr Ala Phe Leu Gln Lys Lys
            260                 265                 270

Tyr Pro Ser Leu Ala Asn Arg Asn Gly Thr Lys Tyr Leu Ala Arg Thr
        275                 280                 285

Leu Asn Arg Leu Leu Met His His Ile Arg Asp Cys Leu Pro Glu Leu
    290                 295                 300

Lys Thr Arg Ile Asn Val Leu Ala Ala Gln Tyr Gln Ser Leu Leu Asn
305                 310                 315                 320

Ser Tyr Gly Glu Pro Val Asp Asp Lys Ser Ala Thr Leu Leu Gln Leu
                325                 330                 335

Ile Thr Lys Phe Ala Thr Glu Tyr Cys Asn Thr Ile Glu Gly Thr Ala
            340                 345                 350

Lys Tyr Ile Glu Thr Ser Glu Leu Cys Gly Gly Ala Arg Ile Cys Tyr
        355                 360                 365

Ile Phe His Glu Thr Phe Gly Arg Thr Leu Glu Ser Val Asp Pro Leu
    370                 375                 380

Gly Gly Leu Asn Thr Ile Asp Ile Leu Thr Ala Ile Arg Asn Ala Thr
385                 390                 395                 400

Gly Pro Arg Pro Ala Leu Phe Val Pro Glu Val Ser Phe Glu Leu Leu
                405                 410                 415

Val Lys Arg Gln Ile Lys Arg Leu Glu Glu Pro Ser Leu Arg Cys Val
            420                 425                 430

Glu Leu Val His Glu Glu Met Gln Arg Ile Ile Gln His Cys Ser Asn
        435                 440                 445

Tyr Ser Thr Gln Glu Leu Leu Arg Phe Pro Lys Leu His Asp Ala Ile
    450                 455                 460

Val Glu Val Val Thr Cys Leu Leu Arg Lys Arg Leu Pro Val Thr Asn
465                 470                 475                 480

Glu Met Val His Asn Leu Val Ala Ile Glu Leu Ala Tyr Ile Asn Thr
                485                 490                 495

Lys His Pro Asp Phe Ala Asp Ala Cys Gly Leu Met Asn Asn Asn Ile
            500                 505                 510

Glu Glu Gln Arg Arg Asn Arg Leu Ala Arg Glu Leu Pro Ser Ala Val
        515                 520                 525

Ser Arg Asp Lys Val Ala Ser Gly Gly Gly Gly Val Gly Asp Gly Val
    530                 535                 540

Gln Glu Pro Thr Thr Gly Asn Trp Arg Gly Met Leu Lys Thr Ser Lys
545                 550                 555                 560
```

-continued

```
Ala Glu Glu Leu Leu Ala Glu Glu Lys Ser Lys Pro Ile Pro Ile Met
            565                 570                 575

Pro Ala Ser Pro Gln Lys Gly His Ala Val Asn Leu Leu Asp Val Pro
            580                 585                 590

Val Pro Val Ala Arg Lys Leu Ser Ala Arg Glu Gln Arg Asp Cys Glu
        595                 600                 605

Val Ile Glu Arg Leu Ile Lys Ser Tyr Phe Leu Ile Val Arg Lys Asn
    610                 615                 620

Ile Gln Asp Ser Val Pro Lys Ala Val Met His Phe Leu Val Asn His
625                 630                 635                 640

Val Lys Asp Thr Leu Gln Ser Glu Leu Val Gly Gln Leu Tyr Lys Ser
            645                 650                 655

Ser Leu Leu Asp Asp Leu Leu Thr Glu Ser Glu Asp Met Ala Gln Arg
            660                 665                 670

Arg Lys Glu Ala Ala Asp Met Leu Lys Ala Leu Gln Gly Ala Ser Gln
        675                 680                 685

Ile Ile Ala Glu Ile Arg Glu Thr His Leu Trp
    690                 695


<210> SEQ ID NO 41
<211> LENGTH: 954
<212> TYPE: PRT
<213> ORGANISM: Homo sapiens

<400> SEQUENCE: 41

Met Ala Glu Pro Gly His Ser His His Leu Ser Ala Arg Val Arg Gly
1               5                   10                  15

Arg Thr Glu Arg Arg Ile Pro Arg Leu Trp Arg Leu Leu Leu Trp Ala
            20                  25                  30

Gly Thr Ala Phe Gln Val Thr Gln Gly Thr Gly Pro Glu Leu His Ala
        35                  40                  45

Cys Lys Glu Ser Glu Tyr His Tyr Glu Tyr Thr Ala Cys Asp Ser Thr
    50                  55                  60

Gly Ser Arg Trp Arg Val Ala Val Pro His Thr Pro Gly Leu Cys Thr
65                  70                  75                  80

Ser Leu Pro Asp Pro Ile Lys Gly Thr Glu Cys Ser Phe Ser Cys Asn
                85                  90                  95

Ala Gly Glu Phe Leu Asp Met Lys Asp Gln Ser Cys Lys Pro Cys Ala
            100                 105                 110

Glu Gly Arg Tyr Ser Leu Gly Thr Gly Ile Arg Phe Asp Glu Trp Asp
        115                 120                 125

Glu Leu Pro His Gly Phe Ala Ser Leu Ser Ala Asn Met Glu Leu Asp
    130                 135                 140

Asp Ser Ala Ala Glu Ser Thr Gly Asn Cys Thr Ser Ser Lys Trp Val
145                 150                 155                 160

Pro Arg Gly Asp Tyr Ile Ala Ser Asn Thr Asp Glu Cys Thr Ala Thr
                165                 170                 175

Leu Met Tyr Ala Val Asn Leu Lys Gln Ser Gly Thr Val Asn Phe Glu
            180                 185                 190

Tyr Tyr Tyr Pro Asp Ser Ser Ile Ile Phe Glu Phe Phe Val Gln Asn
        195                 200                 205

Asp Gln Cys Gln Pro Asn Ala Asp Asp Ser Arg Trp Met Lys Thr Thr
    210                 215                 220

Glu Lys Gly Trp Glu Phe His Ser Val Glu Leu Asn Arg Gly Asn Asn
225                 230                 235                 240
```

-continued

```
Val Leu Tyr Trp Arg Thr Thr Ala Phe Ser Val Trp Thr Lys Val Pro
                245                 250                 255

Lys Pro Val Leu Val Arg Asn Ile Ala Ile Thr Glu Lys Gly Ser Ser
            260                 265                 270

Ser Cys Asn Val Arg Pro Ala Cys Thr Asp Lys Asp Tyr Phe Tyr Thr
        275                 280                 285

His Thr Ala Cys Asp Ala Asn Gly Glu Thr Gln Leu Met Tyr Lys Trp
    290                 295                 300

Ala Lys Pro Lys Ile Cys Ser Glu Asp Leu Glu Gly Ala Val Lys Leu
305                 310                 315                 320

Pro Ala Ser Gly Val Lys Thr His Cys Pro Pro Cys Asn Pro Gly Phe
                325                 330                 335

Phe Lys Thr Asn Asn Ser Thr Cys Gln Pro Cys Pro Tyr Gly Ser Tyr
            340                 345                 350

Ser Asn Gly Ser Asp Cys Thr Arg Cys Pro Ala Gly Thr Glu Pro Ala
        355                 360                 365

Val Gly Phe Glu Tyr Lys Trp Trp Asn Thr Leu Pro Thr Asn Met Glu
    370                 375                 380

Thr Thr Val Leu Ser Gly Ile Asn Phe Glu Tyr Lys Gly Met Thr Gly
385                 390                 395                 400

Trp Glu Val Ala Gly Asp His Ile Tyr Thr Ala Ala Gly Ala Ser Asp
                405                 410                 415

Asn Asp Phe Met Ile Leu Thr Leu Val Val Pro Gly Phe Arg Pro Pro
            420                 425                 430

Gln Ser Val Met Ala Asp Thr Glu Asn Lys Glu Val Ala Arg Ile Thr
        435                 440                 445

Phe Val Phe Glu Thr Leu Cys Ser Val Asn Cys Glu Leu Tyr Phe Met
    450                 455                 460

Val Gly Val Asn Ser Arg Thr Asn Thr Pro Val Glu Thr Trp Lys Gly
465                 470                 475                 480

Ser Lys Gly Lys Gln Ser Tyr Thr Tyr Ile Ile Glu Glu Asn Thr Thr
                485                 490                 495

Thr Ser Phe Thr Trp Ala Phe Gln Arg Thr Thr Phe His Glu Ala Ser
            500                 505                 510

Arg Lys Tyr Thr Asn Asp Val Ala Lys Ile Tyr Ser Ile Asn Val Thr
        515                 520                 525

Asn Val Met Asn Gly Val Ala Ser Tyr Cys Arg Pro Cys Ala Leu Glu
    530                 535                 540

Ala Ser Asp Val Gly Ser Ser Cys Thr Ser Cys Pro Ala Gly Tyr Tyr
545                 550                 555                 560

Ile Asp Arg Asp Ser Gly Thr Cys His Ser Cys Pro Thr Asn Thr Ile
                565                 570                 575

Leu Lys Ala His Gln Pro Tyr Gly Val Gln Ala Cys Val Pro Cys Gly
            580                 585                 590

Pro Gly Thr Lys Asn Asn Lys Ile His Ser Leu Cys Tyr Asn Asp Cys
        595                 600                 605

Thr Phe Ser Arg Asn Thr Pro Thr Arg Thr Phe Asn Tyr Asn Phe Ser
    610                 615                 620

Ala Leu Ala Asn Thr Val Thr Leu Ala Gly Gly Pro Ser Phe Thr Ser
625                 630                 635                 640

Lys Gly Leu Lys Tyr Phe His His Phe Thr Leu Ser Leu Cys Gly Asn
                645                 650                 655
```

-continued

```
Gln Gly Arg Lys Met Ser Val Cys Thr Asp Asn Val Thr Asp Leu Arg
            660                 665                 670

Ile Pro Glu Gly Glu Ser Gly Phe Ser Lys Ser Ile Thr Ala Tyr Val
        675                 680                 685

Cys Gln Ala Val Ile Ile Pro Pro Glu Val Thr Gly Tyr Lys Ala Gly
    690                 695                 700

Val Ser Ser Gln Pro Val Ser Leu Ala Asp Arg Leu Ile Gly Val Thr
705                 710                 715                 720

Thr Asp Met Thr Leu Asp Gly Ile Thr Ser Pro Ala Glu Leu Phe His
                725                 730                 735

Leu Glu Ser Leu Gly Ile Pro Asp Val Ile Phe Phe Tyr Arg Ser Asn
            740                 745                 750

Asp Val Thr Gln Ser Cys Ser Ser Gly Arg Ser Thr Thr Ile Arg Val
        755                 760                 765

Arg Cys Ser Pro Gln Lys Thr Val Pro Gly Ser Leu Leu Leu Pro Gly
    770                 775                 780

Thr Cys Ser Asp Gly Thr Cys Asp Gly Cys Asn Phe His Phe Leu Trp
785                 790                 795                 800

Glu Ser Ala Ala Ala Cys Pro Leu Cys Ser Val Ala Asp Tyr His Ala
                805                 810                 815

Ile Val Ser Ser Cys Val Ala Gly Ile Gln Lys Thr Thr Tyr Val Trp
            820                 825                 830

Arg Glu Pro Lys Leu Cys Ser Gly Gly Ile Ser Leu Pro Glu Gln Arg
        835                 840                 845

Val Thr Ile Cys Lys Thr Ile Asp Phe Trp Leu Lys Val Gly Ile Ser
    850                 855                 860

Ala Gly Thr Cys Thr Ala Ile Leu Leu Thr Val Leu Thr Cys Tyr Phe
865                 870                 875                 880

Trp Lys Lys Asn Gln Lys Leu Glu Tyr Lys Tyr Ser Lys Leu Val Met
                885                 890                 895

Asn Ala Thr Leu Lys Asp Cys Asp Leu Pro Ala Ala Asp Ser Cys Ala
            900                 905                 910

Ile Met Glu Gly Glu Asp Val Glu Asp Asp Leu Ile Phe Thr Ser Lys
        915                 920                 925

Lys Ser Leu Phe Gly Lys Ile Lys Ser Phe Thr Ser Lys Gln Pro Ala
    930                 935                 940

Pro Val Thr Ile Ser Leu Ser Glu Asp Ser
945                 950


<210> SEQ ID NO 42
<211> LENGTH: 595
<212> TYPE: PRT
<213> ORGANISM: Homo sapiens

<400> SEQUENCE: 42

Met Thr Met Thr Leu His Thr Lys Ala Ser Gly Met Ala Leu Leu His
1               5                   10                  15

Gln Ile Gln Gly Asn Glu Leu Glu Pro Leu Asn Arg Pro Gln Leu Lys
            20                  25                  30

Ile Pro Leu Glu Arg Pro Leu Gly Glu Val Tyr Leu Asp Ser Ser Lys
        35                  40                  45

Pro Ala Val Tyr Asn Tyr Pro Glu Gly Ala Ala Tyr Glu Phe Asn Ala
    50                  55                  60

Ala Ala Ala Ala Asn Ala Gln Val Tyr Gly Gln Thr Gly Leu Pro Tyr
65                  70                  75                  80
```

-continued

```
Gly Pro Gly Ser Glu Ala Ala Ala Phe Gly Ser Asn Gly Leu Gly Gly
                85                  90                  95

Phe Pro Pro Leu Asn Ser Val Ser Pro Ser Pro Leu Met Leu Leu His
            100                 105                 110

Pro Pro Pro Gln Leu Ser Pro Phe Leu Gln Pro His Gly Gln Gln Val
        115                 120                 125

Pro Tyr Tyr Leu Glu Asn Glu Pro Ser Gly Tyr Thr Val Arg Glu Ala
    130                 135                 140

Gly Pro Pro Ala Phe Tyr Arg Pro Asn Ser Asp Asn Arg Arg Gln Gly
145                 150                 155                 160

Gly Arg Glu Arg Leu Ala Ser Thr Asn Asp Lys Gly Ser Met Ala Met
                165                 170                 175

Glu Ser Ala Lys Glu Thr Arg Tyr Cys Ala Val Cys Asn Asp Tyr Ala
            180                 185                 190

Ser Gly Tyr His Tyr Gly Val Trp Ser Cys Glu Gly Cys Lys Ala Phe
        195                 200                 205

Phe Lys Arg Ser Ile Gln Gly His Asn Asp Tyr Met Cys Pro Ala Thr
    210                 215                 220

Asn Gln Cys Thr Ile Asp Lys Asn Arg Arg Lys Ser Cys Gln Ala Cys
225                 230                 235                 240

Arg Leu Arg Lys Cys Tyr Glu Val Gly Met Met Lys Gly Gly Ile Arg
                245                 250                 255

Lys Asp Arg Arg Gly Gly Arg Met Leu Lys His Lys Arg Gln Arg Asp
            260                 265                 270

Asp Gly Glu Gly Arg Gly Glu Val Gly Ser Ala Gly Asp Met Arg Ala
        275                 280                 285

Ala Asn Leu Trp Pro Ser Pro Leu Met Ile Lys Arg Ser Lys Lys Asn
    290                 295                 300

Ser Leu Ala Leu Ser Leu Thr Ala Asp Gln Met Val Ser Ala Leu Leu
305                 310                 315                 320

Asp Ala Glu Pro Pro Ile Leu Tyr Ser Glu Tyr Asp Pro Thr Arg Pro
                325                 330                 335

Phe Ser Glu Ala Ser Met Met Gly Leu Leu Thr Asn Leu Ala Asp Arg
            340                 345                 350

Glu Leu Val His Met Ile Asn Trp Ala Lys Arg Val Pro Gly Phe Val
        355                 360                 365

Asp Leu Thr Leu His Asp Gln Val His Leu Leu Glu Cys Ala Trp Leu
    370                 375                 380

Glu Ile Leu Met Ile Gly Leu Val Trp Arg Ser Met Glu His Pro Val
385                 390                 395                 400

Lys Leu Leu Phe Ala Pro Asn Leu Leu Leu Asp Arg Asn Gln Gly Lys
                405                 410                 415

Cys Val Glu Gly Met Val Glu Ile Phe Asp Met Leu Leu Ala Thr Ser
            420                 425                 430

Ser Arg Phe Arg Met Met Asn Leu Gln Gly Glu Glu Phe Val Cys Leu
        435                 440                 445

Lys Ser Ile Ile Leu Leu Asn Ser Gly Val Tyr Thr Phe Leu Ser Ser
    450                 455                 460

Thr Leu Lys Ser Leu Glu Glu Lys Asp His Ile His Arg Val Leu Asp
465                 470                 475                 480

Lys Ile Thr Asp Thr Leu Ile His Leu Met Ala Lys Ala Gly Leu Thr
                485                 490                 495
```

-continued

```
Leu Gln Gln Gln His Gln Arg Leu Ala Gln Leu Leu Leu Ile Leu Ser
            500                 505                 510

His Ile Arg His Met Ser Asn Lys Gly Met Glu His Leu Tyr Ser Met
        515                 520                 525

Lys Cys Lys Asn Val Val Pro Leu Tyr Asp Leu Leu Leu Glu Met Leu
    530                 535                 540

Asp Ala His Arg Leu His Ala Pro Thr Ser Arg Gly Gly Ala Ser Val
545                 550                 555                 560

Glu Glu Thr Asp Gln Ser His Leu Ala Thr Ala Gly Ser Thr Ser Ser
                565                 570                 575

His Ser Leu Gln Lys Tyr Tyr Ile Thr Gly Glu Ala Glu Gly Phe Pro
            580                 585                 590

Ala Thr Val
        595


<210> SEQ ID NO 43
<211> LENGTH: 1575
<212> TYPE: PRT
<213> ORGANISM: Homo sapiens

<400> SEQUENCE: 43

Met Ile Lys Asp Trp Thr Lys Glu His Val Lys Lys Trp Val Asn Glu
1               5                   10                  15

Asp Leu Lys Ile Asn Glu Gln Tyr Gly Gln Ile Leu Leu Ser Glu Glu
            20                  25                  30

Val Thr Gly Leu Val Leu Gln Glu Leu Thr Glu Lys Asp Leu Val Glu
        35                  40                  45

Met Gly Leu Pro Trp Gly Pro Ala Leu Leu Ile Lys Arg Ser Tyr Asn
    50                  55                  60

Lys Leu Asn Ser Lys Ser Pro Glu Ser Asp Asn His Asp Pro Gly Gln
65                  70                  75                  80

Leu Asp Asn Ser Lys Pro Ser Lys Thr Glu His Gln Lys Asn Pro Lys
                85                  90                  95

His Thr Lys Lys Glu Glu Glu Asn Ser Met Ser Ser Asn Ile Asp Tyr
            100                 105                 110

Asp Pro Arg Glu Ile Arg Asp Ile Lys Gln Glu Glu Ser Ile Leu Met
        115                 120                 125

Lys Glu Asn Val Leu Asp Glu Val Ala Asn Ala Lys His Lys Lys Lys
    130                 135                 140

Gly Lys Leu Lys Pro Glu Gln Leu Thr Cys Met Pro Tyr Pro Phe Asp
145                 150                 155                 160

Gln Phe His Asp Ser His Arg Tyr Ile Glu His Tyr Thr Leu Gln Pro
                165                 170                 175

Glu Thr Gly Ala Leu Asn Leu Ile Asp Pro Ile His Glu Phe Lys Ala
            180                 185                 190

Leu Thr Asn Thr Glu Thr Ala Thr Glu Val Asp Ile Lys Met Lys Phe
        195                 200                 205

Ser Asn Glu Val Phe Arg Phe Ala Ser Ala Cys Met Asn Ser Arg Thr
    210                 215                 220

Asn Gly Thr Ile His Phe Gly Val Lys Asp Lys Pro His Gly Glu Ile
225                 230                 235                 240

Val Gly Val Lys Ile Thr Ser Lys Ala Ala Phe Ile Asp His Phe Asn
                245                 250                 255

Val Met Ile Lys Lys Tyr Phe Glu Glu Ser Glu Ile Asn Glu Ala Lys
            260                 265                 270
```

-continued

```
Lys Cys Ile Arg Glu Pro Arg Phe Val Glu Val Leu Leu Gln Asn Asn
        275                 280                 285

Thr Pro Ser Asp Arg Phe Val Ile Glu Val Asp Thr Ile Pro Lys His
    290                 295                 300

Ser Ile Cys Asn Asp Lys Tyr Phe Tyr Ile Gln Met Gln Ile Cys Lys
305                 310                 315                 320

Asp Lys Ile Trp Lys Gln Asn Gln Asn Leu Ser Leu Phe Val Arg Glu
                325                 330                 335

Gly Ala Ser Ser Arg Asp Ile Leu Ala Asn Ser Lys Gln Arg Asp Val
            340                 345                 350

Asp Phe Lys Ala Phe Leu Gln Asn Leu Lys Ser Leu Val Ala Ser Arg
        355                 360                 365

Lys Glu Ala Glu Glu Glu Tyr Gly Met Lys Ala Met Lys Lys Glu Ser
    370                 375                 380

Glu Gly Leu Lys Leu Val Lys Leu Leu Ile Gly Asn Arg Asp Ser Leu
385                 390                 395                 400

Asp Asn Ser Tyr Tyr Asp Trp Tyr Ile Leu Val Thr Asn Lys Cys His
                405                 410                 415

Pro Asn Gln Ile Lys His Leu Asp Phe Leu Lys Glu Ile Lys Trp Phe
            420                 425                 430

Ala Val Leu Glu Phe Asp Pro Glu Ser Met Ile Asn Gly Val Val Lys
        435                 440                 445

Ala Tyr Lys Glu Ser Arg Val Ala Asn Leu His Phe Pro Asn Gln Tyr
    450                 455                 460

Glu Asp Lys Thr Thr Asn Met Trp Glu Lys Ile Ser Thr Leu Asn Leu
465                 470                 475                 480

Tyr Gln Gln Pro Ser Trp Ile Phe Cys Asn Gly Arg Ser Asp Leu Lys
                485                 490                 495

Ser Glu Thr Tyr Lys Pro Leu Glu Pro His Leu Trp Gln Arg Glu Arg
            500                 505                 510

Ala Ser Glu Val Arg Lys Leu Ile Leu Phe Leu Thr Asp Glu Asn Ile
        515                 520                 525

Met Thr Arg Gly Lys Phe Leu Val Val Phe Leu Leu Leu Ser Ser Val
    530                 535                 540

Glu Ser Pro Gly Asp Pro Leu Ile Glu Thr Phe Trp Ala Phe Tyr Gln
545                 550                 555                 560

Ala Leu Lys Gly Met Glu Asn Met Leu Cys Ile Ser Val Asn Ser His
                565                 570                 575

Ile Tyr Gln Arg Trp Lys Asp Leu Leu Gln Thr Arg Met Lys Met Glu
            580                 585                 590

Asp Glu Leu Thr Asn His Ser Ile Ser Thr Leu Asn Ile Glu Leu Val
        595                 600                 605

Asn Ser Thr Ile Leu Lys Leu Lys Ser Val Thr Arg Ser Ser Arg Arg
    610                 615                 620

Phe Leu Pro Ala Arg Gly Ser Ser Ser Val Ile Leu Glu Lys Lys Lys
625                 630                 635                 640

Glu Asp Val Leu Thr Ala Leu Glu Ile Leu Cys Glu Asn Glu Cys Thr
                645                 650                 655

Glu Thr Asp Ile Glu Lys Asp Lys Ser Lys Phe Leu Glu Phe Lys Lys
            660                 665                 670

Ser Lys Glu Glu His Phe Tyr Arg Gly Gly Lys Val Ser Trp Trp Asn
        675                 680                 685
```

-continued

```
Phe Tyr Phe Ser Ser Glu Asn Tyr Ser Ser Asp Phe Val Lys Arg Asp
    690                 695                 700

Ser Tyr Glu Lys Leu Lys Asp Leu Ile His Cys Trp Ala Glu Ser Pro
705                 710                 715                 720

Lys Pro Ile Phe Ala Lys Ile Ile Asn Leu Tyr His His Pro Gly Cys
                725                 730                 735

Gly Gly Thr Thr Leu Ala Met His Val Leu Trp Asp Leu Lys Lys Asn
            740                 745                 750

Phe Arg Cys Ala Val Leu Lys Asn Lys Thr Thr Asp Phe Ala Glu Ile
        755                 760                 765

Ala Glu Gln Val Ile Asn Leu Val Thr Tyr Arg Ala Lys Ser His Gln
    770                 775                 780

Asp Tyr Ile Pro Val Leu Leu Leu Val Asp Asp Phe Glu Glu Gln Glu
785                 790                 795                 800

Asn Val Tyr Phe Leu Gln Asn Ala Ile His Ser Val Leu Ala Glu Lys
                805                 810                 815

Asp Leu Arg Tyr Glu Lys Thr Leu Val Ile Ile Leu Asn Cys Met Arg
            820                 825                 830

Ser Arg Asn Pro Asp Glu Ser Ala Lys Leu Ala Asp Ser Ile Ala Leu
        835                 840                 845

Asn Tyr Gln Leu Ser Ser Lys Glu Gln Arg Ala Phe Gly Ala Lys Leu
    850                 855                 860

Lys Glu Ile Glu Lys Gln His Lys Asn Cys Glu Asn Phe Tyr Ser Phe
865                 870                 875                 880

Met Ile Met Lys Ser Asn Phe Asp Glu Thr Tyr Ile Glu Asn Val Val
                885                 890                 895

Arg Asn Ile Leu Lys Gly Gln Asp Val Asp Ser Lys Glu Ala Gln Leu
            900                 905                 910

Ile Ser Phe Leu Ala Leu Leu Ser Ser Tyr Val Thr Asp Ser Thr Ile
        915                 920                 925

Ser Val Ser Gln Cys Glu Ile Phe Leu Gly Ile Ile Tyr Thr Ser Thr
    930                 935                 940

Pro Trp Glu Pro Glu Ser Leu Glu Asp Lys Met Gly Thr Tyr Ser Thr
945                 950                 955                 960

Leu Leu Ile Lys Thr Glu Val Ala Glu Tyr Gly Arg Tyr Thr Gly Val
                965                 970                 975

Arg Ile Ile His Pro Leu Ile Ala Leu Tyr Cys Leu Lys Glu Leu Glu
            980                 985                 990

Arg Ser Tyr His Leu Asp Lys Cys  Gln Ile Ala Leu Asn  Ile Leu Glu
        995                 1000                1005

Glu Asn  Leu Phe Tyr Asp Ser  Gly Ile Gly Arg Asp  Lys Phe Gln
    1010                1015                1020

His Asp  Val Gln Thr Leu Leu  Leu Thr Arg Gln Arg  Lys Val Tyr
    1025                1030                1035

Gly Asp  Glu Thr Asp Thr Leu  Phe Ser Pro Leu Met  Glu Ala Leu
    1040                1045                1050

Gln Asn  Lys Asp Ile Glu Lys  Val Leu Ser Ala Gly  Ser Arg Arg
    1055                1060                1065

Phe Pro  Gln Asn Ala Phe Ile  Cys Gln Ala Leu Ala  Arg His Phe
    1070                1075                1080

Tyr Ile  Lys Glu Lys Asp Phe  Asn Thr Ala Leu Asp  Trp Ala Arg
    1085                1090                1095

Gln Ala  Lys Met Lys Ala Pro  Lys Asn Ser Tyr Ile  Ser Asp Thr
```

-continued

```
    1100                1105                1110

Leu Gly  Gln Val Tyr Lys Ser  Glu Ile Lys Trp Trp  Leu Asp Gly
    1115                1120                1125

Asn Lys  Asn Cys Arg Ser Ile  Thr Val Asn Asp Leu  Thr His Leu
    1130                1135                1140

Leu Glu  Ala Ala Glu Lys Ala  Ser Arg Ala Phe Lys  Glu Ser Gln
    1145                1150                1155

Arg Gln  Thr Asp Ser Lys Asn  Tyr Glu Thr Glu Asn  Trp Ser Pro
    1160                1165                1170

Gln Lys  Ser Gln Arg Arg Tyr  Asp Met Tyr Asn Thr  Ala Cys Phe
    1175                1180                1185

Leu Gly  Glu Ile Glu Val Gly  Leu Tyr Thr Ile Gln  Ile Leu Gln
    1190                1195                1200

Leu Thr  Pro Phe Phe His Lys  Glu Asn Glu Leu Ser  Lys Lys His
    1205                1210                1215

Met Val  Gln Phe Leu Ser Gly  Lys Trp Thr Ile Pro  Pro Asp Pro
    1220                1225                1230

Arg Asn  Glu Cys Tyr Leu Ala  Leu Ser Lys Phe Thr  Ser His Leu
    1235                1240                1245

Lys Asn  Leu Gln Ser Asp Leu  Lys Arg Cys Phe Asp  Phe Phe Ile
    1250                1255                1260

Asp Tyr  Met Val Leu Leu Lys  Met Arg Tyr Thr Gln  Lys Glu Ile
    1265                1270                1275

Ala Glu  Ile Met Leu Ser Lys  Lys Val Ser Arg Cys  Phe Arg Lys
    1280                1285                1290

Tyr Thr  Glu Leu Phe Cys His  Leu Asp Pro Cys Leu  Leu Gln Ser
    1295                1300                1305

Lys Glu  Ser Gln Leu Leu Gln  Glu Glu Asn Cys Arg  Lys Lys Leu
    1310                1315                1320

Glu Ala  Leu Arg Ala Asp Arg  Phe Ala Gly Leu Leu  Glu Tyr Leu
    1325                1330                1335

Asn Pro  Asn Tyr Lys Asp Ala  Thr Thr Met Glu Ser  Ile Val Asn
    1340                1345                1350

Glu Tyr  Ala Phe Leu Leu Gln  Gln Asn Ser Lys Lys  Pro Met Thr
    1355                1360                1365

Asn Glu  Lys Gln Asn Ser Ile  Leu Ala Asn Ile Ile  Leu Ser Cys
    1370                1375                1380

Leu Lys  Pro Asn Ser Lys Leu  Ile Gln Pro Leu Thr  Thr Leu Lys
    1385                1390                1395

Lys Gln  Leu Arg Glu Val Leu  Gln Phe Val Gly Leu  Ser His Gln
    1400                1405                1410

Tyr Pro  Gly Pro Tyr Phe Leu  Ala Cys Leu Leu Phe  Trp Pro Glu
    1415                1420                1425

Asn Gln  Glu Leu Asp Gln Asp  Ser Lys Leu Ile Glu  Lys Tyr Val
    1430                1435                1440

Ser Ser  Leu Asn Arg Ser Phe  Arg Gly Gln Tyr Lys  Arg Met Cys
    1445                1450                1455

Arg Ser  Lys Gln Ala Ser Thr  Leu Phe Tyr Leu Gly  Lys Arg Lys
    1460                1465                1470

Gly Leu  Asn Ser Ile Val His  Lys Ala Lys Ile Glu  Gln Tyr Phe
    1475                1480                1485

Asp Lys  Ala Gln Asn Thr Asn  Ser Leu Trp His Ser  Gly Asp Val
    1490                1495                1500
```

-continued

```
Trp Lys  Lys Asn Glu Val Lys  Asp Leu Leu Arg Arg  Leu Thr Gly
    1505                 1510                 1515

Gln Ala  Glu Gly Lys Leu Ile  Ser Val Glu Tyr Gly  Thr Glu Glu
    1520                 1525                 1530

Lys Ile  Lys Ile Pro Val Ile  Ser Val Tyr Ser Gly  Pro Leu Arg
    1535                 1540                 1545

Ser Gly  Arg Asn Ile Glu Arg  Val Ser Phe Tyr Leu  Gly Phe Ser
    1550                 1555                 1560

Ile Glu  Gly Pro Leu Ala Tyr  Asp Ile Glu Val Ile
    1565                 1570                 1575


<210> SEQ ID NO 44
<211> LENGTH: 1770
<212> TYPE: PRT
<213> ORGANISM: Homo sapiens

<400> SEQUENCE: 44

Met Asp Gly Met Thr Glu Ala Cys Ile Lys Gly Gly Ile Glu Ala Cys
1               5                   10                  15

Tyr Ala Ala Val Ser Cys Val Cys Thr Leu Leu Gly Ala Leu Asp Glu
            20                  25                  30

Leu Ser Gln Gly Lys Gly Leu Ser Glu Gly Gln Val Gln Leu Leu Leu
        35                  40                  45

Leu Arg Leu Glu Glu Leu Lys Asp Gly Ala Glu Trp Ser Arg Asp Ser
    50                  55                  60

Met Glu Ile Asn Glu Ala Asp Phe Arg Trp Gln Arg Arg Val Leu Ser
65                  70                  75                  80

Ser Glu His Thr Pro Trp Glu Ser Gly Asn Glu Arg Ser Leu Asp Ile
                85                  90                  95

Ser Ile Ser Val Thr Thr Asp Thr Gly Gln Thr Thr Leu Glu Gly Glu
            100                 105                 110

Leu Gly Gln Thr Thr Pro Glu Asp His Ser Gly Asn His Lys Asn Ser
        115                 120                 125

Leu Lys Ser Pro Ala Ile Pro Glu Gly Lys Glu Thr Leu Ser Lys Val
    130                 135                 140

Leu Glu Thr Glu Ala Val Asp Gln Pro Asp Val Val Gln Arg Ser His
145                 150                 155                 160

Thr Val Pro Tyr Pro Asp Ile Thr Asn Phe Leu Ser Val Asp Cys Arg
                165                 170                 175

Thr Arg Ser Tyr Gly Ser Arg Tyr Ser Glu Ser Asn Phe Ser Val Asp
            180                 185                 190

Asp Gln Asp Leu Ser Arg Thr Glu Phe Asp Ser Cys Asp Gln Tyr Ser
        195                 200                 205

Met Ala Ala Glu Lys Asp Ser Gly Arg Ser Asp Val Ser Asp Ile Gly
    210                 215                 220

Ser Asp Asn Cys Ser Leu Ala Asp Glu Glu Gln Thr Pro Arg Asp Cys
225                 230                 235                 240

Leu Gly His Arg Ser Leu Arg Thr Ala Ala Leu Ser Leu Lys Leu Leu
                245                 250                 255

Lys Asn Gln Glu Ala Asp Gln His Ser Ala Arg Leu Phe Ile Gln Ser
            260                 265                 270

Leu Glu Gly Leu Leu Pro Arg Leu Leu Ser Leu Ser Asn Val Glu Glu
        275                 280                 285

Val Asp Thr Ala Leu Gln Asn Phe Ala Ser Thr Phe Cys Ser Gly Met
```

-continued

```
    290                 295                 300

Met His Ser Pro Gly Phe Asp Gly Asn Ser Ser Leu Ser Phe Gln Met
305                 310                 315                 320

Leu Met Asn Ala Asp Ser Leu Tyr Thr Ala Ala His Cys Ala Leu Leu
                325                 330                 335

Leu Asn Leu Lys Leu Ser His Gly Asp Tyr Tyr Arg Lys Arg Pro Thr
            340                 345                 350

Leu Ala Pro Gly Val Met Lys Asp Phe Met Lys Gln Val Gln Thr Ser
        355                 360                 365

Gly Val Leu Met Val Phe Ser Gln Ala Trp Ile Glu Glu Leu Tyr His
    370                 375                 380

Gln Val Leu Asp Arg Asn Met Leu Gly Glu Ala Gly Tyr Trp Gly Ser
385                 390                 395                 400

Pro Glu Asp Asn Ser Leu Pro Leu Ile Thr Met Leu Thr Asp Ile Asp
                405                 410                 415

Gly Leu Glu Ser Ser Ala Ile Gly Gly Gln Leu Met Ala Ser Ala Ala
            420                 425                 430

Thr Glu Ser Pro Phe Ala Gln Ser Arg Arg Ile Asp Asp Ser Thr Val
        435                 440                 445

Ala Gly Val Ala Phe Ala Arg Tyr Ile Leu Val Gly Cys Trp Lys Asn
    450                 455                 460

Leu Ile Asp Thr Leu Ser Thr Pro Leu Thr Gly Arg Met Ala Gly Ser
465                 470                 475                 480

Ser Lys Gly Leu Ala Phe Ile Leu Gly Ala Glu Gly Ile Lys Glu Gln
                485                 490                 495

Asn Gln Lys Glu Arg Asp Ala Ile Cys Met Ser Leu Asp Gly Leu Arg
            500                 505                 510

Lys Ala Ala Arg Leu Ser Cys Ala Leu Gly Val Ala Ala Asn Cys Ala
        515                 520                 525

Ser Ala Leu Ala Gln Met Ala Ala Ala Ser Cys Val Gln Glu Glu Lys
    530                 535                 540

Glu Glu Arg Glu Ala Gln Glu Pro Ser Asp Ala Ile Thr Gln Val Lys
545                 550                 555                 560

Leu Lys Val Glu Gln Lys Leu Glu Gln Ile Gly Lys Val Gln Gly Val
                565                 570                 575

Trp Leu His Thr Ala His Val Leu Cys Met Glu Ala Ile Leu Ser Val
            580                 585                 590

Gly Leu Glu Met Gly Ser His Asn Pro Asp Cys Trp Pro His Val Phe
        595                 600                 605

Arg Val Cys Glu Tyr Val Gly Thr Leu Glu His Asn His Phe Ser Asp
    610                 615                 620

Gly Ala Ser Gln Pro Pro Leu Thr Ile Ser Gln Pro Gln Lys Ala Thr
625                 630                 635                 640

Gly Ser Ala Gly Leu Leu Gly Asp Pro Glu Cys Glu Gly Ser Pro Pro
                645                 650                 655

Glu His Ser Pro Glu Gln Gly Arg Ser Leu Ser Thr Ala Pro Val Val
            660                 665                 670

Gln Pro Leu Ser Ile Gln Asp Leu Val Arg Glu Gly Ser Arg Gly Arg
        675                 680                 685

Ala Ser Asp Phe Arg Gly Gly Ser Leu Met Ser Gly Ser Ser Ala Ala
    690                 695                 700

Lys Val Val Leu Thr Leu Ser Thr Gln Ala Asp Arg Leu Phe Glu Asp
705                 710                 715                 720
```

-continued

```
Ala Thr Asp Lys Leu Asn Leu Met Ala Leu Gly Gly Phe Leu Tyr Gln
                725                 730                 735

Leu Lys Lys Ala Ser Gln Ser Gln Leu Phe His Ser Val Thr Asp Thr
            740                 745                 750

Val Asp Tyr Ser Leu Ala Met Pro Gly Glu Val Lys Ser Thr Gln Asp
        755                 760                 765

Arg Lys Ser Ala Leu His Leu Phe Arg Leu Gly Asn Ala Met Leu Arg
    770                 775                 780

Ile Val Arg Ser Lys Ala Arg Pro Leu Leu His Val Met Arg Cys Trp
785                 790                 795                 800

Ser Leu Val Ala Pro His Leu Val Glu Ala Ala Cys His Lys Glu Arg
                805                 810                 815

His Val Ser Gln Lys Ala Val Ser Phe Ile His Asp Ile Leu Thr Glu
            820                 825                 830

Val Leu Thr Asp Trp Asn Glu Pro Pro His Phe His Phe Asn Glu Ala
        835                 840                 845

Leu Phe Arg Pro Phe Glu Arg Ile Met Gln Leu Glu Leu Cys Asp Glu
    850                 855                 860

Asp Val Gln Asp Gln Val Val Thr Ser Ile Gly Glu Leu Val Glu Val
865                 870                 875                 880

Cys Ser Thr Gln Ile Gln Ser Gly Trp Arg Pro Leu Phe Ser Ala Leu
                885                 890                 895

Glu Thr Val His Gly Gly Asn Lys Ser Glu Met Lys Glu Tyr Leu Val
            900                 905                 910

Gly Asp Tyr Ser Met Gly Lys Gly Gln Ala Pro Val Phe Asp Val Phe
        915                 920                 925

Glu Ala Phe Leu Asn Thr Asp Asn Ile Gln Val Phe Ala Asn Ala Ala
    930                 935                 940

Thr Ser Tyr Ile Met Cys Leu Met Lys Phe Val Lys Gly Leu Gly Glu
945                 950                 955                 960

Val Asp Cys Lys Glu Ile Gly Asp Cys Ala Pro Ala Pro Gly Ala Pro
                965                 970                 975

Ser Thr Asp Leu Cys Leu Pro Ala Leu Asp Tyr Leu Arg Arg Cys Ser
            980                 985                 990

Gln Leu Leu Ala Lys Ile Tyr Lys  Met Pro Leu Lys Pro  Ile Phe Leu
        995                 1000                1005

Ser Gly  Arg Leu Ala Gly Leu  Pro Arg Arg Leu Gln  Glu Gln Ser
    1010                1015                1020

Ala Ser  Ser Glu Asp Gly Ile  Glu Ser Val Leu Ser  Asp Phe Asp
    1025                1030                1035

Asp Asp  Thr Gly Leu Ile Glu  Val Trp Ile Ile Leu  Leu Glu Gln
    1040                1045                1050

Leu Thr  Ala Ala Val Ser Asn  Cys Pro Arg Gln His  Gln Pro Pro
    1055                1060                1065

Thr Leu  Asp Leu Leu Phe Glu  Leu Leu Arg Asp Val  Thr Lys Thr
    1070                1075                1080

Pro Gly  Pro Gly Phe Gly Ile  Tyr Ala Val Val His  Leu Leu Leu
    1085                1090                1095

Pro Val  Met Ser Val Trp Leu  Arg Arg Ser His Lys  Asp His Ser
    1100                1105                1110

Tyr Trp  Asp Met Ala Ser Ala  Asn Phe Lys His Ala  Ile Gly Leu
    1115                1120                1125
```

-continued

```
Ser Cys  Glu Leu Val Val Glu  His Ile Gln Ser Phe  Leu His Ser
    1130                 1135                 1140

Asp Ile  Arg Tyr Glu Ser Met  Ile Asn Thr Met Leu  Lys Asp Leu
    1145                 1150                 1155

Phe Glu  Leu Leu Val Ala Cys  Val Ala Lys Pro Thr  Glu Thr Ile
    1160                 1165                 1170

Ser Arg  Val Gly Cys Ser Cys  Ile Arg Tyr Val Leu  Val Thr Ala
    1175                 1180                 1185

Gly Pro  Val Phe Thr Glu Glu  Met Trp Arg Leu Ala  Cys Cys Ala
    1190                 1195                 1200

Leu Gln  Asp Ala Phe Ser Ala  Thr Leu Lys Pro Val  Lys Asp Leu
    1205                 1210                 1215

Leu Gly  Cys Phe His Ser Gly  Thr Glu Ser Phe Ser  Gly Glu Gly
    1220                 1225                 1230

Cys Gln  Val Arg Val Ala Ala  Pro Ser Ser Ser Pro  Ser Ala Glu
    1235                 1240                 1245

Ala Glu  Tyr Trp Arg Ile Arg  Ala Met Ala Gln Gln  Val Phe Met
    1250                 1255                 1260

Leu Asp  Thr Gln Cys Ser Pro  Lys Thr Pro Asn Asn  Phe Asp His
    1265                 1270                 1275

Ala Gln  Ser Cys Gln Leu Ile  Ile Glu Leu Pro Pro  Asp Glu Lys
    1280                 1285                 1290

Pro Asn  Gly His Thr Lys Lys  Ser Val Ser Phe Arg  Glu Ile Val
    1295                 1300                 1305

Val Ser  Leu Leu Ser His Gln  Val Leu Leu Gln Asn  Leu Tyr Asp
    1310                 1315                 1320

Ile Leu  Leu Glu Glu Phe Val  Lys Gly Pro Ser Pro  Gly Glu Glu
    1325                 1330                 1335

Lys Thr  Ile Gln Val Pro Glu  Ala Lys Leu Ala Gly  Phe Leu Arg
    1340                 1345                 1350

Tyr Ile  Ser Met Gln Asn Leu  Ala Val Ile Phe Asp  Leu Leu Leu
    1355                 1360                 1365

Asp Ser  Tyr Arg Thr Ala Arg  Glu Phe Asp Thr Ser  Pro Gly Leu
    1370                 1375                 1380

Lys Cys  Leu Leu Lys Lys Val  Ser Gly Ile Gly Gly  Ala Ala Asn
    1385                 1390                 1395

Leu Tyr  Arg Gln Ser Ala Met  Ser Phe Asn Ile Tyr  Phe His Ala
    1400                 1405                 1410

Leu Val  Cys Ala Val Leu Thr  Asn Gln Glu Thr Ile  Thr Ala Glu
    1415                 1420                 1425

Gln Val  Lys Lys Val Leu Phe  Glu Asp Asp Glu Arg  Ser Thr Asp
    1430                 1435                 1440

Ser Ser  Gln Gln Cys Ser Ser  Glu Asp Glu Asp Ile  Phe Glu Glu
    1445                 1450                 1455

Thr Ala  Gln Val Ser Pro Pro  Arg Gly Lys Glu Lys  Arg Gln Trp
    1460                 1465                 1470

Arg Ala  Arg Met Pro Leu Leu  Ser Val Gln Pro Val  Ser Asn Ala
    1475                 1480                 1485

Asp Trp  Val Trp Leu Val Lys  Arg Leu His Lys Leu  Cys Met Glu
    1490                 1495                 1500

Leu Cys  Asn Asn Tyr Ile Gln  Met His Leu Asp Leu  Glu Asn Cys
    1505                 1510                 1515

Met Glu  Glu Pro Pro Ile Phe  Lys Gly Asp Pro Phe  Phe Ile Leu
```

-continued

```
    1520                1525                1530

Pro Ser  Phe Gln Ser Glu Ser  Ser Thr Pro Ser Thr  Gly Gly Phe
    1535                1540                1545

Ser Gly  Lys Glu Thr Pro Ser  Glu Asp Asp Arg Ser  Gln Ser Arg
    1550                1555                1560

Glu His  Met Gly Glu Ser Leu  Ser Leu Lys Ala Gly  Gly Gly Asp
    1565                1570                1575

Leu Leu  Leu Pro Pro Ser Pro  Lys Val Glu Lys Lys  Asp Pro Ser
    1580                1585                1590

Arg Lys  Lys Glu Trp Trp Glu  Asn Ala Gly Asn Lys  Ile Tyr Thr
    1595                1600                1605

Met Ala  Ala Asp Lys Thr Ile  Ser Lys Leu Met Thr  Glu Tyr Lys
    1610                1615                1620

Lys Arg  Lys Gln Gln His Asn  Leu Ser Ala Phe Pro  Lys Glu Val
    1625                1630                1635

Lys Val  Glu Lys Lys Gly Glu  Pro Leu Gly Pro Arg  Gly Gln Asp
    1640                1645                1650

Ser Pro  Leu Leu Gln Arg Pro  Gln His Leu Met Asp  Gln Gly Gln
    1655                1660                1665

Met Arg  His Ser Phe Ser Ala  Gly Pro Glu Leu Leu  Arg Gln Asp
    1670                1675                1680

Lys Arg  Pro Arg Ser Gly Ser  Thr Gly Ser Ser Leu  Ser Val Ser
    1685                1690                1695

Val Arg  Asp Ala Glu Ala Gln  Ile Gln Ala Trp Thr  Asn Met Val
    1700                1705                1710

Leu Thr  Val Leu Asn Gln Ile  Gln Ile Leu Pro Asp  Gln Thr Phe
    1715                1720                1725

Thr Ala  Leu Gln Pro Ala Val  Phe Pro Cys Ile Ser  Gln Leu Thr
    1730                1735                1740

Cys His  Val Thr Asp Ile Arg  Val Arg Gln Ala Val  Arg Glu Trp
    1745                1750                1755

Leu Gly  Arg Val Gly Arg Val  Tyr Asp Ile Ile Val
    1760                1765                1770
```